United States Patent
Lu et al.

(10) Patent No.: US 12,180,215 B2
(45) Date of Patent: *Dec. 31, 2024

(54) SUBSTITUTED PYRROLO[3,4-D]IMIDAZOLES AS JAK INHIBITORS

(71) Applicant: HENAN MEDINNO PHARMACEUTICAL TECHNOLOGY CO., LTD., Zhengzhou (CN)

(72) Inventors: Liang Lu, Shanghai (CN); Hai Huang, Zhengzhou (CN); Longzheng Zhang, Zhengzhou (CN); Saisai Zhao, Jiyuan (CN); Jixuan Zhang, Zhengzhou (CN)

(73) Assignee: HENAN MEDINNO PHARMACEUTICAL TECHNOLOGY CO., LTD. (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/169,580

(22) Filed: Feb. 15, 2023

(65) Prior Publication Data

US 2023/0192711 A1    Jun. 22, 2023

Related U.S. Application Data

(63) Continuation of application No. 17/410,965, filed on Aug. 24, 2021, now Pat. No. 11,629,148, which is a continuation of application No. PCT/CN2020/076231, filed on Feb. 21, 2020.

(30) Foreign Application Priority Data

Feb. 25, 2019 (CN) .......................... 201910137984.0
Sep. 17, 2019 (CN) .......................... 201910877661.5

(51) Int. Cl.
*A61K 31/4188* (2006.01)
*C07D 487/04* (2006.01)

(52) U.S. Cl.
CPC .................. *C07D 487/04* (2013.01)

(58) Field of Classification Search
CPC ................ A61K 31/4188; C07D 487/04
USPC ........................... 514/393; 548/303.1
See application file for complete search history.

(56) References Cited

U.S. PATENT DOCUMENTS

| | | |
|---|---|---|
| 6,313,129 B1 | 11/2001 | Uckun et al. |
| 11,629,148 B2 | 4/2023 | Lu et al. |
| 2017/0071946 A1 | 3/2017 | Coe et al. |

FOREIGN PATENT DOCUMENTS

| | | |
|---|---|---|
| CL | 2014000122 A1 | 8/2014 |
| CN | 101401807 A | 4/2009 |
| CN | 103717599 A | 4/2014 |
| CN | 108349972 A | 7/2018 |
| CN | 110461839 A | 11/2019 |
| CN | 110573508 A | 12/2019 |
| CN | 111606908 A | 9/2020 |
| CN | 114075200 A | 2/2022 |
| JP | 2014522865 A | 9/2014 |
| JP | 2017515836 A | 6/2017 |
| JP | 2018531982 A | 11/2018 |
| WO | 2013014567 A1 | 1/2013 |
| WO | 2017077283 A1 | 5/2017 |
| WO | 2017077288 A1 | 5/2017 |
| WO | 2017079205 A1 | 5/2017 |
| WO | 2018204238 A1 | 11/2018 |
| WO | 2020173400 A1 | 9/2020 |
| WO | 2022033562 A1 | 2/2022 |

OTHER PUBLICATIONS

Wolff, Manfred E., Ed. Burger's Medicinal Chemistry and Drug Discovery—Fifth Edition, vol. 1: Principles and Practice, New York: John Wiley & Sons, 1994, 975-977.*

(Continued)

*Primary Examiner* — Douglas M Willis

(74) *Attorney, Agent, or Firm* — MASCHOFF BRENNAN

(57) ABSTRACT

The present disclosure relates to a class of JAK inhibitor compounds and uses thereof. Specifically, the present disclosure discloses a compound represented by formula (G), isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof. The present disclosure also relates to the application of the compounds in medicine.

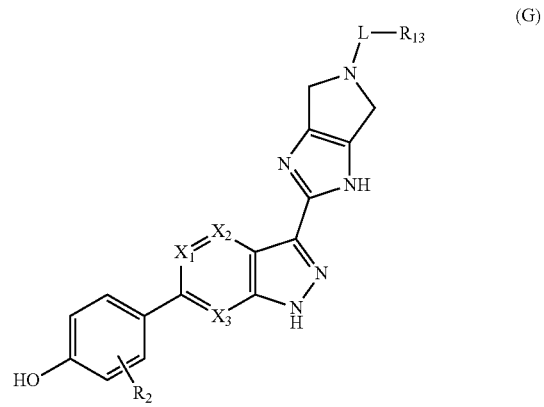

19 Claims, 8 Drawing Sheets

(56) References Cited

OTHER PUBLICATIONS

The Technical Examination Report issued by the Brazilian Patent and Trademark Office dated May 18, 2023 for the Brazilian Patent Application No. BR 11 2021 016751-0 [Translation of the Office Action included].
Eberl et al. "Chemical Proteomics Reveals Target Selectivity of Clinical Jak Inhibitors in Human Primary Cells," Scientific Reports, 9(1), 14159, Oct. 2019.
Tomaselli et al. "Epigenetic Polypharmacology: A New Frontier for Epi-Drug Discovery," Medicinal Research Reviews, 40(1), 190-244, Jan. 2020.
Zhang et al. "Recent Advances in Indazole-Containing Derivatives: Synthesis and Biological Perspectives," Molecules, 23(11), 2783, Oct. 2018.
Turner et al. "Identification of an Indazole-Based Pharmacophore for the Inhibition of FGFR Kinases Using Fragment-Led De Novo Design," ACS medicinal chemistry letters, 8(12), 1264-1268, Dec. 2017.
Atallah, E. et al., Prospect of JAK2 inhibitor therapy in myeloproliferative neoplasms, Expert Reviews Anticancer Therapy, 9(5), 663-670, May 2009.
Barosi, G. et al., Novel strategies for patients with chronic myeloproliferative disorders, Current Opinion in Hematology, 16(2), 129-134, Mar. 2009.
Borie, D.C. et al., JAK3 inhibition as a new concept for immune suppression, Current Opinion in Investigational Drugs, 4(11), 1297-1303, Nov. 2003. (Abstract).
Dörwald, F. Zaragoza, Side Reactions in Organic Synthesis: A Guide to Successful Synthesis Design, Weinheim: WILEY-VCH Verlag Gmbh & Co. KGaA, 2005, Preface.
Jones, P. et al., Design and Synthesis of a Pan-Janus Kinase Inhibitor Clinical Candidate (PF-06263276) Suitable for Inhaled and Topical Delivery for the Treatment of Inflammatory Diseases of the Lungs and Skin, Journal of Medicinal Chemistry, 60(2), 767-786, Jan. 2017.
Jordan, V. C., Tamoxifen: A Most Unlikely Pioneering Medicine, Nature Reviews: Drug Discovery, 2, 205-213, Mar. 2003.
Kisseleva, T. et al., Signaling through the JAK/STAT pathway, recent advances and future challenges, Gene, 285 (1-2), 1-24, Feb. 2002.
Santos, F. et al., Phase 2 study of CEP-701, an orally available JAK2 inhibitor, in patients with primary or post-polycythemia vera/essential thrombocythemia myelofibrosis, Blood, The Journal of the American Society of Hematology, 115(6), 1131-1136, Feb. 2010.
Stahl, P. H. et al., Handbook of Pharmaceutical Salts: Properties, Selection, and Use, Chemistry International, 24 (3), 20, 2002. (Abstract).
Yamaoka, K. et al., The Janus kinases (Jaks), Genome Biology, 5(12), 253-253.6, Nov. 2004.
The first Office Action issued by the Chilean Patent Office dated Oct. 24, 2022 for the Chilean Patent Application No. 202102244.
The first Office Action issued by the China National Intellectual Property Administration (CNIPA) dated Dec. 23, 2020 for the Chinese Patent Application No. 202010110961.3.
The second Office Action issued by the China National Intellectual Property Administration (CNIPA) dated Mar. 12, 2021 for the Chinese Patent Application No. 202010110961.3.
The Extended European Search Report for the European Patent Application No. 20763885.9, issued on Nov. 14, 2022.
The first Office Action issued by the European Patent Office dated Apr. 3, 2023 for the European Patent Application No. 20763885.9.
International Search Report and Written Opinion for PCT/CN2020/076231, mailed May 15, 2020.
International Search Report and Written Opinion for PCT/CN2021/112352, mailed Oct. 14, 2021.
International Search Report and Written Opinion for PCT/CN2021/112351, mailed Nov. 4, 2021.
The first Office Action issued by the Intellectual Property Office of Singapore dated Jan. 23, 2023 for the Singapore Patent Application No. 11202109300Q.
Luo, W. et al., Targeting JAK-STAT Signaling to Control Cytokine Release Syndrome in COVID-19, Trends in Pharmacological Sciences, 41(8), 531-543, Aug. 2020.
Hackam, D. G. et al., Translation of Research Evidence From Animals to Humans, JAMA, 296(14), 1731-1732, Oct. 2006.
Oetjen, L. K. et al., Sensory Neurons Co-opt Classical Immune Signaling Pathways to Mediate Chronic Itch, Cell, 171(1), 217-228, Sep. 2017.
Jones et al.; "Design and Syntheiss of a Pan-JAnus Kinase Inhibitor Clinical Canidate (PF-06263267) Suitable for Inhaled and Topical Delivery for the Treatment of Inflammatory Diseases of the Lungs and Skin"; J Med Chem. Jan. 26, 2017;60(2):767-786. doi: 10.1021/acs.jmedchem.6b01634. Epub Jan. 4, 2017. PMID: 27983835.
Japanese Patent Office; Office Action dated Feb. 9, 2024 issued in JP App No. 2021-572695; 8 pages.
Japanese Patent Office; Office Action dated Jan. 9, 2024 issued in JP App No. 2023-507516; 6 pages.
Japanese Patent Office; Office Action dated Feb. 19, 2024 issued in JP App No. 2023-507517; 6 pages.
China National Intellectual Property Adminstration; Office Action issued in CN App No. 202010818212.6 dated Aug. 13, 2024.
China National Intellectual Property Adminstration; Office Action issued in CN App No. 202010818470.4 dated Aug. 9, 2024.
Spinelli, Francesca Romana et al.; "HiJAKing SARS-CoV-2? The potential role of JAK inhibitors in the management of COVID-19"; Sci Immunol. May 8, 2020;5(47):eabc5367. doi: 10.1126/sciimmunol. abc5367. PMID: 32385052.
Bagca; Bakiey Goker et al.; "The potential of JAK/STAT pathway inhibition by ruxolitinib in the treatment of COVID-19"; Cytokine and Growth Factor Reviews 54; Jun. 20, 2020; pp. 51-61; DOI: https://doi.org/10.1016/j.cytogfr.2020.06.013.
Hasselbalch; Hans Carl; "Rationals for treatment with januskinase 1/2 inhibition of severely ill patients with COVID-19 pneumonia"; Ugeskr Læger; Jun. 15, 2020;182:V04200234 (Including English translation).

* cited by examiner

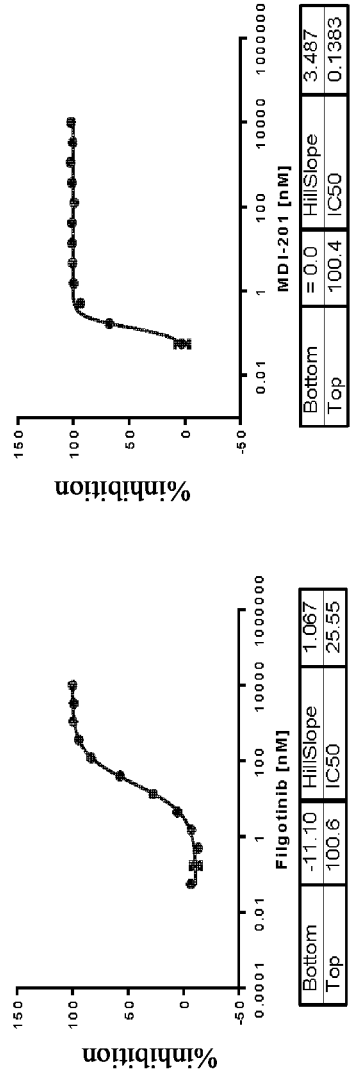
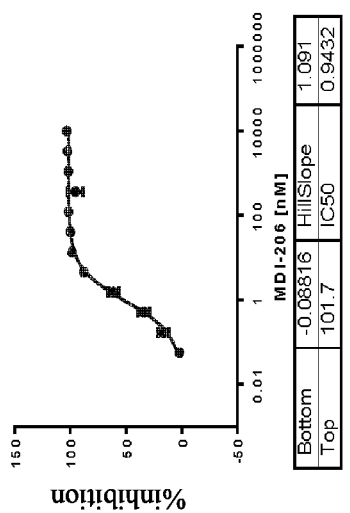
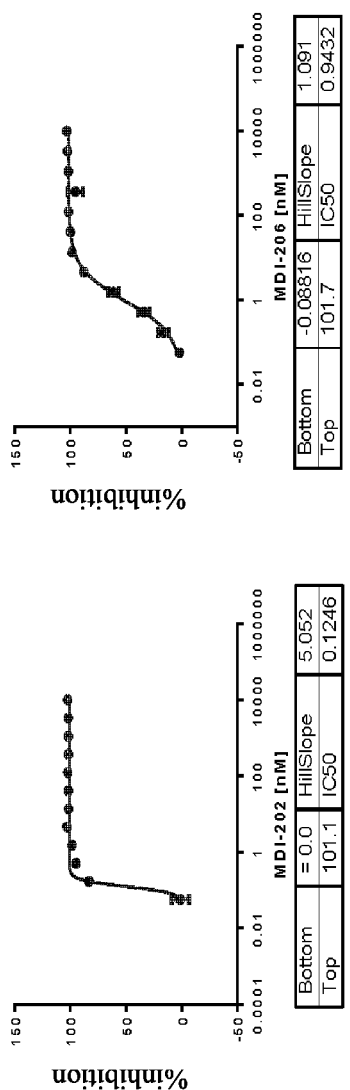
Fig. 5A
Fig. 5B
Fig. 5C
Fig. 5D

Filgotinib dose titration in JAK2 ADP-Glo assay

MDI-201 dose titration in JAK2 ADP-Glo assay

MDI-202 dose titration in JAK2 ADP-Glo assay

MDI-206 dose titration in JAK2 ADP-Glo assay

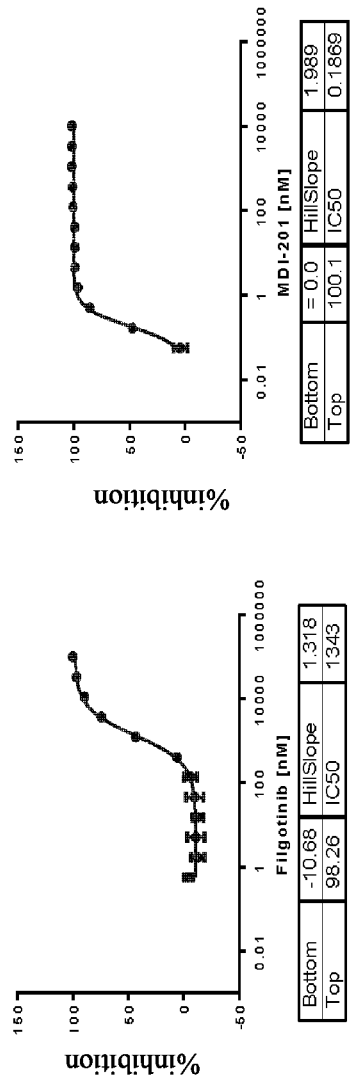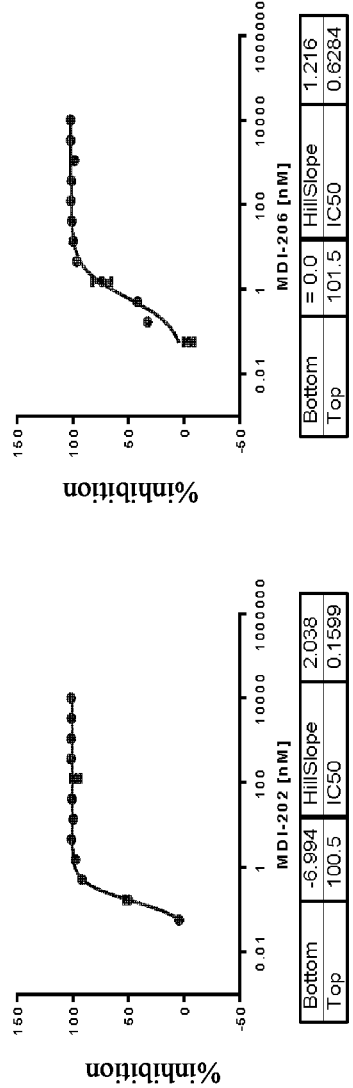

Filgotinib dose titration in TYK2 ADP-Glo assay

MDI-201 dose titration in TYK2 ADP-Glo assay

MDI-202 dose titration in TYK2 ADP-Glo assay

MDI-206 dose titration in TYK2 ADP-Glo assay

SUBSTITUTED PYRROLO[3,4-D]IMIDAZOLES AS JAK INHIBITORS

CROSS-REFERENCE TO RELATED APPLICATION

This application is a continuation of U.S. patent application Ser. No. 17/410,965, filed on Aug. 24, 2021, which is a continuation of International Patent Application No. PCT/CN2020/076231, filed on Feb. 21, 2020, which claims priority to Chinese Patent Application No. 201910877661.5, filed on Sep. 17, 2019 and Chinese Patent Application No. 201910137984.0, filed on Feb. 25, 2019, all of which are incorporated herein by reference in their entireties.

TECHNICAL FIELD

The present disclosure provides a class of novel compounds with pharmacological activity, which can be used to inhibit Janus kinase (JAK). The present disclosure also relates to a composition comprising the compound, and use of the compound and the composition in the preparation of a medicament for the treatment and/or prevention of JAK-related diseases or disorders.

BACKGROUND

Protein kinases are a family of enzymes that catalyze phosphorylation of specific residues in proteins, and are broadly classified into tyrosine and serine/threonine kinases. Inappropriate kinase activities caused by mutations, overexpression or inappropriate regulation, abnormal regulation or dysregulation, and excessive or insufficient production of growth factors or cytokines are involved in many diseases, including but not limited to cancers, cardiovascular diseases, allergies, asthma and other respiratory diseases, autoimmune diseases, inflammatory diseases, bone diseases, metabolic disorders and neurological and neurodegenerative disorders (such as Alzheimer's disease). Inappropriate kinase activity triggers a variety of biological cell responses associated with cell growth, cell differentiation, cell function, survival, apoptosis, and cell motility related to the aforementioned diseases and other related diseases. Therefore, protein kinases have become an important class of enzymes as targets for therapeutic intervention. In particular, the JAK family of cellular protein tyrosine kinases plays an important role in cytokine signal transduction (Kisseleva et al., Gene, 2002, 285, 1; Yamaoka et al., Genome Biology 2004, 5, 253).

Since the first JAK inhibitor was discovered in the early 1990s, the development of JAK inhibitors has gone through nearly 30 years. JAK is a family of intracellular non-receptor tyrosine kinases, which plays an important role in cytokine receptor signaling pathway by interacting with signal transducer and activator of transcription (STAT). JAK/STAT signaling pathway is involved in many important biological processes such as cell proliferation, differentiation, apoptosis and immune regulation. Compared with other signal pathways, the transmission process of this signal pathway is relatively simple. It is mainly composed of three components, namely tyrosine kinase associated receptor, tyrosine kinase JAK, signal transducer and activator of transcription STAT.

Many cytokines and growth factors transmit signals through the JAK-STAT signal pathway, including interleukins (such as IL-2 to IL-7, IL-9, IL-10, IL-15, IL-21, and the like), GM-CSF (granulocyte/macrophage colony stimulating factor), GH (growth hormone), EGF (epidermal growth factor), PRL (prolactin), EPO (erythropoietin), TPO (thrombopoietin), PDGF (platelet derived factors) and interferons (including IFN-α, IFN-β, IFN-γ and the like) and so on. These cytokines and growth factors have corresponding receptors on the cell membrane. The common feature of these receptors is that the receptor itself does not have kinase activity, but its intracellular segment has a binding site for tyrosine kinase JAK. After the receptor binds to a ligand, tyrosine residues of various target proteins are phosphorylated by activation of JAK that binds to the receptor to realize signal transfer from the extracellular to the intracellular.

JAK is a cytoplasmic tyrosine kinase that transduces cytokine signals from membrane receptors to STAT transcription factors. As mentioned above, JAK is the abbreviation of Janus kinase in English. In Roman mythology, Janus is the double-faced god in charge of the beginning and the end. The reason why it is called Janus kinase is that JAK can phosphorylate cytokine receptors that it binds to, and also phosphorylate multiple signal molecules containing specific SH2 domains. The JAK protein family includes 4 members: JAK1, JAK2, JAK3, and TYK2. They have 7 JAK homology domains (JH) in structure in which the JH1 domain is a kinase domain having the function of encoding kinase proteins; JH2 domain is a "pseudo" kinase domain, which regulates the activity of JH1; and JH3-JH7 constitute a four-in-one domain, which regulates the binding of JAK proteins to receptors.

STAT is a type of cytoplasmic protein that can bind to DNA in the regulatory region of target genes, and is a downstream substrate of JAK. Seven members of the STAT family have been discovered, namely STAT1, STAT2, STAT3, STAT4, STAT5A, STAT5B and STAT6. STAT protein can be divided into the following functional segments in structure including N-terminal conserved sequence, DNA binding region, SH3 domain, SH2 domain and C-terminal transcription activation region. Among them, the segment of the most conserved in sequence and most important in function is the SH2 domain, which has the same core sequence "GTFLLRFSS" as the SH2 domain of tyrosine kinase Src.

JAK-STAT signaling pathway has a wide range of functions and is involved in many important biological processes such as cell proliferation, differentiation, apoptosis, and immune regulation. At present, the research related to disease and drug innovation mainly focuses on inflammatory diseases and neoplastic diseases in which the inflammatory diseases mainly include rheumatoid arthritis, canine dermatitis, psoriasis, ulcerative colitis and Crohn's disease; and the neoplastic diseases mainly involve myelofibrosis, polycythemia vera and primary platelets hyperplasia. In addition, mutations in JAK molecule itself can also cause acute myeloid leukemia (AML), acute lymphocytic leukemia (ALL), ductal breast carcinoma and non-small cell lung cancer (NSCLC), polycythemia vera (PV), essential thrombocythemia (ET), idiopathic myelofibrosis (IMF), chronic myeloid leukemia (CML), and the like.

JAK is a very important drug target. JAK inhibitors developed for this target are mainly used to screen therapeutic drugs for blood system diseases, tumors, rheumatoid arthritis and psoriasis. JAK-1, JAK-2 and TYK-2 are expressed in various tissue cells of human body. JAK-3 is mainly expressed in various hematopoietic tissue cells, mainly in bone marrow cells, thymocytes, NK cells and activated B lymphocytes and T lymphocytes. Studies have shown that JAK2 inhibitors are suitable for myeloproliferative diseases (Santos et al., Blood, 2010, 115:1131; Barosi G. and Rosti V., Curr. Opin. Hematol., 2009, 16:129; Atallah E. and Versotvsek S., 2009 Exp. Rev. Anticancer Ther. 9:663), and JAK3 inhibitors are suitable as immunosuppressive agents (such as, U.S. Pat. No. 6,313,129; Borie et al., Curr. Opin. Investigational Drugs, 2003, 4:1297).

Currently, JAK inhibitors approved by the FDA and EMA include Tofacitinib, Ruxolitinib, and Oclacitinib. JAK inhibitors in the middle and late stages of clinical research include Filgotinib, Peficitinib and so on.

Tofacitinib, a JAK3 inhibitor, was developed by Pfizer and was approved by the FDA in November 2012 for the treatment of moderate to severe rheumatoid arthritis (RA) due to inadequate response or intolerance to methotrexate in adult patients. It is the first oral JAK inhibitor approved for RA treatment. After that, it was approved by Japan PMDA for listing in March 2013 under the trade name Xeljanz. On Mar. 16, 2017, Pfizer China announced that the CFDA had formally approved Pfizer's application for the marketing of the oral JAK inhibitor. It was reported that the drug was approved for the treatment of adult patients with moderate to severe rheumatoid arthritis having inadequate response or intolerance to methotrexate. At present, Tofacitinib is close to being approved for indications such as psoriasis, ulcerative colitis, juvenile idiopathic arthritis; and clinical trials for the treatment of indications such as Crohn's disease and alopecia areata have also entered the mid- to late-stage. The main side effects of Tofacitinib are serious infection rate and increased low-density lipoprotein level. The most common adverse effects are upper respiratory tract infection, headache, diarrhea, nasal congestion, sore throat and nasopharyngitis. In addition, it has been have reported that Tofacitinib can cause side effects such as anemia and neutropenia in clinical studies.

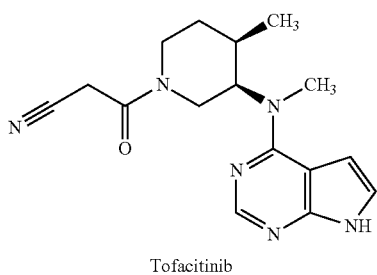 [SMILES: C[C@@H]1CCN(C(=O)CC#N)C[C@@H]1N(C)c1ncnc2[nH]ccc12]

Tofacitinib

Ruxolitinib, a JAK1 and JAK2 inhibitor, was jointly developed by Incyte and Novartis and was approved by the FDA of US in November 2011. It is also the first approved drug specifically for the treatment of myelofibrosis. It was approved by EMA in August 2012 and approved by Japan PMDA for listing in July 2014. The drug is sold by Incyte in the United States under the trade name Jakafi; and is sold by Novartis in Europe and Japan under the trade name Jakavi. Ruxolitinib is under a number of clinical trials in the middle and late stages, wherein the indications include a variety of cancers, GVHD (rejection reaction), alopecia areata, allergic dermatitis, rheumatoid arthritis, vitiligo, psoriasis, and the like. The most common hematological adverse effects with an incidence of >20% of Ruxolitinib are low platelet counts and anemia. The most common non-hematological adverse effects with an incidence of >10% are ecchymosis, dizziness and headache.

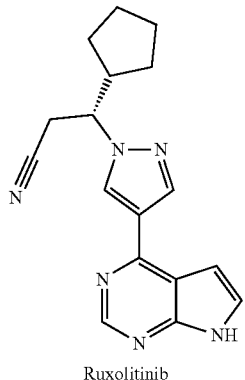 [SMILES: N#CC[C@H](C1CCCC1)n1cc(-c2ncnc3[nH]ccc23)cn1]

Ruxolitinib

Olatinib, approved by the FDA of US in 2013, is used to control itching and atopic dermatitis caused by canine allergic dermatitis. Olatinib is a new type of JAK and JAK1-dependent cytokine inhibitor. Olatinib is not only a very effective JAK1 inhibitor, but can also inhibit the function of JAK1-dependent cytokines in some anti-allergic, inflammation and pruritic reactions. It has little effect on cytokines that are not involved in activation of JAK1. Oral administration of 0.4-0.6 mg/kg Olatinib twice a day is safe and effective for the treatment of itching caused by allergic dermatitis. During the treatment, Olatinib can relieve itching within 24 hours. In experiments, more than 70% of experimental animals (dogs) alleviated the itching response by more than 50% on the 7th day. However, Olatinib cannot yet be used to treat human diseases.

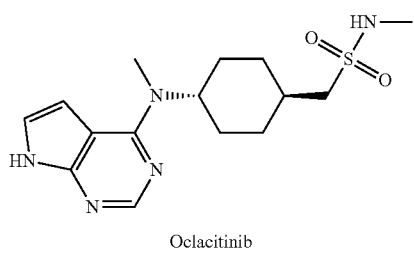 [SMILES: CNS(=O)(=O)C[C@H]1CC[C@H](N(C)c2ncnc3[nH]ccc23)CC1]

Oclacitinib

Filgotinib, a JAK1 inhibitor, passed Phase III clinical trials in September 2018 for the treatment of rheumatoid arthritis. At the same time, the study of Filgotinib for the treatment of ulcerative colitis and Crohn's disease is currently in clinical phase II/III trials. Filgotinib is a selective JAK1 inhibitor with IC50 of 10 nM, 28 nM, 810 nM and 116 nM for JAK1, JAK2, JAK3 and TYK2, respectively.

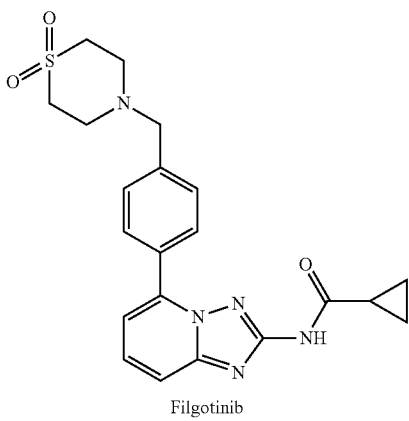 [SMILES: O=C(Nc1nc2cccc(-c3ccc(CN4CCS(=O)(=O)CC4)cc3)n2n1)C1CC1]

Filgotinib

Peficitinib, a JAK1 and JAK3 inhibitor, developed by Astellas, is currently in Phase III clinical trial for the treatment of rheumatoid arthritis. The Phase II clinical study for the treatment of psoriasis has been completed. Peficitinib is a new oral JAK inhibitor. Peficitinib inhibits the enzyme activities of JAK1, JAK2, JAK3 and TYK2 with IC50 of 3.9 nM, 5.0 nM, 0.71 nM and 4.8 nM, respectively.

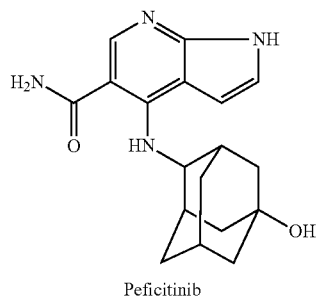 [SMILES: NC(=O)c1cnc2[nH]ccc2c1NC1C2CC3CC1CC(O)(C3)C2]

Peficitinib

Although some JAK inhibitors have been approved for listing, and a large number of JAK inhibitors are still in clinical research, these JAK inhibitors are not satisfactory in terms of efficacy or safety. Therefore, there is always a need for JAK inhibitors with better efficacy and/or fewer side effects.

SUMMARY

It is one object of the present disclosure to provide a novel JAK inhibitor alternative to existing JAK inhibitors, so as to provide more options for the treatment of JAK-related diseases.

A further object of the present disclosure is to provide a novel JAK inhibitor with better efficacy and/or better safety than existing JAK inhibitors.

In a first aspect, the present disclosure provides a compound of Formula (G) as a JAK inhibitor

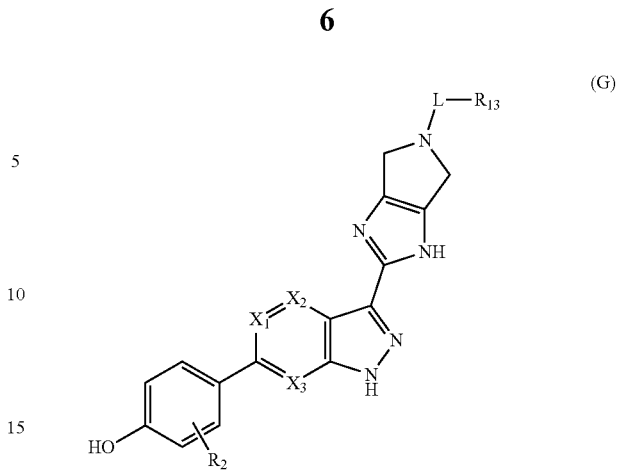

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, wherein L is C=O, O=S=O, $CH_2$ or a bond; and
$X_1$ is N or $CR_{14}$; and
$X_2$ is N or $CR_{15}$; and
$X_3$ is N or $CR_{16}$; and
$R_{14}$, $R_{15}$, $R_{16}$ are each independently selected from H, —OH, —SH, —CN, halogen, —$NO_2$, —$SF_5$, —S—$C_{1-4}$ alkyl, $C_{1-6}$ alkyl, $C_{2-8}$ alkenyl, $C_{2-8}$ alkynyl, $C_{1-6}$ alkoxy, $C_{3-7}$ cycloalkyl, 3-7 membered heterocycloalkyl, $C_{5-7}$ aryl, 5-7 membered heteroaryl, —N($R_9$)($R_{10}$), —N($R_{11}$)(C(=O) $R_{12}$), —C(=O)—N($R_9$)($R_{10}$), —C(=O)—$R_{12}$, —C(=O)—$OR_{12}$, —OC(=O)$R_{12}$, —N($R_{11}$)(S(=O)$_2R_{12}$), —S(=O)$_2$—N($R_9$)($R_{10}$), —$SR_{12}$ and —$OR_{12}$, in which the —S—$C_{1-4}$ alkyl, $C_{1-6}$ alkyl, $C_{1-6}$ alkoxy, $C_{3-7}$ cycloalkyl, and 3-7 membered heterocycloalkyl are optionally substituted with 1, 2 or 3 substitutes selected from halogen, —OH, —$NH_2$, —NH($CH_3$), —N($CH_3$)$_2$, —CN, $C_{1-4}$ alkyl, $C_{3-7}$ cycloalkyl, $C_{1-4}$ hydroxyalkyl, —S—$C_{1-4}$ alkyl, —C(=O) H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, —N($C_{1-4}$ alkyl)(C(=O) $C_{1-4}$ alkyl), $C_{1-4}$ haloalkyl, $C_{1-4}$ alkoxy and $C_{1-4}$ haloalkoxy; and $R_{13}$ is H, —N($R_{17}$)($R_{18}$), $C_{1-6}$ alkoxy, —$SR_{12}$, —$OR_{12}$, —CN, halogen, —$NO_2$, —$SF_5$, —S—$C_{1-4}$ alkyl, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, or 5-11 membered bicyclic heteroalkyl, and $R_{13}$ is substituted with 0, 1, 2, 3 or 4 $R_1$(s), in which $R_{17}$ and $R_{18}$ are each independently selected from H, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, $C_{3-7}$ heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, and 5-11 membered bicyclic heteroalkyl and are optionally substituted with one or more substitutes each independently selected from —OH, —CN, —SH, halogen, —$NO_2$, —$SF_5$, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, —N($R_9$)($R_{10}$), —N($R_{11}$)(C(=O)$R_{12}$), —C(=O)—N($R_9$)($R_{10}$), —C(=O)—$R_{12}$, —C(=O)—$OR_{12}$, —OC(=O)$R_{12}$, —N($R_{11}$)(S(=O)$_2R_{12}$), —S(=O)$_2$—N($R_9$)($R_{10}$), —$SR_{12}$ and —$OR_{12}$, in which the —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2 or 3 substitutes each independently selected from halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$; or $R_{17}$, $R_{18}$ and the N atom connected thereto together form a 3-14 membered ring; and 0, 1, 2, 3 or 4 $R_2$(s) are present in formula (G), and $R_2$ is selected from H, halogen, —OH, —NO$_2$, —CN, —SF$_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, —N($R_9$)($R_{10}$), —N($R_{11}$)(C(=O)$R_{12}$), —C(=O)—N($R_9$)($R_{10}$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$; and $R_1$ is selected from H, halogen, —OH, —NO$_2$, —CN, —SF$_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$bicycloalkyl, 5-11 membered bicyclic heteroalkyl, —N($R_9$)($R_{10}$), —N($R_{11}$)(C(=O)$R_{12}$), —C(=O)—N($R_9$)($R_{10}$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4$(s); and $R_3$ and $R_4$ are each independently selected from H, halogen, —OH, —NO$_2$, —CN, —SF$_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, —N($R_5$)($R_6$), —N($R_{11}$)(C(=O)$R_{12}$), —CON($R_7$)($R_8$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, 3 or 4 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$; and $R_5$, $R_6$, $R_7$, $R_8$, $R_9$, $R_{10}$, $R_{11}$, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein the substituents included in the above group are each optionally substituted with 1, 2, 3 or 4 substituent(s) each independently selected from the group consisting of halogen, —CF$_3$, —OH, —NH$_2$, —NH(CH$_3$), —N(CH$_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy and $C_{1-4}$ haloalkoxy.

In some preferred embodiments of the present disclosure, an isotopically labeled compound of the above-mentioned compound of formula (G) is provided. In some more preferred embodiments of the present disclosure, an isotopically labeled compound of the compound of formula (G) is provided, wherein all Hs are each independently and optionally substituted with D.

In some preferred embodiments of the present disclosure, in formula (G), $X_1$ is N. In some preferred embodiments of the present disclosure, in formula (G), $X_2$ is N. In some preferred embodiments of the present disclosure, in formula (G), $X_3$ is N. In some preferred embodiments of the present disclosure, in formula (G), $X_1$ is CR$_{14}$, $X_2$ is N or CR$_{15}$, and $X_3$ is CR$_{16}$. In some preferred embodiments of the present disclosure, in formula (G), $X_1$ is CR$_{14}$, $X_2$ is CR$_{15}$, and $X_3$ is CR$_{16}$. In some preferred embodiments of the present disclosure, in formula (G), $X_1$ is CR$_{14}$, $X_2$ is CR$_{15}$, $X_3$ is CR$_{16}$, and $R_{14}$, $R_{15}$, and $R_{16}$ are each independently selected from H, —OH, —CN, halogen, $C_{1-6}$ alkyl, $C_{1-6}$ alkoxy, $C_{3-7}$ cycloalkyl, and 3-7 membered heterocycloalkyl. In some preferred embodiments of the present disclosure, in formula (G), $X_1$ is CR$_{14}$, $X_2$ is N, $X_3$ is CR$_{16}$, and $R_{14}$ and $R_{16}$ are each independently selected from H, —OH, —CN, halogen, $C_{1-6}$ alkyl, $C_{1-6}$ alkoxy, $C_{3-7}$ cycloalkyl, and 3-7 membered heterocycloalkyl. In some preferred embodiments of the present disclosure, in formula (G), $X_1$, $X_2$, and $X_3$ are the same. In some preferred embodiments of the present disclosure, in formula (G), $X_1$, $X_2$ and $X_3$ are CH. In some preferred embodiments of the present disclosure, in formula (G), $X_1$, $X_2$ and $X_3$ are N. In some preferred embodiments of the present disclosure, in formula (G), $X_1$ is C(CH$_3$), $X_2$ and $X_3$ are CH. In some preferred embodiments of the present disclosure, in formula (G), $X_2$ is C(CH$_3$), $X_1$ and $X_3$ are CH. In some preferred embodiments of the present disclosure, in formula (G), $X_3$ is C(CH$_3$), $X_1$ and $X_2$ are CH. In some preferred embodiments of the present disclosure, in formula (G), $X_1$ is N, $X_2$ and $X_3$ are CH. In some preferred embodiments of the present disclosure, in formula (G), $X_2$ is N, $X_1$ and $X_3$ are CH. In some preferred embodiments of the present disclosure, in formula (G), $X_3$ is N, $X_1$ and $X_2$ are CH.

In some more preferred embodiments of the present disclosure, there is provided an isotopically labeled compound of the compound of formula (G), wherein all H are each independently and optionally substituted with D, and $X_1$, $X_2$ and $X_3$ are the same. In some more preferred embodiments of the present disclosure, there is provided an isotopically labeled compound of the compound of formula (G), wherein all Hs are each independently and optionally substituted with D, and $X_1$, $X_2$ and $X_3$ are all CH. In some more preferred embodiments of the present disclosure, there is provided an isotopically labeled compound of the compound of formula (G), wherein all Hs are each independently and optionally substituted with D, and $X_1$, $X_2$ and $X_3$ are N. In some more preferred embodiments of the present disclosure, there is provided an isotopically labeled compound of the compound of formula (G), wherein all H are each independently and optionally substituted with D, and $X_1$ is $C(CH_3)$, $X_2$ and $X_3$ are both CH. In some more preferred embodiments of the present disclosure, there is provided an isotopically labeled compound of the compound of formula (G), wherein all Hs are each independently and optionally substituted with D, and $X_2$ is $C(CH_3)$, $X_1$ and $X_3$ are both CH. In some more preferred embodiments of the present disclosure, there is provided an isotopically labeled compound of the compound of formula (G), wherein all Hs are each independently and optionally substituted with D, and $X_3$ is $C(CH_3)$, and $X_1$ and $X_2$ are both CH. In some more preferred embodiments of the present disclosure, there is provided an isotopically labeled compound of the compound of formula (G), wherein all Hs are each independently and optionally substituted with D, and $X_1$ is N, $X_2$ and $X_3$ are both CH. In some more preferred embodiments of the present disclosure, there is provided an isotopically labeled compound of the compound of formula (G), wherein all Hs are each independently and optionally substituted with D, and $X_2$ is N, $X_1$ and $X_3$ are both CH. In some more preferred embodiments of the present disclosure, there is provided an isotopically labeled compound of the compound of formula (G), wherein all Hs are each independently and optionally substituted with D, and $X_3$ is N, and $X_1$ and $X_2$ are both CH.

In some preferred embodiments of the present disclosure, in formula (G), L is C=O, O=S=O or $CH_2$. In some particularly preferred embodiments of the present disclosure, in formula (G), L is C=O. In some particularly preferred embodiments of the present disclosure, in formula (G), L is O=S=O. In some particularly preferred embodiments of the present disclosure, in formula (G), L is $CH_2$. In other embodiments of the present disclosure, in formula (G), L is a bond.

In some particularly preferred embodiments of the present disclosure, in formula (G), $X_1$, $X_2$ and $X_3$ are all CH, and L is C=O.

In some particularly preferred embodiments of the present disclosure, in formula (G), $X_1$, $X_2$ and $X_3$ are all CH, and L is O=S=O.

In some particularly preferred embodiments of the present disclosure, in formula (G), $X_1$, $X_2$ and $X_3$ are all CH, and L is $CH_2$.

In some particularly preferred embodiments of the present disclosure, in formula (G), $X_1$, $X_2$ and $X_3$ are all CH, and L is a bond.

In some particularly preferred embodiments of the present disclosure, in formula (G), $X_1$, $X_2$ and $X_3$ are all N, and L is C=O.

In some particularly preferred embodiments of the present disclosure, in formula (G), $X_1$, $X_2$ and $X_3$ are all N, and L is O=S=O.

In some particularly preferred embodiments of the present disclosure, in formula (G), $X_1$, $X_2$ and $X_3$ are all N, and L is $CH_2$.

In some particularly preferred embodiments of the present disclosure, in formula (G), $X_1$, $X_2$ and $X_3$ are all N, and L is a bond.

In some particularly preferred embodiments of the present disclosure, in formula (G), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is C=O.

In some particularly preferred embodiments of the present disclosure, in formula (G), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is O=S=O.

In some particularly preferred embodiments of the present disclosure, in formula (G), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is $CH_2$.

In some particularly preferred embodiments of the present disclosure, in formula (G), $X_1$, $X_2$ and $X_3$ are all $CR_{14}$, wherein $R_{14}$ is selected from —OH, —CN, halogen, $C_{1-6}$ alkyl, $C_{1-6}$ alkoxy, $C_{3-7}$ cycloalkyl, and 3-7 membered heterocycloalkyl, and L is a bond.

In some particularly preferred embodiments of the present disclosure, in formula (G), $X_1$ is $C(CH_3)$, $X_2$ and $X_3$ are both CH, and L is C=O.

In some particularly preferred embodiments of the present disclosure, in formula (G), $X_1$ is $C(CH_3)$, $X_2$ and $X_3$ are both CH, and L is O=S=O.

In some particularly preferred embodiments of the present disclosure, in formula (G), $X_1$ is $C(CH_3)$, $X_2$ and $X_3$ are both CH, and L is $CH_2$.

In some particularly preferred embodiments of the present disclosure, in formula (G), $X_1$ is $C(CH_3)$, $X_2$ and $X_3$ are both CH, and L is a bond.

In some particularly preferred embodiments of the present disclosure, in formula (G), $X_2$ is $C(CH_3)$, $X_1$ and $X_3$ are both CH, and L is C=O.

In some particularly preferred embodiments of the present disclosure, in formula (G), $X_2$ is $C(CH_3)$, $X_1$ and $X_3$ are both CH, and L is O=S=O.

In some particularly preferred embodiments of the present disclosure, in formula (G), $X_2$ is $C(CH_3)$, $X_1$ and $X_3$ are both CH, and L is $CH_2$.

In some particularly preferred embodiments of the present disclosure, in formula (G), $X_2$ is $C(CH_3)$, $X_1$ and $X_3$ are both CH, and L is a bond.

In some particularly preferred embodiments of the present disclosure, in formula (G), $X_3$ is $C(CH_3)$, $X_1$ and $X_2$ are both CH, and L is C=O.

In some particularly preferred embodiments of the present disclosure, in formula (G), $X_3$ is $C(CH_3)$, $X_1$ and $X_2$ are both CH, and L is O=S=O.

In some particularly preferred embodiments of the present disclosure, in formula (G), $X_3$ is $C(CH_3)$, $X_1$ and $X_2$ are both CH, and L is $CH_2$.

In some particularly preferred embodiments of the present disclosure, in formula (G), $X_3$ is $C(CH_3)$, $X_1$ and $X_2$ are both CH, and L is a bond.

In some particularly preferred embodiments of the present disclosure, in formula (G), $X_1$ is N, $X_2$ and $X_3$ are both CH, and L is C=O.

In some particularly preferred embodiments of the present disclosure, in formula (G), $X_1$ is N, $X_2$ and $X_3$ are both CH, and L is O=S=O.

In some particularly preferred embodiments of the present disclosure, in formula (G), $X_1$ is N, $X_2$ and $X_3$ are both CH, and L is $CH_2$.

In some particularly preferred embodiments of the present disclosure, in formula (G), $X_1$ is N, $X_2$ and $X_3$ are both CH, and L is a bond.

In some particularly preferred embodiments of the present disclosure, in formula (G), $X_2$ is N, $X_1$ and $X_3$ are both CH, and L is C=O.

In some particularly preferred embodiments of the present disclosure, in formula (G), $X_2$ is N, $X_1$ and $X_3$ are both CH, and L is O=S=O.

In some particularly preferred embodiments of the present disclosure, in formula (G), $X_2$ is N, $X_1$ and $X_3$ are both CH, and L is $CH_2$.

In some particularly preferred embodiments of the present disclosure, in formula (G), $X_2$ is N, $X_1$ and $X_3$ are both CH, and L is a bond.

In some particularly preferred embodiments of the present disclosure, in formula (G), $X_3$ is N, $X_1$ and $X_2$ are both CH, and L is C=O.

In some particularly preferred embodiments of the present disclosure, in formula (G), $X_3$ is N, $X_1$ and $X_2$ are both CH, and L is O=S=O.

In some particularly preferred embodiments of the present disclosure, in formula (G), $X_3$ is N, $X_1$ and $X_2$ are both CH, and L is $CH_2$.

In some particularly preferred embodiments of the present disclosure, in formula (G), $X_3$ is N, $X_1$ and $X_2$ are both CH, and L is a bond.

In some preferred embodiments of the present disclosure, in formula (G), $R_{13}$ is H, —N($R_{17}$)($R_{18}$), $C_{1-6}$ alkoxy, —OH, —SH, —CN, halogen, —$NO_2$, —$SF_5$, —S—$C_{1-4}$ alkyl, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, or 5-11 membered bicyclic heteroalkyl, in which $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —$NO_2$, -and $SF_5$, wherein $R_{13}$ is optionally substituted with 1, 2, 3 or 4 $R_1$(s). In some preferred embodiments of the present disclosure, in formula (G), $R_{13}$ is H, —N($R_{17}$)($R_{18}$), $C_{1-6}$ alkoxy, —OH, —SH, —CN, halogen, —$NO_2$, —$SF_5$, —S—$C_{1-4}$ alkyl, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, or 11-15 membered tricyclyl and $R_{17}$ and $R_{18}$ are defined as above, wherein $R_{13}$ is optionally substituted with 1, 2, 3 or 4 $R_1$(s). In some preferred embodiments of the present disclosure, in formula (G), $R_{13}$ is H, —N($R_{17}$)($R_{18}$), $C_{1-6}$ alkoxy, $C_{1-6}$ alkyl, or $C_{3-7}$ cycloalkyl, 3-7 membered heterocycloalkyl, $C_{5-7}$ aryl, or 5-7 membered heteroaryl, and $R_{17}$ and $R_{18}$ are defined as above, wherein $R_{13}$ is optionally substituted with 1, 2, 3 or 4 $R_1$(s). In some preferred embodiments of the present disclosure, in formula (G), $R_{13}$ is —N($R_{17}$)($R_{18}$), $C_{1-6}$ alkoxy, $C_{1-6}$ alkyl, or $C_{3-7}$ cycloalkyl, 4-6 membered heterocycloalkyl, phenyl, or 5-6 membered heteroaryl, and $R_{17}$ and $R_{18}$ are defined as above, wherein $R_{13}$ is optionally substituted with 1, 2, or 3 $R_1$(s). In some preferred embodiments of the present disclosure, in formula (G), $R_{13}$ is —N($R_{17}$)($R_{18}$), $C_{1-3}$ alkoxy, $C_{3-6}$ cycloalkyl, 4-6 membered heterocycloalkyl, phenyl, 5-6 membered heteroaryl or $C_{1-4}$ alkyl, and $R_{17}$ and $R_{18}$ are defined as above, wherein $R_{13}$ is optionally substituted with 1, 2, or 3 $R_1$(s). In some preferred embodiments of the present disclosure, in formula (G), $R_{13}$ is —N(H)($C_{1-3}$ alkyl), —N(H)(3-6 membered cycloalkyl), —N(H) (4-6 membered heterocycloalkyl), —N($C_{1-3}$ alkyl) ($C_{1-3}$ alkyl), $C_{1-3}$ alkoxy, $C_{3-6}$ cycloalkyl, 4-6 membered azacycloalkyl or oxacycloalkyl, phenyl, 5-6 membered azaaryl or $C_{1-4}$ alkyl; or $R_{13}$ is —N($R_{17}$)($R_{18}$), and $R_{17}$ and $R_{18}$ and the N atom connected thereto together form a 4-10 membered ring (where $R_{13}$ is optionally substituted with 1, 2, or 3 $R_1$(s)). In some particularly preferred embodiments of the present disclosure, in formula (G), $R_{13}$ is cyclopropyl, cyclobutyl, cyclopentyl, cyclohexyl, methyl, ethyl, propyl, butyl, methoxy, ethoxy, propoxy, —N(H)($CH_3$), —N(H)($CH_2CH_3$), —N(H)($CH_2CH_2OH$), —N(H)($CH_2CH_2CN$), —N($CH_3$)($CH_3$), —N(H)(cyclopropyl), —N(H)(cyclobutyl), —N(H)(tetrahydrofuranyl), pyrazinyl, pyridazinyl, pyrrolidinyl, pyrazolyl, piperidinyl, phenyl, azetidinyl, morpholinyl, piperazinyl or tetrahydropyranyl; or $R_{13}$ is —N($R_{17}$)($R_{18}$), and $R_{17}$ and $R_{18}$ and the N atom connected thereto together form a 7-membered ring (where $R_{13}$ is optionally substituted with 1, 2, or 3 $R_1$(s)). In some particularly preferred embodiments of the present disclosure, in formula (G), $R_{13}$ is cyclopropyl. In some particularly preferred embodiments of the present disclosure, in formula (G), $R_{13}$ is cyclobutyl. In some particularly preferred embodiments of the present disclosure, in formula (G), $R_{13}$ is cyclopentyl. In some particularly preferred embodiments of the present disclosure, in formula (G), $R_{13}$ is cyclohexyl. In some particularly preferred embodiments of the present disclosure, in formula (G), $R_{13}$ is a methyl group. In some particularly preferred embodiments of the present disclosure, in formula (G), $R_{13}$ is an ethyl group. In some particularly preferred embodiments of the present disclosure, in formula (G), $R_{13}$ is propyl. In some particularly preferred embodiments of the present disclosure, in formula (G), $R_{13}$ is a butyl group. In some particularly preferred embodiments of the present disclosure, in formula (G), $R_{13}$ is pyrazinyl. In some particularly preferred embodiments of the present disclosure, in formula (G), $R_{13}$ is a pyridazinyl. In some particularly preferred embodiments of the present disclosure, in formula (G), $R_{13}$ is a pyrrolidinyl. In some particularly preferred embodiments of the present disclosure, in formula (G), $R_{13}$ is pyrazolyl. In some particularly preferred embodiments of the present disclosure, in formula (G), $R_{13}$ is piperidinyl. In some particularly preferred embodiments of the present disclosure, in formula (G), $R_{13}$ is phenyl. In some particularly preferred embodiments of the present disclosure, in formula (G), $R_{13}$ is azetidinyl. In some particularly preferred embodiments of the present disclosure, in formula (G), $R_{13}$ is morpholinyl. In some particularly preferred embodiments of the present disclosure, in formula (G), $R_{13}$ is piperazinyl. In some particularly preferred embodiments of the present disclosure, in formula (G), $R_{13}$ is tetrahydropyranyl. In some particularly preferred embodiments of the present disclosure, in formula (G), $R_{13}$ is methoxy. In some particularly preferred embodiments of the present disclosure, in formula (G), $R_{13}$ is ethoxy. In some particularly preferred embodiments of the present disclosure, in formula (G), $R_{13}$ is —N(H)($CH_3$). In some particularly preferred embodiments of the present disclosure, in formula (G), $R_{13}$ is —N(H)($CH_2CH_3$). In some particularly preferred embodiments of the present disclosure, in formula (G), $R_{13}$ is —N(H)($CH_2CH_2OH$). In some particularly preferred embodiments of the present disclosure, in formula (G), $R_{13}$ is —N(H)($CH_2CH_2CN$). In some particularly preferred embodiments of the present disclosure, in formula (G), $R_{13}$ is —N($CH_3$)($CH_3$). In some particularly preferred embodiments of the present disclosure, in formula (G), $R_{13}$ is —N(H) (cyclopropyl). In some particularly preferred embodiments of the present disclosure, in formula (G), $R_{13}$ is —N(H) (cyclobutyl). In some particularly preferred embodiments of the present disclosure, in formula (G), $R_{13}$ is —N(H) (tetrahydrofuranyl). In some particularly preferred embodiments of the present disclosure, in formula (G), $R_{13}$ is —N($R_{17}$)($R_{18}$), and $R_{17}$ and $R_{18}$ and the N atom connected to them together form a 7-membered ring.

In some particularly preferred embodiments of the present disclosure, in formula (G), $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, and SF$_5$. In some particularly preferred embodiments of the present disclosure, in formula (G), $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH, —CN, —SH, halogen, —NO$_2$, and SF$_5$. In some particularly preferred embodiments of the present disclosure, in formula (G), $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH and —CN. In some preferred embodiments of the present disclosure, in formula (G), $R_{17}$ and $R_{18}$ are each independently selected from H, methyl, ethyl, propyl, 3-membered cycloalkyl, 4-membered cycloalkyl, 5-membered cycloalkyl, 5-membered heterocycloalkyl, and 6-membered heterocycloalkyl, and optionally substituted with one or more of —OH and —CN. In some preferred embodiments of the present disclosure, in formula (G), $R_{17}$, $R_{18}$ and the N atom connected thereto together form a 4-10 membered ring. In some preferred embodiments of the present disclosure, in formula (G), $R_{17}$, $R_{18}$ and the N atom connected thereto together form a 7-membered ring.

In some particularly preferred embodiments of the present disclosure, in formula (G), L is C=O, and $R_{13}$ is —N($R_{17}$)($R_{18}$), $C_{1-6}$ alkoxy, —OH, —SH, —CN, halogen, —NO$_2$, —SF$_5$, or —S—$C_{1-4}$ alkyl, and $R_{13}$ is substituted with 0, 1, 2, 3 or 4 $R_1$(s) in which $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, -and SF$_5$, or $R_{17}$, $R_{18}$ and the N atom connected thereto together form a 3-14 membered ring. In some particularly preferred embodiments of the present disclosure, in formula (G), L is C=O, and $R_{13}$ is —N($R_{17}$)($R_{18}$), or $C_{1-6}$ alkoxy, in which $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH, —CN, —SH, halogen, —NO$_2$, -and SF$_5$, or $R_{17}$, $R_{18}$ and the N atom connected thereto together form a 3-10 membered ring. In some particularly preferred embodiments of the present disclosure, in formula (G), L is C=O, and $R_{13}$ is methoxy, ethoxy, propoxy, —N(H)(CH$_3$), —N(H)(CH$_2$CH$_3$), —N(H)(CH$_2$CH$_2$OH), —N(H)(CH$_2$CH$_2$CN), —N(CH$_3$)(CH$_3$), —N(H)(cyclopropyl), —N(H) (cyclobutyl), —N(H) (tetrahydrofuranyl); or $R_{13}$ is —N($R_{17}$)($R_{18}$), and $R_{17}$, $R_{18}$ and the N atom connected thereto together form a 7-membered ring. In some particularly preferred embodiments of the present disclosure, in formula (G), L is C=O, and $R_{13}$ is methoxy. In some particularly preferred embodiments of the present disclosure, in formula (G), L is C=O, and $R_{13}$ is ethoxy. In some particularly preferred embodiments of the present disclosure, in formula (G), L is C=O, and $R_{13}$ is —N(H)(CH$_3$). In some particularly preferred embodiments of the present disclosure, in formula (G), L is C=O, and $R_{13}$ is —N(H)(CH$_2$CH$_3$). In some particularly preferred embodiments of the present disclosure, in formula (G), L is C=O, and $R_{13}$ is —N(H)(CH$_2$CH$_2$OH). In some particularly preferred embodiments of the present disclosure, in formula (G), L is C=O, and $R_{13}$ is —N(H)(CH$_2$CH$_2$CN). In some particularly preferred embodiments of the present disclosure, in formula (G), L is C=O, and $R_{13}$ is —N(CH$_3$)(CH$_3$).

In some particularly preferred embodiments of the present disclosure, in formula (G), L is C=O, and $R_{13}$ is —N(H)(cyclopropyl). In some particularly preferred embodiments of the present disclosure, in formula (G), L is C=O, and $R_{13}$ is —N(H)(cyclobutyl). In some particularly preferred embodiments of the present disclosure, in formula (G), L is C=O, and $R_{13}$ is —N(H)(tetrahydrofuranyl). In some particularly preferred embodiments of the formula (G), L is C=O, and $R_{13}$ is —N($R_{17}$)($R_{18}$), and $R_{17}$, $R_{18}$ and the N atom connected thereto together form a 7-membered ring.

In some particularly preferred embodiments of the present disclosure, in formula (G), one, two or three $R_2$(s) are present and $R_2$ is selected from H, halogen, —OH, —NO$_2$, —CN, —SF$_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, and 4-10 membered heterocycloalkyl, in which the —S—$C_{1-4}$ alkyl, $C_{1-6}$ alkyl, $C_{3-7}$ cycloalkyl, and 4-10 membered heterocycloalkyl are each optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G), one, two or three $R_2$(s) are present and $R_2$ is selected from halogen, $C_{1-6}$ alkyl and $C_{3-6}$ cycloalkyl, in which the $C_{1-6}$ alkyl and $C_{3-6}$ cycloalkyl are each optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G), one, two or three $R_2$(s) are present and $R_2$ is selected from halogen, and $C_{1-6}$ alkyl, in which the $C_{1-6}$ alkyl is optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G), one, or two $R_2$(s) are present and $R_2$ is selected from halogen, and $C_{1-6}$ alkyl. In some particularly preferred embodiments of the present disclosure, in formula (G), one or two $R_2$(s) are present and $R_2$ is selected from fluorine, chlorine, bromine, methyl, ethyl, n-propyl, isopropyl, n-butyl, and isobutyl. In some preferred embodiments of the present disclosure, in formula (G), one or two $R_2$(s) are present, and $R_2$ is selected from fluorine, chlorine, methyl, ethyl, n-propyl, and isopropyl. In some preferred embodiments of the present disclosure, in formula (G), one or two $R_2$(s) are present, and $R_2$ is selected from fluorine, methyl, and ethyl. In some preferred embodiments of the present disclosure, in formula (G), one or two $R_2$ (s) are present, and $R_2$ is selected from fluorine and ethyl. In some preferred embodiments of the present disclosure, in formula (G), one $R_2$ is present, and $R_2$ is selected from fluorine and ethyl. In some preferred embodiments of the present disclosure, in formula (G), two $R_2$(s) are present, and $R_2$ is selected from fluorine and ethyl. In some particularly preferred embodiments of the present disclosure, in formula (G), two $R_2$(s) are present which are respectively fluorine and ethyl. In some particularly preferred embodiments of the present disclosure, in formula (G), one $R_2$ is present, and $R_2$ is an ethyl group.

In some preferred embodiments of the present disclosure, in formula (G), $R_{13}$ is substituted with 0, 1, 2, 3 or 4 $R_1$(s), and each $R_1$ is independently selected from H, halogen, —OH, —NO$_2$, —CN, —SF$_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl, wherein the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and wherein the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3 or 4 $R_4$(s). In some preferred embodiments of the present disclosure, in formula (G), $R_{13}$ is substituted with 0, 1, 2, 3 or 4 $R_1$(s), and each $R_1$ is independently selected from H, halogen, —OH, —$NO_2$, —CN, —$SF_5$, —SH, —S—$C_{1-4}$ alkyl, $C_{1-8}$ alkyl, $C_{3-7}$ cycloalkyl, 3-7 membered heterocycloalkyl, $C_{5-7}$ aryl, and 5-7 membered heteroaryl, wherein the —S—$C_{1-4}$ alkyl, and $C_{1-8}$ alkyl are optionally substituted with 1, 2, 3 or 4 $R_3$(s), and wherein the $C_{3-7}$ cycloalkyl, 3-7 membered heterocycloalkyl, $C_{5-7}$ aryl, and 5-7 membered heteroaryl are optionally substituted with 1, 2, 3, or 4 $R_4$(s). In some preferred embodiments of the present disclosure, in formula (G), $R_{13}$ is substituted with 0, 1, 2, 3 or 4 $R_1$(s), and each $R_1$ is independently selected from halogen, —OH, —CN, $C_{1-8}$ alkyl, $C_{3-7}$ cycloalkyl, 3-7 membered heterocycloalkyl, $C_{5-7}$ aryl, 5-7 membered heteroaryl, wherein the $C_{1-8}$ alkyl is optionally substituted with 1, 2, 3 or 4 $R_3$(s), and wherein the $C_{3-7}$ cycloalkyl, 3-7 membered heterocycloalkyl, $C_{5-7}$ aryl, 5-7 membered heteroaryl are optionally substituted with 1, 2, 3 or 4 $R_4$(s). In some preferred embodiments of the present disclosure, in formula (G), $R_{13}$ is substituted with 0, 1, 2, 3 or 4 $R_1$(s), and each $R_1$ is independently selected from halogen, —OH, —CN, $C_{1-8}$ alkyl, $C_{3-7}$ cycloalkyl, and 3-7 membered heterocycloalkyl, wherein the $C_{1-8}$ alkyl is optionally substituted with 1, 2, or 3 $R_3$(s), and wherein the $C_{3-7}$ cycloalkyl, and 3-7 membered heterocycloalkyl are optionally substituted with 1, 2, or 3 $R_4$(s). In some preferred embodiments of the present disclosure, in formula (G), $R_{13}$ is substituted with 0 or 1 $R_1$, and each $R_1$ is independently selected from halogen, —OH, —CN, $C_{1-6}$ alkyl, $C_{3-7}$ cycloalkyl, 5-7 membered heterocycloalkyl, wherein the $C_{1-6}$ alkyl is optionally substituted with 1, 2, or 3 $R_3$(s), and wherein the $C_{3-7}$ cycloalkyl, and 5-7-membered heterocycloalkyl are optionally substituted with 1, 2, or 3 $R_4$(s). In some preferred embodiments of the present disclosure, in formula (G), $R_{13}$ is substituted with 0 or 1 $R_1$, and each $R_1$ is independently selected from halogen, —OH, —CN, $C_{1-4}$ alkyl, $C_{3-6}$ cycloalkyl, and 5-7 membered heterocycloalkyl, wherein the $C_{1-4}$ alkyl is optionally substituted with 1 or 2 $R_3$(s), and wherein the $C_{3-6}$ cycloalkyl and 5-7 membered heterocycloalkyl are optionally substituted with 1, 2, or 3 $R_4$(s). In some particularly preferred embodiments of the present disclosure, in formula (G), $R_{13}$ is substituted with 0 or 1 $R_1$, and each $R_1$ is independently selected from methyl, ethyl, hydroxyl, —CN, piperidinyl, morpholinyl, piperazinyl, and cyclopropyl, wherein the piperidinyl, morpholinyl, and piperazinyl are optionally substituted with 1, 2, 3 or 4 $C_{1-3}$ alkyl. In some particularly preferred embodiments of the present disclosure, in formula (G), $R_{13}$ is substituted with 0 or 1 $R_1$, and each $R_1$ is independently selected from methyl, ethyl, hydroxy, —CN, piperidinyl, morpholinyl, 1-methylpiperazinyl, and cyclopropyl. In some particularly preferred embodiments of the present disclosure, in formula (G), $R_1$ is absent. In some particularly preferred embodiments of the present disclosure, in formula (G), $R_1$ is 1-methylpiperazinyl. In some particularly preferred embodiments of the present disclosure, in formula (G), $R_1$ is methyl. In some particularly preferred embodiments of the present disclosure, in formula (G), $R_1$ is ethyl. In some particularly preferred embodiments of the present disclosure, in formula (G), $R_1$ is piperidinyl. In some particularly preferred embodiments of the present disclosure, in formula (G), $R_1$ is morpholinyl. In some particularly preferred embodiments of the present disclosure, in formula (G), $R_1$ is hydroxyl. In some particularly preferred embodiments of the present disclosure, in formula (G), $R_1$ is —CN. In some particularly preferred embodiments of the present disclosure, in formula (G), $R_1$ is cyclopropyl.

The preferred options of the respective substituents mentioned in the above various preferred embodiments can be combined with each other in any way, and various combinations thereof are within the scope of the present disclosure. In the most preferred embodiments of the present disclosure, the compound of formula (G) is each specific compound shown in Example 1 to Example 58 herein. That is, the compound of formula (G) is selected from (2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(5-morpholinylpyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone;

(2-(6-(2-ethyl-5-fluoro-4-hydroxyphenyl)-1H-indazol-3-yl)pyrrolo[3,4-d]imidazol-5(1H, 4H,6H)-yl)(1-methylpiperidin-4-yl)ketone;

(2-(6-(2-ethyl-5-fluoro-4-hydroxyphenyl)-1H-indazol-3-yl)pyrrolo[3,4-d]imidazol-5(1H, 4H,6H)-yl)(5-(4-methylpiperzin-1-yl)pyrazin-2-yl)ketone;

(2-(6-(2-ethyl-4-hydroxyphenyl)-1H-indazol-3-yl)pyrrolo[3,4-d]imidazol-5(1H,4H,6H)-yl)(5-(4-methylpiperzin-1-yl)pyrazin-2-yl)ketone;

5-ethyl-2-fluoro-4-(3-(5-(benzenesulfonyl)-1,4,5,6-tetrahydropyrrolo[3,4-d]imidazol-2-yl)-1H-indazol-6-yl)phenol;

5-ethyl-2-fluoro-4-(3-(5-(pyrazin-2ylmethyl)-1,4,5,6-tetrahydropyrrolo[3,4-d]imidazol-2-yl)-1H-indazol-6-yl)phenol;

4-(3-(5-(cyclopropylmethyl)-1,4,5,6-tetrahydropyrrolo[3,4-d]imidazol-2-yl)-1H-indazol-6-yl)-5-ethyl-2-fluorophenol;

Cyclopropyl(2-(6-(2-ethyl-5-fluoro-4-hydroxyphenyl)-1H-indazol-3-yl)pyrrolo[3,4-d]imidazol-5(1H,4H,6H)-yl)ketone;

4-(3-(5-(cyclobutylmethyl)-1,4,5,6-tetrahydropyrrolo[3,4-d]imidazol-2-yl)-1H-indazol-6-yl)-5-ethyl-2-fluorophenol;

Cyclobutyl(2-(6-(2-ethyl-5-fluoro-4-hydroxyphenyl)-1H-indazol-3-yl)pyrrolo[3,4-d]imidazol-5(1H,4H,6H)-yl)ketone;

(2-(6-(2-ethyl-5-fluoro-4-hydroxyphenyl)-1H-indazol-3-yl)pyrrolo[3,4-d]imidazol-5(1H,4H,6H)-yl)(3-hydroxylcyclobutyl)ketone;

(2-(6-(2-ethyl-5-fluoro-4-hydroxyphenyl)-1H-indazol-3-yl)-pyrrolo[3,4-d]imidazol-5-(1H,4H,6H)-yl)(pyridazin-4-yl)ketone;

(2-(6-(2-ethyl-5-fluoro-4-hydroxyphenyl)-1H-indazol-3-yl)-pyrrolo[3,4-d]imidazol-5-(1H,4H,6H)-yl)(pyridazin-3-yl)ketone;

(S)-(2-(6-(2-ethyl-5-fluoro-4-hydroxyphenyl)-1H-indazol-3-yl)-4,6-dihydropyrrolo[3,4-d]imidazol-5-(1H)-yl)(3-hydroxylpyrrolidin-1-yl)ketone;

5-ethyl-2-fluoro-4-(3-(5-(4-hydroxylcyclohexyl)-1,4,5,6-tetrahydropyrrolo[3,4-d]imidazol-2-yl)-1H-indazol-6-yl)phenol;
4-(3-(5-(cyclopropanesulfonyl)-1,4,5,6-tetrahydropyrrolo[3,4-d]imidazol-2-yl)-1H-indazol-6-yl)-5-ethyl-2-fluorophenol;
4-(3-(5-(cyclobutylsulfonyl)-1,4,5,6-tetrahydropyrrolo[3,4-d]imidazol-2-yl)-1H-indazol-6-yl)-5-ethyl-2-fluorophenol;
4-(3-(5-(cyclopentylsulfonyl)-1,4,5,6-tetrahydropyrrolo[3,4-d]imidazol-2-yl)-1H-indazol-6-yl)-5-ethyl-2-fluorophenol;
5-ethyl-2-fluoro-4-(3-(5-((1-methyl-1H-pyrazol-4-yl)methyl)-1,4,5,6-tetrahydropyrrolo[3,4-d]imidazol-2-yl)-1H-indazol-6-yl)phenol;
4-(3-(5-(cyclopentyl-1,4,5,6-tetrahydropyrrolo[3,4-d]imidazol-2-yl)-1H-indazol-6-yl)-5-ethyl-2-fluorophenol;
5-ethyl-2-fluoro-4-(3-(5-(tetrahydro-2H-pyran-4-yl)-1,4,5,6-tetrahydropyrrolo[3,4-d]imidazol-2-yl)-1H-indazol-6-yl)phenol;
1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one;
1-(2-(6-(2-ethyl-5-fluoro-4-hydroxyphenyl)-1H-indazol-3-yl)-4,6-dihydropyrrolo[3,4-d]imidazol-5-(1H)-yl)propan-1-one;
(1-(2-(6-(2-ethyl-5-fluoro-4-hydroxyphenyl)-1H-indazol-3-yl)-4,6-dihydropyrrolo[3,4-d]imidazol-5-(1H)-yl)-2-methylpropan-1-one);
2-cyclopropyl-1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one;
1-(2-(6-(2-ethyl-5-fluoro-4-hydroxyphenyl)-1H-indazol-3-yl)-4,6-dihydropyrrolo[3,4-d]imidazol-5-(1H)-yl)-3-methylbutan-1-one;
(2-(6-(2-ethyl-5-fluoro-4-hydroxyphenyl)-1H-indazol-3-yl)-4,6-dihydropyrrolo[3,4-d]imidazol-5-(1H)-yl)(pyrrolidin-1-yl)ketone;
Azetidin-1-yl((2-(6-(2-ethyl-5-fluoro-4-hydroxyphenyl)-1H-indazol-3-yl)-4,6-dihydropyrrolo[3,4-d]imidazol-5-(1H)-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(piperidin-1-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(morpholino)ketone;
(2-(6-(2-ethyl-5-fluoro-4-hydroxyphenyl)-1H-indazol-3-yl)-4,6-dihydropyrrolo[3,4-d]imidazol-5-(1H)-yl)(4-methylpiperzin-1-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(4-ethylpiperzin-1-yl)ketone;
Cyclopropyl(2-(6-(2-ethyl-5-fluoro-4-hydroxyphenyl)-1H-pyrazolo[4,3-b]pyridin-3-yl)-4,6-dihydropyrrolo[3,4-d]imidazol-5(1H)-yl)ketone;
Cyclopropyl(2-(6-(2-ethyl-5-fluoro-4-hydroxyphenyl)-4-methyl-1H-indazol-3-yl)-4,6-dihydropyrrolo[3,4-d]imidazol-5(1H)-yl)ketone;
(S)-(2-(6-(2-ethyl-5-fluoro-4-hydroxyphenyl)-4-methyl-1H-indazol-3-yl)-4,6-dihydropyrrolo[3,4-d]imidazol-5(1H)-yl)(3-hydroxylpyrrolidin-1-yl)ketone;
Cyclopropyl(2-(6-(2-ethyl-5-fluoro-4-hydroxyphenyl)-1H-pyrazolo[4,3-c]pyridin-3-yl)-4,6-dihydropyrrolo[3,4-d]imidazol-5(1H)-yl)ketone;
(R)-(2-(6-(2-ethyl-5-fluoro-4-hydroxyphenyl)-1H-indazol-3-yl)-4,6-dihydropyrrolo[3,4-d]imidazol-5(1H)-yl)(3-hydroxylpyrrolidin-1-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(3-hydroxylAzetidin-1-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(4-hydroxylpiperidin-1-yl)ketone;
2-(6-(2-ethyl-5-fluoro-4-hydroxyphenyl)-1H-indazol-3-yl)-N-methyl-4,6-dihydropyrrolo[3,4-d]imidazol-5-(1H)-carboxamide;
2-(6-(2-ethyl-5-fluoro-4-hydroxyphenyl)-1H-indazol-3-yl)-N-ethyl-4,6-dihydropyrrolo[3,4-d]imidazol-5-(1H)-carboxamide;
2-(6-(2-ethyl-5-fluoro-4-hydroxyphenyl)-1H-indazol-3-yl)-N-(2-hydroxylethyl)-4,6-dihydropyrrolo[3,4-d]imidazol-5(1H)-carboxamide;
1-(2-(6-(2-ethyl-5-fluoro-4-hydroxyphenyl)-1H-indazol-3-yl)-1,4,5,6-tetrahydropyrrolo[3,4-d]imidazol-5-carbonyl)azetidine-3-nitrile;
1-(2-(6-(2-ethyl-5-fluoro-4-hydroxyphenyl)-1H-indazol-3-yl)-1,4,5,6-tetrahydropyrrolo[3,4-d]imidazol-5-carbonyl)pyrrolidin-3-nitrile;
2-(6-(2-ethyl-5-fluoro-4-hydroxyphenyl)-1H-indazol-3-yl)-N-(tetrahydrofuran-3-yl)-4,6-dihydropyrrolo[3,4-d]imidazol-5(1H)-carboxamide;
Methyl 2-(6-(2-ethyl-5-fluoro-4-hydroxyphenyl)-1H-indazol-3-yl)-4,6-dihydropyrrolo[3,4-d]imidazol-5(1H)-carboxylate;
Ethyl 2-(6-(2-ethyl-5-fluoro-4-hydroxyphenyl)-1H-indazol-3-yl)-4,6-dihydropyrrolo[3,4-d]imidazol-5(1H)-carboxylate;
(S)-(2-(6-(2-ethyl-5-fluoro-4-hydroxyphenyl)-1H-pyrazolo[3,4-b]pyridin-3-yl)-4,6-dihydropyrrolo[3,4-d]imidazol-5(1H)-yl)(3-hydroxylpyrrolidin-1-yl)ketone;
3-(2-(6-(2-ethyl-5-fluoro-4-hydroxyphenyl)-1H-indazol-3-yl)-4,6-dihydropyrrolo[3,4-d]imidazol-5(1H)-yl)-3-oxypropionitrile;
2-(6-(2-ethyl-5-fluoro-4-hydroxyphenyl)-1H-indazol-3-yl)-N,N-dimethyl-4,6-dihydropyrrolo[3,4-d]imidazol-5(1H)-carboxamide;
N-(2-cyanoethyl)-2-(6-(2-ethyl-5-fluoro-4-hydroxyphenyl)-1H-indazol-3-yl)-4,6-dihydropyrrolo[3,4-d]imidazol-5(1H)-carboxamide;
N-cyclopropyl-2-(6-(2-ethyl-5-fluoro-4-hydroxyphenyl)-1H-indazol-3-yl)-4,6-dihydropyrrolo[3,4-d]imidazol-5(1H)-carboxamide;
N-cyclobutyl-2-(6-(2-ethyl-5-fluoro-4-hydroxyphenyl)-1H-indazol-3-yl)-4,6-dihydropyrrolo[3,4-d]imidazol-5(1H)-carboxamide;
(2-(6-(2-ethyl-5-fluoro-4-hydroxyphenyl)-1H-indazol-3-yl)-4,6-dihydropyrrolo[3,4-d]imidazol-5(1H)-yl)(2,6-diazaspiro[3.3]heptan-2-yl)ketone;
(S)-6-(2-ethyl-5-fluoro-4-hydroxyphenyl)-3-(5-prolyl-1,4,5,6-tetrahydropyrrolo[3,4-d]imidazol-2-yl)-1H-indazol; and
(R)-6-(2-ethyl-5-fluoro-4-hydroxyphenyl)-3-(5-prolyl-1,4,5,6-tetrahydropyrrolo[3,4-d]imidazol-2-yl)-1H-indazol.

In the compound of formula (G), when $X_1$, $X_2$, and $X_3$ are the same, the compound of formula (G) can also be represented as a compound of formula (G'):

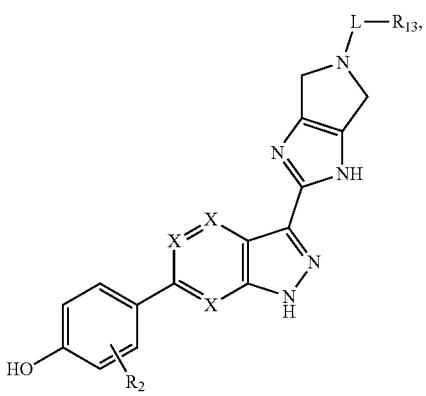

(G')

wherein X is N or $CR_{14}$, and $R_{14}$, $R_{13}$, $R_1$, L, and $R_2$ are as defined in the compound of formula (G).

In a preferred embodiment, the present disclosure provides a compound of Formula (G)'

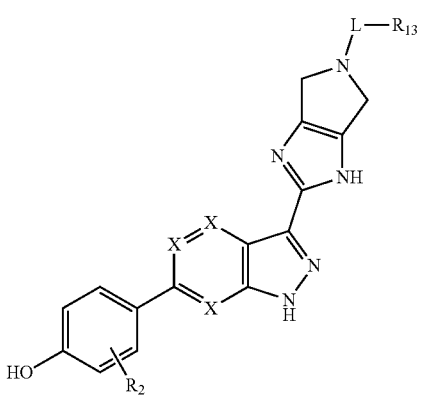

(G')

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof,
wherein
X is N or CH;
L is C=O, O=S=O, $CH_2$ or a bond; and
$R_{13}$ is H, $—N(R_{17})(R_{18})$, $C_{1-6}$ alkoxy, $—SR_{12}$, $—OR_{12}$, —CN, halogen, $—NO_2$, $—SF_5$, $—S—C_{1-4}$ alkyl, $C_{1-6}$ alkyl or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, or 5-11 membered bicyclic heteroalkyl, and $R_{13}$ is substituted with 0, 1, 2, 3 or 4 $R_1(s)$, in which $R_{17}$ and $R_{18}$ are each independently selected from H, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, $C_{3-7}$ heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, and 5-11 membered bicyclic heteroalkyl and are optionally substituted with one or more substitutes each independently selected from —OH, —CN, —SH, halogen, $—NO_2$, $—SF_5$, $—S—C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, $—N(R_9)(R_{10})$, $—N(R_{11})(C(=O)R_{12})$, $—C(=O)—N(R_9)(R_{10})$, $—C(=O)—R_{12}$, $—C(=O)—OR_{12}$, $—OC(=O)R_{12}$, $—N(R_{11})(S(=O)_2R_{12})$, $—S(=O)_2—N(R_9)(R_{10})$, $—SR_{12}$ and $—OR_{12}$, in which the $—S—C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2 or 3 substitutes each independently selected from halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, $—N(R_9)(R_{10})$, $—N(R_{11})(C(=O)R_{12})$, $—C(=O)—OR_{12}$, $—C(=O)H$, $—C(=O)R_{12}$, $—C(=O)—N(R_9)(R_{10})$, $—N(R_{11})(S(=O)_2R_{12})$, $—S(=O)_2—N(R_9)(R_{10})$, $—SR_{12}$ and $—OR_{12}$; or $R_{17}$, $R_{18}$ and the N atom connected thereto together form a 3-14 membered ring; and 0, 1, 2, 3 or 4 $R_2(s)$ are present in formula (G'), and $R_2$ is selected from H, halogen, —OH, $—NO_2$, —CN, $—SF_5$, —SH, $—S—C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, 7-11 membered bicyclic heteroaryl, $—N(R_9)(R_{10})$, $—N(R_{11})(C(=O)R_{12})$, $—C(=O)—N(R_9)(R_{10})$, $—C(=O)—R_{12}$, $—C(=O)—OR_{12}$, $—OC(=O)R_{12}$, $—N(R_{11})(S(=O)_2R_{12})$, $—S(=O)_2—N(R_9)(R_{10})$, $—SR_{12}$ and $—OR_{12}$, in which the $—S—C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, $—N(R_9)(R_{10})$, $—N(R_{11})(C(=O)R_{12})$, $—C(=O)—OR_{12}$, $—C(=O)H$, $—C(=O)R_{12}$, $—C(=O)—N(R_9)(R_{10})$, $—N(R_{11})(S(=O)_2R_{12})$, $—S(=O)_2—N(R_9)(R_{10})$, $—SR_{12}$ and $—OR_{12}$; and $R_1$ is selected from H, halogen, —OH, $—NO_2$, —CN, $—SF_5$, —SH, $—S—C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, $—N(R_9)(R_{10})$, $—N(R_{11})(C(=O)R_{12})$, $—C(=O)—N(R_9)(R_{10})$, $—C(=O)—R_{12}$, $—C(=O)—OR_{12}$, $—OC(=O)R_{12}$, $—N(R_{11})(S(=O)_2R_{12})$, $—S(=O)_2—N(R_9)(R_{10})$, $—SR_{12}$ and $—OR_{12}$, in which the $—S—C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3(s)$, and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4(s)$; and $R_3$ and $R_4$ are each independently selected from H, halogen, —OH, $—NO_2$, —CN, $—SF_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, $—N(R_5)(R_6)$, $—N(R_{11})(C(=O)R_{12})$, $—CON(R_7)(R_8)$, $—C(=O)—R_{12}$, $—C(=O)—OR_{12}$, $—OC(=O)R_{12}$, $—N(R_{11})(S(=O)_2R_{12})$, $—S(=O)_2—N(R_9)(R_{10})$, $—SR_{12}$ and $—OR_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, 3 or 4 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$; and $R_5$, $R_6$, $R_7$, $R_8$, $R_9$, $R_{10}$, $R_{11}$, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein the substituents included in the above group are each optionally substituted with 1, 2, 3 or 4 substituent(s) each independently selected from the group consisting of halogen, —CF$_3$, —OH, —NH$_2$, —NH(CH$_3$), —N(CH$_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy and $C_{1-4}$ haloalkoxy.

In some preferred embodiments of the present disclosure, an isotopically labeled compound of the above-mentioned compound of formula (G') is provided. In some more preferred embodiments of the present disclosure, an isotopically labeled compound of the compound of formula (G') is provided, wherein all Hs are each independently and optionally substituted with D.

In some preferred embodiments of the present disclosure, in formula (G'), X is N. In some more preferred embodiments of the present disclosure, in formula (G'), X is CH.

In some more preferred embodiments of the present disclosure, there is provided an isotopically labeled compound of the compound of formula (G'), wherein all H are each independently and optionally substituted with D, and X is N. In some more preferred embodiments of the present disclosure, there is provided an isotopically labeled compound of the compound of formula (G'), wherein all Hs are each independently and optionally substituted with D, and X is CH.

In some preferred embodiments of the present disclosure, in formula (G'), L is C=O, O=S=O or CH$_2$. In some particularly preferred embodiments of the present disclosure, in formula (G'), L is C=O. In some particularly preferred embodiments of the present disclosure, in formula (G'), L is O=S=O. In some particularly preferred embodiments of the present disclosure, in formula (G'), L is CH$_2$. In other embodiments of the present disclosure, in formula (G'), L is a bond.

In some particularly preferred embodiments of the present disclosure, in formula (G'), X is CH, and L is C=O.

In some particularly preferred embodiments of the present disclosure, in formula (G'), X is CH, and L is O=S=O.

In some particularly preferred embodiments of the present disclosure, in formula (G'), X is CH, and L is CH$_2$.

In some particularly preferred embodiments of the present disclosure, in formula (G'), X is CH, and L is a bond.

In some particularly preferred embodiments of the present disclosure, in formula (G'), X is N, and L is C=O.

In some particularly preferred embodiments of the present disclosure, in formula (G'), X is N, and L is O=S=O.

In some particularly preferred embodiments of the present disclosure, in formula (G'), X is N, and L is CH$_2$.

In some particularly preferred embodiments of the present disclosure, in formula (G'), X is N, and L is a bond.

In some preferred embodiments of the present disclosure, in formula (G'), $R_{13}$ is H, —N($R_{17}$)($R_{18}$), $C_{1-6}$ alkoxy, —OH, —SH, —CN, halogen, —NO$_2$, —SF$_5$, —S—$C_{1-4}$ alkyl, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, or 5-11 membered bicyclic heteroalkyl, in which $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, -and SF$_5$, wherein $R_{13}$ is optionally substituted with 1, 2, 3 or 4 $R_1$(s). In some preferred embodiments of the present disclosure, in formula (G'), $R_{13}$ is H, —N($R_{17}$)($R_{18}$), $C_{1-6}$ alkoxy, —OH, —SH, —CN, halogen, —NO$_2$, —SF$_5$, —S—$C_{1-4}$ alkyl, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, or 11-15 membered tricyclyl and $R_{17}$ and $R_{18}$ are defined as above, wherein $R_{13}$ is optionally substituted with 1, 2, 3 or 4 $R_1$(s). In some preferred embodiments of the present disclosure, in formula (G'), $R_{13}$ is H, —N($R_{17}$)($R_{18}$), $C_{1-6}$ alkoxy, $C_{1-6}$ alkyl, or $C_{3-7}$ cycloalkyl, 3-7 membered heterocycloalkyl, $C_{5-7}$ aryl, or 5-7 membered heteroaryl, and $R_{17}$ and $R_{18}$ are defined as above, wherein $R_{13}$ is optionally substituted with 1, 2, 3 or 4 $R_1$(s). In some preferred embodiments of the present disclosure, in formula (G'), $R_{13}$ is —N($R_{17}$)($R_{18}$), $C_{1-6}$ alkoxy, $C_{1-6}$ alkyl, or $C_{3-7}$ cycloalkyl, 4-6 membered heterocycloalkyl, phenyl, or 5-6 membered heteroaryl, and $R_{17}$ and $R_{18}$ are defined as above, wherein $R_{13}$ is optionally substituted with 1, 2, or 3 $R_1$(s). In some preferred embodiments of the present disclosure, in formula (G'), $R_{13}$ is —N($R_{17}$)($R_{18}$), $C_{1-3}$ alkoxy, $C_{3-6}$ cycloalkyl, 4-6 membered heterocycloalkyl, phenyl, 5-6 membered heteroaryl or $C_{1-4}$ alkyl, and $R_{17}$ and $R_{18}$ are defined as above, wherein $R_{13}$ is optionally substituted with 1, 2, or 3 $R_1$(s). In some preferred embodiments of the present disclosure, in formula (G'), $R_{13}$ is —N(H)($C_{1-3}$ alkyl), —N(H)(3-6 membered cycloalkyl), —N(H) (4-6 membered heterocycloalkyl), —N($C_{1-3}$ alkyl)($C_{1-3}$ alkyl), $C_{1-3}$ alkoxy, $C_{3-6}$ cycloalkyl, 4-6 membered azacycloalkyl or oxacycloalkyl, phenyl, 5-6 membered azaaryl or $C_{1-4}$ alkyl; or $R_{13}$ is —N($R_{17}$)($R_{18}$), and $R_{17}$ and $R_{18}$ and the N atom connected thereto together form a 4-10 membered ring (where $R_{13}$ is optionally substituted with 1, 2, or 3 $R_1$). In some particularly preferred embodiments of the present disclosure, in formula (G'), $R_{13}$ is cyclopropyl, cyclobutyl, cyclopentyl, cyclohexyl, methyl, ethyl, propyl, butyl, methoxy, ethoxy, propoxy, —N(H)(CH$_3$), —N(H)(CH$_2$CH$_3$), —N(H)(CH$_2$CH$_2$OH), —N(H)(CH$_2$CH$_2$CN), —N(CH$_3$)(CH$_3$), —N(H)(cyclopropyl), —N(H)(cyclobutyl), —N(H)(tetrahydrofuranyl), pyrazinyl, pyridazinyl, pyrrolidinyl, pyrazolyl, piperidinyl, phenyl, azetidinyl, morpholinyl, piperazinyl or tetrahydropyranyl; or $R_{13}$ is —N($R_{17}$)($R_{18}$), and $R_{17}$ and $R_{18}$ and the N atom connected thereto together form a 7-membered ring (where $R_{13}$ is optionally substituted with 1, 2, or 3 $R_{1s}$). In some particularly preferred embodiments of the present disclosure, in formula (G'), $R_{13}$ is cyclopropyl. In some particularly preferred embodiments of the present disclosure, in formula (G'), $R_{13}$ is cyclobutyl. In some particularly preferred embodiments of the present disclosure, in formula (G'), $R_{13}$ is cyclopentyl. In some particularly preferred embodiments of the present disclosure, in formula (G'), $R_{13}$ is cyclohexyl. In some particularly preferred embodiments of the present disclosure, in formula (G'), $R_{13}$ is a methyl group. In some particularly preferred embodiments of the present disclosure, in formula (G'), $R_{13}$ is an ethyl group. In some particularly preferred embodiments of the present disclosure, in formula (G'), $R_{13}$ is propyl. In some particularly preferred embodiments of the present disclosure, in formula (G'), $R_{13}$ is a butyl group. In some particularly preferred embodiments of the present disclosure, in formula (G'), $R_{13}$ is pyrazinyl. In some particularly preferred embodiments of the present disclosure, in formula (G'), $R_{13}$ is a pyridazinyl. In some particularly preferred embodiments of the present disclosure, in formula (G'), $R_{13}$ is a pyrrolidinyl. In some particularly preferred embodiments of the present disclosure, in formula (G'), $R_{13}$ is pyrazolyl. In some particularly preferred embodiments of the present disclosure, in formula (G'), $R_{13}$ is piperidinyl. In some particularly preferred embodiments of the present disclosure, in formula (G'), $R_{13}$ is phenyl. In some particularly preferred embodiments of the present disclosure, in formula (G'), $R_{13}$ is azetidinyl. In some particularly preferred embodiments of the present disclosure, in formula (G'), $R_{13}$ is morpholinyl. In some particularly preferred embodiments of the present disclosure, in formula (G'), $R_{13}$ is piperazinyl. In some particularly preferred embodiments of the present disclosure, in formula (G'), $R_{13}$ is tetrahydropyranyl. In some particularly preferred embodiments of the present disclosure, in formula (G'), $R_{13}$ is methoxy. In some particularly preferred embodiments of the present disclosure, in formula (G'), $R_{13}$ is ethoxy. In some particularly preferred embodiments of the present disclosure, in formula (G'), $R_{13}$ is —N(H)(CH$_3$). In some particularly preferred embodiments of the present disclosure, in formula (G'), $R_{13}$ is —N(H)(CH$_2$CH$_3$). In some particularly preferred embodiments of the present disclosure, in formula (G'), $R_{13}$ is —N(H)(CH$_2$CH$_2$OH). In some particularly preferred embodiments of the present disclosure, in formula (G'), $R_{13}$ is —N(H)(CH$_2$CH$_2$CN). In some particularly preferred embodiments of the present disclosure, in formula (G'), $R_{13}$ is —N(CH$_3$)(CH$_3$). In some particularly preferred embodiments of the present disclosure, in formula (G'), $R_{13}$ is —N(H) (cyclopropyl). In some particularly preferred embodiments of the present disclosure, in formula (G'), $R_{13}$ is —N(H) (cyclobutyl). In some particularly preferred embodiments of the present disclosure, in formula (G'), $R_{13}$ is —N(H) (tetrahydrofuranyl). In some particularly preferred embodiments of the present disclosure, in formula (G'), $R_{13}$ is —N($R_{17}$)($R_{18}$), and $R_{17}$ and $R_{18}$ and the N atom connected to them together form a 7-membered ring.

In some particularly preferred embodiments of the present disclosure, in formula (G'), $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, and SF$_5$. In some particularly preferred embodiments of the present disclosure, in formula (G'), $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH, —CN, —SH, halogen, —NO$_2$, and SF$_5$. In some particularly preferred embodiments of the present disclosure, in formula (G'), $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH and —CN. In some preferred embodiments of the present disclosure, in formula (G'), $R_{17}$ and $R_{18}$ are each independently selected from H, methyl, ethyl, propyl, 3-membered cycloalkyl, 4-membered cycloalkyl, 5-membered cycloalkyl, 5-membered heterocycloalkyl, and 6-membered heterocycloalkyl, and optionally substituted with one or more of —OH and —CN. In some preferred embodiments of the present disclosure, in formula (G'), $R_{17}$, $R_{18}$ and the N atom connected thereto together form a 4-10 membered ring. In some preferred embodiments of the present disclosure, in formula (G'), $R_{17}$, $R_{18}$ and the N atom connected thereto together form a 7-membered ring.

In some particularly preferred embodiments of the present disclosure, in formula (G'), L is C=O, and $R_{13}$ is —N($R_{17}$)($R_{18}$), $C_{1-6}$ alkoxy, —OH, —SH, —CN, halogen, —NO$_2$, —SF$_5$, or —S—$C_{1-4}$ alkyl, and $R_{13}$ is substituted with 0, 1, 2, 3 or 4 $R_1$(s) in which $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, -and SF$_5$, or $R_{17}$, $R_{18}$ and the N atom connected thereto together form a 3-14 membered ring. In some particularly preferred embodiments of the present disclosure, in formula (G'), L is C=O, and $R_{13}$ is —N($R_{17}$)($R_{18}$), or $C_{1-6}$ alkoxy, in which $R_{17}$ and $R_{18}$ are each independently selected from H, $C_{1-6}$ alkyl, $C_{3-7}$ cycloalkyl, and $C_{3-7}$ heterocycloalkyl and are optionally substituted with one or more of —OH, —CN, —SH, halogen, —NO$_2$, -and SF$_5$, or $R_{17}$, $R_{18}$ and the N atom connected thereto together form a 3-10 membered ring. In some particularly preferred embodiments of the present disclosure, in formula (G'), L is C=O, and $R_{13}$ is methoxy, ethoxy, propoxy, —N(H)(CH$_3$), —N(H)(CH$_2$CH$_3$), —N(H) (CH$_2$CH$_2$OH), —N(H)(CH$_2$CH$_2$CN), —N(CH$_3$)(CH$_3$), —N(H)(cyclopropyl), —N(H) (cyclobutyl), —N(H) (tetrahydrofuranyl); or $R_{13}$ is —N($R_{17}$)($R_{18}$), and $R_{17}$, $R_{18}$ and the N atom connected thereto together form a 7-membered ring. In some particularly preferred embodiments of the present disclosure, in formula (G'), L is C=O, and $R_{13}$ is methoxy. In some particularly preferred embodiments of the present disclosure, in formula (G'), L is C=O, and $R_{13}$ is ethoxy. In some particularly preferred embodiments of the present disclosure, in formula (G'), L is C=O, and $R_{13}$ is —N(H) (CH$_3$). In some particularly preferred embodiments of the present disclosure, in formula (G'), L is C=O, and $R_{13}$ is —N(H)(CH$_2$CH$_3$). In some particularly preferred embodiments of the present disclosure, in formula (G'), L is C=O, and $R_{13}$ is —N(H)(CH$_2$CH$_2$OH). In some particularly preferred embodiments of the present disclosure, in formula (G'), L is C=O, and $R_{13}$ is —N(H)(CH$_2$CH$_2$CN). In some particularly preferred embodiments of the present disclosure, in formula (G'), L is C=O, and $R_{13}$ is —N(CH$_3$)(CH$_3$). In some particularly preferred embodiments of the present disclosure, in formula (G'), L is C=O, and $R_{13}$ is —N(H) (cyclopropyl). In some particularly preferred embodiments of the present disclosure, in formula (G'), L is C=O, and $R_{13}$ is —N(H)(cyclobutyl). In some particularly preferred embodiments of the present disclosure, in formula (G'), L is C=O, and $R_{13}$ is —N(H)(tetrahydrofuranyl). In some particularly preferred embodiments of the present disclosure, in the formula (G'), L is C=O, and $R_{13}$ is —N($R_{17}$)($R_{18}$), and $R_{17}$, $R_{18}$ and the N atom connected thereto together form a 7-membered ring.

In some particularly preferred embodiments of the present disclosure, in formula (G'), one, two or three $R_2$(s) are present and $R_2$ is selected from H, halogen, —OH, —NO$_2$, —CN, —SF$_5$, —SH, —S—$C_{1-4}$ alkyl, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, and 4-10 membered heterocycloalkyl, in which the —S—$C_{1-4}$ alkyl, $C_{1-6}$ alkyl, $C_{3-7}$ cycloalkyl, and 4-10 membered heterocycloalkyl are each optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G'), one, two or three $R_2$(s) are present and $R_2$ is selected from halogen, $C_{1-6}$ alkyl and $C_{3-6}$ cycloalkyl, in which the $C_{1-6}$ alkyl and $C_{3-6}$ cycloalkyl are each optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G'), one, two or three $R_2$(s) are present and $R_2$ is selected from halogen, and $C_{1-6}$ alkyl, in which the $C_{1-6}$ alkyl is optionally substituted with 1, 2 or 3 substituent(s) each independently selected from the group consisting of halogen, —OH, —NH$_2$, —NH(CH$_3$), —N(CH$_3$)$_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (G'), 1, or two $R_2$(s) are present and $R_2$ is selected from halogen, and $C_{1-6}$ alkyl. In some particularly preferred embodiments of the present disclosure, in formula (G'), one or two $R_2$(s) are present and $R_2$ is selected from fluorine, chlorine, bromine, methyl, ethyl, n-propyl, isopropyl, n-butyl, and isobutyl. In some preferred embodiments of the present disclosure, in formula (G'), one or two $R_2$(s) are present, and $R_2$ is selected from fluorine, chlorine, methyl, ethyl, n-propyl, and isopropyl. In some preferred embodiments of the present disclosure, in formula (G'), one or two $R_2$ (s) are present, and $R_2$ is selected from fluorine, methyl, and ethyl. In some preferred embodiments of the present disclosure, in formula (G'), one or two $R_2$(s) are present, and $R_2$ is selected from fluorine and ethyl. In some preferred embodiments of the present disclosure, in formula (G'), one $R_2$ is present, and $R_2$ is selected from fluorine and ethyl. In some preferred embodiments of the present disclosure, in formula (G'), two $R_2$(s) are present, and $R_2$ is selected from fluorine and ethyl. In some particularly preferred embodiments of the present disclosure, in formula (G'), two $R_2$(s) are present which are respectively fluorine and ethyl. In some particularly preferred embodiments of the present disclosure, in formula (G'), one $R_2$ is present, and $R_2$ is an ethyl group.

In some preferred embodiments of the present disclosure, in formula (G'), $R_{13}$ is substituted with 0, 1, 2, 3 or 4 $R_1$(s), and each $R_1$ is independently selected from H, halogen, —OH, —NO$_2$, —CN, —SF$_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, wherein the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and wherein the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3 or 4 $R_4$(s). In some preferred embodiments of the present disclosure, in formula (G'), $R_{13}$ is substituted with 0, 1, 2, 3 or 4 $R_1$(s), and each $R_1$ is independently selected from H, halogen, —OH, —NO$_2$, —CN, —SF$_5$, —SH, —S—$C_{1-4}$ alkyl, $C_{1-8}$ alkyl, $C_{3-7}$ cycloalkyl, 3-7 membered heterocycloalkyl, $C_{5-7}$ aryl, 5-7 membered heteroaryl, wherein the —S—$C_{1-4}$ alkyl, and $C_{1-8}$ alkyl are optionally substituted with 1, 2, 3 or 4 $R_3$(s), and wherein the $C_{3-7}$ cycloalkyl, 3-7 membered heterocycloalkyl, $C_{5-7}$ aryl, and 5-7 membered heteroaryl are optionally substituted with 1, 2, 3, or 4 $R_4$(s). In some preferred embodiments of the present disclosure, in formula (G'), $R_{13}$ is substituted with 0, 1, 2, 3 or 4 $R_1$(s), and each $R_1$ is independently selected from halogen, —OH, —CN, $C_{1-8}$ alkyl, $C_{3-7}$ cycloalkyl, 3-7 membered heterocycloalkyl, $C_{5-7}$ aryl, 5-7 membered heteroaryl, wherein the $C_{1-8}$ alkyl is optionally substituted with 1, 2, 3 or 4 $R_3$(s), and wherein the $C_{3-7}$ cycloalkyl, 3-7 membered heterocycloalkyl, $C_{5-7}$ aryl, 5-7 membered heteroaryl are optionally substituted with 1, 2, 3 or 4 $R_4$(s). In some preferred embodiments of the present disclosure, in formula (G'), $R_{13}$ is substituted with 0, 1, 2, 3 or 4 $R_1$(s), and each $R_1$ is independently selected from halogen, —OH, —CN, $C_{1-8}$ alkyl, $C_{3-7}$ cycloalkyl, and 3-7 membered heterocycloalkyl, wherein the $C_{1-8}$ alkyl is optionally substituted with 1, 2, or 3 $R_3$(s), and wherein the $C_{3-7}$ cycloalkyl, and 3-7 membered heterocycloalkyl are optionally substituted with 1, 2, or 3 $R_4$. In some preferred embodiments of the present disclosure, in formula (G'), $R_{13}$ is substituted with 0 or 1 $R_1$, and each $R_1$ is independently selected from halogen, —OH, —CN, $C_{1-6}$ alkyl, $C_{3-7}$ cycloalkyl, 5-7 membered heterocycloalkyl, wherein the $C_{1-6}$ alkyl is optionally substituted with 1, 2, or 3 $R_3$(s), and wherein the $C_{3-7}$ cycloalkyl, and 5-7-membered heterocycloalkyl are optionally substituted with 1, 2, or 3 $R_4$(s). In some preferred embodiments of the present disclosure, in formula (G'), $R_{13}$ is substituted with 0 or 1 $R_1$, and each $R_1$ is independently selected from halogen, —OH, —CN, $C_{1-4}$ alkyl, $C_{3-6}$ cycloalkyl, and 5-7 membered heterocycloalkyl, wherein the $C_{1-4}$ alkyl is optionally substituted with 1 or 2 $R_3$, and wherein the $C_{3-6}$ cycloalkyl and 5-7 membered heterocycloalkyl are optionally substituted with 1, 2, or 3 $R_4$(s). In some particularly preferred embodiments of the present disclosure, in formula (G'), $R_{13}$ is substituted with 0 or 1 $R_1$, and each $R_1$ is independently selected from methyl, ethyl, hydroxyl, —CN, piperidinyl, morpholinyl, piperazinyl, and cyclopropyl, wherein the piperidinyl, morpholinyl, and piperazinyl are optionally substituted with 1, 2, 3 or 4 $C_{1-3}$ alkyl. In some particularly preferred embodiments of the present disclosure, in formula (G'), $R_{13}$ is substituted with 0 or 1 $R_1$, and each $R_1$ is independently selected from methyl, ethyl, hydroxy, —CN, piperidinyl, morpholinyl, 1-methylpiperazinyl, and cyclopropyl. In some particularly preferred embodiments of the present disclosure, in formula (G'), $R_1$ is absent. In some particularly preferred embodiments of the present disclosure, in formula (G'), $R_1$ is 1-methylpiperazinyl. In some particularly preferred embodiments of the present disclosure, in formula (G'), $R_1$ is methyl. In some particularly preferred embodiments of the present disclosure, in formula (G'), $R_1$ is ethyl. In some particularly preferred embodiments of the present disclosure, in formula (G'), $R_1$ is piperidinyl. In some particularly preferred embodiments of the present disclosure, in formula (G'), $R_1$ is morpholinyl. In some particularly preferred embodiments of the present disclosure, in formula (G'), $R_1$ is hydroxyl. In some particularly preferred embodiments of the present disclosure, in formula (G'), $R_1$ is —CN. In some particularly preferred embodiments of the present disclosure, in formula (G'), $R_1$ is cyclopropyl.

The preferred options of the respective substituents mentioned in the above various preferred embodiments can be combined with each other in any way, and various combinations thereof are within the scope of the present disclosure.

In the compound of formula (G'), when $R_{13}$ is a ring, the compound of formula (G') can also be represented as a compound of the following formula (I):

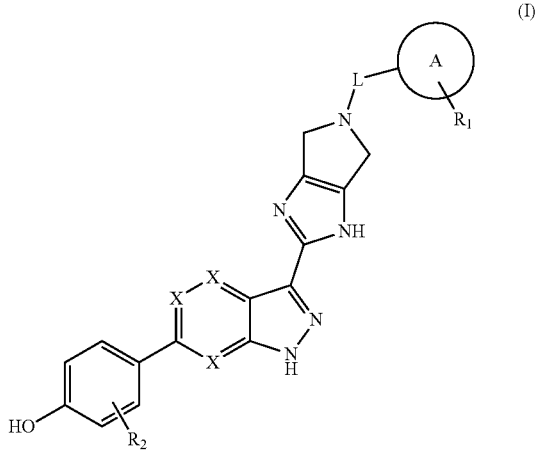
(I)

wherein the ring A is $C_{3-7}$ cycloalkyl, 3.7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicyclic alkyl group or 5-11 membered bicyclic heteroalkyl, which may be optionally substituted with $R_1$, and L, $R_1$, $R_2$, and X are defined as above in the compound of formula (G').

In particular, the present disclosure provides a compound of formula (I) as a JAK inhibitor:

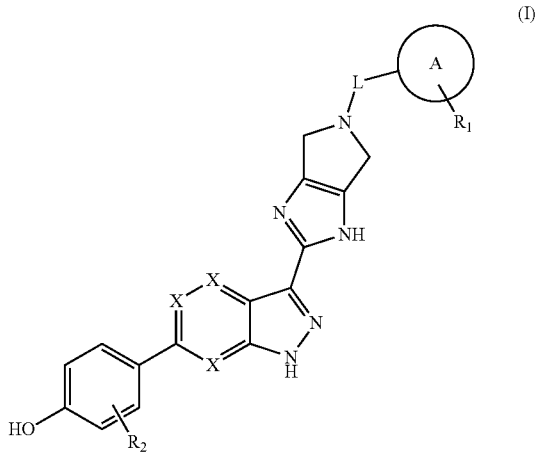
(I)

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, in which
L is C=O, O=S=O, CH₂ or a bond; and
X is CH or N;
The ring A is $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, or 11-15 membered tricyclyl;
0, 1, 2, 3 or 4 $R_1(s)$ are present in formula (I), and $R_1$ is selected from H, halogen, $C_{1-8}$ alkyl, $C_{2-8}$ alkenyl, $C_{2-8}$ alkynyl, $C_{1-8}$ alkoxy, $C_{3-7}$ cycloalkyl, 3-7 membered heterocycloalkyl, $C_{5-7}$ aryl, 5-7 membered heteroaryl, $C_{7-11}$ bicyclic aryl, and 7-11 membered bicyclic heteroaryl, in which the $C_{1-8}$ alkyl, $C_{2-8}$ alkenyl, $C_{2-8}$ alkynyl, and $C_{1-8}$ alkoxy are optionally substituted with 1, 2, 3 or 4 $R_3(s)$, and in which the $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl are optionally substituted with 1, 2, 3 or 4 $R_4(s)$, 0, 1, 2, 3 or 4 $R_2(s)$ are present in formula (I), and $R_2$ is selected from H, halogen, —OH, —NO₂, —CN, —SF₅, $C_{1-6}$alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, —N(R₉)(R₁₀), —N(R₁₁)(C(=O)R₁₂), —C(=O)—N(R₉)(R₁₀), —C(=O)—R₁₂, —C(=O)—OR₁₂, —OC(=O)R₁₂, —N(R₁₁)(S(=O)₂R₁₂), —S(=O)₂—N(R₉)(R₁₀), —SR₁₂ and —OR₁₂, in which the $C_{1-6}$ alkyl, $C_{3-7}$ cycloalkyl and 4-10 membered heterocycloalkyl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N(R₉)(R₁₀), —N(R₁₁)(C(=O)R₁₂), —C(=O)—OR₁₂, —C(=O)H, —C(=O)R₁₂, —C(=O)—N(R₉)(R₁₀), —N(R₁₁)(S(=O)₂R₁₂), —S(=O)₂—N(R₉)(R₁₀), —SR₁₂ and —OR₁₂;

$R_3$ is selected from halogen, cyano, $C_{1-3}$ alkyl, hydroxy, $C_{1-6}$ alkoxy, —N(R₅)(R₆), —CON(R₇)(R₈) or 3-7 membered heterocycloalkyl, in which the 3-7 membered heterocycloalkyl is optionally substituted with 1, 2, 3 or 4 $R_4(s)$;

$R_4$ is selected from halogen, $C_{1-3}$ alkyl, hydroxyl, $C_{1-6}$ alkoxy, —NH₂, —NHCH₃ or —N(CH₃)₂;

$R_5$, $R_6$, $R_7$, $R_8$ are each independently hydrogen or $C_{1-4}$ alkyl;

$R_9$ is selected from H, $C_{1-4}$ alkyl, $C_{1-4}$ haloalkyl or $C_{3-7}$ cycloalkyl;

$R_{10}$ is H or selected from the group consisting of $C_{1-4}$ alkyl, $C_{1-4}$ haloalkyl, $C_{3-7}$ cycloalkyl, 4-10 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2, 3 or 4 substituent(s) each independently selected from the group consisting of —OH, —NH₂, —NH(CH₃), —N(CH₃)₂, —CN, $C_{1-4}$ alkyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—NH₂, —C(=O)—N($C_{1-4}$ alkyl)₂, $C_{1-4}$ haloalkyl, $C_{1-4}$ alkoxy and $C_{1-4}$ haloalkoxy;

$R_{11}$ is selected from H, $C_{1-4}$ alkyl and $C_{3-7}$ cycloalkyl; and
$R_{12}$ is selected from the group consisting of $C_{1-6}$ alkyl, $C_{3-7}$ cycloalkyl, 4- to 14-membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2 or 3 substituent(s) each independently selected from the group consisting of halogen, —CF₃, —CN, —OH, —NH₂, —NH(CH₃), —N(CH₃)₂, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy and $C_{1-4}$ haloalkoxy.

In some preferred embodiments of the present disclosure, in formula (I), L is C=O, O=S=O or CH₂. In some particularly preferred embodiments of the present disclosure, in formula (I), L is C=O. In some particularly preferred embodiments of the present disclosure, in formula (I), L is O=S=O. In some particularly preferred embodiments of the present disclosure, in formula (I), L is CH₂. In other embodiments of the present disclosure, in formula (I), L is a bond.

In some particularly preferred embodiments of the present disclosure, in formula (I), X is CH. In other some embodiments of the present disclosure, in formula (I), X is N.

In some particularly preferred embodiments of the present disclosure, in formula (I), X is CH, and L is C=O.

In some particularly preferred embodiments of the present disclosure, in formula (I), X is CH, and L is O=S=O.

In some particularly preferred embodiments of the present disclosure, in formula (I), X is CH, and L is $CH_2$.

In some particularly preferred embodiments of the present disclosure, in formula (I), X is CH, and L is a bond.

In some particularly preferred embodiments of the present disclosure, in formula (I), X is N, and L is C=O.

In some particularly preferred embodiments of the present disclosure, in formula (I), X is N, and L is O=S=O.

In some particularly preferred embodiments of the present disclosure, in formula (I), X is N, and L is $CH_2$.

In some particularly preferred embodiments of the present disclosure, in formula (I), X is N, and L is a bond.

In some preferred embodiments of the present disclosure, in formula (I), the ring A is $C_{3-7}$ cycloalkyl, 3-7 membered heterocycloalkyl, $C_{5-7}$ aryl, 5-7 membered heteroaryl, where the ring A is optionally substituted with 1, 2, 3 or 4 $R_1(s)$. In some preferred embodiments of the present disclosure, in formula (I), the ring A is $C_{5-6}$ cycloalkyl, 5-6 membered heterocycloalkyl, phenyl, 5-6 membered heteroaryl wherein the ring A is optionally substituted with 1, 2, 3 or 4 $R_1(s)$. In some preferred embodiments of the present disclosure, in formula (I), the ring A is 5-6 membered heterocycloalkyl, phenyl, 5-6 membered heteroaryl wherein the ring A is optionally substituted with 1, 2, 3 or 4 $R_1(s)$. In some preferred embodiments of the present disclosure, in formula (I), the ring A is 5-6 membered azacycloalkyl, phenyl, 5-6 membered azaaryl, where the ring A is optionally substituted with 1, 2, 3 or 4 $R_1(s)$. In some preferred embodiments of the present disclosure, in formula (I), the ring A is pyrazinyl, pyrazolyl, piperidinyl or phenyl, where the ring A is optionally substituted with 1, 2, 3 or 4 $R_1(s)$. In some particularly preferred embodiments of the present disclosure, in formula (I), the ring A is pyrazinyl. In some particularly preferred embodiments of the present disclosure, in formula (I), the ring A is pyrazolyl. In some particularly preferred embodiments of the present disclosure, in formula (I), the ring A is piperidinyl. In some particularly preferred embodiments of the present disclosure, in formula (I), the ring A is phenyl.

In some preferred embodiments of the present disclosure, in formula (I), $R_1$ is absent or $R_1$ is selected from $C_{1-8}$ alkyl, $C_{2-8}$ alkenyl, $C_{2-8}$ alkynyl, $C_{1-8}$ alkoxy, $C_{3-7}$ cycloalkyl, 3-7 membered heterocycloalkyl, $C_{5-7}$ aryl, and 5-7 membered heteroaryl, wherein the $C_{1-8}$ alkyl, $C_{2-8}$ alkenyl, $C_{2-8}$ alkynyl, and $C_{1-8}$ alkoxy are optionally substituted with 1, 2, 3 or 4 $R(s)_3$, and wherein the $C_{3-7}$ cycloalkyl, 3-7 membered heterocycloalkyl, $C_{5-7}$ aryl, and 5-7 membered heteroaryl group are optionally substituted with 1, 2, 3, or 4 $R_4(s)$. In some preferred embodiments of the present disclosure, in formula (I), $R_1$ is absent or $R_1$ is selected from $C_{1-8}$ alkyl, $C_{3-7}$ cycloalkyl, 3-7 membered heterocycloalkyl, $C_{5-7}$ aryl, 5-7 membered heteroaryl, wherein the $C_{1-8}$ alkyl group is optionally substituted with 1, 2, 3 or 4 $R_3(s)$, and wherein the $C_{3-7}$ cycloalkyl group, 3-7 membered heterocycloalkyl, $C_{5-7}$ aryl, 5-7 membered heteroaryl are optionally substituted with 1, 2, 3, or 4 $R_4(s)$. In some preferred embodiments of the present disclosure, in formula (I), $R_1$ is absent or $R_1$ is selected from $C_{1-8}$ alkyl, and 3-7 membered heterocycloalkyl, wherein the $C_{1-8}$ alkyl is optionally substituted with 1, 2, 3, or 4 $R_3(s)$, and wherein the 3-7 membered heterocycloalkyl is optionally substituted with 1, 2, 3, or 4 $R_4(s)$. In some preferred embodiments of the present disclosure, in formula (I), $R_1$ is absent or $R_1$ is selected from $C_{1-6}$ alkyl, 5-7 membered heterocycloalkyl, wherein the $C_{1-6}$ alkyl is optionally substituted with 1, 2, 3, or 4 $R_3(s)$, and wherein the 5-7 membered heterocycloalkyl is optionally substituted with 1, 2, 3, or 4 $R_4(s)$. In some preferred embodiments of the present disclosure, in formula (I), $R_1$ is absent or $R_1$ is selected from $C_{1-6}$ alkyl, 5-7 membered heterocycloalkyl, wherein the $C_{1-6}$ alkyl is optionally substituted with 1 or 2 $R_3$, and wherein the 5-7 membered heterocycloalkyl is optionally substituted with 1, 2, 3 or 4 $C_{1-3}$ alkyl. In some preferred embodiments of the present disclosure, in formula (I), $R_1$ is absent or $R_1$ is selected from $C_{1-4}$ alkyl, and 5-7 membered heterocycloalkyl, wherein the $C_{1-4}$ alkyl is optionally substituted with 1 or 2 $R_3$, and wherein the 5-7 membered heterocycloalkyl is optionally substituted with 1, 2, 3 or 4 $C_{1-3}$ alkyl. In some preferred embodiments of the present disclosure, in formula (I), $R_1$ is absent or $R_1$ is selected from methyl, piperidinyl, morpholinyl, piperazinyl, wherein the piperidinyl, morpholinyl, and piperazinyl are optionally substituted with 1, 2, 3 or 4 $C_{1-3}$ alkyl groups. In some preferred embodiments of the present disclosure, in formula (I), $R_1$ is absent or $R_1$ is selected from methyl, piperidinyl, morpholinyl, and 1-methylpiperazinyl. In some particularly preferred embodiments of the present disclosure, in formula (I), $R_1$ is absent. In some particularly preferred embodiments of the present disclosure, in formula (I), $R_1$ is 1-methylpiperazinyl. In some particularly preferred embodiments of the present disclosure, in formula (I), $R_1$ is methyl. In some particularly preferred embodiments of the present disclosure, in formula (I), $R_1$ is piperidinyl. In some particularly preferred embodiments of the present disclosure, in formula (I), $R_1$ is morpholinyl.

In some particularly preferred embodiments of the present disclosure, in formula (I), one, two or three $R_2(s)$ are present and $R_2$ is selected from halogen, $C_{1-6}$ alkyl, and $C_{3-6}$ cycloalkyl, in which the $C_{1-6}$ alkyl, and $C_{3-6}$ cycloalkyl are each optionally substituted with 1, 2 or 3 substituent(s) each independently selected from the group consisting of halogen, —OH, —$NH_2$, —$NH(CH_3)$, —$N(CH_3)_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one, two or three $R_2(s)$ are present and $R_2$ is selected from halogen, and $C_{1-6}$ alkyl, in which the $C_{1-6}$ alkyl is optionally substituted with 1, 2 or 3 substituent(s) each independently selected from the group consisting of halogen, —OH, —$NH_2$, —$NH(CH_3)$, —$N(CH_3)_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one or two $R_2(s)$ are present and $R_2$ is selected from fluorine, chlorine, bromine, methyl, ethyl, n-propyl, isopropyl, n-butyl, and isobutyl. In some preferred embodiments of the present disclosure, in formula (I), one or two $R_2(s)$ are present, and $R_2$ is selected from fluorine, chlorine, methyl, ethyl, n-propyl, and isopropyl. In some preferred embodiments of the present disclosure, in formula (I), one or two $R_2$ (s) are present, and $R_2$ is selected from fluorine, methyl, and ethyl. In some preferred embodiments of the present disclosure, in formula (I), one or two $R_2$ (s) are present, and $R_2$ is selected from fluorine and ethyl. In some preferred embodiments of the present disclosure, in formula (I), one $R_2$ is present, and $R_2$ is selected from fluorine and ethyl. In some preferred embodiments of the present disclosure, in formula (I), two $R_2(s)$ are present, and $R_2$ is selected from fluorine and ethyl. In some particularly preferred embodiments of the present disclosure, in formula (I), two $R_2(s)$ are present which are respectively fluorine and ethyl. In some particularly preferred embodiments of the present disclosure, in formula (I), one $R_2$ is present, and $R_2$ is an ethyl group.

The preferred options of the respective substituents mentioned in the above various preferred embodiments can be combined with each other in any way, and various combinations thereof are within the scope of the present disclosure.

In particular, the present disclosure provides a compound of formula (I) as a JAK inhibitor:

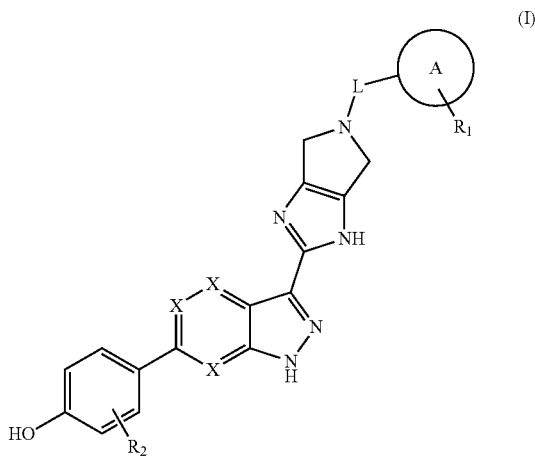

(I)

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, in which L is C=O, and O=S=O;

X is CH;

The ring A is 5-7 membered heteroaryl or $C_{5-7}$ aryl;

0, 1, 2, 3 or 4 $R_1$(s) are present in formula (I), and $R_1$ is selected from $C_{1-8}$ alkyl, and 3-7 membered heterocycloalkyl, in which the $C_{1-8}$ alkyl is optionally substituted with 1, 2, 3 or 4 $R_3$(s), and in which the 3-7 membered heterocycloalkyl is optionally substituted with 1, 2, 3 or 4 $R_4$(s), 1, 2, or 3 $R_2$(s) are present in formula (I), and $R_2$ is selected from H, halogen, —OH, —NO$_2$, —CN, —SF$_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, —N(R$_9$)(R$_{10}$), —N(R$_{11}$)(C(=O)R$_{12}$), —C(=O)—N(R$_9$)(R$_{10}$), —C(=O)—R$_{12}$, —C(=O)—OR$_{12}$, —OC(=O)R$_{12}$, —N(R$_{11}$)(S(=O)$_2$R$_{12}$), —S(=O)$_2$—N(R$_9$)(R$_{10}$), —SR$_{12}$ and —OR$_{12}$, in which the $C_{1-6}$ alkyl, $C_{3-7}$ cycloalkyl and 4-10 membered heterocycloalkyl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N(R$_9$)(R$_{10}$), —N(R$_{11}$)(C(=O)R$_{12}$), —C(=O)—OR$_{12}$, —C(=O)H, —C(=O)R$_{12}$, —C(=O)—N(R$_9$)(R$_{10}$), —N(R$_{11}$)(S(=O)$_2$R$_{12}$), —S(=O)$_2$—N(R$_9$)(R$_{10}$), —SR$_{12}$ and —OR$_{12}$;

$R_3$ is selected from halogen, cyano, $C_{1-3}$ alkyl, hydroxy, $C_{1-6}$ alkoxy, —N(R$_5$)(R$_6$), —CON(R$_7$)(R$_8$) or 3-7 membered heterocycloalkyl, in which the 3-7 membered heterocycloalkyl is optionally substituted with 1, 2, 3 or 4 $R_4$(s);

$R_4$ is selected from halogen, $C_{1-3}$ alkyl, hydroxyl, $C_{1-6}$ alkoxy, —NH$_2$, —NHCH$_3$ or —N(CH$_3$)$_2$;

$R_5$, $R_6$, $R_7$, $R_8$ are each independently hydrogen or $C_{1-4}$ alkyl;

$R_9$ is selected from H, $C_{1-4}$ alkyl, $C_{1-4}$ haloalkyl or $C_{3-7}$ cycloalkyl;

$R_{10}$ is H or selected from the group consisting of $C_{1-4}$ alkyl, $C_{1-4}$ haloalkyl, $C_{3-7}$ cycloalkyl, 4-10 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2, 3 or 4 substituent(s) each independently selected from the group consisting of —OH, —NH$_2$, —NH(CH$_3$), —N(CH$_3$)$_2$, —CN, $C_{1-4}$ alkyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy and $C_{1-4}$ haloalkoxy;

$R_{11}$ is selected from H, $C_{1-4}$ alkyl and $C_{3-7}$ cycloalkyl; and $R_{12}$ is selected from the group consisting of $C_{1-6}$ alkyl, $C_{3-7}$ cycloalkyl, 4- to 14-membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2 or 3 substituent(s) each independently selected from the group consisting of halogen, —CF$_3$, —CN, —OH, —NH$_2$, —NH(CH$_3$), —N(CH$_3$)$_2$, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy and $C_{1-4}$ haloalkoxy.

In some preferred embodiments of the present disclosure, in formula (I), L is O=S=O. In some preferred embodiments of the present disclosure, in formula (I), L is C=O.

In some preferred embodiments of the present disclosure, in formula (I), the ring A is 5-6 membered heteroaryl or phenyl wherein the ring A is optionally substituted with 1, 2, 3 or 4 $R_1$(s). In some preferred embodiments of the present disclosure, in formula (I), the ring A is pyrazinyl, pyrazolyl, or phenyl, where the ring A is optionally substituted with 1, 2, 3 or 4 $R_1$(s). In some particularly preferred embodiments of the present disclosure, in formula (I), the ring A is pyrazinyl. In some particularly preferred embodiments of the present disclosure, in formula (I), the ring A is phenyl.

In some preferred embodiments of the present disclosure, in formula (I), $R_1$ is absent or $R_1$ is selected from $C_{1-8}$ alkyl, and 3-7 membered heterocycloalkyl, wherein the $C_{1-8}$ alkyl is optionally substituted with 1, 2, 3, or 4 $R_3$(s), and wherein the 3-7 membered heterocycloalkyl is optionally substituted with 1, 2, 3, or 4 $R_4$(s). In some preferred embodiments of the present disclosure, in formula (I), $R_1$ is absent or $R_1$ is selected from $C_{1-6}$ alkyl, 5-7 membered heterocycloalkyl, wherein the $C_{1-6}$ alkyl is optionally substituted with 1, 2, 3, or 4 $R_3$(s), and wherein the 5-7 membered heterocycloalkyl is optionally substituted with 1, 2, 3, or 4 $R_4$(s). In some preferred embodiments of the present disclosure, in formula (I), $R_1$ is absent or $R_1$ is selected from $C_{1-6}$ alkyl, 5-7 membered heterocycloalkyl, wherein the $C_{1-6}$ alkyl is optionally substituted with 1 or 2 $R_3$(s), and wherein the 5-7 membered heterocycloalkyl is optionally substituted with 1, 2, 3 or 4 $C_{1-3}$ alkyl. In some preferred embodiments of the present disclosure, in formula (I), $R_1$ is absent or $R_1$ is selected from $C_{1-4}$ alkyl, and 5-7 membered heterocycloalkyl, wherein the $C_{1-4}$ alkyl is optionally substituted with 1 or 2 $R_3$, and wherein the 5-7 membered heterocycloalkyl is optionally substituted with 1, 2, 3 or 4 $C_{1-3}$ alkyl. In some preferred embodiments of the present disclosure, in formula (I), $R_1$ is absent or $R_1$ is selected from methyl, piperidinyl, morpholinyl, wherein the piperidinyl, and morpholinyl are optionally substituted with 1, 2, 3 or 4 $C_{1-3}$ alkyl groups. In some preferred embodiments of the present disclosure, in formula (I), $R_1$ is absent or $R_1$ is selected from methyl, piperidinyl, and morpholinyl. In some particularly preferred embodiments of the present disclosure, in formula (I), $R_1$ is absent. In some particularly preferred embodiments of the present disclosure, in formula (I), $R_1$ is methyl. In some particularly preferred embodiments of the present disclosure, in formula (I), $R_1$ is piperidinyl. In some particularly preferred embodiments of the present disclosure, in formula (I), $R_1$ is morpholinyl.

In some particularly preferred embodiments of the present disclosure, in formula (I), one or two $R_2$(s) are present and $R_2$ is selected from halogen, $C_{1-6}$ alkyl, and $C_{3-6}$ cycloalkyl, in which the $C_{1-6}$ alkyl, and $C_{3-6}$ cycloalkyl are each optionally substituted with 1, 2 or 3 substituent(s) each independently selected from the group consisting of halogen, —OH, —$NH_2$, —$NH(CH_3)$, —$N(CH_3)_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), one, or two $R_2$(s) are present and $R_2$ is selected from halogen, and $C_{1-6}$ alkyl, in which the $C_{1-6}$ alkyl is optionally substituted with 1, 2 or 3 substituent(s) each independently selected from the group consisting of halogen, —OH, —$NH_2$, —$NH(CH_3)$, —$N(CH_3)_2$, —CN, $C_{1-4}$ alkyl, $C_{1-4}$ haloalkyl, $C_{1-4}$ alkoxy, and $C_{1-4}$ haloalkoxy. In some particularly preferred embodiments of the present disclosure, in formula (I), two $R_2$s are present and $R_2$ is selected from fluorine, chlorine, bromine, methyl, ethyl, n-propyl, isopropyl, n-butyl, and isobutyl. In some preferred embodiments of the present disclosure, in formula (I), two $R_2$s are present, and $R_2$ is selected from fluorine, chlorine, methyl, ethyl, n-propyl, and isopropyl. In some preferred embodiments of the present disclosure, in formula (I), two $R_2$s are present, and $R_2$ is selected from fluorine, methyl, and ethyl. In some preferred embodiments of the present disclosure, in formula (I), two $R_2$s are present, and $R_2$ is selected from fluorine and ethyl. In some preferred embodiments of the present disclosure, in formula (I), two $R_2$(s) are present, and $R_2$ is selected from fluorine and ethyl. In some particularly preferred embodiments of the present disclosure, in formula (I), two $R_2$(s) are present which are respectively fluorine and ethyl.

The preferred options of the respective substituents mentioned in the above various preferred embodiments can be combined with each other in any way, and various combinations thereof are within the scope of the present disclosure.

In a more preferred embodiment of the present disclosure, the compound of formula (I) is selected from (2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(5-morpholinylpyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone;

(2-(6-(2-ethyl-5-fluoro-4-hydroxyphenyl)-1H-indazol-3-yl)pyrrolo[3,4-d]imidazol-5(1H, 4H,6H)-yl)(1-methylpiperidin-4-yl)ketone;

(2-(6-(2-ethyl-5-fluoro-4-hydroxyphenyl)-1H-indazol-3-yl)pyrrolo[3,4-d]imidazol-5(1H,4H,6H)-yl)(5-(4-methylpiperzin-1-yl)pyrazin-2-yl)ketone;

(2-(6-(2-ethyl-4-hydroxyphenyl)-1H-indazol-3-yl)pyrrolo[3,4-d]imidazol-5(1H,4H,6H)-yl)(5-(4-methylpiperzin-1-yl)pyrazin-2-yl)ketone;

5-ethyl-2-fluoro-4-(3-(5-(benzenesulfonyl)-1,4,5,6-tetrahydropyrrolo[3,4-d]imidazol-2-yl)-1H-indazol-6-yl)phenol;

5-ethyl-2-fluoro-4-(3-(5-(pyrazin-2ylmethyl)-1,4,5,6-tetrahydropyrrolo[3,4-d]imidazol-2-yl)-1H-indazol-6-yl)phenol;

4-(3-(5-(cyclopropylmethyl)-1,4,5,6-tetrahydropyrrolo[3,4-d]imidazol-2-yl)-1H-indazol-6-yl)-5-ethyl-2-fluorophenol;

Cyclopropyl (2-(6-(2-ethyl-5-fluoro-4-hydroxyphenyl)-1H-indazol-3-yl)pyrrolo[3,4-d]imidazol-5(1H,4H,6H)-yl)ketone;

4-(3-(5-(cyclobutylmethyl)-1,4,5,6-tetrahydropyrrolo[3,4-d]imidazol-2-yl)-1H-indazol-6-yl)-5-ethyl-2-fluorophenol;

Cyclobutyl (2-(6-(2-ethyl-5-fluoro-4-hydroxyphenyl)-1H-indazol-3-yl)pyrrolo[3,4-d]imidazol-5(1H,4H,6H)-yl)ketone;

(2-(6-(2-ethyl-5-fluoro-4-hydroxyphenyl)-1H-indazol-3-yl)-pyrrolo[3,4-d]imidazol-5-(1H,4H,6H)-yl)(pyridazin-4-yl)ketone;

(2-(6-(2-ethyl-5-fluoro-4-hydroxyphenyl)-1H-indazol-3-yl)-pyrrolo[3,4-d]imidazol-5-(1H,4H,6H)-yl)(pyridazin-3-yl)ketone;

4-(3-(5-(cyclopropanesulfonyl)-1,4,5,6-tetrahydropyrrolo[3,4-d]imidazol-2-yl)-1H-indazol-6-yl)-5-ethyl-2-fluorophenol;

4-(3-(5-(cyclobutylsulfonyl)-1,4,5,6-tetrahydropyrrolo[3,4-d]imidazol-2-yl)-1H-indazol-6-yl)-5-ethyl-2-fluorophenol;

4-(3-(5-(cyclopentylsulfonyl)-1,4,5,6-tetrahydropyrrolo[3,4-d]imidazol-2-yl)-1H-indazol-6-yl)-5-ethyl-2-fluorophenol;

5-ethyl-2-fluoro-4-(3-(5-((1-methyl-1H-pyrazol-4-yl)methyl)-1,4,5,6-tetrahydropyrrolo[3,4-d]imidazol-2-yl)-1H-indazol-6-yl)phenol;

4-(3-(5-(cyclopentyl-1,4,5,6-tetrahydropyrrolo[3,4-d]imidazol-2-yl)-1H-indazol-6-yl)-5-ethyl-2-fluorophenol;

5-ethyl-2-fluoro-4-(3-(5-(tetrahydro-2H-pyran-4-yl)-1,4,5,6-tetrahydropyrrolo[3,4-d]imidazol-2-yl)-1H-indazol-6-yl)phenol;

(2-(6-(2-ethyl-5-fluoro-4-hydroxyphenyl)-1H-indazol-3-yl)-4,6-dihydropyrrolo[3,4-d]imidazol-5-(1H)-yl)(pyrrolidin-1-yl)ketone;

Azetidin-1-yl ((2-(6-(2-ethyl-5-fluoro-4-hydroxyphenyl)-1H-indazol-3-yl)-4,6-dihydropyrrolo[3,4-d]imidazol-5-(1H)-yl)ketone;

(2-(6-(2-ethyl-5-fluoro-4-hydroxyphenyl)-1H-indazol-3-yl)-4,6-dihydropyrrolo[3,4-d]imidazol-5-(1H)-yl)(piperidin-1-yl)ketone;

(2-(6-(2-ethyl-5-fluoro-4-hydroxyphenyl)-1H-indazol-3-yl)-4,6-dihydropyrrolo[3,4-d]imidazol-5-(1H)-yl)(morpholino)ketone;

(2-(6-(2-ethyl-5-fluoro-4-hydroxyphenyl)-1H-indazol-3-yl)-4,6-dihydropyrrolo[3,4-d]imidazol-5-(1H)-yl)(4-methylpiperzin-1-yl)ketone;

(2-(6-(2-ethyl-5-fluoro-4-hydroxyphenyl)-1H-indazol-3-yl)-4,6-dihydropyrrolo[3,4-d]imidazol-5-(1H)-yl)(4-ethylpiperzin-1-yl)ketone;

Cyclopropyl(2-(6-(2-ethyl-5-fluoro-4-hydroxyphenyl)-1H-pyrazolo[4,3-b]pyridin-3-yl)-4,6-dihydropyrrolo[3,4-d]imidazol-5(1H)-yl)ketone;

Cyclopropyl(2-(6-(2-ethyl-5-fluoro-4-hydroxyphenyl)-4-methyl-1H-indazol-3-yl)-4,6-dihydropyrrolo[3,4-d]imidazol-5(1H)-yl)ketone;

(S)-(2-(6-(2-ethyl-5-fluoro-4-hydroxyphenyl)-4-methyl-1H-indazol-3-yl)-4,6-dihydropyrrolo[3,4-d]imidazol-5(1H)-yl)(3-hydroxylpyrrolidin-1-yl)ketone;

Cyclopropyl(2-(6-(2-ethyl-5-fluoro-4-hydroxyphenyl)-1H-pyrazolo[4,3-c]pyridin-3-yl)-4,6-dihydropyrrolo[3,4-d]imidazol-5(1H)-yl)ketone;

(R)-(2-(6-(2-ethyl-5-fluoro-4-hydroxyphenyl)-1H-indazol-3-yl)-4,6-dihydropyrrolo[3,4-d]imidazol-5(1H)-yl)(3-hydroxylpyrrolidin-1-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(3-hydroxylAzetidin-1-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(4-hydroxylpiperidin-1-yl)ketone;

1-(2-(6-(2-ethyl-5-fluoro-4-hydroxyphenyl)-1H-indazol-3-yl)-1,4,5,6-tetrahydropyrrolo[3,4-d]imidazol-5-carbonyl)azetidine-3-nitrile;

1-(2-(6-(2-ethyl-5-fluoro-4-hydroxyphenyl)-1H-indazol-3-yl)-1,4,5,6-tetrahydropyrrolo[3,4-d]imidazol-5-carbonyl)pyrrolidin-3-nitrile;

(S)-(2-(6-(2-ethyl-5-fluoro-4-hydroxyphenyl)-1H-pyrazolo[3,4-b]pyridin-3-yl)-4,6-dihydropyrrolo[3,4-d]imidazol-5(1H)-yl)(3-hydroxylpyrrolidin-1-yl)ketone;

(S)-6-(2-ethyl-5-fluoro-4-hydroxyphenyl)-3-(5-prolyl-1,4,5,6-tetrahydropyrrolo[3,4-d]imidazol-2-yl)-1H-indazol; and (R)-6-(2-ethyl-5-fluoro-4-hydroxyphenyl)-3-(5-prolyl-1,4,5,6-tetrahydropyrrolo[3,4-d]imidazol-2-yl)-1H-indazol.

In some of the most preferred embodiments of the present disclosure, the compound of formula (I) is each specific compound shown in Example 1 to Example 8 herein.

That is, the compound of formula (I) is selected from (2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(5-morpholinpyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone;

5-ethyl-2-fluoro-4-{3-[5-(1-methylpiperidin-4-carbonyl)-1H,4H,5H,6H-pyrrolo[3,4-d]imidazol-2-yl]-1H-indazol-6-yl}phenol;

5-ethyl-2-fluoro-4-{3-[5-(4-methylpiperazin-1-carbonyl)-1H,4H,5H,6H-pyrrolo[3,4-d]imidazol-2-yl]-1H-indazol-6-yl}phenol;

3-ethyl-4-{3-[5-(4-methylpiperazin-1-carbonyl)-1H,4H,5H,6H-pyrrolo[3,4-d]imidazol-2-yl]-1H-indazol-6-yl}phenol;

5-ethyl-2-fluoro-4-(3-(5-(bemzenesulfonyl)-1,4,5,6-tetrahydropyrrolo[3,4-d]imidazol-2-yl)-1H-indazol-6-yl)phenol; and 5-ethyl-2-fluoro-4-(3-(5-(pyrazin-2-methyl)-1,4,5,6-tetrahydropyrrolo[3,4-d]imidazol-2-yl)-1H-indazol-6-yl)phenol.

For simplicity, hereinafter, the term "a compound as shown by Formula (G)" or "a compound of Formula (G)" or "a compound of the invention" or "a compound according to the invention" also encompasses any optical isomer, geometric isomer, tautomer or a mixture of various isomers of the compound of Formula (G); the term "a compound as shown by Formula (G')" or "a compound of Formula (G')" or "a compound of the invention" or "a compound according to the invention" also encompasses any optical isomer, geometric isomer, tautomer or a mixture of various isomers of the compound of Formula (G'); and the term "a compound as shown by Formula (I)" or "a compound of Formula (I)" or "a compound of the invention" or "a compound according to the invention" also encompasses any optical isomer, geometric isomer, tautomer or a mixture of various isomers of the compound of Formula (I).

The term "optical isomer" refers that when a compound has one or more chiral centers, each chiral center may have an R configuration or an S configuration, and the various isomers thus constituted are known as an optical isomer. Optical isomers comprise all diastereomers, enantiomers, meso forms, racemates or mixtures thereof. For example, optical isomers can be separated by a chiral chromatography or by chiral synthesis.

The term "geometric isomer" refers that when a double bond is present in a compound, the compound may exist as a cis isomer, a trans isomer, an E isomer, or a Z isomer. A geometric isomer comprises a cis isomer, trans isomer, E isomer, Z isomer, or a mixture thereof.

The term "tautomer" refers to an isomer that is formed by rapid movement of an atom at two positions in a single molecule. It will be understood by those skilled in the art that tautomers can be mutually transformed, and in a certain state, may coexist by reaching an equilibrium state. As used herein, the term "a compound as shown by Formula (G)" also encompasses any tautomer of the compound of Formula (G); "a compound as shown by Formula (G')" also encompasses any tautomer of the compound of Formula (G'); and "a compound as shown by Formula (I)" also encompasses any tautomer of the compound of Formula (I).

Unless otherwise indicated, reference to "a compound as shown by Formula (G)" or "a compound of Formula (G)" or "a compound of the invention" or "a compound according to the invention" herein also encompasses isotopically-labeled compounds obtained by replacing any atom of the compound with its isotopic atom; reference to "a compound as shown by Formula (G')" or "a compound of Formula (G')" or "a compound of the invention" or "a compound according to the invention" herein also encompasses isotopically-labeled compounds obtained by replacing any atom of the compound with its isotopic atom; and reference to "a compound as shown by Formula (I)" or "a compound of Formula (I)" or "a compound of the invention" or "a compound according to the invention" herein also encompasses isotopically-labeled compounds obtained by replacing any atom of the compound with its isotopic atom.

The invention comprises all pharmaceutically acceptable isotopically-labeled compounds of Formula (G) wherein one or more atoms are replaced by atoms having the same atomic number but different atomic mass or mass number than those normally found in nature. The invention comprises all pharmaceutically acceptable isotopically-labeled compounds of Formula (G') wherein one or more atoms are replaced by atoms having the same atomic number but different atomic mass or mass number than those normally found in nature. The invention comprises all pharmaceutically acceptable isotopically-labeled compounds of Formula (I) wherein one or more atoms are replaced by atoms having the same atomic number but different atomic mass or mass number than those normally found in nature.

Examples of isotopes suitable for inclusion in the compounds of the invention include isotopes of hydrogen, such as $^2$H (D) and $^3$H (T), of carbon, such as $^{11}$C, $^{13}$C and $^{14}$C, of chlorine, such as $^{36}$Cl, of fluorine, such as $^{18}$F, of iodine, such as $^{123}$I and $^{125}$I, of nitrogen, such as $^{13}$N and $^{15}$N, of oxygen, such as $^{15}$O, $^{17}$O and $^{18}$O, and of sulphur, such as $^{35}$S.

Certain isotopically-labelled compounds of formula (G), for example, those incorporating a radioactive isotope, are useful in drug and/or substrate tissue distribution studies. Certain isotopically-labelled compounds of formula (G'), for example, those incorporating a radioactive isotope, are useful in drug and/or substrate tissue distribution studies. Certain isotopically-labelled compounds of formula (I), for example, those incorporating a radioactive isotope, are useful in drug and/or substrate tissue distribution studies. The radioactive isotopes deuterium, i.e. $^2$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (G) can generally be prepared by conventional techniques known to those skilled in the art or by processes analogous to those described in the accompanying Examples and Preparations using an appropriate isotopically-labeled reagents in place of the non-labeled reagent previously employed. Isotopically-labeled compounds of formula (G') can generally be prepared by conventional techniques known to those skilled in the art or by processes analogous to those described in the accompanying Examples and Preparations using an appropriate isotopically-labeled reagents in place of the non-labeled reagent previously employed. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

The compound of formula (G) may exist in the form of a pharmaceutically acceptable salt, for example, an acid addition salt and/or a base addition salt of the compound of formula (G). Unless otherwise indicated, "a pharmaceutically acceptable salt" as used herein includes acid addition salts or base addition salts that may appear in the compound of formula (G). The compound of formula (G') may exist in the form of a pharmaceutically acceptable salt, for example, an acid addition salt and/or a base addition salt of the compound of formula (G'). Unless otherwise indicated, "a pharmaceutically acceptable salt" as used herein includes acid addition salts or base addition salts that may appear in the compound of formula (G'). The compound of formula (I) may exist in the form of a pharmaceutically acceptable salt, for example, an acid addition salt and/or a base addition salt of the compound of formula (I). Unless otherwise indicated, "a pharmaceutically acceptable salt" as used herein includes acid addition salts or base addition salts that may appear in the compound of formula (I).

The pharmaceutically acceptable salt of the compound of formula (G), the compound of formula (G') and the compound of formula (I) include acid addition salts and base addition salts thereof. Suitable acid addition salts are formed from acids that form non-toxic salts. Examples include but are not limited to: acetate, adipate, aspartate, benzoate, benzenesulfonate, bicarbonate/carbonate, bisulfate/sulfate, borate, camphor sulfonate, citrate, cyclohexamine sulfonate, ethanedisulfonate, formate, fumarate, glucoheptonate, gluconate, glucuronate, hexafluorophosphate, 2-(4-hydroxybenzyl) benzoate, hydrochloride/chloride, hydrobromide/bromide, hydroiodide/iodide, 2-isethionate, lactate, malate, maleate, malonate, methanesulfonate, methyl sulfate, naphthalate, 2-naphthalenesulfonate, nicotinate, nitrate, orotate, oxalate, palmitate, phosphate/hydrogen phosphate/dihydrogen phosphate, pyroglutamate, glucarate, stearate, salicylate, tannate, tartrate, tosylate and trifluoroacetate. Suitable base addition salts are formed from bases that form non-toxic salts. Examples thereof include, but are not limited to: aluminum, arginine, calcium, choline, diethylamine, diethanolamine, glycine, lysine, magnesium, meglumine, ethanolamine, potassium, sodium, tromethamine, and zinc salts. It is also possible to form half salts of acids and bases, such as hemisulfate and hemicalcium salts. For a review of suitable salts, please refer to Handbook of Pharmaceutical Salts: Properties, Selection and Use by Stahl and Wermuth (Wiley-VCH, 2002). Methods for preparing pharmaceutically acceptable salts of the compounds described herein are known to those skilled in the art.

Certain compounds of the invention may exist in unsolvated form as well as solvated forms, including hydrated forms. In general, the compounds of formula (G), the compounds of formula (G') and the compounds of formula (I), whether present in solvated form or in unsolvated form, are included within the scope of the invention.

Certain compounds of the invention may exist in different crystalline or amorphous forms, and the compounds of formula (G), the compounds of formula (G') and the compounds of Formula (I) present in any forms, are included within the scope of the invention.

To avoid ambiguity, the definitions of some terms used herein are given below. Unless otherwise stated, the meanings of the terms used herein are as follows.

The term "pharmaceutically acceptable" means that the corresponding compound, carrier or molecule is suitable for administration to humans. Preferably, the term refers to it is approved by regulatory agencies such as CFDA (China), EMEA (Europe), FDA (United States), and other national regulatory agencies to be suitable for mammals, preferably humans.

The "prodrug" refers to a derivative that is converted into a compound of the present disclosure by a reaction with enzymes, gastric acid, and the like in the living body under physiological conditions, for example, through oxidation, reduction, hydrolysis, and the like catalyzed by enzymes.

The "metabolite" refers to all molecules derived from any compound of the present disclosure in a cell or organism, preferably a human.

The term "hydroxy" refers to —OH.

The term "halogen" or "halo" refers to —F, —Cl, —Br, or —I.

The term "cyano" refers to —CN.

In the present disclosure, when there are multiple substituents of a certain type, each substituent is independently selected from each other, and these substituents may be the same or different. For example, when there are 2, 3, or 4 $R_1$s, these $R_1$s may be the same or different. For example, when there are 2, 3, or 4 $R_2$s, these $R_2$s may be the same or different. For example, when $R_1$ and $R_2$ are both —N($R_9$)($R_{10}$), $R_9$ and $R_{10}$ contained in $R_1$ and $R_2$ can be independently selected, that is, $R_9$ in $R_1$ and $R_9$ in $R_2$ can be the same or different, and $R_{10}$ in $R_1$ and $R_{10}$ in $R_2$ may be the same or different. For example, when there are two $R_1$s, and the two $R_1$s are both —N($R_9$)($R_{10}$), $R_9$ and $R_{10}$ in the two $R_1$s can be selected independently, that is, $R_9$ in the first $R_1$ and $R_9$ in the second $R_1$ may be the same or different, and $R_{10}$ in the first $R_1$ and $R_{10}$ in the second $R_1$ may be the same or different. The above statement applies to $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$.

As used herein, the term "substituted" means that one or more (preferably 1 to 5, more preferably 1 to 3) hydrogen atoms in a group are independently replaced by a corresponding number of substituents.

As used herein, the term "independently" means that when the number of substituents is more than one, these substituents may be the same or different.

As used herein, the term "optional" or "optionally" means that the event described therein may or may not occur. For example, an "optionally substituted" group means that the group may be unsubstituted or substituted.

As used herein, the term "heteroatom" as used herein refers to oxygen (O), nitrogen (N), or $S(O)_m$ in which m may be 0, 1 or 2, i.e. a sulfur atom S, or a sulfoxide group SO, or a sulfonyl group $S(O)_2$).

As used herein, the term "alkyl" refers to saturated aliphatic hydrocarbons, including straight and branched chains. In some embodiments, the alkyl group has 1-8, or 1-6, or 1-3 carbon atoms. For example, the term "$C_{1-8}$ alkyl" refers to a straight or branched chain group of atoms having 1-8 carbon atoms. The term "$C_{1-8}$ alkyl" includes the terms "$C_{1-6}$ alkyl", "$C_1$-$C_3$ alkyl" and "$C_1$-$C_4$ alkyl" in its definition. Examples of alkyl groups include, but are not limited to, methyl, ethyl, propyl, isopropyl, butyl, isobutyl, sec-butyl, tert-butyl, pentyl, 2-pentyl, 3-pentyl, isopentyl, neopentyl, (R)-2-methylbutyl, (S)-2-methylbutyl, 3-methylbutyl, 2,3-dimethylpropyl, 2,3-dimethylbutyl, hexyl, and the like. The alkyl group may be optionally substituted with one or more (for example, 1 to 5) suitable substituent(s).

As used herein, the term "alkenyl" refers to an aliphatic hydrocarbon having at least one carbon-carbon double bond, including straight and branched chains having at least one carbon-carbon double bond. In some embodiments, alkenyl groups have 2-8 carbon atoms, 2-6 carbon atoms, 3-6 carbon atoms, or 2-4 carbon atoms. For example, the term "$C_{2-8}$ alkenyl" refers to a linear or branched unsaturated atomic group (having at least one carbon-carbon double bond) having 2-8 carbon atoms. The double bond may or may not be the point of attachment of another group. Alkenyl groups include, but are not limited to, vinyl, 1-propenyl, 2-propenyl, 2-methyl-2-propenyl, butenyl, pentenyl, 3-hexenyl, and the like. Alkenyl groups may be optionally substituted with one or more (for example, 1 to 5) suitable substituent(s). When the compound of formula (I) contains an alkenyl group, the alkenyl group may be present in the pure E form, the pure Z form, or any mixture thereof.

As used herein, the term "alkynyl" refers to an aliphatic hydrocarbon having at least one carbon-carbon triple bond, including straight and branched chains having at least one carbon-carbon triple bond. In some embodiments, an alkynyl group has 2-8 carbon atoms, 2-6 carbon atoms, 3-6 carbon atoms, or 2-4 carbon atoms. For example, the term "$C_{2-8}$ alkynyl" refers to a linear or branched unsaturated atomic group (having at least one carbon-carbon triple bond) having 2-8 carbon atoms. The triple bond may or may not be the point of attachment of another group. Alkynyl groups include, but are not limited to, ethynyl, 1-propynyl, 2-propynyl, 2-methyl-2-propynyl, butynyl, pentynyl, 3-hexynyl, and the like. The alkynyl group may be optionally substituted with one or more (for example, 1 to 5) suitable substituent(s).

As used herein, the term "$C_{3-7}$ cycloalkyl" refers to a cycloalkyl group having 3-7 carbon atoms forming a ring, such as cyclopropyl, cyclobutyl, cyclopentyl, cyclohexyl, cyclohexenyl, cycloheptyl. The cycloalkyl may be optionally substituted with one or more suitable substituent(s).

As used herein, the term "n-membered heterocycloalkyl" refers to a cycloalkyl group having m ring-forming carbon atoms and (n-m) ring-forming heteroatoms, the heteroatoms being selected from O, S and N. For example, 3-7 membered heterocycloalkyl includes, but not limited to, oxetane, thietane, azetidine, tetrahydrofuran, tetrahydrothiophene, pyrrolidine, tetrahydropyran, tetrahydrothiopyran, piperidine, morpholine, piperazine, oxepane, thiepane, and azepine. The heterocycloalkyl may be optionally substituted with one or more suitable substituent(s).

As used herein, the term "$C_{5-7}$ aryl" refers to an aryl group having an aromatic ring containing 5-7 carbon atoms, preferably phenyl.

As used herein, the term "n-membered heteroaryl" refers to a heteroaryl group having m carbon atoms forming an aromatic ring and (n-m) heteroatoms forming an aromatic ring, the heteroatoms being selected from O, S and N. For example, 5-7 membered heteroaryl includes but not limited to pyrazine, pyrazole, pyrrole, furan, thiophene, thiazole, and pyridine. The heteroaryl may be optionally substituted with one or more suitable substituent(s).

As used herein, the term "$C_{7-11}$ bicyclic aryl" refers to a bicyclic aryl group having 7-11 carbon atoms, such as naphthalene, indene and the like. The bicyclic aryl may be optionally substituted with one or more suitable substituent(s).

As used herein, the term "n-membered bicyclic heteroaryl" refers to a bicyclic heteroaryl group having m carbon atoms forming an aromatic bicyclic ring and (n-m) heteroatoms forming an aromatic bicyclic ring, and the heteroatoms are selected from O, S and N. For example, 7-11 membered bicyclic heteroaryl includes, but not limited to, quinoline, isoquinoline, benzothiazole, and the like. The bicyclic heteroaryl may be optionally substituted with one or more suitable substituent(s).

As used herein, the term "11-15 membered tricyclyl" includes but not limited to acridine and the like. The 11-15 membered tricyclyl may be optionally substituted with one or more suitable substituent(s).

As used herein, the term "haloalkyl" refers to an alkyl group having one or more halogen substituent(s) (up to perhaloalkyl, that is, each hydrogen atom of the alkyl is replaced by a halogen atom). For example, the term "$C_{1-6}$ haloalkyl" refers to a $C_{1-6}$ alkyl group with one or more halogen substituent(s) (up to perhaloalkyl, that is, each hydrogen atom of the alkyl group is replaced by a halogen atom). As another example, the term "$C_{1-4}$ haloalkyl" refers to a $C_{1-4}$ alkyl group with one or more halogen substituent(s) (up to perhaloalkyl, that is, each hydrogen atom of the alkyl group is replaced by a halogen atom); the term "$C_{1-3}$ haloalkyl" refers to a $C_{1-3}$ alkyl group with one or more halogen substituent(s) (up to perhaloalkyl, that is, each hydrogen atom of the alkyl group is replaced by a halogen atom); and the term "$C_{1-2}$ haloalkyl" refers to a $C_{1-2}$ alkyl group (i.e. methyl or ethyl) with one or more halogen substituent(s) (up to perhaloalkyl, that is, each hydrogen atom of the alkyl group is replaced by a halogen atom). As another example, the term "$C_1$ haloalkyl" refers to a methyl group with 1, 2, or 3 halogen substituent(s). Examples of haloalkyl groups include: $CF_3$, $C_2F_5$, $CHF_2$, $CH_2F$, $CH_2CF_3$, $CH_2Cl$, and the like.

As used herein, the term "alkoxy" refers to alkyl with a single bond attached to an oxygen atom. The point of attachment of the alkoxy group to a molecule is through the oxygen atom. Alkoxy can be described as alkyl-O—. The term "$C_{1-6}$ alkoxy" refers to a linear or branched alkoxy group containing 1 to 6 carbon atoms. The term "$C_{1-6}$ alkoxy" includes the term "$C_{1-3}$ alkoxy" in its definition. Alkoxy includes, but not limited to, methoxy, ethoxy, propoxy, isopropoxy, butoxy, hexoxy, and the like. The alkoxy group may be optionally substituted with one or more suitable substituent(s).

Herein, a numerical range relating to the number of substituents, the number of carbon atoms, or the number of ring members represents an enumeration of all integers in the range, and the range is only a simplified representation thereof. For example:

"1-4 substituent(s)" means 1, 2, 3 or 4 substituent(s);
"1-3 substituent(s)" means a 1, 2 or 3 substituent(s);
"3 to 12-membered ring" means a 3, 4, 5, 6, 7, 8, 9, 10, 11 or 12-membered ring;
"3 to 14-membered ring" means a 3, 4, 5, 6, 7, 8, 9, 10, 11, 12, 13 or 14-membered ring;
"3 to 8 membered ring" means a 3, 4, 5, 6, 7, or 8 membered ring;
"1-12 carbon atoms" or "$C_{1-12}$" means 1 ($C_1$), 2 ($C_2$), 3 ($C_3$), 4 ($C_4$), 5 ($C_5$), 6 ($C_6$), 7 ($C_7$), 8 ($C_8$), 9 ($C_9$), 10 ($C_{10}$), 11 ($C_{11}$) or 12 ($C_{12}$) carbon atoms;
"1-6 carbon atoms" or "$C_{1-6}$" means 1 ($C_1$), 2 ($C_2$), 3 ($C_3$), 4 ($C_4$), 5 ($C_5$) or 6 ($C_6$) carbon atoms;
"1-4 carbon atoms" or "$C_{1-4}$" means 1 ($C_1$), 2 ($C_2$), 3 ($C_3$), 4 ($C_4$) carbon atoms;
"2-6 carbon atoms" or "$C_2$-6" means 2 ($C_2$), 3 ($C_3$), 4 ($C_4$), 5 ($C_5$) or 6 ($C_6$) carbon atoms;
"$C_3$-8" means 3 ($C_3$), 4 ($C_4$), 5 ($C_5$), 6 ($C_6$), 7 ($C_7$), 8 ($C_8$) carbon atoms; and
"3 to 8 ring members" means 3, 4, 5, 6, 7, or 8 ring members.

Thus, a numerical range associated with the number of substituents, the number of carbon atoms, or the number of ring members also encompasses any one of its subranges, and each subrange is also considered to be disclosed herein.

In a second aspect, the present disclosure provides a pharmaceutical composition comprising the above mentioned compounds, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, and one or more pharmaceutically acceptable carriers, adjuvants or excipients.

The pharmaceutical compositions of the invention may be formulated as suitable dosage forms for oral, external (including not limited to external application, spraying, and the like), parenteral (including subcutaneous, intramuscular, intradermal and intravenous), bronchial or nasal administration as desire. Preferably, the pharmaceutical compositions of the invention may be formulated as suitable dosage forms for oral or external administration. More preferably, the pharmaceutical compositions of the invention may be formulated as suitable dosage forms for oral administration.

If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, paste, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. The pharmaceutical compositions are prepared by conventional techniques appropriate to the desired preparation containing appropriate amounts of the active ingredient, that is, the compound of Formula (G), the compound of Formula (G') or the compound of Formula (I) according to the invention.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil), and injectable organic esters such as ethyl oleate.

These compositions may also contain excipients such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylatedisostearyl alcohols, polyoxyethylene sorbitol and sorbitan esters, microcrystalline cellulose, aluminum metahydroxide, bentonite, agar-agar and tragacanth, or mixtures of these substances, and the like.

Dosage forms for topical administration of a compound of the invention include paste, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The external dosage form of the compound of the present disclosure may be in the form of a water-in-oil (W/O) or oil-in-water (O/W) emulsion, a multi-emulsion form, such as a water-in-oil-in-water (W/O/W) form or an oil-in-water-oil (O/W/O) emulsion, or in the form of water dispersion or lipid dispersion, gel or aerosol.

The external dosage form of the compound of the present disclosure may contain additives and aids, such as emulsifiers, thickeners, gelling agents, water fixatives, spreading agents, stabilizers, dyes, fragrances, and preservatives. Suitable emulsifiers include stearic acid, triethanolamine and PEG-40-stearate. Suitable thickeners include glyceryl monostearate and PEG600. Suitable preservatives include propyl paraben and chlorocresol. Suitable spreading agents include dimethicone and polydimethylcyclosiloxane. Suitable water fixatives include polyethylene glycol, preferably polyethylene glycol 600.

The external dosage form of the compound of the present disclosure may include pastes, lotions, gels, emulsions, microemulsions, sprays, skin patches, and the like, which can be applied topically to treat atopic dermatitis, eczema, psoriasis, and scleroderma, itching, vitiligo, hair loss and other skin diseases. In particular, the external dosage form of the compound of the present disclosure is pastes, which can be applied topically to treat skin diseases such as atopic dermatitis, eczema, psoriasis, scleroderma, itching, vitiligo, and hair loss and other skin diseases.

The amount of the compound of formula (G), the compound of formula (G') or the compound of formula (I) in the pharmaceutical composition and dosage form can be appropriately determined by those skilled in the art as needed. For example, the compound of formula (G), the compound of formula (G') or the compound of formula (I) can be present in the pharmaceutical composition or dosage form in a therapeutically effective amount.

In a third aspect, the present disclosure provides use of the compound as described above, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, or the composition as described above in the preparation of a medicament for the treatment and/or prevention of JAK-related diseases or disorders.

"Diseases or disorders related to JAK" include but not limited to: Arthritis, including rheumatoid arthritis, juvenile arthritis and psoriatic arthritis; Autoimmune diseases or disorders, including single organ or single cell type autoimmune disorders, such as Hashimoto's thyroiditis, autoimmune hemolytic anemia, pernicious anemia of autoimmune atrophic gastritis, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis and membranous glomerulopathy, those involving systemic autoimmune disorders (e.g. systemic lupus erythematosus, rheumatoid arthritis, Sjogren's syndrome, Reiter's syndrome, polymyositis-dermatomyositis, systemic sclerosis, polyarteritis nodosa, multiple sclerosis and bullous pemphigoid) and other O-cell (humoral) or T-cell autoimmune diseases (including Kogan syndrome), ankylosing spondylitis, Wegener's Granuloma, autoimmune alopecia, type I diabetes or juvenile-onset diabetes or thyroiditis;

Cancer or tumor, including digestive/gastrointestinal cancer, colorectal cancer, liver cancer, skin cancer (including mast cell tumor and squamous cell carcinoma), breast cancer, ovarian cancer, prostate cancer, lymphoma, leukemia (including acute myeloid leukemia and chronic myeloid leukemia), kidney cancer, lung cancer, muscle cancer, bone cancer, bladder cancer, brain cancer, melanoma (including oral and metastatic melanoma), Kaposi's sarcoma, myeloma (including multiple myeloma), myeloproliferative disorders, proliferative diabetic retinopathy or disorders related to angiogenesis (including solid tumors);

Diabetes, including type I diabetes or diabetic complications;

Eye diseases, disorders or conditions, including autoimmune diseases of eyes, keratoconjunctivitis, vernal conjunctivitis, uveitis (including uveitis and lens uveitis related to Behcet's disease), keratitis, herpetic keratitis, keratitis conus, corneal epithelial dystrophy, leukoplakia, ocular pemphigus, Moran ulcer, scleritis, Grave's eye disease, Vogt-Koyanagi-Harada syndrome, keratoconjunctivitis sicca (dry eye), blisters, iridocyclitis, sarcoidosis, endocrine ophthalmopathy, sympathetic ophthalmia, allergic conjunctivitis, or ocular neovascularization;

Intestinal inflammation, allergies or conditions, including Crohn's disease and/or ulcerative colitis, inflammatory bowel disease, celiac disease, proctitis, eosinophilic gastroenteritis or mastocytosis;

Neurodegenerative diseases, including motor neuron disease, Alzheimer's disease, Parkinson's disease, amyotrophic lateral sclerosis, Huntington's disease, neurodegenerative disease caused by cerebral ischemia or traumatic injury, stroke, glutamate neurotoxicity or hypoxia; stroke ischemia/reperfusion injury, myocardial ischemia, renal ischemia, heart attack, cardiac hypertrophy, atherosclerosis and arteriosclerosis, organ hypoxia or platelet aggregation;

Skin diseases, conditions or disorders, including atopic dermatitis, eczema, psoriasis, scleroderma, itching or other pruritic conditions, vitiligo, hair loss;

Allergies, including mammalian allergic dermatitis (including equine allergic diseases, such as bite allergies), summer eczema, *Culex* mosquito itch syndrome (sweet itch), emphysema, inflammatory airway disease, recurrent airway obstruction, airway overreaction, or chronic obstructive pulmonary disease;

Asthma and other obstructive airway diseases, including chronic or refractory asthma, advanced asthma, bronchitis, bronchial asthma, allergic asthma, endogenous asthma, exogenous asthma or dusty asthma; and Transplant rejection, including islet transplant rejection, bone marrow transplant rejection, graft versus host disease, organ and cell transplant rejection (for example bone marrow, cartilage, cornea, heart, intervertebral disc, pancreatic islets, kidney, limbs, liver, lung, muscle, myoblasts, nerve, pancreas, skin, small intestine or trachea) or xenotransplantation.

In a fourth aspect, the present disclosure provides a method for treating JAK-related diseases or disorders, the method comprising administrating a therapeutically effective amount of the compound as described above or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, or the composition as described above to patients in need. Among them, the patient is preferably a mammal, and more preferably a human patient. The route of administration can be oral, topical (including but not limited to external application, spraying, and the like), parenteral (including subcutaneous, intramuscular, cortical, and intravenous) administration, bronchial administration, or nasal administration. Among them, it is preferably administered orally or topically. It is more preferably administered orally.

Unexpectedly, the compound of the present disclosure demonstrated excellent efficacy as a JAK kinase inhibitor in experiments that is superior to existing JAK kinase inhibitors, such as Filgotinib, and had good safety potentially.

Preferably, the present disclosure provides the following embodiments:

1. A compound of Formula (G),

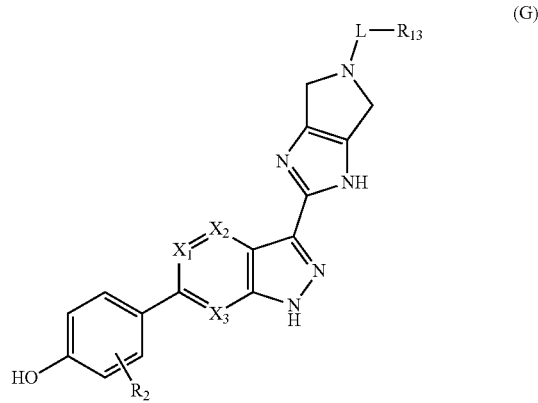

(G)

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, in which L is C=O, O=S=O, CH$_2$ or a bond; and
X$_1$ is N or CR$_{14}$; and
X$_2$ is N or CR$_{15}$; and
X$_3$ is N or CR$_{16}$; and R$_{14}$, R$_{15}$, R$_{16}$ are each independently selected from H, —OH, —SH, —CN, halogen, —NO$_2$, —SF$_5$, —S—C$_{1-4}$ alkyl, C$_{1-6}$ alkyl, C$_{2-8}$ alkenyl, C$_{2-8}$ alkynyl, C$_{1-6}$ alkoxy, C$_{3-7}$ cycloalkyl, 3-7 membered heterocycloalkyl, C$_{5-7}$ aryl, 5-7 membered heteroaryl, —N(R$_9$)(R$_{10}$), —N(R$_{11}$)(C(=O)R$_{12}$), —C(=O)—N(R$_9$)(R$_{10}$), —C(=O)—R$_{12}$, —C(=O)—OR$_{12}$, —OC(=O)R$_{12}$, —N(R$_{11}$)(S(=O)$_2$R$_{12}$), —S(=O)$_2$—N(R$_9$)(R$_{10}$), —SR$_{12}$ and —OR$_{12}$, in which the —S—C$_{1-4}$ alkyl, C$_{1-6}$ alkyl, C$_{1-6}$ alkoxy, C$_{3-7}$ cycloalkyl, and 3-7 membered heterocycloalkyl are optionally substituted with 1, 2 or 3 substitutes selected from halogen, —OH, —NH$_2$, —NH(CH$_3$), —N(CH$_3$)$_2$, —CN, C$_{1-4}$ alkyl, C$_{3-7}$ cycloalkyl, C$_{1-4}$ hydroxyalkyl, —S—C$_{1-4}$ alkyl, —C(=O)H, —C(=O)—C$_{1-4}$ alkyl, —C(=O)—O—C$_{1-4}$ alkyl, —C(=O)—NH$_2$, —C(=O)—N(C$_{1-4}$ alkyl)$_2$, —N(C$_{1-4}$ alkyl)(C(=O) C$_{1-4}$ alkyl), C$_{1-4}$ haloalkyl, C$_{1-4}$ alkoxy and C$_{1-4}$ haloalkoxy; and R$_{13}$ is H, —N(R$_{17}$)(R$_{18}$), C$_{1-6}$ alkoxy, —SR$_{12}$, —OR$_{12}$, —CN, halogen, —NO$_2$, —SF$_5$, —S—C$_{1-4}$ alkyl, C$_{1-6}$ alkyl or C$_{3-7}$ cycloalkyl, 3-7 membered heterocycloalkyl, C$_{5-7}$ aryl, 5-7 membered heteroaryl, C$_{7-11}$ bicyclic aryl, 7-11 membered bicyclic heteroaryl, 11-15 membered tricyclyl, C$_{5-11}$bicycloalkyl, or 5-11 membered bicyclic heteroalkyl, and R$_{13}$ is substituted with 0, 1, 2, 3 or 4 R$_1$(s), in which R$_{17}$, and R$_{18}$ are each independently selected from H, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, C$_{3-7}$ heterocycloalkyl, C$_{5-7}$ aryl, 5-7 membered heteroaryl, C$_{7-11}$ bicyclic aryl, 7-11 membered bicyclic heteroaryl, 11-15 membered tricyclyl, C$_{5-11}$bicycloalkyl, and 5-11 membered bicyclic heteroalkyl and are optionally substituted with one or more substitutes each independently selected from —OH, —CN, —SH, halogen, —NO$_2$, —SF$_5$, —S—C$_{1-4}$ alkyl, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, 4-10 membered heterocycloalkyl, C$_{5-7}$ aryl, 5-7 membered heteroaryl, C$_{7-11}$ bicyclic aryl, 7-11 membered bicyclic heteroaryl, —N(R$_9$)(R$_{10}$), —N(R$_{11}$)(C(=O)R$_{12}$), —C(=O)—N(R$_9$)(R$_{10}$), —C(=O)—R$_{12}$, —C(=O)—OR$_{12}$, —OC(=O)R$_{12}$, —N(R$_{11}$)(S(=O)$_2$R$_{12}$), —S(=O)$_2$—N(R$_9$)(R$_{10}$), —SR$_{12}$ and —OR$_{12}$, wherein the —S—C$_{1-4}$ alkyl, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, 4-10 membered heterocycloalkyl, C$_{5-7}$ aryl, 5-7 membered heteroaryl, C$_{7-11}$ bicyclic aryl, and 7-11 membered bicyclic heteroaryl are optionally substituted with 1, 2 or 3 substitutes each independently selected from halogen, —CN, —OH, C$_{1-4}$ alkyl, C$_{1-4}$ alkoxy, C$_{1-4}$ haloalkyl, C$_{1-4}$ haloalkoxy, C$_{3-6}$ cycloalkyl, —N(R$_9$)(R$_{10}$), —N(R$_{11}$)(C(=O)R$_{12}$), —C(=O)—OR$_{12}$, —C(=O)H, —C(=O)R$_{12}$, —C(=O)—N(R$_9$)(R$_{10}$), —N(R$_{11}$)(S(=O)$_2$R$_{12}$), —S(=O)$_2$—N(R$_9$)(R$_{10}$), —SR$_{12}$ and —OR$_{12}$; or R$_{17}$, R$_{18}$ and the N atom connected thereto together form a 3-14 membered ring; and 0, 1, 2, 3 or 4 R$_2$(s) are present in formula (G), and R$_2$ is selected from H, halogen, —OH, —NO$_2$, —CN, —SF$_5$, —SH, —S—C$_{1-4}$ alkyl, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, 4-10 membered heterocycloalkyl, C$_{5-7}$ aryl, 5-7 membered heteroaryl, C$_{7-11}$ bicyclic aryl, 7-11 membered bicyclic heteroaryl, —N(R$_9$)(R$_{10}$), —N(R$_{11}$)(C(=O)R$_{12}$), —C(=O)—N(R$_9$)(R$_{10}$), —C(=O)—R$_{12}$, —C(=O)—OR$_{12}$, —OC(=O)R$_{12}$, —N(R$_{11}$)(S(=O)$_2$R$_{12}$), —S(=O)$_2$—N(R$_9$)(R$_{10}$), —SR$_{12}$ and —OR$_{12}$, in which the —S—C$_{1-4}$ alkyl, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, 4-10 membered heterocycloalkyl, C$_{5-7}$ aryl, 5-7 membered heteroaryl, C$_{7-11}$ bicyclic aryl, and 7-11 membered bicyclic heteroaryl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—O$R_{12}$, —C(═O)H, —C(═O)$R_{12}$, —C(═O)—N($R_9$)($R_{10}$), —N($R_{11}$)(S(═O)$_2$$R_{12}$), —S(═O)$_2$—N($R_9$)($R_{10}$), —S$R_{12}$ and —O$R_{12}$; and $R_1$ is selected from H, halogen, —OH, —NO$_2$, —CN, —SF$_5$, —SH, —S—$C_{1-4}$ alkyl, $C_{1-8}$ alkyl, $C_{2-8}$ alkenyl, $C_{2-8}$ alkynyl, $C_{1-8}$ alkoxy, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, 5-11 membered bicyclic heteroalkyl, —N($R_9$)($R_{10}$), —N($R_{11}$)(C(═O)$R_{12}$), —C(═O)—N($R_9$)($R_{10}$), —C(═O)—$R_{12}$, —C(═O)—O$R_{12}$, —OC(═O)$R_{12}$, —N($R_{11}$)(S(═O)$_2$$R_{12}$), —S(═O)$_2$—N($R_9$)($R_{10}$), —S$R_{12}$ and —O$R_{12}$, in which the —S—$C_{1-4}$ alkyl, $C_{1-8}$ alkyl, $C_{2-8}$ alkenyl, $C_{2-8}$ alkynyl, and $C_{1-8}$ alkoxy are optionally substituted with 1, 2, 3, or 4 $R_3$(s), and in which the $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are optionally substituted with 1, 2, 3, or 4 $R_4$(s); and $R_3$ and $R_4$ are each independently selected from H, halogen, —OH, —NO$_2$, —CN, —SF$_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 3-10 membered heterocycloalkyl, $C_{5-7}$ aryl, 5-7 membered heteroaryl, $C_{7-11}$ bicyclic aryl, 7-11 membered bicyclic heteroaryl, —N($R_5$)($R_6$), —N($R_{11}$)(C(═O)$R_{12}$), —CON($R_7$)($R_8$), —C(═O)—$R_{12}$, —C(═O)—O$R_{12}$, —OC(═O)$R_{12}$, —N($R_{11}$)(S(═O)$_2$$R_{12}$), —S(═O)$_2$—N($R_9$)($R_{10}$), —S$R_{12}$ and —O$R_{12}$, in which the $C_{1-6}$ alkyl, $C_{3-7}$ cycloalkyl, 3-10 membered heterocycloalkyl, $C_{5-7}$ aryl, 5-7 membered heteroaryl, $C_{7-11}$ bicyclic aryl, and 7-11 membered bicyclic heteroaryl are each optionally substituted with 1, 2, 3 or 4 substituent(s) each independently selected from the group consisting of halogen, —CN, —OH, $C_{1-4}$ alkyl, $C_{1-6}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(═O)$R_{12}$), —C(═O)—O$R_{12}$, —C(═O)H, —C(═O)$R_{12}$, —C(═O)—N($R_9$)($R_{10}$), —N($R_{11}$)(S(═O)$_2$$R_{12}$), —S(═O)$_2$—N($R_9$)($R_{10}$), —S$R_{12}$ and —O$R_{12}$; and $R_5$, $R_6$, $R_7$, $R_8$, $R_9$, $R_{10}$, Ru, and $R_{12}$ are each independently H or selected from the group consisting of $C_{1-6}$ alkyl, $C_{1-4}$ haloalkyl, $C_{3-7}$ cycloalkyl, 4-14 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein the substituents included in the above group are each optionally substituted with 1, 2, 3 or 4 substituent(s) each independently selected from the group consisting of halogen, —CF$_3$, —OH, —NH$_2$, —NH(CH$_3$), —N(CH$_3$)$_2$, —CN, oxo, $C_{1-4}$ alkyl, $C_{2-6}$ alkenyl, $C_{2-6}$ alkynyl, $C_{3-7}$ cycloalkyl, $C_{1-4}$ hydroxyalkyl, —S—$C_{1-4}$ alkyl, —C(═O)H, —C(═O)—$C_{1-4}$ alkyl, —C(═O)—O—$C_{1-4}$ alkyl, —C(═O)—NH$_2$, —C(═O)—N($C_{1-4}$ alkyl)$_2$, $C_{1-4}$ haloalkyl, $C_{1-4}$ alkoxy and $C_{1-4}$ haloalkoxy.

2. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, which is an isotopically labeled compound of the compound of formula (G), wherein all Hs are each independently optionally substituted with D.

3. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_1$ is N.

4. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_2$ is N.

5. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_3$ is N.

6. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_1$ is C$R_{14}$, $X_2$ is N or C$R_{15}$, and $X_3$ is C$R_{16}$.

7. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_1$, $X_2$ and $X_3$ are the same.

8. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 2, wherein $X_1$, $X_2$ and $X_3$ are the same.

9. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 1, wherein $X_1$, $X_2$ and $X_3$ are CH.

10. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 8, wherein $X_1$, $X_2$ and $X_3$ are CH.

11. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein L is C═O, O═S═O or CH$_2$.

12. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein $R_{13}$ is H, —N($R_{17}$)($R_{18}$), $C_{1-6}$ alkoxy, —OH, —SH, —CN, halogen, —NO$_2$, —SF$_5$, —S—$C_{1-4}$ alkyl, $C_{1-6}$ alkyl, or $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, 11-15 membered tricyclyl, $C_{5-11}$ bicycloalkyl, or 5-11 membered bicyclic heteroalkyl, and $R_{13}$ is substituted with 0, 1, 2, 3 or 4 $R_1$(s), in which $R_{17}$ and $R_{18}$ are each independently selected from H, $C_{1-6}$ alkyl, $C_{1-6}$ alkoxy, $C_{3-7}$ cycloalkyl, $C_{3-7}$ heterocycloalkyl, $C_{5-7}$ aryl, and 5-7 membered heteroaryl, and are optionally substituted with one or more of —OH, —CN, —SH, halogen, —NO$_2$, -and SF$_5$.

13. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{13}$ is H, —N(R$_{17}$)(R$_{18}$), C$_{1-6}$ alkoxy, —OH, —SH, —CN, halogen, —NO$_2$, —SF$_5$, —S—C$_{1-4}$ alkyl, C$_{1-6}$ alkyl, C$_{3-7}$ cycloalkyl, 3-7 membered heterocycloalkyl, C$_{5-7}$ aryl, 5-7 membered heteroaryl, C$_{7-11}$ bicyclic aryl, 7-11 membered bicyclic heteroaryl, or 11-15 membered tricyclyl, and R$_{13}$ is substituted with 0, 1, 2, 3 or 4 R$_1$(s).

14. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{13}$ is H, —N(R$_{17}$)(R$_{18}$), C$_{1-6}$ alkoxy, C$_{1-6}$ alkyl, C$_{3-7}$ cycloalkyl, 3-7 membered heterocycloalkyl, C$_{5-7}$ aryl, or 5-7 membered heteroaryl, and R$_{13}$ is substituted with 0, 1, 2, 3, or 4 R$_1$(s).

15. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{13}$ is —N(R$_{17}$)(R$_{18}$), C$_{1-6}$ alkoxy, C$_{1-6}$ alkyl, C$_{3-7}$ cycloalkyl, 4-6 membered heterocycloalkyl, phenyl, or 5-6 membered heteroaryl, and R$_{13}$ is substituted with 0, 1, 2, or 3 R$_1$(s).

16. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{17}$ and R$_{18}$ are each independently selected from H, C$_{1-6}$ alkyl, C$_{3-7}$ cycloalkyl, and C$_{3-7}$ heterocycloalkyl, and are optionally substituted with one or more of —OH, —CN, —SH, halogen, —NO$_2$, -and SF$_5$.

17. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{17}$, R$_{18}$ and the N atom connected thereto together form a 4-10 membered ring.

18. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein L is C=O, and R$_{13}$ is —N(R$_{17}$)(R$_{18}$), C$_{1-6}$ alkoxy, —OH, —SH, —CN, halogen, —NO$_2$, —SF$_5$, or —S—C$_{1-4}$ alkyl, and R$_{13}$ is substituted with 0, 1, 2, 3 or 4 R$_1$(s) in which R$_{17}$ and R$_{18}$ are each independently selected from H, C$_{1-6}$ alkyl, C$_{1-6}$ alkoxy, C$_{3-7}$ cycloalkyl, C$_{3-7}$ heterocycloalkyl, C$_{5-7}$ aryl, and 5-7 membered heteroaryl, and are optionally substituted with one or more of —OH, —CN, —SH, halogen, —NO$_2$, -and SF$_5$, or R$_{17}$, R$_{18}$ and the N atom connected thereto together form a 4-10 membered ring.

19. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein 1, 2 or 3 R$_2$(s) are present and R$_2$ is selected from H, halogen, —OH, —NO$_2$, —CN, —SF$_5$, —SH, —S—C$_{1-4}$ alkyl, C$_{1-6}$ alkyl, C$_{1-6}$ alkoxy, C$_{1-6}$ haloalkoxy, C$_{2-6}$ alkenyl, C$_{2-6}$ alkynyl, C$_{3-7}$ cycloalkyl, and 4-10 membered heterocycloalkyl, in which the —S—C$_{1-4}$ alkyl, C$_{1-6}$ alkyl, C$_{3-7}$ cycloalkyl, and 4-10 membered heterocycloalkyl are each optionally substituted with 1, 2 or 3 substituent(s) each independently selected from the group consisting of halogen, —OH, —NH$_2$, —NH(CH$_3$), —N(CH$_3$)$_2$, —CN, C$_{1-4}$ alkyl, C$_{1-4}$ haloalkyl, C$_{1-4}$ alkoxy, and C$_{1-4}$ haloalkoxy.

20. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein 1, 2 or 3 R$_2$(s) are present, and R$_2$ is selected from halogen, C$_{1-6}$ alkyl, and C$_{3-6}$ cycloalkyl in which the C$_{1-6}$ alkyl and C$_{3-6}$ cycloalkyl are each optionally substituted with 1, 2 or 3 substituent(s) each independently selected from the group consisting of halogen, —OH, —NH$_2$, —NH(CH$_3$), —N(CH$_3$)$_2$, —CN, C$_{1-4}$ alkyl, C$_{1-4}$ haloalkyl, C$_{1-4}$ alkoxy, and C$_{1-4}$ haloalkoxy.

21. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 15, wherein 1 or 2 R$_2$(s) are present, and R$_2$ is selected from halogen, and C$_{1-6}$ alkyl.

22. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein R$_{13}$ is substituted with 0 or 1 R$_1$, and R$_1$ is selected from halogen, —OH, C$_{1-6}$ alkyl, 5-7 membered heterocycloalkyl, and C$_{3-7}$ cycloalkyl, in which the C$_{1-6}$ alkyl is optionally substituted with 1, 2, or 3 R$_3$(s) and in which the 5-7 membered heterocycloalkyl, and C$_{3-7}$ cycloalkyl is optionally substituted with 1, 2, 3 or 4 C$_{1-3}$ alkyl.

23. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 10, wherein the compound is selected from a group consisting of:

(2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(5-morpholinylpyrazin-2-yl)ketone;

(2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone;

(2-(6-(2-ethyl-5-fluoro-4-hydroxyphenyl)-1H-indazol-3-yl)pyrrolo[3,4-d]imidazol-5(1H, 4H,6H)-yl)(1-methylpiperidin-4-yl)ketone;

(2-(6-(2-ethyl-5-fluoro-4-hydroxyphenyl)-1H-indazol-3-yl)pyrrolo[3,4-d]imidazol-5(1H, 4H,6H)-yl)(5-(4-methylpiperzin-1-yl)pyrazin-2-yl)ketone;

(2-(6-(2-ethyl-4-hydroxyphenyl)-1H-indazol-3-yl)pyrrolo[3,4-d]imidazol-5(1H,4H,6H)-yl)(5-(4-methylpiperzin-1-yl)pyrazin-2-yl)ketone;
5-ethyl-2-fluoro-4-(3-(5-(benzenesulfonyl)-1,4,5,6-tetrahydropyrrolo[3,4-d]imidazol-2-yl)-1H-indazol-6-yl)phenol;
5-ethyl-2-fluoro-4-(3-(5-(pyrazin-2ylmethyl)-1,4,5,6-tetrahydropyrrolo[3,4-d]imidazol-2-yl)-1H-indazol-6-yl)phenol;
4-(3-(5-(cyclopropylmethyl)-1,4,5,6-tetrahydropyrrolo[3,4-d]imidazol-2-yl)-1H-indazol-6-yl)-5-ethyl-2-fluorophenol;
Cyclopropyl(2-(6-(2-ethyl-5-fluoro-4-hydroxyphenyl)-1H-indazol-3-yl)pyrrolo[3,4-d]imidazol-5(1H,4H,6H)-yl)ketone;
4-(3-(5-(cyclobutylmethyl)-1,4,5,6-tetrahydropyrrolo[3,4-d]imidazol-2-yl)-1H-indazol-6-yl)-5-ethyl-2-fluorophenol;
Cyclobutyl(2-(6-(2-ethyl-5-fluoro-4-hydroxyphenyl)-1H-indazol-3-yl)pyrrolo[3,4-d]imidazol-5(1H,4H,6H)-yl)ketone;
(2-(6-(2-ethyl-5-fluoro-4-hydroxyphenyl)-1H-indazol-3-yl)pyrrolo[3,4-d]imidazol-5(1H,4H,6H)-yl)(3-hydroxylcyclobutyl)ketone;
(2-(6-(2-ethyl-5-fluoro-4-hydroxyphenyl)-1H-indazol-3-yl)-pyrrolo[3,4-d]imidazol-5-(1H,4H,6H)-yl)(pyridazin-4-yl)ketone;
(2-(6-(2-ethyl-5-fluoro-4-hydroxyphenyl)-1H-indazol-3-yl)-pyrrolo[3,4-d]imidazol-5-(1H,4H,6H)-yl)(pyridazin-3-yl)ketone;
(S)-(2-(6-(2-ethyl-5-fluoro-4-hydroxyphenyl)-1H-indazol-3-yl)-4,6-dihydropyrrolo[3,4-d]imidazol-5-(1H)-yl)(3-hydroxylpyrrolidin-1-yl)ketone;
5-ethyl-2-fluoro-4-(3-(5-(4-hydroxylcyclohexyl)-1,4,5,6-tetrahydropyrrolo[3,4-d]imidazol-2-yl)-1H-indazol-6-yl)phenol;
4-(3-(5-(cyclopropanesulfonyl)-1,4,5,6-tetrahydropyrrolo[3,4-d]imidazol-2-yl)-1H-indazol-6-yl)-5-ethyl-2-fluorophenol;
4-(3-(5-(cyclobutylsulfonyl)-1,4,5,6-tetrahydropyrrolo[3,4-d]imidazol-2-yl)-1H-indazol-6-yl)-5-ethyl-2-fluorophenol;
4-(3-(5-(cyclopentylsulfonyl)-1,4,5,6-tetrahydropyrrolo[3,4-d]imidazol-2-yl)-1H-indazol-6-yl)-5-ethyl-2-fluorophenol;
5-ethyl-2-fluoro-4-(3-(5-((1-methyl-1H-pyrazol-4-yl)methyl)-1,4,5,6-tetrahydropyrrolo[3,4-d]imidazol-2-yl)-1H-indazol-6-yl)phenol;
4-(3-(5-(cyclopentyl-1,4,5,6-tetrahydropyrrolo[3,4-d]imidazol-2-yl)-1H-indazol-6-yl)-5-ethyl-2-fluorophenol;
5-ethyl-2-fluoro-4-(3-(5-(tetrahydro-2H-pyran-4-yl)-1,4,5,6-tetrahydropyrrolo[3,4-d]imidazol-2-yl)-1H-indazol-6-yl)phenol;
1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one;
1-(2-(6-(2-ethyl-5-fluoro-4-hydroxyphenyl)-1H-indazol-3-yl)-4,6-dihydropyrrolo[3,4-d]imidazol-5-(1H)-yl)propan-1-one;
1-(2-(6-(2-ethyl-5-fluoro-4-hydroxyphenyl)-1H-indazol-3-yl)-4,6-dihydropyrrolo[3,4-d]imidazol-5-(1H)-yl)-2-methylpropan-1-one;
2-cyclopropyl-1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one;
1-(2-(6-(2-ethyl-5-fluoro-4-hydroxyphenyl)-1H-indazol-3-yl)-4,6-dihydropyrrolo[3,4-d]imidazol-5-(1H)-yl)-3-methylbutan-1-one;
(2-(6-(2-ethyl-5-fluoro-4-hydroxyphenyl)-1H-indazol-3-yl)-4,6-dihydropyrrolo[3,4-d]imidazol-5-(1H)-yl)(pyrrolidin-1-yl)ketone;
Azetidin-1-yl((2-(6-(2-ethyl-5-fluoro-4-hydroxyphenyl)-1H-indazol-3-yl)-4,6-dihydropyrrolo[3,4-d]imidazol-5-(1H)-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(piperidin-1-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(morpholino)ketone;
(2-(6-(2-ethyl-5-fluoro-4-hydroxyphenyl)-1H-indazol-3-yl)-4,6-dihydropyrrolo[3,4-d]imidazol-5-(1H)-yl)(4-methylpiperzin-1-yl)ketone;
(2-(6-(2-ethyl-5-fluoro-4-hydroxyphenyl)-1H-indazol-3-yl)-4,6-dihydropyrrolo[3,4-d]imidazol-5-(1H)-yl)(4-ethylpiperzin-1-yl)ketone;
Cyclopropyl(2-(6-(2-ethyl-5-fluoro-4-hydroxyphenyl)-1H-pyrazolo[4,3-b]pyridin-3-yl)-4,6-dihydropyrrolo[3,4-d]imidazol-5(1H)-yl)ketone;
Cyclopropyl(2-(6-(2-ethyl-5-fluoro-4-hydroxyphenyl)-4-methyl-1H-indazol-3-yl)-4,6-dihydropyrrolo[3,4-d]imidazol-5(1H)-yl)ketone;
(S)-(2-(6-(2-ethyl-5-fluoro-4-hydroxyphenyl)-4-methyl-1H-indazol-3-yl)-4,6-dihydropyrrolo[3,4-d]imidazol-5(1H)-yl)(3-hydroxylpyrrolidin-1-yl)ketone;
Cyclopropyl(2-(6-(2-ethyl-5-fluoro-4-hydroxyphenyl)-1H-pyrazolo[4,3-c]pyridin-3-yl)-4,6-dihydropyrrolo[3,4-d]imidazol-5(1H)-yl)ketone;
(R)-(2-(6-(2-ethyl-5-fluoro-4-hydroxyphenyl)-1H-indazol-3-yl)-4,6-dihydropyrrolo[3,4-d]imidazol-5(1H)-yl)(3-hydroxylpyrrolidin-1-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(3-hydroxylAzetidin-1-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(4-hydroxylpiperidin-1-yl)ketone;
2-(6-(2-ethyl-5-fluoro-4-hydroxyphenyl)-1H-indazol-3-yl)-N-methyl-4,6-dihydropyrrolo[3,4-d]imidazol-5-(1H)-carboxamide;
2-(6-(2-ethyl-5-fluoro-4-hydroxyphenyl)-1H-indazol-3-yl)-N-ethyl-4,6-dihydropyrrolo[3,4-d]imidazol-5-(1H)-carboxamide;
2-(6-(2-ethyl-5-fluoro-4-hydroxyphenyl)-1H-indazol-3-yl)-N-(2-hydroxylethyl)-4,6-dihydropyrrolo[3,4-d]imidazol-5(1H)-carboxamide;
1-(2-(6-(2-ethyl-5-fluoro-4-hydroxyphenyl)-1H-indazol-3-yl)-1,4,5,6-tetrahydropyrrolo[3,4-d]imidazol-5-carbonyl)azetidine-3-nitrile;
1-(2-(6-(2-ethyl-5-fluoro-4-hydroxyphenyl)-1H-indazol-3-yl)-1,4,5,6-tetrahydropyrrolo[3,4-d]imidazol-5-carbonyl)pyrrolidin-3-nitrile;
2-(6-(2-ethyl-5-fluoro-4-hydroxyphenyl)-1H-indazol-3-yl)-N-(tetrahydrofuran-3-yl)-4,6-dihydropyrrolo[3,4-d]imidazol-5(1H)-carboxamide;
Methyl 2-(6-(2-ethyl-5-fluoro-4-hydroxyphenyl)-1H-indazol-3-yl)-4,6-dihydropyrrolo[3,4-d]imidazol-5(1H)-carboxylate;
Ethyl 2-(6-(2-ethyl-5-fluoro-4-hydroxyphenyl)-1H-indazol-3-yl)-4,6-dihydropyrrolo[3,4-d]imidazol-5(1H)-carboxylate;
(S)-(2-(6-(2-ethyl-5-fluoro-4-hydroxyphenyl)-1H-pyrazolo[3,4-b]pyridin-3-yl)-4,6-dihydropyrrolo[3,4-d]imidazol-5(1H)-yl)(3-hydroxylpyrrolidin-1-yl)ketone;
3-(2-(6-(2-ethyl-5-fluoro-4-hydroxyphenyl)-1H-indazol-3-yl)-4,6-dihydropyrrolo[3,4-d]imidazol-5(1H)-yl)-3-oxypropionitrile;
2-(6-(2-ethyl-5-fluoro-4-hydroxyphenyl)-1H-indazol-3-yl)-N,N-dimethyl-4,6-dihydropyrrolo[3,4-d]imidazol-5(1H)-carboxamide;

N-(2-cyanoethyl)-2-(6-(2-ethyl-5-fluoro-4-hydroxyphenyl)-1H-indazol-3-yl)-4,6-dihydropyrrolo[3,4-d]imidazol-5(1H)-carboxamide;

N-cyclopropyl-2-(6-(2-ethyl-5-fluoro-4-hydroxyphenyl)-1H-indazol-3-yl)-4,6-dihydropyrrolo[3,4-d]imidazol-5(1H)-carboxamide;

N-cyclobutyl-2-(6-(2-ethyl-5-fluoro-4-hydroxyphenyl)-1H-indazol-3-yl)-4,6-dihydropyrrolo[3,4-d]imidazol-5(1H)-carboxamide;

(2-(6-(2-ethyl-5-fluoro-4-hydroxyphenyl)-1H-indazol-3-yl)-4,6-dihydropyrrolo[3,4-d]imidazol-5(1H)-yl)(2,6-diazaspiro[3.3]heptan-2-yl)ketone;

(S)-6-(2-ethyl-5-fluoro-4-hydroxyphenyl)-3-(5-prolyl-1,4,5,6-tetrahydropyrrolo[3,4-d]imidazol-2-yl)-1H-indazol; and (R)-6-(2-ethyl-5-fluoro-4-hydroxyphenyl)-3-(5-prolyl-1,4,5,6-tetrahydropyrrolo[3,4-d]imidazol-2-yl)-1H-indazol.

24. A pharmaceutical composition, comprising the compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 1 to 23, and one or more pharmaceutically acceptable carriers, adjuvants or excipients.

25. Use of the compound, or isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof according to any one of embodiments 1 to 23 or the pharmaceutical composition of embodiment 24 in the manufacture of a medicament for the treatment and/or prevention of a JAK-related disease or disorder.

26. The use according to embodiment 25, wherein the JAK-related disease or disorder is selected from the group consisting of arthritis, autoimmune diseases or disorders, cancer or tumor, diabetes, eye diseases, disorders or conditions, intestinal inflammation, allergies or conditions, neurodegenerative diseases, skin diseases, conditions or disorders, allergies, asthma and other obstructive airway diseases, and transplant rejection.

27. A compound of Formula (I),

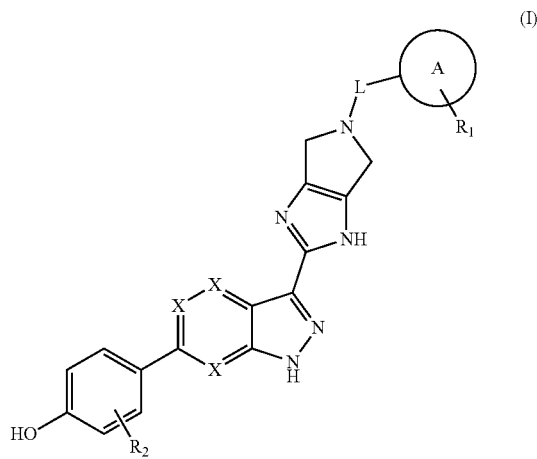

(I)

or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof, in which L is C=O, O=S=O, $CH_2$ or a bond; and X is CH or N;

The ring A is $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl, or 11-15 membered tricyclyl;

0, 1, 2, 3 or 4 $R_1$(s) are present in formula (I), and $R_1$ is selected from H, halogen, $C_{1-8}$ alkyl, $C_{2-8}$ alkenyl, $C_{2-8}$ alkynyl, $C_{1-8}$ alkoxy, $C_{3-7}$ cycloalkyl, 3-7 membered heterocycloalkyl, $C_{5-7}$ aryl, 5-7 membered heteroaryl, $C_{7-11}$ bicyclic aryl, and 7-11 membered bicyclic heteroaryl, in which the $C_{1-8}$ alkyl, $C_{2-8}$ alkenyl, $C_{2-8}$ alkynyl, and $C_{1-8}$ alkoxy are optionally substituted with 1, 2, 3 or 4 $R_3$(s), and in which the $C_{3-7}$ cycloalkyl, 3-7 membered heterocycloalkyl, $C_{5-7}$ aryl, 5-7 membered heteroaryl, $C_{7-11}$ bicyclic aryl, 7-11 membered bicyclic heteroaryl are optionally substituted with 1, 2, 3 or 4 $R_4$(s), 0, 1, 2, 3 or 4 $R_2$(s) are present in formula (I), and $R_2$ is selected from H, halogen, —OH, —$NO_2$, —CN, —$SF_5$, $C_{1-6}$alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, —N($R_9$)($R_{10}$), —N($R_{11}$)(C(=O)$R_{12}$), —C(=O)—N($R_9$)($R_{10}$), —C(=O)—$R_{12}$, —C(=O)—O$R_{12}$, —OC(=O)$R_{12}$, —N($R_{11}$)(S(=O)$_2R_{12}$), —S(=O)$_2$—N($R_9$)($R_{10}$), —S$R_{12}$ and —O$R_{12}$, in which the $C_{1-6}$ alkyl, $C_{3-7}$ cycloalkyl and 4-10 membered heterocycloalkyl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N($R_9$)($R_{10}$), —N($R_{11}$)(C(=O)$R_{12}$), —C(=O)—O$R_{12}$, —C(=O)H, —C(=O)$R_{12}$, —C(=O)—N($R_9$)($R_{10}$), —N($R_{11}$)(S(=O)$_2R_{12}$), —S(=O)$_2$—N($R_9$)($R_{10}$), —S$R_{12}$ and —O$R_{12}$;

$R_3$ is selected from halogen, cyano, $C_{1-3}$ alkyl, hydroxy, $C_{1-6}$ alkoxy, —N($R_5$)($R_6$), —CON($R_7$)($R_8$) or 3-7 membered heterocycloalkyl, in which the 3-7 membered heterocycloalkyl is optionally substituted with 1, 2, 3 or 4 $R_4$(s);

$R_4$ is selected from halogen, $C_{1-3}$ alkyl, hydroxyl, $C_{1-6}$ alkoxy, —$NH_2$, —$NHCH_3$ or —$N(CH_3)_2$;

$R_5$, $R_6$, $R_7$, $R_8$ are each independently hydrogen or $C_{1-4}$ alkyl;

$R_9$ is selected from H, $C_{1-4}$ alkyl, $C_{1-4}$ haloalkyl or $C_{3-7}$ cycloalkyl;

$R_{10}$ is H or selected from the group consisting of $C_{1-4}$ alkyl, $C_{1-4}$ haloalkyl, $C_{3-7}$ cycloalkyl, 4-10 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2, 3 or 4 substituent(s) each independently selected from the group consisting of —OH, —$NH_2$, —$NH(CH_3)$, —$N(CH_3)_2$, —CN, $C_{1-4}$ alkyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—N($C_{1-4}$ alkyl)$_2$, $C_{1-4}$ haloalkyl, $C_{1-4}$ alkoxy and $C_{1-4}$ haloalkoxy;

$R_{11}$ is selected from H, $C_{1-4}$ alkyl and $C_{3-7}$ cycloalkyl; and $R_{12}$ is selected from the group consisting of $C_{1-6}$ alkyl, $C_{3-7}$ cycloalkyl, 4- to 14-membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2 or 3 substituent(s) each independently selected from the group consisting of halogen, —$CF_3$, —CN, —OH, —$NH_2$, —$NH(CH_3)$, —$N(CH_3)_2$, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy and $C_{1-4}$ haloalkoxy.

28. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 27, wherein L is C=O, O=S=O or $CH_2$.

29. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 27, wherein X is CH.

30. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein the ring A is $C_{3-7}$ cycloalkyl, 3-7 membered heterocycloalkyl, $C_{5-7}$ aryl, or 5-7 membered heteroaryl.

31. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein the ring A is 5-6 membered heteroaryl, or phenyl.

32. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein 0, or 1 $R_1$ is present, and $R_1$ is selected from $C_{1-6}$ alkyl, and 5-7 membered heterocycloalkyl in which the $C_{1-6}$ alkyl is optionally substituted with 1 or 2 $R_3$, and in which the 5-7 membered heterocycloalkyl is optionally substituted with 1, 2, 3 or 4 $C_{1-3}$ alkyl.

33. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein 1 or 2 $R_2$(s) are present, and $R_2$ is selected from halogen, $C_{1-6}$ alkyl and $C_{3-6}$ cycloalkyl, in which the $C_{1-6}$ alkyl and $C_{3-6}$ cycloalkyl are each optionally substituted with 1, 2 or 3 substituent(s) each independently selected from the group consisting of halogen, —OH, —$NH_2$, —$NH(CH_3)$, —$N(CH_3)_2$, —CN, $C_{1-4}$ alkyl, $C_{1-4}$ haloalkyl, $C_{1-4}$ alkoxy, and $C_{1-4}$ haloalkoxy.

34. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein
L is C=O, and O=S=O;
X is CH;
The ring A is 5-7 membered heteroaryl or $C_{5-7}$ aryl;
0, 1, 2, 3 or 4 $R_1$(s) are present in formula (I), and $R_1$ is selected from $C_{1-8}$ alkyl, and 3-7 membered heterocycloalkyl, in which the $C_{1-8}$ alkyl is optionally substituted with 1, 2, 3 or 4 $R_3$(s), and in which the 3-7 membered heterocycloalkyl is optionally substituted with 1, 2, 3 or 4 $R_4$(s),
1, 2, or 3 $R_2$(s) are present in formula (I), and $R_2$ is selected from H, halogen, —OH, —$NO_2$, —CN, —$SF_5$, $C_{1-6}$ alkyl, $C_{1-6}$ alkoxy, $C_{1-6}$ haloalkoxy, $C_{2-6}$ alkenyl, $C_{2-6}$ alkynyl, $C_{3-7}$ cycloalkyl, 4-10 membered heterocycloalkyl, —$N(R_9)(R_{10})$, —$N(R_{11})(C(=O)R_{12})$, —C(=O)—$N(R_9)(R_{10})$, —C(=O)—$R_{12}$, —C(=O)—$OR_{12}$, —OC(=O)$R_{12}$, —$N(R_{11})(S(=O)_2R_{12})$, —$S(=O)_2$—$N(R_9)(R_{10})$, —$SR_{12}$ and —$OR_{12}$, in which the $C_{1-6}$ alkyl, $C_{3-7}$ cycloalkyl and 4-10 membered heterocycloalkyl are each optionally substituted with 1, 2 or 3 substituent(s) each independently selected from the group consisting of halogen, —CN, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —$N(R_9)(R_{10})$, —$N(R_{11})(C(=O)R_{12})$, —C(=O)—$OR_{12}$, —C(=O)H, —C(=O)$R_{12}$, —C(=O)—$N(R_9)(R_{10})$, —$N(R_{11})(S(=O)_2R_{12})$, —$S(=O)_2$—$N(R_9)(R_{10})$, —$SR_{12}$ and —$OR_{12}$;
$R_3$ is selected from halogen, cyano, $C_{1-3}$ alkyl, hydroxy, $C_{1-6}$ alkoxy, —$N(R_5)(R_6)$, —$CON(R_7)(R_8)$ or 3-7 membered heterocycloalkyl, in which the 3-7 membered heterocycloalkyl is optionally substituted with 1, 2, 3 or 4 $R_4$(s);
$R_4$ is selected from halogen, $C_{1-3}$ alkyl, hydroxyl, $C_{1-6}$ alkoxy, —$NH_2$, —$NHCH_3$ or —$N(CH_3)_2$;
$R_5$, $R_6$, $R_7$, $R_8$ are each independently hydrogen or $C_{1-4}$ alkyl;
$R_9$ is selected from H, $C_{1-4}$ alkyl, $C_{1-4}$ haloalkyl or $C_{3-7}$ cycloalkyl;
$R_{10}$ is H or selected from the group consisting of $C_1$-4 alkyl, $C_{1-4}$ haloalkyl, $C_{3-7}$ cycloalkyl, 4-10 membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2, 3 or 4 substituent(s) each independently selected from the group consisting of —OH, —$NH_2$, —$NH(CH_3)$, —$N(CH_3)_2$, —CN, $C_{1-4}$ alkyl, $C_{3-7}$ cycloalkyl, $C_{1-4}$ hydroxyalkyl, —S—$C_{1-4}$ alkyl, —C(=O)H, —C(=O)—$C_{1-4}$ alkyl, —C(=O)—O—$C_{1-4}$ alkyl, —C(=O)—$NH_2$, —C(=O)—$N(C_{1-4}$ alkyl$)_2$, $C_{1-4}$ haloalkyl, $C_{1-4}$ alkoxy and $C_{1-4}$ haloalkoxy;
$R_{11}$ is selected from H, $C_{1-4}$ alkyl and $C_{3-7}$ cycloalkyl; and
$R_{12}$ is selected from the group consisting of $C_{1-6}$ alkyl, $C_{3-7}$ cycloalkyl, 4- to 14-membered heterocycloalkyl, $C_{6-10}$ aryl, 5-10 membered heteroaryl, ($C_{3-7}$ cycloalkyl)-$C_{1-4}$ alkyl-, (4-10 membered heterocycloalkyl)-$C_{1-4}$ alkyl-, ($C_{6-10}$ aryl)-$C_{1-4}$ alkyl- and (5-10 membered heteroaryl)-$C_{1-4}$ alkyl-, wherein each substituent included in the above group is optionally substituted with 1, 2 or 3 substituent(s) each independently selected from the group consisting of halogen, —$CF_3$, —CN, —OH, —$NH_2$, —$NH(CH_3)$, —$N(CH_3)_2$, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy and $C_{1-4}$ haloalkoxy.

35. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 34, wherein the ring A is 5-6 membered heteroaryl, or phenyl.

36. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 34, wherein 0 or 1 $R_1$ is present, and $R_1$ is selected from $C_{1-6}$ alkyl, and 5-7 membered heterocycloalkyl, wherein the $C_{1-6}$ alkyl is optionally substituted by 1 or 2 $R_3$, and wherein the 5-7 membered heterocycloalkyl group is optionally substituted with 1, 2, 3, or 4 $C_{1-3}$ alkyl.

37. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to embodiment 34, wherein 1 or 2 $R_2$(s) are present, and $R_2$ is selected from halogen, $C_{1-6}$ alkyl and $C_{3-6}$ cycloalkyl, wherein the $C_{1-6}$ alkyl and $C_{3-6}$ cycloalkyl are each optionally substituted with 1, 2 or 3 substituent(s) each independently selected from the group consisting of halogen, —OH, —$NH_2$, —NH($CH_3$), —N($CH_3$)$_2$, —CN, $C_{1-4}$ alkyl, $C_{1-4}$ haloalkyl, $C_{1-4}$ alkoxy and $C_{1-4}$ haloalkoxy.

38. The compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27 to 29, wherein the compound is selected from a group consisting of:
(2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(5-morpholinpyrazin-2-yl)ketone;
(2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone;
5-ethyl-2-fluoro-4-{3-[5-(1-methylpiperidin-4-carbonyl)-1H,4H,5H,6H-pyrrolo[3,4-d]imidazol-2-yl]-1H-indazol-6-yl}phenol;
5-ethyl-2-fluoro-4-{3-[5-(4-methylpiperazin-1-carbonyl)-1H,4H,5H,6H-pyrrolo[3,4-d]imidazol-2-yl]-1H-indazol-6-yl}phenol;
3-ethyl-4-{3-[5-(4-methylpiperazin-1-carbonyl)-1H,4H,5H,6H-pyrrolo[3,4-d]imidazol-2-yl]-1H-indazol-6-yl}phenol;
5-ethyl-2-fluoro-4-(3-(5-(bemzenesulfonyl)-1,4,5,6-tetrahydropyrrolo[3,4-d]imidazol-2-yl)-1H-indazol-6-yl)phenol; and
5-ethyl-2-fluoro-4-(3-(5-(pyrazin-2-methyl)-1,4,5,6-tetrahydropyrrolo[3,4-d]imidazol-2-yl)-1H-indazol-6-yl)phenol.

39. A pharmaceutical composition, comprising the compound, or an isotopically labeled compound thereof, or an optical isomer thereof, a geometric isomer thereof, a tautomer thereof or a mixture of various isomers, or a pharmaceutically acceptable salt thereof, or a prodrug thereof, or a metabolite thereof according to any one of embodiments 27-38, and one or more pharmaceutically acceptable carriers, adjuvants or excipients.

40. Use of the compound, or isotopically labeled compound thereof, or optical isomer thereof, geometric isomer thereof, a tautomer thereof or a mixture of various isomers, or a pharmaceutically acceptable salt thereof, or a prodrug thereof, or a metabolite thereof according to any one of embodiments 27-38 or the pharmaceutical composition of embodiment 39 in the manufacture of a medicament for the treatment and/or prevention of a JAK-related disease or disorder.

41. The use according to embodiment 40, wherein the JAK-related disease or disorder is selected from the group consisting of arthritis, autoimmune diseases or disorders, cancer or tumor, diabetes, eye diseases, disorders or conditions, intestinal inflammation, allergies or conditions, neurodegenerative diseases, skin diseases, conditions or disorders, allergies, asthma and other obstructive airway diseases, and transplant rejection.

The present invention will be further illustrated and described below in conjunction with the drawings and specific examples.

DESCRIPTION OF THE DRAWINGS

FIGS. 5A to 5D show IC50 curve of JAK1 experiments for MDI-201, MDI-202, and MDI-206, in which Filgotinib was used as a positive control.
FIGS. 7A to 7D show IC50 curve of JAK3 experiments for MDI-201, MDI-202, and MDI-206, in which Filgotinib was used as a positive control.

EXAMPLES

Figure 1:
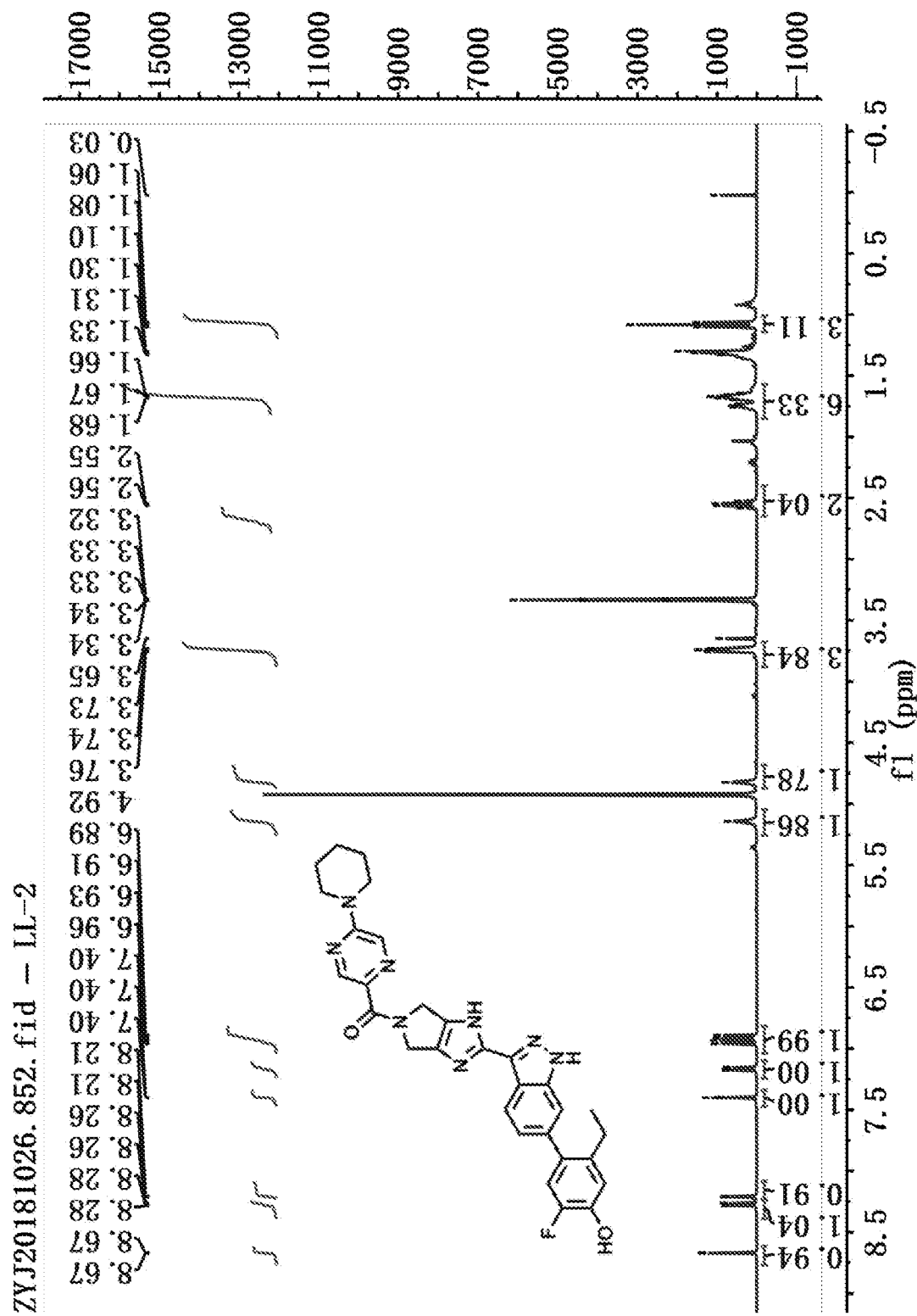
FIG. 1 shows the NMR spectrum of compound MDI-2.
Figure 2:
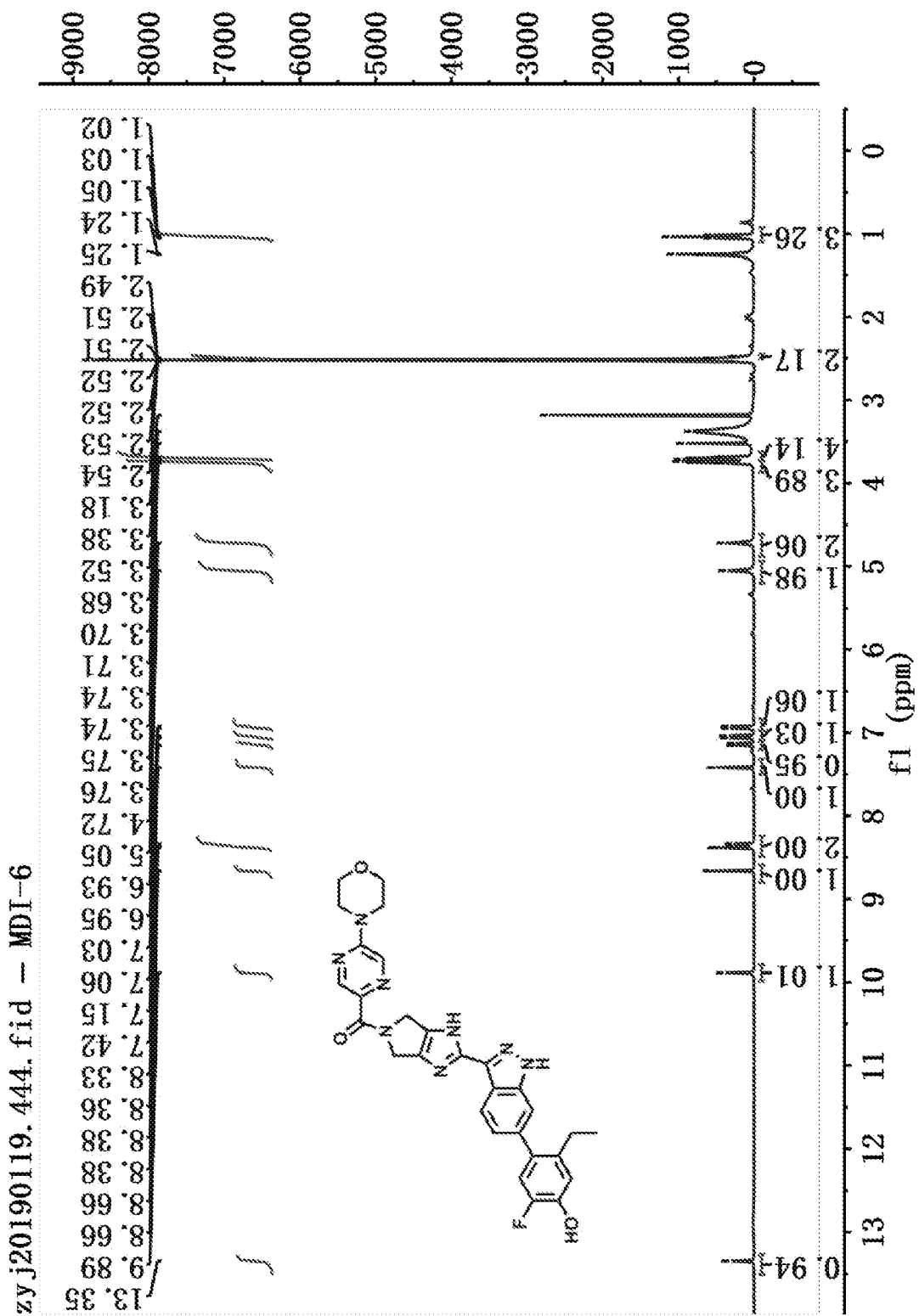
FIG. 2 shows the NMR spectrum of compound MDI-201.
Figure 3:
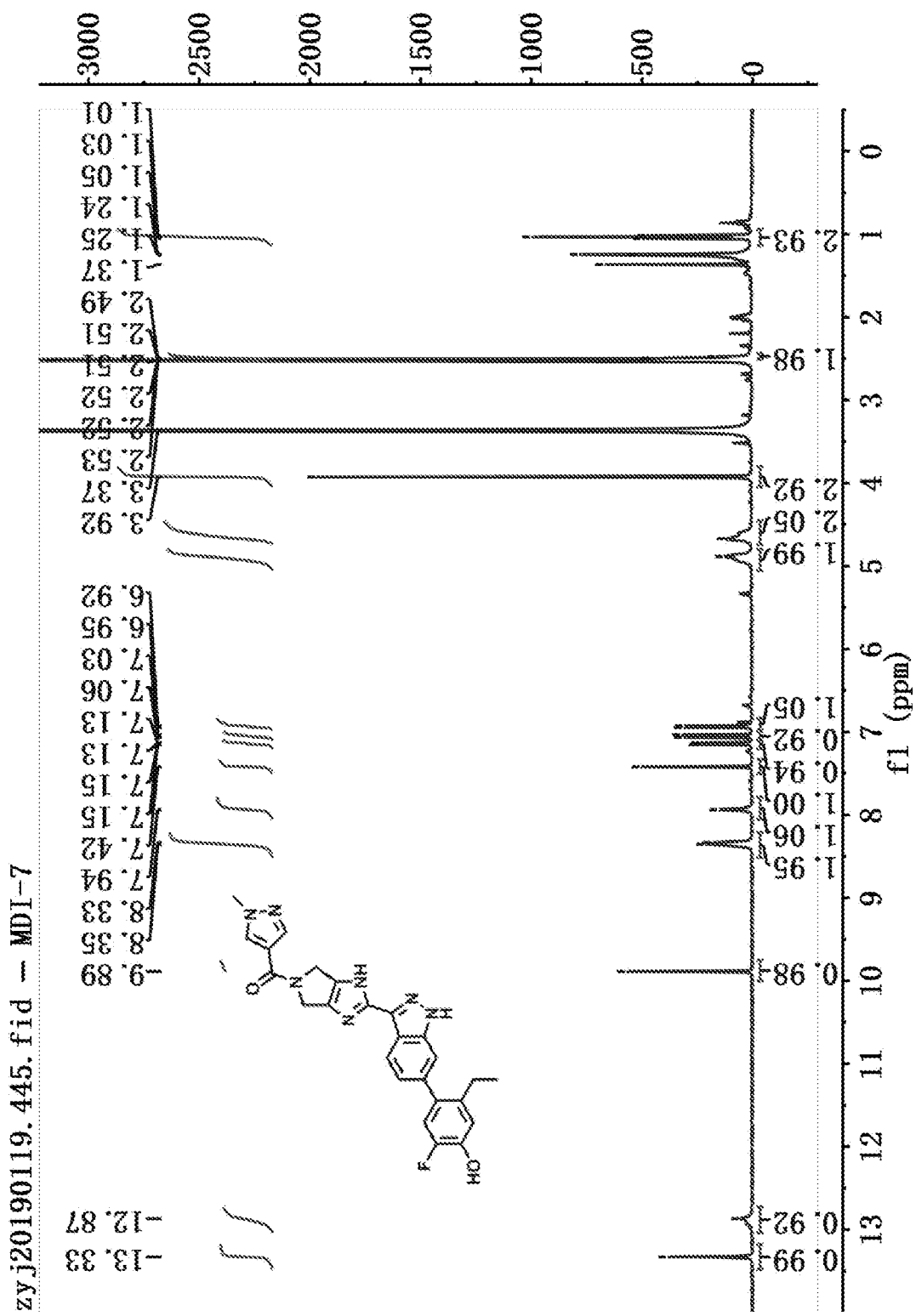
FIG. 3 shows the NMR spectrum of compound MDI-202.
Figure 4:
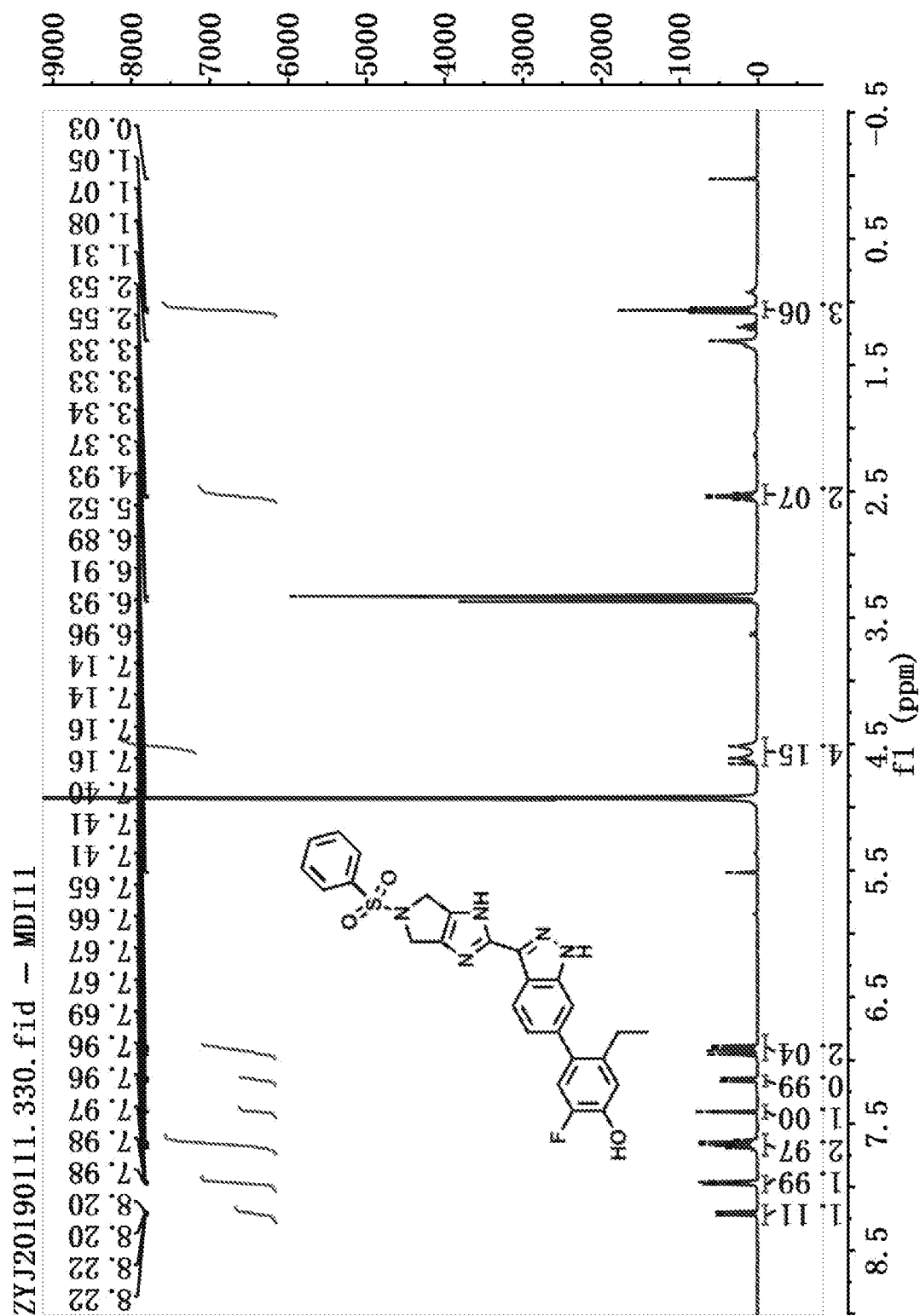
FIG. 4 shows the NMR spectrum of compound MDI-206.
Figure 6A:
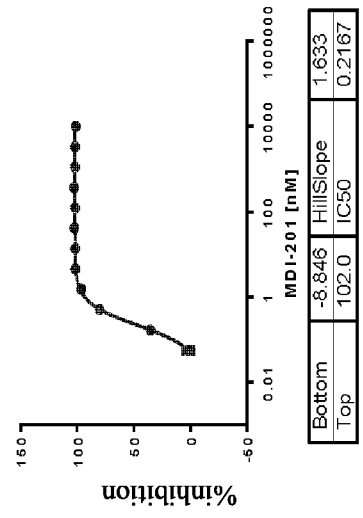
FIGS. 6A to 6D show IC50 curve of JAK2 experiments for MDI-201, MDI-202, and MDI-206, in which Filgotinib was used as a positive control.
Figure 6B:
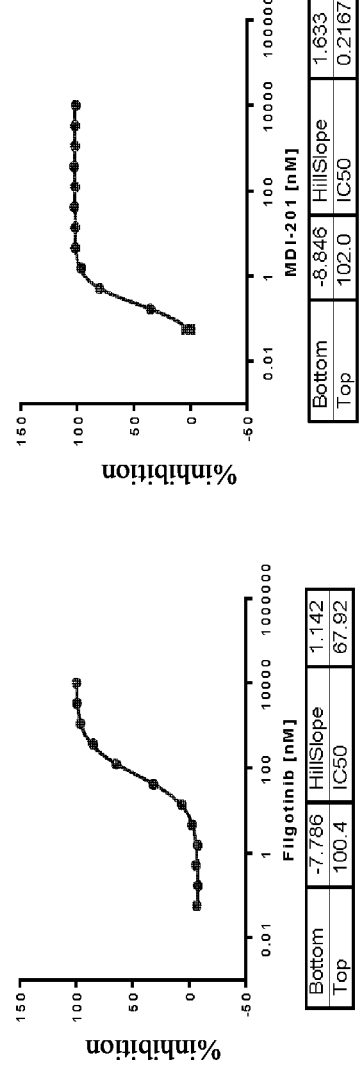
Figure 6C:
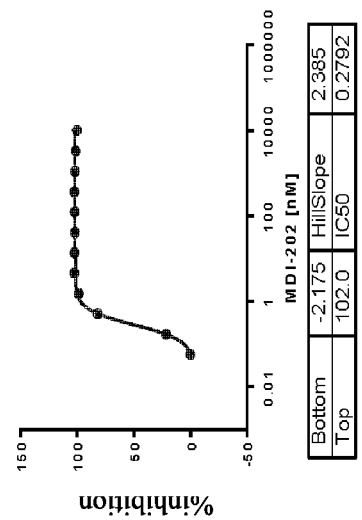
Figure 6D:
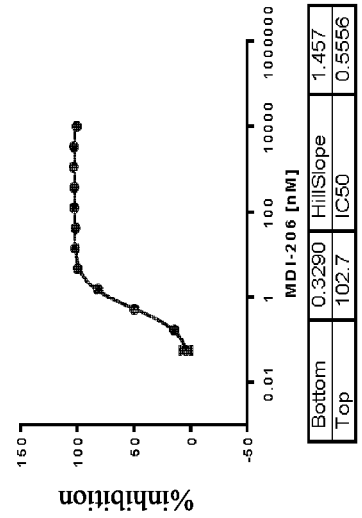
Figure 8A:
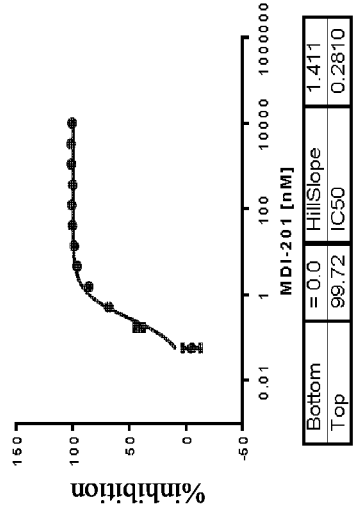
FIGS. 8A to 8D show IC50 curve of TYK2 experiments for MDI-201, MDI-202, and MDI-206, in which Filgotinib was used as a positive control.
Figure 8B:
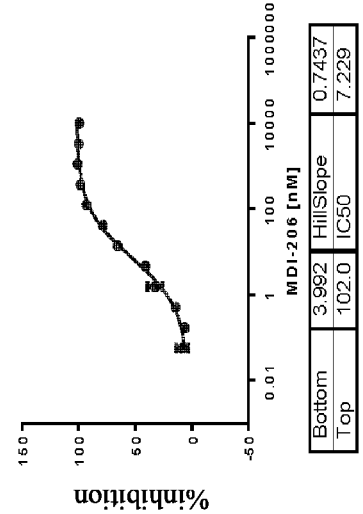
Figure 8C:
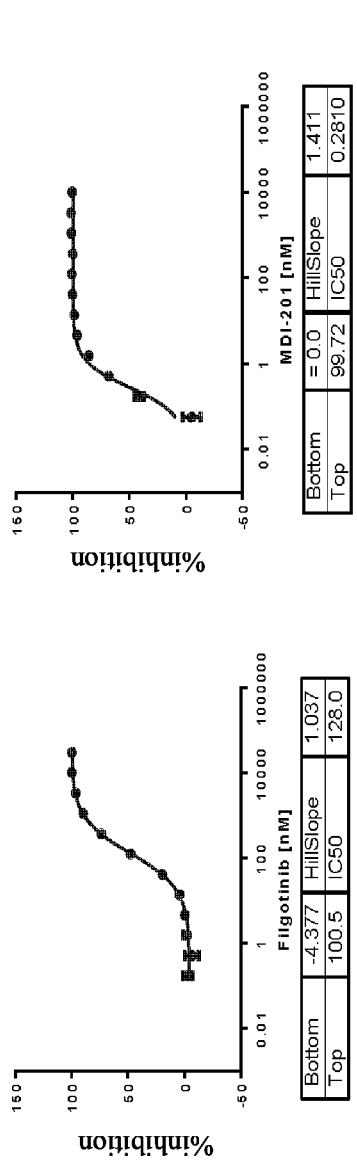
Figure 8D:
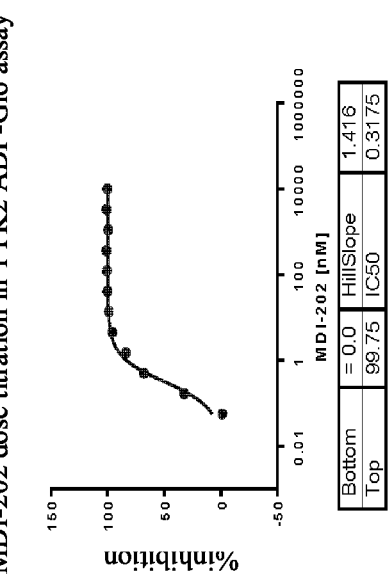

The compounds of formula (G), the compounds of formula (G') or the compounds of formula (I) of the present disclosure can be synthesized by various methods familiar to those skilled in the art of organic synthesis. The following specific examples give some exemplary synthesis methods of the compounds of formula (G), the compounds of formula (G') or the compounds of formula (I), and these methods are well-known in the field of synthetic chemistry. Obviously, referring to the exemplary embodiments of the present application, those skilled in the art can appropriately adjust reactants, reaction conditions, and protective groups to easily design other synthetic routes for compounds of formula (G), formula (G') or formula (I).

The following further describes the present disclosure in conjunction with examples. Nevertheless, these examples do not limit the scope of the present disclosure.

Example 1:(2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone (MDI-2)

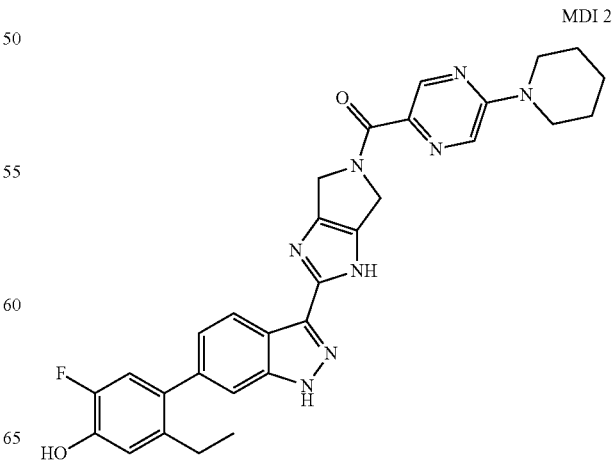

Synthetic Route of Target Compound 8 (i.e. MDI-2):
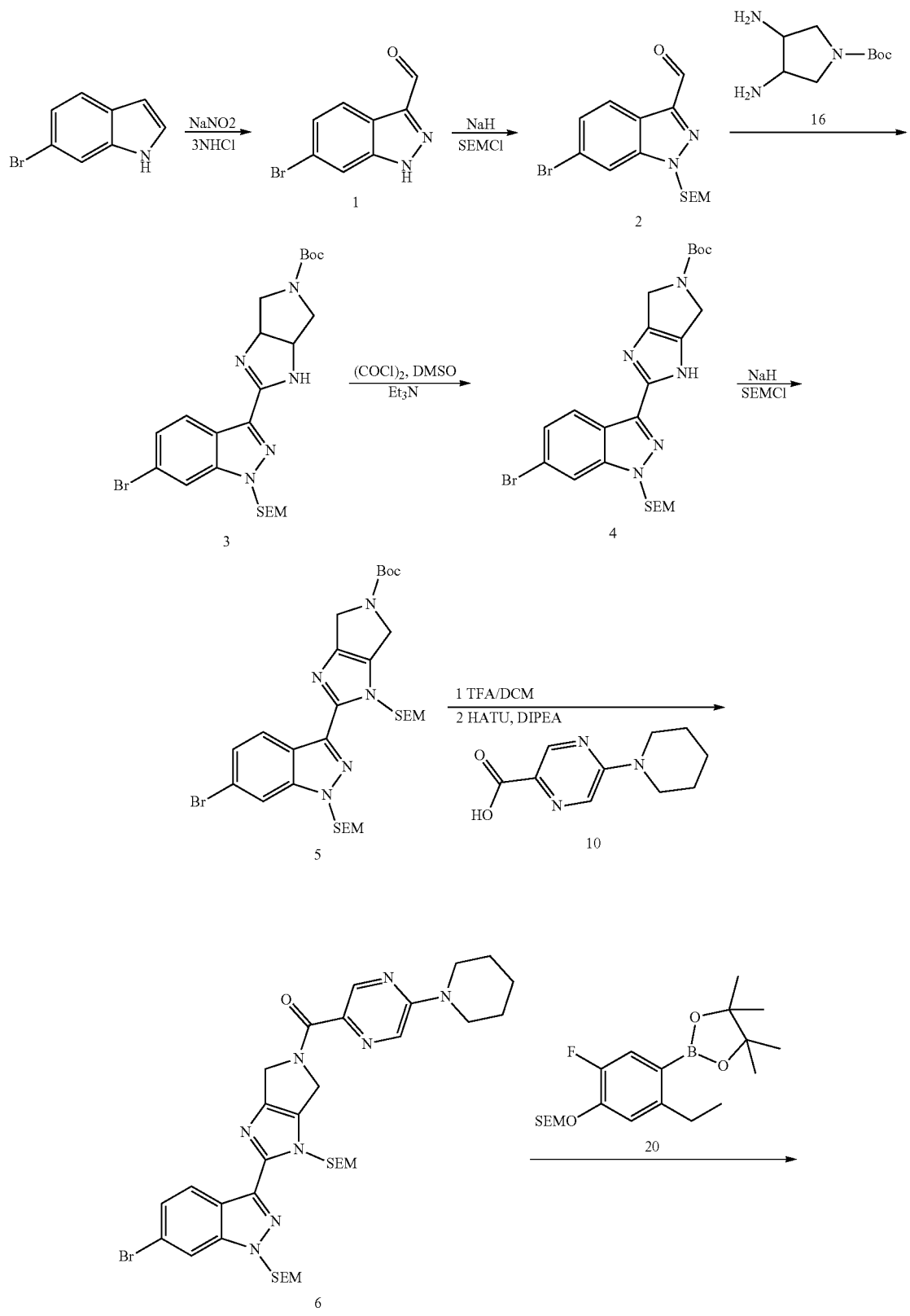

-continued
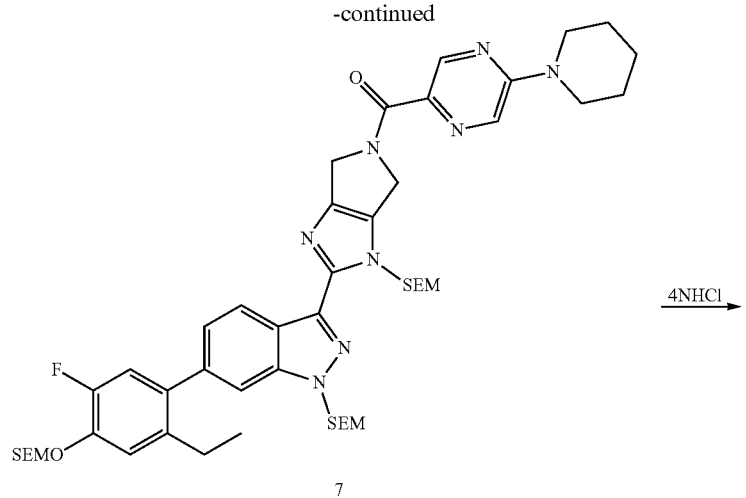
7
4NHCl →
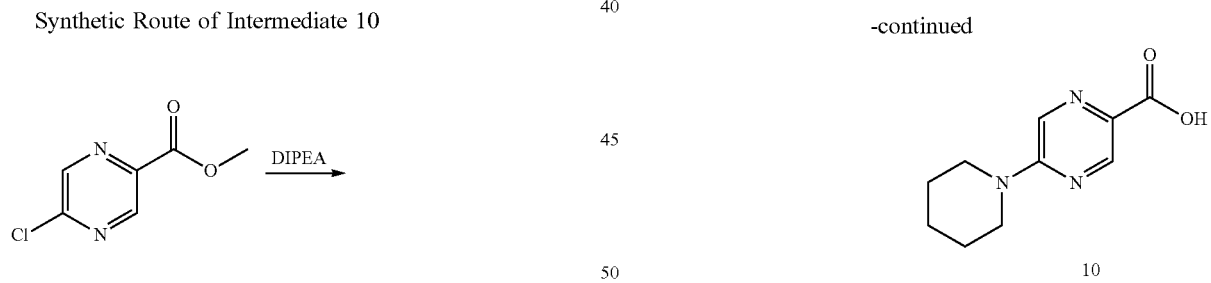
8
Synthetic Route of Intermediate 10
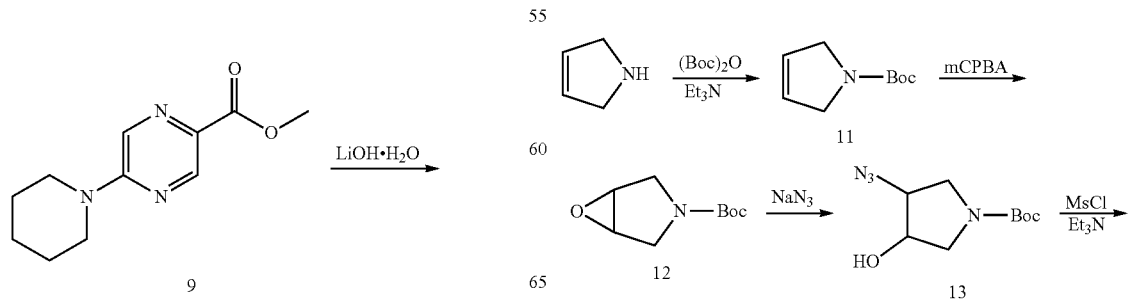
Synthetic Route of Intermediate 16

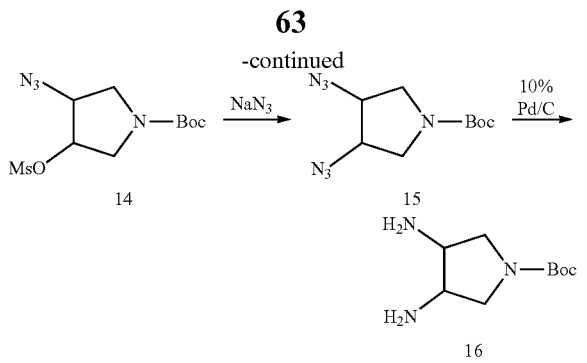

Synthetic Route of Intermediate 20

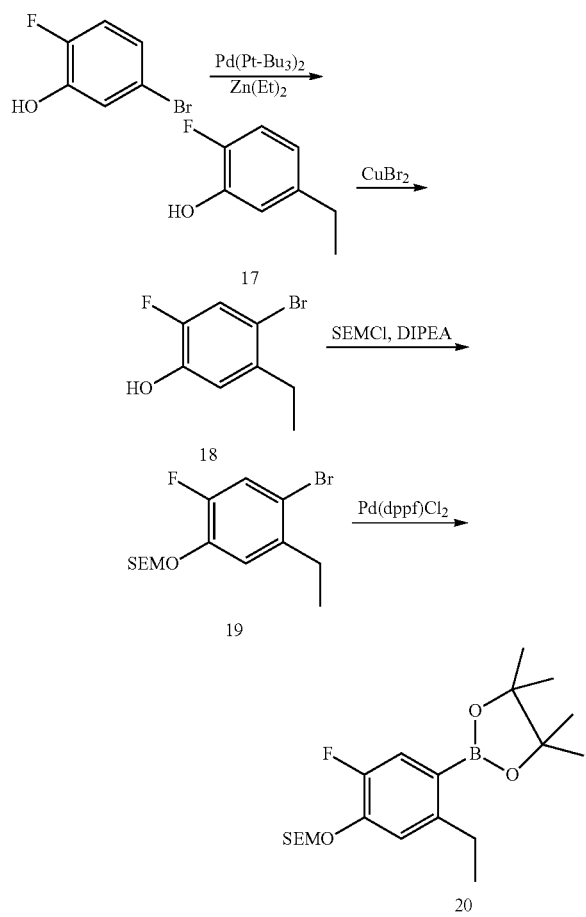

Synthesis Method

Synthesis of Intermediate 1:6-bromo-1H-indazole-3-formaldehyde

Sodium nitrite (14.00 g, 200 mmol) was dissolved in 75 ml DMF and 100 ml water, and then cooled to 0° C. Under nitrogen protection, 3N HCl (23 ml, 68.9 mmol) was slowly added dropwise and after addition, the reaction was carried out for 10 minutes. At 0° C., to the reaction solution, 6-bromoindole (5.00 g, 25.5 mmol) in DMF (35 ml) was slowly added dropwise. After the dropwise addition was complete, the reaction was continued at room temperature overnight. The resulting mixture was extracted with ethyl acetate 3 times, and then the organic phases were combined, washed 3 times with water, washed with saturated brine, dried over anhydrous sodium sulfate, concentrated, and purified by silica gel column to afford the intermediate 1, with a yield of 83.6%.

$^1$H NMR (400 MHz, CDCl3) δ 10.29 (s, 1H), 8.24 (d, J=8.0 Hz, 1H), 7.80 (d, J=4.0 Hz, 1H), 7.52 (dd, J=8.0 Hz, J=4.0 Hz, 1H).

Synthesis of Intermediate 2: 6-bromo-1-((2-(trimethylsilyl)ethoxy) methyl)-1H-indazole-3-formaldehyde Intermediate 1 (1.56 g, 6.93 mmol) was dissolved in dry tetrahydrofuran, and then cooled to 0° C. Sodium hydride (0.33 g, 8.32 mmol) was added slowly, the reaction was carried out at room temperature for 1 hour, and then cooled to 0° C. After that, 2-(trimethylsilyl)ethoxymethyl chloride (1.73 g, 10.40 mmol) was added dropwise and the reaction was carried out at room temperature overnight. The reaction was quenched by adding water. The resulting mixture was extracted twice with ethyl acetate, and the organic phases were combined and washed with water and saturated brine, dried over anhydrous sodium sulfate, concentrated, and purified by silica gel column to afford Intermediate 2, with a yield of 49.2%.

$^1$H NMR (400 MHz, CDCl3) δ 10.25 (s, 1H), 8.22 (dd, J=8.0 Hz, J=4.0 Hz 1H), 7.88 (dd, J=4.0 Hz, J=4.0 Hz, 1H), 7.52 (dd, J=4.0 Hz, J=4.0 Hz, 1H), 5.81 (s, 2H), 3.63-3.58 (m, 2H), 0.97-0.93 (m, 2H), 0.04 (s, 9H).

Synthesis of Intermediate 16: Tert-butyl 3,4-diaminopyrrolidinyl-1-carboxylate

1. Synthesis of Intermediate 11: Tert-butyl 2,5-dihydro-1H-pyrrole-1-carboxylate 3-pyrroline (10.0 g, 0.15 mol) was dissolved in 400 ml dichloromethane and triethylamine (40.6 ml, 0.29 mol), and then cooled to 0° C. (Boc)$_2$O (37.9 g, 0.17 mol) was slowly added. The reaction was carried out at room temperature overnight. Water was added and the mixture was extracted twice with dichloromethane. The organic phases was combined, washed with water three times, washed with saturated brine, dried over anhydrous sodium sulfate, concentrated, and purified by silica gel column to afford Intermediate 11 with a yield of 91.0%.

2. Synthesis of Intermediate 12: Tert-butyl 6-oxa-3-azabicyclo[3.1.0]hexane-3-carboxylate Intermediate 11 (24.5 g, 0.15 mol) was dissolved in 450 ml of dichloromethane, and then cooled to 0° C. M-chloroperoxybenzoic acid (37.5 g, 0.22 mol) was slowly added in batches. The reaction was carried out at room temperature overnight. After that, saturated sodium thiosulfate (40 ml) was added, and then stirred for 30 minutes. The aqueous phase was extracted twice with dichloromethane, washed with saturated potassium carbonate solution, water and saturated brine, dried over anhydrous sodium sulfate, concentrated, and purified by silica gel column to afford Intermediate 12 with a yield of 84.9%.

$^1$H NMR (400 MHz, CDCl3) δ 3.85 (d, J=12.0 Hz, 1H), 3.77 (d, J=12.0 Hz, 1H), 3.69-3.67 (m, 2H), 3.36-3.30 (m, 2H), 1.45 (s, 9H).

3. Synthesis of Intermediate 13: Tert-butyl 3-azido-4-hydroxyl pyrrolidinyl-1-carboxylate Intermediate 12 (20.8 g, 0.12 mol) was dissolved in 150 ml 1,4-dioxane and 50 ml water, and then sodium azide (24.0 g, 0.37 mol) was added. The mixture was heated to 106° C. and reacted for 18 hours, then cooled to room temperature, followed by adding 100 ml of saturated brine. The resulting mixture was extracted with dichloromethane (250 ml*4), and the organic phases were combined, washed with saturated brine, dried over anhydrous sodium sulfate, and concentrated to afford Intermediate 13, with a yield of 100%.

$^1$H NMR (400 MHz, CDCl3) δ 4.27-4.24 (m, 1H), 3.94 (s, 1H), 3.73-3.59 (m, 2H), 3.41-3.36 (m, 2H), 1.47 (s, 9H).

4. Synthesis of Intermediate 14: Tert-butyl 3-azido-4-((methanesulfonyl)oxy)pyrrolidinyl-1-carboxylate Intermediate 13 (28.0 g, 0.12 mol) was dissolved in 350 ml of dichloromethane and triethylamine (37.3 g, 0.37 mol), and cooled to 0° C., followed by slowly adding methanesulfonyl chloride (16.9 g, 0.15 mol) dropwise. After the addition, the reaction was carried out at room temperature for 2 hours, the reaction was quenched with water, and the resulting mixture was extracted twice with dichloromethane. The organic phases was combined, washed with saturated sodium bicarbonate solution, water and saturated brine, dried over anhydrous sodium sulfate, and concentrated to afford Intermediate 14, with a yield of 98.0%.

5. Synthesis of Intermediate 15: Tert-butyl 3,4-diazidopyrrolidinyl-1-carboxylate Intermediate 14 (36.9 g, 0.12 mol) was dissolved in 250 ml DMF, to which sodium azide (23.5 g, 0.36 mol) was added. The mixture was heated to 90° C., reacted for 2 days, and cooled to room temperature, following by adding 750 ml of water. The resulting mixture was extracted with butyl tert-butyl ether (400 ml*4), and the organic phases were combined, washed with saturated brine, dried with anhydrous sodium sulfate, and purified by silica gel column to afford Intermediate 15 with a yield of 62.2%.

6. Synthesis of Intermediate 16: Tert-butyl 3,4-diaminopyrrolidinyl-1-carboxylate Intermediate 15 (18.9 g, 0.08 mol) was dissolved in 200 ml methanol, and 10% Pd/C was added where it was replaced with hydrogen 3 times. The mixture was heated to 40° C., and reacted for 2 days. The resulting mixture was filtered and concentrated to afford Intermediate 16, with a yield of 78%.

$^1$H NMR (400 MHz, CDCl3) δ 3.51-3.49 (m, 2H), 3.40-3.36 (m, 2H), 3.21-3.11 (m, 2H), 1.47 (s, 9H).

Synthesis of Intermediate 3: Tert-butyl 2-(6-bromol-((2-(trimethylsilyl)ethoxy)methyl)-1H-indazol-3-yl)3,4,6,6a-tetrahydropyrrolo[3,4-d]imidazole-5(1H)-carboxylate Intermediate 2 (1.56 g, 6.93 mmol) and tert-butyl 3,4-diaminopyrroline-1-carboxylate (1.56 g, 6.93 mmol) were dissolved in 5 ml of hexafluoroisopropanol and heated to 40° C. for 2 days. The resulting mixture was concentrated and purified by a silica gel column to afford Intermediate 3 with a yield of 54.7%.

Synthesis of Intermediate 4: Tert-butyl 2-(6-bromo-1-((2-(trimethylsilyl) ethoxy)methyl)-1H-indazol-3-yl)4,6-dihydropyrrolo[3,4-d]imidazole-5(1H)-carboxylate Oxalyl chloride (0.53 g, 4.20 mmol) was dissolved in dry 15 ml dichloromethane, and cooled to −78° C. under the protection of nitrogen. DMSO (0.61 g, 7.84 mmol) was slowly added dropwise. After the addition was complete, it was allowed to react for 30 minutes. Intermediate 3 (1.00 g, 1.87 mmol) in dichloromethane was slowly added dropwise. After the dropwise addition, it was allowed to react for 30 minutes. Dry triethylamine (1.89 g, 18.66 mmol) was added slowly dropwise, and it was allowed to react for 10 minutes. The temperature was increased slowly and the reaction was carried out at room temperature for 2 hours. The reaction was quenched with saturated ammonium chloride solution and the resulting mixture was extracted twice with dichloromethane, and the organic layers were combined, washed with water and saturated brine, dried over anhydrous sodium sulfate, concentrated, and purified by silica gel column to afford Intermediate 4 with a yield of 36.3%.

$^1$H NMR (400 MHz, CDCl3) δ 8.36 (d, J=4.0 Hz, 1H), 7.78 (d, J=4.0 Hz, 1H), 7.44 (dd, J=8.0 Hz, J=4.0 Hz, 1H), 5.69 (s, 2H), 4.64-4.52 (m, 4H), 3.67-3.56 (m, 2H), 1.56 (s, 9H), 0.95-0.89 (m, 2H), 0.03 (s, 9H).

Synthesis of Intermediate 5: Tert-butyl 2-(6-bromol-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate Intermediate 4 (110 mg, 0.21 mmol) was dissolved in dry tetrahydrofuran, and cooled to 0° C. Sodium hydride (12.3 mg, 0.31 mmol) was added and it allowed to react at room temperature for 30 minutes. The mixture was cooled to 0° C. 2-(tri methylsilyl)ethoxymethyl chloride (41.2 mg, 0.25 mmol) was added slowly dropwise, and it allowed to react at room temperature for 4 hours. The reaction was quenched with water and the resulting mixture was extracted twice with ethyl acetate. The organic phases were combined, washed with water and saturated brine, dried over anhydrous sodium sulfate, concentrated, and purified by silica gel column to intermediate 5 with a yield of 73.1%.

$^1$H NMR (400 MHz, CDCl3) δ 8.41-8.36 (m, 1H), 7.79 (s, 1H), 7.44 (dd, J=8.0 Hz, J=4.0 Hz, 1H), 5.94 (d, J=12.0 Hz, 2H), 5.73 (s, 2H), 4.65-4.52 (m, 4H), 3.63-3.57 (m, 4H), 1.56 (s, 9H), 0.96-0.91 (m, 4H), 0.03 (s, 18H)).

Synthesis of Intermediate 10: 5-(piperidin-1-yl)pyrazine-2 carboxylic acid

1. Synthesis of Intermediate 9: Methyl 5-(piperidin-1-yl)pyrazine-2-carboxylate Methyl 5-chloro-pyrazine-2-carboxylate (1.72 g, 10 mmol) was dissolved in 10 ml DMF, and N,N-diisopropylethylamine (4.3 ml, 25.0 mmol) and piperidine hydrochloride (1.45 g, 12.0 mmol) were added. The mixture was stirred overnight at room temperature. Under vigorous stirring, water was added. A solid was precipitated, filtered, and the filter cake was washed with water, and dried to afford Intermediate 9 with a yield of 80.0%.

2. Synthesis of Intermediate 10: 5-(piperidin-1-yl)pyrazin-2-carboxylic acid

Intermediate 9 (430 mg, 1.95 mmol) was dissolved in 20 ml of tetrahydrofuran and 20 ml of water, to which lithium hydroxide (163 mg, 3.88 mmol) was added. The reaction was carried out at room temperature for 4 hours. The mixture was concentrated by distilling off tetrahydrofuran under reduced pressure, and the pH was adjusted to 4 with 1N HCl. A solid precipitated, filtered, and the filter cake was washed with water, and dried to afford Intermediate 10 with a yield of 91.5%.
$^1$H NMR (400 MHz, CDCl3) δ 8.84 (s, 1H), 8.02 (s, 1H), 3.76-3.73 (m, 4H), 1.78-1.65 (m, 6H).

Synthesis of Intermediate 6: (2-(6-bromol-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(5-(piperidin-1-yl)pyrazin-2-yl)ketone Intermediate 10 (34.3 mg, 0.17 mmol) and N,N-diisopropylethylamine (58.2 mg, 0.45 mmol) were dissolved in DMF, HATU (85.7 mg, 0.22 mmol) was added, and the reaction was carried out at room temperature for 10 minutes. Intermediate 5 (100 mg, 0.15 mmol) was dissolved in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in DMF and was then slowly added to the previous reaction solution. It was allowed to react overnight at room temperature.

The reaction was quenched with water, and the resulting mixture was extracted twice with ethyl acetate. The organic phases were combined, washed with water and saturated brine, dried over anhydrous sodium sulfate, concentrated, and purified by silica gel column to afford intermediate 6 with a yield of 57.3%.
$^1$H NMR (400 MHz, CDCl$_3$) δ 8.87 (d, J=8.0 Hz, 1H), 8.41-8.37 (m, 1H), 8.09-8.04 (m, 1H), 7.80 (s, 1H), 7.44-7.41 (m, 1H), 5.96 (s, 2H), 5.75 (d, J=8.0 Hz, 2H), 5.28 (s, 1H), 5.19 (s, 1H), 4.99 (s, 1H), 4.91 (s, 1H), 3.74-3.68 (m, 4H), 3.67-3.64 (m, 2H), 3.63-3.59 (m, 2H), 1.71-1.68 (m, 6H), 0.95-0.91 (m, 4H), 0.03 (s, 9H), 0.02 (s, 9H).

Synthesis of Intermediate 20: (2-((5-ethyl-2-fluoro-4-(4,4,5,5-tetramethyl-1,3,2-dioxaboran-2-yl)phenoxy)methoxy)ethyl)trimethylsilane 1. Synthesis of Intermediate 17: 5-ethyl-2-fluorophenol 5-bromo-2-fluorophenol (200.0 mg, 1.05 mmol) and bis(tri-tert-butylphosphorus) palladium (10.7 mg, 0.02 mmol) was dissolved in 10 ml THF. The atmosphere was replaced with nitrogen, which was repeated 3 times. The temperature was lowered to 10-20° C. 1 mol/L diethyl zinc solution (2.3 ml, 2.30 mmol) was added dropwise.

After the addition was completed, the temperature was heated up to 50° C. It was allowed to react overnight, and the temperature was cooled to 0° C. The reaction was quenched with water, and filtered with celite. The celite pad was washed with ethyl acetate. The resulting filtrate was extracted with ethyl acetate, and the organic phases were combined, washed with saturated sodium chloride solution, and dried over anhydrous sodium sulfate. After drying, it was concentrated and separated by column chromatography to afford an oily liquid with a yield of 65.1%.
$^1$H NMR (400 MHz, CDCl$_3$) δ6.97 (d, J=8.0 Hz, 1H), 6.85 (d, J=12.0 Hz, 1H), 6.69-6.65 (m, 1H), 2.61-2.55 (m, 2H), 1.21 (t, J=8.0 Hz, 3H).

2. Synthesis of Intermediate 18: 4-bromo-5-ethyl-2-fluorophenol

Intermediate 17 (200.1 mg, 1.43 mmol) was dissolved in 6 ml of acetonitrile, to which CuBr$_2$ (957.5 mg, 4.29 mmol) was added. The mixture was stirred at room temperature for 3 hours. The reaction was quenched with water, extracted with ethyl acetate, and the organic phase was washed with saturated sodium chloride solution and dried over anhydrous sodium sulfate. It was concentrated and separated by column chromatography to afford a colorless oil, yield: 78.1%.
$^1$H NMR (400 MHz, CDCl3) δ7.25 (d, J=12.0 Hz, 1H), 6.89 (d, J=12.0 Hz, 1H), 2.69-2.63 (m, 2H), 1.19 (t, J=12.0 Hz, 3H).

3. Synthesis of Intermediate 19: (2-((4-bromo-5-ethyl-2-fluorophenoxy)methoxy)ethyl)trimethylsilane Intermediate 18 (220.0 mg, 1.00 mmol) was dissolved in 6 ml DCM, DIPEA (130.5 mg, 1.10 mmol) was added, and the temperature was reduced to 0° C. SEMCl (168.2 mg, 1.10 mmol) was added dropwise at 0° C. After the addition, the temperature was raised to room temperature, and it was allowed to react for 8 hours. The reaction was quenched with water, and extracted with DCM. The organic phase was washed with saturated sodium chloride solution, and dried over anhydrous sodium sulfate. It was concentrated to afford a colorless oil, the crude yield: 99.1%.
$^1$H NMR (400 MHz, CDCl3) δ7.26 (d, J=12.0 Hz, 1H), 6.89 (d, J=12.0 Hz, 1H), 5.24 (s, 2H) 3.82-3.78 (m, 2H) 2.67-2.62 (m, 2H), 1.19 (t, J=12.0 Hz, 3H), 0.98-0.94 (m, 2H), 0.01 (s, 9H).

4. Synthesis of Intermediate 20: (2-((5-ethyl-2-fluoro-4-(4,4,5,5-tetramethyl-1,3,2-dioxaboran-2-yl)phenoxy)methoxy)ethyl)trimethylsilane Compound 19 (280.0 mg, 0.80 mmol), pinacol borate (206.1 mg, 0.80 mmol), Pd(dppf)Cl$_2$ (59.2 mg, 0.08 mmol) and KOAc (237.5 mg, 2.40 mmol) were dissolved in 1, 4-dioxane (6 ml). The atmosphere was replaced with nitrogen, which was repeated 3 times. The mixture was heated to 100° C. and it was allowed to react overnight. After the reaction was completed, it was quenched with water, extracted with ethyl acetate, and the organic phase was washed with saturated sodium chloride solution, and dried over anhydrous sodium sulfate. It was concentrated and separated by column chromatography to afford a colorless oil, yield: 56.2%.
$^1$H NMR (400 MHz, CDCl3) δ7.48 (d, J=12.0 Hz, 1H), 7.02 (d, J=8.0 Hz, 1H), 5.28 (s, 2H), 3.82-3.78 (m, 2H) 2.89-2.83 (m, 2H), 1.35 (s, 12H), 1.17 (t, J=8.0 Hz, 3H), 0.98-0.94 (m, 2H), 0.01 (s, 9H).

Synthesis of Intermediate 7: (2-(6-(2-ethyl-5-fluoro-4-((2-(trimethylsilyl)ethoxy)methyl)hydroxyphenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(5-(piperidin-1-yl)pyrazin-2-yl)ketone Intermediate 6 (65.0 mg, 0.09 mmol), (2-((5-ethyl-2-fluoro-4-(4,4,5,5-tetramethyl-1,3,2-dioxaboran-2-yl)phenoxy)methoxy)ethyl)trimethylsilane (40.9 mg, 0.10 mmol), Pd(dppf)Cl$_2$ (6.3 mg, 0.01 mmol) and potassium phosphate (25.3 mg, 0.26 mmol) were dissolved in 1,4-dioxane (10 ml) and water (2 ml). The atmosphere was replaced with nitrogen 3 times. The mixture was heated to 100° C., reacted overnight, and cooled to room temperature. Water was added and the mixture was extracted 2 times with ethyl acetate. The organic phases were combined, washed with water and saturated brine, dried over anhydrous sodium sulfate, concentrated, and purified by silica gel column to afford Intermediate 7 with a yield of 52.8%.

$^1$H NMR (400 MHz, CDCl3) δ 8.87 (dd, J=8.0 Hz, J=4.0 Hz, 1H), 8.54 (dd, J=8.0 Hz, J=20.0 Hz, 1H), 8.10 (dd, J=8.0 Hz, 1H), 7.48 (s, 1H), 7.27 (s, 1H), 7.20 (d, J=8.0 Hz, 1H), 7.06 (d, J=12.0 Hz, 1H), 6.00 (s, 2H), 5.79 (d, J=4.0 Hz, 2H), 5.35 (s, 2H), 5.33 (s, 1H), 5.29 (s, 1H), 5.20 (s, 1H), 5.01 (s, 1H), 3.91 (t, J=8.0 Hz, J=20.0 Hz, 2H), 3.76-3.74 (m, 4H), 3.64-3.62 (m, 4H), 2.58 (t, J=8.0 Hz, J=16.0 Hz, 2H), 1.74-1.72 (m, 6H), 1.10-1.06 (m, 3H), 0.95-0.91 (m, 6H), 0.06 (s, 9H), 0.04 (s, 9H), 0.03 (s, 9H).

Synthesis of Compound 8 (i.e. MDI-2): (2-(6-(2-ethyl-5-fluoro-4-hydroxyphenyl)-1H-indazol-3-yl)-4,6-dihydropyrrolo[3,4-d]imidazol-5(1H)-yl)(5-(piperidin-1-yl)pyrazin-2-yl)ketone Intermediate 7 (43.0 mg, 0.05 mmol) was dissolved in methanol (4 ml), to which concentrated hydrochloric acid (2 ml) was added. The mixture was heated to 50° C., reacted for 6 hours, and concentrated. The resulting solid was dissolved in 1 ml methanol, pH was adjusted to 8-9 with sodium bicarbonate solution, and then the resulting mixture was extracted 4 times with dichloromethane. The organic phases were combined, dried over anhydrous sodium sulfate, and purified by a preparation plate to afford 4.5 mg of the final product with a yield of 18.0%.

$^1$H NMR (400 MHz, MeOD-d4) δ 8.67 (s, 1H), 8.28 (dd, J=8.0 Hz, J=4.0 Hz, 1H), 8.21 (s, 1H), 7.40 (s, 1H), 7.18 (dd, J=8.0 Hz, J=4.0 Hz, 1H), 6.96-6.89 (m, 2H), 5.14 (s, 2H), 4.82 (s, 2H), 3.76-3.73 (m, 4H), 2.58 (dd, J=12.0 Hz, J=8.0 Hz, 2H), 1.76-1.66 (m, 6H), 1.10 (t, J=8.0 Hz, 3H).

Example 2: (2-(6-(2-ethyl-5-fluoro-4-hydroxyphenyl)-1H-indazol-3-yl)-4,6-dihydropyrrolo[3,4-d]imidazol-5(1H)-yl)(5-morpholinepyrazin-2-yl)ketone (MDI-201)

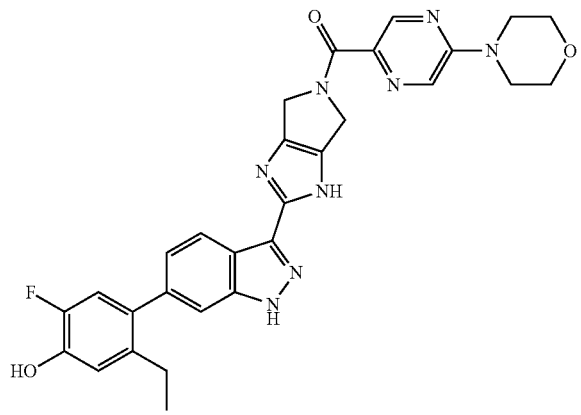

Synthetic Route of MDI-201:

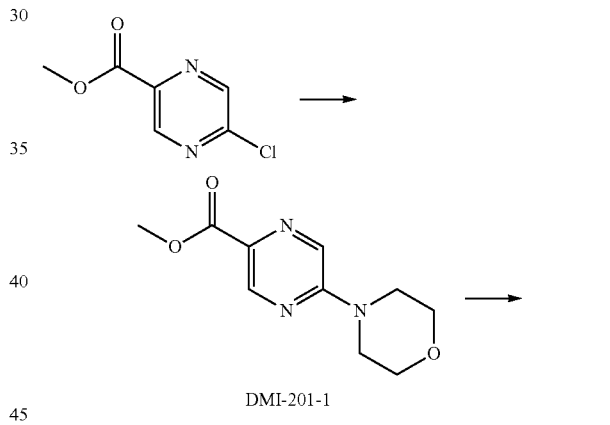

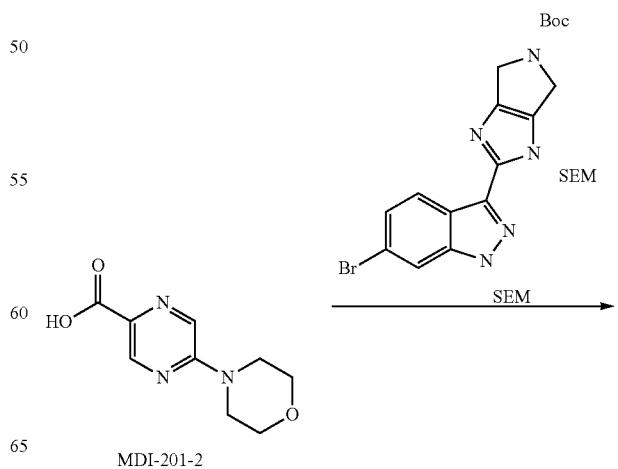

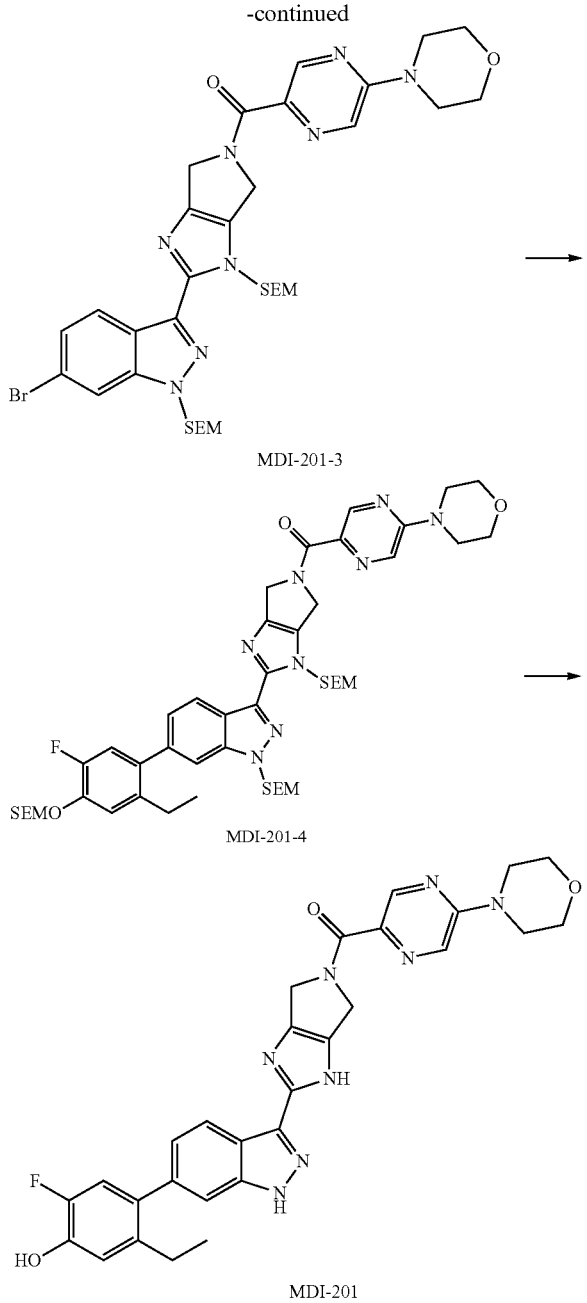

MDI-201-3

MDI-201-4

MDI-201

Synthesis Method

Synthesis of Intermediate MDI-201-1: Methyl 5-morpholine pyrazin-2-carboxylate

Methyl 5-chloro-pyrazine-2-carboxylate (1.5 g, 8.7 mmol) was dissolved in 10 ml DMF, and N,N-diisopropylethylamine (3.0 ml, 17.4 mmol) and morpholine (0.91 g, 10.4 mmol) were added. The mixture was stirred overnight at room temperature. Under vigorous stirring, water was added and a solid precipitated out, and filtered. The resulting filter cake was washed with water, and dried to afford the intermediate MDI-201-1 with a yield of 72.2%.

Synthesis of Intermediate MDI-201-2: 5-morpholinepyrazin-2-carboxylic acid

The intermediate MDI-201-1 (1.4 g, 6.27 mmol) was dissolved in 20 ml of tetrahydrofuran and 20 ml of water, lithium hydroxide (0.32 g, 7.53 mmol) was added, and the reaction was carried out at room temperature for 4 hours. The reaction mixture was concentrated by distilling off tetrahydrofuran under reduced pressure and adjusted with 1N HCl to pH=4. A solid precipitated out, and filtered. The resulting filter cake was washed with water, and dried to afford the intermediate MDI-201-2 with a yield of 99.1%.

$^1$H NMR (400 MHz, CDCl3) δ 8.92 (s, 1H), 8.04 (s, 1H), 3.88-3.86 (m, 4H), 3.80-3.77 (m, 4H).

Synthesis of Intermediate MDI-201-3: (2-(6-bromol-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(5-morpholinepyrazin-2-yl)ketone The intermediate MDI-201-2 (27.4 mg, 0.13 mmol) and N,N-diisopropylethylamine (46.0 mg, 0.36 mmol) was dissolved in DMF, to which HATU (67.8 mg, 0.18 mmol) was added. It was allowed to react at room temperature for 10 minutes. Intermediate tert-butyl 2-(6-bromol-((2-(trimethylsilyl)ethoxy)methyl)-1H-indazol-3-yl)-1-((2-(trimethylsilyl) ethoxy)methyl)-4,6-dihydropyrrolo[3,4-d]imidazole-5 (1H)-carboxylate (80 mg, 0.12 mmol) was dissolved in 5 ml dichloromethane, to which 1 ml of trifluoroacetic acid was added. The mixture was stirred at room temperature for 30 minutes, and concentrated to give a residue. The residue was dissolved in dichloromethane and concentrated to dryness, which was repeated 3 times. The resulting residue was dissolved in DMF, and then slowly added to the previous reaction solution. It was allowed to react at room temperature overnight, and water was added to quench the reaction. The mixture was extracted twice with ethyl acetate and the organic phases were combined, washed with water and saturated brine, dried over anhydrous sodium sulfate, concentrated, and purified on a silica gel column to afford intermediate MDI-201-3 with a yield of 47.8%.

$^1$H NMR (400 MHz, CDCl$_3$) δ 8.91 (d, J=8.0 Hz, 1H), 8.44-8.36 (m, 1H), 8.10 (d, J=8.0 Hz, 1H), 7.80 (s, 1H), 7.46-7.41 (m, 1H), 5.96 (s, 2H), 5.74 (d, J=4.0 Hz, 2H), 5.27 (s, 1H), 5.19 (s, 1H), 5.00 (s, 1H), 4.92 (s, 1H), 3.90-3.88 (m, 4H), 3.75-3.72 (m, 4H), 3.64-3.58 (m, 4H), 0.96-0.89 (m, 4H), 0.03 (s, 9H), 0.02 (s, 9H).

Synthesis of Intermediate MDI-201-4: (2-(6-(2-ethyl-5-fluoro-4-((2-(trimethylsilyl)ethoxy)methyl) hydroxyphenyl)1-((2-(trimethylsilyl)ethoxy)methyl)-1H-indazol-3-yl)-1-((2-(trimethylsilyl)ethoxy) methyl)-4,6-dihydropyrrolo[3,4-d]imidazol-5(1H)-yl)(5-morpholinepyrazin-2-yl)ketone The intermediate MDI-201-3 (43.0 mg, 0.06 mmol), (2-((5-ethyl-2-fluoro-4-(4,4,5,5-tetramethyl-1,3,2-dioxaborolan-2-yl)phenoxy)methoxy)ethyl) trimethylsilane (27.1 mg, 0.07 mmol), Pd(dppf)Cl2 (4.2 mg, 0.006 mmol) and potassium phosphate (36.2 mg, 0.17 mmol) were dissolved in 1,4-dioxane (10 ml) and water (2 ml). The atmosphere was replaced with nitrogen, which was repeated 3 times. The mixture was heated to 100° C., reacted overnight, cooled to room temperature. Water was added and the resulting mixture was extracted with ethyl acetate twice. The organic phases were combined, washed with water and saturated brine, dried over anhydrous sodium sulfate, concentrated, and purified by silica gel column to afford intermediate MDI-201-4 with a yield of 40.9%.

¹H NMR (400 MHz, CDCl3) δ 8.91 (dd, J=4.0 Hz, J=4.0 Hz, 1H), 8.52 (dd, J=8.0 Hz, J=16.0 Hz, 1H), 8.10 (dd, J=8.0 Hz, J=4.0 Hz, 1H), 7.49 (s, 1H), 7.27 (s, 1H), 7.20 (d, J=8.0 Hz, 1H), 7.06 (d, J=12.0 Hz, 1H), 6.00 (s, 2H), 5.79 (d, J=4.0 Hz, 2H), 5.35 (s, 2H), 5.29 (s, 1H), 5.20 (s, 1H), 5.02 (s, 1H), 4.94 (s, 1H)), 3.91-3.86 (m, 6H), 3.76-3.72 (m, 4H), 3.65-3.61 (m, 4H), 2.58 (t, J=8.0 Hz, 2H), 1.10-1.03 (m, 3H), 0.95-0.91 (m, 6H), 0.06 (s, 9H), 0.04 (s, 9H), 0.03 (s, 9H).

Synthesis of MDI-201:(2-(6-(2-ethyl-5-fluoro-4-hydroxyphenyl)-1H-indazol-3-yl)-4,6-dihydropyrrolo[3,4-d]imidazol-5(1H)-yl)(5-morpholinepyrazin-2-yl)ketone The intermediate MDI-201-4 (22.0 mg, 0.02 mmol) was dissolved in methanol (4 ml), to which concentrated hydrochloric acid (2 ml) was added. The mixture was heated to 50° C., reacted for 6 hours, and concentrated. The resulting solid was dissolved with 1 ml methanol, to which 2 ml concentrated aqueous ammonia was added. The resulting mixture was concentrated to a residue. The residue was dissolved in methanol and concentrated to dryness, which was repeated 3 times. The resulting residue was and purified by a preparation plate to afford 8 mg of the final product, with a yield of 61.9%.

¹H NMR (400 MHz, DMSO-d6) δ 13.35 (s, 1H), 9.89 (s, 1H), 8.66 (d, J=4.0 Hz, 1H), 8.38-8.33 (m, 2H), 7.42 (s, 1H), 7.15 (d, J=8.0 Hz, 1H), 7.06 (d, J=12.0 Hz, 1H), 6.95 (d, J=8.0 Hz, 1H), 5.05 (s, 2H), 4.72 (s, 2H), 3.76-3.74 (m, 4H), 3.71-3.68 (m, 4H), 2.52 (dd, J=12.0 Hz, J=4.0 Hz, 2H), 1.05 (t, J=8.0 Hz, 3H).

Example 3: (2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone (MDI-202)

Synthetic Route of MDI-202:

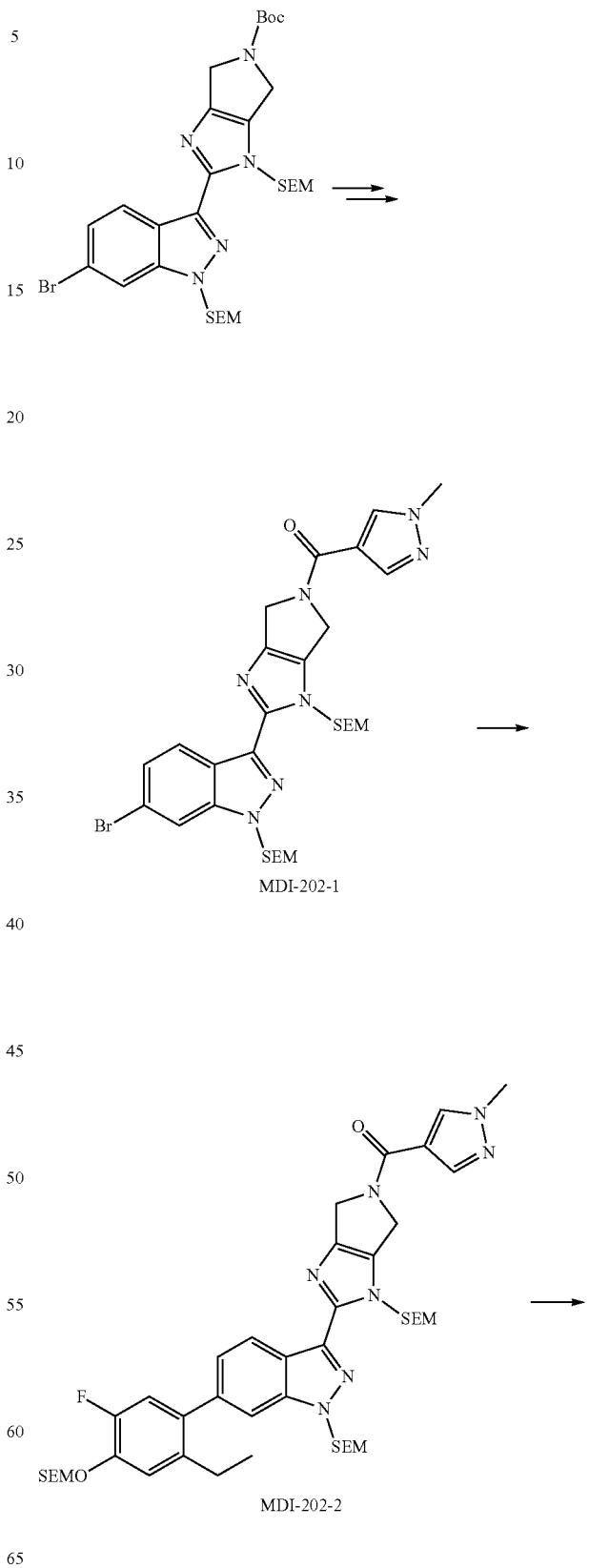

-continued

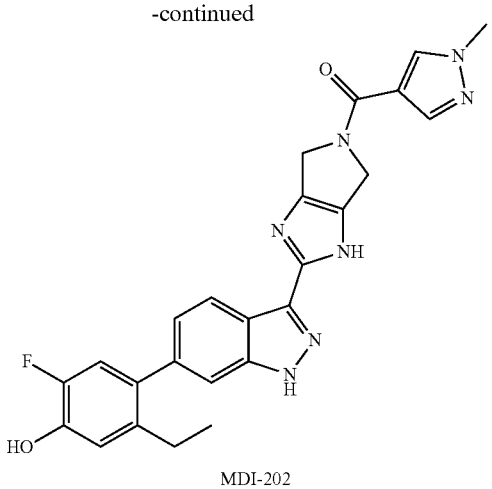

MDI-202

Synthesis Method

Synthesis of Intermediate MDI-202-1: (2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(1-methyl-1H-pyrazol-4-yl)ketone The intermediate 1-methyl-1H-pyrazole-4-carboxylic acid (16.5 mg, 0.13 mmol) and N,N-diisopropylethylamine (46.0 mg, 0.36 mmol) were dissolved in DMF, to which HATU (67.8 mg, 0.18 mmol) was added. It was allowed to react at room temperature for 10 minutes. Intermediate tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate (80 mg, 0.12 mmol) was dissolved in 5 ml dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in DMF and then slowly added to the previous reaction solution. It was allowed to react at room temperature overnight, and water was added to quench the reaction. The resulting mixture was extracted twice with ethyl acetate, and the organic phases were combined, washed with water and saturated brine, dried over anhydrous sodium sulfate, concentrated, and purified by silica gel column to afford intermediate MDI-202-1 with a yield of 41.3%.

$^1$H NMR (400 MHz, CDCl3) δ 8.43 (dd, J=8.0 Hz, J=20.0 Hz, 1H), 7.98 (d, J=4.0 Hz, 2H), 7.81 (s, 1H), 7.45 (d, J=8.0 Hz, 1H), 5.96 (s, 2H), 5.75 (s, 2H), 5.02-4.85 (m, 4H), 4.01 (s, 3H), 3.64-3.59 (m, 4H), 0.97-0.91 (m, 4H), 0.03 (s, 9H), 0.02 (s, 9H).

Synthesis of Intermediate MDI-202-2: (2-(6-(2-ethyl-5-fluoro-4-((2-(trimethylsilyl)ethoxy)methyl)hydroxyphenyl)1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(1-methyl-1H-pyrazol-4-yl)ketone The intermediate MDI-202-1 (33 mg, 0.05 mmol), (2-((5-ethyl-2-fluoro-4-(4,4,5,5-tetramethyl-1,3,2-dioxaborolan-2-yl)phenoxy)methoxy)ethyl) trimethylsilane (23.3 mg, 0.06 mmol), Pd(dppf)Cl$_2$ (3.6 mg, 0.005 mmol) and potassium phosphate (31.3 mg, 0.15 mmol) were dissolved in 1,4-dioxane (10 ml) and water (2 ml). The atmosphere was replaced with nitrogen, which was repeated 3 times and the mixture was heated to 100° C., reacted overnight, and cooled to room temperature. Water was added and the mixture was extracted with ethyl acetate twice. The organic phases were combined, washed with water and saturated brine, dried over anhydrous sodium sulfate, concentrated, and purified by silica gel column to afford intermediate MDI-202-2 with a yield of 85.0%.

$^1$H NMR (400 MHz, CDCl3) δ 8.48 (d, J=8.0 Hz, 1H), 7.98 (d, J=4.0 Hz, 2H), 7.49 (s, 1H), 7.20 (s, 1H), 7.18 (d, J=8.0 Hz, 1H), 7.06 (d, J=12.0 Hz, 1H), 6.00 (s, 2H), 5.79 (s, 2H), 5.35 (s, 2H), 5.04-4.87 (m, 4H), 4.01 (s, 3H), 3.91 (t, J=8.0 Hz, J=20.0 Hz, 2H), 3.67-3.61 (m, 4H), 2.58 (d, J=8.0 Hz, 2H), 1.11-1.07 (m, 3H), 0.95-0.91 (m, 6H), 0.06 (s, 9H), 0.03 (s, 9H), 0.02 (s, 9H).

Synthesis of Compound MDI-202: (2-(6-(2-ethyl-5-fluoro-4-hydroxyphenyl)-1H-indazol-3-yl)-4,6-dihydropyrrolo[3,4-d]imidazol-5(1H)-yl)(1-methyl-1H-pyrazol-4-yl)ketone The intermediate MDI-202-2 (36.0 mg, 0.04 mmol) was dissolved in methanol (4 ml), to which concentrated hydrochloric acid (2 ml) was added. The mixture was heated to 50° C., reacted for 6 hours, and concentrated. The solid was dissolved with 1 ml methanol, to which 2 ml of concentrated aqueous ammonia was added. The mixture was concentrated to give a residue. The residue was dissolved in methanol and was concentrated to dryness, which was repeated 3 times. The resulting residue was purified by a preparation plate to afford 5.0 mg of the final product with a yield of 25.4%.

$^1$H NMR (400 MHz, DMSO-d6) δ 13.33 (s, 1H), 12.87 (s, 1H), 9.89 (s, 1H), 8.35 (d, J=8.0 Hz, 2H), 7.94 (s, 1H), 7.42 (s, 1H), 7.15 (d, J=8.0 Hz, 1H), 7.06 (d, J=12.0 Hz, 1H), 6.95 (d, J=12.0 Hz, 1H), 4.89 (s, 2H), 4.67 (s, 2H), 3.92 (s, 3H), 2.51-2.48 (m, 2H), 1.05 (t, J=8.0 Hz, 3H).

Example 4: (2-(6-(2-ethyl-5-fluoro-4-hydroxyphenyl)-1H-indazol-3-yl)pyrrolo[3,4-d]imidazol-5(1H,4H,6H)-yl)(1-methylpiperidin-4-yl)ketone (MDI-203)

MDI-203 may also be named as 5-ethyl-2-fluoro-4-{3-[5-(1-methylpiperidin-4-carbonyl)-1H,4H,5H,6H-pyrrolo[3,4-d]imidazol-2-yl]-1H-indazol-6-yl}phenol.

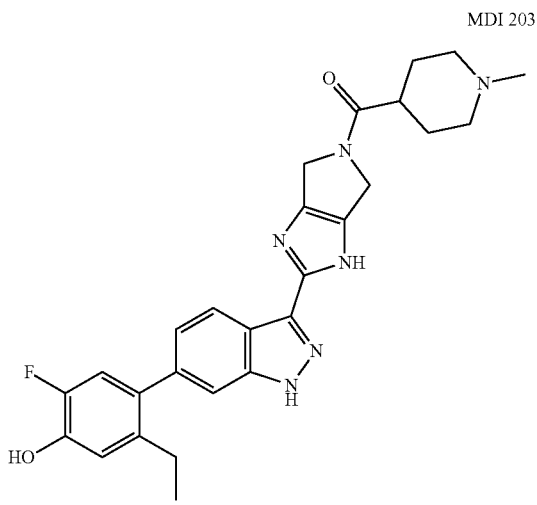 [SMILES: CCc1cc(O)c(F)cc1-c1ccc2c(-c3nc4c([nH]3)CN(C(=O)C3CCN(C)CC3)C4)n[nH]c2c1]

MDI 203

Synthetic Route of MDI-203:

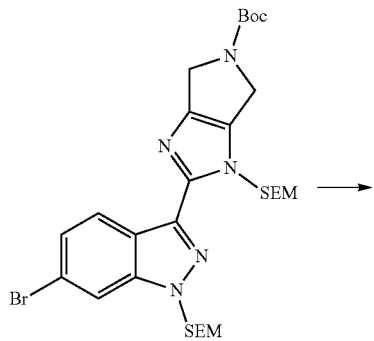

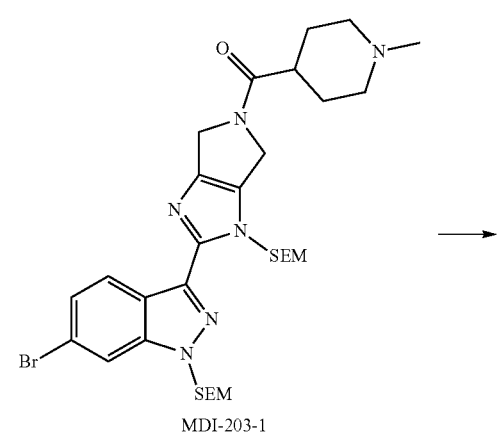

MDI-203-1

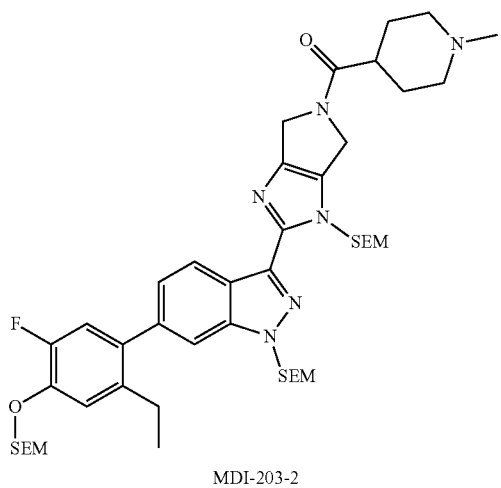

MDI-203-2

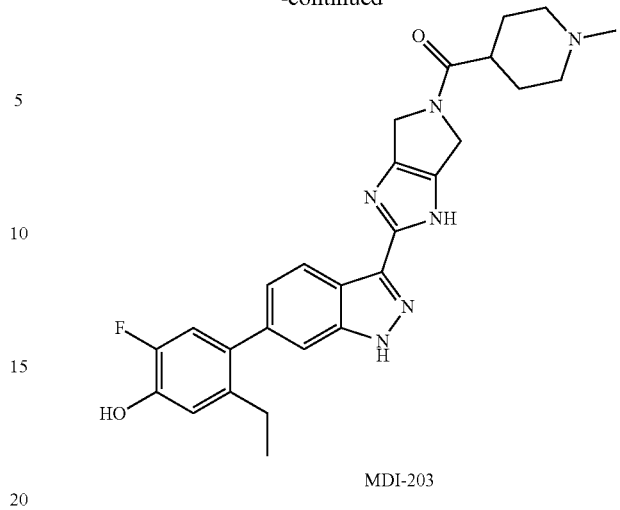

MDI-203

Synthesis Method

Synthesis of Intermediate MDI-203-1: (2-(6-bromo-1-((2-(trimethylsilyl)ethoxy)methyl)-1H-indazol-3-yl)-1-((2-(trimethylsilyl)ethoxy)methyl) pyrrolo[3,4-d]imidazol-5(1H,4H,6H)-yl)(1-methylpiperidin-4-yl) ketone 1-methylpiperidine-4-carboxylic acid (18.6 mg, 0.13 mmol) and N,N-diisopropylethylamine (46.0 mg, 0.36 mmol) was dissolved in DMF, to which HATU (67.8 mg, 0.18 mmol) was added. It was allowed to react at room temperature for 10 minutes. Intermediate tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate (80 mg, 0.12 mmol) was dissolved in 5 ml dichloromethane, to which 1 ml of trifluoroacetic acid was added. The reaction mixture was stirred at room temperature for 30 minutes, and concentrated to give a residue. The residue was dissolved in dichloromethane and concentrated to dryness (to remove trifluoroacetic acid), which was repeated 3 times. Then the resulting residue was dissolved in DMF, which was slowly added to the previous reaction solution. It was allowed to react at room temperature overnight. Water was added to quench the reaction. The resulting mixture was extracted twice with ethyl acetate and the organic phases were combined, washed with water and saturated brine, dried over anhydrous sodium sulfate, concentrated, and purified by silica gel column to afford intermediate MDI-203-1 with a yield of 40.2%.

$^1$H NMR (400 MHz, CDCl3) δ8.29-8.22 (m, 1H), 7.76 (s, 1H), 7.41-7.26 (m, 1H), 5.85 (s, 2H), 5.69 (s, 2H), 4.88-4.59 (m, 4H), 3.63-3.54 (m, 6H), 3.21-2.81 (m, 5H), 2.28-2.01 (m, 4H), 0.93-0.83 (m, 5H), 0.03 (s, 9H), 0.02 (s, 9H).

Synthesis of Intermediate MDI-203-2: (2-(6-(2-ethyl-5-fluoro-4-((2-(trimethylsilyl)ethoxy)methoxy)phenyl)1-((2-(trimethylsilyl)ethoxy)methyl)-1H-indazol-3-yl)-1-((2-(trimethylsilyl)ethoxy)methyl) pyrrolo[3,4-d]imidazol-5(1H, 4H,6H)-yl)(1-methylpiperidin-4-yl)ketone The intermediate MDI-203-1 (41.29 mg, 0.06 mmol), (2-((5-ethyl-2-fluoro-4-(4,4,5,5-tetramethyl-1,3,2-dioxaborolan-2-yl)phenoxy)methoxy)ethyl)trimethylsilane (27.1 mg, 0.07 mmol), Pd(dppf)Cl2 (4.2 mg, 0.006 mmol) and potassium phosphate (36.2 mg, 0.17 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted with ethyl acetate twice. The organic phases were combined, washed with water and saturated brine, dried over anhydrous sodium sulfate, concentrated, and purified by silica gel column to afford intermediate MDI-203-2 with a yield of 40.9%.

¹H NMR (400 MHz, CDCl3) δ8.50-8.44 (m, 1H), 7.49 (s, 1H), 7.22 (dd, J=12.0 Hz, 2H), 7.04 (d, J=12.0 Hz, 1H), 5.98 (d, J=12.0 Hz, 2H), 5.78 (s, 2H), 5.34 (s, 2H), 4.84-4.69 (m, 4H), 3.90-3.86 (m, 2H), 3.66-3.58 (m, 4H), 3.38-3.30 (m, 2H), 2.61-2.54 (m, 5H), 2.13-2.05 (m, 4H), 1.10-1.01 (m, 5H), 0.97-0.89 (m, 3H), 0.03 (s, 9H), 0.02 (s, 18H).

Synthesis of Compound MDI-203: (2-(6-(2-ethyl-5-fluoro-4-hydroxyphenyl)-1H-indazol-3-yl)pyrrolo[3,4-d]imidazol-5(1H,4H,6H)-yl)(1-methylpiperidin-4-yl)ketone Intermediate MDI-203-2 (26.4 mg, 0.03 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, to which 2 ml concentrated ammonia water was added. It was concentrated to give a residue. The residue was dissolved in methanol and concentrated to dryness (to remove ammonia water), which was repeated 3 times. After separation, 5.0 mg of the final product was obtained with a yield of 34.2%.

¹H NMR (400 MHz, DMSO-d6) δ 13.35 (s, 1H), 9.87 (s, 1H), 9.24 (s, 1H), 8.32 (d, J=8.0 Hz, 1H), 7.42 (s, 1H), 7.22 (d, J=8.0 Hz, 1H), 7.03 (d, J=12.0 Hz, 1H), 6.96 (d, J=12.0 Hz, 1H), 4.80 (s, 2H), 4.48 (s, 2H), 3.04-3.01 (m, 2H), 2.79 (s, 3H), 2.55-2.51 (m, 2H), 2.05-1.99 (m, 3H), 1.85-1.78 (m, 2H), 1.01-0.98 (m, 3H). The signals of the two H were masked by the water peak (δ=3.37).

Example 5: (2-(6-(2-ethyl-5-fluoro-4-hydroxyphenyl)-1H-indazol-3-yl)pyrrolo[3,4-d]imidazol-5(1H,4H,6H)-yl)(5-(4-methylpiperazin-1-yl)pyrazin-2-yl)ketone (MDI-204)

MDI-204 may also be named as 5-ethyl-2-fluoro-4-{3-[5-(4-methylpiperazine-1-carbonyl)-1H,4H,5H,6H-pyrrolo[3,4-d]imidazol-2-yl]-1H-indazol-6-yl}phenol.

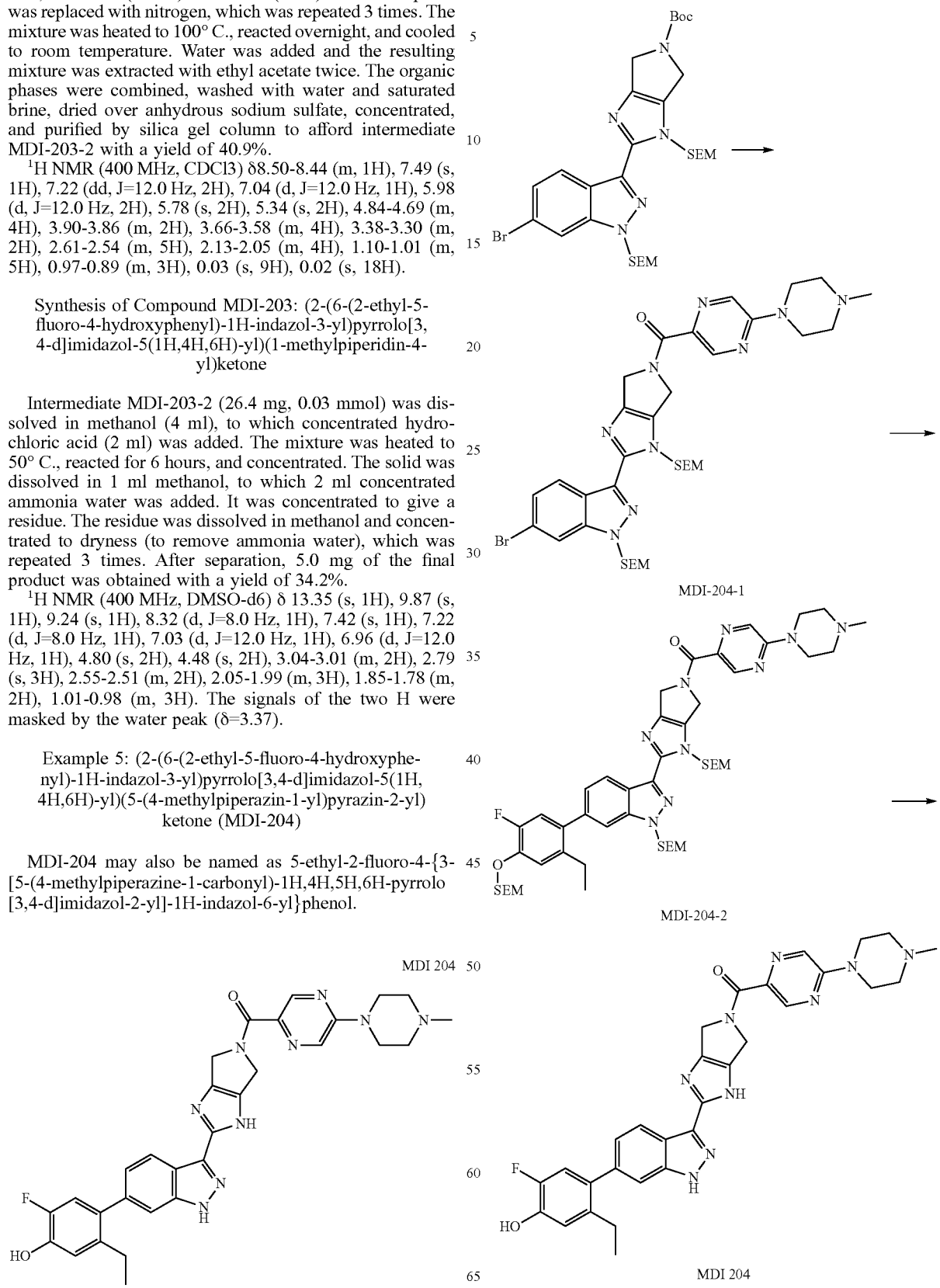

Synthesis Method

Synthesis of Intermediate MDI-204-1: (2-(6-bromo1-((2-(trimethylsilyl) ethoxy)methyl)-1H-indazol-3-yl)-1-((2-(trimethylsilyl)ethoxy)methyl)pyrrolo[3,4-d]imidazol-5(1H, 4H,6H)-yl)(5-(4-methylpiperazin-1-yl)pyrazin-2-yl)ketone 5-(4-methylpiperazin-1-yl)pyrazine-2-carboxylic acid (28.9 mg, 0.13 mmol) and N,N-diisopropylethylamine (46.0 mg, 0.36 mmol) were dissolved in DMF, to which HATU (67.8 mg, 0.18 mmol) was added. It was allowed to react at room temperature for 10 minutes. Intermediate tert-butyl 2-(6-bromo1-((2-(trimethylsilyl)ethoxy)methyl)-1H-indazol-3-yl)-1-((2-(trimethylsilyl ethoxy)methyl)-4,6-dihydropyrrolo[3,4-d]imidazole-5(1H)-carboxylate (80 mg, 0.12 mmol) was dissolved in 5 ml dichloromethane, to which 1 ml of trifluoroacetic acid was added. The reaction mixture was stirred at room temperature for 30 minutes, and concentrated to give a residue. The residue was dissolved in dichloromethane and concentrated to dryness (to remove trifluoroacetic acid), which was repeated 3 times. Then the resulting residue was dissolved in DMF, which was slowly added to the previous reaction solution. It was allowed to react at room temperature overnight. Water was added to quench the reaction, and the resulting mixture was extracted twice with ethyl acetate. The organic phases were combined, washed with water and saturated brine, dried over anhydrous sodium sulfate, concentrated, and purified by silica gel column to afford intermediate MDI-204-1 with a yield of 43%.

$^1$H NMR (400 MHz, CDCl3) δ8.86-8.84 (m, 1H), 8.41-8.33 (m, 1H), 8.07-8.05 (m, 1H), 7.76 (d, J=4.0 Hz, 1H), 7.42-7.38 (m, 1H), 5.92 (s, 2H), 5.70 (d, J=4.0 Hz, 2H), 5.23-4.88 (m, 4H), 3.77-3.65 (m, 4H), 3.61-3.55 (m, 4H), 2.55 (t, J=4.0 Hz, 4H), 2.37 (s, 3H), 0.94-0.83 (m, 4H), 0.03 (s, 9H), 0.02 (s, 9H).

Synthesis of Intermediate MDI-204-2: (2-(6-(2-ethyl-5-fluoro-4-((2-(trimethylsilyl)ethoxy)methoxy)phenyl)1-((2-(trimethylsilyl)ethoxy)methyl)-1H-indazol-3-yl)-1-((2-(trimethylsilyl)ethoxy)methyl)pyrrolo[3,4-d]imidazol-5(1H, 4H,6H)-yl)(5-(4-methylpiperazin-1-yl)pyrazin-2-yl)ketone The intermediate MDI-204-1 (46.0 mg, 0.06 mmol), (2-((5-ethyl-2-fluoro-4-(4,4,5,5-tetramethyl-1,3,2-dioxaborolan-2-yl)phenoxy)methoxy)ethyl)trimethylsilane (27.1 mg, 0.07 mmol), Pd(dppf)Cl$_2$ (4.2 mg, 0.006 mmol) and potassium phosphate (36.2 mg, 0.17 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted with ethyl acetate twice. The organic phases were combined, washed with water and saturated brine, dried over anhydrous sodium sulfate, concentrated, and purified by silica gel column to afford intermediate MDI-204-2 with a yield of 47.2%.

$^1$H NMR (400 MHz, CDCl3) δ8.86-8.84 (m, 1H), 8.51-8.43 (m, 1H), 8.08-8.06 (m, 1H), 7.45 (d, J=4.0 Hz, 1H), 7.26-7.23 (m, 1H), 7.21-7.14 (m, 1H), 7.02 (d, J=8.0 Hz, 1H), 5.97 (s, 2H), 5.75 (d, J=4.0 Hz, 2H), 5.32 (s, 2H), 5.25-5.16 (m, 2H), 4.99-4.90 (m, 2H), 3.87-3.83 (m, 2H), 3.77-3.74 (m, 4H), 3.63-3.56 (m, 4H), 2.56-2.51 (m, 6H), 2.37 (s, 3H), 1.07-1.01 (m, 3H), 0.99-0.88 (m, 6H), 0.03 (s, 9H), −0.07 (s, 9H), −0.09 (s, 9H).

Synthesis of Compound MDI-204: (2-(6-(2-ethyl-5-fluoro-4-hydroxyphenyl)-1H-indazol-3-yl)pyrrolo[3,4-d]imidazol-5(1H,4H,6H)-yl)(5-(4-methylpiperazin-1-yl)pyrazin-2-yl)ketone Intermediate MDI-204-2 (28.7 mg, 0.03 mmol) was dissolved in methanol (4 ml), to which concentrated hydrochloric acid (2 ml) was added. The mixture was heated to 50° C., reacted for 6 hours, and concentrated. The resulting solid was dissolved in 1 ml methanol, to which 2 ml concentrated ammonia water was added. It was concentrated to give a residue. The residue was dissolved in methanol and concentrated to dryness (to remove ammonia water), which was repeated 3 times. After separation, 4.0 mg of the final product was obtained with a yield of 23.51%.

$^1$H NMR (400 MHz, DMSO-d6) δ 13.29 (s, 1H), 12.79 (d, J=16.0 Hz, 1H), 9.85 (s, 1H), 8.62 (s, 1H), 8.36 (s, 1H), 8.34-8.30 (m, 1H), 7.40 (s, 1H), 7.14-7.10 (m, 1H), 7.03 (d, J=12.0 Hz, 1H), 6.92 (d, J=12.0 Hz, 1H), 5.08-4.65 (m, 4H), 2.55-2.49 (m, 6H), 2.24 (s, 3H), 2.03-1.97 (m, 4H), 1.04-1.02 (m, 3H).

Example 6: (2-(6-(2-ethyl-4-hydroxyphenyl)-1H-indazol-3-yl)pyrrolo[3,4-d]imidazol-5(1H,4H,6H)-yl)(5-(4-methylpiperazin-1-yl)pyrazin-2-yl)ketone (MDI-205)

MDI-205 may also be named as 3-ethyl-4-{3-[5-(4-methylpiperazine-1-carbonyl)-1H,4H,5H,6H-pyrrolo[3,4-d]imidazol-2-yl]-1H-indazol-6-yl}phenol.

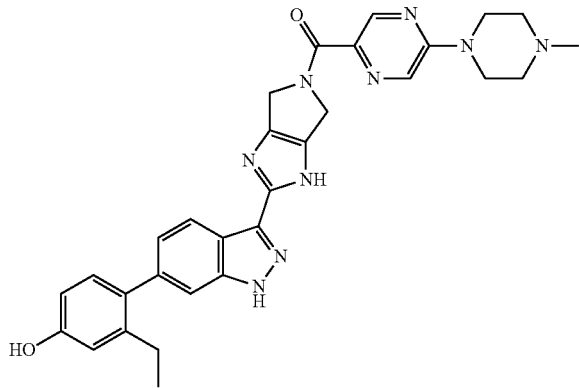

MDI 205

Synthetic Route of MDI-205:
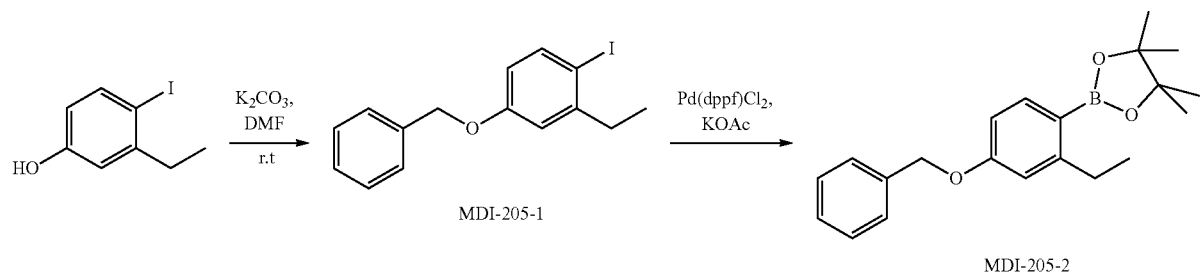
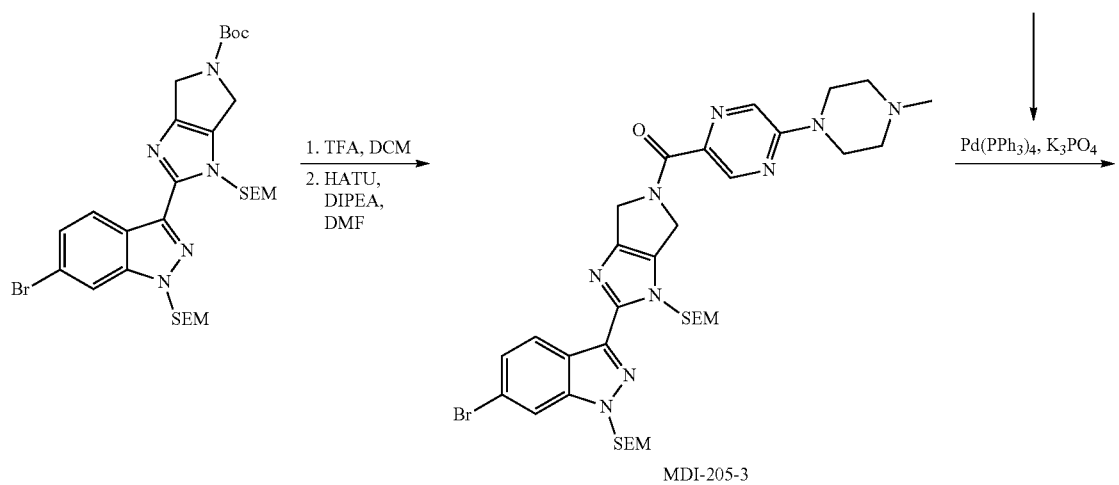
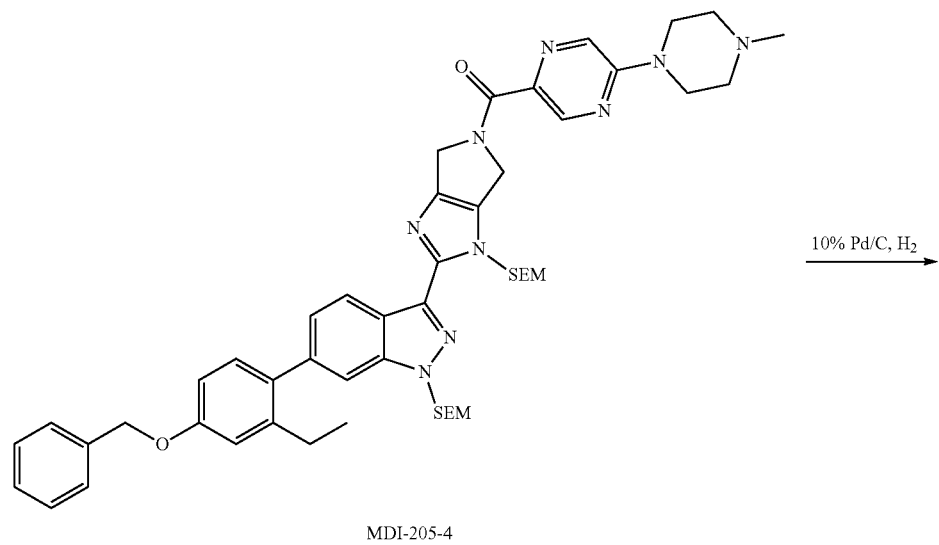

-continued

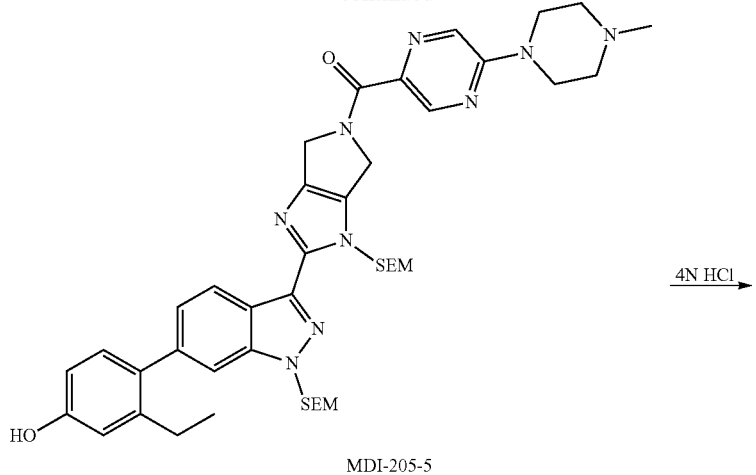

MDI-205-5

4N HCl

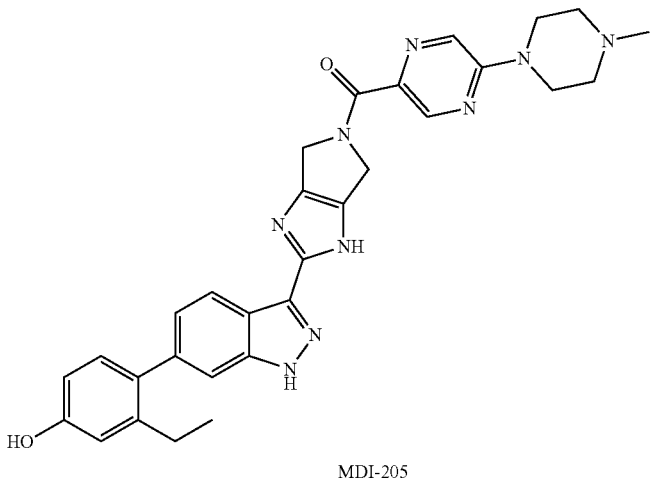

MDI-205

Synthesis Method

Synthesis of Intermediate MDI-205-1: 4-benzyloxy-2-ethyl-iodobenzene 3-ethyl-4-iodophenol (200 mg, 0.81 mmol), benzyl bromide (165.5 mg, 0.97 mmol) and potassium carbonate (222.9 mg, 1.61 mmol) were dissolved in DMF. It was allowed to react at room temperature for two hours. Water was added and the resulting mixture was extracted twice with EA. The organic phases were combined, washed with water, saturated brine, dried over anhydrous sodium sulfate, concentrated, and purified by silica gel column to afford 250 mg of colorless oily product with a yield of 91.7%.

$^1$H NMR (400 MHz, CDCl3) δ7.70 (d, J=8.0 Hz, 1H), 7.46-7.36 (m, 5H), 6.92 (d, J=4.0 Hz, 1H), 6.57 (dd, J=4.0 Hz, J=8.0 Hz, 1H), 5.06 (s, 2H), 2.72 (dd, J=8.0 Hz, J=16.0 Hz, 2H), 1.22 (t, J=8.0 Hz, 3H).

Synthesis of Intermediate MDI-205-2: (2-(4-(phenoxy)-2-ethyl phenyl)-4,4,5,5-tetramethyl-1,3,2-dioxaborane MDI-205-1 (250.0 mg, 0.74 mmol), pinacol borate (225.1 mg, 0.89 mmol), Pd(dppf)Cl$_2$ (54.0 mg, 0.07 mmol) and KOAc (217.6 mg, 2.22 mmol) were dissolved in 1,4-dioxane (10 ml). The atmosphere was replaced with nitrogen, which was repeated 3 times. The mixture was heated to 100° C. and reacted overnight. After the reaction was completed, it was quenched with water, extracted with ethyl acetate, and the organic phase was washed with saturated sodium chloride solution, and dried over anhydrous sodium sulfate. It was concentrated and separated by column chromatography to afford a colorless oil with a yield of 70%.

$^1$H NMR (400 MHz, CDCl3) δ 7.77 (d, J=8.0 Hz, 1H), 7.47-7.34 (m, 5H), 6.86-6.80 (m, 2H), 5.11 (s, 2H), 2.93 (dd, J=8.0 Hz, J=16.0 Hz, 2H), 1.35 (s, 12H), 1.21 (t, J=8.0 Hz, 3H).

Synthesis of Compound MDI-205-3: (2-(6-bromo-1-((2-(trimethylsilyl)ethoxy)methyl)-1H-indazol-3-yl)-1-((2-(trimethylsilyl)ethoxy)methyl) pyrrolo[3,4-d]imidazol-5(1H,4H,6H)-yl)(5-(4-methylpiperazin-1-yl)pyrazin-2-yl)ketone The intermediate 5-(4-methylpiperazin-1-yl)pyrazine-2 carboxylic acid (64.2 mg, 0.29 mmol) and N,N-diisopropylethylamine (93.2 mg, 0.72 mmol) were dissolved in DMF, to which HATU (109.7 mg, 0.29 mmol) was added. It was allowed to react at room temperature for 10 minutes. Intermediate tert-butyl 2-(6-bromoI-((2-(trimethylsilyl)ethoxy) methyl)-1H-indazol-3-yl)-1-((2-(trimethylsilyl)ethoxy) methyl)-4,6-dihydropyrrolo[3,4-d]imidazole-5(1H)-carboxylate (160.0 mg, 0.24 mmol) was dissolved in 5 ml dichloromethane, to which 1 ml of trifluoroacetic acid was added. The reaction mixture was stirred at room temperature for 30 minutes, and concentrated to give a residue. The residue was dissolved in dichloromethane and concentrated to dryness (to remove trifluoroacetic acid), which was repeated 3 times. Then the resulting residue was dissolved in DMF, which was slowly added to the previous reaction solution. It was allowed to react at room temperature overnight. Water was added to quench the reaction, and the resulting mixture was extracted twice with ethyl acetate. The organic phases were combined, washed with water and saturated brine, dried over anhydrous sodium sulfate, concentrated, and purified by silica gel column to afford intermediate MDI-205-3 with a yield of 49.2%.

$^1$H NMR (400 MHz, CDCl3) δ 8.88 (dd, J=8.0 Hz, J=4.0 Hz 1H), 8.42 (dd, J=8.0 Hz, J=20.0 Hz 1H), 8.10 (dd, J=8.0 Hz, J=4.0 Hz 1H), 7.80 (s, 1H), 7.41-7.46 (m, 1H), 5.96 (s, 2H), 5.74 (d, J=4.0 Hz, 2H), 5.27 (s, 1H), 5.19 (s, 1H), 4.99 (s, 1H), 4.91 (s, 1H), 3.80-3.78 (m, 4H), 3.63-3.59 (m, 4H), 2.59-2.56 (m, 4H), 2.40 (s, 3H), 0.97-0.91 (m, 4H), 0.03 (s, 9H), 0.02 (s, 9H).

Synthesis of Compound MDI-205-4: (2-(6-(4-(phenoxy)-2-ethyl-phenyl)1-((2-(trimethylsilyl)ethoxy)methyl)-1H-indazol-3-yl)-1-((2-(trimethylsilyl)ethoxy) methyl)pyrrolo[3,4-d]imidazol-5(1H,4H,6H)-yl)(5-(4-methylpiperazin-1-yl)pyrazin-2-yl)ketone Intermediate MDI-205-3 (91.0 mg, 0.12 mmol), intermediate MDI-205-2 (48.1 mg, 0.14 mmol), Pd(PPh3)4 (13.6 mg, 00.1 mmol) and potassium phosphate (75.4 mg, 0.36 mmol) were dissolved in 1,4-dioxane (20 ml) and water (4 ml). The atmosphere was replaced with nitrogen, which was repeated 3 times. The mixture was heated to 100° C., reacted overnight, and cooled to room temperature. Water was added, and the resulting mixture was extracted 2 times with ethyl acetate. The organic phases were combined, washed with water and saturated brine, dried over anhydrous sodium sulfate, concentrated, and purified by silica gel column to afford intermediate MDI-205-4 with a yield of 44.1%.

$^1$H NMR (400 MHz, CDCl3) δ 8.88 (dd, J=8.0 Hz, J=4.0 Hz 1H), 8.46 (dd, J=4.0 Hz, J=8.0 Hz 1H), 8.11 (dd, J=8.0 Hz, J=4.0 Hz 1H), 7.52-7.31 (m, 6H), 7.27-7.22 (m, 2H), 7.00 (d, J=4.0 Hz, 1H), 6.91 (dd, J=4.0 Hz, J=8.0 Hz, 1H), 6.00 (s, 2H), 5.77 (d, J=4.0 Hz, 2H), 5.20 (s, 1H), 5.19 (s, 1H), 5.15 (s, 2H), 5.01 (s, 1H), 4.93 (s, 1H), 3.81-3.77 (m, 4H), 3.65-3.61 (m, 4H), 2.62-2.57 (m, 6H), 2.40 (s, 3H), 1.10 (t, J=8.0 Hz, 3H), 0.95-0.91 (m, 4H), 0.03 (s, 9H), 0.02 (s, 9H).

Synthesis of Compound MDI-205-5: (2-(6-(2-ethyl-4-hydroxyphenyl)1-((2-(trimethylsilyl)ethoxy)methyl)-1H-indazol-3-yl)-1-((2-(trimethylsilyl)ethoxy)methyl) pyrrolo[3,4-d]imidazol-5(1H,4H,6H)-yl)(5-(4-methylpiperazin-1-yl)pyrazin-2-yl)ketone Intermediate MDI-205-4 (47.0 mg, 0.05 mmol) was dissolved in 10 ml methanol, to which 5 mg 10% Pd/C was added. The atmosphere was replaced with hydrogen, which was repeated three times. It was allowed to react at room temperature overnight. The palladium on carbon was filtered off and the filtrate was concentrated to afford intermediate MDI-205-5 with a yield of 78.0%, which was directly used in the next step.

Synthesis of Compound MDI-205: (2-(6-(2-ethyl-4-hydroxyphenyl)-1H-indazol-3-yl)pyrrolo[3,4-d]imidazol-5(1H,4H,6H)-yl)(5-(4-methylpiperazin-1-yl)pyrazin-2-yl)ketone The intermediate MDI-205-5 (33.0 mg, 0.04 mmol) was dissolved in 4 ML methanol, to which 2 ml concentrated hydrochloric acid was added. The mixture was heated to 50° C., reacted for 6 hours, and concentrated to give a residue. The residue was dissolved in methanol and was concentrated to dryness (to remove hydrochloric acid), which was repeated 3 times. The resulting product was dissolved 1 ml methanol and 2 ml aqueous ammonia was added for neutralization, and the resulting mixture was concentrated to give a residue. The residue was dissolved in methanol and was concentrated to dryness (to remove aqueous ammonia), which was repeated 2 times. The obtained product was purified by a preparation plate to afford 6.2 mg of the product with a yield of 27.7%.

$^1$H NMR (400 MHz, MeOD-d4) δ 8.72 (d, J=4.0 Hz, 1H), 8.28 (dd, J=4.0 Hz, J=8.0 Hz, 2H), 7.40 (s, 1H), 7.18 (dd, J=4.0 Hz, J=8.0 Hz, 1H), 7.09 (d, J=8.0 Hz, 1H), 6.80 (d, J=4.0 Hz, 1H), 6.72-6.69 (m, 1H), 5.17 (s, 2H), 4.85 (s, 2H), 3.83-3.81 (m, 4H), 2.67-2.64 (m, 4H), 2.60 (dd, J=4.0 Hz, J=8.0 Hz, 2H), 2.43 (s, 3H), 1.10 (t, J=8.0 Hz, 3H).

Example 7: 5-ethyl-2-fluoro-4-(3-(5-(benzenesulfonyl)-1,4,5,6-tetrahydro pyrrolo[3,4-d]imidazol-2-yl)-1H-indazol-6-yl)phenol (MDI-206)

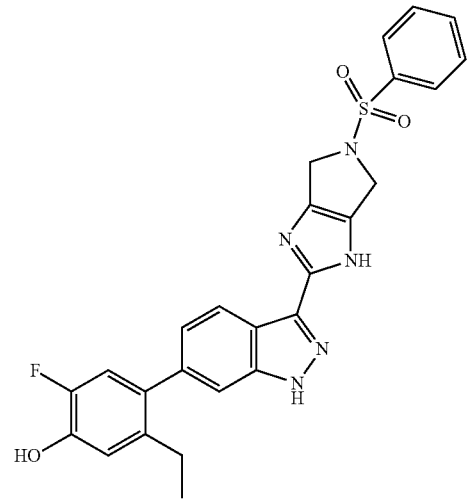

MDI 206

Synthetic Route of MDI-206:

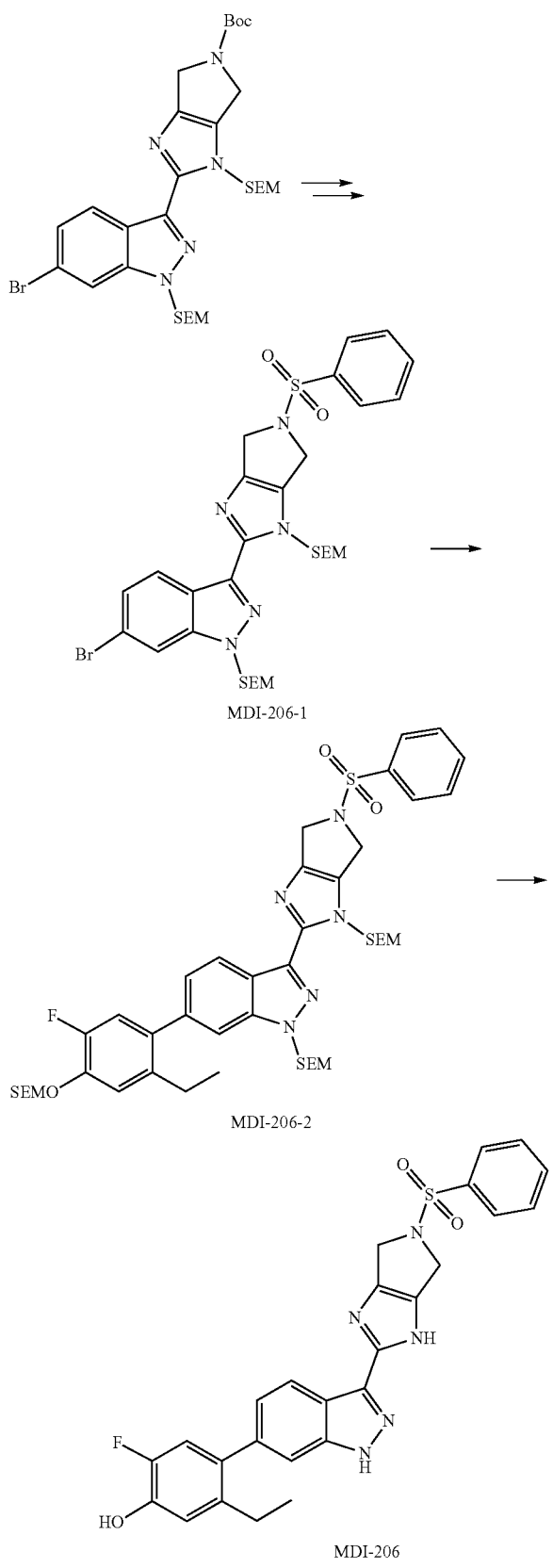

MDI-206-1

MDI-206-2

MDI-206

Synthesis Method

Synthesis of Intermediate MDI-206-1: (6-bromo-3-(5-(benzenesulfonyl)-1-(2-(trimethylsilyl)ethoxy) methyl)-1, 4, 5, 6-tetrahydropyrrolo[3,4-d]imidazol-2-yl)-1-((2-(trimethylsilyl)ethoxy)methyl)-1H-indazole Tert-butyl 2-(6-bromo-1-((2-(trimethylsilyl)ethoxy) methyl)-1H-indazol-3-yl)-1-((2-(trimethylsilyl)ethoxy) methyl)-4,6-dihydropyrrolo[3,4-d]imidazole-5(1H)-carboxylate (100 mg, 0.15 mmol) was dissolved in 5 ml dichloromethane, to which 1 ml of trifluoroacetic acid was added. The mixture was stirred at room temperature for 30 minutes, and concentrated to give a residue (to remove trifluoroacetic acid). The residue was dissolved in dichloromethane and was concentrated to dryness, which was repeated 3 times. The resulting residue was dissolved in 5 ML DCM and Et$_3$N (0.08 ml, 0.59 mmol), cooled to 0° C., and benzenesulfonyl chloride (28.6 mg, 0.16 mmol) was slowly added. It was allowed to react at room temperature for 2 hours, and water was added to quench the reaction. The resulting mixture was extracted twice with DCM, and the organic phases were combined, washed with water and saturated brine, dried over anhydrous sodium sulfate, concentrated, and purified by silica gel column to afford intermediate MDI-206-1 with a yield of 41.4%.

$^1$H NMR (400 MHz, CDCl3) δ 8.32 (d, J=8.0 Hz, 1H), 7.95 (d, J=8.0 Hz, 2H), 7.77 (s, 1H), 7.62-7.55 (m, 3H), 7.42 (d, J=8.0 Hz, 1H), 5.85 (s, 2H), 5.70 (s, 2H), 4.66-4.58 (m, 4H), 3.59-3.51 (m, 4H), 0.94-0.87 (m, 4H), 0.03 (s, 18H).

Synthesis of Intermediate MDI-206-2: (6-(2-ethyl-5-fluoro-4-((2-(trimethylsilyl)ethoxy)methyl)hydroxyphenyl)-3-(5-benzenesulfonyl)-1-((2-(trimethylsilyl)ethoxy)methyl)-1,4,5,6-tetrahydropyrrolo[3,4-d]imidazol-2-yl)-1-((2-(trimethylsilyl)ethoxy) methyl)-1H-indazole The intermediate MDI-206-1 (53.0 mg, 0.08 mmol), (2-((5-ethyl-2-fluoro-4-(4,4,5,5-tetramethyl-1,3,2-dioxaborolan-2-yl)phenoxy)methoxy)ethyl)trimethylsilane (35.8 mg, 0.09 mmol), Pd(dppf)Cl$_2$ (5.5 mg, 0.008 mmol) and potassium phosphate (47.9 mg, 0.23 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted with ethyl acetate twice and the organic phases were combined, washed with water and saturated brine, dried over anhydrous sodium sulfate, concentrated, and purified on a silica gel column to afford intermediate MDI-206-2 with a yield of 74.3%.

$^1$H NMR (400 MHz, CDCl3) δ 8.42 (d, J=8.0 Hz, 1H), 7.96-7.94 (m, 2H), 7.62-7.57 (m, 3H), 7.46 (s, 1H), 7.25 (d, J=8.0 Hz, 1H), 7.19 (d, J=8.0 Hz, 1H), 7.04 (d, J=12.0 Hz, 1H), 5.89 (s, 2H), 5.75 (s, 2H), 5.34 (s, 2H), 4.67-4.60 (m, 4H), 3.90-3.86 (m, 2H), 3.62-3.51 (m, 4H), 2.58 (dd, J=8.0 Hz, J=16.0 Hz, 2H), 1.09-1.05 (m, 3H), 0.93-0.88 (m, 6H), 0.06 (s, 9H), 0.03 (s, 9H), 0.02 (s, 9H).

Synthesis of Compound MDI-206: 5-ethyl-2-fluoro-4-(3-(5-(benzenesulfonyl)-1,4,5,6-tetrahydropyrrolo [3,4-d]imidazol-2-yl)-1H-indazol-6-yl)phenol Intermediate MDI-206-2 (50.0 mg, 0.06 mmol) was dissolved in methanol (4 ml), to which concentrated hydrochloric acid (2 ml) was added. The mixture was heated to 50° C., reacted for 6 hours, and concentrated. The resulting solid was dissolved in 1 ml methanol, and pH was adjusted with sodium bicarbonate solution to 8-9. The resulting mixture was extracted 4 times with dichloromethane, and the organic phases were combined, dried over anhydrous sodium sulfate, and purified by a preparation plate to afford 13 mg of the final product with a yield of 46.2%.

¹H NMR (400 MHz, MeOD-d4) δ 8.22 (d, J=8.0 Hz, 1H), 7.98-7.96 (m, 2H), 7.69-7.65 (m, 3H), 7.41 (s, 1H), 7.16 (d, J=8.0 Hz, 1H), 6.96-6.89 (m, 2H), 4.61-4.52 (m, 4H), 2.57 (dd, J=16.0 Hz, J=8.0 Hz, 2H), 1.08 (t, J=8.0 Hz, 3H).

Example 8: 5-ethyl-2-fluoro-4-(3-(5-(pyrazin-2ylmethyl)-1,4,5,6-tetrahydropyrrolo[3,4-d]imidazol-2-yl)-1H-indazol-6-yl)phenol (MDI-207)

Synthetic Route of MDI-207:

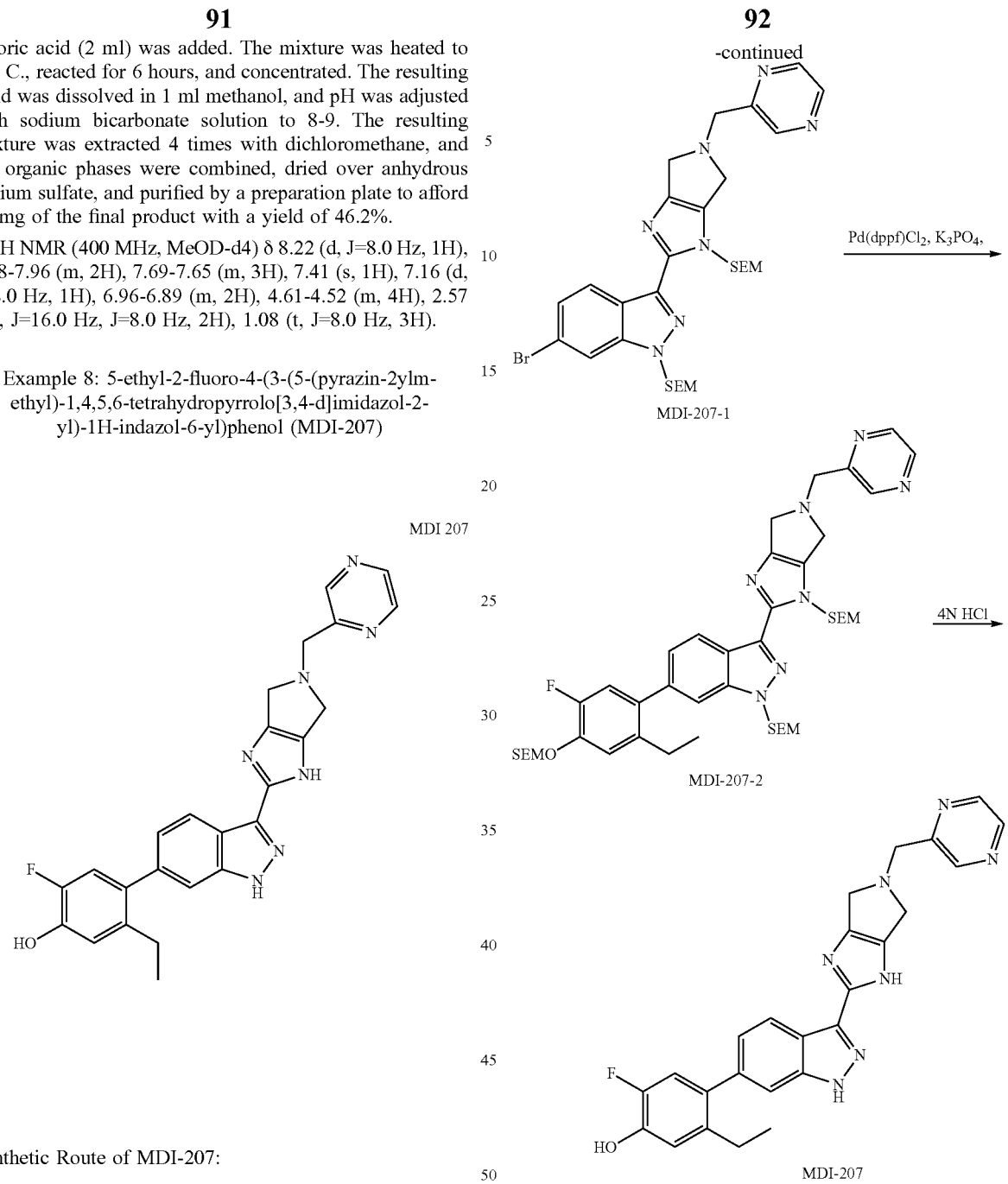

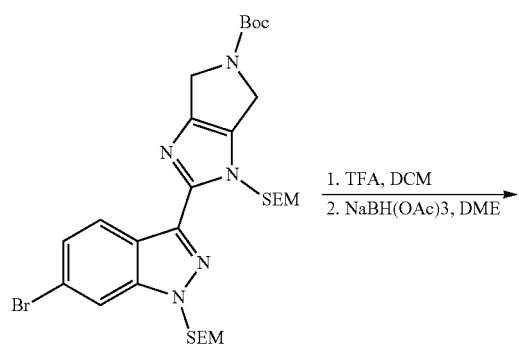

Synthesis Method

Synthesis of Intermediate MDI-207-1: (6-bromo-3-(5-(pyrazin-2ylmethyl)1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol Tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate (47.0 mg, 0.07 mmol) was dissolved in 5 ml dichloromethane, to which 1 ml of trifluoroacetic acid was added. The mixture was stirred at room temperature for 30 minutes. Water was added and saturated sodium bicarbonate solution was used to adjust pH=9. The resulting mixture was extracted with DCM. The organic phase was washed with water and saturated brine, dried over anhydrous sodium sulfate, and concentrated. The resulting solid was dissolved in 1,2-dichloroethane, to which 2-pyrazinecarboxaldehyde (30.6 mg, 0.28 mmol) was added. The mixture was stirred at room temperature for 1 hour, to which sodium triacetylborohydride (60.0 mg, 0.28 mmol) was added. It was allowed to react at room temperature for 4 hours, and water was added to quench the reaction. The resulting mixture was extracted with DCM twice, and the organic phases were combined, washed with water and saturated brine, dried over anhydrous sodium sulfate, concentrated, and purified by silica gel column to afford the product MDI-207-1 with a yield of 49.5%.

$^1$H NMR (400 MHz, CDCl3) δ 8.81 (d, J=4.0 Hz, 1H), 8.60 (dd, J=8.0 Hz, J=4.0 Hz, 1H), 8.54 (d, J=4.0 Hz, 1H), 8.39 (d, J=8.0 Hz, 1H), 7.77 (d, J=4.0 Hz, 1H), 7.41 (dd, J=8.0 Hz, J=4.0 Hz, 1H), 5.88 (s, 2H), 5.72 (s, 2H), 4.28 (s, 2H), 4.12 (dd, J=4.0 Hz, J=12.0 Hz, 4H), 3.62-3.55 (m, 4H), 0.96-0.87 (m, 4H), 0.03 (s, 9H), 0.02 (s, 9H).

Synthesis of Intermediate MDI-207-2: (6-(2-ethyl-5-fluoro-4-((2-(trimethylsilyl)ethoxy)methoxy)phenyl)-3-(5-(pyrazin-2ylmethyl)1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazole The intermediate MDI-207-1 (20.0 mg, 0.03 mmol), the intermediate (2-((5-ethyl-2-fluoro-4-(4,4,5,5-tetramethyl-1,3,2-dioxaborolan-2-yl)phenoxy)methoxy)ethyl) trimethylsilane (14.5 mg, 0.04 mmol), Pd(dppf)Cl$_2$ (2.3 mg, 0.003 mmol) and potassium phosphate (19.4 mg, 0.09 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted with ethyl acetate twice, the organic phases were combined, washed with water and saturated brine, dried over anhydrous sodium sulfate, concentrated, and purified by silica gel column to afford intermediate MDI-207-2 with a yield of 93.0%.

$^1$H NMR (400 MHz, CDCl3) δ 8.82 (d, J=4.0 Hz, 1H), 8.60 (dd, J=8.0 Hz, J=4.0 Hz, 1H), 8.54 (d, J=4.0 Hz, 1H), 8.48 (d, J=8.0 Hz, 1H), 7.47 (d, J=4.0 Hz, 1H), 7.23 (dd, J=8.0 Hz, J=4.0 Hz, 1H), 7.19 (d, J=8.0 Hz, 1H), 7.05 (d, J=12.0 Hz, 1H), 5.92 (s, 2H), 5.77 (s, 2H), 5.34 (s, 2H), 4.30 (s, 2H), 4.13 (dd, J=4.0 Hz, J=12.0 Hz, 4H), 3.88-3.86 (m, 2H), 3.63-3.58 (m, 4H), 2.57 (d, J=8.0 Hz, 2H), 1.07 (t, J=8.0 Hz, 3H), 0.92-0.90 (m, 6H), 0.06 (s, 9H), 0.03 (s, 9H), 0.02 (s, 9H).

Synthesis of Compound MDI-207: 5-ethyl-2-fluoro-4-(3-(5-(pyrazin-2ylmethyl)-1,4,5,6-tetrahydropyrrolo[3,4-d]imidazol-2-yl)-1H-indazol-6-yl)phenol The intermediate MDI-207-2 (24.0 mg, 0.03 mmol) was dissolved in 4 ML methanol, to which 2 ml concentrated hydrochloric acid was added. The mixture was heated to 50° C., reacted for 6 hours, and concentrated to give a residue. The residue was dissolved in methanol and was concentrated to dryness, which was repeated 3 times. The resulting product was dissolved 1 ml methanol and 2 ml aqueous ammonia was added for neutralization, and the resulting mixture was concentrated to give a residue. The residue was dissolved in methanol and was concentrated to dryness, which was repeated 2 times. The obtained product was purified by a preparation plate to afford 8 mg of the product with a yield of 61.8%.

$^1$H NMR (400 MHz, MeOD-d4) δ 8.80 (d, J=4.0 Hz, 1H), 8.65 (dd, J=4.0 Hz, J=4.0 Hz, 1H), 8.56 (d, J=4.0 Hz, 1H), 8.26 (dd, J=4.0 Hz, J=4.0 Hz, 1H), 7.41 (d, J=4.0 Hz, 1H), 7.17 (dd, J=12.0 Hz, J=4.0 Hz, 1H), 6.91-6.89 (m, 2H), 4.30 (s, 2H), 4.07 (s, 4H), 2.56 (dd, J=8.0 Hz, J=16.0 Hz, 2H), 1.07 (t, J=8.0 Hz, 3H).

Example 9: 4-(3-(5-(cyclopropylmethyl)-1,4,5,6-tetrahydropyrrolo[3,4-d]imidazol-2-yl)-1H-indazol-6-yl)-5-ethyl-2-fluorophenol (MDI-208)

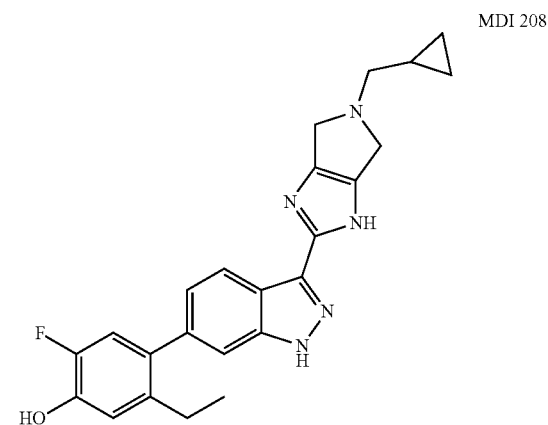 [SMILES: CCc1cc(O)c(F)cc1-c1ccc2c(-c3nc4c([nH]3)CN(CC3CC3)C4)n[nH]c2c1]

Synthetic Route of MDI-208:

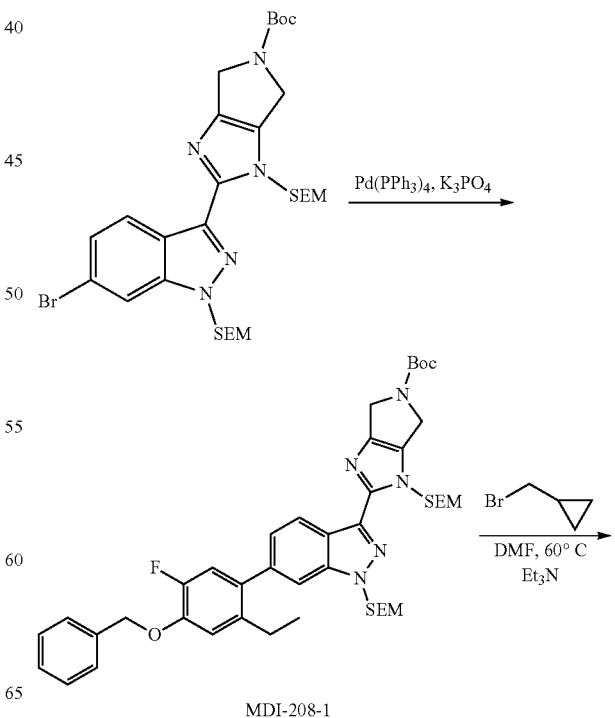

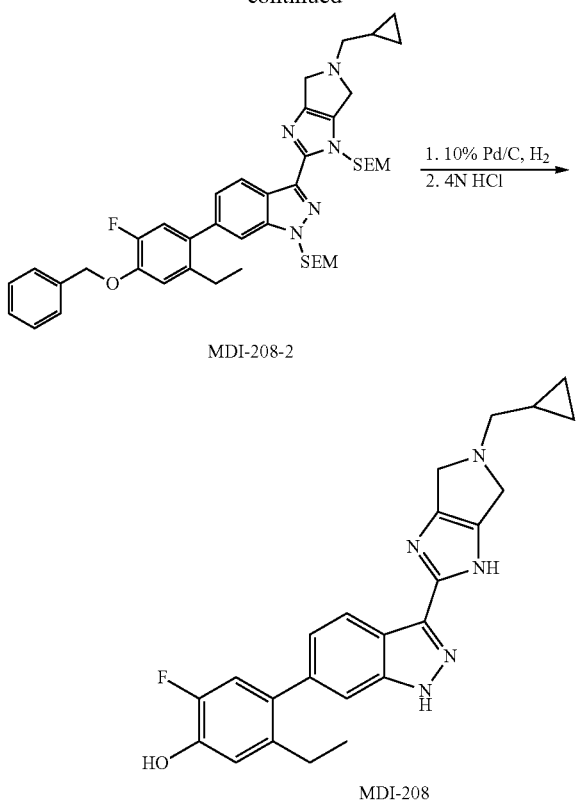

MDI-208-2

MDI-208

Synthesis Method

Synthesis of Intermediate MDI-208-1:(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate Tert-butyl Tert-butyl 2-(6-bromo1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate (500.0 mg, 0.75 mmol), 2-(4-(benzyloxy)-2-ethyl-5-fluorophenyl)-4,4,5,5-tetramethyl-1,3,2-dioxaboran (401.9 mg, 1.13 mmol), Pd(PPh$_3$)$_4$ (86.9 mg, 0.08 mmol) and potassium phosphate (478.9 mg, 2.26 mmol) were dissolved in 1,4-dioxane (30 ml) and water (6 ml). The atmosphere was replaced with nitrogen, which was repeated 3 times. The mixture was heated to 100° C., reacted overnight, and cooled to room temperature. Water was added and the resulting mixture was exacted twice with ethyl acetate, and the organic phases were combined, washed with water and saturated brine, dried over anhydrous sodium sulfate, concentrated, and purified on a silica gel column to afford intermediate MDI-208-1 with a yield of 85.1%.

$^1$H NMR (400 MHz, CDCl3) δ 8.50-8.45 (m, 1H), 7.53-7.37 (m, 6H), 7.26 (d, J=8.0 Hz, 1H), 7.06 (d, J=8.0 Hz, 1H), 6.99 (d, J=12.0 Hz, 1H), 5.97 (d, J=8.0 Hz, 2H), 5.77 (s, 2H), 5.23 (s, 2H), 4.67-4.54 (m, 4H), 3.65-3.59 (m, 4H), 2.55 (d, J=8.0 Hz, 2H), 1.57 (s, 9H), 1.05 (t, J=8.0 Hz, 3H), 0.95-0.89 (m, 4H), 0.02 (s, 9H), 0.01 (s, 9H).

Synthesis of Intermediate MDI-208-2: (6-(4-(benzyloxy)-2-ethyl-5-fluorophenyl)-3-(5-(cyclopropylmethyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazole Tert-butyl 2-(6-(4-(phenoxy)-2-ethyl-5-fluorophenyl)-1-((2-(trimethylsilyl) ethoxy) methyl)-1H-indazol-3-yl)-1-((2-(trimethylsilyl)ethoxy)methyl)-4,6-dihydropyrrolo[3,4-d]imidazol-5(1H)-carboxylate (80.0 mg, 0.10 mmol) was dissolved in 5 ml dichloromethane, to which 1 ml trifluoroacetic acid was added. The mixture was stirred at room temperature for 30 minutes. Water was added and saturated sodium bicarbonate solution was used to adjust pH=9. The resulting mixture was extracted with DCM, and the organic phase was washed with water and saturated brine, dried over anhydrous sodium sulfate, and concentrated. The obtained solid was dissolved in 2 ml DMF, and Et$_3$N (0.1 ml) and bromomethylcyclopropane (27.0 mg, 0.20 mmol) were added. The mixture was heated to 60° C., reacted overnight, and cooled to room temperature. Water was added and the resulting mixture was extracted with EA, washed with water and saturated brine, dried over anhydrous sodium sulfate, concentrated, and purified by silica gel column to afford MDI-208-2 with a yield of 33.5%.

$^1$H NMR (400 MHz, CDCl3) δ 8.48 (d, J=8.0 Hz, 1H), 7.53-7.37 (m, 6H), 7.23 (dd, J=8.0 Hz, J=4.0 Hz, 1H), 7.06 (dd, J=12.0 Hz, J=4.0 Hz, 1H), 6.98 (d, J=8.0 Hz, 1H), 5.94 (d, J=4.0 Hz, 2H), 5.76 (s, 2H), 5.23 (s, 2H), 4.13 (d, J=36.0 Hz, 4H), 3.67-3.58 (m, 4H), 2.80 (d, J=8.0 Hz, 2H), 2.55 (dd, J=12.0 Hz, J=8.0 Hz, 2H), 2.32-2.22 (m, 1H), 1.06 (t, J=8.0 Hz, 3H), 0.92-0.90 (m, 4H), 0.63 (d, J=8.0 Hz, 2H), 0.27 (d, J=4.0 Hz, 2H), 0.03 (s, 9H), 0.02 (s, 9H).

Synthesis of Compound MDI-208: 4-(3-(5-(cyclopropylmethyl)-1,4,5,6-tetrahydropyrrolo[3,4-d]imidazol-2-yl)-1H-indazol-6-yl)-5-ethyl-2-fluorophenol Intermediate MDI-208-2 (28.0 mg, 0.04 mmol) was dissolved in 10 ml methanol, to which 5 mg 10% Pd/C was added. The atmosphere was replaced with hydrogen, which was repeated three times. The mixture was heated to 40° C. and reacted overnight, filtered to remove palladium on carbon, and concentrated. The resulting solid was dissolved in 4 ml methanol, to which 2 ml concentrated hydrochloric acid was added. The mixture was heated to 50° C., reacted for 6 hours and concentrated to give a residue. The residue was dissolved in methanol and concentrated to dryness, which was repeated 3 times. The resulting product was dissolved 1 ml methanol and 2 ml aqueous ammonia was added for neutralization, and the resulting mixture was concentrated to give a residue. The residue was dissolved in methanol and was concentrated to dryness (to remove aqueous ammonia), which was repeated 2 times. The obtained product was purified by a preparation plate to afford 2 mg of the product with a yield of 13.1%.

$^1$H NMR (400 MHz, MeOD-d4) δ 8.27 (dd, J=4.0 Hz, J=8.0 Hz, 1H), 7.42 (s, 1H), 7.17 (dd, J=4.0 Hz, J=8.0 Hz, 1H), 6.97-6.89 (m, 2H), 4.02 (s, 4H), 2.80 (d, J=8.0 Hz, 2H), 2.59-2.53 (m, 2H), 1.10 (m, 4H), 0.66-0.61 (m, 2H), 0.30-0.27 (m, 2H).

Example 10: cyclopropyl (2-(6-(2-ethyl-5-fluoro-4-hydroxyphenyl)-1H-indazol-3-yl)pyrrolo[3,4-d]imidazol-5(1H, 4H,6H)-yl)ketone (MDI-209)

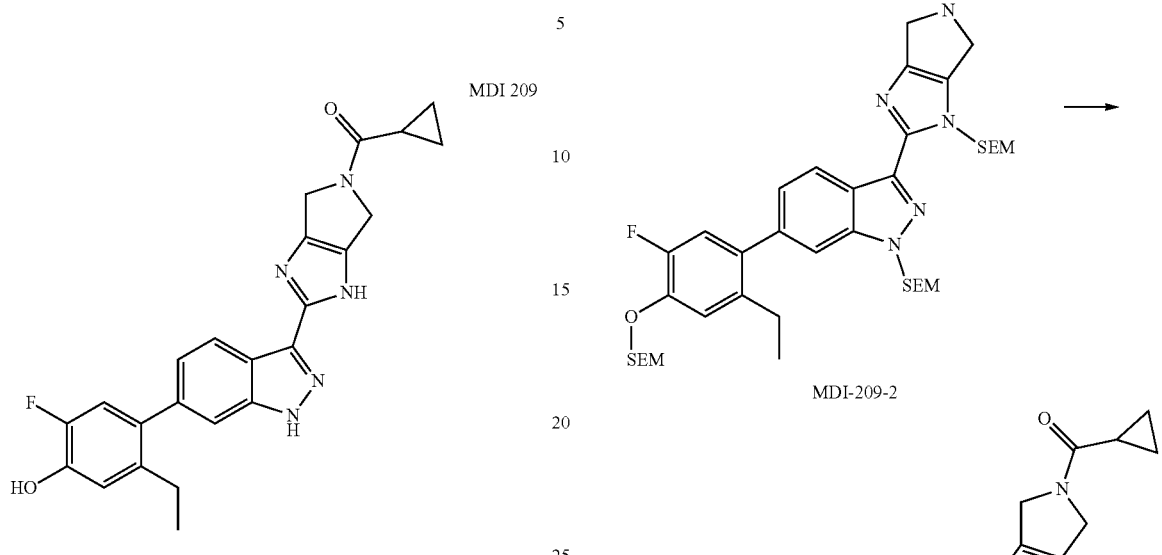

Synthetic Route of MDI-209:

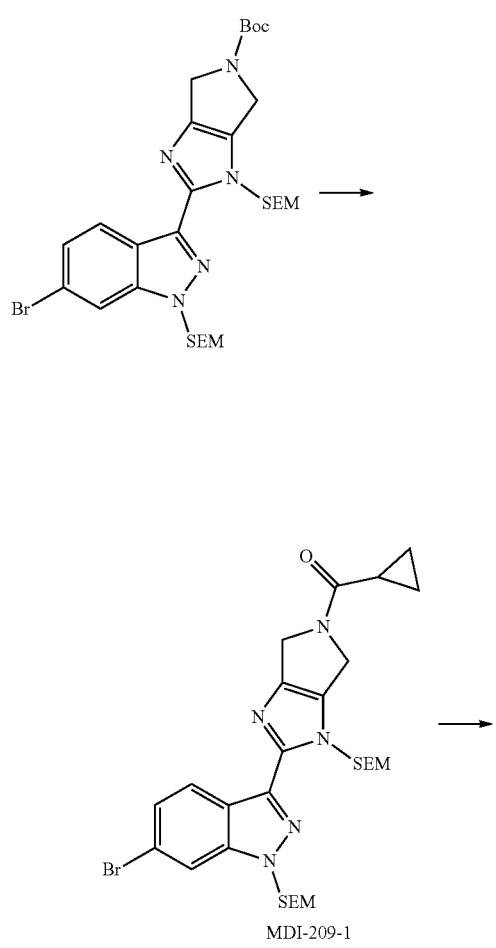

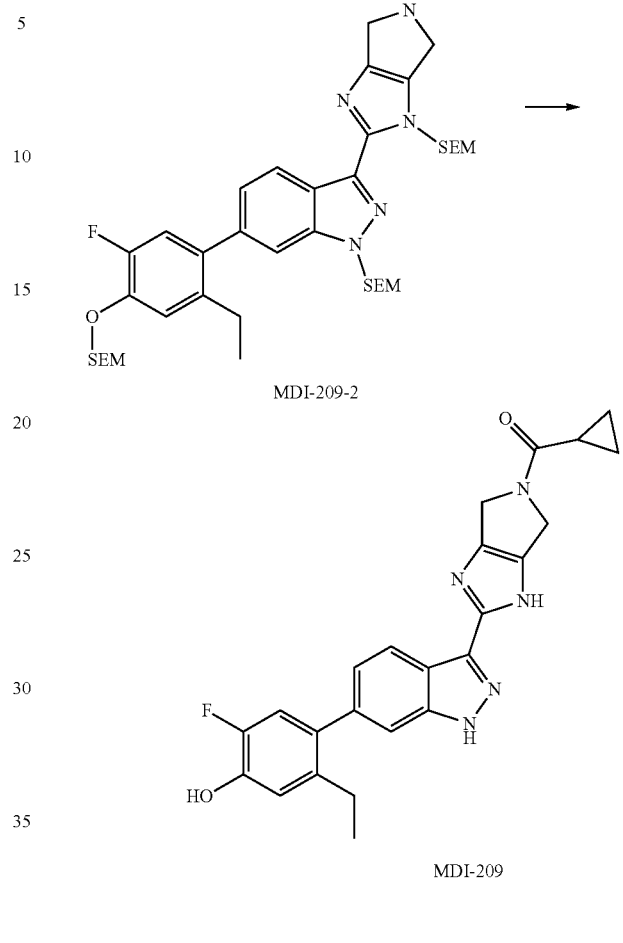

Synthesis Method

Synthesis of Intermediate MDI-209-1: (2-(6-bromo-1-((2-(trimethylsilyl)ethoxy)methyl)-1H-indazol-3-yl)-1-((2-(trimethylsilyl)ethoxy)methyl) pyrrolo[3,4-d]imidazol-5(1H,4H,6H)-yl)(cyclopropyl)ketone The intermediate tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate (80 mg, 0.12 mmol) was dissolved in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 5 ml of DCM, to which triethylamine (24.3 mg, 0.24 mmol) was added. The temperature was lowered to 0° C., and cyclopropylformyl chloride (18.8 mg, 0.18 mmol) was slowly added dropwise. After the dropwise addition was completed, the reaction was warmed up to room temperature and was allowed to react for 1-2 h. Water was added to quench the reaction and liquids were separated. The organic phase was dried over sodium sulfate and concentrated by column chromatography to afford compound MDI-209-1 with a yield of 45%.

$^1$H NMR (400 MHz, CDCl3) δ 8.36 (dd, J=17.8 Hz, J=8.6 Hz, 1H), 7.80-7.79 (m, 1H), 7.41 (d, J=8.6 Hz, 1H), 5.97-

5.92 (m, 2H), 5.71 (d, J=2.4 Hz, 2H), 4.96-4.66 (m, 4H), 3.62-3.54 (m, 4H), 1.78-1.67 (m, 1H), 1.10-1.07 (m, 2H), 0.94-0.84 (m, 6H), −0.05 (s, 9H), −0.08 (s, 9H).

Synthesis of Intermediate MDI-209-2: cyclopropyl (2-(6-(2-ethyl-5-fluoro-4-((2-(trimethylsilyl)ethoxy) methoxy)phenyl)1-((2-(trimethylsilyl)ethoxy) methyl)-1H-indazol-3-yl)-1-((2-(trimethylsilyl) ethoxy)methyl)pyrrolo[3,4-d]imidazol-5(1H, 4H,6H)-yl)ketone The intermediate MDI-209-1 (50.5 mg, 0.08 mmol), (2-((5-ethyl-2-fluoro-4-(4, 4,5,5-tetramethyl-1,3,2-dioxaboran-2-yl)phenoxy)methoxy)ethyl) trimethylsilane (34.8 mg, 0.1 mmol), Pd(dppf)Cl$_2$ (5.9 mg, 0.008 mmol) and potassium phosphate (50.9 mg, 0.24 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted twice with ethyl acetate and the organic phases were combined, washed with water and saturated brine, dried over anhydrous sodium sulfate, concentrated, and purify by silica gel column to afford intermediate MDI-209-2 with a yield of 76.1%.

$^1$H NMR (400 MHz, CDCl3) δ 8.50-8.43 (m, 1H), 7.46-7.45 (m, 1H), 7.25-7.22 (m, 1H), 7.16 (d, J=8.0 Hz, 1H), 7.02 (d, J=12.0 Hz, 1H), 5.99-5.94 (m, 2H), 5.76 (s, 2H), 5.32 (s, 2H), 4.98-4.67 (m, 4H), 3.88-3.84 (m, 2H), 3.64-3.55 (m, 4H), 2.57-2.51 (m, 2H), 1.79-1.68 (m, 1H), 1.07-1.02 (m, 6H), 0.95-0.87 (m, 5H), 0.03 (s, 9H), −0.06-0.08 (m, 18H).

Synthesis of Compound MDI-209: cyclopropyl (2-(6-(2-ethyl-5-fluoro-4-hydroxyphenyl)-1H-indazol-3-yl)pyrrolo[3,4-d]imidazol-5(1H, 4H,6H)-yl)ketone The intermediate MDI-209-2 (50 mg, 0.06 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, to which 2 ml concentrated aqueous ammonia was added. The mixture was concentrated to give a residue. The residue was dissolved in methanol and was concentrated to dryness, which was repeated 3 times. The resulting residue was purified by a preparation plate to afford 10.0 mg of the final product with a yield of 38.1%.

$^1$H NMR (400 MHz, MeOD-d4) δ8.28 (d, J=8.0 Hz, 1H), 7.43 (s, 1H), 7.18 (dd, J=8.4 Hz, J=1.4 Hz, 1H), 6.98 (d, J=12.0 Hz, 1H), 6.92 (d, J=12.0 Hz, 1H), 4.95 (s, 2H), 4.65 (s, 2H), 2.59-2.53 (m, 2H), 1.98-1.89 (m, 1H), 1.08 (t, J=8.0 Hz, 3H), 1.02-1.00 (m, 2H), 0.98-0.92 (m, 2H).

Example 11: 4-(3-(5-(cyclobutylmethyl)-1,4,5,6-tetrahydropyrrolo[3,4-d]imidazol-2-yl)-1H-indazol-6-yl)-5-ethyl-2-fluorophenol (MDI-210)

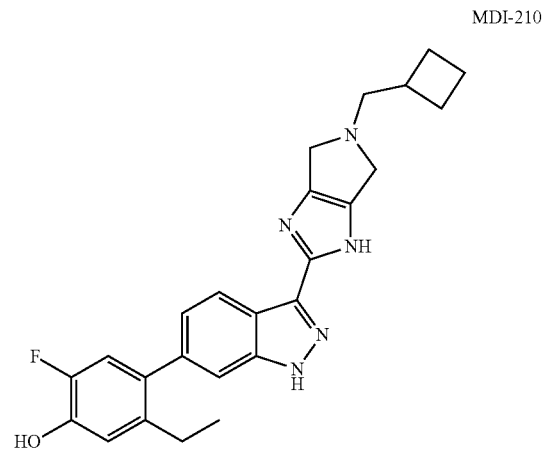 [SMILES: CCc1cc(O)c(F)cc1-c1ccc2c(-c3nc4c([nH]3)CN(CC3CCC3)C4)n[nH]c2c1]

MDI-210

Synthetic Route of MDI-210:

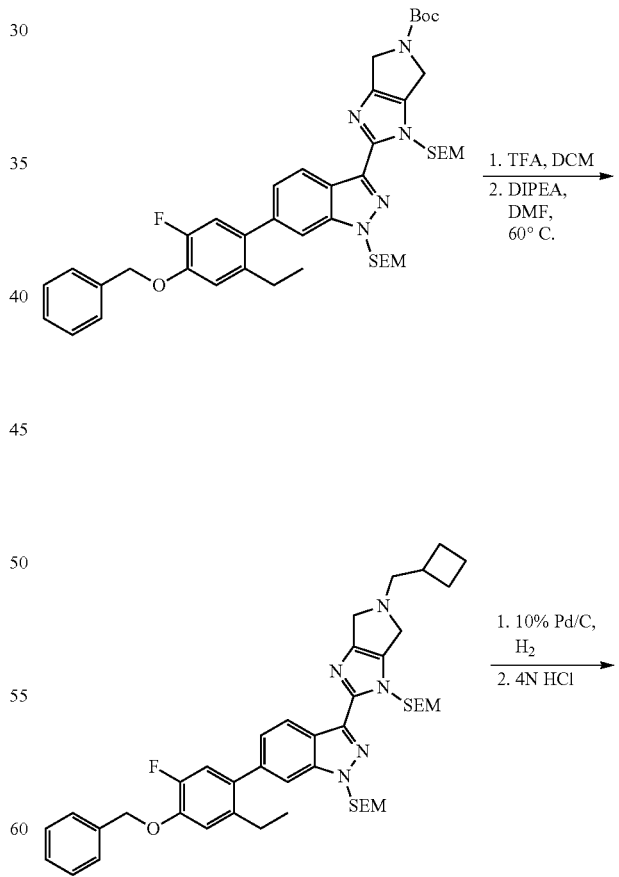

-continued

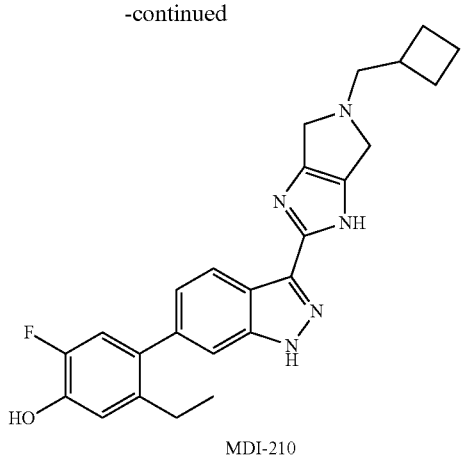

MDI-210

Synthesis Method

Synthesis of Intermediate MDI-210-1: (6-(4-(benzyloxy)-2-ethyl-5-fluorophenyl)-3-(5-(cyclobutylmethyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazole Tert-butyl 2-(6-(4-(phenoxy)-2-ethyl-5-fluorophenyl)-1-((2-(trimethylsilyl) ethoxy)methyl)-1H-indazol-3-yl)-1-((2-(trimethylsilyl)ethoxy)methyl)-4,6-dihydropyrrolo[3,4-d] imidazol-5(1H)-carboxylate (80.0 mg, 0.10 mmol) was dissolved in 5 ml dichloromethane, to which 1 ml trifluoroacetic acid was added. The mixture was stirred at room temperature for 30 minutes. Water was added and saturated sodium bicarbonate solution was used to adjust pH=9. The resulting mixture was extracted with DCM, washed with water and saturated brine, dried over sodium sulfate and concentrated. The obtained solid was dissolved in 3 ml DMF, followed by addition of DIPEA (126.8 mg, 0.98 mmol) and bromomethylcyclobutane (29.3 mg, 0.20 mmol). The mixture was heated to 60° C., reacted overnight, and cooled to room temperature. Water was added and the resulting mixture was extracted with EA, washed with water and saturated brine, dried over anhydrous sodium sulfate, concentrated, and purified by silica gel column to afford MDI-210-1 with a yield of 35.1%.

$^1$H NMR (400 MHz, CDCl3) δ 8.47 (dd, J=8.0 Hz, J=4.0 Hz, 1H), 7.53-7.51 (m, 2H), 7.46-7.37 (m, 4H), 7.23 (dd, J=8.0 Hz, J=4.0 Hz, 1H), 7.06 (d, J=12.0 Hz, 1H), 6.98 (d, J=8.0 Hz, 1H), 5.91 (s, 2H), 5.76 (s, 2H), 5.22 (s, 2H), 4.02 (s, 2H), 3.94 (s, 2H), 3.65-3.56 (m, 4H), 2.93 (d, J=8.0 Hz, 2H), 2.68-2.64 (m, 1H), 2.57 (dd, J=16.0 Hz, J=8.0 Hz, 2H), 2.21-2.14 (m, 2H), 1.97-1.67 (m, 4H), 1.06 (t, J=8.0 Hz, 3H), 0.94-0.89 (m, 4H), 0.02 (s, 18H).

Synthesis of Compound MDI-210: 4-(3-(5-(cyclobutylmethyl)-1,4,5,6-tetrahydropyrrolo[3,4-d]imidazol-2-yl)-1H-indazol-6-yl)-5-ethyl-2-fluorophenol Intermediate MDI-210-1 (35.0 mg, 0.05 mmol) was dissolved in 10 ml methanol, to which 5 mg 10% Pd/C was added. The atmosphere was replaced with hydrogen, which was repeated three times. The mixture was heated to 40° C. and reacted overnight, filtered to remove palladium on carbon, and concentrated. The resulting solid was dissolved in 4 ml methanol, to which 2 ml concentrated hydrochloric acid was added. The mixture was heated to 50° C., reacted for 6 hours and concentrated to give a residue. The residue was dissolved in methanol and was concentrated to dryness, which was repeated 3 times. The resulting product was dissolved 1 ml methanol and 2 ml concentrated aqueous ammonia was added for neutralization, and the resulting mixture was concentrated to give a residue. The residue was dissolved in methanol and was concentrated to dryness, which was repeated 2 times. The obtained product was purified by a preparation plate to afford 4 mg of the product with a yield of 20.7%.

$^1$H NMR (400 MHz, MeOD-d4) δ 8.27 (dd, J=4.0 Hz, J=8.0 Hz, 1H), 7.42 (s, 1H), 7.17 (dd, J=4.0 Hz, J=8.0 Hz, 1H), 6.97-6.89 (m, 2H), 3.98 (s, 4H), 3.00 (d, J=8.0 Hz, 2H), 2.72-2.68 (m, 1H), 2.59-2.53 (m, 2H), 2.21-2.18 (m, 2H), 1.89-1.85 (m, 4H), 1.07 (t, J=8.0 Hz, 3H).

Example 12: cyclobutyl (2-(6-(2-ethyl-5-fluoro-4-hydroxyphenyl)-1H-indazol-3-yl)pyrrolo[3,4-d]imidazol-5(1H, 4H,6H)-yl)ketone (MDI-211)

MDI 211

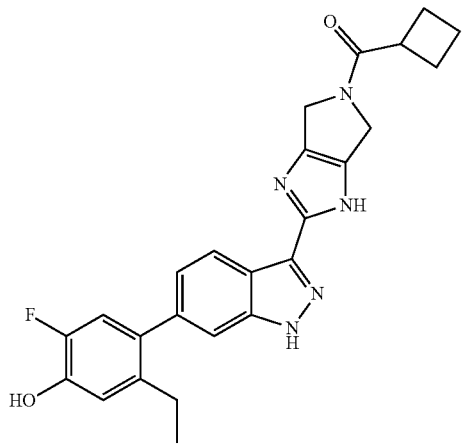

Synthetic Route of MDI-211:

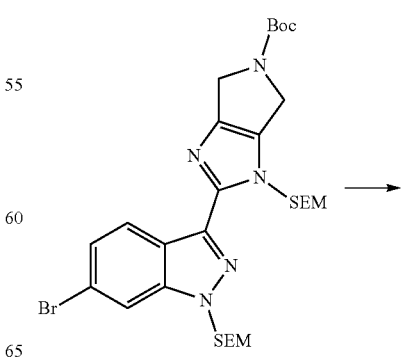

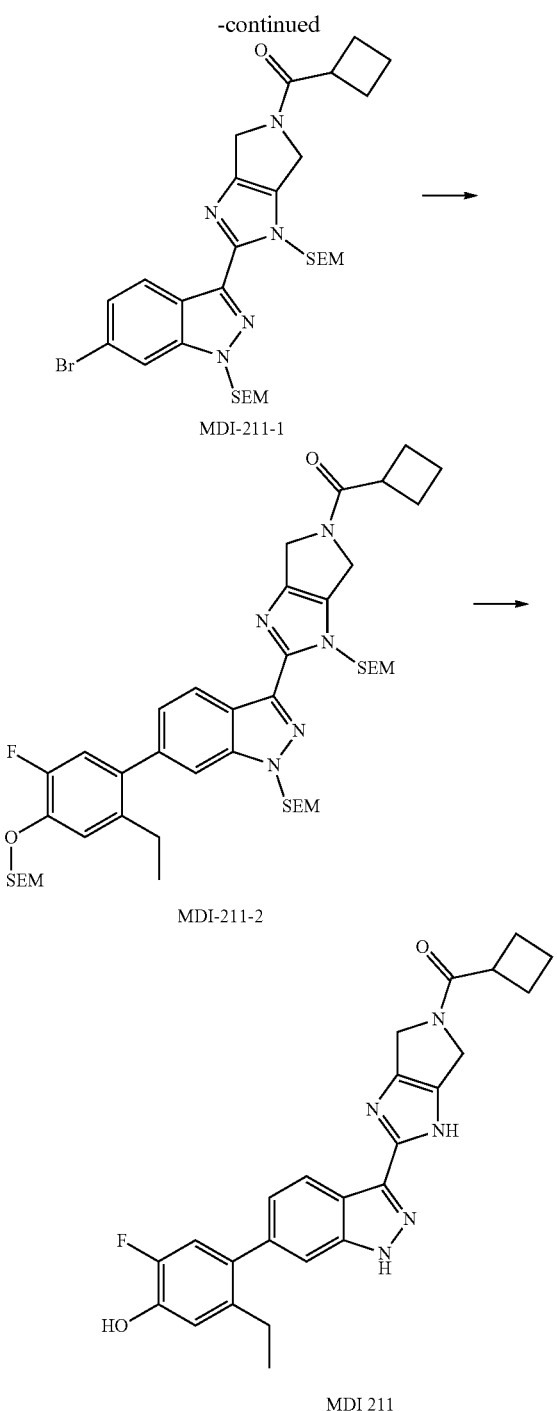

Synthesis Method

Synthesis of Intermediate MDI-211-1: (2-(6-bromo-1-((2-(trimethylsilyl)ethoxy)methyl)-1H-indazol-3-yl)-1-((2-(trimethylsilyl)ethoxy) methyl) pyrrolo[3,4-d]imidazol-5(1H, 4H,6H)-yl)(cyclobutyl)ketone The intermediate tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5 (1H)-carboxylate (80 mg, 0.12 mmol) was dissolved in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 5 ml of DCM, to which triethylamine (24.3 mg, 0.24 mmol) was added. The temperature was reduced to 0° C. and cyclobutyl carbonyl chloride (21.3 mg, 0.18 mmol) was slowly added dropwise. After the dropwise addition was completed, the reaction was warmed up to room temperature and was allowed to react for 1-2 h. Water was added to quench the reaction and liquids were separated. The organic phase was dried over sodium sulfate and concentrated by column chromatography to afford compound MDI-211-1 with a yield of 43%.

$^1$H NMR (400 MHz, CDCl3) δ 8.39-8.31 (m, 1H), 7.77-7.76 (m, 1H), 7.42-7.38 (m, 1H), 5.92-5.89 (m, 2H), 5.71-5.70 (m, 2H), 4.73-4.57 (m, 4H), 3.60-3.54 (m, 4H), 3.37-3.27 (m, 1H), 2.46-2.39 (m, 2H), 2.34-2.20 (m, 3H), 2.10-1.93 (m, 3H), 0.93-0.88 (m, 4H), −0.05 (s, 9H), −0.09 (s, 9H).

Synthesis of Intermediate MDI-211-2: cyclobutyl (2-(6-(2-ethyl-5-fluoro-4-((2-(trimethylsilyl)ethoxy) methoxy)phenyl)1-((2-(trimethylsilyl)ethoxy) methyl)-1H-indazol-3-yl)-1-((2-(trimethylsilyl) ethoxy)methyl)pyrrolo[3,4-d]imidazol-5(1H, 4H,6H)-yl)ketone The intermediate MDI-211-1 (51.6 mg, 0.08 mmol), (2-((5-ethyl-2-fluoro-4-(4, 4,5,5-tetramethyl-1,3,2-dioxaboran-2-yl)phenoxy)methoxy)ethyl)trimethylsilane (34.8 mg, 0.1 mmol), Pd(dppf)Cl$_2$ (5.9 mg, 0.008 mmol) and potassium phosphate (50.9 mg, 0.24 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted twice with ethyl acetate, and the organic phases were combined, washed with water and saturated brine, dried over anhydrous sodium sulfate, concentrated, and purified by silica gel column to afford intermediate MDI-211-2 with a yield of 75.2%.

$^1$H NMR (400 MHz, CDCl3) δ 8.49-8.42 (m, 1H), 7.47-7.45 (m, 1H), 7.25-7.22 (m, 1H), 7.16 (d, J=8.0 Hz, 1H), 7.02 (d, J=12.0 Hz, 1H), 5.96-5.93 (m, 2H), 5.75 (s, 2H), 5.32 (s, 2H), 4.75-4.58 (m, 4H), 3.88-3.83 (m, 2H)), 3.63-3.55 (m, 4H), 3.38-3.28 (m, 1H), 2.57-2.51 (m, 2H), 2.48-2.20 (m, 4H), 2.06-2.00 (m, 1H), 1.96-1.92 (m, 1H), 1.08-1.05 (m, 3H), 0.93-0.85 (m, 6H), 0.03 (s, 9H), −0.06-0.08 (m, 18H).

Synthesis of Compound MDI-211: cyclobutyl (2-(6-(2-ethyl-5-fluoro-4-hydroxyphenyl)-1H-indazol-3-yl)pyrrolo[3,4-d]imidazol-5(1H, 4H,6H)-yl)ketone The intermediate MDI-211-2 (45 mg, 0.054 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, 2 ml of concentrated aqueous ammonia was added, and the mixture was concentrated to give a residue. The residue was dissolved in methanol and was concentrated to dryness, which was repeated 3 times. The resulting residue was separated by a preparation plate to afford 8.2 mg of the final product with a yield of 34.2%.

$^1$H NMR (400 MHz, MeOD-d4) δ 8.27 (d, J=8.0 Hz, 1H), 7.43 (s, 1H), 7.17 (dd, J=8.4, 1.4 Hz, 1H), 6.93 (dd, J=20.0 Hz, J=12.0 Hz, 2H), 4.68-4.63 (m, 4H), 3.54-3.46 (m, 1H), 2.57-2.53 (m, 2H), 2.43-2.26 (m, 4H), 2.16-2.04 (m, 1H), 1.98-1.89 (m, 1H), 1.08 (t, J=8.0 Hz, 3H).
Example 13: (2-(6-(2-ethyl-5-fluoro-4-hydroxyphenyl)-1H-indazol-3-yl)pyrrolo[3,4-d]imidazol-5(1H,4H,6H)-yl)(3-hydroxylcyclobutyl)ketone (MDI-213)
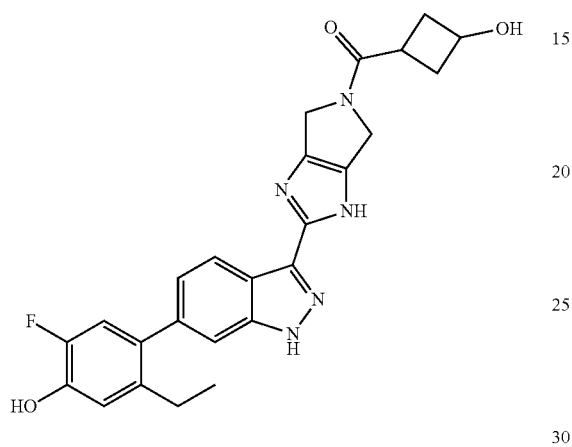
Synthetic Route of MDI-213:
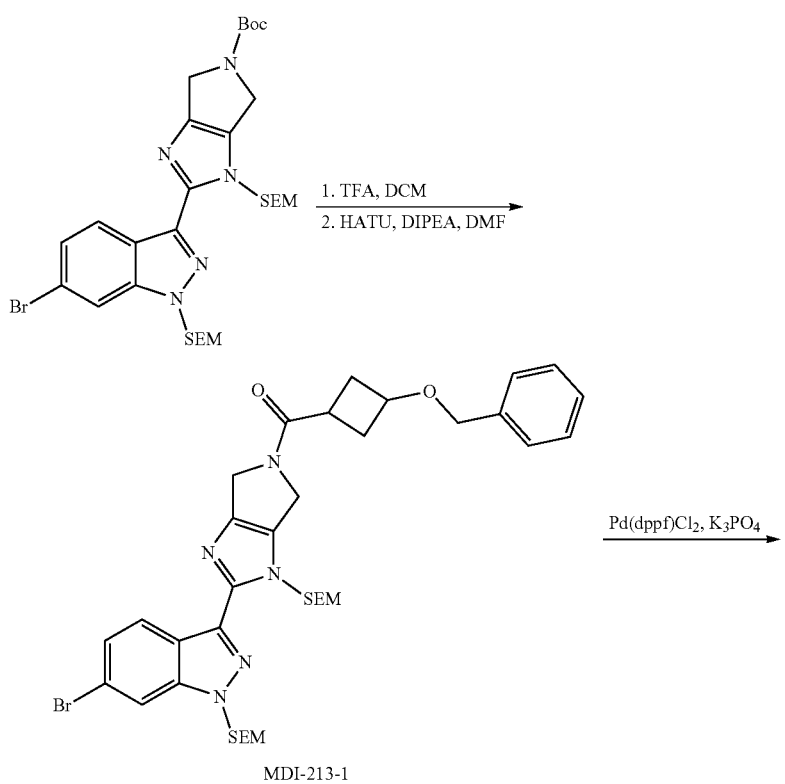

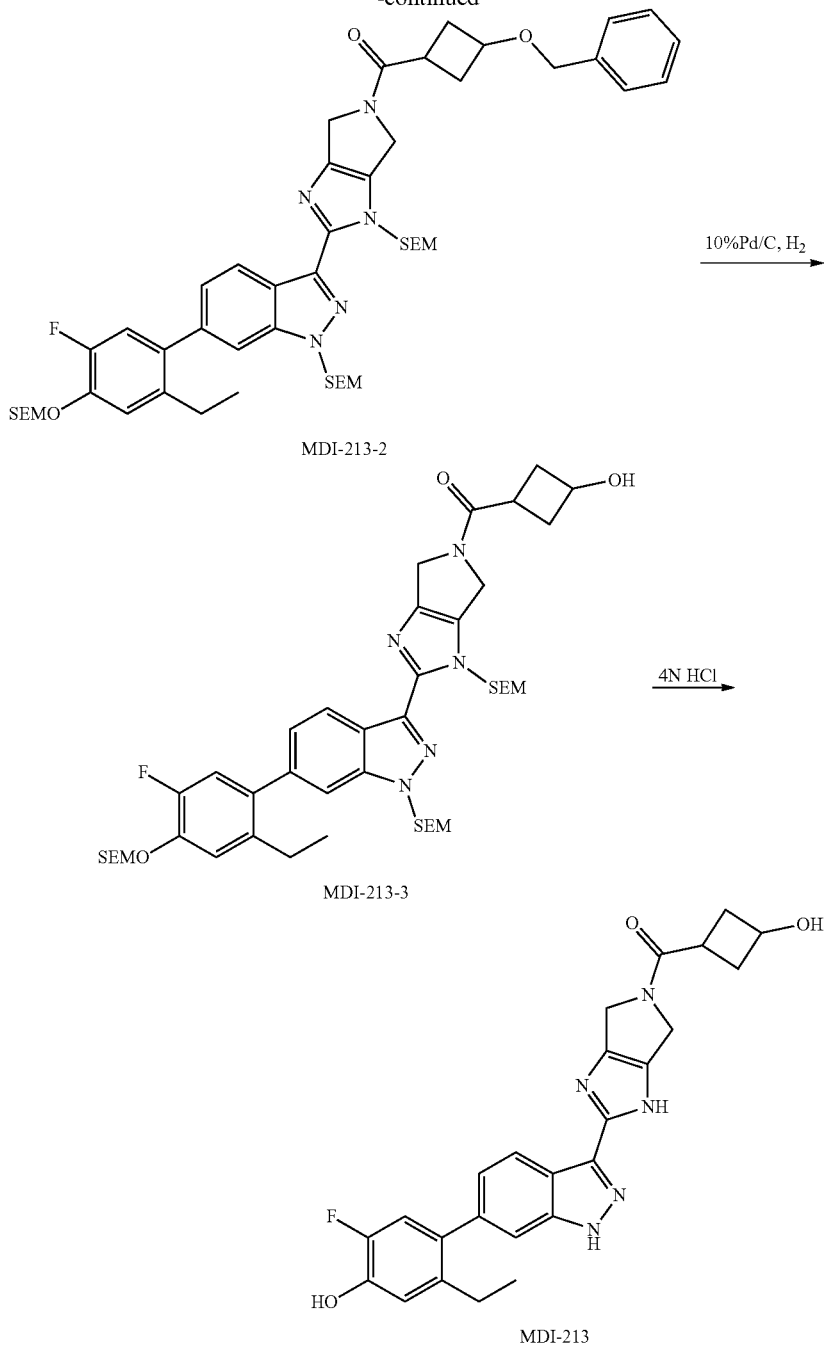

Synthesis Method

Synthesis of Intermediate MDI-213-1: (3-(benzyloxy)cyclobutyl)(2-(6-bromo-1-((2-(trimethylsilyl)ethoxy)methyl)-1H-indazol-3-yl)-1-((2-(trimethylsilyl) ethoxy)methyl)pyrrolo[3,4-d]imidazol-5(1H,4H,6H)-yl)ketone The intermediate 3-benzyloxy-cyclobutanecarboxylic acid (44.6 mg, 0.22 mmol) and N,N-diisopropylethylamine (69.9 mg, 0.54 mmol) were dissolved in DMF, to which HATU (82.3 mg, 0.22 mmol) was added. The mixture was reacted at room temperature for 10 minutes. Intermediate tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate (120.0 mg, 0.18 mmol) was dissolved in 5 ml dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in DMF, and then slowly added to the previous reaction solution. It was allowed to react at room temperature overnight, and water was added to quench the reaction. The resulting mixture was extracted twice with ethyl acetate, and the organic phases were combined, washed with water and saturated brine, dried over anhydrous sodium sulfate, concentrated, and purified by silica gel column to afford intermediate MDI-213-1 with a yield of 35.3%.

$^1$H NMR (400 MHz, CDCl3) δ 8.41 (dd, J=8.0 Hz, J=20.0 Hz, 1H), 7.80-7.78 (m, 1H), 7.43-7.31 (m, 6H), 5.94 (d, J=12.0 Hz, 2H), 5.73 (d, J=4.0 Hz, 2H), 4.76-4.61 (m, 4H), 4.49 (s, 2H), 4.10-4.04 (m, 1H), 3.63-3.57 (m, 4H)), 2.80-2.78 (m, 1H), 2.58-2.53 (m, 2H), 2.46-2.41 (m, 2H), 0.96-0.90 (m, 4H), 0.02 (s, 9H), −0.03 (s, 9H).

Synthesis of Intermediate MDI-213-2: (3-(benzyloxy)cyclobutyl)(2-(6-(2-ethyl-5-fluoro-4-((2-(trimethylsilyl)ethoxy)methoxy)phenyl)-1-((2-(trimethylsilyl) ethoxy)methyl)-1H-indazol-3-yl)-1-((2-(trimethylsilyl)ethoxy)methyl)pyrrolo[3,4-d] imidazol-5(1H, 4H,6H)-yl)ketone Intermediate MDI-213-1 (48.0 mg, 0.06 mmol), intermediate MDI-10-2 (30.4 mg, 0.08 mmol), Pd(dppf)Cl2 (4.7 mg, 0.01 mmol) and potassium phosphate (40.6 mg, 0.19 mmol) were dissolved in 1,4-dioxane (20 ml) and water (4 ml). The atmosphere was replaced with nitrogen, which was repeated 3 times. The mixture was heated to 100° C., reacted overnight, and cooled to room temperature. Water was added, and the resulting mixture was extracted 2 times with ethyl acetate, and the organic phases were combined, washed with water and saturated brine, dried over anhydrous sodium sulfate, concentrated, and purified by silica gel column to afford intermediate MDI-213-2 with a yield of 71.5%.

$^1$H NMR (400 MHz, CDCl3) δ 8.46 (dd, J=8.0 Hz, J=4.0 Hz, 1H), 7.49-7.48 (m, 1H), 7.38-7.32 (m, 5H), 7.28-7.24 (m, 1H), 7.19 (d, J=8.0 Hz, 1H), 7.05 (d, J=12.0 Hz, 1H), 5.99 (d, J=12.0 Hz, 2H), 5.78 (d, J=4.0 Hz, 2H), 5.34 (s, 2H), 4.78-4.62 (m, 4H), 4.50 (s, 2H), 4.12-4.05 (m, 1H), 3.90-3.86 (m, 2H), 3.66-3.58 (m, 4H), 2.80-2.78 (m, 1H), 2.59-2.54 (m, 4H), 2.46-2.44 (m, 2H), 1.10-1.05 (m, 3H), 0.95-0.90 (m, 6H), 0.06 (s, 9H), −0.04 (s, 18H).

Synthesis of Intermediate MDI-213-3: (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl) pyrrolo[3,4-d]imidazol-5(1H,4H,6H)-yl)(3-hydroxylcyclobutyl)ketone Intermediate MDI-213-2 (43.0 mg, 0.05 mmol) was dissolved in 10 ml methanol, and 5 mg of 10% Pd/C was added. The atmosphere was replaced with hydrogen, which was repeated three times. The mixture was reacted overnight at room temperature, filtered off palladium carbon, and concentrated to afford intermediate MDI-213-3, which was directly used in the next step.

Synthesis of Compound MDI-213: (2-(6-(2-ethyl-5-fluoro-4-hydroxyphenyl)-1H-indazol-3-yl)pyrrolo[3,4-d]imidazol-5(1H,4H,6H)-yl)(3-hydroxyl cyclobutyl)ketone The intermediate MDI-213-3 (36.1 mg, 0.05 mmol) was dissolved in 4 ML methanol and 2 ml concentrated hydrochloric acid was added. The mixture was heated to 50° C., reacted for 6 hours, and concentrated to give a residue. The residue was dissolved in methanol and was concentrated to dryness, which was repeated 3 times. The resulting product was dissolved 1 ml methanol and 2 ml aqueous ammonia was added for neutralization, and the resulting mixture was concentrated to give a residue. The residue was dissolved in methanol and was concentrated to dryness, which was repeated 2 times. The obtained product was purified by a preparation plate to afford 4 mg of the product with a yield of 16.4%.

$^1$H NMR (400 MHz, MeOD-d4) δ 8.28 (dd, J=4.0 Hz, J=8.0 Hz, 1H), 7.43-7.42 (m, 1H), 7.19 (dd, J=4.0 Hz, J=8.0 Hz, 1H), 6.97-6.89 (m, 2H), 4.72-4.62 (m, 4H), 4.23-4.20 (m, 1H), 2.95-2.91 (m, 1H), 2.63-2.53 (m, 4H), 2.26-2.18 (m, 2H), 1.10 (t, J=8.0 Hz, 3H).

Example 14: (2-(6-(2-ethyl-5-fluoro-4-hydroxyphenyl)-1H-indazol-3-yl)-pyrrolo[3,4-d]imidazol-5-(1H, 4H,6H)-yl)(pyridazin-4-yl)ketone (MDI-214)

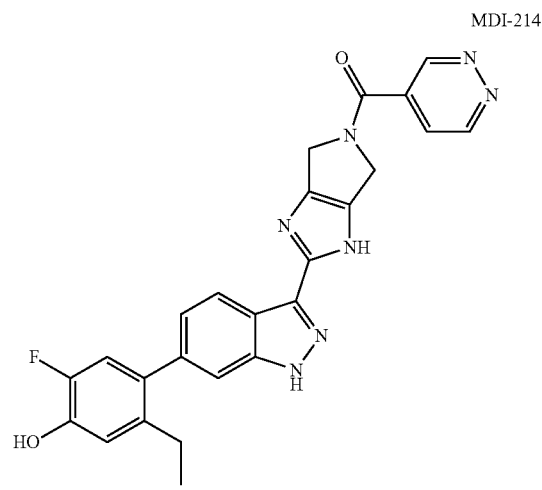 [SMILES: CCc1cc(O)c(F)cc1-c1ccc2c(-c3nc4c([nH]3)CN(C(=O)c3ccnnc3)C4)n[nH]c2c1]

MDI-214

Synthetic Route of MDI-214:

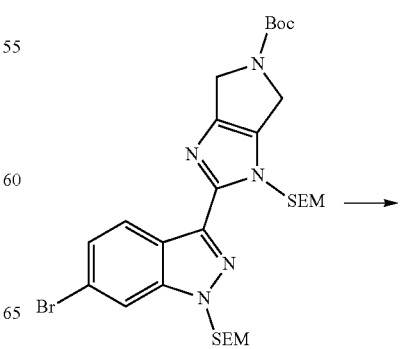

-continued

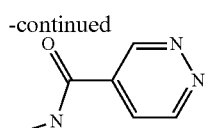

MDI-214-1

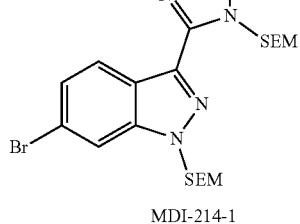

MDI-214-2

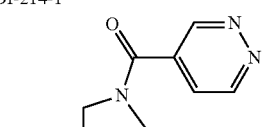

MDI-214

Synthesis Method

Synthesis of Intermediate MDI-214-1: (2-(6-bromo-1-((2-(trimethylsilyl)ethoxy)methyl)-1H-indazol-3-yl)-1-((2-(trimethylsilyl)ethoxy)methyl)-pyrrolo[3,4-d]imidazol-5-(1H, 4H,6H)-yl)(pyridazin-4-yl)ketone Tert-butyl 2-(6-bromo-1-((2-(trimethylsilyl)ethoxy) methyl)-1H-indazol-3-yl)-1-((2-(trimethylsilyl)ethoxy) methyl)-4,6-dihydropyrrolo[3,4-d]imidazol-5(1H)-carboxylate (45 mg, 0.06 mmol) was dissolve in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 5 ml of DMF, followed by addition of pyridazine-4-carboxylic acid (9 mg, 0.07 mmol), HATU (32 mg, 0.08 mmol) and DIPEA (0.05 ml, 0.30 mmol). It was allowed to react at room temperature for 16 hours and water was added to quench the reaction. The mixture was extracted twice with EA, and the organic phases were combined, washed with water and saturated brine, dried over anhydrous sodium sulfate, concentrated, and purified by silica gel column to afford 23 mg of intermediate MDI-214-1 with a yield of 51.2%.

$^1$H NMR (400 MHz, CDCl3) δ 9.45-9.50 (m, 2H), 8.34 (dd, J=38.3 Hz, J=8.6 Hz, 1H), 7.79 (t, J=1.9 Hz, 1H), 7.69-7.66 (m, 1H), 7.45-7.41 (m, 1H), 5.92 (d, J=31.9 Hz, 2H), 5.72 (d, J=5.3 Hz, 2H), 4.95-4.93 (m, 2H), 4.68-4.66 (m, 2H), 3.65-3.54 (m, 4H), 1.08-0.77 (m, 4H), 0.05-0.13 (m, 18H).

Synthesis of Intermediate MDI-214-2: (2-(6-(2-ethyl-5-fluoro-4-((2-(trimethylsilyl)ethoxy)methoxy) phenyl)-1-((2-(trimethylsilyl)ethoxy)methyl)-1H-indazol-3-yl)-1-((2-(trimethylsilyl)ethoxy)methyl)-pyrrolo[3,4-d]imidazol-5-(1H,4H,6H)-yl)(pyridazin-4-yl)ketone The intermediate MDI-214-1 (23 mg, 0.03 mmol), (2-((5-ethyl-2-fluoro-4-(4,4,5,5-tetramethyl-1,3,2-dioxaboran-2-yl)phenoxy)methoxy)ethyl)trimethylsilane (20 mg, 0.05 mmol), Pd(dppf)Cl$_2$ (3 mg, 0.003 mmol) and potassium phosphate (22 mg, 0.10 mmol) were dissolved in 1,4-dioxane (5 ml) and water (1 ml). The atmosphere was replaced with nitrogen, which was repeated 3 times. The mixture was heated to 100° C., reacted for 16 h, and cooled to room temperature. Water was added and the resulting mixture was extracted 2 times with ethyl acetate and the organic phases were combined, washed with water and saturated brine, dried over anhydrous sodium sulfate, concentrated, and purified by silica gel column to afford 25 mg of intermediate MDI-214-2 with a yield of 84.7%.

$^1$H NMR (400 MHz, CDCl3) δ 9.46-9.42 (m, 2H), 8.62-8.31 (m, 1H), 7.71-7.67 (m, 1H), 7.51-7.47 (m, 1H), 7.25 (dd, J=8.4, 1.3 Hz, 1H), 7.18 (dd, J=8.4, 4.0 Hz, 1H), 7.03 (dd, J=11.6, 6.0 Hz, 1H), 5.96 (d, J=31.6 Hz, 2H), 5.78 (d, J=5.2 Hz, 2H), 5.34 (d, J=2.7 Hz, 2H), 5.02-4.95 (m, 2H), 4.71-4.67 (m, 2H), 3.90-3.86 (m, 2H), 3.66-3.62 (m, 4H), 2.57-2.54 (m, 2H), 1.14-0.81 (m, 9H), 0.06 (d, J=2.1 Hz, 9H), −0.04 (dd, J=12.1 Hz, J=8.6 Hz, 18H).

Synthesis of Compound MDI-214: (2-(6-(2-ethyl-5-fluoro-4-hydroxyphenyl)-1H-indazol-3-yl)pyrrolo[3,4-d]imidazol-5-(1H,4H,6H)-yl)(pyridazin-4-yl)ketone Intermediate MDI-214-2 (25 mg, 0.03 mmol) was dissolved in methanol (4 ml), to which concentrated hydrochloric acid (2 ml) was added. The mixture was heated to 50° C., reacted for 6 hours, and concentrated to give a residue. The residue was dissolved in methanol and was concentrated to dryness, which was repeated 3 times. The resulting residue was dissolve in methanol, 1 ml of aqueous ammonia was added, and then the mixture was concentrated, and purified by a preparation plate to afford 4 mg of the final product with a yield of 29.4%.

$^1$H NMR (400 MHz, MeOD-d4) δ 9.48 (dd, J=2.3, J=1.3 Hz, 1H), 9.42 (dd, J=5.2, J=1.3 Hz, 1H), 8.26 (s, 1H), 8.02 (dd, J=5.3, J=2.2 Hz, 1H), 7.43 (d, J=1.1 Hz, 1H), 7.17 (d, J=8.2 Hz, 1H), 6.93 (dd, J=19.7, J=10.4 Hz, 2H), 4.90 (s, 2H), 4.73 (s, 2H), 2.55 (q, J=7.5 Hz, 2H), 1.08 (t, J=7.5 Hz, 3H).

Example 15: (2-(6-(2-ethyl-5-fluoro-4-hydroxyphenyl)-1H-indazol-3-yl)-pyrrolo[3,4-d]imidazol-5-(1H,4H,6H)-yl)(pyridazin-3-yl)ketone (MDI-215)

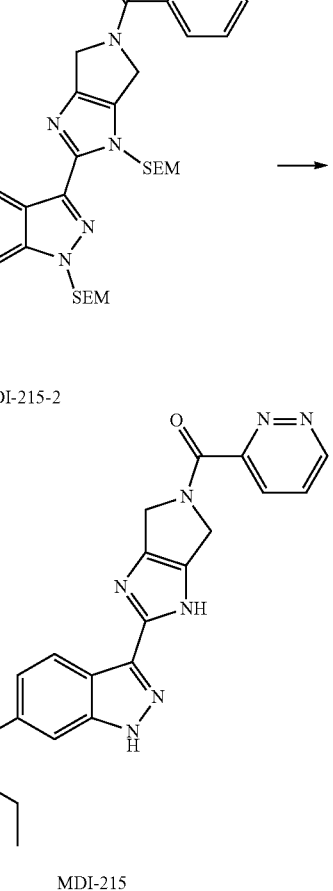

MDI-215

Synthetic Route of MDI-215:

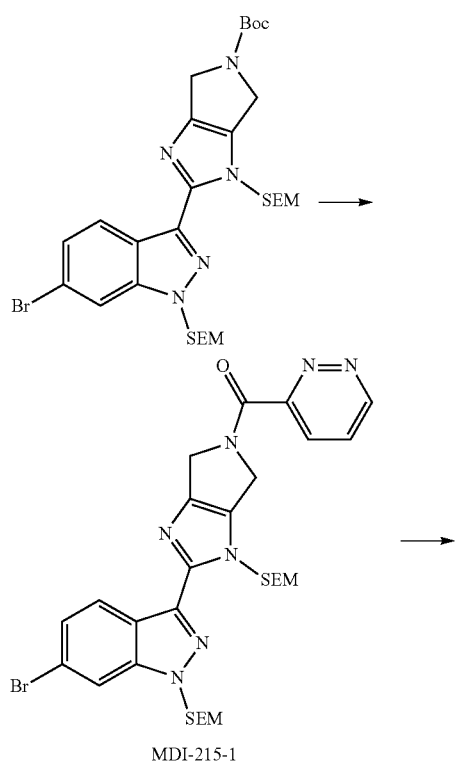

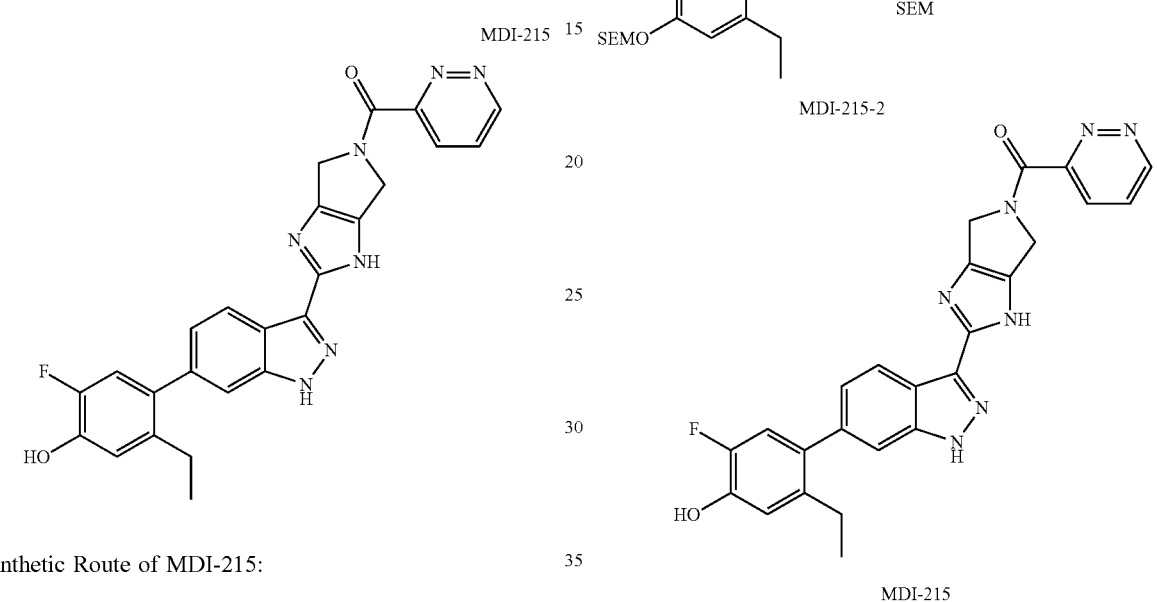

Synthesis Method

Synthesis of Intermediate MDI-215-1: (2-(6-bromo-1-((2-(trimethylsilyl)ethoxy)methyl)-1H-indazol-3-yl)-1-((2-(trimethylsilyl)ethoxy)methyl)-pyrrolo[3,4-d]imidazol-5-(1H,4H,6H)-yl)(pyridazin-3-yl)ketone Tert-butyl 2-(6-bromol-((2-(trimethylsilyl)ethoxy)methyl)-1H-indazol-3-yl)-1-((2-(trimethylsilyl) ethoxy)methyl)-4,6-dihydropyrrolo[3,4-d]imidazole-5(1H)-carboxylate (200 mg, 0.30 mmol) was dissolved in 10 ml dichloromethane, and 2 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 10 ml of DMF, followed by addition of pyridazine-3-carboxylic acid (45 mg, 0.36 mml), HATU (164 mg, 0.43 mmol) and DIPEA (0.18 ml, 1.08 mmol). It was allowed to react at room temperature for 16 hours and water was added to quench the reaction. The resulting mixture was extracted twice with EA, and the organic phases were combined, washed with water and saturated brine, dried over anhydrous sodium sulfate, concentrated and purified by silica gel column to afford 98 mg of intermediate MDI-215-1 with a yield of 49.2%.

$^1$H NMR (400 MHz, CDCl3) δ 9.35-9.30 (m, 1H), 8.40 (dd, J=19.4 Hz, J=8.6 Hz, 1H), 8.25 (dd, J=4.0 Hz, J=8.0 Hz,

1H), 7.79 (dd, J=3.1, J=1.5 Hz, 1H), 7.72-7.68 (m, 1H), 7.46-7.43 (m, 1H), 5.95 (d, J=21.7 Hz, 2H), 5.73 (d, J=3.2 Hz, 2H), 5.40-5.24 (m, 2H), 5.06-4.98 (m, 2H), 3.66-3.56 (m, 4H), 0.98-0.87 (m, 4H), 0.00-0.05 (m, 9H), −0.09 (s, 9H).

Synthesis of Intermediate MDI-215-2: (2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-pyrrolo[3,4-d]imidazol-5-(1H,4H,6H)-yl)(pyridazin-3-yl)ketone The intermediate MDI-215-1 (98 mg, 0.15 mmol), (2-((5-ethyl-2-fluoro-4-(4, 4,5,5-tetramethyl-1,3,2-dioxaboran-2-yl)phenoxy)methoxy)ethyl)trimethylsilane (100 mg, 0.25 mmol), Pd(dppf)Cl$_2$ (15 mg, 0.015 mmol) and potassium phosphate (110 mg, 0.50 mmol) were dissolved in 1,4-dioxane (25 ml) and water (5 ml). The atmosphere was replaced with nitrogen, which was repeated 3 times. The mixture was heated to 100° C., reacted for 16 h, and cooled to room temperature. Water was added and the resulting mixture was extracted twice with ethyl acetate, and the organic phases were combined, washed with water and saturated brine, dried over anhydrous sodium sulfate, concentrated, and purified on a silica gel column to afford 97 mg of intermediate MDI-215-2 with a yield of 77.1%.

$^1$H NMR (400 MHz, CDCl3) δ 9.33-9.32 (d, J=4.0 Hz, 1H), 8.52-8.48 (m, 1H), 8.26-8.21 (m, 1H), 7.71-7.69 (m, 1H), 7.48 (dd, J=2.8 Hz, J=1.2 Hz, 1H), 7.26 (dd, J=8.4 Hz, J=1.3 Hz, 1H), 7.18 (dd, J=8.4 Hz, J=2.4 Hz, 1H), 7.04 (dd, J=11.6 Hz, J=4.2 Hz, 1H), 5.99 (d, J=22.2 Hz, 2H), 5.78 (d, J=3.0 Hz, 2H), 5.40 (d, J=2.4 Hz, 1H), 5.34 (s, 2H), 5.25 (t, J=2.1 Hz, 1H), 5.08-4.99 (m, 2H), 3.90-3.88 (m, 2H), 3.67-3.58 (m, 4H), 2.56 (q, J=7.5 Hz, 2H), 1.10-0.77 (m, 9H), 0.06 (d, J=1.2 Hz, 9H), −0.01-0.10 (m, 18H).

Synthesis of Compound MDI-215: (2-(6-(2-ethyl-5-fluoro-4-hydroxyphenyl)-1H-indazol-3-yl)-pyrrolo[3,4-d]imidazol-5-(1H,4H,6H)-yl)(pyridazin-3-yl)ketone Intermediate MDI-215-2 (97 mg, 0.11 mmol) was dissolved in methanol (10 ml), to which concentrated hydrochloric acid (5 ml) was added. The mixture was heated to 50° C., reacted for 6 hours, and concentrated to give a residue. The residue was dissolved in methanol and was concentrated to dryness, which was repeated 3 times. The resulting residue was dissolve in methanol, 1 ml of aqueous ammonia was added, and the mixture was concentrated, and purified by a preparation plate to afford 10 mg of the final product with a yield of 18.9%.

$^1$H NMR (400 MHz, DMSO-d6) δ 13.31 (s, 1H), 12.83 (d, J=33.0 Hz, 1H), 9.85 (s, 1H), 9.39 (dd, J=5.0 Hz, J=1.7 Hz, 1H), 8.37-8.31 (m, 1H), 8.07 (s, 1H), 7.92 (dd, J=8.5 Hz, J=5.0 Hz, 1H), 7.40 (s, 1H), 7.13 (d, J=8.1 Hz, 1H), 7.03 (d, J=11.9 Hz, 1H), 6.92 (d, J=9.1 Hz, 1H), 4.84-4.45 (m, 4H), 2.49 (q, J=7.5 Hz, 2H), 1.02 (t, J=7.5 Hz, 3H).

Example 16: (S)-(2-(6-(2-ethyl-5-fluoro-4-hydroxyphenyl)-1H-indazol-3-yl)-4,6-dihydropyrrolo[3,4-d]imidazol-5-(1H)-yl)(3-hydroxylpyrrolidin-1-yl)ketone (MDI-216)

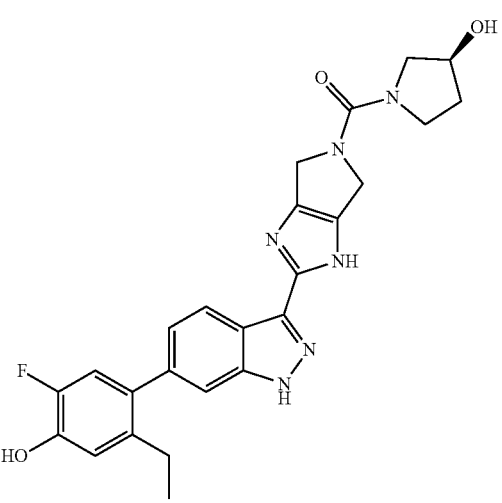

Synthetic Route of MDI-216:

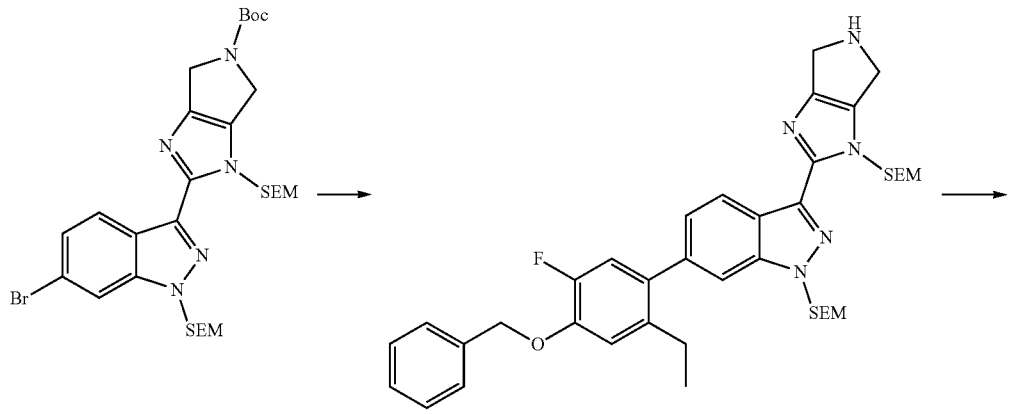

-continued

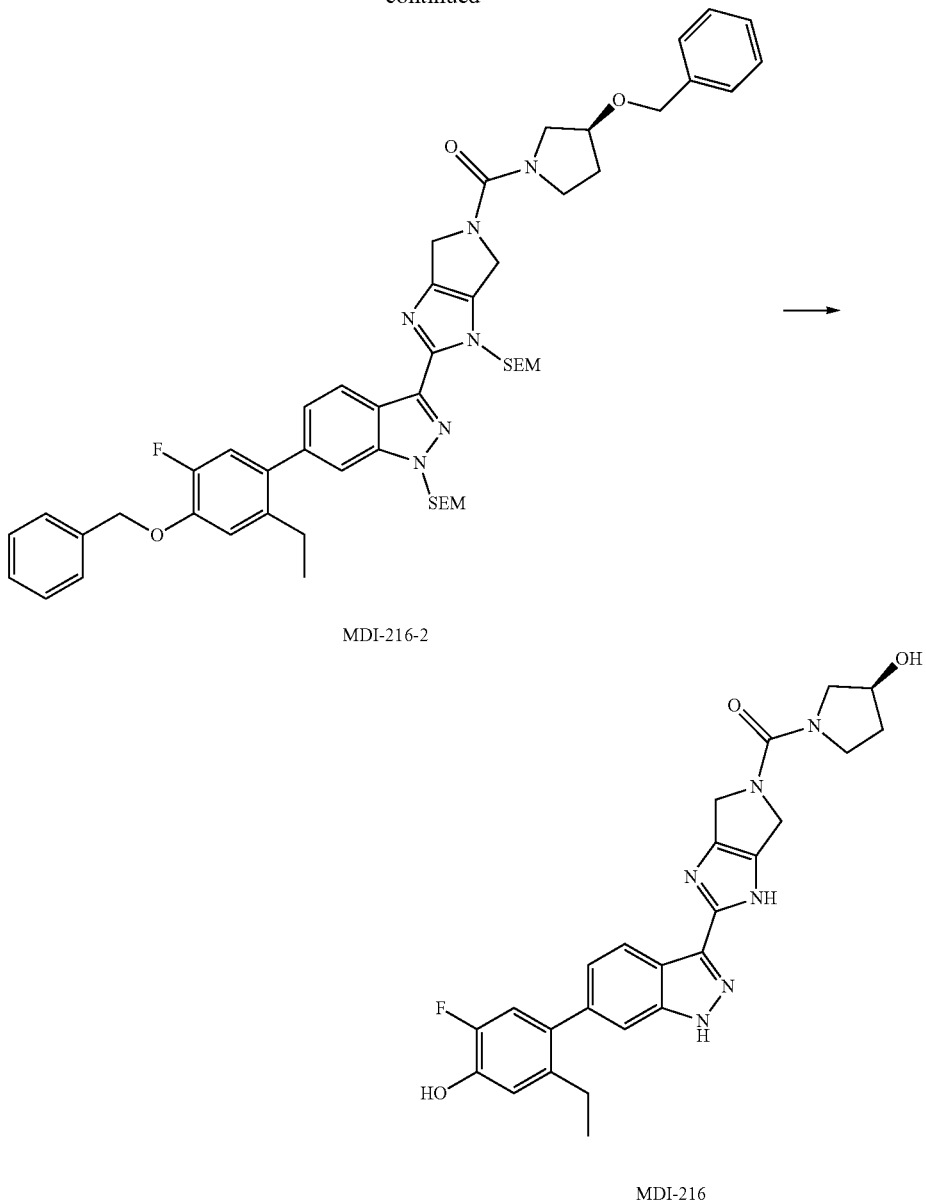

MDI-216-2

MDI-216

Synthesis Method

Synthesis of Intermediate MDI-216-1: 6-(4-(benzyloxy)-2-ethyl-5-fluorophenyl)-1-((2-(trimethylsilyl)ethoxy)methyl)-3-(1-((2-(trimethylsilyl)ethoxy)methyl)-1,4,5,6-tetrahydropyrrolo[3,4-d]imidazol-2-yl)-1H-indazole Tert-butyl 2-(6-bromo-1-((2-(trimethylsilyl)ethoxy)methyl)-1H-indol-3-yl)-1-((2-(trimethylsilyl)ethoxy)methyl)-4,6-dihydropyrrolo[3,4-d]imidazol-5(1H)-carboxylate (500 mg, 0.75 mmol), 2-(4-(benzyloxy)-2-ethyl-5-fluorophenyl)-4,4,5,5-tetramethyl-1,3,2-dioxaborane (401 mg, 1.13 mmol), Pd(dppf)Cl2 (75 mg, 0.075 mmol) and potassium phosphate (495 mg, 2.25 mmol) were dissolved in 1,4-dioxane (30 ml) and water (6 ml). The atmosphere was replaced with nitrogen, which was repeated 3 times. The mixture was heated to 100° C., reacted for 16 hours and cooled to room temperature. Water was added and the resulting mixture was extracted twice with ethyl acetate, and the organic phases were combined, washed with water and saturated brine, dried over anhydrous sodium sulfate, concentrated, and purified by silica gel column. The purified product was dissolved in 25 ml of dichloromethane, and 5 ml of trifluoroacetic acid was added dropwise. The mixture was stirred at room temperature for 30 minutes, and concentrated to give a residue. The residue was dissolved in dichloromethane and was concentrated to dryness, which was repeated 3 times. The resulting residue was purified with silica gel column to afford 210 mg of intermediate MDI-216-1 with a yield of 39.2%.

$^1$H NMR (400 MHz, CDCl3) δ 8.48 (d, J=8.3 Hz, 1H), 7.52 (d, J=7.4 Hz, 1H), 7.49-7.37 (m, 5H), 7.25 (d, J=8.4 Hz, 1H), 7.23-6.96 (m, 2H), 5.93 (s, 2H), 5.77 (s, 2H), 5.23 (s, 2H), 4.21 (d, J=35.1 Hz, 4H), 3.66-3.52 (m, 4H), 2.54 (q,

J=7.6 Hz, 2H), 1.05 (t, J=7.5 Hz, 3H), 0.95-0.89 (m, 4H), 0.02 (s, 9H), −0.05 (d, J=3.4 Hz, 9H).

Synthesis of Intermediate MDI-216-2: (S)-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(3-(benzyloxy)pyrrolidin-1-yl)ketone Triphosgene (25.8 mg, 0.09 mmol) was dissolved in 5 ml of tetrahydrofuran, and intermediate MDI-216-1 (80 mg, 0.09 mmol) in tetrahydrofuran (5 ml) was added dropwise at 0° C. The mixture was stirred at room temperature for 10 minutes and (S)-3-(benzyloxy) pyrrolidine (31.9 mg, 0.18 mmol) in tetrahydrofuran was added. The mixture was stirred at room temperature for 5 minutes, and water was added. The resulting mixture was extracted twice with ethyl acetate, and the organic phases were combined, washed with water and saturated brine, dried over aqueous sodium sulfate, concentrated, and purified by silica gel column to afford 71 mg of intermediate MDI-216-2 with a yield of 86.1%.

¹H NMR (400 MHz, CDCl3) δ 8.46 (d, J=8.3 Hz, 1H), 7.53-7.51 (m, 2H), 7.47-7.42 (m, 3H), 7.39-7.29 (m, 6H), 7.24 (dd, J=8.4 Hz, J=4.0 Hz, 1H), 7.07-6.97 (m, 2H), 5.95 (s, 2H), 5.77 (s, 2H), 5.23 (s, 2H), 4.92-4.88 (m, 2H), 4.76-4.69 (m, 2H), 4.60 (s, 2H), 4.23 (s, 1H), 3.76-3.70 (m, 2H), 3.66-3.58 (m, 6H), 2.54 (q, J=7.5 Hz, 2H), 2.15-2.13 (m, 1H), 2.06-2.02 (m, 1H), 1.05 (t, J=7.5 Hz, 3H), 0.95-0.91 (m, 4H), −0.01-0.11 (m, 18H).

Synthesis of Compound MDI-216: (S)-(2-(6-(2-ethyl-5-fluoro-4-hydroxyphenyl)-1H-indazol-3-yl)-4,6-dihydropyrrolo[3,4-d]imidazol-5-(1H)-yl)(3-hydroxylpyrrolidin-1-yl)ketone Intermediate MDI-216-2 (83 mg, 0.11 mmol) was dissolved in methanol (10 ml), to which 10 mg Pd/C and concentrated hydrochloric acid (5 ml) were added. The mixture was heated to 50° C., reacted for 6 hours, filtered and concentrated to give a residue. The residue was dissolved in methanol and was concentrated to dryness, which was repeated 3 times. The resulting residue was dissolve in methanol, 1 ml of aqueous ammonia was added, and then the mixture was concentrated, and purified by a preparation plate to afford 8 mg of the final product with a yield of 15.2%.

¹H NMR (400 MHz, MeOD-d4) δ 8.27 (d, J=8.4 Hz, 1H), 7.43 (d, J=1.0 Hz, 1H), 7.17 (d, J=8.4 Hz, 1H), 6.97-6.90 (m, 2H), 4.81-4.61 (m, 4H), 4.46-4.44 (m, 1H), 3.79-3.69 (m, 2H), 3.50-3.43 (m, 2H), 2.56 (q, J=7.5 Hz, 2H), 2.09-1.99 (m, 2H), 1.08 (t, J=7.5 Hz, 3H).

Example 17: 5-ethyl-2-fluoro-4-(3-(5-(4-hydroxylcyclohexyl)-1,4,5,6-tetrahydropyrrolo[3,4-d]imidazol-2-yl)-1H-indazol-6-yl)phenol (MDI-217)

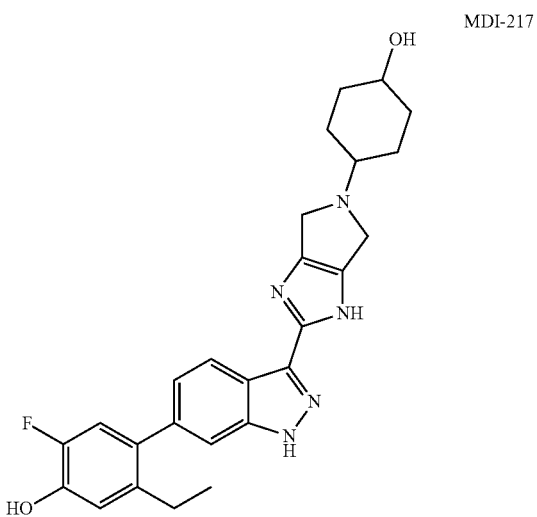 [SMILES: CCc1cc(O)c(F)cc1-c1ccc2c(-c3nc4c([nH]3)CN(C3CCC(O)CC3)C4)n[nH]c2c1]

MDI-217

Synthetic Route of MDI-217:

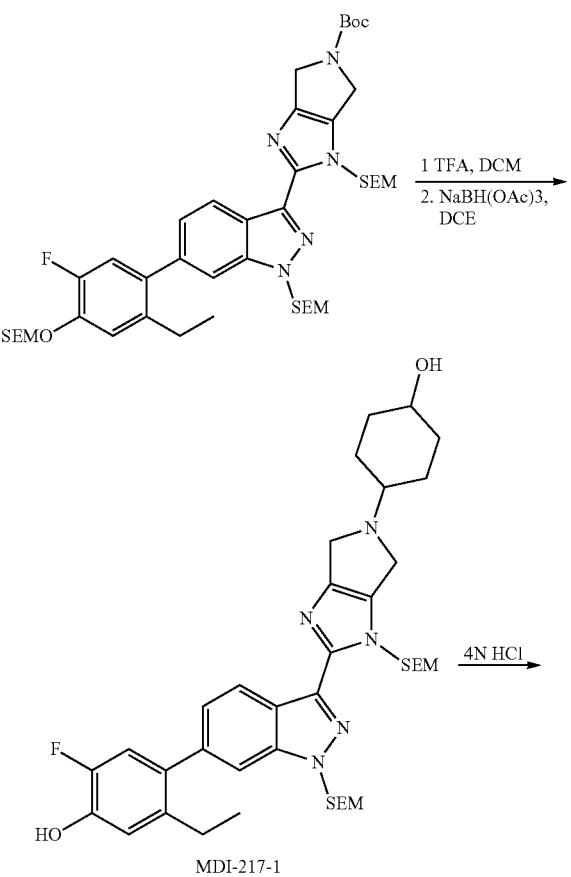

MDI-217-1

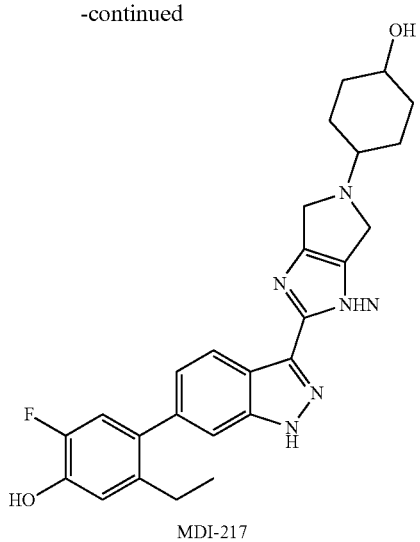

MDI-217

Synthesis Method

Synthesis of Intermediate MDI-217-1: 5-ethyl-2-fluoro-4-(3-(5-(4-hydroxylcyclohexyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol-6-yl)phenol Tert-butyl 2-(6-(2-ethyl-5-fluoro-4-((2-(trimethylsilyl)ethoxy)methoxy) phenyl)1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate (65.0 mg, 0.08 mmol) was dissolved in 5 ml dichloromethane, and 1 ml trifluoroacetic acid was added. The mixture was stirred at room temperature for 30 minutes. Water was added, pH was adjusted with saturated sodium bicarbonate to pH=9, and the resulting mixture was extracted with DCM, washed with water and saturated brine, dried over anhydrous sodium sulfate, and concentrated. The obtained solid was dissolved in 1,2-dichloroethane, and 4-hydroxycyclohexanone (17.4 mg, 0.15 mmol) was added, which was stirred at room temperature for 1 hour. And then sodium triacetyl borohydride (32.3 mg, 0.15 mmol) was added, and it was allowed to react at room temperature for 3 hours. Water was added to quench the reaction, and the resulting mixture was extracted with DCM twice, and the organic phases were combined, washed with water and saturated brine, dried over anhydrous sodium sulfate, concentrated, and purified by silica gel column to afford the product MDI-217-1 with a yield of 38.2%.

$^1$H NMR (400 MHz, CDCl3) δ 8.46 (dd, J=8.0 Hz, J=4.0 Hz, 1H), 7.44 (s, 1H), 7.22 (dd, J=8.0 Hz, J=4.0 Hz, 1H), 7.02-6.95 (m, 2H), 5.93 (d, J=4.0 Hz, 2H), 5.77 (d, J=4.0 Hz, 2H), 4.27-4.07 (m, 4H), 3.76-3.74 (m, 1H), 3.65-3.56 (m, 4H), 2.76-2.74 (m, 1H), 2.55-2.49 (m, 2H), 2.11-2.03 (m, 3H), 1.88-1.86 (m, 2H), 1.74-1.66 (m, 3H), 1.08 (t, J=4.0 Hz, 3H), 0.94-0.89 (m, 4H), 0.02 (s, 9H), −0.05 (s, 9H).

Synthesis of Compound MDI-217: 5-ethyl-2-fluoro-4-(3-(5-(4-hydroxylcyclohexyl)-1,4,5,6-tetrahydropyrrolo[3,4-d]imidazol-2-yl)-1H-indazol-6-yl)phenol Intermediate MDI-217-1 (21.0 mg, 0.03 mmol) was dissolved in 4 ml of methanol, and 2 ml of concentrated hydrochloric acid was added. The mixture was heated to 50° C., reacted for 6 hours, and concentrated to give a residue. The residue was dissolved in methanol and was concentrated to dryness, which was repeated 3 times. To the resulting residue, 1 ml of methanol was added, 2 ml of concentrated aqueous ammonia was added for neutralization, and the mixture was concentrated to give a residue. The residue was dissolved in methanol and was concentrated to dryness, which was repeated 2 times. The resulting residue was purified by a preparation plate to afford 5.3 mg of the product with a yield of 39.5%.

$^1$H NMR (400 MHz, MeOD-d4) δ 8.27 (dd, J=4.0 Hz, J=8.0 Hz, 1H), 7.43-7.42 (m, 1H), 7.19 (dd, J=4.0 Hz, J=8.0 Hz, 1H), 6.96-6.88 (m, 2H), 3.98 (s, 4H), 3.93 (m, 1H), 2.74-2.72 (m, 1H), 2.58 (q, J=8.0 Hz, 2H), 2.04-2.05 (m, 1H), 1.90-1.80 (m, 5H), 1.64-1.62 (m, 2H), 1.10 (t, J=8.0 Hz, J=16.0 Hz, 3H).

Example 18: 4-(3-(5-(cyclopropanesulfonyl)-1,4,5,6-tetrahydropyrrolo[3,4-d]imidazol-2-yl)-1H-indazol-6-yl)-5-ethyl-2-fluorophenol (MDI-218)

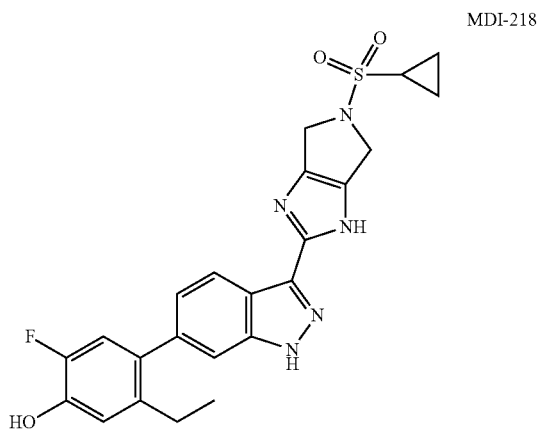 [SMILES: CCc1cc(O)c(F)cc1-c1ccc2c(-c3nc4c([nH]3)CN(S(=O)(=O)C3CC3)C4)n[nH]c2c1]

MDI-218

Synthetic Route of MDI-218:

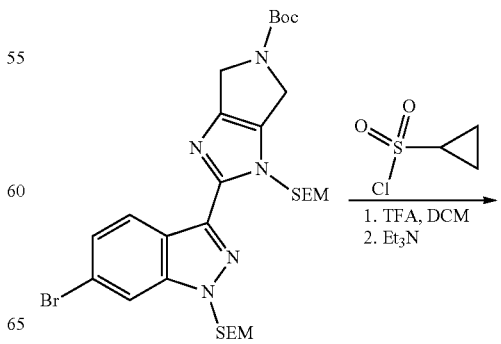

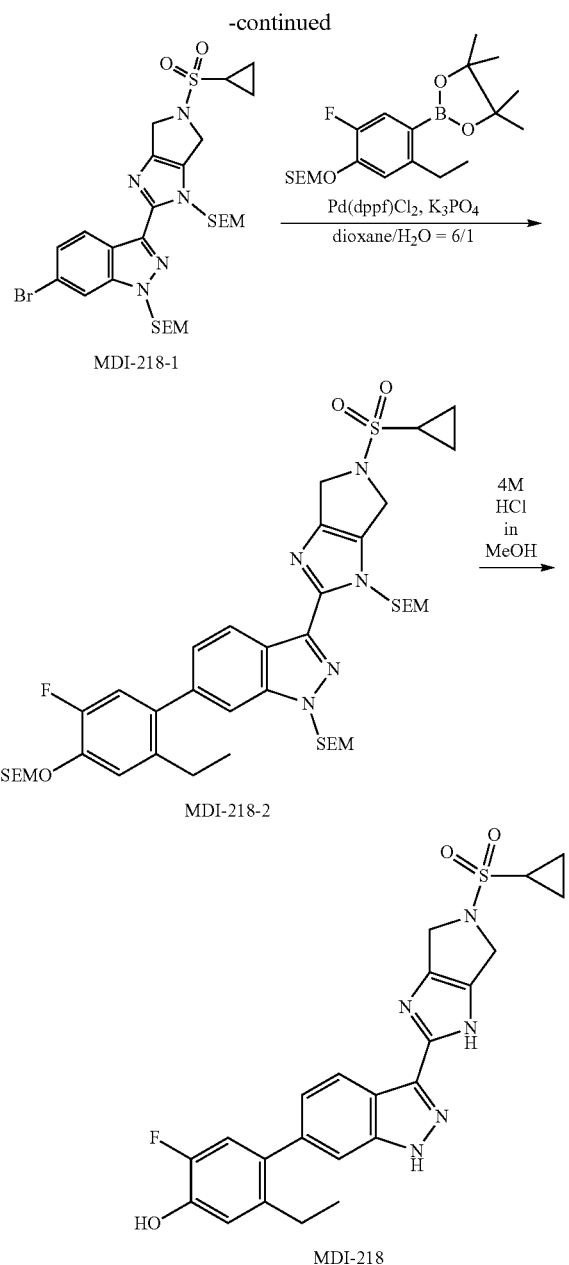

MDI-218-1

MDI-218-2

MDI-218

Synthesis Method

Synthesis of Intermediate MDI-218-1: 6-bromo-3-(5-(cyclopropanesulfonyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol Tert-butyl 2-(6-bromo1-((2-(trimethylsilyl)ethoxy)methyl)-1H-indazol-3-yl)-1-((2-(trimethylsilyl)methyl)-4,6-dihydropyrrolo[3,4-d]imidazol-5(1H)-carboxylate (100 mg, 0.15 mmol) was dissolved in 5 ml dichloromethane, and 1 ml trifluoroacetic acid was added. The mixture was stirred at room temperature for 30 minutes, concentrated, quenched with sodium bicarbonate, and extracted twice with dichloromethane. The organic phases were combined, washed with water and saturated brine, dried over anhydrous sodium sulfate and concentrated. The obtained compound was dissolved in 5 ml DCM and Et3N (0.08 ml, 0.59 mmol), and cooled to 0° C. Cyclopropylsulfonyl chloride (22.4 mg, 0.16 mmol) was slowly added. It was allowed to react at room temperature for 2 hours, and water was added to quench the reaction. The resulting mixture was extracted with DCM twice, and the organic phases were combined, washed with water and saturated brine, dried over anhydrous sodium sulfate, concentrated, and purified by silica gel column to afford intermediate MDI-218-1 with a yield of 36.0%.

$^1$H NMR (400 MHz, CDCl3) δ 8.37 (d, J=8.0 Hz, 1H), 7.80 (d, J=4.0 Hz, 1H), 7.43 (d, J=8.0 Hz, 1H), 5.91 (s, 2H), 5.73 (s, 2H), 4.75-4.74 (m, 2H), 4.66-4.65 (m, 2H), 3.63-3.58 (m, 4H), 2.50-2.44 (m, 1H), 1.33-1.31 (m, 2H), 1.06-1.02 (m, 2H), 0.96-0.91 (m, 4H), 0.00-0.05 (m, 18H).

Synthesis of Intermediate MDI-218-2: 3-(5-cyclopropanesulfonyl)-1-((2-(trimethylsilyl)ethoxy)methyl)-1,4,5,6-tetrahydropyrrolo[3,4-d]imidazol-2-yl)-6-(2-ethyl-5-fluoro-4-((2-(trimethylsilyl)ethoxy)methoxy)phenyl)-1-((2-(trimethylsilyl) ethoxy)methyl)-1H-indazole The intermediate MDI-218-1 (36.0 mg, 0.05 mmol), (2-((5-ethyl-2-fluoro-4-(4, 4,5,5-tetramethyl-1,3,2-dioxaboran-2-yl)phenoxy)methoxy)ethyl)trimethylsilane (25.5 mg, 0.06 mmol), Pd(dppf)Cl2 (3.9 mg, 0.005 mmol) and potassium phosphate (34.2 mg, 0.16 mmol) were dissolved in 1,4-dioxane (6 ml) and water (1 ml). The atmosphere was replaced with nitrogen, which was repeated 3 times. The mixture was heat to 100° C., reacted overnight, and cooled to room temperature. Water was added, and the resulting mixture was extracted twice with ethyl acetate, and the organic phases were combined, washed with water and saturated brine, dried over anhydrous sodium sulfate, concentrated, and purified by silica gel column to afford the intermediate MDI-218-2, the yield was 70.0%.

$^1$H NMR (400 MHz, CDCl3) δ 8.47 (d, J=8.0 Hz, 1H), 7.48 (s, 1H), 7.26 (d, J=7.9 Hz, 1H), 7.18 (d, J=8.0 Hz, 1H), 7.04 (d, J=12.0 Hz, 1H), 5.95 (s, 2H), 5.78 (s, 2H), 5.34 (s, 2H), 4.76 (s, 2H), 4.68 (s, 2H), 3.88 (t, J=8.0 Hz, 2H), 3.68-3.57 (m, 4H), 2.56 (q, J=7.6 Hz, 2H), 2.24 (t, J=7.7 Hz, 1H), 1.12-0.86 (m, 13H), −0.01-0.06 (m, 27H).

Synthesis of Compound MDI-218: 4-(3-(5-(cyclopropanesulfonyl)-1,4,5,6-tetrahydropyrrolo[3,4-d]imidazol-2-yl)-1H-indazol-6-yl)-5-ethyl-2-fluorophenol Intermediate MDI-218-2 (36.0 mg, 0.04 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, and pH was adjusted with sodium bicarbonate to 8-9, and the resulting mixture was extracted 4 times with dichloromethane. The organic phases were combined, dried over anhydrous sodium sulfate, and purified by a preparation plate to afford 16 mg of the final product with a yield of 81.4%.

$^1$H NMR (400 MHz, MeOD-d4) δ 8.27 (d, J=8.0 Hz, 1H), 7.43 (s, 1H), 7.18 (dd, J=8.0 Hz, J=4.0 Hz, 1H), 6.93 (dd,

J=20.0 Hz, J=12.0 Hz, 2H), 4.65 (s, 4H), 2.76-2.69 (m, 1H), 2.60-2.51 (m, 2H), 1.20-1.18 (m, 2H), 1.10-1.06 (m, 5H).

Example 19: 4-(3-(5-(cyclobutylsulfonyl)-1,4,5,6-tetrahydropyrrolo[3,4-d]imidazol-2-yl)-1H-indazol-6-yl)-5-ethyl-2-fluorophenol (MDI-219)

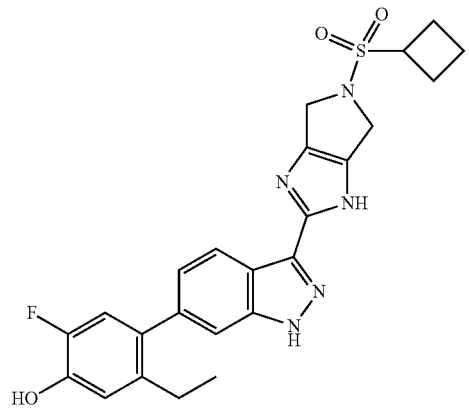

MDI-219

Synthetic Route of MDI-219:

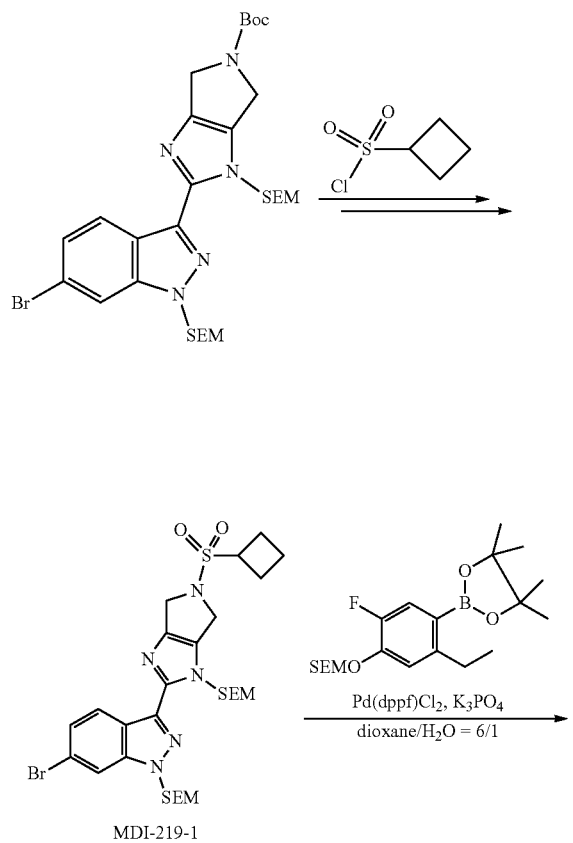

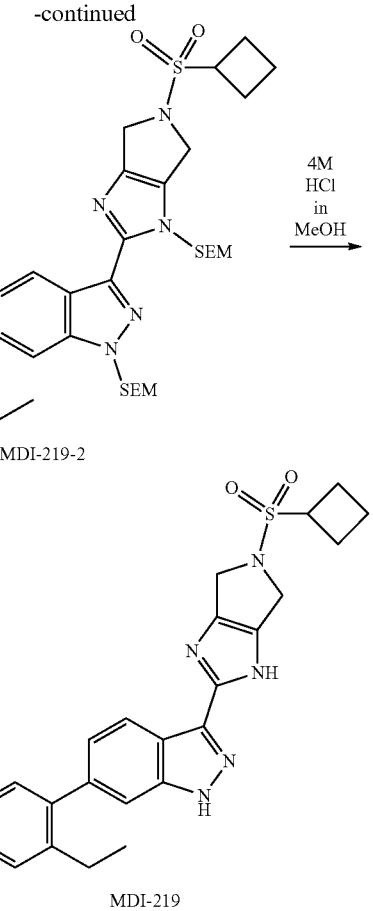

Synthesis Method

Synthesis of Intermediate MDI-219-1: 6-bromo-3-(5-(cyclobutylsulfonyl)-1-(2-(trimethylsilyl)ethoxy)methyl)-1,4,5,6-tetrahydropyrrolo[3,4-d]imidazol-2-yl)-1-(2-(trimethylsilyl)ethoxy)methyl)-1H-indazole Tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-carboxylate (100 mg, 0.15 mmol) was dissolved in 5 ml dichloromethane, and 1 ml trifluoroacetic acid was added. The mixture was stirred at room temperature for 30 minutes, concentrated, and quenched with sodium bicarbonate. The resulting mixture was extracted twice with dichloromethane, and the organic phases were combined, washed with water and saturated brine, dried over anhydrous sodium sulfate and concentrated. The obtained compound was dissolved in 5 ml DCM and Et3N (0.08 ml, 0.59 mmol), and cooled to 0° C.

Cyclobutylsulfonyl chloride (24.6 mg, 0.16 mmol) was slowly added. It was allowed to react at room temperature for 2 hours, and water was added to quench the reaction. The resulting mixture was extracted with DCM twice, and the organic phases were combined, washed with water and saturated brine, dried over anhydrous sodium sulfate, concentrated, and purified by silica gel column to afford intermediate MDI-219-1 with a yield of 32.1%.

$^1$H NMR (400 MHz, CDCl3) δ 8.36 (d, J=8.0 Hz, 1H), 7.79 (s, 1H), 7.43 (d, J=8 Hz, 1H), 5.92 (d, J=4.0 Hz, 2H), 5.73 (s, 2H), 4.70 (s, 2H), 4.60 (s, 2H), 4.03-3.95 (m, 1H), 3.65-3.56 (m, 4H), 2.75-2.64 (m, 2H), 2.37-2.30 (m, 2H), 2.11-2.04 (m, 2H), 0.95-0.90 (m, 4H), 0.00-0.05 (m, 18H).

Synthesis of Intermediate MDI-219-2: 3-(5-(cyclobutylsulfonyl)-1-((2-(trimethylsilyl)ethoxy)methyl)-1,4,5,6-tetrahydropyrrolo[3,4-d]imidazol-2-yl)-6-(2-ethyl-5-fluoro-4-((2-(trimethylsilyl)ethoxy)methoxy)phenyl)-1-((2-(trimethylsilyl)ethoxy)methyl)-1H-indazole The intermediate MDI-219-1 (33.0 mg, 0.05 mmol), (2-((5-ethyl-2-fluoro-4-(4, 4,5,5-tetramethyl-1,3,2-dioxaboran-2-yl)phenoxy)methoxy)ethyl)trimethylsilane (22.6 mg, 0.06 mmol), Pd(dppf)Cl$_2$ (3.5 mg, 0.005 mmol), and potassium phosphate (30.2 mg, 0.14 mmol) were dissolved in 1,4-dioxane (6 ml) and water (1 ml). The atmosphere was replaced with nitrogen, which was repeated 3 times. The mixture was heated to 100° C., reacted overnight, and cooled to room temperature. Water was added, the resulting mixture was extracted twice with ethyl acetate, and the organic phases were combined, washed with water and saturated brine, dried over anhydrous sodium sulfate, concentrated, and purified by silica gel column to afford intermediate MDI-219-2 with a yield of 73.5%.

$^1$H NMR (400 MHz, CDCl3) δ 8.45 (d, J=8.0 Hz, 1H), 7.48 (s, 1H), 7.26 (dd, J=8.3 Hz, J=1.3 Hz, 1H), 7.18 (d, J=8.0 Hz, 1H), 7.07-7.02 (m, 1H), 5.93 (s, 2H), 5.77 (s, 2H), 5.34 (s, 2H), 4.74-4.70 (m, 2H), 4.64-4.60 (m, 2H), 4.00-3.98 (m, 1H), 3.91-3.86 (m, 2H), 3.66-3.58 (m, 4H), 2.75-2.66 (m, 2H), 2.58-2.54 (m, 2H), 2.11-2.02 (m, 4H), 1.10-1.04 (m, 3H), 1.01-0.96 (m, 6H), −0.02-0.05 (m, 27H).

Synthesis of Compound MDI-219: 4-(3-(5-(cyclobutylsulfonyl)-1,4,5,6-tetrahydropyrrolo[3,4-d]imidazol-2-yl)-1H-indazol-6-yl)-5-ethyl-2-fluorophenol Intermediate MDI-219-2 (31.0 mg, 0.04 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, and pH was adjusted with sodium bicarbonate to pH=8-9. The resulting mixture was extracted with dichloromethane 4 times, and the organic phases were combined, dried over anhydrous sodium sulfate, and purified by a preparation plate to afford 12 mg of the final product with a yield of 65.7%.

$^1$H NMR (400 MHz, MeOD-d4) δ 8.26 (d, J=8.0 Hz, 1H), 7.43 (s, 1H), 7.17 (dd, J=8.4 Hz, J=1.4 Hz, 1H), 6.93 (dd, J=20.0 Hz, J=12.0 Hz, 2H), 4.60 (s, 4H), 4.26-4.18 (m, 1H), 2.68-2.52 (m, 4H), 2.40-2.31 (m, 2H), 2.13-2.02 (m, 2H), 1.08 (t, J=7.5 Hz, 3H).

Example 20: 4-(3-(5-(cyclopentylsulfonyl)-1,4,5,6-tetrahydropyrrolo[3,4-d]imidazol-2-yl)-1H-indazol-6-yl)-5-ethyl-2-fluorophenol (MDI-220)

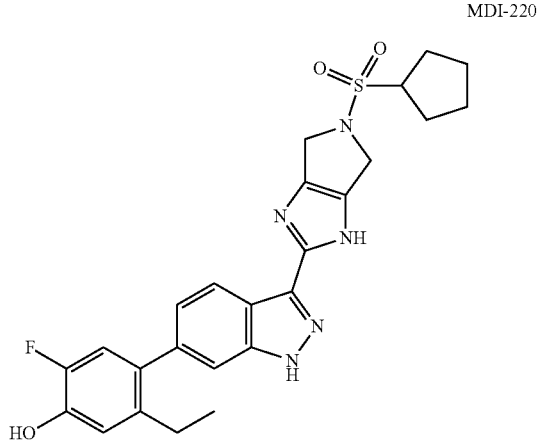 [SMILES: CCc1cc(O)c(F)cc1-c1ccc2c(-c3nc4c([nH]3)CN(S(=O)(=O)C3CCCC3)C4)n[nH]c2c1]

MDI-220

Synthetic Route of MDI-220:

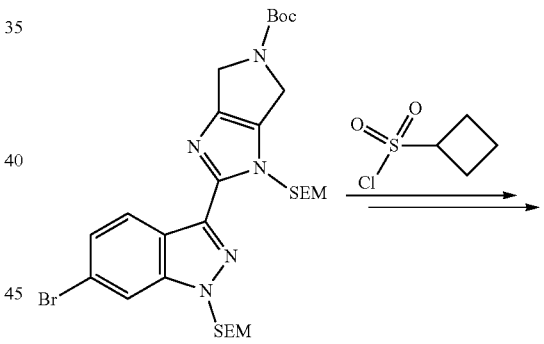

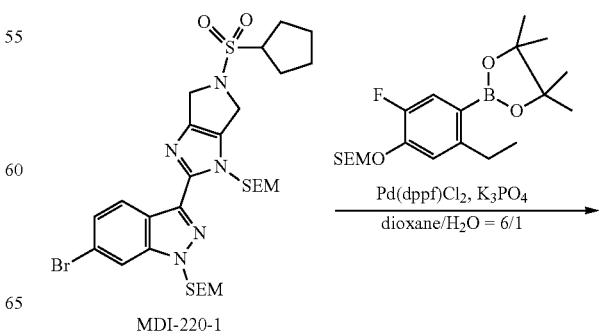

MDI-220-1

-continued

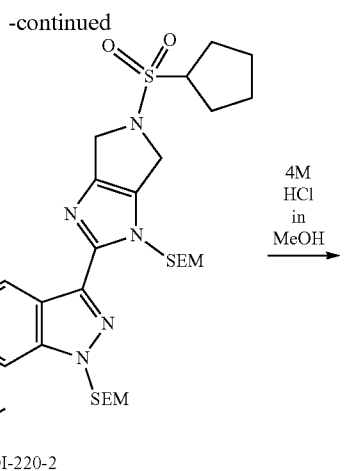

MDI-220-2

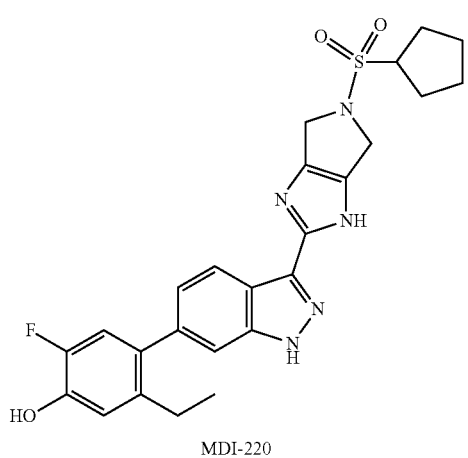

MDI-220

Synthesis Method

Synthesis of Intermediate MDI-220-1: 6-bromo-3-(5-(cyclopentylsulfonyl)-1-((2-(trimethylsilyl)ethoxy)methyl)-1,4,5,6-tetrahydropyrrol[3,4-d]imidazol-2-yl)-1-((2-(trimethylsilyl)ethoxy)methyl)-1H-indazol Tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-carboxylate (100 mg, 0.15 mmol) was dissolved in 5 ml dichloromethane, and 1 ml trifluoroacetic acid was added. The mixture was stirred at room temperature for 30 minutes, concentrated, and quenched with sodium bicarbonate. The resulting mixture was extracted twice with dichloromethane, and the organic phases were combined, washed with water and saturated brine, dried over anhydrous sodium sulfate and concentrated. The obtained compound was dissolved in 5 ml DCM and Et3N (0.08 ml, 0.59 mmol), and cooled to 0° C.

Cyclopentylsulfonyl chloride (26.8 mg, 0.16 mmol) was slowly added and it was allowed to react at room temperature for 2 hours. And then water was added to quench the reaction. The resulting mixture was extracted with DCM twice, and the organic phases were combined, washed with water and saturated brine, dried over anhydrous sodium sulfate, concentrated, and purified by silica gel column to afford intermediate MDI-220-1 with a yield of 38.1%.

$^1$H NMR (400 MHz, CDCl3) δ 8.36 (d, J=8.0 Hz, 1H), 7.80 (s, 1H), 7.43 (dd, J=8.0 Hz, J=1.6 Hz, 1H), 5.90 (s, 2H)), 5.73 (s, 2H), 4.78-4.72 (m, 2H), 4.68-4.62 (m, 2H), 4.33 (t, J=8.0 Hz, 1H), 3.63-3.57 (m, 4H), 2.14-2.03 (m, 4H), 1.75-1.56 (m, 4H), 0.96-0.90 (m, 4H), −0.02-0.05 (m, 18H).

Synthesis of Intermediate MDI-220-2: 3-(5-(cyclopentylsulfonyl)-1-((2-(trimethylsilyl)ethoxy)methyl)-1,4,5,6-tetrahydropyrrolo[3,4-d]imidazol-2-yl)-6-(2-ethyl-5-fluoro-4-((2-(trimethylsilyl)ethoxy)methoxy)phenyl)-1-((2-(trimethylsilyl) ethoxy)methyl)-1H-indazole The intermediate MDI-220-1 (40 mg, 0.06 mmol), (2-((5-ethyl-2-fluoro-4-(4,4,5,5-tetramethyl-1,3,2-dioxaborolan-2-yl)phenoxy)methoxy)ethyl)trimethylsilane (27.3 mg, 0.07 mmol), Pd(dppf)Cl2 (4.2 mg, 0.006 mmol) and potassium phosphate (36.5 mg, 0.17 mmol) were dissolved in 1,4-dioxane (6 ml) and water (1 ml). The atmosphere was replaced with nitrogen, which was repeated 3 times. The mixture was heated to 100° C., reacted overnight, and cooled to room temperature. Water was added and the resulting mixture was extracted with ethyl acetate twice, and the organic phases were combined, washed with water and saturated brine, dried over anhydrous sodium sulfate, concentrated, and purified by silica gel column to afford intermediate MDI-220-2 with a yield of 62.9%.

$^1$H NMR (400 MHz, CDCl3) δ 8.46 (d, J=8.0 Hz, 1H), 7.48 (s, 1H), 7.26 (dd, J=8.0 Hz, J=1.2 Hz, 1H), 7.18 (d, J=8.0 Hz, 1H), 7.04 (d, J=12.0 Hz, 1H), 5.94 (s, 2H), 5.78 (s, 2H), 5.34 (s, 2H), 4.80-4.75 (m, 2H), 4.70-4.65 (m, 2H), 4.33 (t, J=8.0 Hz, 1H), 3.82-3.80 (m, 2H), 3.73-3.58 (m, 4H), 2.58-2.53 (m, 2H), 2.18-2.05 (m, 4H), 1.79-1.58 (m, 4H), 1.11-1.04 (m, 3H), 0.93-0.90 (m, 6H), −0.02-0.06 (m, 27H).

Synthesis of Compound MDI-220: 4-(3-(5-(cyclopentylsulfonyl)-1,4,5,6-tetrahydropyrrolo[3,4-d]imidazol-2-yl)-1H-indazol-6-yl)-5-ethyl-2-fluorophenol Intermediate MDI-220-2 (32.0 mg, 0.04 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, and pH was adjusted with sodium bicarbonate to 8-9. The resulting mixture was extracted 4 times with dichloromethane, and the organic phases were combined, dried over anhydrous sodium sulfate, and purified by a preparation plate to afford 10 mg of the final product with a yield of 55.8%.

$^1$H NMR (400 MHz, MeOD-d4) δ 8.27 (dd, J=8.0 Hz, J=4.0 Hz, 1H), 7.43 (s, 1H), 7.17 (dd, J=8.0 Hz, J=1.4 Hz, 1H), 6.93 (dd, J=20.0 Hz, J=12.0 Hz, 2H), 4.65 (s, 4H), 3.91-3.83 (m, 1H), 2.58-2.52 (m, 2H), 2.13-2.03 (m, 4H), 1.89-1.78 (m, 2H), 1.75-1.64 (m, 2H), 1.08 (t, J=8.0 Hz, 3H).

Example 21: 5-ethyl-2-fluoro-4-(3-(5-((1-methyl-1H-pyrazol-4-yl)methyl)-1,4,5,6-tetrahydropyrrolo[3,4-d]imidazol-2-yl)-1H-indazol-6-yl)phenol (MDI-221)
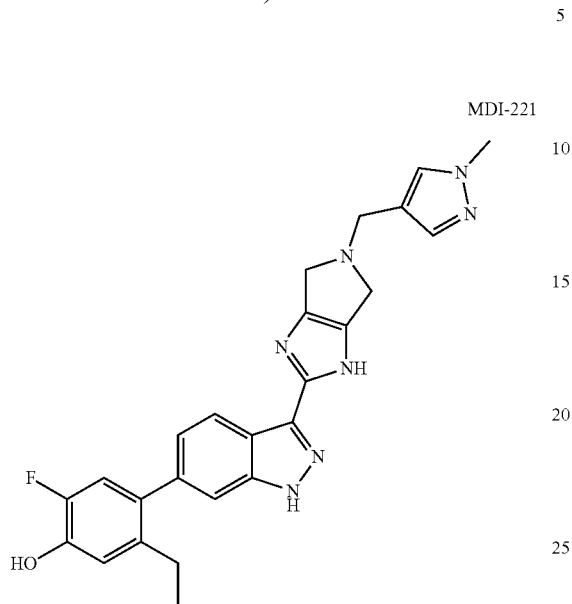
Synthetic Route of MDI-221:
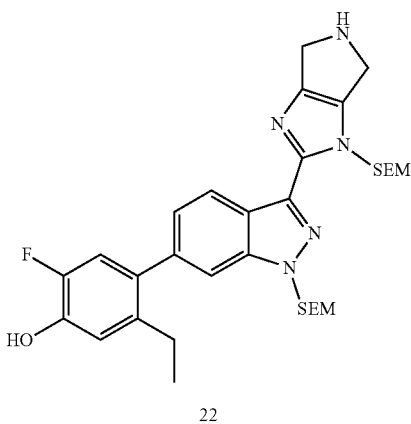
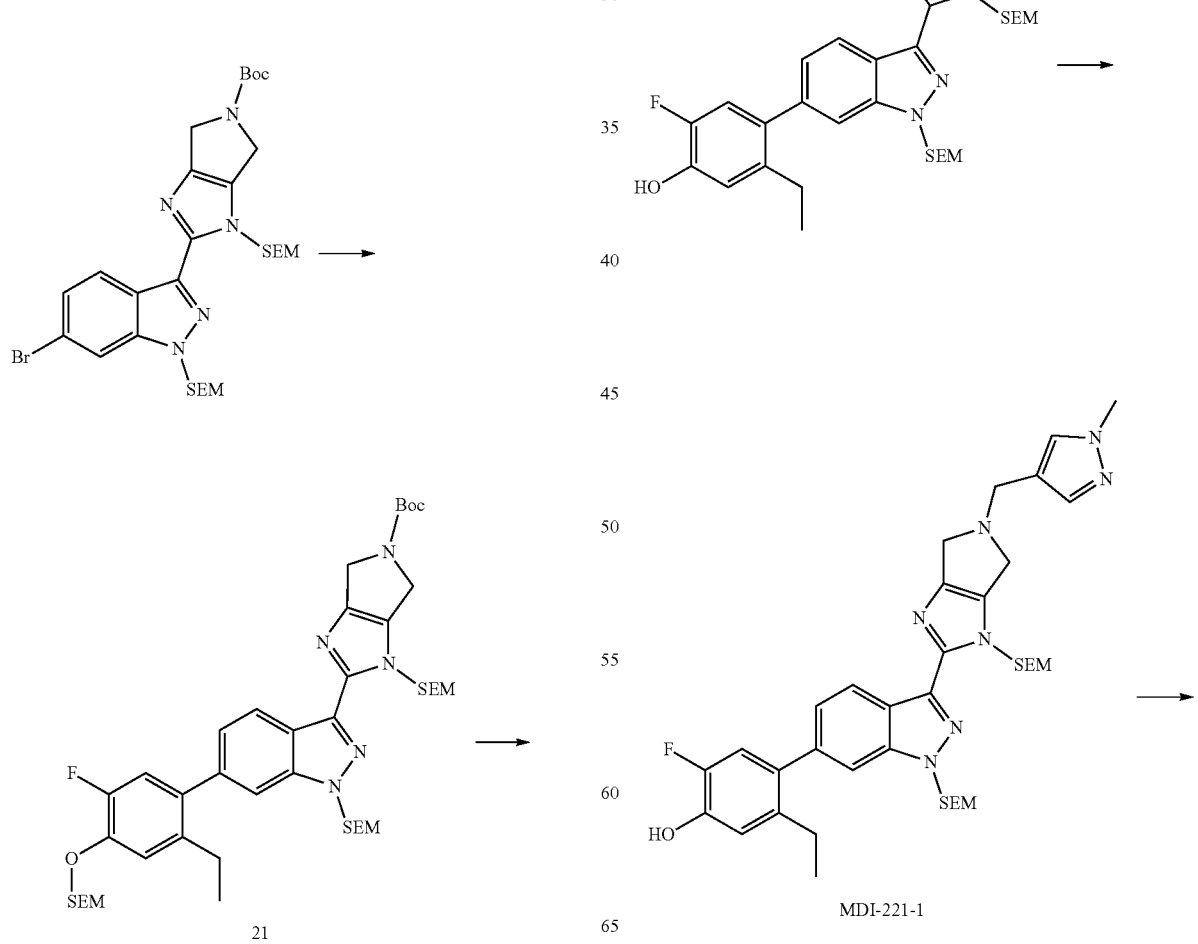

-continued

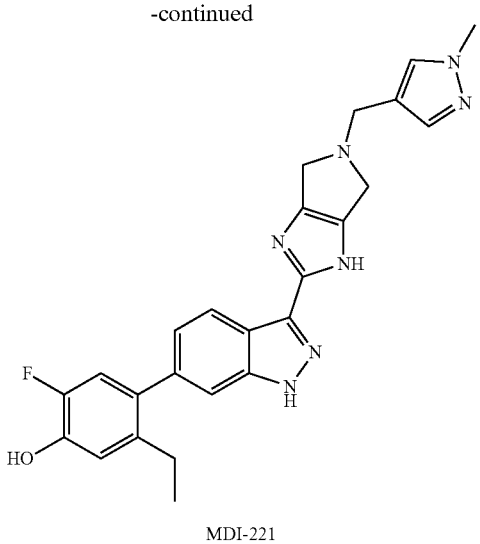

MDI-221

Synthesis Method

Synthesis of Intermediate 21: Tert-butyl 2-(6-(2-ethyl-5-fluoro-4-((2-(trimethylsilyl) ethoxy)methoxy)phenyl)1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate The intermediate tert-butyl 2-(6-bromo-1-((2-(trimethylsilyl)ethoxy)methyl)-1H-indazol-3-yl)-1-((2-(tri methyl silyl)ethoxy)methyl)-4,6-dihydropyrrolo[3,4-d]imidazol-5(1H)-carboxylate (39.8 mg, 0.06 mmol), intermediate (2-((5-ethyl-2-fluoro-4-(4,4,5,5-tetramethyl-1,3,2-dioxaboran-2-yl)phenoxy)methoxy)ethyl)trimethylsilane (27.1 mg, 0.07 mmol), Pd(dppf)Cl2 (4.2 mg, 0.006 mmol) and potassium phosphate (36.2 mg, 0.17 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added and the resulting mixture was extracted twice with ethyl acetate, and the organic phases were combined, washed with water and saturated brine, dried over anhydrous sodium sulfate, concentrated, and purified by silica gel column to afford Intermediate 21 with a yield of 78%.

$^1$H NMR (400 MHz, CDCl3) δ8.46 (dd, J=12.0 Hz, J=8.0 Hz, 1H), 7.45 (s, 1H), 7.24-7.21 (m, 1H), 7.15 (d, J=8.0 Hz, 1H), 7.01 (d, J=12.0 Hz, 1H), 5.93 (d, J=12.0 Hz, 2H), 5.75 (s, 2H), 5.31 (s, 2H), 4.65-4.50 (m, 4H)), 3.88-3.84 (m, 2H), 3.63-3.55 (m, 4H), 2.57-2.51 (m, 2H), 1.54 (s, 9H), 1.07-1.03 (m, 3H), 0.90-0.85 (m, 4H), 0.03 (s, 9H), —0.07 (s, 18H).

Synthesis of Intermediate 22: 5-ethyl-2-fluoro-4-(1-((2-(trimethylsilyl)ethoxy)methyl)-3-((2-trimethylsilyl)ethoxy)methyl)-1,4,5,6-tetrahydropyrrolo[3,4-d]imidazol-2-yl)-1H-indazol-6-yl)phenol The intermediate Tert-butyl 2-(6-(2-ethyl-5-fluoro-4-((2-(trimethylsilyl) ethoxy)methoxy)phenyl)1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate (40 mg, 0.046 mmol) was dissolved in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was purified by silica gel column to afford Intermediate 22 with a yield of 43%.

$^1$H NMR (400 MHz, CDCl3) δ 8.44 (d, J=8.0 Hz, 1H), 7.20 (dd, J=8.3 Hz, J=1.4 Hz, 1H), 6.95 (dd, J=20.0 Hz, J=8.0 Hz, 1H), 5.91 (s, 2H), 5.47 (s, 2H), 4.26-4.16 (m, 4H), 3.64-3.55 (m, 4H), 2.53-2.47 (m, 2H), 1.04 (t, J=8.0 Hz, 3H), 0.92-0.86 (m, 4H), −0.07 (s, 9H), −0.08 (s, 9H).

Synthesis of Intermediate MDI-221-1: 5-ethyl-2-fluoro-4-(3-(5-((1-methyl-1H-pyrazol-4-yl)methyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol-6-yl) phenol 5-ethyl-2-fluoro-4-(1-((2-(trimethylsilyl)ethoxy)methyl)-3-((2-trimethylsilyl) ethoxy)methyl)-1,4,5,6-tetrahydropyrrolo[3,4-d]imidazol-2-yl)-1H-indazol-6-yl)phenol (40 mg, 0.064 mmol) and 1-methyl-1H-pyrazol-4-formaldehyde (8.5 mg, 0.077 mmol) were dissolved in 5 ml 1,2-dichloroethane. It was allowed to react at room temperature for 10 minutes. The reaction was cooled to 0° C. and sodium triacetoxyborohydride (26.9 mg, 0.128 mmol) was added. After the addition was completed, the mixture was warmed to room temperature and reacted for 1-2 h. After the completion of the reaction, water was added to quench the reaction, the resulting mixture was extracted twice with dichloromethane, and the organic phases were combined, washed with water and saturated brine, dried over anhydrous sodium sulfate, concentrated, and purified by silica gel column to afford the intermediate MDI-221-1, yield 43.4%.

$^1$H NMR (400 MHz, CDCl3) δ 8.41 (d, J=8.0 Hz, 1H), 7.51 (s, 1H), 7.40 (d, J=4.0 Hz, 2H), 7.19-7.16 (m, 1H), 6.93 (dd, J=24.0 Hz, J=12.0 Hz, 2H), 5.87 (s, 2H), 5.73 (s, 2H), 4.01-3.98 (m, 4H), 3.95 (s, 2H), 3.91 (s, 3H), 3.62-3.52 (m, 4H), 2.51-2.45 (m, 2H), 1.01 (t, J=6.0 Hz, 3H), 0.91-0.85 (m, 4H), −0.08 (s, 9H), −0.09 (s, 9H).

Synthesis of Compound MDI-221: 5-ethyl-2-fluoro-4-(3-(5-((1-methyl-1H-pyrazol-4-yl)methyl)-1,4,5,6-tetrahydropyrrolo[3,4-d]imidazol-2-yl)-1H-indazol-6-yl) phenol Intermediate MDI-221-1 (28 mg, 0.039 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, and 2 ml concentrated aqueous ammonia was added and concentrated to give a residue. The residue was dissolved in methanol and was concentrated to dryness, which was repeated 3 times. The resulting residue was purified by a preparation plate to afford 5.0 mg of the final product with a yield of 28%.

$^1$H NMR (400 MHz, MeOD-d4) δ 8.25 (d, J=8.0 Hz, 1H), 7.68 (s, 1H), 7.56 (s, 1H), 7.42 (s, 1H), 7.16 (dd, J=8.4 Hz, J=1.4 Hz, 1H), 6.93 (dd, J=20.0 Hz, J=12.0 Hz, 2H), 4.03-3.96 (m, 6H), 3.92 (s, 3H), 2.58-2.53 (m, 2H), 1.08 (t, J=8.0 Hz, 3H).

Example 22: 4-(3-(5-cyclopentyl-1,4,5,6-tetrahydro-pyrrolo[3,4-d]imidazol-2-yl)-1H-indazol-6-yl)-5-ethyl-2-fluorophenol (MDI-224)

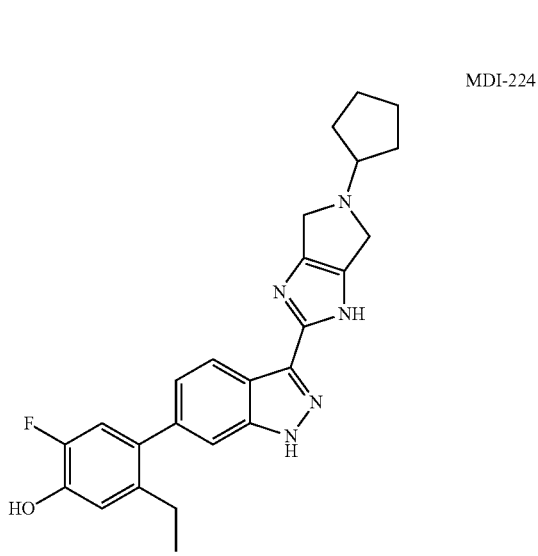 [SMILES: CCc1cc(O)c(F)cc1-c1ccc2c(-c3nc4c([nH]3)CN(C3CCCC3)C4)n[nH]c2c1]

Synthetic Route of MDI-224:

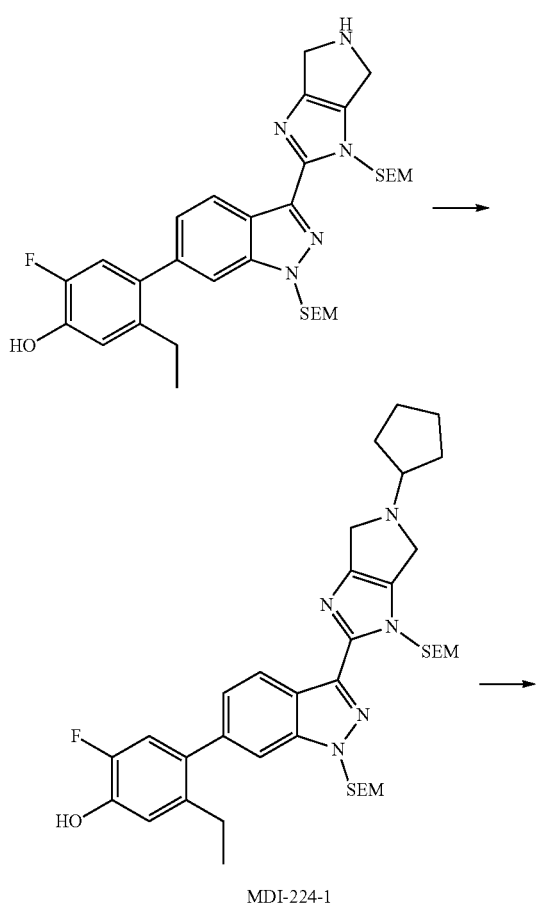

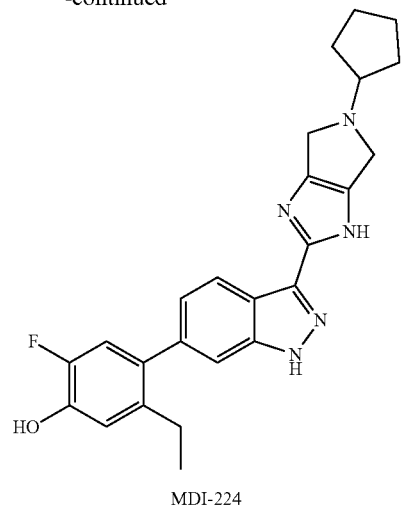

MDI-224

Synthesis Method

Synthesis of Intermediate MDI-224-1: 4-(3-(5-(cyclopentyl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol-6-yl)-5-ethyl-2-fluorophenol 5-ethyl-2-fluoro-4-(1-((2-(trimethylsilyl)ethoxy)methyl)-3-((2-trimethylsilyl)ethoxy)methyl)-1,4,5,6-tetrahydropyrrolo[3,4-d]imidazol-2-yl)-1H-indazol-6-yl)phenol (31.2 mg, 0.05 mmol) and cyclopentanone (5.1 mg, 0.06 mmol) were dissolved in 5 ml 1,2-dichloroethane. It was allowed to react at room temperature for 10 minutes. The reaction was cooled to 0° C., and sodium triacetoxyborohydride (21 mg, 0.1 mmol) was added. After the addition was completed, the mixture was warmed to room temperature and reacted for 1-2 h. After the completion of the reaction, water was added to quench the reaction, the resulting mixture was extracted twice with dichloromethane, and the organic phases were combined, washed with water and saturated brine, dried over anhydrous sodium sulfate, concentrated, and purified by silica gel column to afford the intermediate MDI-221-1 with a yield of 56.8%.

$^1$H NMR (400 MHz, CDCl3) δ 8.40 (d, J=8.0 Hz, 1H), 7.41 (s, 1H), 7.16 (dd, J=8.3 Hz, J=1.4 Hz, 1H), 6.93 (dd, J=24.0 Hz, J=12.0 Hz, 2H), 5.89 (s, 2H), 5.73 (s, 2H), 4.08 (s, 2H), 3.99 (s, 2H), 3.62-3.55 (m, 4H), 3.22-3.19 (m, 1H), 2.50-2.45 (m, 2H), 1.98-1.89 (m, 2H), 1.84-1.75 (m, 2H), 1.70-1.56 (m, 4H), 1.01 (t, J=8.0 Hz, 3H), 0.91-0.86 (m, 4H), −0.08 (s, 9H), −0.09 (s, 9H).

Synthesis of Compound MDI-224: 4-(3-(5-(cyclopentyl-1,4,5,6-tetrahydropyrrolo[3,4-d]imidazol-2-yl)-1H-indazol-6-yl)-5-ethyl-2-fluorophenol Intermediate MDI-224-1 (25 mg, 0.036 mmol) was dissolved in methanol (4 ml), to which concentrated hydrochloric acid (5 ml) was added. The mixture was heated to 50° C., reacted for 6 hours, and concentrated. The solid was dissolved in methanol and 2 ml of concentrated aqueous ammonia was added, and the mixture was concentrated to give a residue.

The residue was dissolved in methanol, and was concentrated to dryness, which was repeated 3 times. The resulting residue was purified by a preparation plate to afford 7.0 mg of the final product with a yield of 45.1%.

$^{1}$H NMR (400 MHz, MeOD-d4) δ 8.26 (d, J=8.0 Hz, 1H), 7.42 (s, 1H), 7.17 (d, J=8.0 Hz, 1H), 6.93 (dd, J=20.0 Hz, J=12.0 Hz, 2H), 4.05-3.94 (m, 4H), 3.27-3.25 (m, 1H), 2.59-2.54 (m, 2H), 2.08-2.01 (m, 2H), 1.87-1.79 (m, 2H), 1.73-1.56 (m, 4H), 1.08 (t, J=8.0 Hz, 3H).

Example 23: 5-ethyl-2-fluoro-4-(3-(5-(tetrahydro-2H-pyran-4-yl)-1,4,5,6-tetrahydropyrrolo[3,4-d]imidazol-2-yl)-1H-indazol-6-yl)phenol (MDI-225)

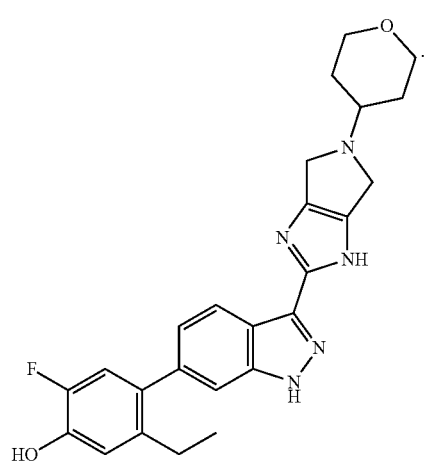

MDI-225

Synthetic Route of MDI-225:

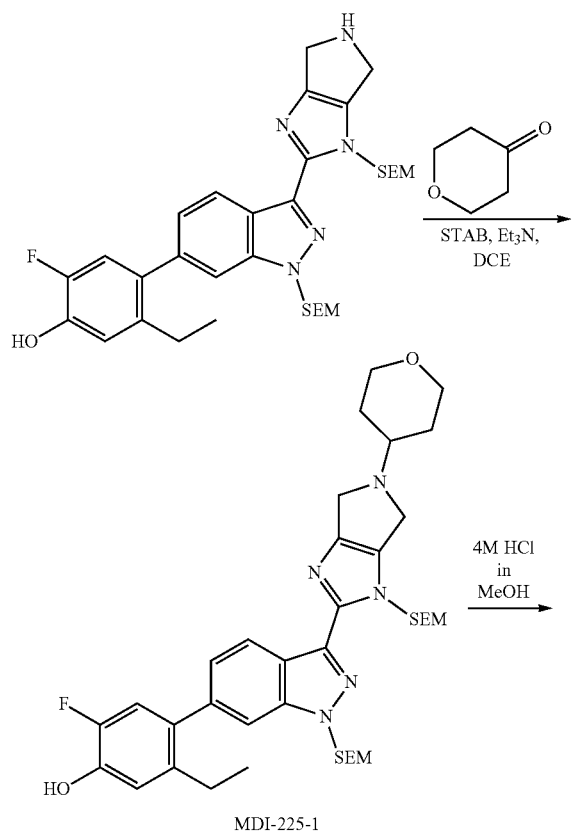

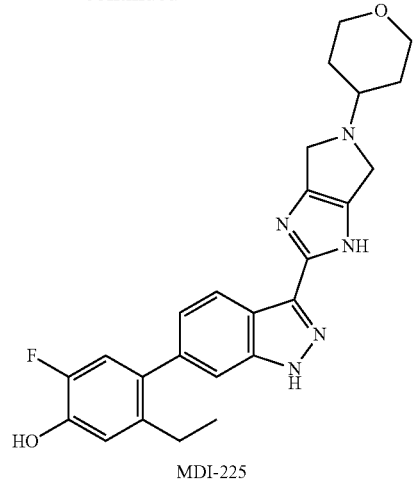

MDI-225

Synthesis Method

Synthesis of Intermediate MDI-225-1: 5-ethyl-2-fluoro-4-(3-(5-(tetrahydro-2H-pyran-4-yl)-1-((2-(trimethylsilyl)ethoxy)methyl)-1,4,5,6-tetrahydropyrrolo[3,4-d]imidazol-2-yl)-1-((2-(trimethylsilyl)ethoxy)methyl)-1H-indazol-6-yl)phenol 5-ethyl-2-fluoro-4-(1-((2-(trimethylsilyl)ethoxy)methyl)-3-(1-((2-(trimethylsilyl)ethoxy)methyl)-1,4,5,6-tetrahydropyrrolo[3,4-d]imidazol-2-yl)-1H-indazol-6-yl)phenol (60 mg, 0.096 mmol) was dissolved in 5 ml 1,2-dichloroethane, and tetrahydropyrone (14 mg, 0.14 mmol) was added. The mixture was stirred at room temperature for 5 minutes, and sodium triacetyl borohydride (41 mg, 0.19 mmol) was added. It was allowed to react at room temperature for 2 hours, and water was added to quench the reaction. The resulting mixture was extracted twice with DCM, and the organic phases were combined, washed with water and saturated brine, dried with anhydrous sodium sulfate, concentrated, and purified by silica gel column to afford intermediate MDI-225-1 with a yield of 51.4%.

$^{1}$H NMR (400 MHz, CDCl3) δ 8.43 (d, J=8.0 Hz, 1H), 7.44 (s, 1H), 7.20 (dd, J=8.0 Hz, J=1.4 Hz, 1H), 6.96 (dd, J=20.0 Hz, J=12.0 Hz, 2H), 5.93 (s, 2H), 5.76 (s, 2H), 4.08 (s, 4H), 4.00 (s, 2H), 3.66-3.56 (m, 4H), 3.55-3.47 (m, 2H), 2.95-2.86 (m, 1H), 2.54-2.46 (m, 2H), 1.99-1.90 (m, 2H), 1.80-1.71 (m, 2H), 1.04 (t, J=8.0 Hz, 3H), 0.95-0.87 (m, 4H), −0.03-0.08 (m, 18H).

Synthesis of Compound MDI-225: 5-ethyl-2-fluoro-4-(3-(5-(tetrahydro-2H-pyran-4-yl)-1,4,5,6-tetrahydropyrrolo[3,4-d]imidazol-2-yl)-1H-indazol-6-yl)phenol Intermediate MDI-225-1 (35.0 mg, 0.05 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, and pH was adjusted with sodium bicarbonate to 8-9. The resulting mixture was extracted 4 times with dichloromethane, and the organic phases were combined, dried over anhydrous sodium sulfate, and purified by a preparation plate to afford 12 mg of the final product with a yield of 64.1%.

¹H NMR (400 MHz, MeOD-d4) δ 8.26 (dd, J=12.0 Hz, J=4.0 Hz, 1H), 7.42 (s, 1H), 7.16 (dd, J=8.0 Hz, J=4.0 Hz, 1H), 6.93 (dd, J=20.0 Hz, J=12.0 Hz, 2H), 4.07-3.99 (m, 6H), 3.52-3.49 (m, 2H), 2.95-2.90 (m, 1H), 2.58-2.53 (m, 2H), 2.00-1.97 (m, 2H), 1.69-1.59 (m, 2H), 1.08 (t, J=8.0 Hz, 3H).

Example 24: 1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one (MDI-226)

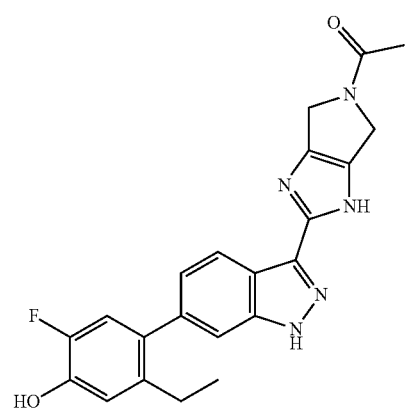

MDI-226

Synthetic Route of MDI-226:

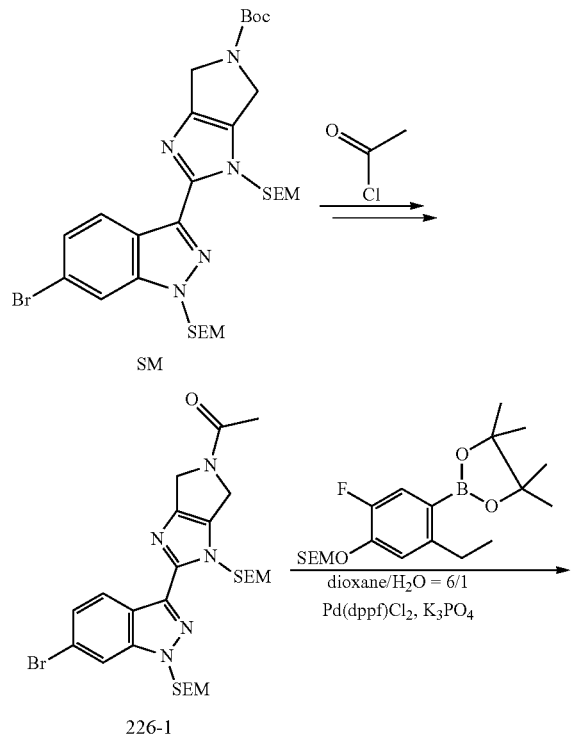

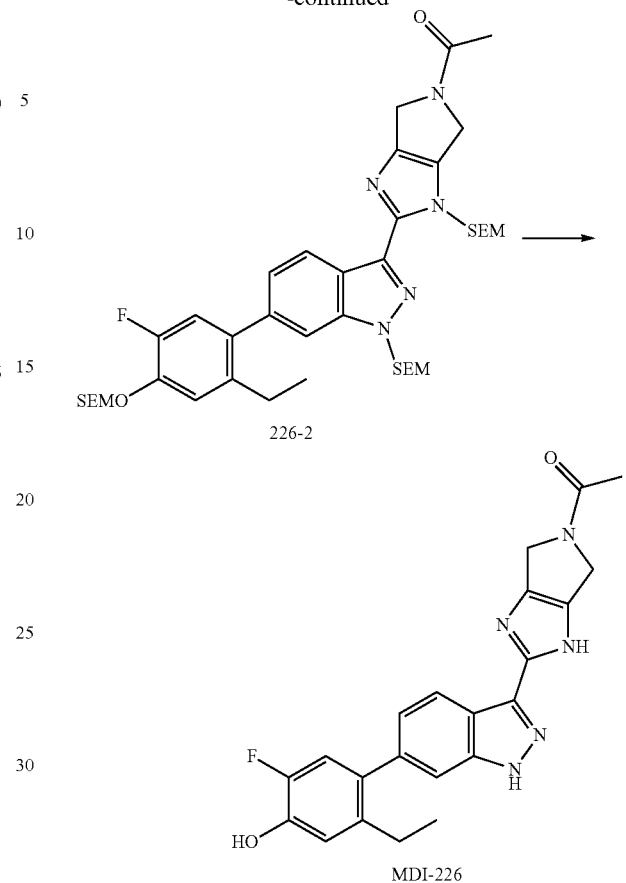

Synthesis Method

Synthesis of Intermediate MDI-226-1: 1-(2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)ethan-1-one Tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-carboxylate (200 mg, 0.30 mmol) was dissolved in 10 ml dichloromethane, and 2 ml trifluoroacetic acid was added. The mixture was stirred at room temperature for 30 minutes, concentrated, and quenched with sodium bicarbonate. The resulting mixture was extracted twice with dichloromethane, and the organic phases were combined, washed with water and saturated brine, dried over anhydrous sodium sulfate and concentrated. The obtained compound was dissolved in 10 ml DCM, and Et3N (0.16 ml, 1.18 mmol) was added. The mixture was cooled to 0° C., and acetyl chloride (25.0 mg, 0.32 mmol) was slowly added. It was allowed to react at room temperature for 2 hours, and water was added to quench the reaction. The resulting mixture was extracted with DCM twice, and the organic phases were combined, washed with water and saturated brine, dried over anhydrous sodium sulfate, concentrated, and purified by silica gel column to afford intermediate MDI-226-1 with a yield of 54.8%.

¹H NMR (400 MHz, chloroform-d) δ 8.36-8.29 (m, 1H), 7.78-7.77 (m, 1H), 7.42-7.39 (m, 1H), 5.93-5.88 (m, 2H), 5.71 (d, J=4 Hz, 2H), 4.76-4.73 (m, 2H), 4.67-4.63 (m, 2H), 3.61-3.54 (m, 4H), 2.20 (s, 3H), 0.94-0.88 (m, 4H)), −0.03-0.09 (m, 18H).

Synthesis of Intermediate MDI-226-2: 1-(2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)ethan-1-one The intermediate MDI-226-1 (100 mg, 0.16 mmol), (2-((5-ethyl-2-fluoro-4-(4,4,5,5-tetramethyl-1,3,2-dioxaboran-2-yl)phenoxy)methoxy)ethyl)trimethylsilane (78.3 mg, 0.20 mmol), Pd(dppf)Cl2 (12.0 mg, 0.016 mmol) and potassium phosphate (104.8 mg, 0.49 mmol) were dissolved in 1,4-dioxane (12 ml) and water (2 ml). The atmosphere was replaced with nitrogen, which was repeated 3 times. The mixture was heated to 100° C., reacted overnight, and cooled to room temperature. Water was added and the resulting mixture was extracted twice with ethyl acetate, and the organic phases were combined, washed with water and saturated brine, dried over anhydrous sodium sulfate, concentrated, and purified by silica gel column to afford the intermediate MDI-226-2 with a yield of 76.2%.

$^1$H NMR (400 MHz, chloroform-d) δ 8.52-8.45 (m, 1H), 7.49 (s, 1H), 7.27-7.25 (m, 1H), 7.18 (d, J=8 Hz, 1H), 7.03 (d, J=12 Hz, 1H) 6.00-5.95 (m, 2H), 5.78 (s, 2H), 5.34 (s, 2H), 4.80-4.77 (m, 2H), 4.71-4.69 (m, 2H), 3.90-3.86 (m, 2H), 3.66-3.58 (m, 4H), 2.59-2.54 (m, 2H), 2.22 (d, J=8 Hz, 3H), 1.10-1.06 (m, 3H), 1.03-0.91 (m, 6H), −0.02-0.06 (m, 27H).

Synthesis of Compound MDI-226: 1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one Intermediate MDI-226-2 (100 mg, 0.13 mmol) was dissolved in methanol (5 ml), to which concentrated hydrochloric acid (2.5 ml) was added. The mixture was heated to 50° C., reacted for 6 hours, and concentrated. The solid was dissolved in 1 ml of methanol, and pH was adjusted to 8-9 with aqueous ammonia. The resulting mixture was concentrated, and purified by silica gel column to afford 5 mg of the final product with a yield of 9.8%.

$^1$H NMR (400 MHz, methanol-d4) δ 8.28 (d, J=8 Hz, 1H), 7.43 (s, 1H), 7.18 (d, J=8 Hz, 1H), 6.94 (dd, J=22, 10 Hz, 2H), 4.79 (s, 2H), 4.65 (s, 2H), 2.59-2.53 (m, 2H), 2.23 (s, 3H), 1.08 (t, J=7.5 Hz, 3H).

Example 25: 1-(2-(6-(2-ethyl-5-fluoro-4-hydroxyphenyl)-1H-indazol-3-yl)-4,6-dihydropyrrolo[3,4-d]imidazol-5-(1H)-yl)propan-1-one (MDI-227)

Synthetic Route of MDI-77

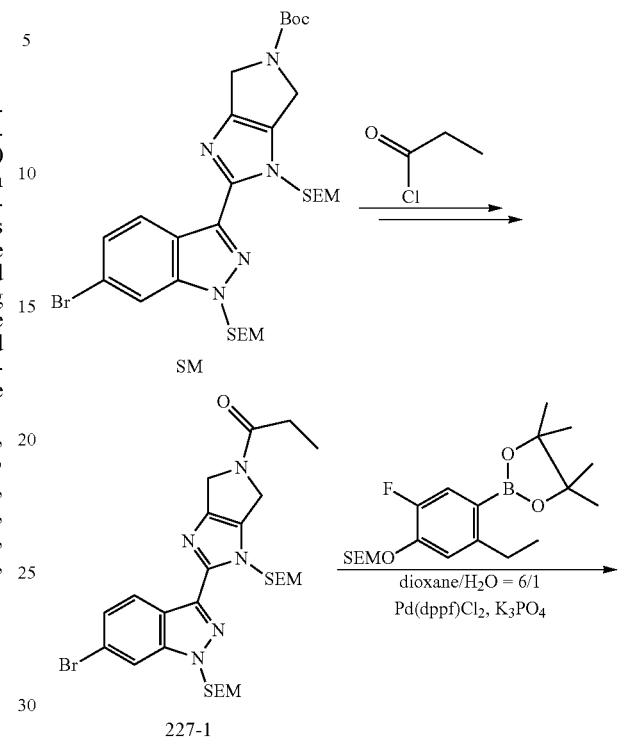

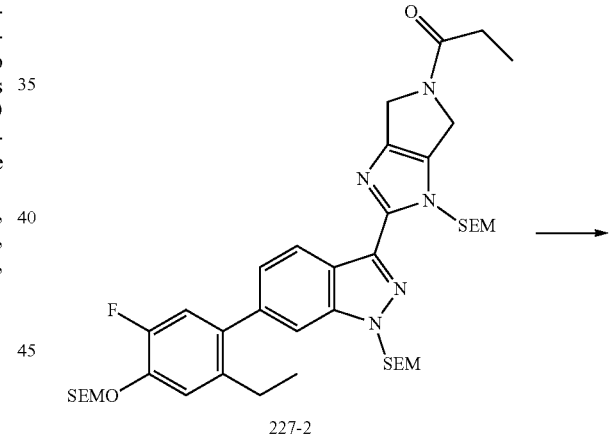

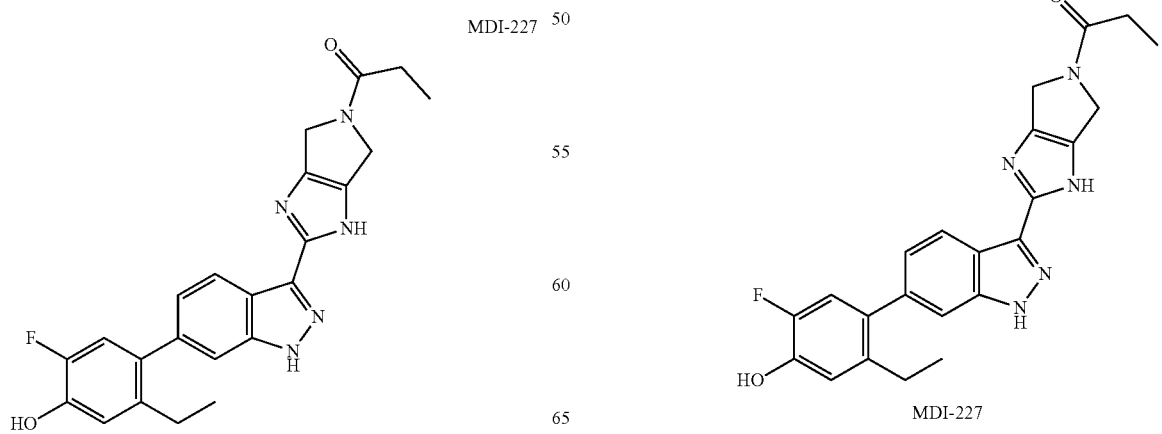

Synthesis Method

Synthesis of Intermediate MDI-227-1: 1-(2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)propan-1-one Tert-butyl 2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-carboxylate (200 mg, 0.30 mmol) was dissolved in 10 ml dichloromethane, and 2 ml trifluoroacetic acid was added. The mixture was stirred at room temperature for 30 minutes, concentrated, and quenched with sodium bicarbonate. The resulting mixture was extracted twice with dichloromethane, and the organic phases were combined, washed with water and saturated brine, dried over anhydrous sodium sulfate and concentrated. The obtained compound was dissolved in 10 ml DCM and Et3N (0.16 ml, 1.18 mmol), and cooled to 0° C.

Propionyl chloride (29 mg, 0.32 mmol) was slowly added. It was allowed to react at room temperature for 2 hours, and water was added to quench the reaction. The resulting mixture was extracted with DCM twice, and the organic phases were combined, washed with water and saturated brine, dried over anhydrous sodium sulfate, concentrated, and purified by silica gel column to afford intermediate MDI-227-1 with a yield of 53.5%.

$^1$H NMR (400 MHz, chloroform-d) δ 8.39-8.32 (m, 1H), 7.77-7.76 (m, 1H), 7.42-7.38 (m, 1H), 5.93-5.89 (m, 2H), 5.71 (d, J=4 Hz, 2H), 4.76-4.70 (m, 2H), 4.65-4.63 (m, 2H), 3.61-3.55 (m, 4H), 2.46-2.40 (m, 2H), 1.25-1.23 (m, 3H), 0.93-0.89 (m, 4H), −0.05-0.08 (m, 18H).

Synthesis of Intermediate MDI-227-2: 1-(2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)propan-1-one The intermediate MDI-227-1 (100 mg, 0.16 mmol), (2-((5-ethyl-2-fluoro-4-(4,4,5,5-tetramethyl-1,3,2-dioxaboran-2-yl)phenoxy)methoxy)ethyl)trimethylsilane (76.5 mg, 0.19 mmol), Pd(dppf)Cl2 (11.8 mg, 0.016 mmol) and potassium phosphate (102.4 mg, 0.48 mmol) were dissolved in 1,4-dioxane (12 ml) and water (2 ml). The atmosphere was replaced with nitrogen, which was repeated 3 times. The mixture was heated to 100° C., reacted overnight, and cooled to room temperature. Water was added, the resulting mixture was extracted twice with ethyl acetate, and the organic phases were combined, washed with water and saturated brine, dried over anhydrous sodium sulfate, concentrated, and purified by silica gel column to afford the intermediate MDI-227-2 with a yield of 76.7%.

$^1$H NMR (400 MHz, chloroform-d) δ 8.52-8.45 (m, 1H), 7.48 (d, J=4 Hz, 1H), 7.28-7.25 (m, 1H), 7.18 (d, J=8 Hz, 1H), 7.04 (d, J=12 Hz, 1H), 5.98 (d, J=12 Hz, 2H), 5.78 (s, 2H), 5.34 (s, 2H), 4.78 (s, 2H), 4.69-4.68 (m, 2H), 3.90-3.86 (m, 2H), 3.66-3.58 (m, 4H), 2.59-2.54 (m, 2H), 2.49-2.40 (m, 2H), 1.31-1.26 (m, 5H)), 1.10-1.05 (m, 3H), 0.96-0.91 (m, 4H), −0.02-0.05 (m, 27H).

Synthesis of Compound MDI-227: 1-(2-(6-(2-ethyl-5-fluoro-4-hydroxyphenyl)-1H-indazol-3-yl)-4,6-dihydropyrrolo[3,4-d]imidazol-5-(1H)-yl) propan-1-one Intermediate MDI-227-2 (100 mg, 0.12 mmol) was dissolved in methanol (5 ml), to which concentrated hydrochloric acid (2.5 ml) was added. The mixture was heated to 50° C., reacted for 6 hours, and concentrated. The solid was dissolved in 1 ml of methanol and pH was adjusted to 8-9 with aqueous ammonia. The resulting mixture was concentrated, and purified by silica gel column to afford 18 mg of final product with a yield of 34.8%.

$^1$H NMR (400 MHz, DMSO-d6) δ 13.29 (s, 1H), 12.80 (s, 1H), 9.85 (s, 1H), 8.33 (d, J=8 Hz, 1H), 7.40 (s, 1H), 7.12 (d, J=8 Hz, 1H), 7.03 (d, J=12 Hz, 1H), 6.92 (d, J=12 Hz, 1H), 4.73-4.58 (m, 2H), 4.50-4.42 (m, 2H), 2.50-2.47 (m, 2H), 2.43-2.37 (m, 2H), 1.08-1.01 (m, 6H).

Example 26: 1-(2-(6-(2-ethyl-5-fluoro-4-hydroxyphenyl)-1H-indazol-3-yl)-4,6-dihydropyrrolo[3,4-d]imidazol-5-(1H)-yl)-2-methylpropan-1-one (MDI-228)

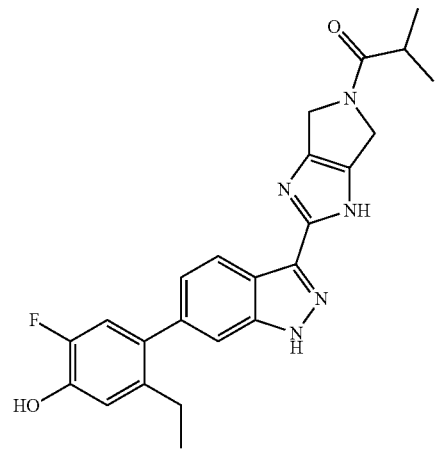

MDI-228

Synthetic Route of MDI-228:

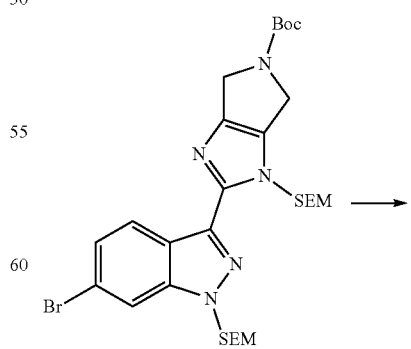

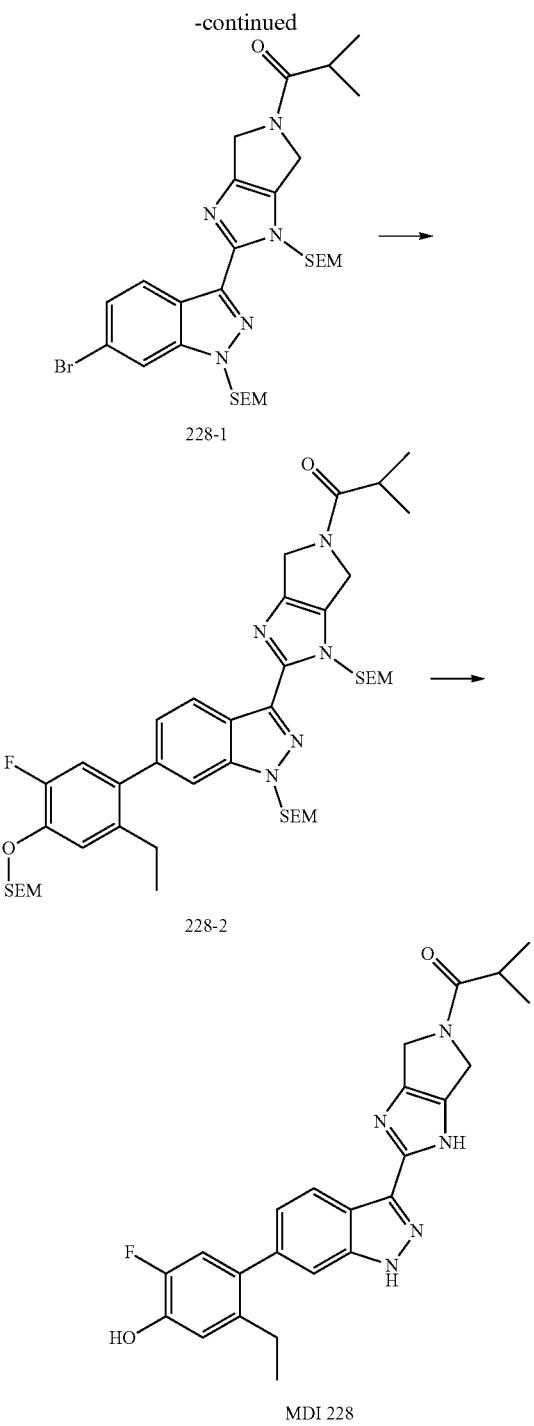

228-1

228-2

MDI 228

Synthesis Method

Synthesis of Intermediate MDI-228-1: (1-(2-(6-bromo1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)-2-methylpropan-1-one)

The intermediate tert-butyl 2-(6-bromol-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate (80 mg, 0.12 mmol) was dissolved in 5 ml of dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 5 ml of DCM, and then triethylamine (24.3 mg, 0.24 mmol) was added. The temperature was lowered to 0° C., and isobutyryl chloride (19.2 mg, 0.18 mmol) was slowly added dropwise. After the dropwise addition was completed, the mixture was warmed to room temperature and reacted for 1-2 h. Water was added to the reaction to quench the reaction. The liquids were separated, and the organic phase was dried over sodium sulfate and concentrated by column chromatography to afford compound MDI-228-1 with a yield of 58.7%.

$^1$H NMR (400 MHz, CDCl3) $^1$H NMR (400 MHz, CDCl3) δ 8.39-8.32 (m, 1H), 7.77-7.76 (m, 1H), 7.42-7.38 (m, 1H), 5.92-5.89 (m, 2H), 5.71-5.69 (m, 2H), 4.83-4.64 (m, 4H), 3.63-3.55 (m, 4H), 2.81-2.70 (m, 1H), 1.22 (d, J=8 Hz, 6H), 0.98-0.86 (m, 4H), —0.05-0.08 (m, 18H).

Synthesis of Intermediate MDI-228-2: 1-(2-(6-(2-ethyl-5-fluoro-4-((2-(trimethylsilyl)ethoxy)methoxy)phenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)-2-methylpropan-1-one The intermediate MDI-228-1 (50.65 mg, 0.08 mmol), (2-((5-ethyl-2-fluoro-4-(4, 4,5,5-tetramethyl-1,3,2-dioxaboran-2-yl)phenoxy)methoxy)ethyl)trimethylsilane (34.8 mg, 0.1 mmol), Pd(dppf)Cl2 (5.9 mg, 0.008 mmol) and potassium phosphate (50.9 mg, 0.24 mmol) were dissolved in 1,4-dioxane (10 ml) and water (2 ml). The atmosphere was replaced with nitrogen, which was repeated 3 times. The mixture was heated to 100° C., reacted overnight, and cooled to room temperature. Water was added, and the resulting mixture was extracted twice with ethyl acetate, and the organic phases were combined, washed with water and saturated brine, dried over anhydrous sodium sulfate, concentrated and purified by silica gel column to afford intermediate MDI-228-2 with a yield of 77.5%.

$^1$H NMR (400 MHz, CDCl3) δ 8.49-8.42 (m, 1H), 7.46-7.45 (m, 1H), 7.25-7.22 (m, 1H), 7.16 (d, J=8 Hz, 1H), 7.02 (d, J=12 Hz, 1H), 5.97-5.92 (m, 2H), 5.76 (s, 2H), 5.32 (s, 2H), 4.83-4.67 (m, 4H), 3.88-3.84 (m, 2H), 3.64-3.56 (m, 4H), 2.82-2.73 (m, 1H), 2.57-2.51 (m, 2H), 1.22 (d, J=8 Hz, 6H), 1.08-0.99 (m, 5H), 0.93-0.88 (m, 4H), 0.03 (s, 9H), −0.06-0.07 (m, 18H).

Synthesis of Compound MDI-228: 1-(2-(6-(2-ethyl-5-fluoro-4-hydroxyphenyl)-1H-indazol-3-yl)-4,6-dihydropyrrolo[3,4-d]imidazol-5-(1H)-yl)-2-methylpropan-1-one Intermediate MDI-228-2 (50 mg, 0.061 mmol) was dissolved in methanol (4 ml), to which concentrated hydrochloric acid (2 ml) was added. The mixture was heated to 50° C., reacted for 6 hours, and concentrated. The solid was dissolved in 1 ml methanol, 2 ml concentrated aqueous ammonia was added, and the mixture was concentrated to give a residue. The residue was dissolved in methanol and was concentrated to dryness, which was repeated 3 times. The resulting residue was purified by a preparation plate to afford 15 mg of the final product with a yield of 57.0%.

¹H NMR (400 MHz, MeOD-d4) δ 8.26 (d, J=8.0 Hz, 1H), 7.43 (s, 1H), 7.17 (d, J=8 Hz, 1H), 6.93 (dd, J=20, 12 Hz, 2H), 4.83-4.59 (m, 4H), 2.94-2.90 (m, 1H), 2.58-2.52 (m, 2H), 1.22 (d, J=8.0 Hz, 6H), 1.08 (t, J=8.0 Hz, 3H).

Example 27: 2-cyclopropyl-1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one (MDI-229)

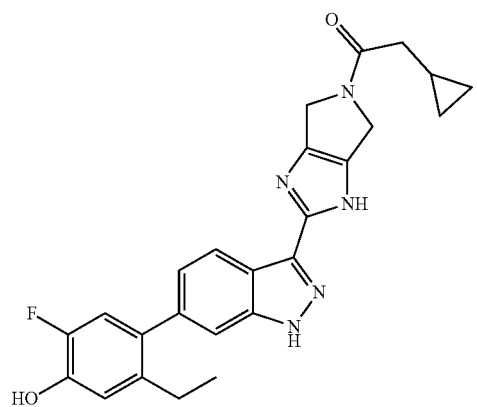

Synthetic Route of MDI-229:

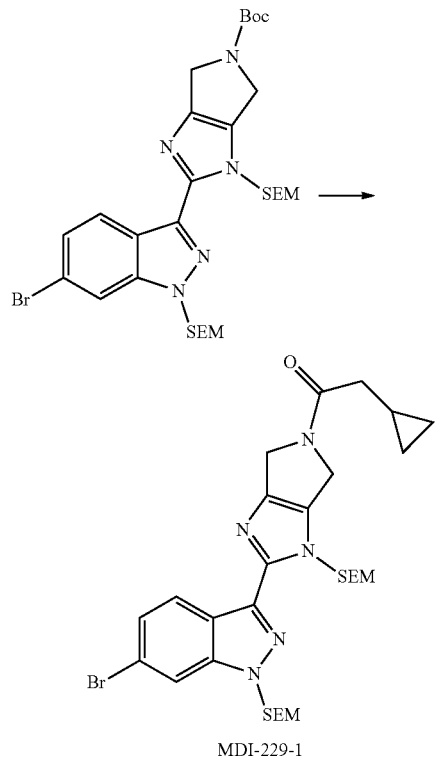

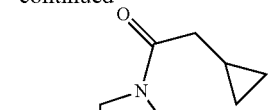

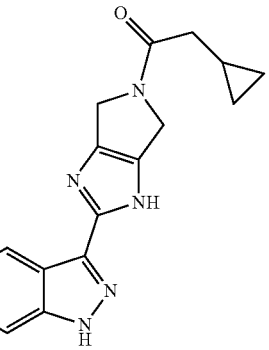

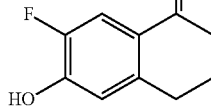

Synthesis Method

Synthesis of Intermediate MDI-229-1: 1-(2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)-2-cyclopropylethan-1-one 2-cyclopropylacetic acid (14.5 mg, 0.14 mmol) and N,N-diisopropylethylamine (46.6 mg, 0.36 mmol) were dissolved in DMF, and HATU (54.9 mg, 0.14 mmol) was added. It was allowed to react at room temperature for 10 minute. Intermediate tert-butyl 2-(6-bromol-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate (80.0 mg, 0.12 mmol) was dissolved in 5 ml dichloromethane, to which 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in DMF, and then was slowly added to the previous reaction solution. It was allowed to react at room temperature overnight, and water was added to quench the reaction. The resulting mixture was extracted twice with ethyl acetate, and the organic phases were combined, washed with water and saturated brine, dried over anhydrous sodium sulfate, concentrated, and purified by silica gel column to afford intermediate MDI-229-1 with a yield of 57.8%.

¹H NMR (400 MHz, CDCl3) δ 8.40 (dd, J=8.0 Hz, J=20.0 Hz, 1H), 7.80 (s, 1H), 7.44-7.41 (m, 1H), 5.92 (s, 2H), 5.74 (s, 2H), 4.78-4.66 (m, 4H), 3.63-3.58 (m, 4H), 2.39-2.35 (m, 2H), 2.04 (s, 1H), 0.96-0.91 (m, 4H), 0.66 (d, J=8.0 Hz, 2H), 0.27 (d, J=4.0 Hz, 2H), 0.02 (s, 18H).

Synthesis of Intermediate MDI-229-2: 2-cyclopropyl-1-(2-(6-(2-ethyl-5-fluoro-4-((2-(trimethylsilyl)ethoxy)methoxy)phenyl)-1-((2-(trimethylsilyl)ethoxy) methyl)-1H-indazol-3-yl)-1-((2-(trimethylsilyl)ethoxy)methyl)-4,6-dihydropyrrolo[3,4-d]imidazol-5-(1H)-yl)ethan-1-one The intermediate MDI-229-1 (45.0 mg, 0.07 mmol), (2-((5-ethyl-2-fluoro-4-(4, 4,5,5-tetramethyl-1,3,2-dioxaboran-2-yl)phenoxy)methoxy)ethyl)trimethylsilane (33.1 mg, 0.08 mmol), Pd(dppf)Cl2 (5.1 mg, 0.007 mmol) and potassium phosphate (44.3 mg, 0.21 mmol) were dissolved in 1,4-dioxane (20 ml) and water (4 ml). The atmosphere was replaced with nitrogen, which was repeated 3 times. The mixture was heated to 100° C., reacted overnight, and cooled to room temperature. Water was added, the resulting mixture was extracted twice with ethyl acetate, and the organic phases were combined, washed with water and saturated brine, dried over anhydrous sodium sulfate, concentrated, and purified by silica gel column to afford intermediate MDI-229-1 with a yield of 55.0%.

¹H NMR (400 MHz, CDCl3) δ 8.50 (dd, J=8.0 Hz, J=16.0 Hz, 1H), 7.49 (s, 1H), 7.27 (s, 1H), 7.19 (d, J=8.0 Hz, 1H), 7.05 (d, J=12.0 Hz, 1H), 5.96 (s, 2H), 5.78 (s, 2H), 5.34 (s, 2H), 4.79-4.66 (m, 4H), 3.88 (t, J=8.0 Hz, 2H), 3.66-3.58 (m, 4H), 2.59-2.54 (m, 2H), 2.39-2.36 (m, 2H), 2.06-2.04 (m, 1H), 1.05 (t, J=8.0 Hz, 3H), 0.96-0.91 (m, 6H), 0.66-0.63 (m, 2H), 0.28-0.26 (m, 2H), 0.06-0.05 (m, 27H).

Synthesis of Compound MDI-229: 2-cyclopropyl-1-(2-(6-(2-ethyl-5-fluoro-4-hydroxyphenyl)-1H-indazol-3-yl)-4,6-dihydropyrrolo[3,4-d]imidazol-5-(1H)-yl)ethan-1-one The intermediate MDI-229-4 was dissolved in 4 ML methanol and 2 ml concentrated hydrochloric acid was added. The mixture was heated to 50° C., reacted for 6 hours, and concentrated to give a residue. The residue was dissolved in methanol and was concentrated to dryness, which was repeated 3 times. The resulting residue was dissolved 1 ml methanol and 2 ml aqueous ammonia was added for neutralization, and the resulting mixture was concentrated to give a residue. The residue was dissolved in methanol and was concentrated to dryness, which was repeated 2 times, thereby obtaining 3.8 mg of the product with a yield of 12.2%.

¹H NMR (400 MHz, MeOD-d4) δ 8.29 (d, J=8.0 Hz, 1H), 7.43 (s, 1H), 7.19-7.17 (m, 1H), 6.98-6.90 (m, 2H), 4.73-4.61 (m, 4H), 2.59-2.53 (m, 2H), 2.46 (d, J=8.0 Hz, 2H), 1.17 (m, 1H), 1.08 (t, J=8.0 Hz, 3H), 0.64-0.59 (m, 2H), 0.30-0.26 (m, 2H).

Example 28: 1-(2-(6-(2-ethyl-5-fluoro-4-hydroxyphenyl)-1H-indazol-3-yl)-4,6-dihydropyrrolo[3,4-d]imidazol-5-(1H)-yl)-3-methylbutan-1-one (MDI-230)

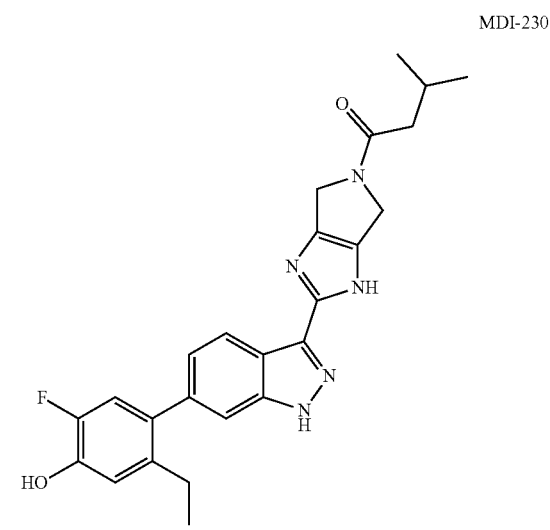 [SMILES: CCc1cc(O)c(F)cc1-c1ccc2c(-c3nc4c([nH]3)CN(C(=O)CC(C)C)C4)n[nH]c2c1]

MDI-230

Synthetic Route of MDI-230:

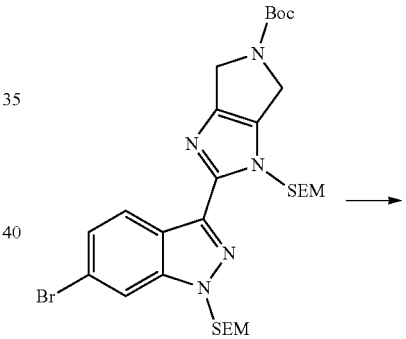

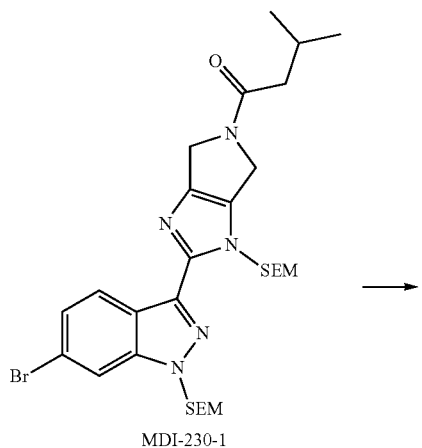

MDI-230-1

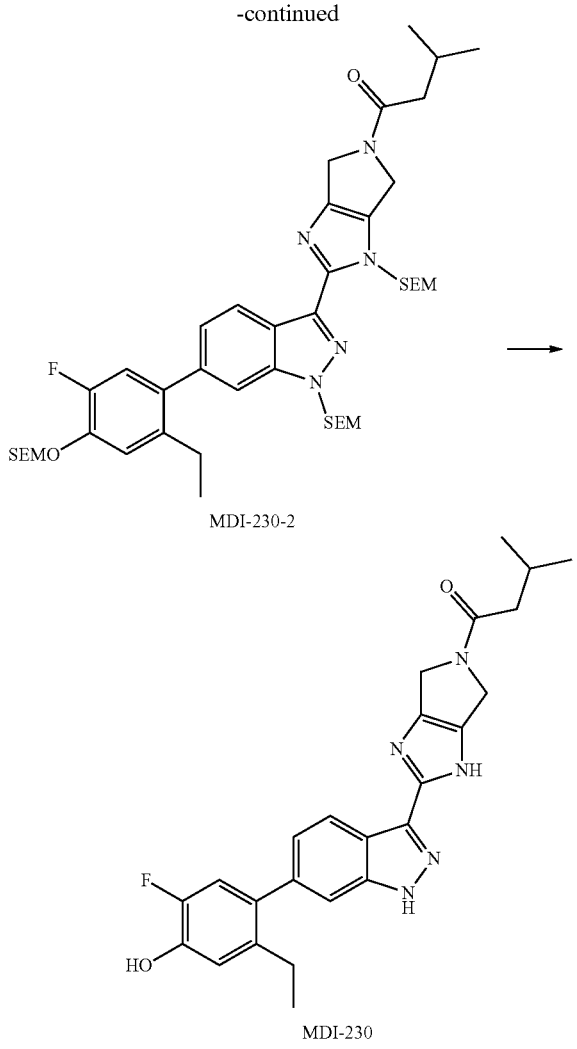

Synthesis Method

Synthesis of Intermediate MDI-230-1: 1-(2-(6-bromo-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)-3-methylbutan-1-one Tert-butyl 2-(6-bromol-((2-(trimethylsilyl)ethoxy) methyl)-1H-indol-3-yl)-1-((2-(trimethylsilyl)ethoxy) methyl)-4,6-dihydropyrrolo[3,4-d]imidazol-5(1H)-carboxylate (100 mg, 0.15 mmol) was dissolve in 5 ml of dichloromethane, and 1 ml of trifluoroacetic acid was added. The mixture was stirred at room temperature for 30 minutes, and concentrated to give a residue. The residue was dissolved in dichloromethane and was concentrated to dryness, which was repeated 3 times. The resulting residue was dissolved in 5 ml of dichloromethane and triethylamine (0.08 ml, 0.59 mmol) and cooled to 0° C. 3-methylbutyryl chloride (36.6 mg, 0.30 mmol) was slowly added. It was allowed to react at room temperature for 2 hours, and water was added to quench the reaction. The resulting mixture was extracted twice with dichloromethane, and the organic phases were combined, washed with saturated brine, dried over anhydrous sodium sulfate, concentrated, and purified by silica gel column to afford 64 mg of intermediate MDI-230-1, with a yield of 65.8%.

$^1$H NMR (400 MHz, CDCl3) δ 8.42-8.35 (m, 1H), 7.80-7.79 (m, 1H), 7.45-7.41 (m, 1H), 5.96-5.91 (m, 2H), 5.74-5.73 (m, 2H), 4.78-4.69 (m, 4H), 3.67-3.58 (m, 4H), 2.31-2.22 (m, 3H), 1.08-1.05 (m, 6H), 0.97-0.90 (m, 4H), −0.02-0.05 (m, 18H).

Synthesis of Intermediate MDI-230-2: 1-(2-(6-(2-ethyl-5-fluoro-4-((2-(trimethylsilyl)ethoxy)methoxy) phenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)-3-methylbutan-1-one The intermediate MDI-230-1 (98 mg, 0.15 mmol), (2-((5-ethyl-2-fluoro-4-(4, 4,5,5-tetramethyl-1,3,2-dioxaboran-2-yl)phenoxy)methoxy)ethyl)trimethylsilane (64 mg, 0.10 mmol), Pd(dppf)Cl2 (10 mg, 0.01 mmol) and potassium phosphate (70 mg, 0.30 mmol) were dissolved in 1,4-dioxane (20 ml) and water (4 ml). The atmosphere was replaced with nitrogen, which was repeated 3 times. The mixture was heat to 100° C., reacted for 16 h, and cooled to room temperature. Water was added, the resulting mixture was extracted twice with ethyl acetate, and the organic phases were combined, washed with water and saturated brine, dried over anhydrous sodium sulfate, concentrated, and purified by silica gel column to afford 50 mg of intermediate MDI-230-2 with a yield of 59.7%.

$^1$H NMR (400 MHz, CDCl3) δ8.52-8.45 (m, 1H), 7.49 (s, 1H), 7.25 (d, J=2.8 Hz, 1H), 7.18 (d, J=8.6 Hz, 1H), 7.04 (d, J=11.8 Hz, 1H), 5.98 (d, J=15.6 Hz, 2H), 5.78 (s, 2H), 5.36 (s, 2H), 4.78-4.72 (m, 4H), 3.91-3.86 (m, 2H), 3.66-3.59 (m, 4H), 2.60 2.56 (m, 2H), 2.32-2.30 (m, 3H), 1.11-1.01 (m, 6H), 0.99-0.89 (m, 7H), 0.03 (s, 9H), −0.03-0.05 (m, 18H).

Synthesis of Compound MDI-230: 1-(2-(6-(2-ethyl-5-fluoro-4-hydroxyphenyl)-1H-indazol-3-yl)-4,6-dihydropyrrolo[3,4-d]imidazol-5-(1H)-yl)-3-methylbutan-1-one The intermediate MDI-230-2 (50 mg, 0.06 mmol) was dissolved in methanol (6 ml), to which concentrated hydrochloric acid (3 ml) was added. It was heated to 50° C. and allowed to react for 6 hours. The reaction mixture was concentrated to give a residue. The residue was dissolved in methanol and concentrated to dryness (to remove hydrochloric acid), which was repeated 3 times. The resulting residue was dissolved in methanol, to which 1 ml ammonia water was added. Then the mixture was concentrated and filtered, the filtrate was concentrated and purified by a preparation plate to afford 15 mg of the final product with a yield of 55.9%.

$^1$H NMR (400 MHz, MeOD-d4) δ 8.29-8.26 (m, 1H), 7.43 (s, 1H), 7.19-7.16 (m, 1H), 6.97-6.89 (m, 2H), 4.75-4.70 (m, 4H), 2.56 (q, J=7.5 Hz, 2H), 2.36 (m, 2H), 2.29-2.20 (m, 1H), 1.10-1.05 (m, 9H).

Example 29: (2-(6-(2-ethyl-5-fluoro-4-hydroxyphenyl)-1H-indazol-3-yl)-4,6-dihydropyrrolo[3,4-d]imidazol-5-(1H)-yl)(pyrrolidin-1-yl)ketone (MDI-231)

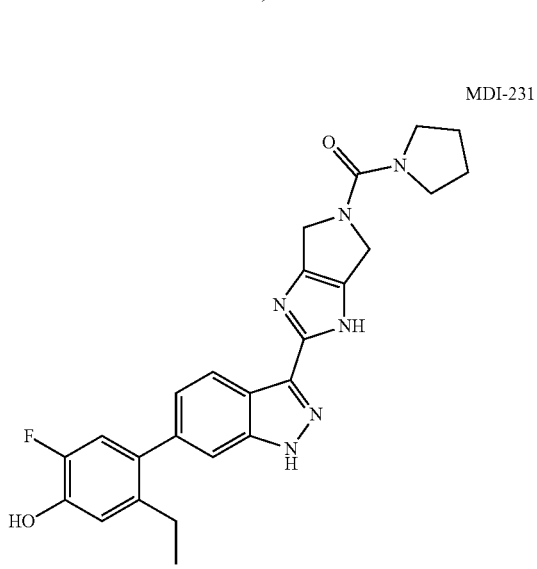

Synthetic Route of MDI-231:

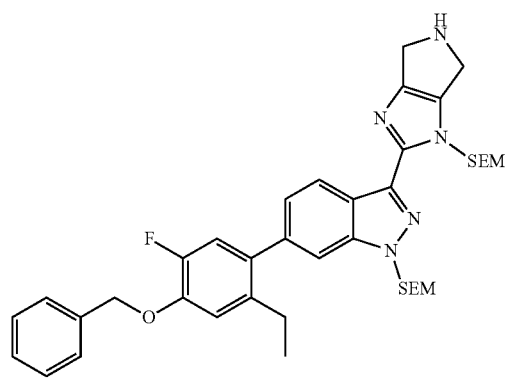

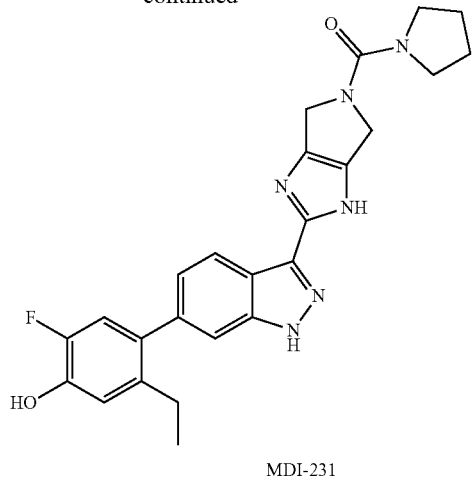

Synthesis Method

Synthesis of intermediate MDI-231-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl) (pyrrolidin-1-yl)ketone Triphosgene (64.4 mg, 0.21 mmol) was dissolved in 15 ml of dichloromethane, to which the intermediate 6-(4-(benzyloxy)-2-ethyl-5-fluorophenyl)-1-((2-(trimethylsilyl) ethoxy)methyl)-3-(1-((2-(Trimethylsilyl)ethoxy)methyl)-1-1,4,5,6-tetrahydropyrrolo[3,4-d]imidazol-2-yl)-1H-indazole (150 mg, 0.21 mmol) in dichloromethane (5 ml) was added dropwise at 0° C., followed by addition of triethylamine (63.6 mg, 0.63 mmol). The mixture was stirred at room temperature for 5 minutes and pyrrolidine (29.8 mg, 0.42 mmol) in dichloromethane was added. The resulting mixture was stirred at room temperature for 10 minutes, and water was added. The resulting mixture was extracted twice with ethyl acetate, and the organic phases were combined, washed with water and saturated brine, dried over anhydrous sodium sulfate, concentrated, and purified by silica gel column to afford 140 mg of intermediate MDI-231-1 with a yield of 82.4%.

$^1$H NMR (400 MHz, CDCl3) δ 8.48 (d, J=8 Hz, 1H), 7.53-7.38 (m, 6H), 7.22 (d, J=8 Hz, 1H), 7.03 (d, J=12 Hz, 1H), 6.95 (d, J=8 Hz, 1H), 5.96 (s, 2H), 5.77 (s, 2H), 5.23 (s, 2H), 4.81 (s, 2H), 4.67 (s, 2H), 3.66-3.59 (m, 4H), 3.53-3.51 (m, 4H), 2.56-2.52 (m, 2H), 1.93-1.88 (m, 4H), 1.03 (t, J=8 Hz, 3H), 0.93-0.87 (m, 4H), −0.05-0.09 (m, 18H).

Synthesis of Compound MDI-231: (2-(6-(2-ethyl-5-fluoro-4-hydroxyphenyl)-1H-indazol-3-yl)-4,6-dihydropyrrolo[3,4-d]imidazol-5-(1H)-yl)(pyrrolidin-1-yl)ketone Intermediate MDI-231-1 (140 mg, 0.173 mmol) was dissolved in methanol (6 ml), to which 15 mg Pd/C was added and concentrated hydrochloric acid (3 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 21 mg of the final product with a yield of 26.3%.

$^1$H NMR (400 MHz, DMSO-d6) δ 13.25 (s, 1H), 12.69 (s, 1H), 9.83 (s, 1H), 8.31 (d, J=8 Hz, 1H), 7.39 (s, 1H), 7.11 (d, J=8 Hz, 1H), 7.02 (d, J=12 Hz, 1H), 6.91 (d, J=12 Hz, 1H), 4.57-4.56 (m, 2H), 4.49-4.48 (m, 2H), 3.32-3.31 (m, 4H), 2.48-2.44 (m, 2H), 1.85-1.79 (m, 4H), 1.02 (t, J=7 Hz, 3H).

Example 30: Azetidin-1-yl(2-(6-(2-ethyl-5-fluoro-4-hydroxyphenyl)-1H-indazol-3-yl)-4,6-dihydropyrrolo[3,4-d]imidazol-5-(1H)-yl)ketone (MDI-232)

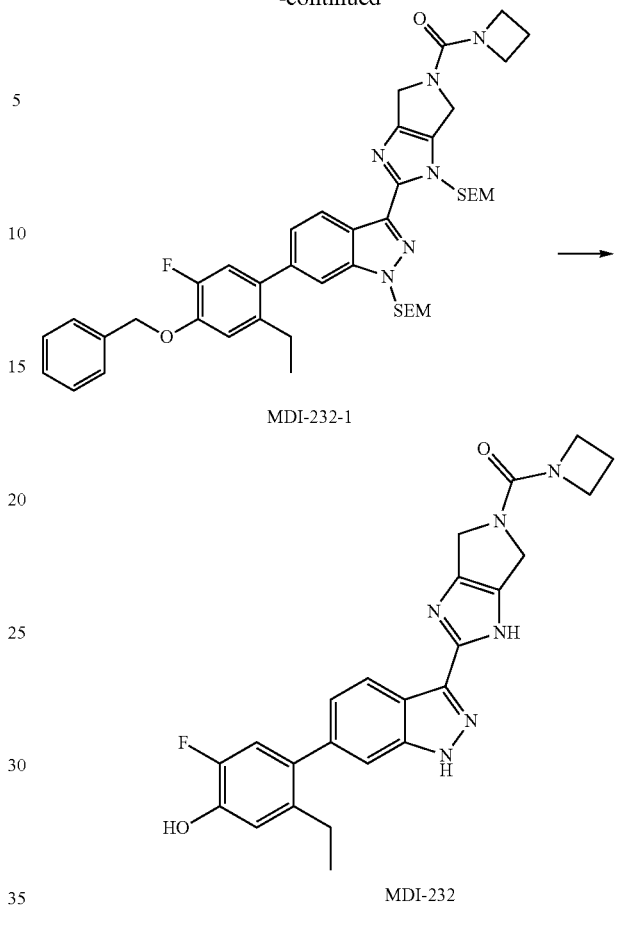

Synthetic Route of MDI-232:

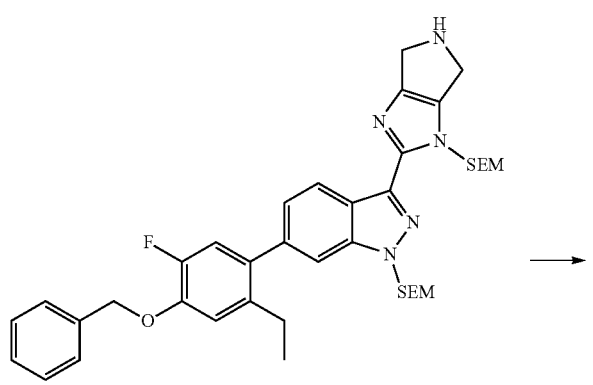

Synthesis Method

Synthesis of Intermediate MDI-232-1: Azetidin-1-yl (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)ketone Triphosgene (49.1 mg, 0.165 mmol) was dissolved in 15 ml of tetrahydrofuran, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (118 mg, 0.165 mmol) in tetrahydrofuran (5 ml) was added dropwise at 0° C. and then triethylamine (50.0 mg, 0.495 mmol) was added. The mixture was stirred at room temperature for 5 minutes, and azetidine (18.8 mg, 0.330 mmol) in tetrahydrofuran was added. The resulting mixture was stirred at room temperature for 10 minutes. Water was added and the resulting mixture was extracted twice with ethyl acetate, and the organic phases were combined, washed with water and saturated brine, dried over anhydrous sodium sulfate, concentrated, and purified by silica gel column to afford 105 mg of intermediate MDI-232-1, with a yield of 79.8%.

$^1$H NMR (400 MHz, CDCl3) δ 8.52 (d, J=8.3 Hz, 1H), 7.58-7.55 (m, 2H), 7.52-7.40 (m, 4H), 7.30-7.28 (m, 1H), 7.11-7.01 (m, 2H), 5.82 (s, 2H), 5.43 (s, 2H), 5.27 (s, 2H), 4.78-4.61 (m, 4H), 4.22-4.19 (m, 4H), 3.70-3.56 (m, 4H), 2.62 (q, J=7.5 Hz, 2H), 2.41-2.36 (m, 2H), 1.03 (t, J=7.5 Hz, 3H), 0.99-0.94 (m, 4H), 0.07 (d, J=2.7 Hz, 18H).

Synthesis of Compound MDI-232: Azetidin-1-yl (2-(6-(2-ethyl-5-fluoro-4-hydroxyphenyl)-1H-indazol-3-yl)-4,6-dihydropyrrolo[3,4-d]imidazol-5-(1H)-yl)ketone Intermediate MDI-232-1 (105 mg, 0.132 mmol) was dissolved in methanol (6 ml), to which 11 mg Pd/C was added and concentrated hydrochloric acid (3 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 25 mg of the final product with a yield of 42.6%.

$^1$H NMR (400 MHz, MeOD-d4) δ 8.29 (dd, J=8.4 Hz, J=4.0 Hz, 1H), 7.43 (s, 1H), 7.19-7.16 (m, 1H), 6.97-6.90 (m, 2H), 4.62-4.53 (m, 4H), 3.69-3.66 (m, 2H), 3.43-3.40 (m, 2H), 2.54 (q, J=7.5 Hz, 2H), 2.09-2.02 (m, 2H), 1.06 (t, J=7.5 Hz, 3H).

Example 31: (2-(6-(2-ethyl-5-fluoro-4-hydroxyphenyl)-1H-indazol-3-yl)-4,6-dihydropyrrolo[3,4-d]imidazol-5-(1H)-yl)(piperidin-1-yl)ketone (MDI-233)

MDI-233

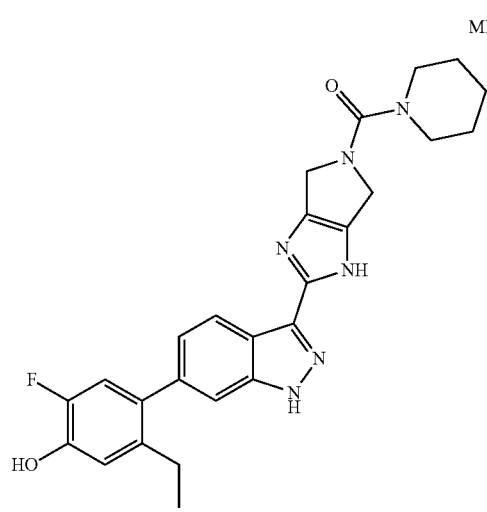

Synthetic Route of MDI-233:

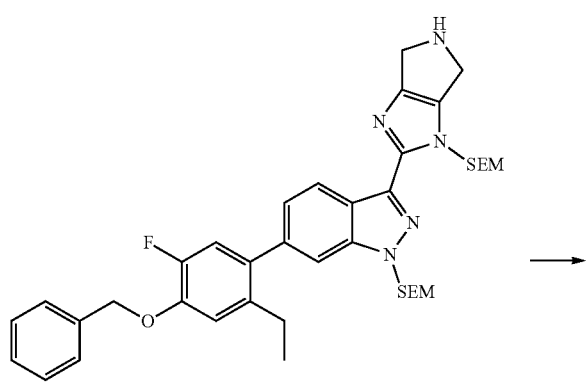

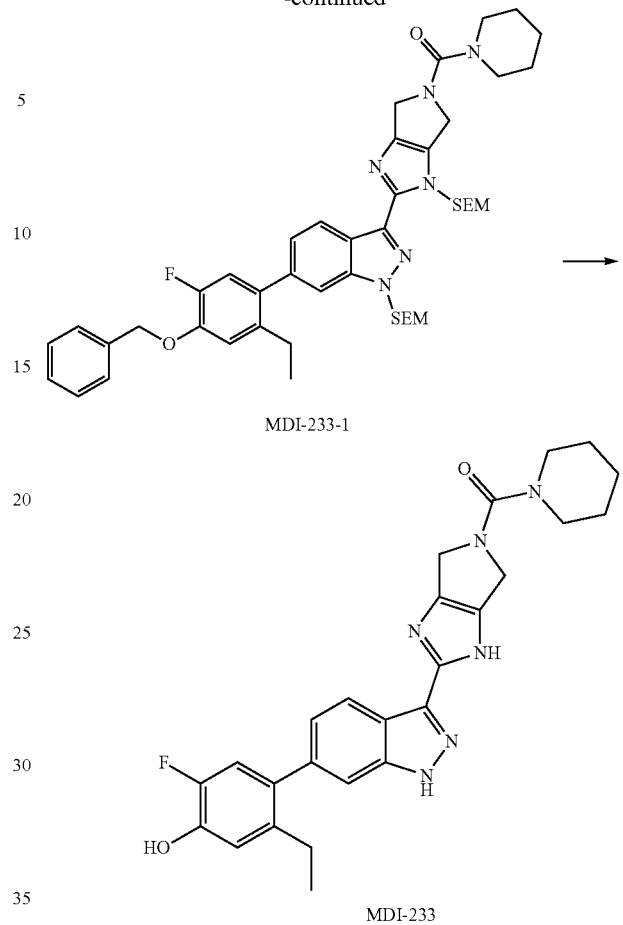

Synthesis Method

Synthesis of Intermediate MDI-233-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(piperidin-1-yl)ketone Triphosgene (54.1 mg, 0.182 mmol) was dissolved in 5 ml of tetrahydrofuran, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (130 mg, 0.182 mmol) in tetrahydrofuran (5 ml) was added dropwise at 0° C., followed by addition of triethylamine (55.2 mg, 0.550 mmol). The mixture was stirred at room temperature for 5 minutes, and piperidine hydrochloride (44.4 mg, 0.364 mmol) in tetrahydrofuran was added. The resulting mixture was stirred at room temperature for 10 minutes. Water was added and the resulting mixture was extracted twice with ethyl acetate, and the organic phases were combined, washed with water and saturated brine, dried over anhydrous sodium sulfate, concentrated, and purified by silica gel column to afford 105 mg of intermediate MDI-233-1, with a yield of 66.6%.

$^1$H NMR (400 MHz, CDCl$_3$) δ 8.44 (d, J=8.3 Hz, 1H), 7.50-7.48 (m, 2H), 7.44-7.35 (m, 4H), 7.23-7.20 (m, 1H), 7.04-6.94 (m, 2H), 5.93 (s, 2H), 5.74 (s, 2H), 5.20 (s, 2H), 4.69 (d, J=54.8 Hz, 4H), 3.64-3.56 (m, 4H), 3.31 (s, 4H), 2.54 (q, J=7.5 Hz, 2H), 1.64 (s, 6H), 1.03 (t, J=7.5 Hz, 3H), 0.93-0.86 (m, 4H), −0.07 (d, J=2.7 Hz, 18H).

Synthesis of Compound MDI-233: (2-(6-(2-ethyl-5-fluoro-4-hydroxyphenyl)-1H-indazol-3-yl)-4,6-dihydropyrrolo[3,4-d]imidazol-5-(1H)-yl)(piperidin-1-yl)ketone Intermediate MDI-233-1 (100 mg, 0.121 mmol) was dissolved in methanol (6 ml), to which 10 mg Pd/C was added and concentrated hydrochloric acid (3 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 33 mg of the final product with a yield of 57.3%.

$^1$H NMR (400 MHz, MeOD-d4) δ 8.25 (d, J=8.4 Hz, 1H), 7.40 (s, 1H), 7.16-7.14 (m, 1H), 6.95-6.87 (m, 2H), 4.83-4.65 (m, 4H), 3.35-3.33 (m, 4H), 2.54 (q, J=7.5 Hz, 2H), 1.67-1.65 (m, 6H), 1.06 (t, J=7.5 Hz, 3H).

Example 32: (2-(6-(2-ethyl-5-fluoro-4-hydroxyphenyl)-1H-indazol-3-yl)-4,6-dihydropyrrolo[3,4-d]imidazol-5-(1H)-yl)(morpholino)ketone (MDI-234)

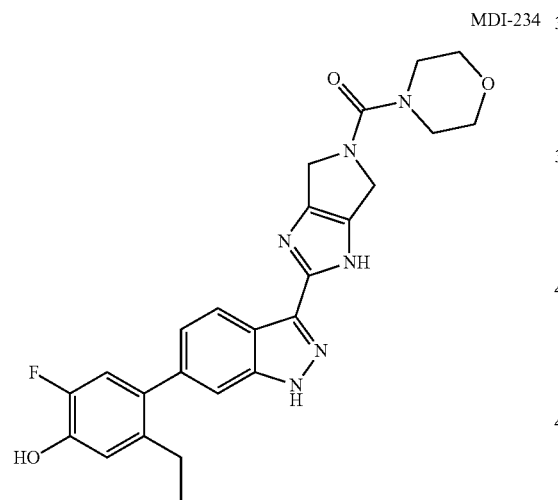

MDI-234

Synthetic Route of MDI-234:

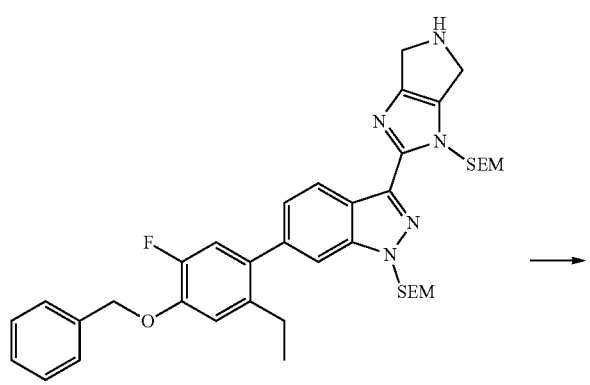

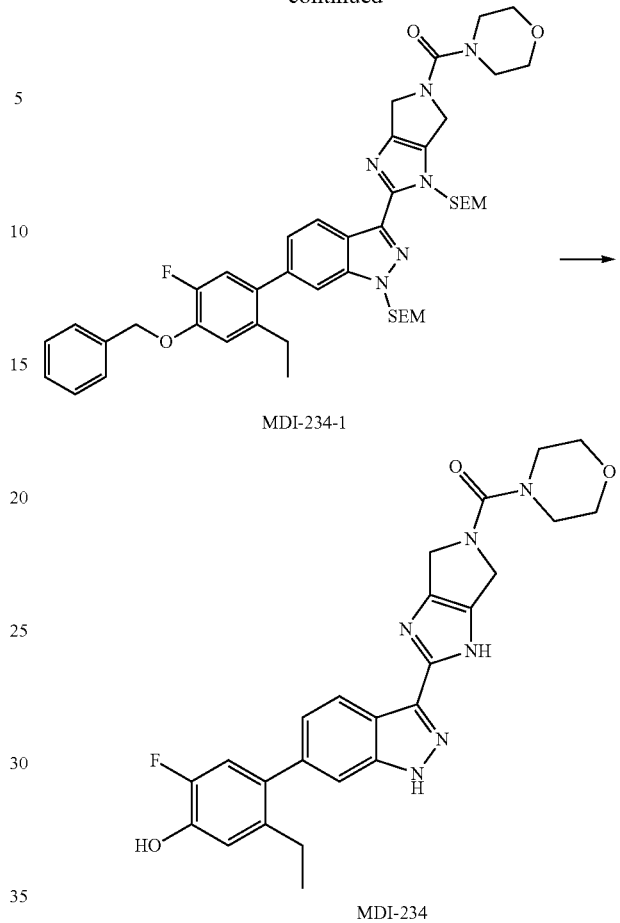

Synthesis Method

Synthesis of Intermediate MDI-234-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(morpholino)ketone Triphosgene (54.1 mg, 0.182 mmol) was dissolved in 5 ml of tetrahydrofuran, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (130 mg, 0.182 mmol) in tetrahydrofuran (5 ml) was added dropwise at 0° C., followed by addition of triethylamine (55.1 mg, 0.546 mmol). The mixture was stirred at room temperature for 5 minutes, and morpholine (31.7 mg, 0.364 mmol) in tetrahydrofuran was added. The resulting mixture was stirred at room temperature for 10 minutes. Water was added and the resulting mixture was extracted twice with ethyl acetate, and the organic phases were combined, washed with water and saturated brine, dried over anhydrous sodium sulfate, concentrated, and purified by silica gel column to afford 120 mg of intermediate MDI-234-1, with a yield of 79.7%.

$^1$H NMR (400 MHz, CDCl$_3$) δ 8.45 (d, J=8.3 Hz, 1H), 7.53-7.51 (m, 2H), 7.47-7.35 (m, 4H), 7.26-7.23 (m, 1H), 7.06-6.97 (m, 2H), 5.96 (s, 2H), 5.77 (s, 2H), 5.23 (s, 2H), 4.68 (d, J=54.8 Hz, 4H), 3.80-3.78 (m, 3H), 3.67-3.59 (m, 4H), 3.43-3.40 (m, 3H), 3.27-3.21 (m, 6H), 2.54 (q, J=7.5 Hz, 2H), 1.05 (t, J=7.5 Hz, 3H), 0.96-0.89 (m, 4H), −0.04 (d, J=2.7 Hz, 18H).

Synthesis of Compound MDI-234: (2-(6-(2-ethyl-5-fluoro-4-hydroxyphenyl)-1H-indazol-3-yl)-4,6-dihydropyrrolo[3,4-d]imidazol-5-(1H)-yl)(morpholino)ketone Intermediate MDI-234-1 (120 mg, 0.145 mmol) was dissolved in methanol (6 ml), to which 12 mg Pd/C was added and concentrated hydrochloric acid (3 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 42 mg of the final product with a yield of 60.9%.

$^1$H NMR (400 MHz, MeOD-d4) δ 8.28 (d, J=8.4 Hz, 1H), 7.43 (s, 1H), 7.19-7.16 (m, 1H), 6.97-6.90 (m, 2H), 4.71-4.66 (m, 4H), 3.78-3.75 (m, 4H), 3.41-3.39 (m, 4H), 2.54 (q, J=7.5 Hz, 2H), 1.06 (t, J=7.5 Hz, 3H).

Example 33: (2-(6-(2-ethyl-5-fluoro-4-hydroxyphenyl)-1H-indazol-3-yl)-4,6-dihydropyrrolo[3,4-d]imidazol-5-(1H)-yl)(4-methylpiperazin-1-yl)ketone (MDI-235)

MDI-235

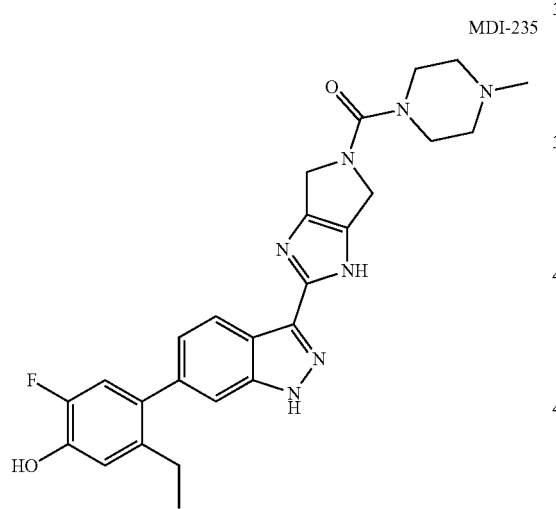

Synthetic Route of MDI-235:

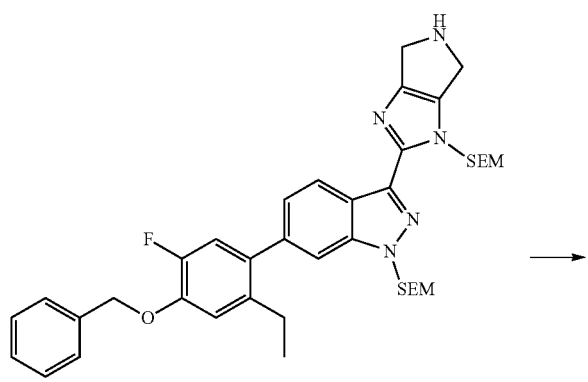

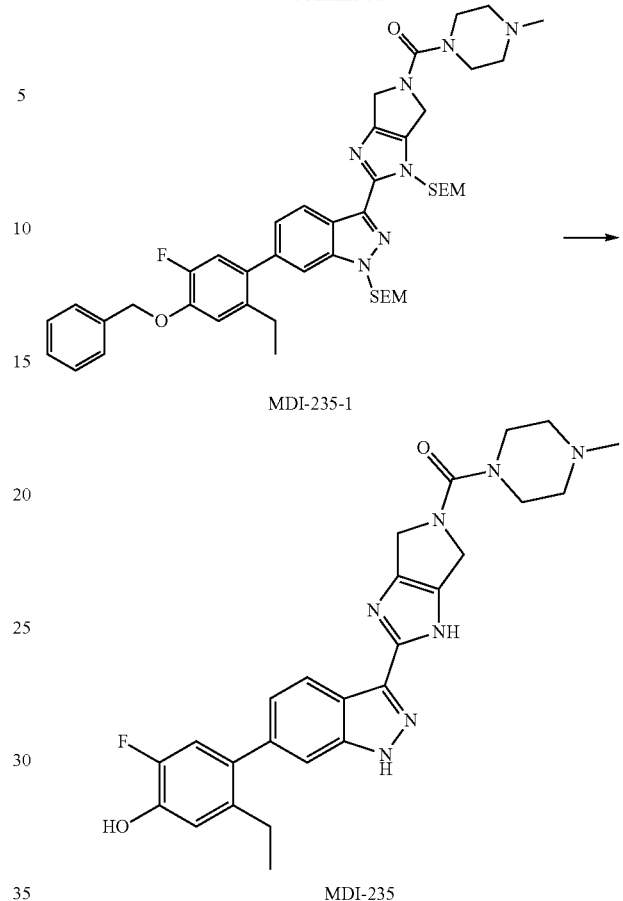

MDI-235-1

MDI-235

Synthesis Method

Synthesis of Intermediate MDI-235-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(4-methylpiperazin-1-yl)ketone Triphosgene (8.3 mg, 0.028 mmol) was dissolved in 5 ml of tetrahydrofuran, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (20 mg, 0.028 mmol) in tetrahydrofuran (5 ml) was added dropwise at 0° C., followed by addition of triethylamine (8.5 mg, 0.084 mmol). The mixture was stirred at room temperature for 5 minutes, and 1-methylpiperazine (5.60 mg, 0.056 mmol) in tetrahydrofuran was added. The resulting mixture was stirred at room temperature for 10 minutes. Water was added and the resulting mixture was extracted twice with ethyl acetate, and the organic phases were combined, washed with water and saturated brine, dried over anhydrous sodium sulfate, concentrated, and purified by silica gel column to afford 20 mg of intermediate MDI-235-1, with a yield of 85.1%.

$^1$H NMR (400 MHz, CDCl$_3$) δ 8.44 (d, J=8.3 Hz, 1H), 7.50-7.48 (m, 2H), 7.44-7.33 (m, 4H), 7.23-7.21 (m, 1H), 7.04-6.94 (m, 2H), 5.93 (s, 2H), 5.75 (s, 2H), 5.20 (s, 2H), 4.70 (d, J=54.8 Hz, 4H), 3.64-3.56 (m, 4H), 3.43-3.41 (m,

4H), 2.56-2.49 (m, 6H), 2.34 (s, 3H), 1.03 (t, J=7.5 Hz, 3H), 0.93-0.86 (m, 4H), −0.07 (d, J=2.7 Hz, 18H).

Synthesis of Compound MDI-235: (2-(6-(2-ethyl-5-fluoro-4-hydroxyphenyl)-1H-indazol-3-yl)-4,6-dihydropyrrolo[3,4-d]imidazol-5-(1H)-yl)(4-methylpiperazin-1-yl)ketone Intermediate MDI-235-1 (20 mg, 0.024 mmol) was dissolved in methanol (6 ml), to which 5 mg Pd/C was added and concentrated hydrochloric acid (3 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 3 mg of the final product with a yield of 14.8%.

$^1$H NMR (400 MHz, MeOD-d4) δ 8.25 (d, J=8.4 Hz, 1H), 7.40 (s, 1H), 7.16-7.14 (m, 1H), 6.95-6.87 (m, 2H), 4.83-4.66 (m, 4H), 3.44-3.41 (m, 4H), 2.56-2.51 (m, 6H), 2.35 (s, 3H), 1.06 (t, J=7.5 Hz, 3H).

Example 34: (2-(6-(2-ethyl-5-fluoro-4-hydroxyphenyl)-1H-indazol-3-yl)-4,6-dihydropyrrolo[3,4-d]imidazol-5-(1H)-yl)(4-ethylpiperazin-1-yl)ketone (MDI-236)

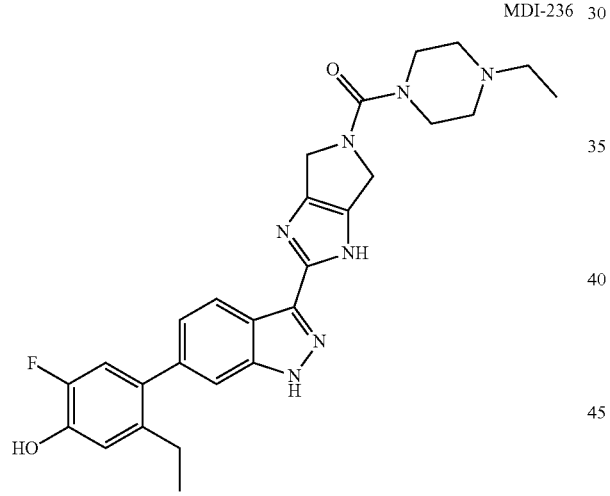

MDI-236

Synthetic Route of MDI-236:

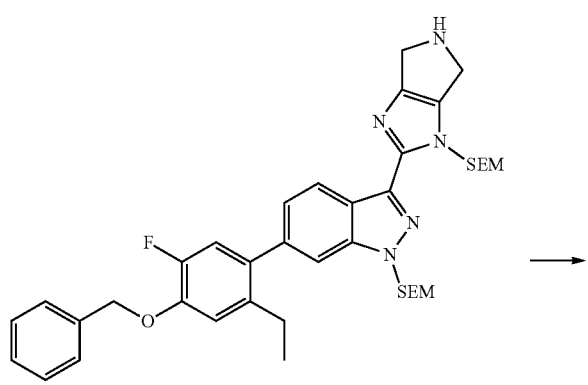

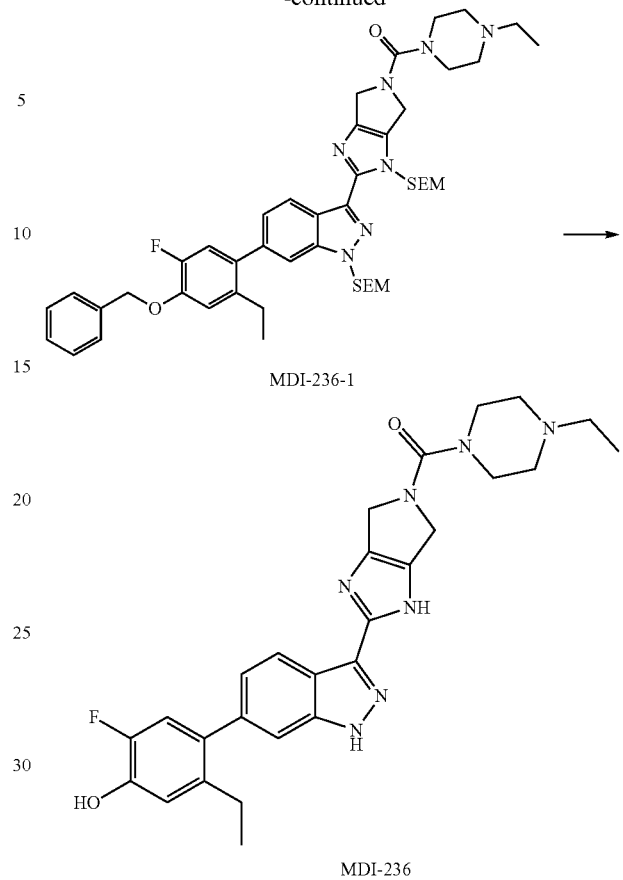

Synthesis Method

Synthesis of Intermediate MDI-236-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(4-ethyl piperazin-1-yl)ketone Triphosgene (54.07 mg, 0.182 mmol) was dissolved in 15 ml of dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (20 mg, 0.028 mmol) in dichloromethane (5 ml) was added dropwise at 0° C., followed by addition of triethylamine (55.2 mg, 0.55 mmol). The mixture was stirred at room temperature for 5 minutes, and 1-ethylpiperazine (41.5 mg, 0.364 mmol) in dichloromethane was added. The resulting mixture was stirred at room temperature for 10 minutes. Water was added and the resulting mixture was extracted twice with ethyl acetate, and the organic phases were combined, washed with water and saturated brine, dried over anhydrous sodium sulfate, concentrated, and purified by silica gel column to afford 100 mg of intermediate MDI-236-1, with a yield of 64.3%.

$^1$H NMR (400 MHz, CDCl$_3$) δ 8.44 (d, J=8 Hz, 1H), 8.28 (s, 1H), 7.50-7.33 (m, 5H), 7.22 (d, J=8 Hz, 1H), 7.03 (d, J=12 Hz, 1H), 6.95 (d, J=8 Hz, 1H), 5.93 (s, 2H), 5.74 (s, 2H), 5.20 (s, 2H), 4.77 (s, 2H), 4.63 (s, 2H), 3.63-3.61 (m,

4H), 3.43-3.42 (m, 4H), 2.53-2.46 (m, 8H), 1.03 (t, J=6 Hz, 3H), 0.93-0.86 (m, 7H), −0.06-0.08 (m, 18H).

Synthesis of Compound MDI-236: (2-(6-(2-ethyl-5-fluoro-4-hydroxyphenyl)-1H-indazol-3-yl)-4,6-dihydropyrrolo[3,4-d]imidazol-5-(1H)-yl)(4-ethylpiperazin-1-yl)ketone Intermediate MDI-236-1 (100 mg, 0.117 mmol) was dissolved in methanol (10 ml), to which 10 mg Pd/C was added and concentrated hydrochloric acid (5 ml) was added dropwise. The mixture was heated to 50° C., reacted for 6 hours, filtered, and concentrated to give a residue. The residue was dissolved in methanol and was concentrated to dryness, which was repeated 3 times. The resulting residue was dissolved in methanol, and 1 ml of ammonia was added. The resulting mixture was concentrated, and purified by a preparation plate to afford 21 mg of the final product with a yield of 35.6%.

$^1$H NMR (400 MHz, MeOD-d4) δ 8.27 (d, J=8 Hz, 1H), 7.43 (s, 1H), 7.17 (d, J=8 Hz, 1H), 6.96 (d, J=12 Hz, 1H), 6.91 (d, J=8 Hz, 1H), 4.75-4.60 (m, 4H), 3.48-3.44 (m, 4H), 2.61-2.48 (m, 8H), 1.17 (t, J=8 Hz, 3H), 1.08 (t, J=8 Hz, 3H).

Example 35: cyclopropyl (2-(6-(2-ethyl-5-fluoro-4-hydroxyphenyl)-1H-pyrazolo[4,3-b]pyridine-3-yl)-4,6-dihydropyrrolo[3,4-d]imidazol-5(1H)-yl)ketone (MDI-237)

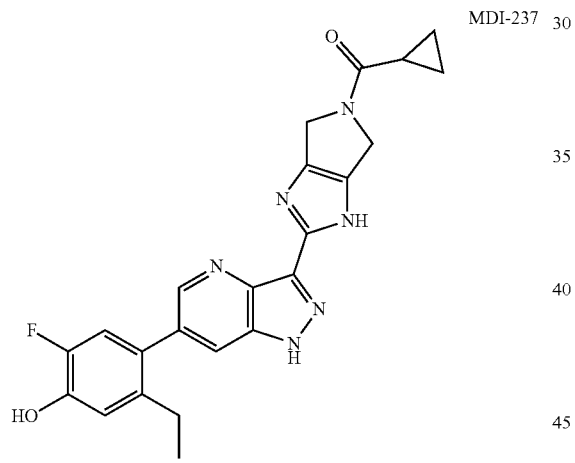

MDI-237

Synthetic Route of MDI-237:

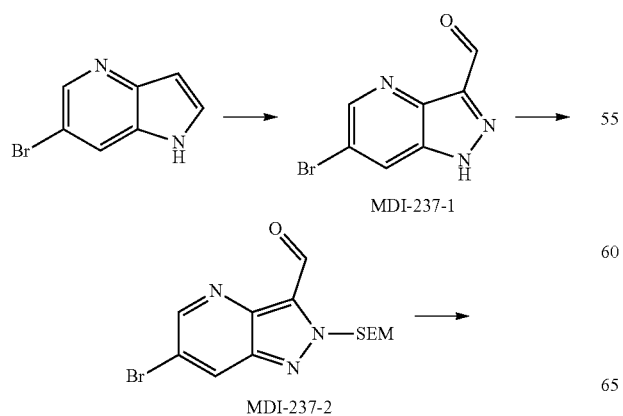

MDI-237-1

MDI-237-2

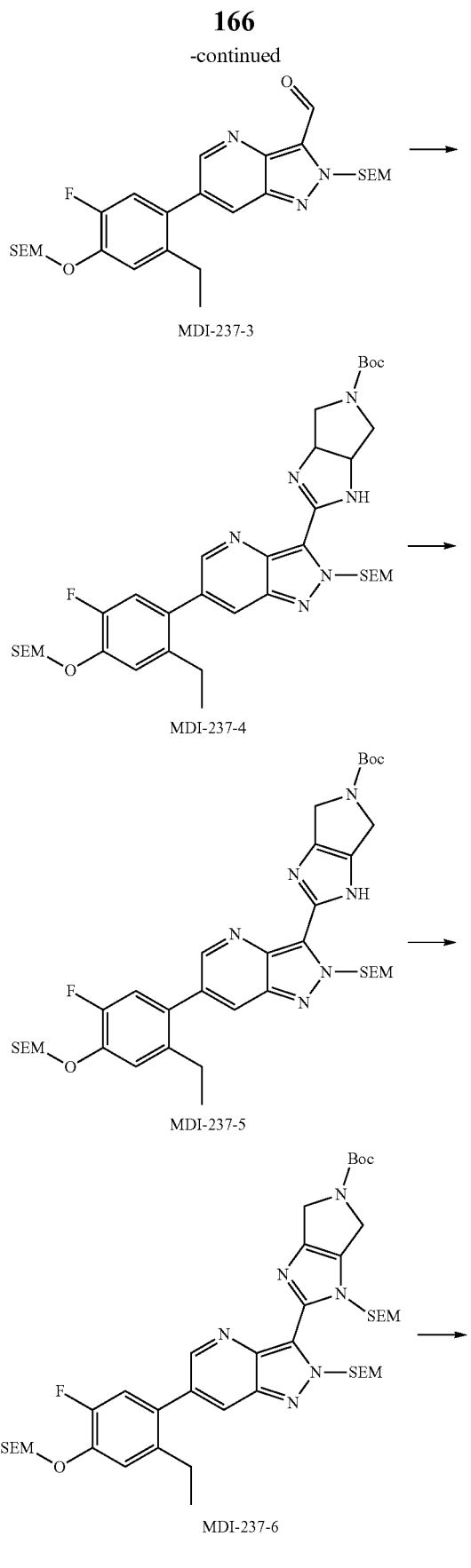

MDI-237-3

MDI-237-4

MDI-237-5

MDI-237-6

-continued

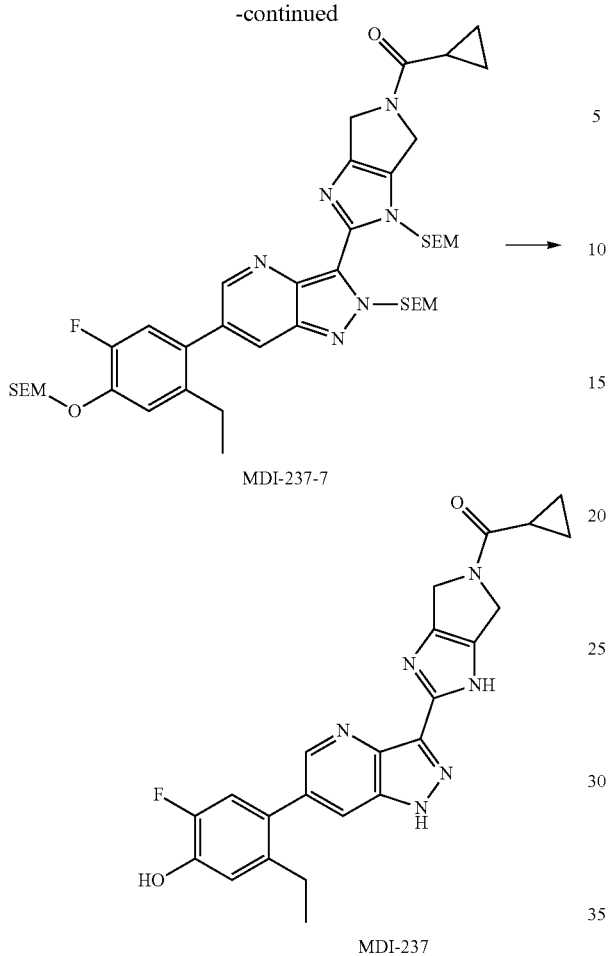

MDI-237-7

MDI-237

Synthesis Method

Synthesis of Intermediate MDI-237-1: 6-bromo-1H-pyrazolo[4,3-b]pyridine-3-formaldehyde Sodium nitrite (2.81 g, 40.72 mmol) was dissolved in 12 ml DMF and 16 ml water, and cooled to 0° C. Under nitrogen protection, 2N HCl (17.7 ml, 35.4 mmol) was slowly added dropwise, and after the addition was complete, the reaction continued for 10 minutes.

At 0° C., 6-bromo-4-azaindole (1.0 g, 5.08 mmol) in DMF (8 ml) was slowly added to the reaction solution dropwise. After the addition was completed, it was allowed to react at room temperature overnight. After the reaction was completed, 50 ml of water was added to the reaction. The resulting mixture was stirred at room temperature for 0.5 hours, and filtered with suction to afford 580 mg of intermediate MDI-237-1 with a yield of 50.5%.

$^1$H NMR (400 MHz, DMSO) δ 14.52 (s, 1H), 10.27 (s, 1H), 8.80 (d, J=2.0 Hz, 1H), 8.55 (d, J=2.0 Hz, 1H).

Synthesis of Intermediate MDI-237-2: 6-bromo-1-((2-(trimethylsilyl) ethoxy)methyl)-2H-pyrazolo[4,3-b]pyridine-3-formaldehyde The intermediate MDI-237-1 (250 mg, 1.11 mmol) was dissolved in 5 ml DMF, and then was cooled to 0° C. NaH (60%) (53.1 mg, 1.33 mmol) was added in batches at 0° C.

After the addition was completed, it was allowed to react for 30 minutes, and then SEMCl (276.6 mg, 1.66 mmol) was added dropwise to the reaction. After the dropwise addition was completed, the temperature was raised to room temperature for reaction. After the reaction was completed, it was quenched with water, and the resulting mixture was extracted with ethyl acetate, and the organic phase was washed with saturated brine, dried over anhydrous sodium sulfate, and concentrated by column chromatography to afford 157.4 mg of intermediate MDI-237-2 with a yield of 39.9%.

$^1$H NMR (400 MHz, CDCl3) δ 10.57 (s, 1H), 8.82 (d, J=2.0 Hz, 1H), 8.39 (d, J=2.0 Hz, 1H), 6.14 (s, 2H), 3.69-3.65 (m, 2H), 0.98-0.92 (m, 2H), −0.03 (s, 9H).

Synthesis of Intermediate MDI-237-3: 6-(2-ethyl-5-fluoro-4-((2-(trimethylsilanyl)ethoxy)methoxy)phenyl)-2-((2-(trimethylsilanyl)ethoxy)methyl)-2H-pyrazolo[4,3-b]pyridine-3-formaldehyde The intermediate MDI-237-2 (176 mg, 0.49 mmol), (2-((5-ethyl-2-fluoro-4-(4,4,5,5-tetramethyl-1,3,2-dioxaborolan-2-yl)phenoxy)methoxy)ethyl)trimethylsilane (196 mg, 0.49 mmol), Pd(dppf)Cl2 (36.1 mg, 0.05 mmol) and potassium carbonate (205 mg, 1.48 mmol) were dissolved in 1,4-dioxane (20 ml) and water (4 ml). The atmosphere was replaced with nitrogen, which was repeated 3 times. The mixture was heated to 100° C., reacted overnight, and cooled to room temperature. Water was added, the resulting mixture was extracted with ethyl acetate twice, and the organic phases were combined, washed with water and saturated brine, dried over anhydrous sodium sulfate, concentrated, and purified by silica gel column to afford 169.5 mg of intermediate MDI-237-3 with a yield of 62.7%.

$^1$H NMR (400 MHz, CDCl3) δ 10.58 (s, 1H), 8.76 (d, J=2.0 Hz, 1H), 8.08 (d, J=2.0 Hz, 1H), 7.21 (d, J=8.3 Hz, 1H), 7.02 (d, J=11.3 Hz, 1H), 6.19 (s, 2H), 5.33 (s, 2H), 3.88-3.83 (m, 2H), 3.72-3.69 (m, 2H), 2.59-2.53 (m, 2H), 1.10 (t, J=8.0 Hz, 3H), 1.02-0.94 (m, 4H), 0.03 (s, 9H), −0.03 (s, 9H).

Synthesis of Intermediate MDI-237-4: tert-butyl 2-(6-(2-ethyl-5-fluoro-4-((2-(trimethylsilanyl) ethoxy)methoxy)phenyl)-2-((2-(trimethylsilanyl) ethoxy)methyl)-2H-pyrazolo[4,3-b]pyridine-3-yl)-3a,4,6,6a-tetrahydropyrrolo[3,4-d]imidazol-5(1H)-carboxylate The intermediate MDI-237-3 (170 mg, 0.31 mmol) and tert-butyl 3,4-diaminopyrroline-1-carboxylate (69.0 mg, 0.34 mmol) were dissolved in 10 ml tert-butanol, to which I2 (98.8 mg, 0.39 mmol) and K2CO3 (129 mg, 0.93 mmol) were added. The mixture was heated to 70° C. and reacted for 3 hours. After the reaction was completed, aqueous sodium thiosulfate was added to quench the reaction. The resulting mixture was extract twice with ethyl acetate, and the organic phases were combined, washed with water and saturated brine, dried with anhydrous sodium sulfate, concentrated, and purified by silica gel column to afford 150 mg of intermediate MDI-237-4 with a yield of 66.2%.

$^1$H NMR (400 MHz, CDCl3) δ 8.54 (d, J=1.9 Hz, 1H), 7.99 (d, J=1.9 Hz, 1H), 7.20 (d, J=8.3 Hz, 1H), 7.01 (d, J=11.3 Hz, 1H), 6.60-6.20 (m, 2H), 5.33 (s, 2H), 5.00-4.87 (m, 1H), 4.58-4.46 (m, 1H), 3.88-3.83 (m, 2H), 3.79-3.64 (m, 6H), 2.58-2.52 (m, 2H), 1.57 (s, 9H), 1.09 (t, J=8.0 Hz, 3H), 1.02-0.96 (m, 4H), 0.03 (s, 9H), −0.03 (s, 9H).

Synthesis of Intermediate MDI-237-5: Tert-butyl 2-(6-(2-ethyl-5-fluoro-4-((2-(trimethylsilanyl)ethoxy)methoxy)phenyl)-2-((2-(trimethylsilanyl)ethoxy)methyl)-2H-pyrazolo[4,3-b]pyridine-3-yl)-4,6-dihydropyrrolo[3,4-d]imidazol-5(1H)-carboxylate Intermediate MDI-237-4 (100 mg, 0.14 mmol) and 2-iodoyl benzoic acid (77.0 mg, 0.28 mmol) were dissolved in 10 ml DMSO, heated to 45° C. and reacted for 5 hours. After the reaction was completed, the reaction was quenched by aqueous sodium thiosulfate. The resulting mixture was extracted twice with ethyl acetate, and the organic phases were combined, washed with water and saturated brine, dried over anhydrous sodium sulfate, concentrated, and purified by silica gel column to afford 75.0 mg of intermediate MDI-237-5, with a yield 75.2%.

$^1$H NMR (400 MHz, CDCl3) δ 11.78 (d, J=8.8 Hz, 1H), 8.52-8.50 (m, 1H), 7.99-7.98 (m, 1H), 7.21 (d, J=8.4 Hz, 1H), 7.03 (d, J=11.3 Hz, 1H), 6.44 (s, 2H), 5.33 (s, 2H), 4.66-4.51 (m, 4H), 3.88-3.79 (m, 4H), 2.60-2.54 (m, 2H), 1.54 (s, 9H), 1.11 (t, J=8.0 Hz, 3H), 1.03-0.98 (m, 4H), 0.03 (s, 9H), −0.05 (s, 9H).

Synthesis of Intermediate MDI-237-6: tert-butyl 2-(6-(2-ethyl-5-fluoro-4-((2-(trimethylsilanyl)ethoxy)methoxy)phenyl)-2-((2-(trimethylsilanyl)ethoxy)methyl)-2H-pyrazolo[4,3-b]pyridine-3-yl)-1-((2-(trimethylsilyl)ethoxy)methyl)-4,6-dihydropyrrolo[3,4-d]imidazol-5(1H)-carboxylate The intermediate MDI-237-5 (20.0 mg, 0.03 mmol) was dissolved in 10 ml of THF, the temperature was reduced to 0° C., and then NaH (60%) (1.2 mg, 0.03 mmol) was added. The reaction mixture was stirred for 0.5 hours. SEMCl (5.1 mg, 0.03 mmol) was added to the mixture, which was warmed to room temperature and stirred for 1 hour. After the reaction was completed, water was added to quench the reaction. The resulting mixture was extracted twice with ethyl acetate, and the organic phases were combined, washed with water and saturated brine, dried over anhydrous sodium sulfate, concentrated and purified by silica gel column to afford 15.0 mg of intermediate MDI-237-6 with a yield of 63.5%.

$^1$H NMR (400 MHz, CDCl3) δ 8.54 (d, J=2.0 Hz, 1H), 8.00 (t, J=2.1 Hz, 1H), 7.20 (d, J=8.3 Hz, 1H), 7.03 (d, J=11.4 Hz, 1H), 6.13 (d, J=4.5 Hz, 2H), 5.57 (d, J=3.7 Hz, 2H), 5.33 (s, 2H), 4.66-4.50 (m, 4H), 3.88-3.84 (m, 2H), 3.75-3.64 (m, 2H), 3.43-3.38 (m, 2H), 2.60-2.54 (m, 2H), 1.54 (s, 9H), 1.11 (t, J=8.0 Hz, 3H), 1.02-0.98 (m, 2H), 0.93-0.88 (m, 2H), 0.82-0.77 (m, 2H), 0.03 (s, 9H), −0.03 (s, 9H), −0.06 (s, 9H).

Synthesis of Intermediate MDI-237-7: cyclopropyl (2-(6-(2-ethyl-5-fluoro-4-((2-(trimethylsilanyl)ethoxy)methoxy)phenyl)-2-((2-(trimethylsilanyl)ethoxy)methyl)-2H-pyrazolo[4,3-b]pyridine-3-yl)-1-((2-(trimethylsilyl)ethoxy)methyl)-4,6-dihydropyrrolo[3,4-d]imidazol-5(1H)-yl)ketone Intermediate MDI-237-6 (30.0 mg, 0.04 mmol) was dissolved in 10 ml DCM, to which zinc bromide (31.6 mg, 0.14 mmol) was added. The mixture was stirred for 5 hours, and water was added to the reaction to quench the reaction. The resulting mixture was extracted twice with DCM, and the organic phases were combined, washed with aqueous ammonia, then washed with water and saturated brine, dried over anhydrous sodium sulfate, and concentrated. The crude product was dissolved in 10 ml DCM, to which DIPEA (5.4 mg, 0.04 mmol) was added and then the mixture was cooled down 0° C. Then, cyclopropylformyl chloride (4.4 mg, 0.04 mmol) was added dropwise. After the addition was complete, the temperature was raised to room temperature for reaction. After the reaction was completed, water was added to quench the reaction, and the resulting mixture was extracted twice with DCM, and the organic phases were combined, wash with water and saturated brine, dried over anhydrous sodium sulfate, and concentrate to afford 23.0 mg of crude MDI-237-7, which was directly used in the next reaction. The crude yield was 79.6%.

Synthesis of Compound MDI-237: cyclopropyl (2-(6-(2-ethyl-5-fluoro-4-hydroxyphenyl)-1H-pyrazolo[4,3-b]pyridine-3-yl)-4,6-dihydropyrrolo[3,4-d]imidazol-5(1H)-yl)ketone The intermediate MDI-237-7 (23.0 mg, 0.03 mmol) was dissolved in 4 ml MeOH, to which 2 ml concentrated hydrochloric acid was added. After the addition, the temperature was raised to 50° C. for reaction. After 6 hours of reaction, the temperature was lowered to room temperature, and the reaction solvent was evaporated by concentration under reduced pressure. After that, 4 ml methanol and 0.5 ml aqueous ammonia were added. After concentration, the residue was subject to thin layer chromatography to afford 3.2 mg of white solid MDI-237 with a yield of 26.5%.

$^1$H NMR (400 MHz, DMSO) δ 13.60 (s, 1H), 12.60-12.48 (m, 1H), 10.02 (s, 1H), 8.53 (d, J=1.6 Hz, 1H), 7.95 (s, 1H), 7.16 (d, J=11.8 Hz, 1H), 6.98 (d, J=9.1 Hz, 1H), 4.91-4.41 (m, 4H), 2.51-2.47 (m, 2H), 1.96-1.84 (m, 1H)), 1.03 (t, J=8.0 Hz, 3H), 0.87-0.80 (m, 4H). LC-MS m/z (ESI) [M+H]+ calculated value for $C_{23}H_{22}FN_6O_2$: 433.2; measured value: 433.2.

Example 36: cyclopropyl (2-(6-(2-ethyl-5-fluoro-4-hydroxyphenyl)-4-methyl-1H-indazol-3-yl)-4,6-dihydropyrrolo[3,4-d]imidazol-5(1H)-yl)ketone (MDI-239)

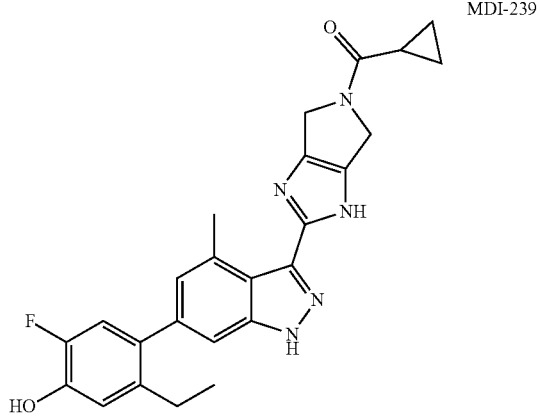 [SMILES: CCc1cc(O)c(F)cc1-c1cc(C)c2c(-c3nc4c([nH]3)CN(C(=O)C3CC3)C4)n[nH]c2c1]

MDI-239

Synthetic Route of MDI-239:

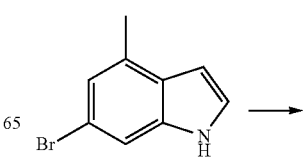

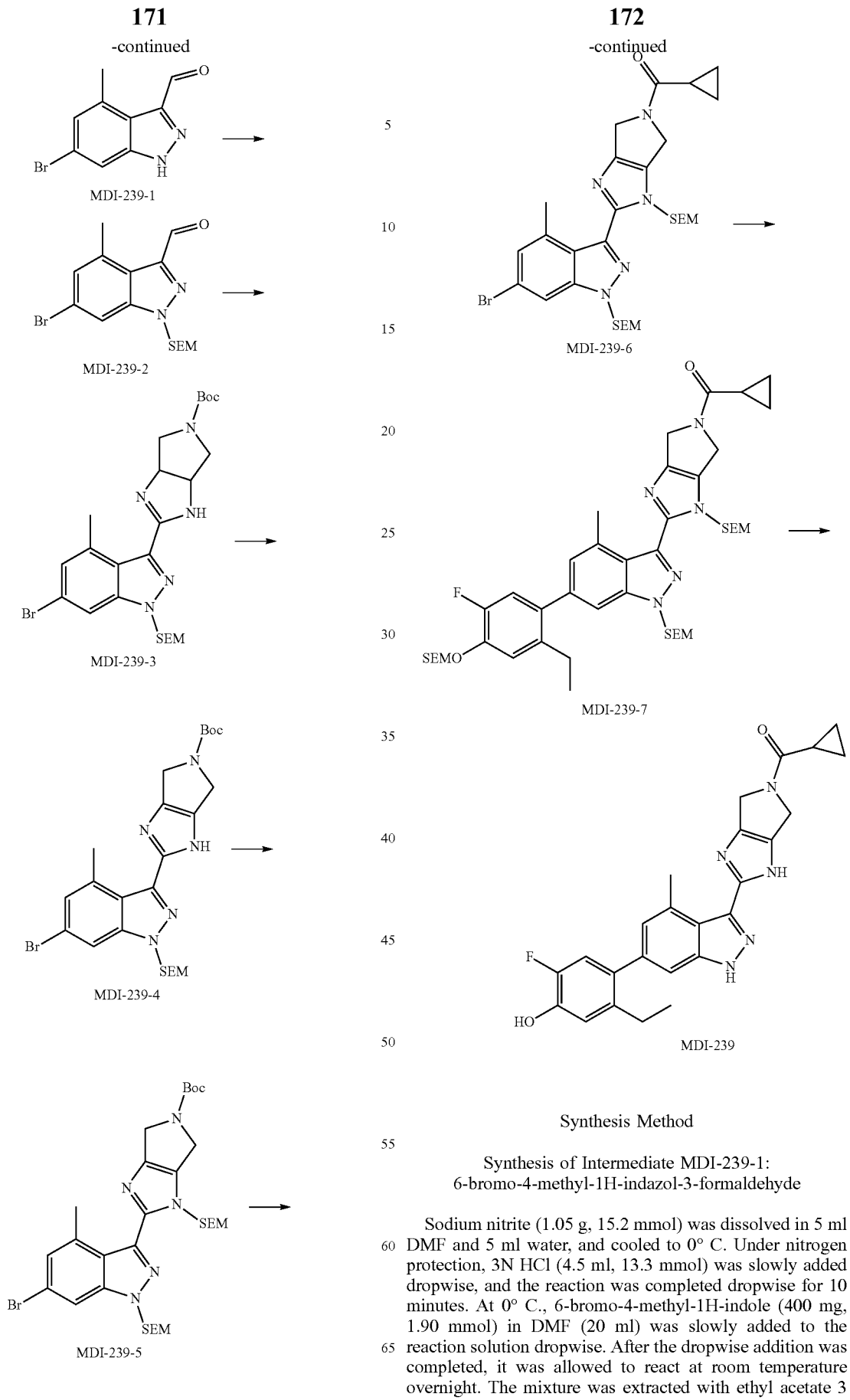

Synthesis Method

Synthesis of Intermediate MDI-239-1:
6-bromo-4-methyl-1H-indazol-3-formaldehyde

Sodium nitrite (1.05 g, 15.2 mmol) was dissolved in 5 ml DMF and 5 ml water, and cooled to 0° C. Under nitrogen protection, 3N HCl (4.5 ml, 13.3 mmol) was slowly added dropwise, and the reaction was completed dropwise for 10 minutes. At 0° C., 6-bromo-4-methyl-1H-indole (400 mg, 1.90 mmol) in DMF (20 ml) was slowly added to the reaction solution dropwise. After the dropwise addition was completed, it was allowed to react at room temperature overnight. The mixture was extracted with ethyl acetate 3 times, and the organic phases were combined, washed 3 times with water, washed with saturated brine, dried over anhydrous sodium sulfate, concentrated, and purified by silica gel column to afford 388 mg of intermediate MDI-239-1 with a yield of 84.3%.

$^1$H NMR (400 MHz, CDCl3) δ 10.61 (s, 1H), 10.24 (s, 1H), 7.58 (d, J=1.3 Hz, 1H), 7.27 (d, J=1.2 Hz, 1H), 2.90 (s, 3H).

Synthesis of Intermediate MDI-239-2: 6-bromo-4-methyl-1-((2-(trimethylsilyl)ethoxy)methyl)-1H-indazol-3-formaldehyde Intermediate MDI-239-1 (388 mg, 1.62 mmol) was dissolved in 25 ml of dry tetrahydrofuran, and cooled to 0° C. Sodium hydride (60%) (117 mg, 4.86 mmol) was slowly added, and the mixture was stirred for 10 minutes. 2-(Trimethylsilyl)ethoxymethyl chloride (540 mg, 3.24 mmol) was added slowly dropwise, and the reaction was carried out at room temperature for 1 hour. Water was added to quench the reaction, and the resulting mixture was extracted twice with ethyl acetate, and the organic phases were combined, washed with water and saturated brine, dried over anhydrous sodium sulfate, concentrated, and purified by silica gel column to afford 371 mg of intermediate MDI-239-2 with a yield of 61.9%.

$^1$H NMR (400 MHz, CDCl3) δ 10.20 (s, 1H), 7.68 (s, 1H), 7.30 (s, 1H), 5.78 (s, 2H), 3.61-3.57 (m, 2H), 2.89 (s, 3H), 0.96-0.89 (m, 2H), −0.02 (s, 9H).

Synthesis of Intermediate MDI-239-3: tert-butyl 2-(6-bromo-4-methyl-1-((2-(trimethylsilyl)ethoxy)methyl)-1H-indazol-3-yl)-3a,4,6,6a-tetrahydropyrrolo[3,4-d]imidazol-5(1H)-carboxylate The intermediate MDI-239-2 (371 mg, 1.00 mmol) and tert-butyl 3,4-diaminopyrroline-1-carboxylate (242 mg, 1.20 mmol) were dissolved in 10 ml tert-butanol, followed by addition of iodine (317 mg, 1.25 mmol) and potassium carbonate (414 mg, 3.00 mmol), and the reaction was carried out at 70° C. for 3 hours. The reaction was quenched by adding a saturated aqueous solution of sodium thiosulfate and the resulting mixture was extracted twice with ethyl acetate. The organic phases were combined, washed with water and saturated brine, dried over anhydrous sodium sulfate, concentrated, and purified by silica gel column to afford 330 mg of intermediate MDI-239-3 with a yield of 60.0%.

$^1$H NMR (400 MHz, CDCl3) δ 7.62 (s, 1H), 7.20 (s, 1H), 5.68 (s, 2H), 4.77-4.66 (m, 2H), 3.77-3.60 (m, 4H), 3.57-3.53 (m, 2H), 2.89 (s, 3H), 1.46 (s, 9H), 0.94-0.89 (m, 2H), −0.02 (s, 9H).

Synthesis of Intermediate MDI-239-4: tert-butyl 2-(6-bromo-4-methyl-1-((2-(trimethylsilyl)ethoxy)methyl)-1H-indazol-3-yl)-4,6-dihydropyrrolo[3,4-d]imidazol-5(1H)-carboxylate MDI-239-3 (330 mg, 0.60 mmol) was dissolved in 15 ml DMSO, and IBX (252 mg, 0.90 mmol) was added. It was allowed to react at 50° C. for 16 hours. The reaction was quenched by adding water, and resulting mixture was extracted twice with ethyl acetate.

The organic phases were combined, washed with water and saturated brine, dried over anhydrous sodium sulfate, concentrated, and purified on a silica gel column to afford 240 mg of intermediate MDI-239-4 with a yield of 73.0%.

$^1$H NMR (400 MHz, CDCl3) δ 7.60 (s, 1H), 7.19 (s, 1H), 5.67 (s, 2H), 4.62-4.50 (m, 4H), 3.67-3.54 (m, 2H), 2.98 (d, J=7.2 Hz, 3H), 1.55 (s, 9H), 0.98-0.89 (m, 2H), −0.03 (s, 9H).

Synthesis of Intermediate MDI-239-5: tert-butyl 2-(6-bromo-4-methyl-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate Intermediate MDI-239-4 (145 mg, 0.26 mmol) was dissolved in 15 ml of dry tetrahydrofuran, and cooled to 0° C. Sodium hydride (60%) (19.0 mg, 0.79 mmol) was slowly added, and the mixture was stirred for 10 minutes. 2-(Trimethylsilyl)ethoxymethyl chloride (86.7 mg, 0.52 mmol) was added slowly dropwise. After the addition, the reaction was carried out at room temperature for 1 hour. The reaction was quenched by adding water, the resulting mixture was extracted twice with ethyl acetate, and the organic phases were combined, washed with water and saturated brine, dried over anhydrous sodium sulfate, concentrated, and purified by silica gel column to afford 148 mg of intermediate MDI-239-5 with a yield of 84.0%.

$^1$H NMR (400 MHz, CDCl3) δ 7.67 (s, 1H), 7.17 (s, 1H), 5.73 (s, 2H), 5.44 (d, J=4.7 Hz, 2H), 4.65-4.51 (m, 4H), 3.61-3.57 (m, 2H), 3.38-3.34 (m, 2H), 2.54 (d, J=5.8 Hz, 3H), 1.56 (s, 9H), 0.97-0.88 (m, 4H), −0.02 (s, 9H), −0.11 (s, 9H).

Synthesis of Intermediate MDI-239-6: (2-(6-bromo-4-methyl-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(cyclopropyl)ketone Intermediate MDI-239-5 (148 mg, 0.22 mmol) was dissolved in 15 ml of dichloromethane, and zinc bromide (197 mg, 0.87 mmol) was added. The mixture was stirred at 25° C. for 4 hours, and 10 ml of aqueous ammonia was added to the reaction solution. After liquid separation, the organic phase was washed with saturated sodium bicarbonate, and saturated sodium chloride, dried over anhydrous sodium sulfate, and concentrated. The concentrate was dissolved in 10 ml of dichloromethane and triethylamine (66.8 mg, 0.66 mmol), and cooled to 0° C. Cyclopropionyl chloride (46.0 mg, 0.44 mmol) was slowly added, and it was allowed to react at room temperature for 1 hour. The reaction was quenched by adding water. The resulting mixture was extracted with dichloromethane twice, and the organic phases were combined, washed with water and saturated brine, dried over anhydrous sodium sulfate, concentrated, and purified by silica gel column to afford intermediate MDI-239-694 mg, with a yield of 65.8%.

$^1$H NMR (400 MHz, CDCl3) δ 7.70 (s, 1H), 7.20 (s, 1H), 5.75 (s, 2H), 5.48 (d, J=15.8 Hz, 2H), 5.00-4.69 (m, 4H), 3.63-3.59 (m, 2H), 3.46-3.34 (m, 2H), 2.57 (d, J=7.7 Hz, 3H), 2.09-2.05 (m, 1H), 1.09-1.00 (m, 4H), 0.98-0.89 (m, 4H), 0.00-0.05 (m, 18H).

Synthesis of Intermediate MDI-239-7: cyclopropyl (2-(6-(2-ethyl-5-fluoro-4-((2-(trimethylsilanyl)ethoxy)methoxy)phenyl)-4-methyl-1-((2-(trimethylsilanyl)ethoxy)methyl)-1H-indazol-3-yl)-1-((2-(trimethylsilyl)ethoxy)methyl)-4,6-dihydropyrrolo[3,4-d]imidazol-5(1H)-yl)ketone The intermediate MDI-239-6 (40.0 mg, 0.06 mmol), (2-((5-ethyl-2-fluoro-4-(4,4,5,5-tetramethyl-1,3,2-dioxaborolan-2-yl)phenoxy)methoxy)ethyl)trimethylsilane (36.8 mg, 0.09 mmol), tetrakistriphenylphosphine palladium (6.9 mg, 0.01 mmol) and potassium phosphate (39.4 mg, 0.19 mmol) were dissolved in 1,4-dioxane (10 ml) and water (2 ml). The atmosphere was replaced with nitrogen, which was repeated 3 times. The mixture was heated to 100° C., reacted for 16 hours, and cooled to room temperature. Water was added, the resulting mixture was extracted twice with ethyl acetate, and the organic phases were combined, washed with water and saturated brine, dried over anhydrous sodium sulfate, concentrated, and purified by a silica gel column to afford 27.3 mg of intermediate MDI-239-7 with a yield of 52.6%.

$^1$H NMR (400 MHz, CDCl3) δ 7.36 (s, 1H), 7.17 (d, J=8.4 Hz, 1H), 7.06-6.92 (m, 2H), 5.79 (d, J=7.0 Hz, 2H), 5.53 (d, J=14.4 Hz, 2H), 5.33 (d, J=5.3 Hz, 2H), 5.00-4.69 (m, 4H), 3.90-3.86 (m, 2H), 3.64-3.58 (m, 2H), 3.42-3.37 (m, 2H), 2.64-2.56 (m, 5H), 2.06-2.03 (m, 1H), 1.13-1.07 (m, 4H), 1.05-1.01 (m, 3H), 0.95-0.89 (m, 6H), 0.02 (s, 9H), −0.03-0.12 (m, 18H).

Synthesis of Compound MDI-239: cyclopropyl (2-(6-(2-ethyl-5-fluoro-4-hydroxyphenyl)-4-methyl-1H-indazol-3-yl)-4,6-dihydropyrrolo[3,4-d]imidazol-5(1H)-yl)ketone Intermediate MDI-239-7 (27.3 mg, 0.03 mmol) was dissolved in methanol (6 ml), to which concentrated hydrochloric acid (3 ml) was added. The mixture was heated to 50° C., reacted for 6 hours, and concentrated to give a residue. The residue was dissolved in methanol, and was concentrated to dryness, which was repeated 3 times. The resulting residue was dissolved in methanol, and 1 ml aqueous ammonia was added. The mixture was concentrated, and filtered. The resulting filtrate was concentrated, and purified by a preparation plate to afford 5.1 mg of the final product with a yield of 34.7%.

$^1$H NMR (400 MHz, MeOD) δ 7.27 (s, 1H), 6.95-6.88 (m, 3H), 4.96 (s, 2H), 4.66 (s, 2H), 2.63 (s, 3H), 2.55 (q, J=7.5 Hz, 2H), 1.98-1.92 (m, 1H), 1.07 (t, J=7.5 Hz, 3H), 1.04-0.92 (m, 4H).

Example 37: (S)-(2-(6-(2-ethyl-5-fluoro-4-hydroxyphenyl)-4-methyl-1H-indazol-3-yl)-4,6-dihydropyrrolo[3,4-d]imidazol-5(1H)-yl)(3-hydroxylpyrrolidin-1-yl)ketone (MDI-240)

Synthetic Route of MDI-240

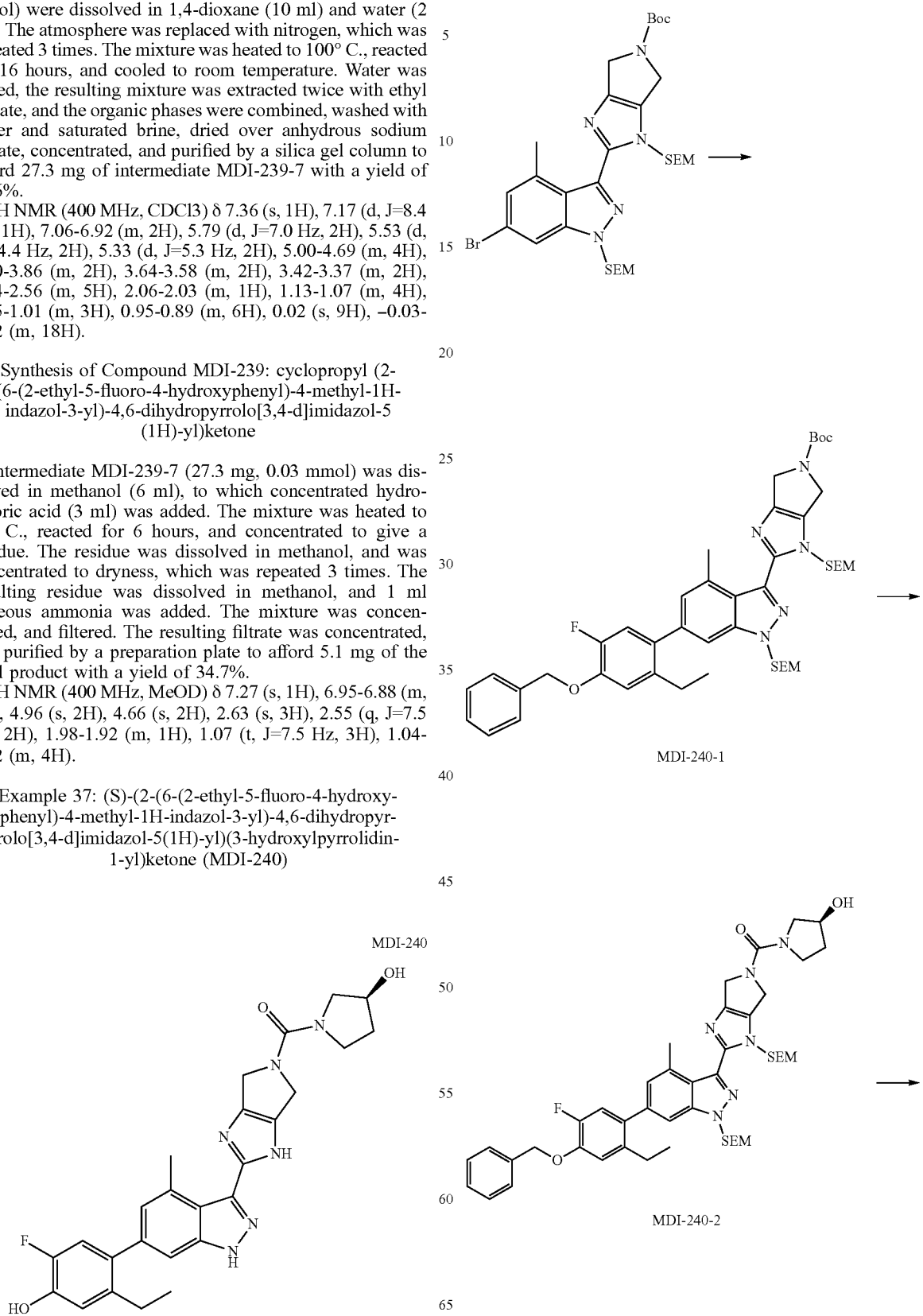

-continued

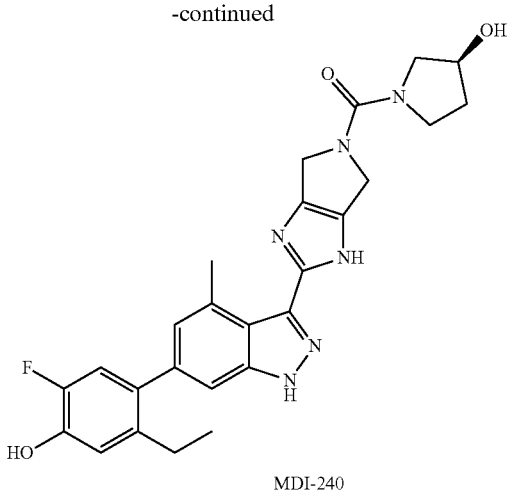

MDI-240

Synthesis Method

Synthesis of Intermediate MDI-240-1: tert-butyl 2-(6-(4-(benzyloxy)-2-ethyl-5-fluorophenyl)-4-methyl-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-carboxylate Tert-butyl 2-(6-bromo-4-methyl-1-(((2-(trimethylsilanyl)ethoxy)methyl)-1H-indazol-3-yl)-1-(((2-(trimethylsilanyl)ethoxy)methyl)-4,6-dihydropyrrolo[3,4-d]imidazol-5(1H)-carboxylate (60.0 mg, 0.09 mmol), 2-(4-(benzyloxy)-2-ethyl-5-fluorophenyl)-4,4,5,5-tetramethyl-1,3,2-dioxaborane (47.2 mg, 0.13 mmol), tetrakistriphenylphosphine palladium (10.4 mg, 0.01 mmol) and potassium phosphate (55.9 mg, 0.26 mmol) were dissolved in 1,4-dioxane (10 ml) and water (2 ml). The atmosphere was replaced with nitrogen, which was repeated 3 times. The mixture was heated to 100° C., reacted for 16 hours, and cooled to room temperature. Water was added, the resulting mixture was extracted 2 times with ethyl acetate, and the organic phases were combined, washes with water and saturated brine, dried over anhydrous sodium sulfate, concentrated and purified by a silica gel column to afford 63.2 mg of the intermediate MDI-240-1 with a yield of 86.7%.

$^1$H NMR (400 MHz, CDCl3) δ 7.52 (d, J=7.4 Hz, 2H), 7.46-7.34 (m, 4H), 7.03-6.96 (m, 3H), 5.77 (s, 2H), 5.50 (d, J=4.1 Hz, 2H), 5.22 (s, 2H), 4.67-4.53 (m, 4H), 3.64-3.60 (m, 2H), 3.40-3.35 (m, 2H), 2.59-2.51 (m, 5H), 1.56 (s, 9H), 1.06 (t, J=7.5 Hz, 3H), 0.98-0.89 (m, 4H), −0.04 (s, 9H), −0.12 (s, 9H).

Synthesis of intermediate MDI-240-2: (S)-(2-(6-(4-(benzyloxy)-2-ethyl-5-fluorophenyl)-4-methyl-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(3-hydroxyl pyrrolidin-1-yl)ketone Intermediate MDI-240-1 (63.2 mg, 0.08 mmol) was dissolved in 10 ml of dichloromethane, and zinc bromide (68.7 mg, 0.31 mmol) was added. The mixture was stirred at 25° C. for 4 hours, and 6 ml of aqueous ammonia was added to the reaction solution. After liquid separation, the organic phase was washed with saturated sodium bicarbonate and saturated sodium chloride, dried over anhydrous sodium sulfate, and concentrated. The concentrate was dissolved in 8 ml dichloromethane, at 0° C. triphosgene (22.5 mg, 0.08 mmol) was added, and triethylamine (76.7 mg, 0.76 mmol) was slowly added dropwise. The mixture was stirred at room temperature for 10 minutes, and (S)-pyrrolidine butan-3-ol (13.2 mg, 0.15 mmol) in dichloromethane was added. The mixture was stirred at room temperature for 20 minutes. Water was added, the resulting mixture was extracted twice with ethyl acetate, and the organic phases were combined, washed with water and saturated brine, dried over anhydrous sodium sulfate, concentrated and purified by silica gel column to afford 44.0 mg of intermediate MDI-240-2 with a yield of 68.9%.

$^1$H NMR (400 MHz, CDCl3) δ 7.51 (d, J=7.0 Hz, 2H), 7.45-7.34 (m, 4H), 7.03-6.95 (m, 3H), 5.77 (s, 2H), 5.49 (s, 2H), 5.22 (s, 2H), 4.76-4.53 (m, 4H), 4.46-4.44 (m, 1H), 3.64-3.54 (m, 4H), 3.44-3.33 (m, 4H), 2.57-2.51 (m, 5H), 2.06-1.90 (m, 2H), 1.05 (t, J=7.5 Hz, 3H), 1.00-0.88 (m, 4H), −0.04 (s, 9H), −0.13 (s, 9H).

Synthesis of Compound MDI-240: (S)-(2-(6-(2-ethyl-5-fluoro-4-hydroxyphenyl)-4-methyl-1H-indazol-3-yl)-4,6-dihydropyrrolo[3,4-d]imidazol-5(1H)-yl)(3-hydroxylpyrrolidin-1-yl)ketone MDI-240-2 (44.0 mg, 0.05 mmol) was dissolved in 6 ml methanol, to which 5 mg 10% palladium on carbon was added. The atmosphere was replaced with hydrogen. It was allowed to react at 40° C. for 1 hour. After the reaction was completed, the resulting mixture was filtered, and the filtrate was concentrated. The concentrate was dissolved in 6 ml methanol, and 3 ml concentrated hydrochloric acid was added. It was allowed to react for 7 hours at 50° C., and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified by a preparation plate to afford 5.7 mg of the final product with a yield of 22.3%.

$^1$H NMR (400 MHz, MeOD) δ 7.27 (s, 1H), 6.95-6.88 (m, 3H), 4.85-4.82 (m, 2H), 4.62-4.59 (m, 2H), 4.46-4.45 (m, 1H), 3.79-3.69 (m, 2H), 3.64-3.57 (m, 1H), 3.46-3.42 (m, 1H), 2.61 (s, 3H), 2.56 (q, J=7.5 Hz, 2H), 2.09-1.98 (m, 2H), 1.07 (t, J=7.5 Hz, 3H).

Example 38: cyclopropyl(2-(6-(2-ethyl-5-fluoro-4-hydroxyphenyl)-1H-pyrazolo[4,3-c]pyridine-3-yl)-4,6-dihydropyrrolo[3,4-d]imidazol-5(1H)-yl)ketone (MDI-242)

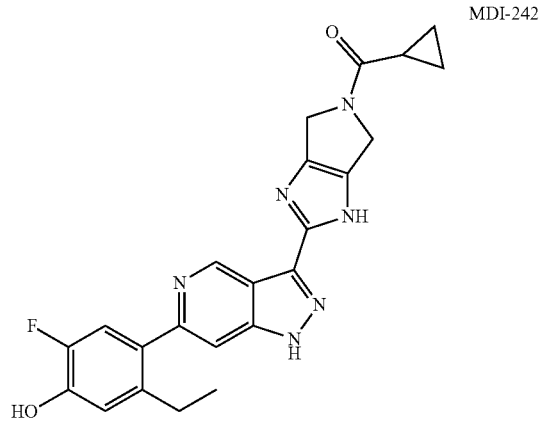 [SMILES: CCc1cc(O)c(F)cc1-c1cc2[nH]nc(-c3nc4c([nH]3)CN(C(=O)C3CC3)C4)c2cn1]

MDI-242

Synthetic Route of MDI-242:

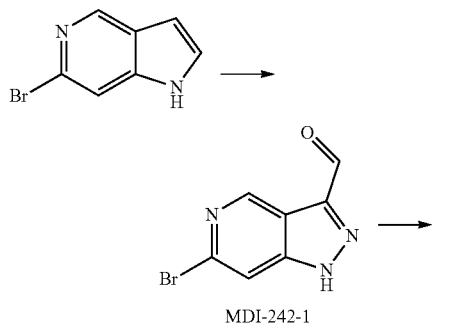
MDI-242-1

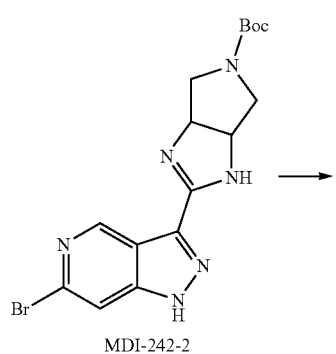
MDI-242-2

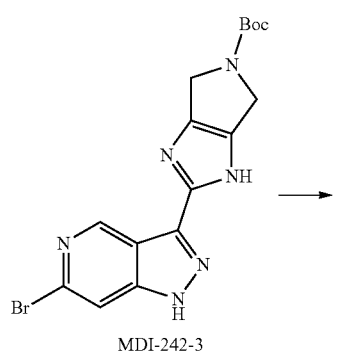
MDI-242-3

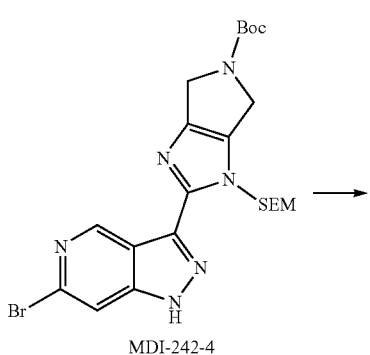
MDI-242-4

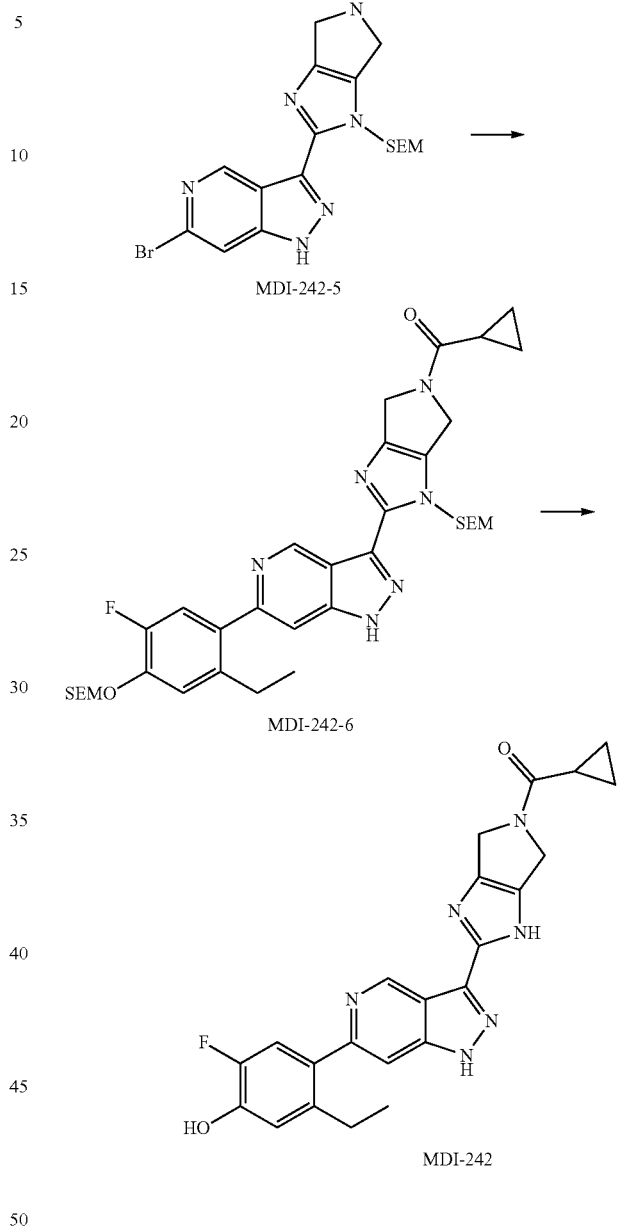

Synthesis Method

Synthesis of Intermediate MDI-242-1: 6-bromo-1H-pyrazolo[4,3-c]pyridine-3-formaldehyde Sodium nitrite (1.68 g, 24.4 mmol) was dissolved in 15 ml DMF and 15 ml water, and 3N HCl (7.1 ml, 21.3 mmol) was added at 0° C. The mixture was stirred for 10 minutes, and 6-bromo-1H-pyrrolo[3,2-c]pyridine (600 mg, 3.04 mmol) in DMF (15 ml) was added dropwise at 0° C. It was allowed to react at room temperature for 30 minutes, and to react at 50° C. for 3 hours. The resulting mixture was extracted 3 times with ethyl acetate, and the organic phases were combined, washed with water and saturated brine, dried over anhydrous sodium sulfate, concentrated, and purified by silica gel column to afford 350 mg of intermediate MDI-242-1 with a yield of 50.9%.

$^1$H NMR (400 MHz, CDCl3) δ 10.40 (s, 1H), 9.25 (s, 1H), 7.88 (s, 1H).

Synthesis of Intermediate MDI-242-2: tert-butyl 2-(6-bromo-1H-pyrazolo[4,3-c]pyridine-3-yl)-3a,4,6,6a-tetrahydropyrrolo[3,4-d]imidazol-5(1H)-carboxylate Intermediate MDI-242-1 (350 mg, 1.55 mmol) was dissolved in 15 ml tert-butanol, followed by addition of tert-butyl 3,4-diaminopyrrolidine-1-carboxylate (3734 mg, 1.86 mmol), potassium carbonate (775 mg, 5.57 mmol) and iodine (590 mg, 2.32 mmol). The mixture was stirred at 60° C. for 3 hours, and aqueous saturated sodium thiosulfate was added. The resulting mixture was extracted 3 times with ethyl acetate, and the organic phases were combined, washed with water and saturated brine, dried over anhydrous sodium sulfate, concentrated, and purified by silica gel column to afford 240 mg of intermediate MDI-242-2 with a yield of 38.1%.

$^1$H NMR (400 MHz, CDCl3) δ 9.29 (d, J=0.9 Hz, 1H), 7.78 (d, J=1.0 Hz, 1H), 5.00-4.95 (m, 1H), 4.52-4.49 (m, 1H), 3.77-3.70 (m, 3H), 3.57-3.53 (m, 1H), 1.42 (s, 9H).

Synthesis of Intermediate MDI-242-3: Tert-butyl 2-(6-bromo-1H-pyrazolo[4,3-c]pyridine-3-yl)-4,6-dihydropyrrolo[3,4-d]imidazol-5(1H)-carboxylate Intermediate MDI-242-2 (240 mg, 0.59 mmol) was dissolved in 15 ml DMSO, and IBX (330 mg, 1.18 mmol) was added. The mixture was stirred overnight at 45° C., and extracted 3 times with ethyl acetate. The organic phases were combined, washed with water and saturated brine, dried over anhydrous sodium sulfate, concentrated, and purified by silica gel column to afford 100 mg of intermediate MDI-242-3, with a yield of 41.9%.

$^1$H NMR (400 MHz, CDCl3) δ 9.46 (d, J=6.1 Hz, 1H), 7.78 (s, 1H), 4.65-4.53 (m, 4H), 1.54 (s, 9H).

Synthesis of Intermediate MDI-242-4: Tert-butyl 2-(6-bromo-1H-pyrazolo[4,3-c]pyridine-3-yl)-1-((2-(trimethylsilyl)ethoxy)methyl)-4,6-dihydropyrrolo[3,4-d]imidazol-5(1H)-carboxylate Intermediate MDI-242-3 (100 mg, 0.25 mmol) was dissolved in 15 ml THF and cooled to 0° C. NaH (60%) (21.7 mg, 0.54 mmol) was added and the mixture was stirred at 0° C. for 20 minutes. After that, SEM-Cl (103 mg, 0.62 mmol) was added. It was allowed to react for 2 hours. The resulting mixture was extracted 3 times with ethyl acetate, and the organic phases were combined, washed with water and saturated brine, dried over anhydrous sodium sulfate, concentrated, and purified on silica gel column to afford 100 mg of intermediate MDI-242-4 with a yield of 75.7%.

$^1$H NMR (400 MHz, CDCl3) δ 9.53-9.51 (m, 1H), 7.77 (d, J=1.2 Hz, 1H), 5.85 (d, J=7.2 Hz, 2H), 4.65-4.52 (m, 4H), 3.66-3.61 (m, 2H), 1.54 (s, 9H), 0.90-0.86 (m, 2H), −0.02 (s, 9H).

Synthesis of Intermediate MDI-242-5: (2-(6-bromo-1H-pyrazolo[4,3-c]pyridine-3-yl)-1-((2-(trimethylsilyl)ethoxy)methyl)-4,6-dihydropyrrolo[3,4-d]imidazol-5(1H)-yl)(cyclopropyl)ketone Intermediate MDI-242-4 (100 mg, 0.19 mmol) was dissolved in 5 ml of dichloromethane, and zinc bromide (168 mg, 0.75 mmol) was added. The mixture was stirred at room temperature for 4 hours and aqueous ammonia was added. The resulting mixture was extracted twice with dichloromethane, and the organic phases were combined, washed with water and saturated brine, dried over anhydrous sodium sulfate, and concentrated. The obtained compound was dissolved in 5 ml of dichloromethane, and triethylamine (56.6 mg, 0.56 mmol) was added. The mixture was cooled to 0° C., and cyclopropylformyl chloride (29.3 mg, 0.28 mmol) was added. It was allowed to react at room temperature for 2 hours. Water was added to quench the reaction, and the resulting mixture was extracted twice with dichloromethane, and the organic phases were combined, washed with water and saturated brine, dried over anhydrous sodium sulfate, concentrated, and purified by silica gel column to afford 60.0 mg of intermediate MDI-242-5 with a yield of 63.8%.

$^1$H NMR (400 MHz, CDCl3) δ 9.53 (d, J=7.4 Hz, 1H), 7.78 (d, J=2.4 Hz, 1H), 5.86 (s, 2H), 4.97-4.67 (m, 4H), 3.68-3.61 (m, 2H), 1.77-1.72 (m, 1H), 1.13-1.09 (m, 2H), 0.99-0.89 (m, 4H), −0.05 (s, 9H).

Synthesis of Intermediate MDI-242-6: cyclopropyl (2-(6-(2-ethyl-5-fluoro-4-((2-(trimethylsilyl)ethoxy)methoxy)phenyl)-1H-pyrazolo[4,3-c]pyridine-3-yl)-1-((2-(trimethylsilyl)ethoxy)methyl)-4,6-dihydropyrrolo[3,4-d]imidazol-5(1H)-yl)ketone Intermediate MDI-242-5 (60 mg, 0.12 mmol) was dissolved in 5 ml dioxane and 1 ml water, followed by addition of (2-((5-ethyl-2-fluoro-4-(4,4,5,5-tetramethyl-1,3,2-dioxaborolan-2-yl)phenoxy)methoxy)ethyl)trimethylsilane (56.7 mg, 0.14 mmol), Pd(PPh$_3$)$_4$ (13.8 mg, 0.01 mmol) and potassium carbonate (49.4 mg, 0.36 mmol). The atmosphere was replaced with nitrogen. The mixture was stirred at 100° C. for 2 hours. Water was added to quench the reaction, and the resulting mixture was extracted twice with ethyl acetate, and the organic phases were combined, washed with water and saturated brine, dried over anhydrous sodium sulfate, concentrated, and purified by silica gel column to afford 40 mg of intermediate MDI-242-6 with a yield of 48.4%.

$^1$H NMR (400 MHz, CDCl3) δ 9.79 (d, J=8.7 Hz, 1H), 7.58 (d, J=1.2 Hz, 1H), 7.26-7.18 (m, 2H), 5.95-5.90 (m, 2H), 5.33 (s, 2H), 5.00-4.70 (m, 4H), 3.86-3.82 (m, 2H), 3.69-3.62 (m, 2H), 2.74-2.68 (m, 2H), 1.79-1.70 (m, 1H), 1.14-1.08 (m, 5H), 1.02-0.96 (m, 4H), 0.92-0.88 (m, 2H), 0.03 (s, 9H), −0.02-0.04 (m, 9H).

Synthesis of Compound MDI-242: cyclopropyl (2-(6-(2-ethyl-5-fluoro-4-hydroxyphenyl)-1H-pyrazolo[4,3-c]pyridine-3-yl)-4,6-dihydropyrrolo[3,4-d]imidazol-5(1H)-yl)ketone (MDI-242)

Intermediate MDI-242-6 (40 mg, 0.06 mmol) was dissolved in 4 ml of methanol, and 2 ml of concentrated hydrochloric acid was added. The mixture was heated to 50° C., reacted for 6 hours, and concentrated. The solid was dissolved in 1 ml of methanol, and pH was adjusted with aqueous ammonia to 8-9. The resulting mixture was concentrated and purified by a preparation plate to afford 8.0 mg of the final product with a yield of 32.0%.

$^1$H NMR (400 MHz, MeOD) δ 9.61 (d, J=1.0 Hz, 1H), 7.77 (d, J=1.1 Hz, 1H), 7.16 (d, J=11.6 Hz, 1H), 6.93 (d, J=8.8 Hz, 1H), 5.07-4.88 (m, 4H), 4.68-4.62 (m, 2H), 2.69-2.64 (m, 2H), 1.98-1.89 (m, 1H), 1.09-1.05 (m, 3H)), 1.01-0.98 (m, 2H), 0.96-0.94 (m, 2H).

Example 39: (R)-(2-(6-(2-ethyl-5-fluoro-4-hydroxyphenyl)-1H-indazol-3-yl)-4,6-dihydropyrrolo[3,4-d]imidazol-5(1H)-yl)(3-hydroxylpyrrolidin-1-yl)ketone (MDI-243)

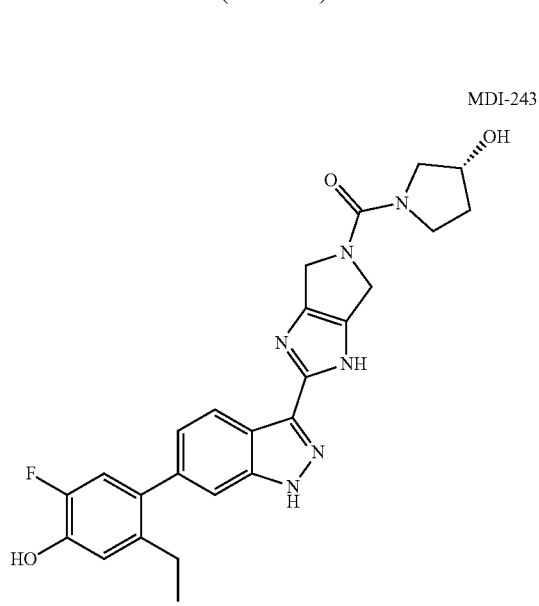

Synthetic Route of MDI-243:

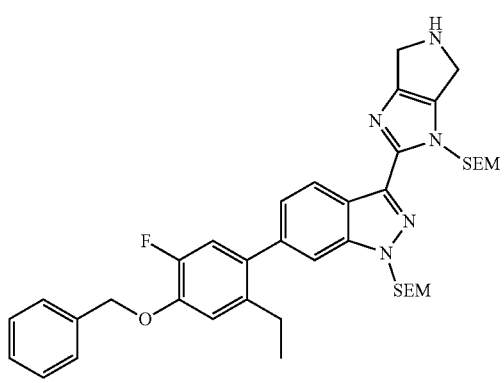

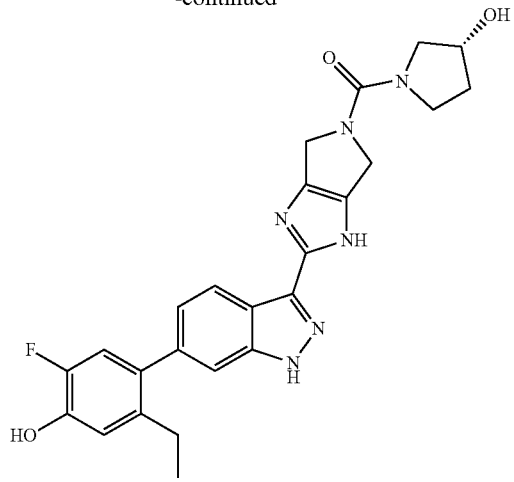

Synthesis Method

Synthesis of Intermediate MDI-243-1: (R)-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(3-hydroxylpyrrolidin-1-yl)ketone Triphosgene (54.1 mg, 0.18 mmol) was dissolved in 10 ml of dichloromethane, and at 0° C., the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (130 mg, 0.18 mmol) in dichloromethane (5 ml), was added dropwise. After the addition, anhydrous triethylamine (55.2 mg, 0.55 mmol) was added dropwise. The mixture was stirred at room temperature for 10 minutes. TLC monitored that the raw materials disappeared. (R)-Pyrrolidin-3-ol (31.8 mg, 0.36 mmol) in dichloromethane (5 ml) was added. The resulting mixture was stirred at room temperature for 20 minutes. Water was added to quench the reaction and the resulting mixture was extracted twice with ethyl acetate, and the organic phases were combined, washed with saturated brine, dried over anhydrous sodium sulfate, concentrated, and purified by silica gel column to afford 118 mg of intermediate MDI-243-1, with a yield of 78.4%.

$^1$H NMR (400 MHz, CDCl3) δ 8.47 (d, J=8.3 Hz, 1H), 7.75-7.73 (m, 2H), 7.47-7.35 (m, 4H), 7.25 (d, J=8.4 Hz, 1H), 7.06-6.96 (m, 2H), 5.96 (s, 2H), 5.78 (s, 2H), 5.23 (s, 2H), 4.95-4.56 (m, 4H), 4.50-4.45 (m, 1H), 3.79-3.72 (m, 2H), 3.66-3.58 (m, 5H), 3.46-3.42 (m, 1H), 2.54 (q, J=7.6 Hz, 2H), 2.06-2.01 (m, 2H), 1.06 (t, J=7.5 Hz, 3H), 0.99-0.89 (m, 4H), 0.02 (s, 9H), −0.05 (d, J=3.4 Hz, 9H).

Synthesis of Compound MDI-243: (R)-(2-(6-(2-ethyl-5-fluoro-4-hydroxyphenyl)-1H-indazol-3-yl)-4,6-dihydropyrrolo[3,4-d]imidazol-5-(1H)-yl)(3-hydroxylpyrrolidin-1-yl)ketone MDI-243-1 (118 mg, 0.14 mmol) was dissolved in 20 ml methanol, and 20 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 12 ml methanol and 6 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 8 ml methanol, and 0.8 ml aqueous ammonia was added. The resulting mixture was concentrated, and purified to afford 28 mg of the final product with a yield of 41.2%.

$^{1}$H NMR (400 MHz, MeOD) δ 8.27 (d, J=8.4 Hz, 1H), 7.43 (d, J=1.0 Hz, 1H), 7.17 (d, J=8.4 Hz, 1H), 6.98-6.90 (m, 2H), 4.82-4.60 (m, 4H), 4.47-4.45 (m, 1H), 3.79-3.70 (m, 2H), 3.60-3.57 (m, 1H), 3.46-3.43 (m, 1H), 2.56 (q, J=7.5 Hz, 2H), 2.09-1.98 (m, 2H), 1.08 (t, J=7.5 Hz, 3H).

Example 40: (2-(6-(2-ethyl-5-fluoro-4-hydroxyphenyl)-1H-indazol-3-yl)-4,6-dihydropyrrolo[3,4-d]imidazol-5(1H)-yl)(3-hydroxylazetidin-1-yl)ketone (MDI-244)

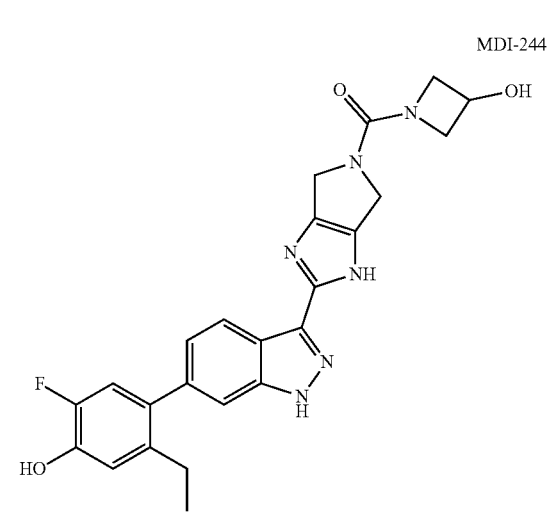 [SMILES: CCc1cc(O)c(F)cc1-c1ccc2c(-c3nc4c([nH]3)CN(C(=O)N3CC(O)C3)C4)n[nH]c2c1]

MDI-244

Synthetic Route of MDI-244:

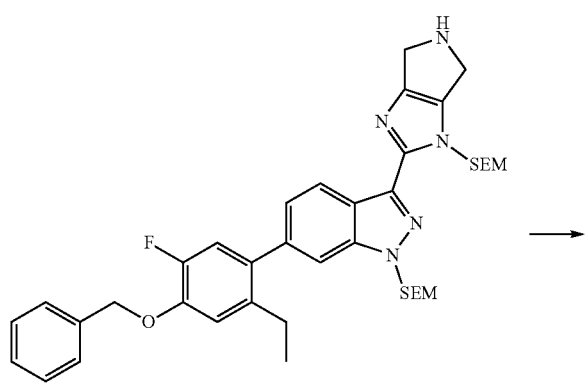

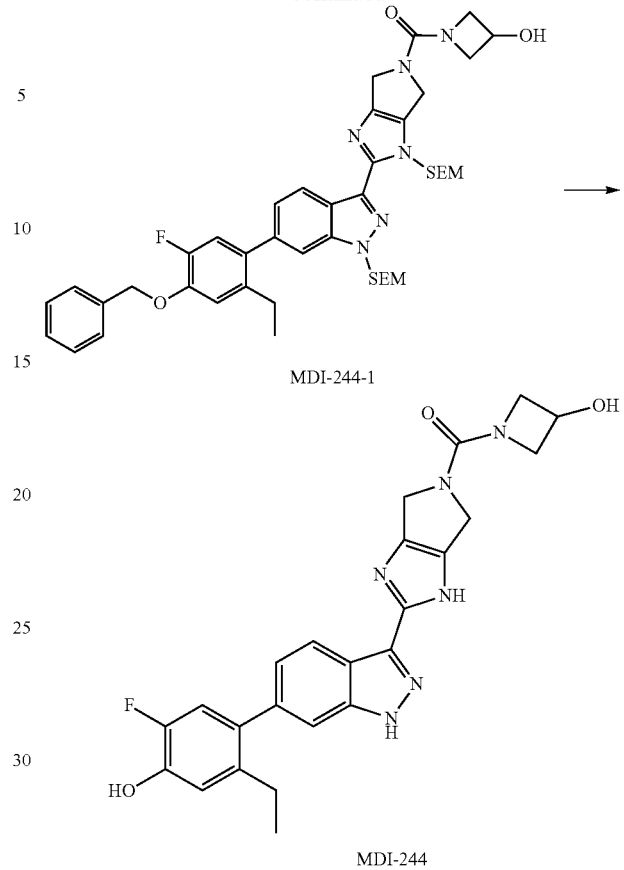

Synthesis Method

Synthesis of Intermediate MDI-244-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)(3-hydroxylazetidin-1-yl)ketone Triphosgene (54.1 mg, 0.18 mmol) was dissolved in 10 ml of dichloromethane, and at 0° C., the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (130 mg, 0.18 mmol) in dichloromethane (5 ml), was added dropwise. After the addition, anhydrous triethylamine (185 mg, 1.8 mmol) was added dropwise. The mixture was stirred at room temperature for 10 minutes. TLC monitored that the raw materials disappeared. Azetidine-3-ol (26.7 mg, 0.36 mmol) in dichloromethane (5 ml) was added. The resulting mixture was stirred at room temperature for 20 minutes. Water was added to quench the reaction and the resulting mixture was extracted twice with ethyl acetate, and the organic phases were combined, washed with saturated brine, dried over anhydrous sodium sulfate, concentrated, and purified by silica gel column to afford 110 mg of intermediate MDI-244-1, with a yield of 74.3%.

$^{1}$H NMR (400 MHz, CDCl$_3$) δ 8.45 (d, J=8.3 Hz, 1H), 7.73-7.51 (m, 2H), 7.48-7.35 (m, 4H), 7.25 (d, J=8.4 Hz, 1H), 7.06-6.96 (m, 2H), 5.96 (s, 2H), 5.76 (s, 2H), 5.23 (s, 2H), 4.73-4.58 (m, 4H), 4.39-4.31 (m, 2H), 4.22-4.18 (m,

1H), 4.03-4.00 (m, 1H), 3.88-3.85 (m, 1H), 3.65-3.57 (m, 4H), 2.54 (q, J=7.6 Hz, 2H), 1.05 (t, J=7.5 Hz, 3H), 0.99-0.89 (m, 4H), 0.02 (s, 9H), −0.05 (d, J=3.4 Hz, 9H).

Synthesis of Compound MDI-244: (2-(6-(2-ethyl-5-fluoro-4-hydroxyphenyl)-1H-indazol-3-yl)-4,6-dihydropyrrolo[3,4-d]imidazol-5-(1H)-yl)(3-hydroxylazetidin-1-yl)ketone MDI-241-1 (110 mg, 0.14 mmol) was dissolved in 20 ml methanol, and 20 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 12 ml methanol and 6 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 8 ml methanol, and 0.8 ml aqueous ammonia was added. The resulting mixture was concentrated, and purified to afford 34 mg of the final product with a yield of 54.4%.

$^1$H NMR (400 MHz, MeOD-d4) δ 8.27 (d, J=8.4 Hz, 1H), 7.43 (s, 1H), 7.18 (d, J=8.4 Hz, 1H), 6.97-6.90 (m, 2H), 4.62-4.56 (m, 4H), 4.00-3.94 (m, 1H), 3.70-3.66 (m, 1H), 3.62-3.55 (m, 1H), 3.51-3.46 (m, 1H), 3.41-3.37 (m, 1H), 2.56 (q, J=7.5 Hz, 2H), 1.08 (t, J=7.5 Hz, 3H).

Example 41: (2-(6-(2-ethyl-5-fluoro-4-hydroxyphenyl)-1H-indazol-3-yl)-4,6-dihydropyrrolo[3,4-d]imidazol-5(1H)-yl)(4-hydroxylpiperidin-1-yl)ketone (MDI-245)

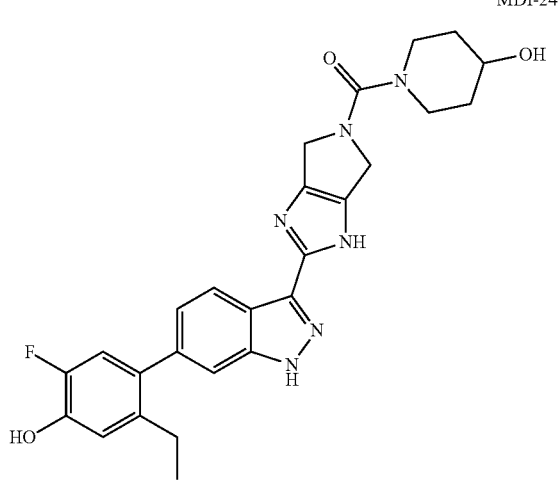

MDI-245

Synthetic Route of MDI-245:

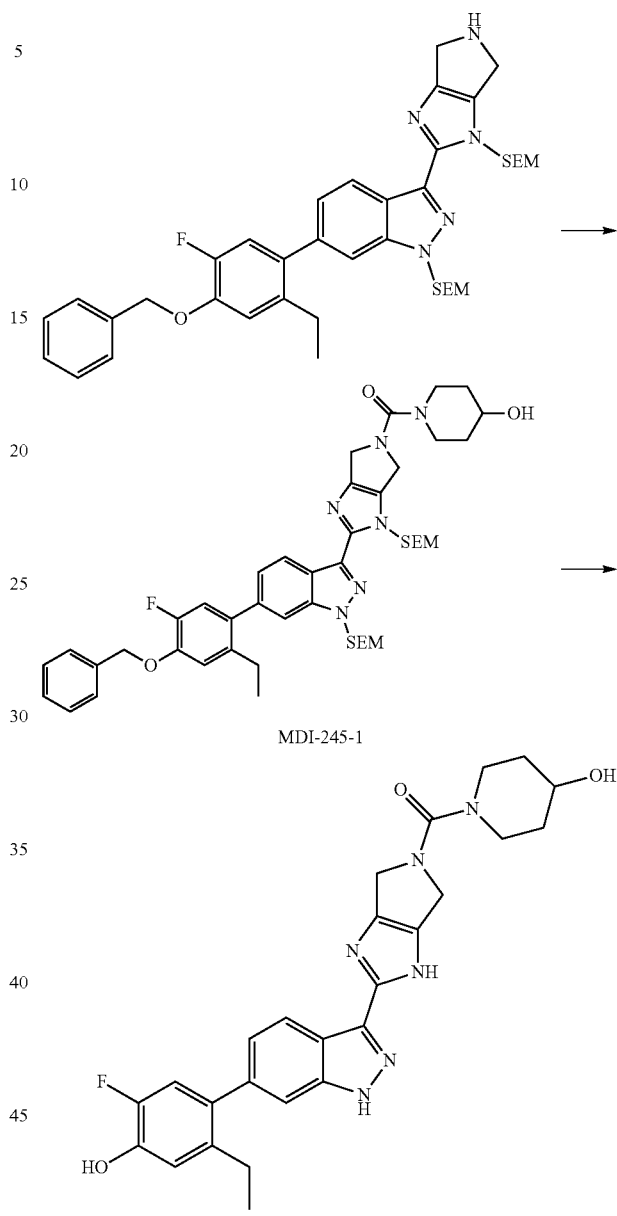

Synthesis Method

Synthesis of Intermediate MDI-245-1: (2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5-(1H)-yl)(4-hydroxylpiperidin-1-yl)ketone Triphosgene (54.1 mg, 0.18 mmol) was dissolved in 10 ml of dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (130 mg, 0.18 mmol) in dichloromethane (5 ml) was added dropwise at 0° C., followed by addition of anhydrous triethylamine (185 mg, 1.8 mmol). The mixture was stirred at room temperature for 10 minutes. TLC monitored that the raw materials disappeared. Piperidin-4-ol (36.9 mg, 0.36 mmol) in dichloromethane (5 ml) was added. The resulting mixture was stirred at room temperature for 20 minutes. Water was added to quench the reaction and the resulting mixture was extracted twice with ethyl acetate, and the organic phases were combined, washed with saturated brine, dried over anhydrous sodium sulfate, concentrated, and purified by silica gel column to afford 116 mg of intermediate MDI-245-1, with a yield of 75.7%.

$^1$H NMR (400 MHz, CDCl3) δ 8.46 (d, J=8.3 Hz, 1H), 7.53-7.51 (m, 2H), 7.47-7.35 (m, 4H), 7.25 (d, J=8.4 Hz, 1H), 7.06-6.97 (m, 2H), 5.96 (s, 2H), 5.75 (s, 2H), 5.37 (s, 2H), 4.79-4.66 (m, 4H), 3.95-3.92 (m, 1H), 3.75-3.72 (m, 2H), 3.66-3.52 (m, 4H), 3.12-3.07 (m, 2H), 2.54 (q, J=7.6 Hz, 2H), 2.02-1.91 (m, 2H), 1.68-1.63 (m, 2H), 1.06 (t, J=7.5 Hz, 3H), 0.99-0.89 (m, 4H), 0.02 (s, 9H), −0.05 (d, J=3.4 Hz, 9H).

Synthesis of Compound MDI-245: (2-(6-(2-ethyl-5-fluoro-4-hydroxyphenyl)-1H-indazol-3-yl)-4,6-dihydropyrrolo[3,4-d]imidazol-5-(1H)-yl)(4-hydroxylpiperidin-1-yl)ketone MDI-243-1 (116 mg, 0.14 mmol) was dissolved in 20 ml methanol, and 20 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 12 ml methanol and 6 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 8 ml methanol, and 0.8 ml aqueous ammonia was added. The resulting mixture was concentrated, and purified to afford 30 mg of the final product with a yield of 44.4%.

$^1$H NMR (400 MHz, MeOD) δ 8.27 (d, J=8.4 Hz, 1H), 7.43 (s, 1H), 7.18 (d, J=8.4 Hz, 1H), 6.97-6.90 (m, 2H), 4.72-4.65 (m, 4H), 3.88-3.82 (m, 1H), 3.76-3.73 (m, 2H), 3.13-3.06 (m, 2H), 2.56 (q, J=7.5 Hz, 2H), 1.97-1.95 (m, 2H), 1.63-1.55 (m, 2H), 1.08 (t, J=7.5 Hz, 3H).

Example 42: 2-(6-(2-ethyl-5-fluoro-4-hydroxyphenyl)-1H-indazol-3-yl)-N-methyl-4,6-dihydropyrrolo[3,4-d]imidazol-5-(1H)-carboxamide (MDI-246)

MDI-246 的 Synthetic Route:

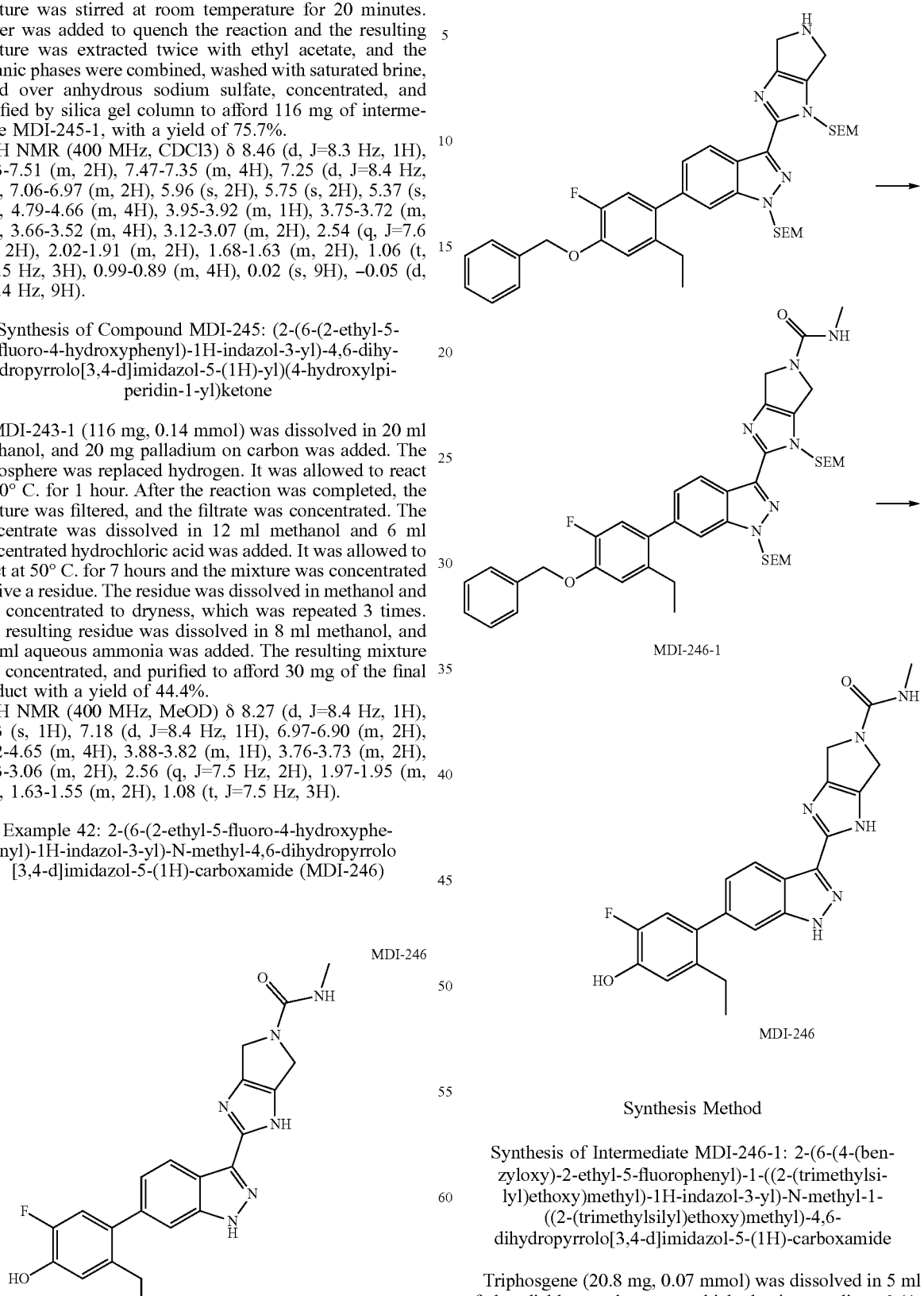

Synthesis Method

Synthesis of Intermediate MDI-246-1: 2-(6-(4-(benzyloxy)-2-ethyl-5-fluorophenyl)-1-((2-(trimethylsilyl)ethoxy)methyl)-1H-indazol-3-yl)-N-methyl-1-((2-(trimethylsilyl)ethoxy)methyl)-4,6-dihydropyrrolo[3,4-d]imidazol-5-(1H)-carboxamide Triphosgene (20.8 mg, 0.07 mmol) was dissolved in 5 ml of dry dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-

1,4,5,6-tetrahydropyrrolo[3,4-d]imidazol-2-yl)-1H-indazole (50 mg, 0.07 mmol) in dichloromethane (5 ml) was added dropwise at 0° C., then anhydrous triethylamine (70.9 mg, 0.70 mmol) was added slowly. The mixture was stirred at room temperature for 10 minutes. TLC monitored that the raw materials disappeared. Methylamine hydrochloride (9.5 mg, 0.14 mmol) was added. The resulting mixture was stirred at room temperature for 2 hours. Water was added to quench the reaction and the resulting mixture was extracted twice with dichloromethane, and the organic phases were combined, washed with saturated brine, dried over anhydrous sodium sulfate, concentrated, and purified by silica gel column to afford 42 mg of intermediate MDI-246-1, with a yield of 77.8%.

$^1$H NMR (400 MHz, CDCl3) δ 8.47 (d, J=8.3 Hz, 1H), 7.53-7.51 (m, 2H), 7.47-7.37 (m, 4H), 7.25 (d, J=8.4 Hz, 1H), 7.07-6.96 (m, 2H), 5.96 (s, 2H), 5.78 (s, 2H), 5.23 (s, 2H), 4.72-4.54 (m, 4H), 3.65-3.58 (m, 4H), 2.64 (s, 3H), 2.56 (q, J=7.6 Hz, 2H), 1.08 (t, J=7.5 Hz, 3H), 0.95-0.89 (m, 4H), 0.02 (s, 9H), −0.04-0.05 (m, 9H).

Synthesis of Compound MDI-246: 2-(6-(2-ethyl-5-fluoro-4-hydroxyphenyl)-1H-indazol-3-yl)-N-methyl-4,6-dihydropyrrolo[3,4-d]imidazol-5-(1H)-carboxamide MDI-246-1 (42 mg, 0.055 mmol) was dissolved in 10 ml methanol, and 8 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 10.3 mg of the final product with a yield of 45.1%.

$^1$H NMR (400 MHz, MeOD) δ 8.27 (d, J=8.4 Hz, 1H), 7.43 (s, 1H), 7.18 (d, J=8.4 Hz, 1H), 6.97-6.90 (m, 2H), 4.56 (s, 4H), 2.84 (s, 3H), 2.56 (q, J=7.5 Hz, 2H), 1.08 (t, J=7.5 Hz, 3H).

Example 43: 2-(6-(2-ethyl-5-fluoro-4-hydroxyphenyl)-1H-indazol-3-yl)-N-ethyl-4,6-dihydropyrrolo[3,4-d]imidazol-5-(1H)-carboxamide (MDI-247)

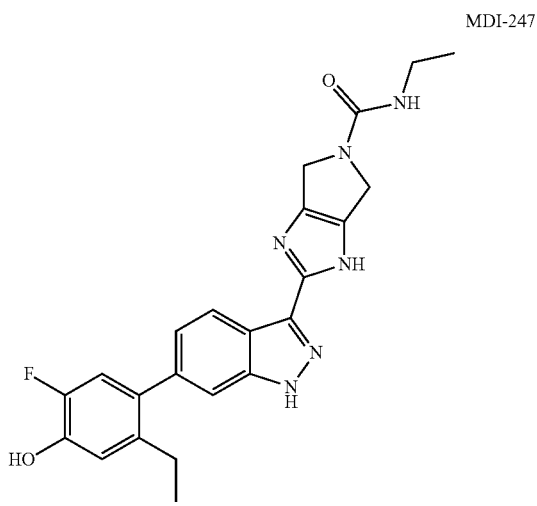 [SMILES: CCNC(=O)N1Cc2nc(-c3n[nH]c4cc(-c5cc(F)c(O)cc5CC)ccc34)[nH]c2C1]

MDI-247

Synthetic Route of MDI-247:

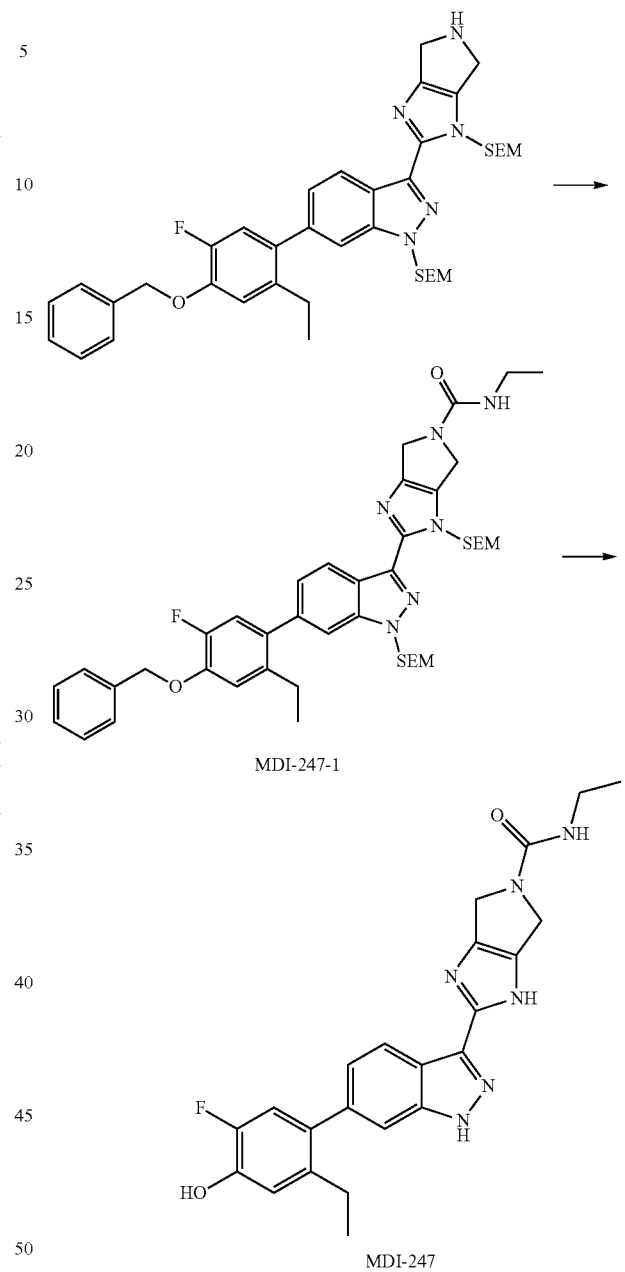

MDI-247-1

MDI-247

Synthesis Method

Synthesis of Intermediate MDI-247-1: 2-(6-(4-(benzyloxy)-2-ethyl-5-fluorophenyl)-1-((2-(trimethylsilyl)ethoxy)methyl)-1H-indazol-3-yl)-N-ethyl-1-((2-(trimethylsilyl)ethoxy)methyl)-4,6-dihydropyrrolo[3,4-d]imidazol-5-(1H)-carboxamide Triphosgene (22.9 mg, 0.08 mmol) was dissolved in 6 ml of dry dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (55 mg, 0.08 mmol) in dichloromethane (5 ml) was added dropwise at 0° C., then anhydrous triethylamine (78.0 mg, 0.8 mmol) was added slowly. The mixture was stirred at room temperature for 10 minutes. TLC monitored that the raw materials disappeared. Ethylamine hydrochloride (12.6 mg, 0.16 mmol) was added. The resulting mixture was stirred at room temperature for 20 hours. Water was added to quench the reaction and the resulting mixture was extracted twice with ethyl acetate, and the organic phases were combined, washed with saturated brine, dried over anhydrous sodium sulfate, concentrated, and purified by silica gel column to afford 47 mg of intermediate MDI-247-1, with a yield of 77.7%.

$^1$H NMR (400 MHz, CDCl3) δ 8.46 (d, J=8.3 Hz, 1H), 7.53-7.51 (m, 2H), 7.47-7.35 (m, 4H), 7.25 (d, J=8.4 Hz, 1H), 7.07-6.97 (m, 2H), 5.96 (s, 2H), 5.78 (s, 2H), 5.23 (s, 2H), 4.72-4.54 (m, 4H), 3.65-3.58 (m, 4H), 3.45-3.38 (m, 2H), 2.54 (q, J=7.6 Hz, 2H), 1.18-1.14 (m, 3H), 1.05 (t, J=7.5 Hz, 3H), 0.95-0.89 (m, 4H), 0.02 (s, 9H), −0.05 (d, J=3.4 Hz, 9H).

Synthesis of Compound MDI-247: 2-(6-(2-ethyl-5-fluoro-4-hydroxyphenyl)-1H-indazol-3-yl)-N-ethyl-4,6-dihydropyrrolo[3,4-d]imidazol-5-(1H)-carboxamide MDI-247-1 (47 mg, 0.06 mmol) was dissolved in 10 ml methanol, and 8 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 11 mg of the final product with a yield of 42.4%.

$^1$H NMR (400 MHz, MeOD) δ 8.27 (d, J=8.4 Hz, 1H), 7.43 (s, 1H), 7.18 (d, J=8.4 Hz, 1H), 6.98-6.90 (m, 2H), 4.57 (s, 4H), 3.38-3.28 (m, 2H), 2.56 (q, J=7.5 Hz, 2H), 1.21 (t, J=7.2 Hz, 3H), 1.08 (t, J=7.5 Hz, 3H).

Example 44: 2-(6-(2-ethyl-5-fluoro-4-hydroxyphenyl)-1H-indazol-3-yl)-N-(2-hydroxyethyl)-4,6-dihydropyrrolo[3,4-d]imidazol-5(1H)-carboxamide (MDI-248)

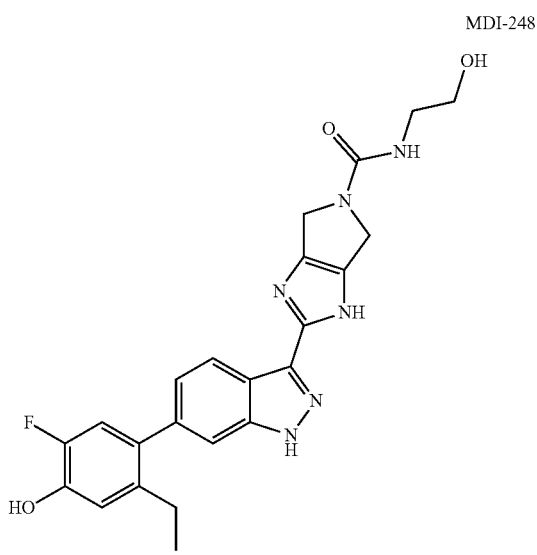 [SMILES: CCc1cc(O)c(F)cc1-c1ccc2c(-c3nc4c([nH]3)CN(C(=O)NCCO)C4)n[nH]c2c1]

MDI-248

Synthetic Route of MDI-248:

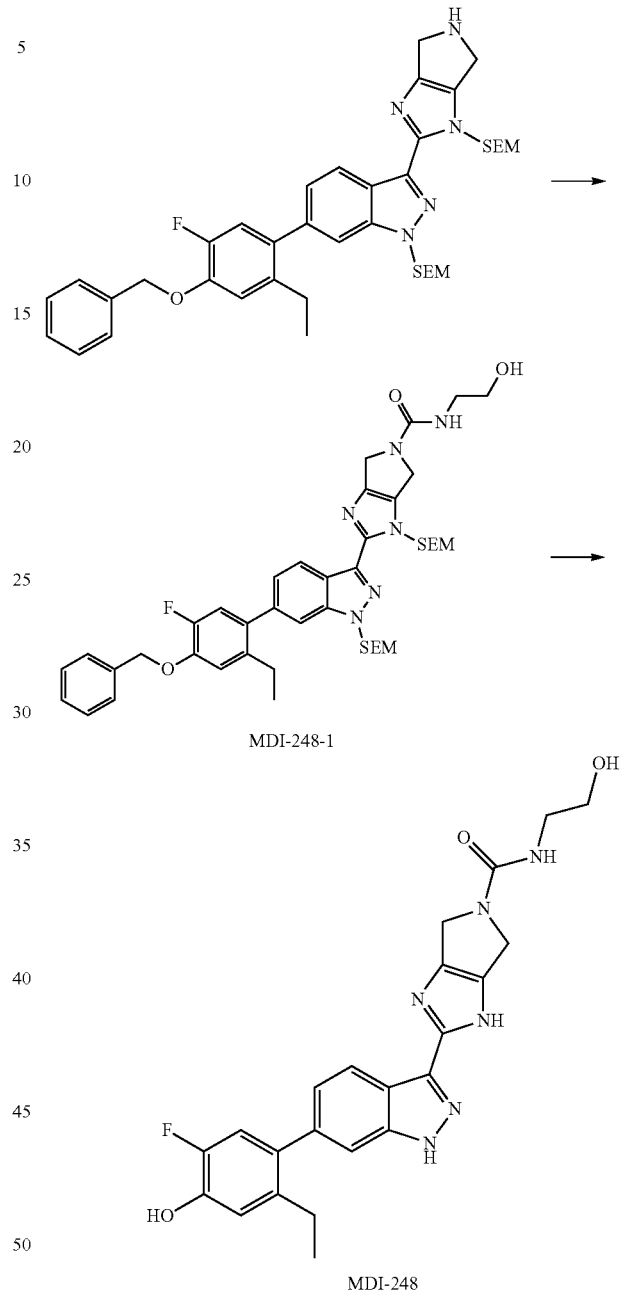

MDI-248-1

MDI-248

Synthesis Method

Synthesis of Intermediate MDI-248-1: 2-(6-(4-(benzyloxy)-2-ethyl-5-fluorophenyl)-1-((2-(trimethylsilyl)ethoxy)methyl)-1H-indazol-3-yl)-N-(2-hydroxylethyl)-1-((2-(trimethylsilyl)ethoxy)methyl)-4,6-dihydropyrrolo[3,4-d]imidazol-5-(1H)-carboxamide Triphosgene (22.9 mg, 0.08 mmol) was dissolved in 6 ml of dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (55 mg, 0.08 mmol) in dichloromethane (5 ml) was added dropwise at 0° C., then anhydrous triethylamine (78 mg, 0.8 mmol) was added slowly. The mixture was stirred at room temperature for 10 minutes. TLC monitored that the raw materials disappeared. Ethanolamine (9.4 mg, 0.16 mmol) in dichloromethane (5 ml) was added. The resulting mixture was stirred at room temperature for 1 hour. Water was added to quench the reaction and the resulting mixture was extracted twice with dichloromethane, and the organic phases were combined, washed with saturated brine, dried over anhydrous sodium sulfate, concentrated, and purified by silica gel column to afford 44 mg of intermediate MDI-248-1, with a yield of 71.3%.

$^1$H NMR (400 MHz, CDCl$_3$) δ 8.46 (d, J=8.3 Hz, 1H), 7.73-7.51 (m, 2H), 7.48-7.35 (m, 4H), 7.27-7.24 (m, 1H), 7.07-6.97 (m, 2H), 5.96 (s, 2H), 5.78 (s, 2H), 5.23 (s, 2H), 4.73-4.57 (m, 4H), 3.65-3.53 (m, 6H), 3.33-3.29 (m, 2H), 2.54 (q, J=7.6 Hz, 2H), 1.05 (t, J=7.5 Hz, 3H), 0.95-0.89 (m, 4H), 0.02 (s, 9H), −0.05 (s, 9H).

Synthesis of Compound MDI-248: 2-(6-(2-ethyl-5-fluoro-4-hydroxyphenyl)-1H-indazol-3-yl)-N-(2-hydroxylethyl)-4,6-dihydropyrrolo[3,4-d]imidazol-5(1H)-carboxamide MDI-248-1 (44 mg, 0.06 mmol) was dissolved in 10 ml methanol, and 8 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 14 mg of the final product with a yield of 56.6%.

$^1$H NMR (400 MHz, MeOD) δ 8.28 (d, J=8.4 Hz, 1H), 7.43 (s, 1H), 7.18 (d, J=8.4 Hz, 1H), 6.97-6.90 (m, 2H), 4.59 (s, 4H), 3.68 (t, J=5.8 Hz, 2H), 3.40 (t, J=5.8 Hz, 2H), 2.56 (q, J=7.5 Hz, 2H), 1.08 (t, J=7.5 Hz, 3H)

Example 45: 1-(2-(6-(2-ethyl-5-fluoro-4-hydroxyphenyl)-1H-indazol-3-yl)-1,4,5,6-tetrahydropyrrolo[3,4-d]imidazol-5-carbonyl)Azetidin-3-nitrile (MDI-249)

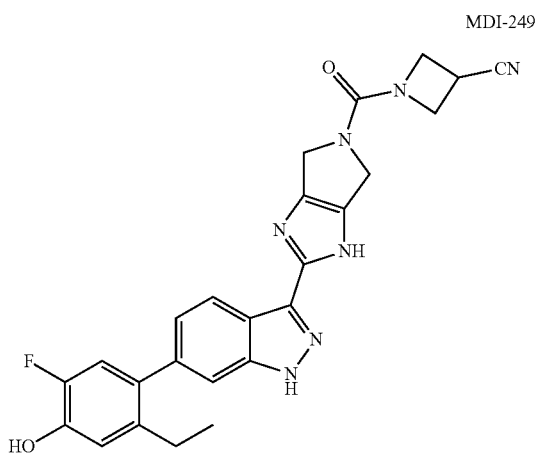 [SMILES: CCc1cc(O)c(F)cc1-c1ccc2c(-c3nc4c([nH]3)CN(C(=O)N3CC(C#N)C3)C4)n[nH]c2c1]

MDI-249

Synthetic Route of MDI-249:

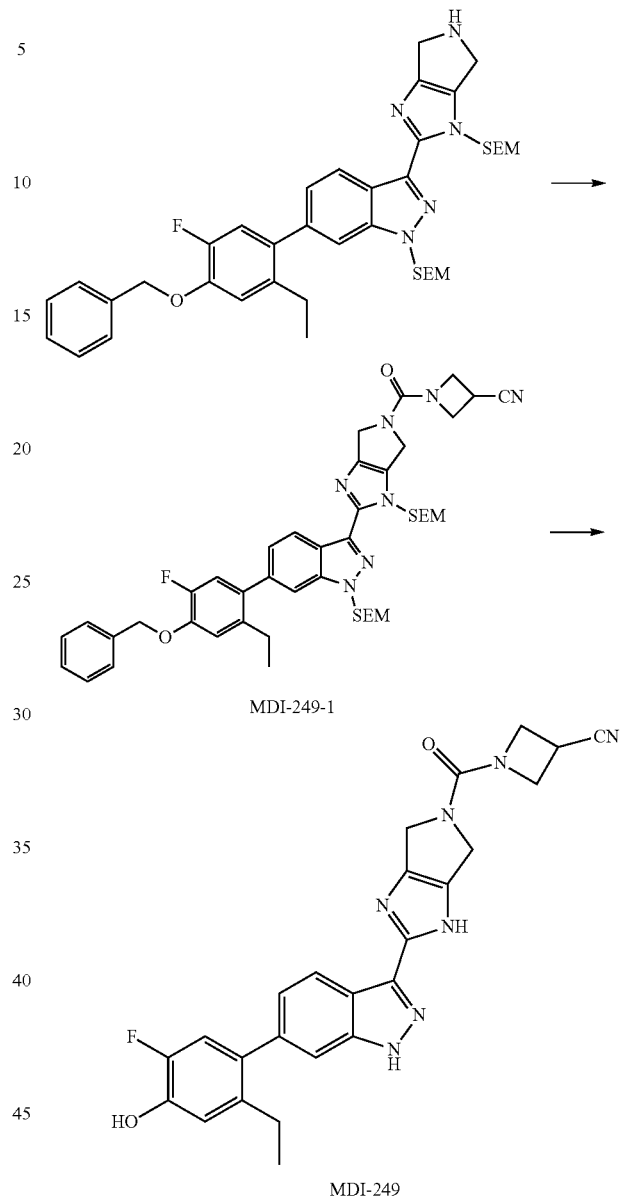

MDI-249-1

MDI-249

Synthesis Method

Synthesis of Intermediate MDI-249-1: 1-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-1,4,5,6-tetrahydropyrrolo[3,4-d]imidazole-5-carbonyl)azetidine-3-nitrile Triphosgene (15.8 mg, 0.05 mmol) was dissolved in 5 ml of dry dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (38 mg, 0.05 mmol) in dichloromethane (5 ml) was added dropwise at 0° C., then anhydrous triethylamine (53.9 mg, 0.50 mmol) was added slowly. The mixture was stirred at room temperature for 10 minutes. TLC monitored that the raw materials disappeared. Azetidine-3-nitrile hydrochloride (8.8 mg, 0.10 mmol) was added. The resulting mixture was stirred at room temperature for 2 hours. Water was added to quench the reaction and the resulting mixture was extracted twice with dichloromethane, and the organic phases were combined, washed with saturated brine, dried over anhydrous sodium sulfate, concentrated, and purified by silica gel column to afford 26 mg of intermediate MDI-249-1, with a yield of 59.4%.

$^1$H NMR (400 MHz, CDCl$_3$) δ 8.45 (d, J=8.3 Hz, 1H), 7.53-7.51 (m, 2H), 7.48-7.36 (m, 4H), 7.25 (d, J=8.4 Hz, 1H), 7.06-6.97 (m, 2H), 5.96 (s, 2H), 5.77 (s, 2H), 5.23 (s, 2H), 4.72-4.56 (m, 4H), 4.42-4.34 (m, 2H), 4.26-4.17 (m, 2H), 3.65-3.58 (m, 4H), 3.46-3.39 (m, 1H), 2.53 (q, J=7.6 Hz, 2H), 1.05 (t, J=7.5 Hz, 3H), 0.95-0.89 (m, 4H), 0.02 (s, 9H), −0.04-0.05 (m, 9H).

Synthesis of Compound MDI-249: 1-(2-(6-(2-ethyl-5-fluoro-4-hydroxyphenyl)-1H-indazol-3-yl)-1,4,5,6-tetrahydropyrrolo[3,4-d]imidazol-5-carbonyl)azetidin-3-nitrile MDI-249-1 (26 mg, 0.03 mmol) was dissolved in 10 ml methanol, and 6 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 5.3 mg of the final product with a yield of 33.5%.

$^1$H NMR (400 MHz, MeOD) δ 8.28 (d, J=8.4 Hz, 1H), 7.43 (s, 1H), 7.18 (d, J=8.4 Hz, 1H), 6.97-6.90 (m, 2H), 4.60 (s, 4H), 3.86-3.81 (m, 2H), 3.65-3.53 (m, 2H), 3.19-3.13 (m, 1H), 2.56 (q, J=7.5 Hz, 2H), 1.08 (t, J=7.5 Hz, 3H).

Example 46: 1-(2-(6-(2-ethyl-5-fluoro-4-hydroxyphenyl)-1H-indazol-3-yl)-1,4,5,6-tetrahydropyrrolo[3,4-d]imidazol-5-carbonyl)pyrrolidin-3-nitrile (MDI-250)

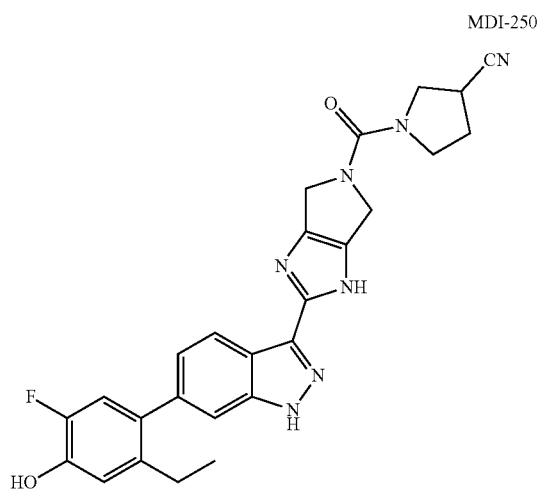 [SMILES: CCc1cc(O)c(F)cc1-c1ccc2c(-c3nc4c([nH]3)CN(C(=O)N3CCC(C#N)C3)C4)n[nH]c2c1]

MDI-250

Synthetic Route of MDI-250:

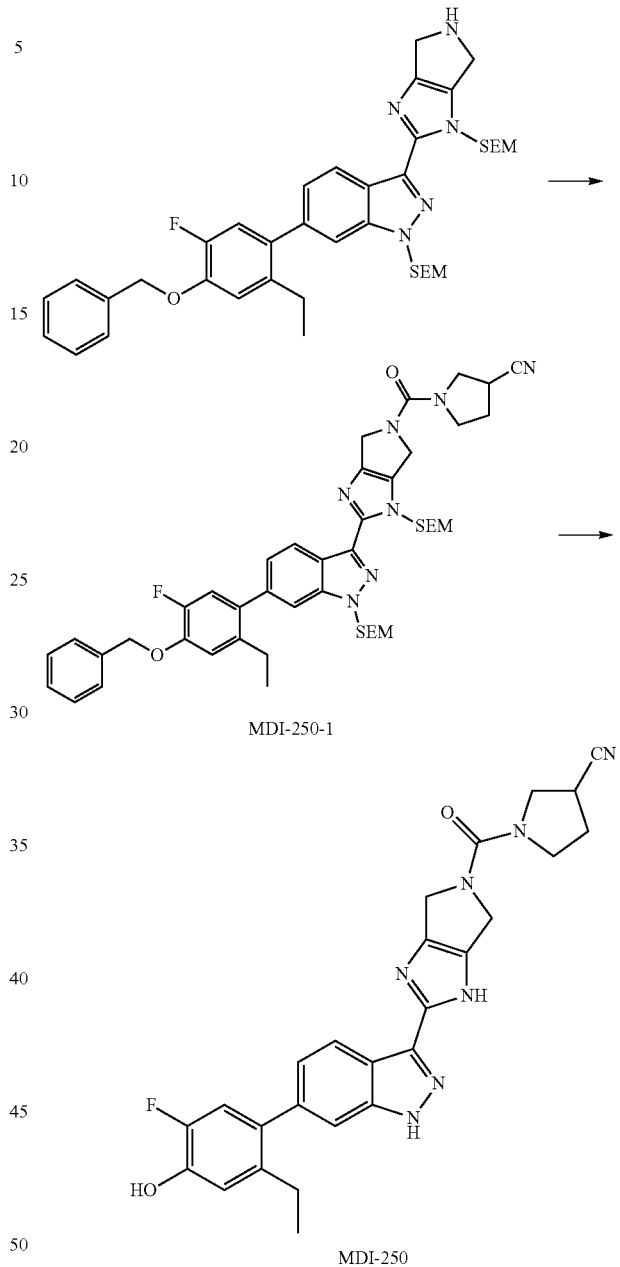

Synthesis Method

Synthesis of Intermediate MDI-250-1: 1-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-1,4,5,6-tetrahydropyrrolo[3,4-d]imidazole-5-carbonyl)pyrrolidine-3-nitrile Triphosgene (14.9 mg, 0.05 mmol) was dissolved in 6 ml of dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (36 mg, 0.05 mmol) in dichloromethane (5 ml) was added dropwise at 0° C., then anhydrous triethylamine (51.1 mg, 0.50 mmol) was added slowly. The mixture was stirred at room temperature for 10 minutes. TLC monitored that the raw materials disappeared. Pyrrolidine-3-nitrile hydrochloride (9.7 mg, 0.10 mmol) was added. The resulting mixture was stirred at room temperature for 20 minutes. Water was added to quench the reaction and the resulting mixture was extracted twice with ethyl acetate, and the organic phases were combined, washed with saturated brine, dried over anhydrous sodium sulfate, concentrated, and purified by silica gel column to afford 26 mg of intermediate MDI-250-1, with a yield of 61.6%.

$^1$H NMR (400 MHz, CDCl3) δ 8.46 (d, J=8.3 Hz, 1H), 7.53-7.51 (m, 2H), 7.47-7.35 (m, 4H), 7.25 (d, J=8.4 Hz, 1H), 7.06-6.97 (m, 2H), 5.96 (s, 2H), 5.77 (s, 2H), 5.23 (s, 2H), 4.80-4.67 (m, 4H), 3.79-3.46 (m, 8H), 3.12-3.05 (m, 1H), 2.54 (q, J=7.6 Hz, 2H), 2.38-2.16 (m, 2H), 1.05 (t, J=7.5 Hz, 3H), 0.96-0.89 (m, 4H), 0.02 (s, 9H), −0.05 (d, J=3.4 Hz, 9H).

Synthesis of Compound MDI-250: 1-(2-(6-(2-ethyl-5-fluoro-4-hydroxyphenyl)-1H-indazol-3-yl)-1,4,5,6-tetrahydropyrrolo[3,4-d]imidazol-5-carbonyl) pyrrolidin-3-nitrile MDI-250-1 (26 mg, 0.03 mmol) was dissolved in 10 ml methanol, and 6 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 4 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 6 mg of the final product with a yield of 39.8%.

$^1$H NMR (400 MHz, MeOD) δ 8.27 (d, J=8.4 Hz, 1H), 7.43 (s, 1H), 7.18 (d, J=8.4 Hz, 1H), 6.98-6.90 (m, 2H), 4.70 (s, 4H), 3.89-3.85 (m, 1H), 3.78-3.76 (m, 1H), 3.70-3.59 (m, 2H), 3.23-3.18 (m, 1H), 2.56 (q, J=7.5 Hz, 2H), 2.42-2.19 (m, 2H), 1.08 (t, J=7.5 Hz, 3H).

Example 47: 2-(6-(2-ethyl-5-fluoro-4-hydroxyphenyl)-1H-indazol-3-yl)-N-(tetrahydrofuran-3-yl)-4,6-dihydropyrrolo[3,4-d]imidazol-5(1H)-carboxamide (MDI-251)

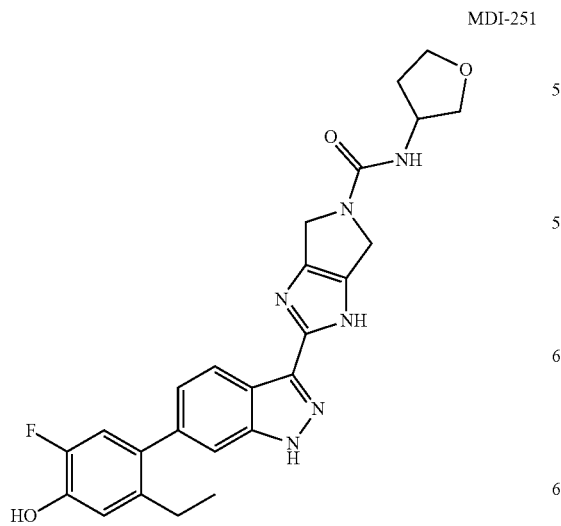

MDI-251

Synthetic Route of MDI-251:

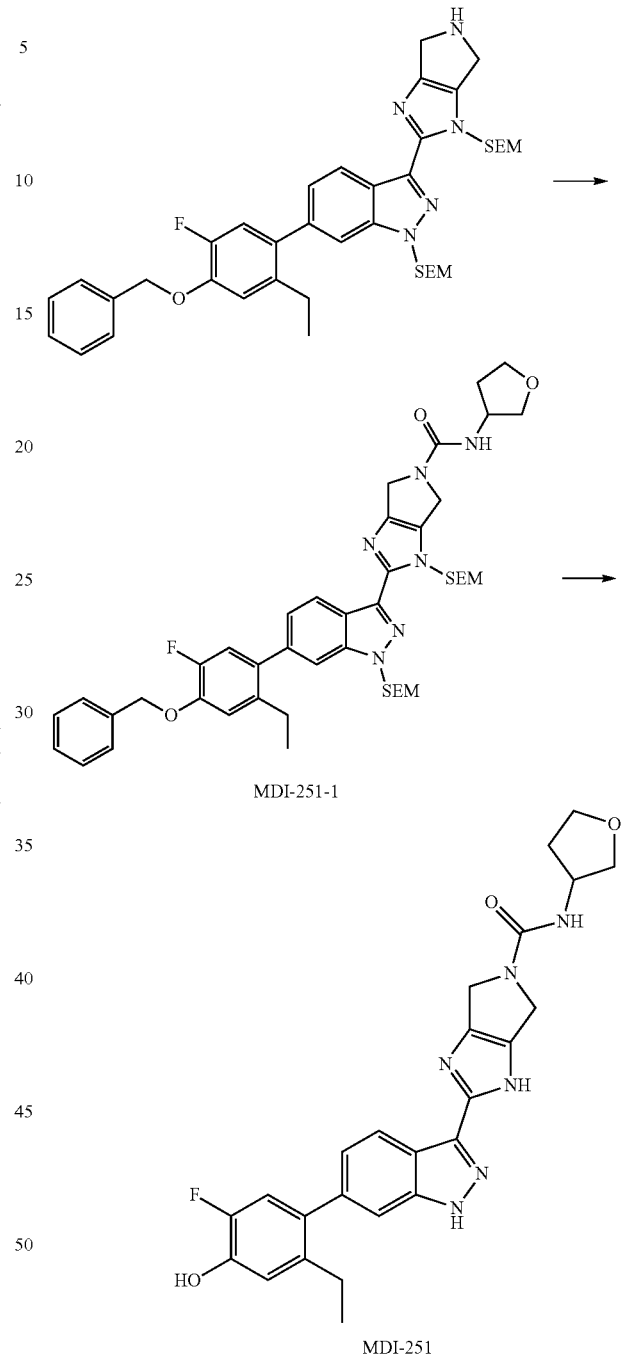

MDI-251-1

MDI-251

Synthesis Method

Synthesis of intermediate MDI-251-1: 2-(6-(4-(benzyloxy)-2-ethyl-5-fluorophenyl)-1-((2-(trimethylsilyl)ethoxy)methyl)-1H-indazol-3-yl)-N-(tetrahydrofuran-3-yl)-1-(((2-(trimethylsilyl)ethoxy)methyl)-4,6-dihydropyrrolo[3,4-d]imidazole-5(1H)-carboxamide Triphosgene (19.1 mg, 0.06 mmol) was dissolved in 6 ml of dry dichloromethane, to which the intermediate 6-(4-

(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (46 mg, 0.06 mmol) in dichloromethane (5 ml) was added dropwise at 0° C., then anhydrous triethylamine (65.3 mg, 0.6 mmol) was added slowly. The mixture was stirred at room temperature for 10 minutes. TLC monitored that the raw materials disappeared. Tetrahydrofuran-3-amine hydrochloride (16.4 mg, 0.13 mmol) was added. It was allowed to react at 38° C. for 5 hours. Water was added to quench the reaction and the resulting mixture was extracted twice with dichloromethane, and the organic phases were combined, washed with saturated brine, dried over anhydrous sodium sulfate, concentrated, and purified by silica gel column to afford 32 mg of intermediate MDI-251-1, with a yield of 60.3%.

$^1$H NMR (400 MHz, CDCl$_3$) δ 8.46 (d, J=8.3 Hz, 1H), 7.73-7.51 (m, 2H), 7.47-7.35 (m, 4H), 7.27-7.24 (m, 1H), 7.07-6.97 (m, 2H), 5.96 (s, 2H), 5.77 (s, 2H), 5.23 (s, 2H), 4.70-4.53 (m, 4H), 4.51-4.41 (m, 1H), 4.06-3.58 (m, 8H), 2.54 (q, J=7.6 Hz, 2H), 2.40-1.99 (m, 2H), 1.05 (t, J=7.5 Hz, 3H), 0.95-0.89 (m, 4H), 0.02 (s, 9H), −0.05 (s, 9H).

Synthesis of Compound MDI-251: 2-(6-(2-ethyl-5-fluoro-4-hydroxyphenyl)-1H-indazol-3-yl)-N-(tetrahydrofuran-3-yl)-4,6-dihydropyrrolo[3,4-d]imidazol-5(1H)-carboxamide MDI-251-1 (32 mg, 0.04 mmol) was dissolved in 10 ml methanol, and 6 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 3 mg of the final product with a yield of 16.3%.

$^1$H NMR (400 MHz, MeOD) δ 8.28 (d, J=8.4 Hz, 1H), 7.43 (s, 1H), 7.18 (d, J=8.4 Hz, 1H), 6.97-6.90 (m, 2H), 4.63 (s, 4H), 4.45-4.40 (m, 1H), 4.03-3.94 (m, 2H), 3.87-3.81 (m, 1H), 3.71-3.68 (m, 1H), 2.56 (q, J=7.5 Hz, 2H), 2.32-1.87 (m, 2H), 1.08 (t, J=7.5 Hz, 3H).

Example 48: Methyl 2-(6-(2-ethyl-5-fluoro-4-hydroxyphenyl)-1H-indazol-3-yl)-4,6-dihydropyrrolo[3,4-d]imidazol-5(1H)-carboxylate (MDI-252)

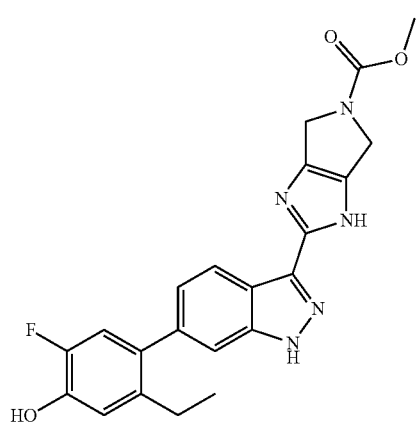

MDI-252

Synthetic Route of MDI-252:

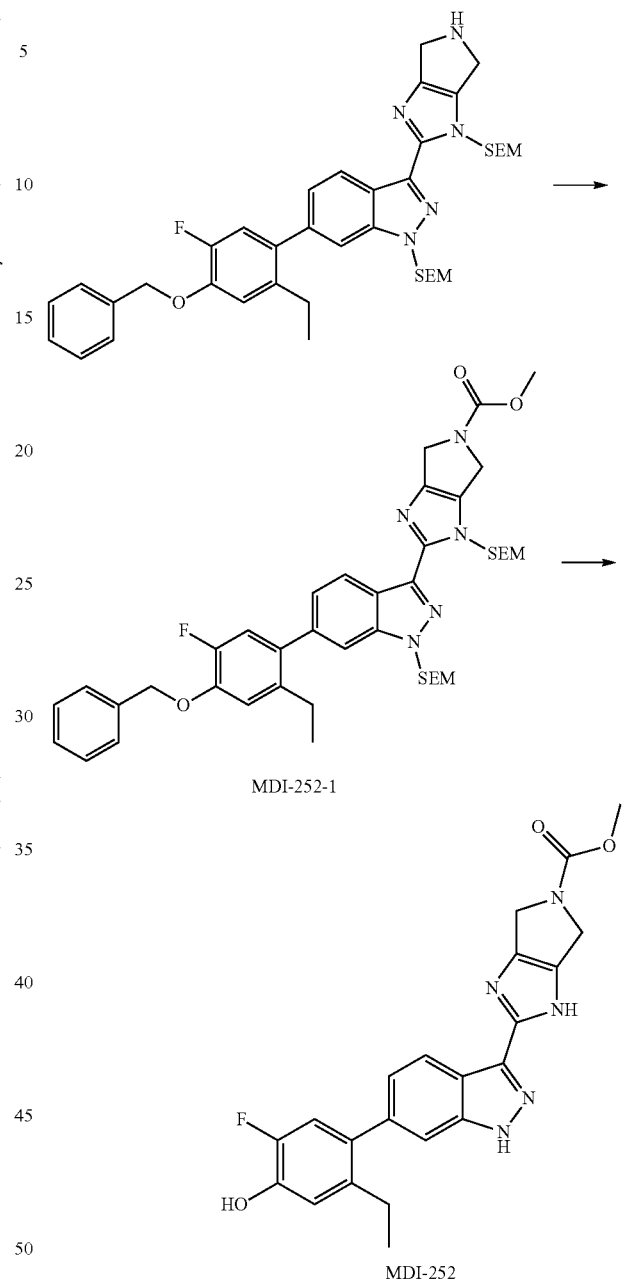

MDI-252-1

MDI-252

Synthesis Method

Synthesis of Intermediate MDI-252-1: Methyl 2-(6-(4-(benzyloxy)-2-ethyl-5-fluorophenyl)-1-((2-(trimethylsilyl)ethoxy)methyl)-1H-indazol-3-yl)-1-((2-((trimethylsilyl)ethoxy)methyl)-4,6-dihydropyrrolo[3,4-d]imidazol-5(1H)-carboxylate Triphosgene (16.6 mg, 0.06 mmol) was dissolved in 5 ml of dry dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (40 mg, 0.06 mmol) in dichloromethane (5 ml) was added dropwise at 0° C., then anhydrous triethylamine (56.8 mg, 0.56 mmol) was added slowly. The mixture was stirred at room temperature for 10 minutes. TLC monitored that the raw materials disappeared. The reaction mixture was concentrated and was dissolved in 10 ml of methanol. DMAP (6.9 mg, 0.06 mmol) was added. It was allowed to react at 70° C. for 4 hours. The reaction mixture was concentrated to which water was added. The resulting mixture was extracted twice with dichloromethane, and the organic phases were combined, washed with saturated brine, dried over anhydrous sodium sulfate, concentrated, and purified by silica gel column to afford 30 mg of intermediate MDI-252-1, with a yield of 69.4%.

$^1$H NMR (400 MHz, CDCl3) δ 8.44-8.39 (m, 1H), 7.53-7.51 (m, 2H), 7.48-7.36 (m, 4H), 7.23 (d, J=8.4 Hz, 1H), 7.05-6.96 (m, 2H), 5.95 (s, 2H), 5.78 (s, 2H), 5.23 (s, 2H), 4.75-4.59 (m, 4H), 3.85 (s, 3H), 3.66-3.57 (m, 4H), 2.53 (q, J=7.6 Hz, 2H), 1.04 (t, J=7.5 Hz, 3H), 0.95-0.88 (m, 4H), 0.02 (s, 9H), −0.04-0.05 (m, 9H).

Synthesis of Compound MDI-252: Methyl 2-(6-(2-ethyl-5-fluoro-4-hydroxyphenyl)-1H-indazol-3-yl)-4,6-dihydropyrrolo[3,4-d]imidazol-5(1H)-carboxylate MDI-252-1 (30 mg, 0.04 mmol) was dissolved in 10 ml methanol, and 6 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml methanol and 3 ml concentrated hydrochloric acid was added. It was allowed to react at 50° C. for 7 hours and the mixture was concentrated to give a residue. The residue was dissolved in methanol and was concentrated to dryness, which was repeated 3 times. The resulting residue was dissolved in 5 ml methanol, and 0.5 ml aqueous ammonia was added. The resulting mixture was concentrated, and purified to afford 8 mg of the final product with a yield of 48.9%.

$^1$H NMR (400 MHz, MeOD) δ 8.28 (d, J=8.4 Hz, 1H), 7.43 (s, 1H), 7.18 (d, J=8.4 Hz, 1H), 6.97-6.90 (m, 2H), 4.61 (s, 4H), 3.83 (s, 3H), 2.56 (q, J=7.5 Hz, 2H), 1.08 (t, J=7.5 Hz, 3H).

Example 49: Ethyl 2-(6-(2-ethyl-5-fluoro-4-hydroxyphenyl)-1H-indazol-3-yl)-4,6-dihydropyrrolo[3,4-d]imidazol-5(1H)-carboxylate (MDI-253)

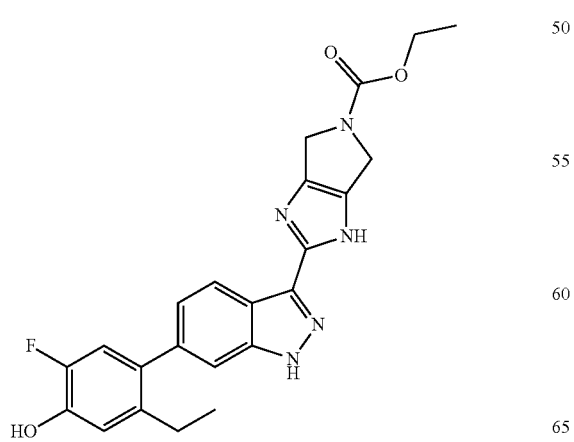

MDI-253

Synthetic Route of MDI-253:

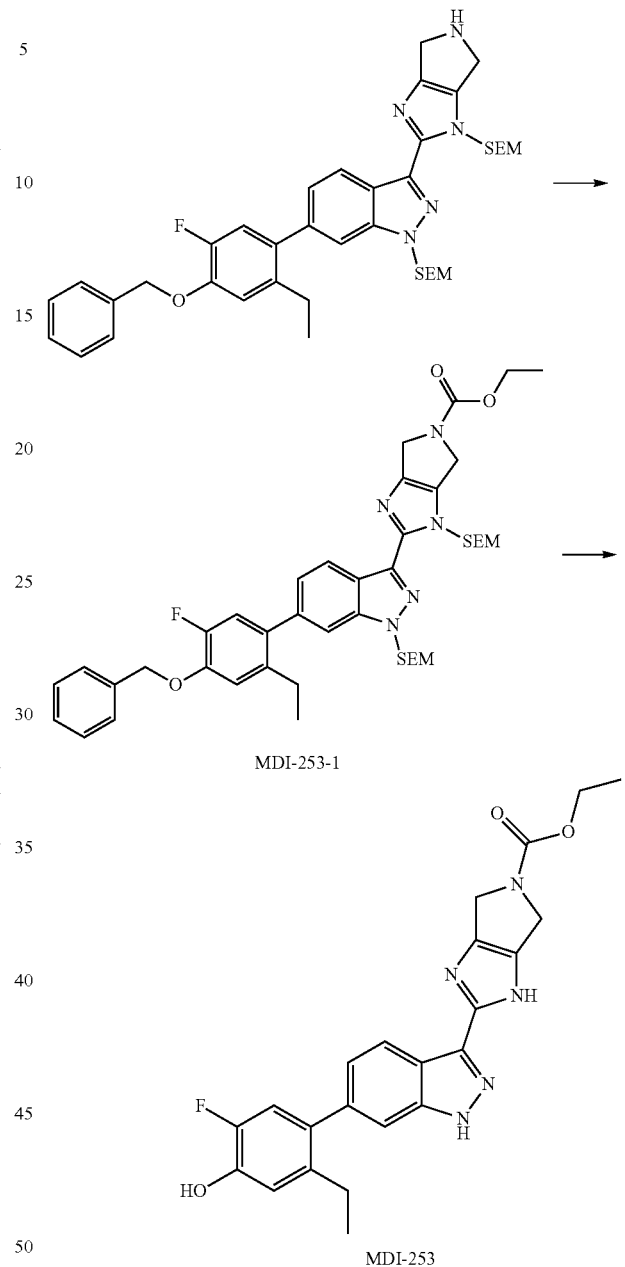

Synthesis Method

Synthesis of Intermediate MDI-253-1: Ethyl 2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazole-5(1H)-carboxylate Triphosgene (20.1 mg, 0.07 mmol) was dissolved in 5 ml of dry dichloromethane, to which the intermediate 6-(4-(benzyloxy)-2-ethyl-5-fluorophenyl)-1-((2-(trimethylsilyl)ethoxy)methyl)-3-(1-((2-(trimethylsilyl)ethoxy)methyl)-1-1,4,5,6-tetrahydropyrrolo[3,4-d]imidazol-2-yl)-1H-indazole (48 mg, 0.07 mmol) in dichloromethane (5 ml) was added dropwise at 0° C., then anhydrous triethylamine (68.1 mg, 0.67 mmol) was added slowly. The mixture was stirred at room temperature for 10 minutes. TLC monitored that the raw materials disappeared. The reaction mixture was concentrated and was dissolved in 10 ml ethanol. DMAP (8.2 mg, 0.07 mmol) was added. It was allowed to react at 80° C. for 4 hours. The reaction mixture was concentrated to which water was added. The resulting mixture was extracted twice with dichloromethane, and the organic phases were combined, washed with saturated brine, dried over anhydrous sodium sulfate, concentrated, and purified by silica gel column to afford 33 mg of intermediate MDI-253-1, with a yield of 62.5%.

$^1$H NMR (400 MHz, CDCl3) δ 8.50-8.45 (m, 1H), 7.53-7.51 (m, 2H), 7.47-7.37 (m, 4H), 7.25 (d, J=8.4 Hz, 1H), 7.07-6.96 (m, 2H), 5.96 (s, 2H), 5.77 (s, 2H), 5.23 (s, 2H), 4.72-4.59 (m, 4H), 4.29-4.25 (m, 2H), 3.65-3.58 (m, 4H), 2.54 (q, J=7.6 Hz, 2H), 1.38-1.34 (m, 3H), 1.05 (t, J=7.5 Hz, 3H), 0.95-0.89 (m, 4H), 0.02 (s, 9H), −0.05 (s, 9H).

Synthesis of Compound MDI-253: Ethyl 2-(6-(2-ethyl-5-fluoro-4-hydroxyphenyl)-1H-indazol-3-yl)-4,6-dihydropyrrolo[3,4-d]imidazole-5(1H)-carboxylate MDI-253-1 (33 mg, 0.04 mmol) was dissolved in 10 ml ethanol, and 6 mg palladium on carbon was added. The atmosphere was replaced hydrogen. It was allowed to react at 40° C. for 1 hour. After the reaction was completed, the mixture was filtered, and the filtrate was concentrated. The concentrate was dissolved in 6 ml ethanol and 3 ml concentrated hydrochloric acid was added. It was allowed to react at 50° C. for 7 hours and the mixture was concentrated to give a residue. The residue was dissolved in ethanol and was concentrated to dryness, which was repeated 3 times. The resulting residue was dissolved in 5 ml ethanol, and 0.5 ml aqueous ammonia was added. The resulting mixture was concentrated, and purified to afford 10 mg of the final product with a yield of 54.8%.

$^1$H NMR (400 MHz, MeOD) δ 8.27 (d, J=8.4 Hz, 1H), 7.43 (s, 1H), 7.18 (d, J=8.4 Hz, 1H), 6.97-6.90 (m, 2H), 4.60 (s, 4H), 4.26 (q, J=7.1 Hz, 2H), 2.57 (q, J=7.5 Hz, 2H), 1.36 (t, J=7.1 Hz, 3H), 1.08 (t, J=7.5 Hz, 3H).

Example 50: (S)-(2-(6-(2-ethyl-5-fluoro-4-hydroxyphenyl)-1H-pyrazolo[3,4-b]pyridine-3-yl)-4,6-dihydropyrrolo[3,4-d]imidazol-5(1H)-yl)(3-hydroxylpyrrolidin-1-yl)ketone (MDI-255)

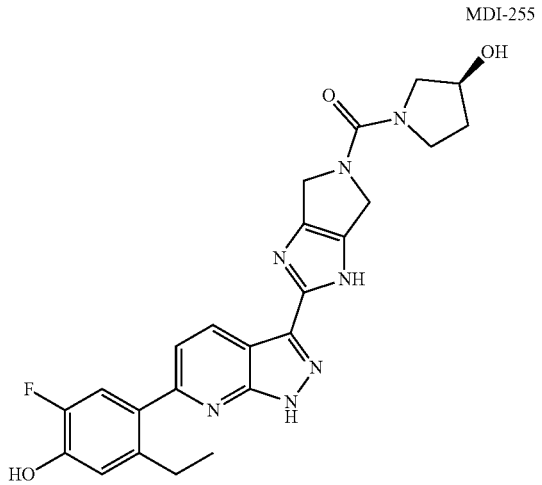 [SMILES: CCc1cc(O)c(F)cc1-c1ccc2c(-c3nc4c([nH]3)CN(C(=O)N3CC[C@H](O)C3)C4)n[nH]c2n1]

MDI-255

Synthetic Route of MDI-255:

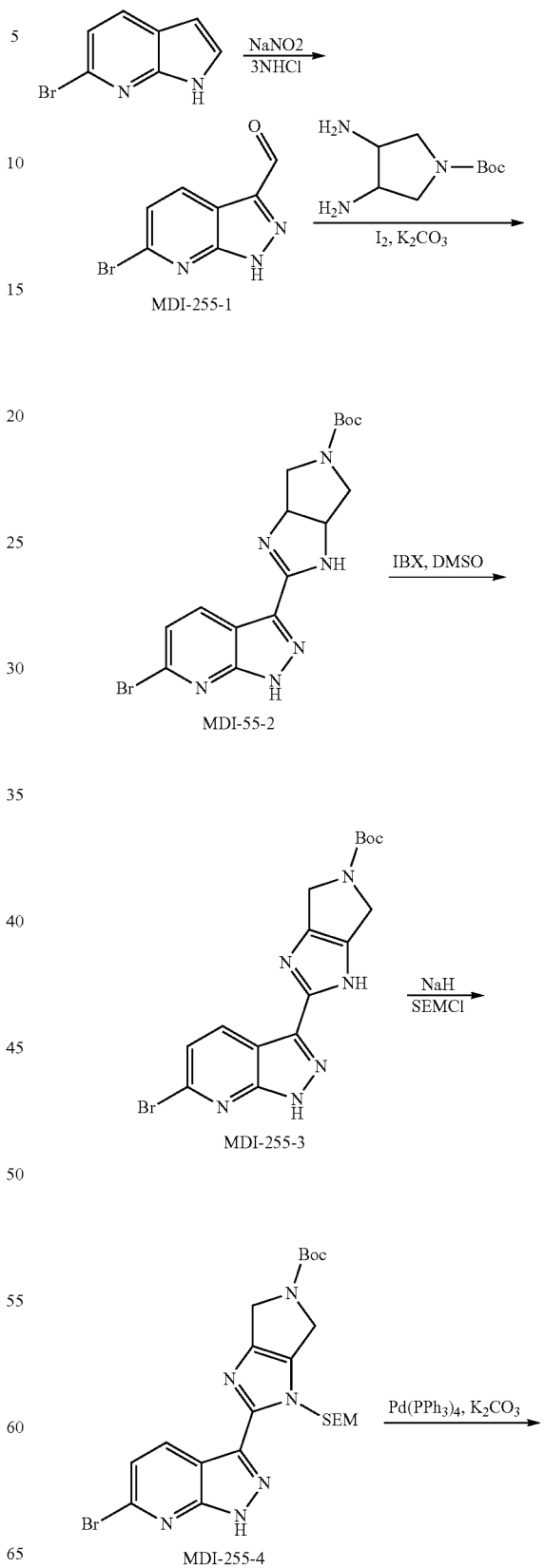

207
-continued

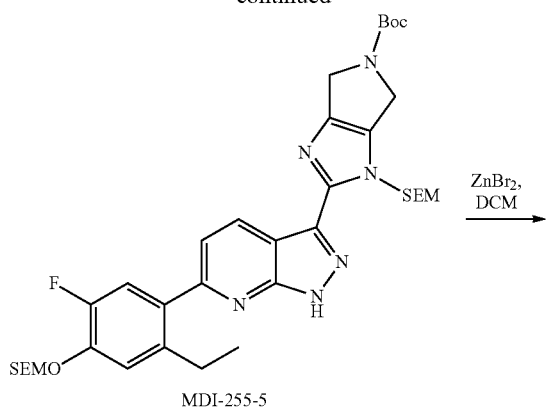
MDI-255-5

ZnBr₂, DCM →

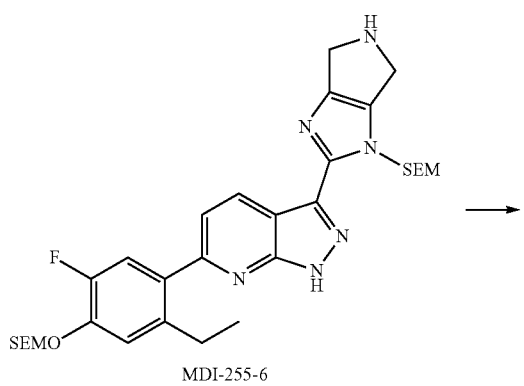
MDI-255-6

→

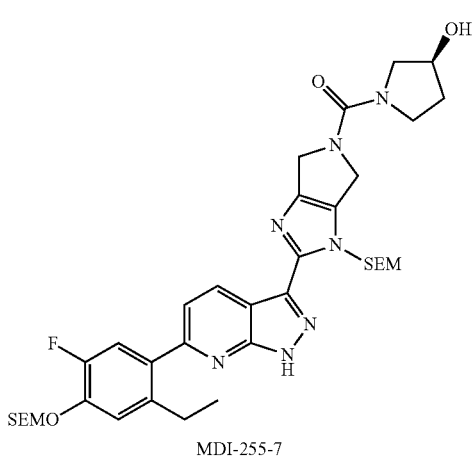
MDI-255-7

4NHCl →

208
-continued

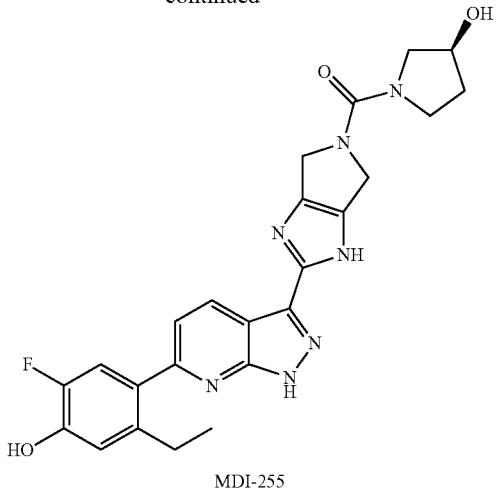
MDI-255

Synthesis Method

Synthesis of Intermediate MDI-551-1: 6-bromo-1H-pyrazolo[3,4-b]pyridine-3-formaldehyde Sodium nitrite (2.80 g, 40.6 mmol) was dissolved in 15 ml DMF and 20 ml water, and cooled to 0° C. 3N HCl (11.9 ml, 35.6 mmol) was slowly added dropwise, and after the addition, the reaction was carried out for 10 minutes. At 0° C., 6-bromo-1H-pyrrolo[2,3-b]pyridine (1.00 g, 5.08 mmol) in DMF (15 ml) was slowly added to the reaction solution dropwise. After the addition, the mixture was heated to 50° C. It was allowed to react for 5 hours. The resulting mixture was extracted with ethyl acetate 3 times, and the organic phases were combined, washed 3 times with water, washed with saturated brine, dried over anhydrous sodium sulfate, concentrated, and purified by silica gel column to afford 540 mg of intermediate MDI-255-1 with a yield of 47.0%.

$^1$H NMR (400 MHz, CDCl3) δ 10.36 (s, 1H), 8.40 (d, J=8.0 Hz, 1H), 7.70 (d, J=8.0 Hz, 1H).

Synthesis of Intermediate MDI-255-2: Tert-butyl 2-(6-bromo-1H-pyrazolo[3,4-b]pyridine-3-yl)-3a,4,6,6a-tetrahydropyrrolo[3,4-d]imidazol-5(1H)-carboxylate Intermediate MDI-255-1 (540 mg, 2.39 mmol) and tert-butyl 3,4-diaminopyrroline-1-carboxylate (529 mg, 2.63 mmol) were dissolved in 30 ml tert-butanol and stirred at room temperature for 30 minutes, followed by addition of I₂ (759 mg, 2.99 mmol) and K₂CO₃ (989.1 mg, 7.17 mmol). The mixture was heated to 70° C. for 3 hours, and cooled to room temperature. Saturated sodium thiosulfate was added and the mixture was stirred for 20 minutes until the color of iodine disappeared. The resulting mixture was extracted twice with ethyl acetate, and the organic phases were combined, washed with water and saturated brine, dried over anhydrous sodium sulfate, concentrated, and purified by silica gel column to afford 396 mg of intermediate MDI-255-2 with a yield of 40.7%.

$^1$H NMR (400 MHz, CDCl3) δ 8.46 (d, J=8.0 Hz, 1H), 7.62 (d, J=8.0 Hz, 1H), 4.99-4.94 (m, 1H), 4.54-4.50 (m, 1H), 3.76-3.68 (m, 3H), 3.60-3.58 (m, 1H), 1.45 (s, 9H).

Synthesis of Intermediate MDI-255-3: Tert-butyl 2-(6-bromo-1H-pyrazolo[3,4-b]pyridine-3-yl)-4,6-dihydropyrrolo[3,4-d]imidazol-5(1H)-carboxylate MDI-255-2 (396 mg, 0.97 mmol) was dissolved in 6 ml DMSO, and IBX (543 mg, 1.94 mmol) was added. It was allowed to react at 50° C. for 6 hours. The reaction was quenched by adding water. The resulting mixture was extracted twice with ethyl acetate and the organic phases were combined, washed with water and saturated brine, dried over anhydrous sodium sulfate, concentrated, and purified on a silica gel column to afford 227 mg of intermediate MDI-255-3 with a yield of 57.6%.

$^1$H NMR (400 MHz, CDCl3) δ 10.59 (s, 1H), 8.64 (dd, J=8.0 Hz, J=12.0 Hz, 1H), 7.64 (d, J=8.0 Hz, 1H), 4.67-4.53 (m, 4H), 1.56 (s, 9H).

Synthesis of Intermediate MDI-255-4: Tert-butyl 2-(6-bromo-1H-pyrazolo[3,4-b]pyridine-3-yl)-1-((2-(trimethylsilyl)ethoxy)methyl)-4,6-dihydropyrrolo[3,4-d]imidazol-5(1H)-carboxylate Intermediate MDI-255-3 (227 mg, 0.56 mmol) was dissolved in 15 ml of dry tetrahydrofuran, and cooled to 0° C., to which sodium hydride (60%) (67.2 mg, 1.68 mmol) was slowly added. The mixture was stirred for 10 minutes. 2-(Trimethylsilyl)ethoxymethyl chloride (280.3 mg, 1.68 mmol) was added slowly dropwise, and after the addition, the reaction was carried out at room temperature for 1 hour. Water was added to quench the reaction. The resulting mixture was extracted twice with ethyl acetate, and the organic phases were combined, washed with water and saturated brine, dried over anhydrous sodium sulfate, concentrated, and purified by silica gel column to afford 126 mg of intermediate MDI-255-4 with a yield of 42.0%.

$^1$H NMR (400 MHz, CDCl3) δ 8.72 (dd, J=8.0 Hz, J=12.0 Hz, 1H), 7.63 (dd, J=8.0 Hz, J=4.0 Hz, 1H), 5.90 (d, J=8.0 Hz, 2H), 4.67-4.52 (m, 4H), 3.69-3.64 (m, 2H), 1.56 (s, 9H), 1.01-0.97 (m, 2H), 0.02 (s, 9H).

Synthesis of Intermediate MDI-255-5: Tert-butyl 2-(6-(2-ethyl-5-fluoro-4-((2-(trimethylsilyl)ethoxy)methoxy)phenyl)-1H-pyrazolo[3,4-b]pyridine-3-yl)-1-((2-(trimethylsilyl)ethoxy)methyl)-4,6-dihydropyrrolo[3,4-d]imidazol-5(1H)-carboxylate Intermediate MDI-255-4 (126 mg, 0.24 mmol), (2-((5-ethyl-2-fluoro-4-(4,4,5,5-tetramethyl-1,3,2-dioxaborolan-2-yl)phenoxy)methoxy)ethyl)trimethylsilane (143 mg, 0.36 mmol), Pd(PPh3)4 (27.2 mg, 0.02 mmol) and potassium carbonate (99.4 mg, 0.72 mmol) were dissolved in 1,4-dioxane (20 ml) and water (4 ml). The atmosphere was replaced with nitrogen, which was repeated 3 times. The mixture was heated to 100° C., reacted for 3 hours, cooled to room temperature. Water was added, and the resulting mixture was extracted twice with ethyl acetate. The organic phases were combined, washed with water and saturated brine, dried over anhydrous sodium sulfate, concentrated, and purified on a silica gel column to afford 83 mg of intermediate MDI-255-5 with a yield of 47.7%.

$^1$H NMR (400 MHz, CDCl3) δ 8.88 (dd, J=8.0 Hz, J=12.0 Hz, 1H), 7.52 (d, J=8.0 Hz, 1H), 7.25-7.21 (m, 2H), 5.95 (d, J=8.0 Hz, 2H), 5.36 (s, 2H), 4.69-4.54 (m, 4H), 3.89-3.84 (m, 2H), 3.72-3.65 (m, 2H), 2.82-2.76 (m, 2H)), 1.59 (s, 9H), 1.18-1.12 (m, 3H), 1.04-0.99 (m, 4H), 0.05 (s, 9H), 0.02 (s, 9H).

Synthesis of Intermediate MDI-255-6: 6-(2-ethyl-5-fluoro-4-((2-(trimethylsilanyl)ethoxy)methoxy)phenyl)-3-(1-((2-(trimethylsilanyl)ethoxy)methyl)-1,4,5,6-tetrahydropyrrolo[3,4-d]imidazol-2-yl)-1H-pyrazolo[3,4-b]pyridine Intermediate MDI-255-5 (83 mg, 0.11 mmol) was dissolved in 15 ml of dichloromethane, and zinc bromide (103 mg, 0.46 mmol) was added. The mixture was stirred at 25° C. for 4 hours, and 10 ml of aqueous ammonia was added to the reaction solution. After liquid separation, the organic phase was washed with saturated sodium bicarbonate and saturated sodium chloride, dried over anhydrous sodium sulfate, and concentrated to afford 65 mg of intermediate MDI-255-6, with a yield of 95.6%. The crude product was directly used in the next step.

Synthesis of Intermediate MDI-255-7: (S)-(2-(6-(2-ethyl-5-fluoro-4-((2-(trimethylsilyl)ethoxy)methoxy)phenyl)-1H-pyrazolo[3,4-b]pyridine-3-yl)-1-(((2-(trimethylsilyl)ethoxy)methyl)-4,6-dihydropyrrolo[3,4-d]imidazol-5(1H)-yl)(3-hydroxyl pyrrolidin-1-yl) ketone Intermediate MDI-241-6 (20 mg, 0.03 mmol) was dissolved in 5 ml of dry dichloromethane, and cooled to 0° C., to which triphosgene (9.5 mg, 0.03 mmol) was added, and triethylamine (32.3 mg, 0.32 mmol) was added dropwise. After the addition, the mixture was stirred at room temperature for 10 minutes, to which (S)-3-hydroxypyrrolidine hydrochloride (7.7 mg, 0.06 mmol) was added. The mixture was stirred at room temperature for 1 hour. Water was added and the resulting mixture was extracted twice with dichloromethane. The organic phases were combined, washed with water and saturated brine, dried over anhydrous sodium sulfate, and concentrated to afford 19 mg of intermediate MDI-255-7. The crude product was directly used in the next step.

Synthesis of Compound MDI-255: (S)-(2-(6-(2-ethyl-5-fluoro-4-hydroxyphenyl)-1H-pyrazolo[3,4-b]pyridine-3-yl)-4,6-dihydropyrrolo[3,4-d]imidazol-5(1H)-yl)(3-hydroxylpyrrolidin-1-yl)ketone Intermediate MDI-255-1 (19 mg, 0.03 mmol) was dissolved in 4 ml of methanol, to which 2 ml of concentrated hydrochloric acid was added. The mixture was heated to 50° C., reacted for 6 hours, and concentrated to give a residue. The residue was dissolved in methanol and was concentrated to dryness, which was repeated 3 times. The resulting residue was dissolved in methanol to which 1 ml of aqueous ammonia was added to neutralize. The resulting mixture was concentrated and purified by a preparation plate to afford 4.9 mg of the final product 4.9 mg with a total yield of the two steps of 32.0%.

$^1$H NMR (400 MHz, DMSO) δ 13.61 (s, 1H), 10.22 (s, 1H), 8.78 (d, J=8.0 Hz, 1H), 7.71 (d, J=8.0 Hz, 1H), 7.34 (d, J=12.0 Hz, 1H), 6.97 (d, J=8.0 Hz, 1H), 4.93 (d, J=4.0 Hz, 1H), 4.75-4.42 (m, 4H), 4.30-4.27 (m, 1H), 3.58-3.53 (m, 2H), 3.41-3.40 (m, 1H), 3.26-3.23 (m, 1H), 2.73-2.71 (m, 2H), 2.01-1.79 (m, 2H), 1.09 (t, J=8.0 Hz, 3H).

Example 51: 3-(2-(6-(2-ethyl-5-fluoro-4-hydroxyphenyl)-1H-indazol-3-yl)-4,6-dihydropyrrolo[3,4-d]imidazol-5(1H)-yl)-3-oxypropionitrile (MDI-256)

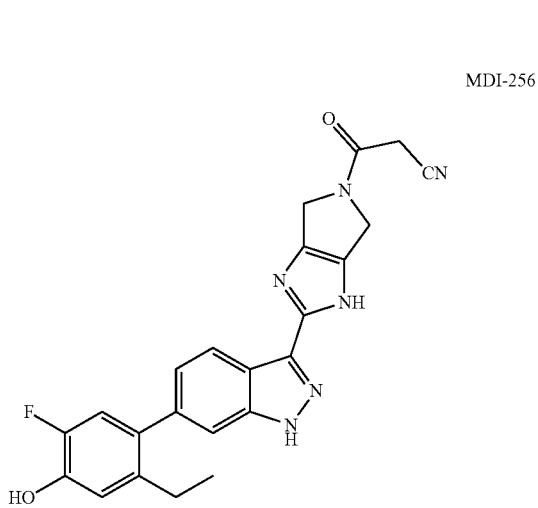 [SMILES: CCc1cc(O)c(F)cc1-c1ccc2c(-c3nc4c([nH]3)CN(C(=O)CC#N)C4)n[nH]c2c1]

Synthetic Route of MDI-256:

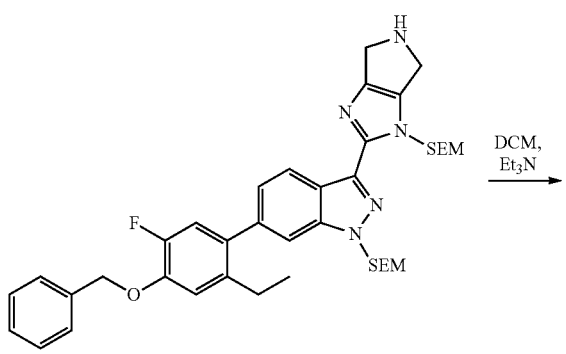

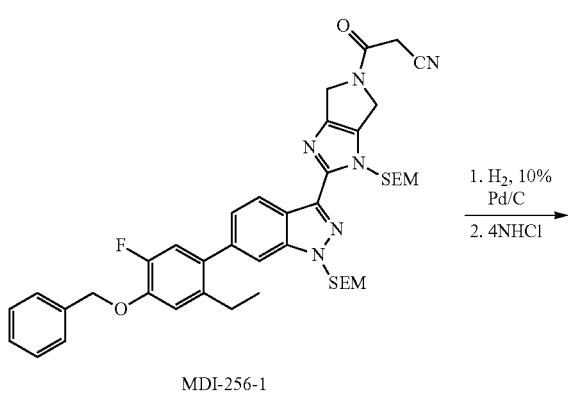

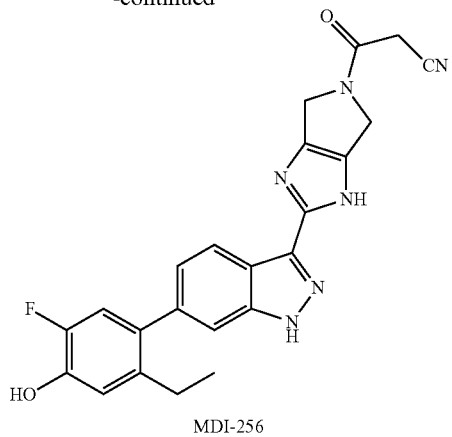

Synthesis Method

Synthesis of Intermediate MDI-256-1: 3-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-4,6-dihydropyrrolo[3,4-d]imidazol-5(1H)-yl)-3-oxypropionitrile 6-(4-(benzyloxy)-2-ethyl-5-fluorophenyl)-1-((2-(trimethylsilyl)ethoxy) methyl)-3-(1-((2-(trimethylsilyl)ethoxy)methyl)-1,4,5,6-tetrahydropyrrolo[3,4-d]imidazol-2-yl)-1H-indole (50 mg, 0.07 mmol) was dissolved in 5 ml of dichloromethane, to which Et3N (21.2 mg, 0.21 mmol) was added. The mixture was cooled to 0° C. and to which 2-cyanoacetyl chloride (8.7 mg, 0.08 mmol) was slowly added. It was allowed to react at room temperature for 1 hour, and water was added to quench the reaction. The resulting mixture was extracted twice with dichloromethane, and the organic phases were combined, washed with water and saturated brine, dried over anhydrous sodium sulfate, concentrated, and purified by silica gel column to afford 31 mg of intermediate MDI-256-1 with a yield of 56.7%.

Synthesis of Compound MDI-256: 3-(2-(6-(2-ethyl-5-fluoro-4-hydroxyphenyl)-1H-indazol-3-yl)-4,6-dihydropyrrolo[3,4-d]imidazol-5(1H)-yl)-3-oxypropionitrile Intermediate MDI-256-1 (31 mg, 0.04 mmol) was dissolved in methanol (6 ml), and 6 mg 10% Pd/C was added. The atmosphere was replaced with hydrogen 3 times. The mixture was heated to 40° C., reacted for 1 hour, filtered, and concentrated, to which 4 ml of methanol and 1 ml of concentrated hydrochloric acid were added. The mixture was heated to 50° C., reacted for 6 hours, and concentrated to give a residue. The residue was dissolved in methanol and was concentrated to dryness, which was repeated 3 times. The resulting residue was dissolved in methanol, to which 1 ml of aqueous ammonia was added to neutralize. The resulting mixture was concentrated and purified by a preparation plate to afford 3 mg of the final product with a yield of 17.4%.

$^1$H NMR (400 MHz, MeOD) δ 8.27 (d, J=8.0 Hz, 1H), 7.43 (s, 1H), 7.18 (d, J=8.0 Hz, 1H), 6.97 (dd, J=8.0 Hz, J=20.0 Hz, 2H), 4.77-4.70 (m, 4H), 3.62 (s, 2H), 2.59-2.53 (m, 2H), 1.09 (t, J=8.0 Hz, 3H).

Example 52: 2-(6-(2-ethyl-5-fluoro-4-hydroxyphenyl)-1H-indazol-3-yl)-N,N-dimethyl-4,6-dihydropyrrolo[3,4-d]imidazol-5(1H)-carboxamide (MDI-257)

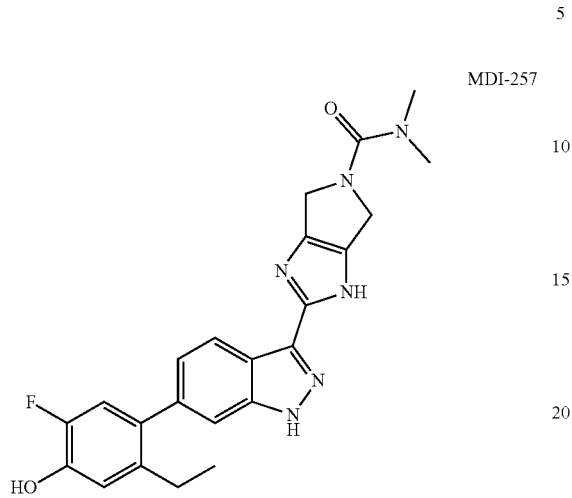

MDI-257

Synthetic Route of MDI-257:

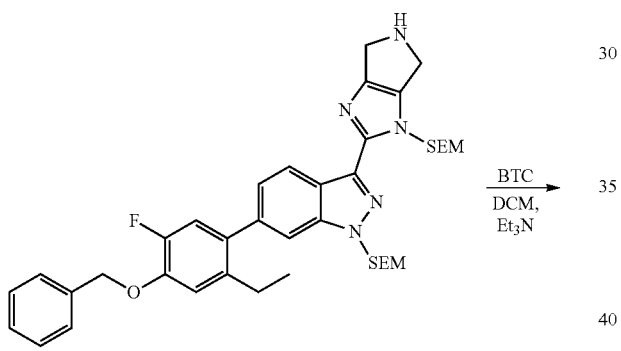

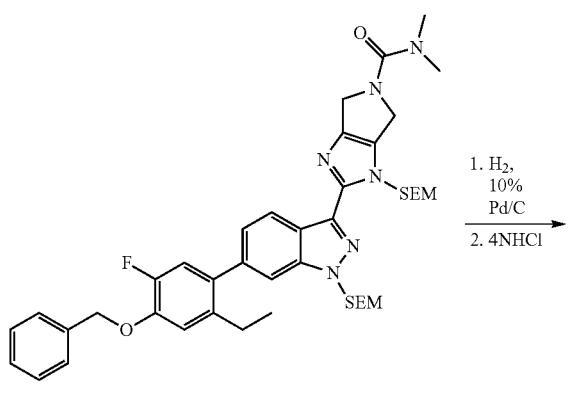

MDI-257-1

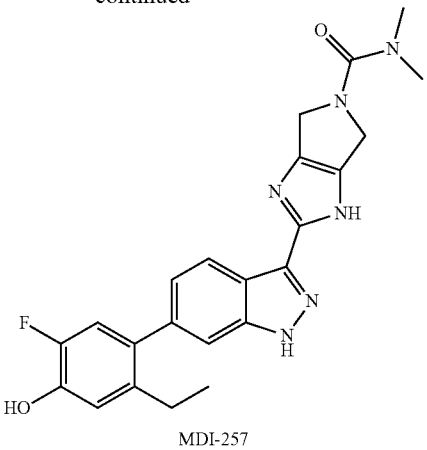

MDI-257

Synthesis Method

Synthesis of Intermediate MDI-257-1: 2-(6-(4-(benzyloxy)-2-ethyl-5-fluorophenyl)-1-((2-(trimethylsilyl)ethoxy)methyl)-1H-indazol-3-yl)-N,N-dimethyl-1-((2-(trimethylsilyl)ethoxy)methyl)-4,6-dihydropyrrolo[3,4-d]imidazol-5(1H)-carboxamide The synthesis process was similar to that of the intermediate MDI-246-1 with the exception that dimethylamine hydrochloride was used instead of methylamine hydrochloride.

Synthesis of Compound MDI-257: 2-(6-(2-ethyl-5-fluoro-4-hydroxyphenyl)-1H-indazol-3-yl)-N,N-dimethyl-4,6-dihydropyrrolo[3,4-d]imidazol-5(1H)-carboxamide Intermediate MDI-257-1 (41 mg, 0.05 mmol) was dissolved in methanol (6 ml), and 8 mg 10% Pd/C was added. The atmosphere was replaced with hydrogen 3 times. The mixture was heated to 40° C., reacted for 1 hour, filtered, and concentrated, to which 4 ml of methanol and 1 ml of concentrated hydrochloric acid were added. The mixture was heated to 50° C., reacted for 6 hours, and concentrated to give a residue. The residue was dissolved in methanol, and was concentrated to dryness, which was repeated 3 times. The resulting residue was dissolved in methanol, to which 1 ml of ammonia was added to neutralize. The resulting mixture was concentrated and purified by a preparation plate to afford 8 mg of the final product with a yield of 35.2%.

$^1$H NMR (400 MHz, DMSO) δ 13.28 (s, 1H), 9.85 (s, 1H), 8.32 (d, J=8.0 Hz, 1H), 7.40 (s, 1H), 7.13 (d, J=8.0 Hz, 1H), 7.03 (d, J=12.0 Hz, 1H), 6.93 (d, J=12.0 Hz, 1H), 4.54-4.53 (m, 4H), 2.85 (s, 6H), 2.50-2.46 (m, 2H), 1.04 (t, J=8.0 Hz, 3H).

Example 53: N-(2-cyanoethyl)-2-(6-(2-ethyl-5-fluoro-4-hydroxyphenyl)-1H-indazol-3-yl)-4,6-dihydropyrrolo[3,4-d]imidazole-5(1H)-carboxamide (MDI-258)

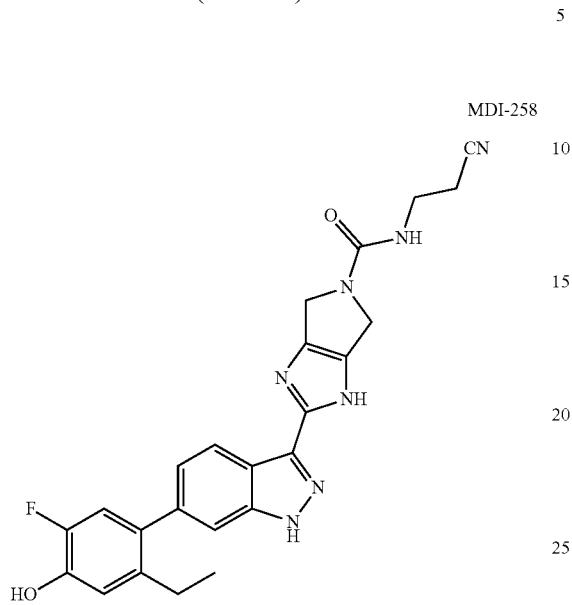

MDI-258

Synthetic Route of MDI-258:

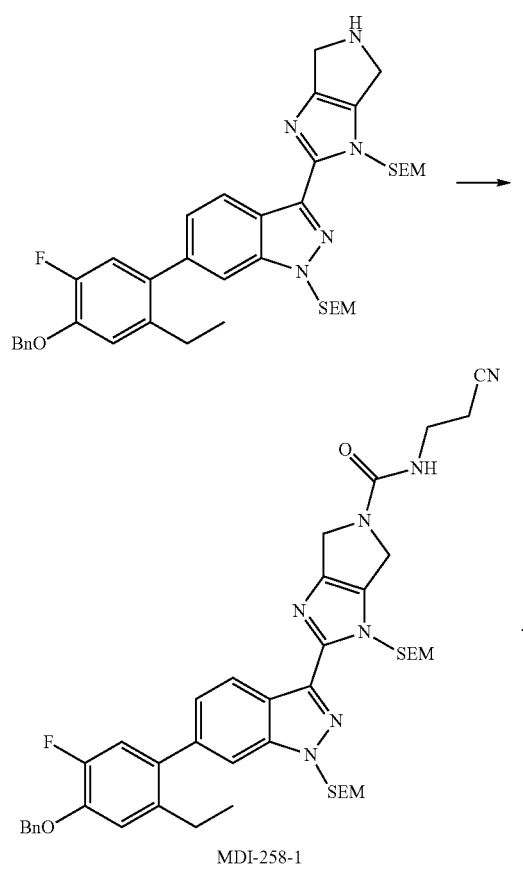

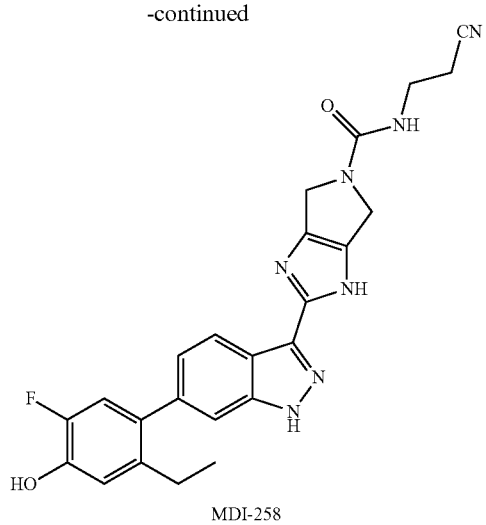

MDI-258

Synthesis Method

Synthesis of Intermediate MDI-258-1: 2-(6-(4-(benzyloxy)-2-ethyl-5-fluorophenyl)-1-((2-(trimethylsilyl)ethoxy)methyl)-1H-indazol-3-yl)-N-(2-cyanoethyl)-1-((2-(trimethylsilyl)ethoxy)methyl)-4,6-dihydropyrrolo[3,4-d]imidazol-5(1H)-carboxamide The synthesis process was similar to that of the intermediate MDI-246-1 with the exception that 3-aminopropionitrile was used instead of methylamine hydrochloride.

Synthesis of Compound MDI-258: N-(2-cyanoethyl)-2-(6-(2-ethyl-5-fluoro-4-hydroxyphenyl)-1H-indazol-3-yl)-4,6-dihydropyrrolo[3,4-d]imidazol-5(1H)-carboxamide Intermediate MDI-258-1 (36 mg, 0.04 mmol) was dissolved in methanol (4 ml), and 3.6 mg 10% Pd/C was added. The atmosphere was replaced with hydrogen 3 times. The mixture was heated to 40° C., reacted for 1 hour, filtered, and concentrated. The concentrated product was dissolved in 4 ml of methanol to which 2 ml of concentrated hydrochloric acid was added. The mixture was heated to 60° C., reacted for 6 hours, and concentrated. The solid was dissolved in methanol, which was adjusted with aqueous ammonia to pH=8-9. The resulting mixture was concentrated and purified by a preparation plate to afford 7.0 mg of the final product with a yield of 34.2%.

$^1$H NMR (400 MHz, MeOD) δ 8.25 (d, J=8.4 Hz, 1H), 7.41 (s, 1H), 7.16 (d, J=8.4 Hz, 1H), 6.91 (dd, J=20.8, 10.3 Hz, 2H), 4.61-4.54 (m, 4H), 3.55-3.50 (m, 2H), 2.66-2.51 (m, 4H), 1.06 (t, J=7.5 Hz, 3H).

217

Example 54: N-cyclopropyl-2-(6-(2-ethyl-5-fluoro-4-hydroxyphenyl)-1H-indazol-3-yl)-4,6-dihydropyrrolo[3,4-d]imidazol-5(1H)-carboxamide (MDI-259)

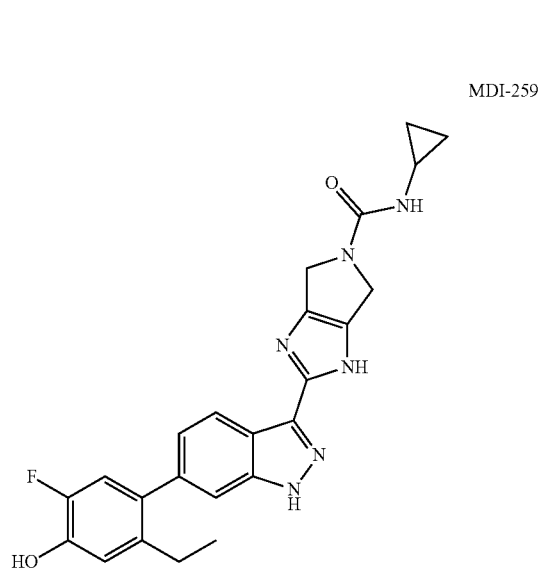 [SMILES: CCc1cc(O)c(F)cc1-c1ccc2c(-c3nc4c([nH]3)CN(C(=O)NC3CC3)C4)n[nH]c2c1]

MDI-259

Synthetic Route of MDI-259:

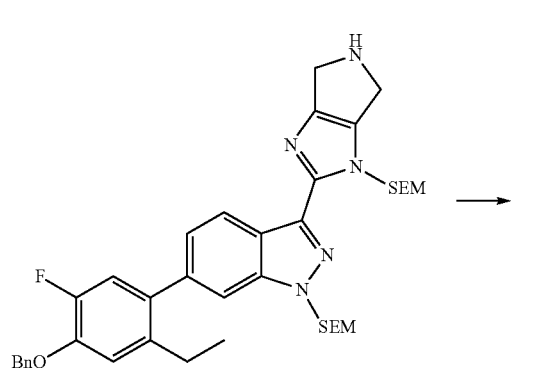

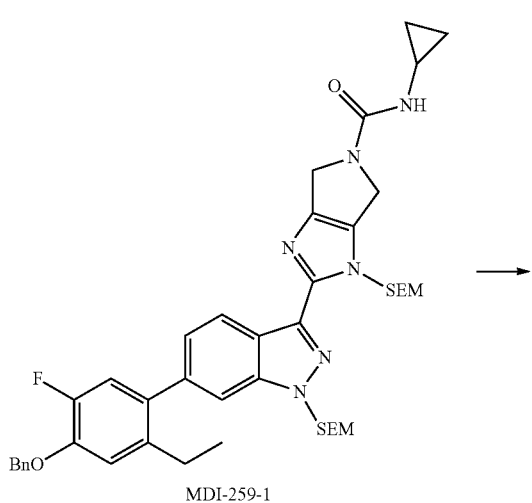

MDI-259-1

218

-continued

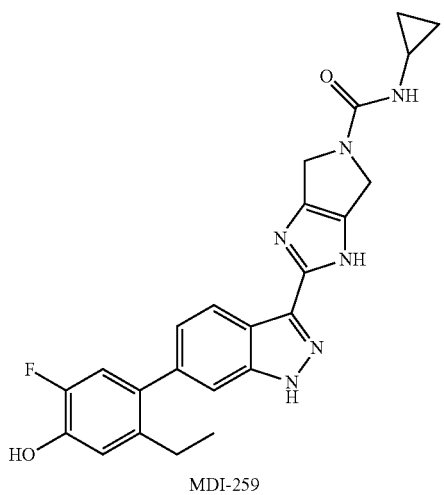

MDI-259

Synthesis Method

Synthesis of Intermediate MDI-259-1: 2-(6-(4-(benzyloxy)-2-ethyl-5-fluorophenyl)-1-((2-(trimethylsilyl)ethoxy)methyl)-1H-indazol-3-yl)-N-cyclopropyl-1-(((2-(trimethylsilyl)ethoxy)methyl)-4,6-dihydropyrrolo[3,4-d]imidazol-5(1H)-carboxamide The synthesis process was similar to that of the intermediate MDI-246-1 with the exception that cyclopropylamine was used instead of methylamine hydrochloride.

Synthesis of Compound MDI-259: N-cyclopropyl-2-(6-(2-ethyl-5-fluoro-4-hydroxyphenyl)-1H-indazol-3-yl)-4,6-dihydropyrrolo[3,4-d]imidazol-5(1H)-carboxamide Intermediate MDI-259-1 (36 mg, 0.04 mmol) was dissolved in methanol (4 ml), and 3.6 mg 10% Pd/C was added. The atmosphere was replaced with hydrogen 3 times. The mixture was heated to 40° C., reacted for 1 hour, filtered, and concentrated. The concentrated product was dissolved in 4 ml of methanol to which 2 ml of concentrated hydrochloric acid was added. The mixture was heated to 60° C., reacted for 6 hours, and concentrated. The solid was dissolved in methanol, which was adjusted with aqueous ammonia to pH=8-9. The resulting mixture was concentrated and purified by a preparation plate to afford 8.0 mg of the final product with a yield of 39.6%.

$^1$H NMR (400 MHz, MeOD) δ 8.25 (d, J=8.4 Hz, 1H), 7.43 (s, 1H), 7.16 (dd, J=8.4, 1.4 Hz, 1H), 6.91 (dd, J=20.6, 10.4 Hz, 2H), 4.66-4.48 (m, 4H), 2.68-2.62 (m, 1H), 2.59-2.53 (m, 2H), 1.08 (t, J=7.5 Hz, 3H), 0.76-0.71 (m, 2H), 0.60-0.56 (m, 2H).

Example 55: N-cyclobutyl-2-(6-(2-ethyl-5-fluoro-4-hydroxyphenyl)-1H-indazol-3-yl)-4,6-dihydropyrrolo[3,4-d]imidazol-5(1H)-carboxamide (MDI-260)

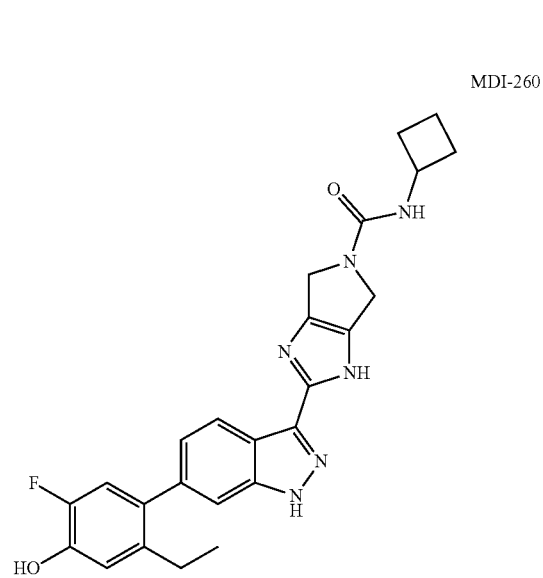 [SMILES: CCc1cc(O)c(F)cc1-c1ccc2c(-c3nc4c([nH]3)CN(C(=O)NC3CCC3)C4)n[nH]c2c1]

MDI-260

Synthetic Route of MDI-260:

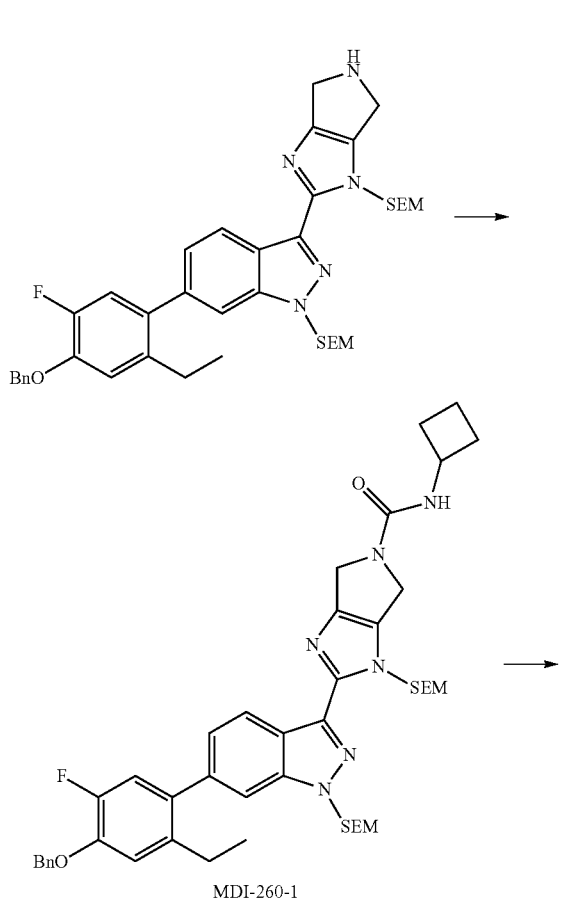

MDI-260-1

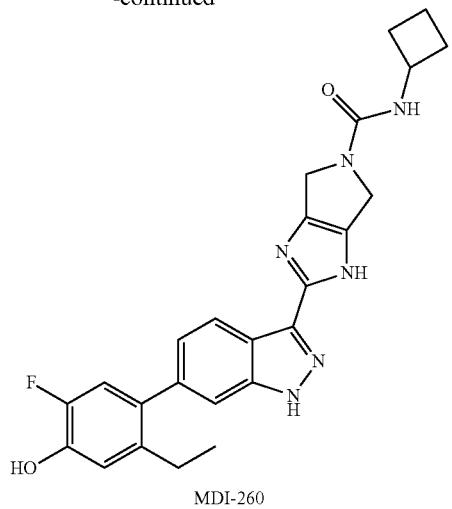

MDI-260

Synthesis Method

Synthesis of Intermediate MDI-260-1: 2-(6-(4-(benzyloxy)-2-ethyl-5-fluorophenyl)-1-((2-(trimethylsilyl)ethoxy)methyl)-1H-indazol-3-yl)-N-cyclobutyl-1-(((2-(trimethylsilyl)ethoxy)methyl)-4,6-dihydropyrrolo[3,4-d]imidazol-5(1H)-carboxamide The synthesis process was similar to that of the intermediate MDI-246-1 with the exception that cyclobutylamine was used instead of methylamine hydrochloride.

Synthesis of Compound MDI-260: N-cyclobutyl-2-(6-(2-ethyl-5-fluoro-4-hydroxyphenyl)-1H-indazol-3-yl)-4,6-dihydropyrrolo[3,4-d]imidazol-5(1H)-carboxamide Intermediate MDI-260-1 (37 mg, 0.04 mmol) was dissolved in methanol (4 ml), and 3.7 mg 10% Pd/C was added. The atmosphere was replaced with hydrogen 3 times. The mixture was heated to 40° C., reacted for 1 hour, filtered, and concentrated. The concentrated product was dissolved in 4 ml of methanol to which 2 ml of concentrated hydrochloric acid was added. The mixture was heated to 60° C., reacted for 6 hours, and concentrated. The solid was dissolved in methanol, which was adjusted with aqueous ammonia to pH=8-9. The resulting mixture was concentrated and purified by a preparation plate to afford 4.0 mg of the final product with a yield of 19.0%.

$^1$H NMR (400 MHz, MeOD) δ 8.27 (d, J=8.4 Hz, 1H), 7.43 (s, 1H), 7.18 (d, J=8.4 Hz, 1H), 7.01-6.85 (m, 2H), 4.57 (s, 4H), 4.35-4.31 (m, 1H), 2.59-2.53 (m, 2H), 2.36-2.30 (m, 2H), 2.11-2.04 (m, 2H), 1.76-1.69 (m, 2H), 1.08 (t, J=7.5 Hz, 3H).

Example 56: (2-(6-(2-ethyl-5-fluoro-4-hydroxyphenyl)-1H-indazol-3-yl)-4,6-dihydropyrrolo[3,4-d]imidazol-5(1H)-yl)(2,6-diazaspiro[3.3]heptan-2-yl)ketone (MDI-261)
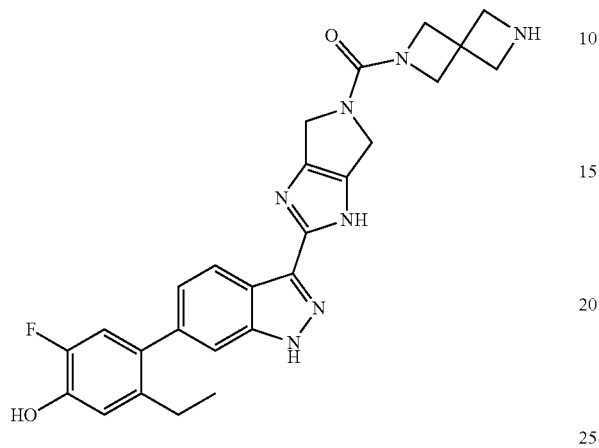
Synthetic Route of MDI-261:
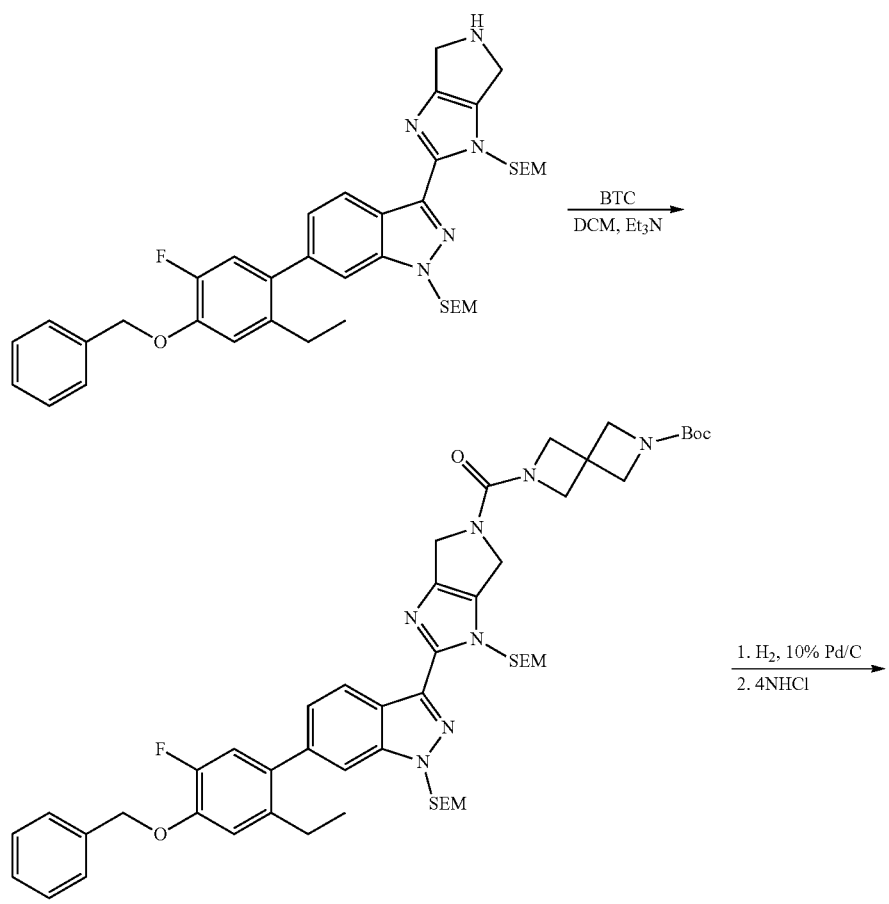

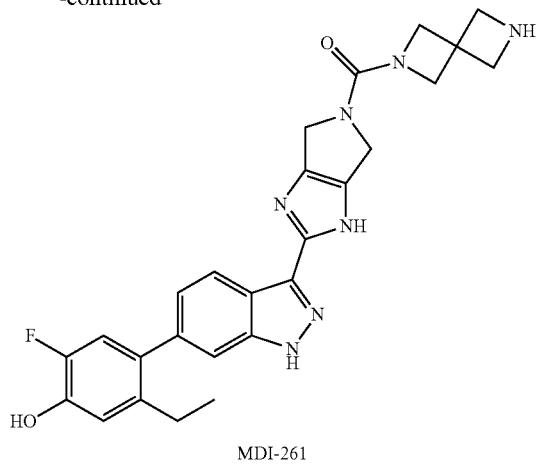

MDI-261

Synthesis Method

Synthesis of Intermediate MDI-261-1: Tert-butyl 6-(2-(6-(4-(benzyloxy)-2-ethyl-5-fluorophenyl)-1-((2-(trimethylsilyl)ethoxy)methyl)-1H-indazol-3-yl)-1-((2-(trimethylsilyl)ethoxy)methyl)-1,4,5,6-tetrahydropyrrolo[3,4-d]imidazol-5-carbonyl)-2,6-diazaspiro[3.3]heptane-2-carboxylate The synthesis process was similar to that of the intermediate MDI-246-1 with the exception that tert-butyl 2,6-diazaspiro[3.3]heptane-2-carboxylate oxalate was used instead of methylamine hydrochloride.

Synthesis of Compound MDI-261: (2-(6-(2-ethyl-5-fluoro-4-hydroxyphenyl)-1H-indazol-3-yl)-4,6-dihydropyrrolo[3,4-d]imidazol-5(1H)-yl)(2,6-diazaspiro[3.3]heptan-2-yl)ketone Intermediate MDI-261-1 (52 mg, 0.06 mmol) was dissolved in methanol (6 ml), and 10.1 mg 10% Pd/C was added. The atmosphere was replaced with hydrogen, which was repeated 3 times. The mixture was heated to 40° C., reacted for 1 hour, filtered, and concentrated, followed by addition of 4 ml of methanol and 1 ml of concentrated hydrochloric acid. The mixture was heated to 50° C., reacted for 6 hours, and concentrated to give a residue. The residue was dissolved in methanol, and was concentrated to dryness, which was repeated 3 times. The resulting residue was dissolved in methanol, to which 1 ml of ammonia was added to neutralize. The resulting mixture was concentrated and purified by a preparation plate to afford 6 mg of the final product with a yield of 22.2%.

$^1$H NMR (400 MHz, MeOD) δ 8.28 (d, J=8.0 Hz, 1H), 7.45 (s, 1H), 7.19 (d, J=8.0 Hz, 1H), 6.95 (dd, J=12.0 Hz, J=12.0 Hz, 2H), 4.90 (s, 2H), 4.66 (s, 2H), 4.22 (d, J=12.0 Hz, 2H), 4.02-3.94 (m, 4H), 3.60 (d, J=4.0 Hz, 2H), 2.59-2.54 (m, 2H), 1.09 (t, J=8.0 Hz, 3H).

Example 57: (S)-6-(2-ethyl-5-fluoro-4-hydroxyphenyl)-3-(5-prolyl-1,4,5,6-tetrahydropyrrolo[3,4-d]imidazol-2-yl)-1H-indazol (MDI-262)

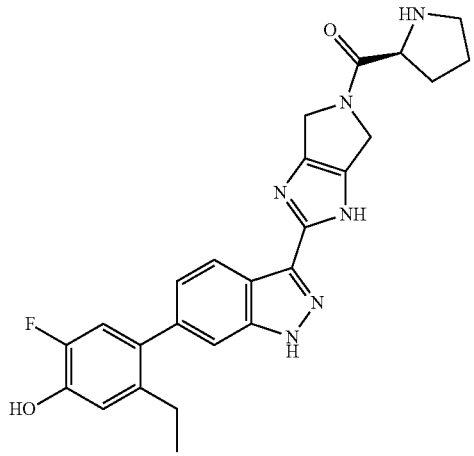

MDI-262

Synthetic Route of MDI-262:

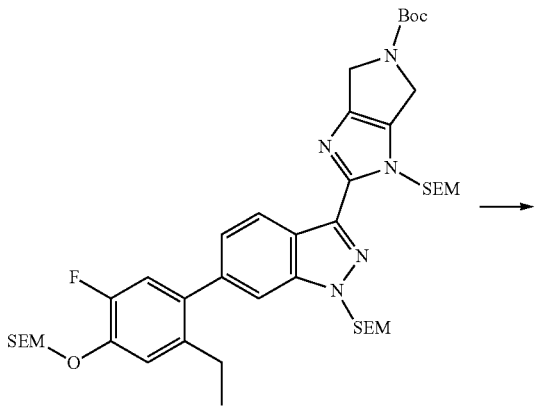

-continued

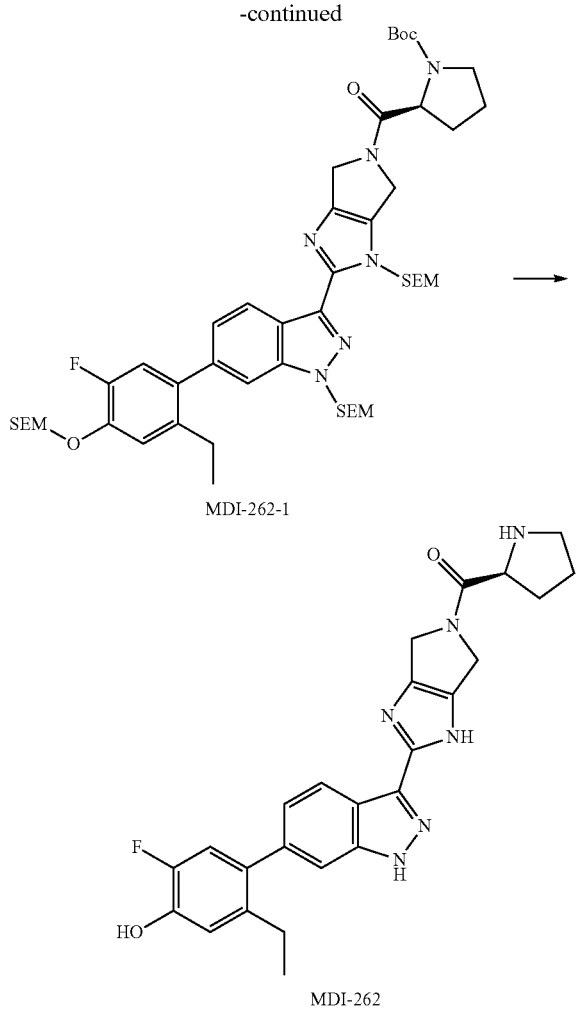

MDI-262-1

MDI-262

Synthesis Method

Synthesis of Intermediate MDI-262-1: Tert-butyl (S)-2-(2-(6-(2-ethyl-5-fluoro-4-((2-(trimethylsilyl) ethoxy)methoxy)phenyl)-1-((2-(trimethylsilyl) ethoxy) methyl)-1H-indazol-3-yl)-1-((2-(trimethylsilyl)ethoxy)methyl)-1,4,5,6-tetrahydropyrrolo[3,4-d] imidazol-5-carbonyl)pyrrolidin-1-carboxylate Tert-butyl 2-(6-(2-ethyl-5-fluoro-4-((2-(trimethylsilyl)ethoxy)methoxy) phenyl)1-((2-(trimethylsilyl)ethoxy) methyl)-1H-indazol-3-yl)-1-((2-(trimethylsilyl)ethoxy) methyl)-4,6-dihydropyrrolo[3,4-d]imidazol-5(1H)-carboxylate (65.0 mg, 0.08 mmol) was dissolved in 10 ml DCM, to which zinc bromide (68.6 mg, 0.31 mmol) was added. The mixture was stirred for 5 hours, and water was added to quench the reaction. The resulting mixture was extracted with DCM twice, and the organic phases were combined, washed with aqueous ammonia, then washed with water and saturated brine, dried over anhydrous sodium sulfate, and concentrated. The obtained crude product was dissolved in 10 ml DMF, to which Boc-L-proline (19.7 mg, 0.09 mmol), HATU (34.71 mg, 0.09 mmol), and DIPEA (11.8 mg, 0.09 mmol) were added. After the addition, it was allowed to react at room temperature. Water was added to quench the reaction. The resulting mixture was extracted twice with ethyl acetate, and the organic phases were combined, washed with water and saturated brine, dried over anhydrous sodium sulfate and concentrated to afford 43.0 mg of intermediate MDI-262-1 with a yield of 59.4%.

$^1$H NMR (400 MHz, CDCl3) δ 8.50-8.41 (m, 1H), 7.47-7.45 (m, 1H), 7.25-7.22 (m, 1H), 7.16 (d, J=8.0 Hz, 1H), 7.01 (d, J=10.3 Hz, 1H), 6.05-5.87 (m, 2H), 5.76-5.75 (m, 2H), 5.31 (s, 2H), 5.02-4.23 (m, 5H), 3.89-3.83 (m, 2H), 3.70-3.42 (m, 6H), 2.57-2.51 (m, 2H), 2.37-1.88 (m, 3H), 1.73-1.70 (m, 1H), 1.47 (s, 9H), 1.07-0.98 (m, 5H), 0.94-0.88 (m, 4H), 0.03 (s, 9H), −0.06-0.08 (m, 18H).

Synthesis of Compound MDI-262: (S)-6-(2-ethyl-5-fluoro-4-hydroxyphenyl)-3-(5-prolyl-1,4,5,6-tetrahydropyrrolo[3,4-d]imidazol-2-yl)-1H-indazole The intermediate MDI-262-1 (33.0 mg, 0.04 mmol) was dissolved in 4 ml MeOH, to which 2 ml concentrated hydrochloric acid was added. After the addition, the temperature was raised to 50° C. for reaction. After 6 hours of reaction, the temperature was reduced to room temperature, and the reaction solvent was evaporated by concentration under reduced pressure, followed by addition of 4 ml methanol and 0.5 ml aqueous ammonia. After concentration, the residue was subject to thin layer chromatography to afford 1.8 mg of white solid MDI-262 with a yield of 11.3%.

$^1$H NMR (400 MHz, MeOD) δ 8.28 (d, J=8.0 Hz, 1H), 7.44 (s, 1H), 7.18 (d, J=8.5 Hz, 1H), 6.96 (d, J=11.7 Hz, 1H), 6.91 (d, J=8.9 Hz, 1H), 4.80-4.64 (m, 4H), 4.09-4.05 (m, 1H), 3.26-3.22 (m, 2H), 2.59-2.53 (m, 2H), 2.06-1.86 (m, 4H), 1.08 (t, J=8.0 Hz, 3H). LC-MS m/z (ESI) [M+H]$^+$ calculated value for $C_{25}H_{26}FN_6O_2$: 461.2; measured value: 461.2.

Example 58: (R)-6-(2-ethyl-5-fluoro-4-hydroxyphenyl)-3-(5-prolyl-1,4,5,6-tetrahydropyrrolo[3,4-d] imidazol-2-yl)-1H-indazol (MDI-263)

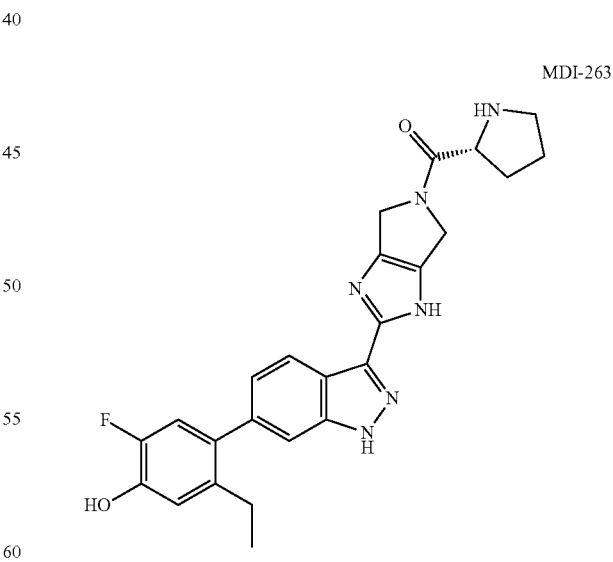

MDI-263

The synthesis process was similar to that of MDI-262, with the exception that Boc-D-proline was used instead of Boc-L-proline.

$^1$H NMR (400 MHz, MeOD) δ 8.27 (d, J=8.0 Hz, 1H), 7.44 (s, 1H), 7.18 (d, J=8.4 Hz, 1H), 6.96 (d, J=12.2 Hz, 1H), 6.91 (d, J=8.8 Hz, 1H), 4.82-4.60 (m, 4H), 4.21-4.15 (m,

1H), 3.33-3.23 (m, 1H), 3.08-2.99 (m, 1H), 2.59-2.53 (m, 2H), 2.08-1.86 (m, 4H), 1.08 (t, J=8.0 Hz, 3H).

Example 59: Evaluation I of Pharmacological Activity

1. Experimental Principle

A drug screening system based on kinases JAK1, JAK2, JAK3, and TYK2 was used to detect the inhibitory ability of small molecule compounds on kinase activity. A kinase undergoes an enzymatic reaction with its substrates IRS1, IGF1Rtide, and Poly (4:1 Glu, Tyr), consuming ATP to produce ADP, wherein the ADP-Glo reagent and luminescence method can be used to detect the amount of the product to reflect the activity of the kinase.

2. Experimental Scheme 2.1 Experimental Materials and Instruments

| Item | Name | Source/Supplier | Catalogue No. |
|---|---|---|---|
| 1 | HEPES | Life Technologies | 15630-080 |
| 2 | BRIJ 35 detergent (10%) | Merck | 203728 |
| 3 | MgCl2 | Sigma | M1028 |
| 4 | EGTA | Sigma | E3889 |
| 5 | ADP-Glo Kinase Assay | Promega | V9101 |
| 6 | JAK1 | Invitrogen | PV4774 |
| 7 | JAK2 | Invitrogen | PV4210 |
| 8 | JAK3 | Invitrogen | PV3855 |
| 9 | TYK2 | Invitrogen | PV4790 |
| 10 | ATP | Promega | V915B |
| 11 | IRS1 | Signalchem | I40-58-1000 |
| 12 | IGF1Rtide | Signalchem | I15-58 |
| 13 | Poly (4:1 Glu, Tyr) | Sigma | P0275 |
| 14 | Topseal A | PerkinElmer | E5341 |
| 15 | OptiPlate-384 | PerkinElmer | 6007290 |
| 16 | 384-Well Polypropylene microplate | Labcyte | PP-0200 |
| 17 | Envision | Perkin Elmer | 2104 |
| 18 | Echo | Labcyte | 550 |
| 19 | Centrifuge | Eppendorf | 5810R |

2.2 Experimental Methods 2.2.1 Kinase Reaction Reagent Formulation 2.2.1.1 1× Kinase Reaction Buffer (400 mL)

| Name | Stock Concentration | Volume | Final Concentration |
|---|---|---|---|
| HEPES | 1M (20X) | 20 mL | 50 mM |
| MgCl2 | 1M (100X) | 4 mL | 10 mM |
| BRIJ-35 | 10%(1000X) | 400 µL | 0.01% |
| EGTA | Powder | 152 mg | 1 mM |
| ddH2O | | 375.6 mL | |

2 mM DTT, ready to use 2.2.1.2 2× Kinase Formulation

| Name | Stock concentration | Volume | 2X Final Concentration | Final Concentration |
|---|---|---|---|---|
| JAK1 | 7072.4 nM (884X) | 0.8 µL | 8 nM | 4 nM |
| 1X Kinase Reaction Buffer | | 706.5 µL | | |

JAK2 kinase solution

| Name | Stock concentration | Volume | 2X Final Concentration | Final Concentration |
|---|---|---|---|---|
| JAK2 | 4955 nM (4955X) | 0.2 µL | 1 nM | 0.5 nM |
| 1X Kinase Reaction Buffer | | 990.8 µL | | |

JAK3 kinase solution

| Name | Stock concentration | Volume | 2X Final Concentration | Final Concentration |
|---|---|---|---|---|
| JAK3 | 5341.2 nM (5341.2X) | 0.2 µL | 1 nM | 0.5 nM |
| 1X Kinase Reaction Buffer | | 1068 µL | | |

TYK2 kinase solution

| Name | Stock concentration | Volume | 2X Final Concentration | Final Concentration |
|---|---|---|---|---|
| TYK2 | 6104.7 nM (763X) | 1 µL | 8 nM | 4 nM |
| 1X Kinase Reaction Buffer | | 762 µL | | |

2.2.1.3 2× Substrate Mixture Formulation

JAK1 substrate mixture solution

| Name | Stock concentration | Volume | 2X Final Concentration | Final Concentration |
|---|---|---|---|---|
| ATP | 10 mM (250X) | 2.8 µL | 40 µM | 20 µM |
| IRS1 | 1 mg/mL(10X) | 70 µL | 0.1 mg/mL | 0.05 mg/mL |
| 1X Kinase Reaction Buffer | | 627.2 µL | | |

JAK2 substrate mixture solution

| Name | Stock concentration | Volume | 2X Final Concentration | Final Concentration |
|---|---|---|---|---|
| ATP | 10 mM (500X) | 1.4 µL | 20 µM | 10 µM |
| IGF1Rtide | 1 mg/mL (50X) | 14 µL | 0.02 mg/mL | 0.01 mg/mL |
| 1X Kinase Reaction Buffer | | 684.6 µL | | |

| JAK3 substrate mixture solution | | | | |
|---|---|---|---|---|
| Name | Stock concentration | Volume | 2X Final Concentration | Final Concentration |
| ATP | 10 mM (500X) | 1.4 μL | 20 μM | 10 μM |
| Poly (4:1 Glu, Tyr) Peptide | 5 mg/mL (83.3X) | 8.4 μL | 0.06 mg/mL | 0.03 mg/mL |
| 1X Kinase Reaction Buffer | | 690.2 μL | | |

| TYK2 substrate mixture solution | | | | |
|---|---|---|---|---|
| Name | Stock concentration | Volume | 2X Final Concentration | Final Concentration |
| ATP | 10 mM (500X) | 1.4 μL | 20 μM | 10 μM |
| IRS1 | 1 mg/mL (16.67X) | 42 μL | 0.06 mg/mL | 0.03 mg/mL |
| 1X Kinase Reaction Buffer | | 656.6 μL | | |

2.2.1.4 Compounds to be Tested

| Name | Mass/mg | Molecular weight | Concentration/mM |
|---|---|---|---|
| Filgotinib | 5.0 | 420.5 | 10 |
| MDI-2 | 3.3 | 552.24 | 10 |
| MDI-201 | 2.0 | 554.59 | 10 |
| MDI-202 | 1.9 | 471.50 | 10 |
| MDI-206 | 2.0 | 503.55 | 10 |
| MDI-203 | 1.8 | 488.57 | 10 |
| MDI-204 | 2.1 | 567.63 | 10 |
| MDI-205 | 1.9 | 549.64 | 10 |
| MDI-207 | 1.5 | 455.50 | 10 |
| MDI-209 | 1.9 | 431.47 | 10 |
| MDI-211 | 1.6 | 445.50 | 10 |
| MDI-213 | 1.5 | 461.50 | 10 |
| MDI-217 | 1.6 | 461.54 | 10 |

2.2.2 Kinase Reaction Experiment Procedure 2.2.2.1 JAK1 & JAK2 Kinase Reaction Experimental Procedure a) Dilute Filgotinib (10 mM stock solution) by 10 times, and dilute a compound solution to be tested by 10 times with 100% DMSO, and then perform a series of dilutions at a ratio of 1:3 in a 384-well dilution plate (Labcyte, PP-0200). Concentrations of Filgotinib: 1000, 333.33, 111.11, 37.04, 12.35, 4.12, 1.37, 0.46, 0.15, 0.05, 0.02, and 0 μM; and concentrations of the compound to be tested: 1000, 333.33, 111.11, 37.04, 12.35, 4.12, 1.37, 0.46, 0.15, 0.05, and 0 μM.

b) Use Echo to transfer 0.1 μL of the compound solution to be tested (prepared in step a) to a 384-well reaction plate (PE, 6007290), and centrifuge it at 1000 rpm/min for 1 min.

c) Transfer 5 μL of kinase (prepared according to 2.2.1.2) to the 384-well reaction plate (prepared in step b), centrifuge it at 1000 rpm/min for 1 min, and incubate it at 25° C. for 15 min.

d) Transfer 5 μL of the substrate mixture (prepared according to 2.2.1.3) to the 384-well reaction plate, centrifuge it at 1000 rpm/min for 1 min, and incubate it at 25° C. for 60 min. In the reaction system, the final concentrations of Filgotinib are 10, 3.33, 1.11, 0.37, 0.12, 0.04, 0.014, 0.0046, 0.0015, 0.0005, and 0 μM. The final concentrations of the compound to be tested are: 10, 3.33, 1.11, 0.37, 0.12, 0.04, 0.014, 0.0046, 0.0015, 0.0005, and 0 μM. The final concentration of DMSO is 1%.

e) Transfer 10 μL of ADP-Glo to the 384-well reaction plate, centrifuge it at 1000 rpm/min for 1 min, and incubate it at 25° C. for 40 min.

f) Transfer 20 μL of Detection solution to the 384-well reaction plate, centrifuge it at 1000 rpm/min for 1 min, and incubate it at 25° C. for 40 min.

g) Use Envision multi-function plate reader to read the RLU (Relative luminescence unit) signal. The signal intensity is used to characterize the degree of kinase activity.

2.2.2.2 JAK3 Kinase Reaction Experimental Procedure a) Dilute Filgotinib (10 mM stock solution) and a compound solution to be tested by 10 times with 100% DMSO, and then perform a series of dilutions at a ratio of 1:3 in a 384-well dilution plate (Labcyte, PP-0200). Filgotinib concentrations are: 10000, 3333.33, 1111.11, 370.37, 123.46, 41.15, 13.72, 4.57, 1.52, 0.51, 0.17, and 0 μM; and concentrations of the compound to be tested are: 1000, 333.33, 111.11, 37.04, 12.35, 4.12, 1.37, 0.46, 0.15, 0.05, and 0 μM.

b) Use Echo to transfer 0.1 μL of the compound solution to be tested (prepared in step a) to a 384-well reaction plate (PE, 6007290), and centrifuge it at 1000 rpm/min for 1 min.

c) Transfer 5 μL of kinase (prepared according to 2.2.1.2) to the 384-well reaction plate (prepared in step b), centrifuge it at 1000 rpm/min for 1 min, and incubate it at 25° C. for 15 min.

d) Transfer 5 μL of the substrate mixture (prepared according to 2.2.1.3) to the 384-well reaction plate, centrifuge it at 1000 rpm/min for 1 min, and incubate it at 25° C. for 60 min. In the reaction system, the final concentrations of Filgotinib are 100, 33.33, 11.11, 3.70, 1.23, 0.412, 0.137, 0.046, 0.015, 0.005, 0.002, and 0 μM. The final concentrations of the compound to be tested are: 10, 3.33, 1.11, 0.37, 0.12, 0.04, 0.014, 0.0046, 0.0015, 0.0005, and 0 μM. The final concentration of DMSO is 1%.

e) Transfer 10 μLADP-Glo to the 384-well reaction plate, centrifuge it at 1000 rpm/min for 1 min, and incubate it at 25° C. for 40 min.

f) Transfer 20 μL of Detection solution to the 384-well reaction plate, centrifuge it at 1000 rpm/min for 1 min, and incubate it at 25° C. for 40 min.

g) Use Envision multi-function plate reader to read the RLU (Relative luminescence unit) signal. The signal intensity is used to characterize the degree of kinase activity.

2.2.2.3 TYK2 Kinase Reaction Experimental Procedure a) Dilute Filgotinib (10 mM stock solution) by 3.3 times, and a compound solution to be tested by 10 times with 100% DMSO, and then perform a series of dilutions at a ratio of 1:3 in a 384-well dilution plate (Labcyte, PP-0200). The concentrations of Filgotinib are: 3000, 1000, 333.33, 111.11, 37.04, 12.35, 4.12, 1.37, 0.46, 0.15, 0.05, and 0 μM; and the concentrations of the compound to be tested are: 1000, 333.33, 111.11, 37.04, 12.35, 4.12, 1.37, 0.46, 0.15, 0.05, and 0 μM.

b) Use Echo to transfer 0.1 μL of the compound solution to be tested (prepared in step a) to a 384-well reaction plate (PE, 6007290), and centrifuge it at 1000 rpm/min for 1 min.

c) Transfer 5 μL of kinase (prepared according to 2.2.1.2) to the 384-well reaction plate (prepared in step b), centrifuge it at 1000 rpm/min for 1 min, and incubate it at 25° C. for 15 min.

d) Transfer 5 μL of the substrate mixture (prepared according to 2.2.1.3) to the 384-well reaction plate, centrifuge it at 1000 rpm/min for 1 min, and incubate it at 25° C.

for 60 min. In the reaction system, the final concentrations of Filgotinib are 30, 10, 3.3333, 1.1111, 0.3704, 0.1235, 0.0412, 0.0137, 0.0046, 0.0015, 0.0005, and 0 μM. The final concentrations of the compound to be tested are: 10, 3.33, 1.11, 0.37, 0.12, 0.04, 0.014, 0.0046, 0.0015, 0.0005, and 0 μM. The final concentration of DMSO is 1%.

e) Transfer 10 μL of ADP-Glo to the 384-well reaction plate, centrifuge it at 1000 rpm/min for 1 min, and incubate it at 25° C. for 40 min.

f) Transfer 20 μL of Detection solution to the 384-well reaction plate, centrifuge it at 1000 rpm/min for 1 min, and incubate it at 25° C. for 40 min.

g) Use Envision multi-function plate reader to read the RLU (Relative luminescence unit) signal. The signal intensity is used to characterize the degree of kinase activity.

2.2.3 Experimental Data Processing Method

Compound inhibition rate (% inh)=(negative control−compound)/(negative control−positive control)*100%

Negative control: DMSO
Positive control: 10 μM/100 μM/30 μM Filgotinib
IC50 (half inhibitory concentration) of the compound can be obtained using the following nonlinear fitting formula:

$$Y=\text{Bottom}+(\text{Top}-\text{Bottom})/(1+10^{((\text{Log IC50}-X)*\text{HillSlope})})$$

X: log value of the compound concentration
Y: Compound inhibition rate (% inh)
Z' factor calculation equation:

$$Z'=1-3(\text{SDmin}+\text{SDmax})/(\text{AVEmax}-\text{AVEmin})$$

in which:
Min is the RLU value of the positive control 10 μM/100 μM/30 μM Filgotinib, and Max is the RLU value of the negative control; and
SD is the standard error, and AVE is the average value of RLU.

3. Experimental Results 3.1 Quality Control Results of Binding Experiment 3.1.1 Quality Control Result of JAK1 Binding Experiment Z'=0.77CV % (min)=0% CV % (max)=6.2%

3.1.2 Quality Control Result of JAK2 Binding Experiment

Z'=0.78CV % (min)=2.9% CV % (max)=5.7%

3.1.3 Quality Control Result of JAK3 Binding Experiment

Z'=0.71CV % (min)=7.0% CV % (max)=11.3%

3.1.4 Quality Control Result of TYK2 Binding Experiment

Z'=0.77CV % (min)=3.9% CV % (max)=6.8%

3.2 Summary of Test Results as Obtained

| Item | Tested compound | Hillslope | IC50 (nM) |
|---|---|---|---|
| JAK1 Experiment | Filgotinib | 1.067 | 25.550 |
|  | MDI-2 | 1.356 | 0.8056 |
|  | MDI-201 | 3.487 | 0.138 |
|  | MDI-202 | 5.052 | 0.125 |
|  | MDI-206 | 1.091 | 0.943 |
| JAK2 Experiment | Filgotinib | 1.142 | 67.920 |
|  | MDI-2 | 1.271 | 0.7723 |
|  | MDI-201 | 1.633 | 0.217 |
|  | MDI-202 | 2.385 | 0.279 |
|  | MDI-206 | 1.457 | 0.556 |
| JAK3 Experiment | Filgotinib | 1.318 | 1343 |
|  | MDI-2 | 1.569 | 0.7649 |
|  | MDI-201 | 1.989 | 0.187 |
|  | MDI-202 | 2.038 | 0.160 |
|  | MDI-206 | 1.216 | 0.628 |
| TYK2 Experiment | Filgotinib | 1.037 | 128.0 |
|  | MDI-2 |  | 1.630 |
|  | MDI-201 | 1.411 | 0.281 |
|  | MDI-202 | 1.416 | 0.318 |
|  | MDI-206 | 0.744 | 7.229 |

For brevity, only IC50 values are shown for the below tested compounds.

| Item | Tested compound | IC50 (nM) |
|---|---|---|
| JAK1 Experiment | Filgotinib | 25.550 |
|  | MDI-203 | 0.160 |
|  | MDI-204 | 0.152 |
|  | MDI-205 | 0.121 |
|  | MDI-207 | 0.120 |
|  | MDI-209 | 0.128 |
|  | MDI-211 | 0.162 |
|  | MDI-213 | 0.146 |
|  | MDI-217 | 0.122 |
| JAK2 Experiment | Filgotinib | 67.920 |
|  | MDI-203 | 0.208 |
|  | MDI-204 | 0.176 |
|  | MDI-205 | 0.158 |
|  | MDI-207 | 0.160 |
|  | MDI-209 | 0.165 |
|  | MDI-211 | 0.198 |
|  | MDI-213 | 0.166 |
|  | MDI-217 | 0.217 |
| JAK3 Experiment | Filgotinib | 1343 |
|  | MDI-203 | 0.212 |
|  | MDI-204 | 0.238 |
|  | MDI-205 | 0.178 |
|  | MDI-207 | 0.132 |
|  | MDI-209 | 0.158 |
|  | MDI-211 | 0.160 |
|  | MDI-213 | 0.116 |
|  | MDI-217 | 0.137 |
| TYK2 Experiment | Filgotinib | 128.0 |
|  | MDI-203 | 0.328 |
|  | MDI-204 | 0.200 |
|  | MDI-205 | 0.194 |
|  | MDI-207 | 0.474 |
|  | MDI-209 | 0.281 |
|  | MDI-211 | 0.266 |
|  | MDI-213 | 0.146 |
|  | MDI-217 | 0.391 |

The above experimental results demonstrate that: MDI-2, MDI-201, MDI-202, MDI-206, MDI-203, MDI-204, MDI-207, MDI-209, MDI-211, MDI-213, and MDI-217 can inhibit JAK1, JAK2, JAK3, and TYK2 at an extremely low concentration, and the inhibitory activities of the compounds in these examples are much higher than that of Filgotinib.

Example 60: Evaluation II of Pharmacological Activity

1. Experimental Principle

The experimental principle of the pharmacological activity evaluation in this example is the same as that described in Example 59, but the experimental materials or instruments as used, and/or some specific test condition parameters (such as the kinase formulation, substrate formulation, kinase reaction experiment procedures, and the like) were varied and adjusted.

2. Experimental Scheme
2.1 Experimental Materials and Instruments

| No. | Name | Source/Supplier | Catalogue No. |
|---|---|---|---|
| 1 | HEPES | Life Technologies | 15630-080 |
| 2 | BRIJ 35 detergent (10%) | Sigma | 1018940100 |
| 3 | MgCl2 | Sigma | M1028 |
| 4 | EGTA | Sigma | E3889 |
| 5 | ADP-Glo Kinase Assay | Promega | V9101 |
| 6 | JAK1 | Carna | 08-144 |
| 7 | JAK2 | Carna | 08-045 |
| 8 | JAK3 | Carna | 08-046 |
| 9 | TYK2 | Carna | 08-147 |
| 10 | ATP | Promega | V915B |
| 11 | IRS1 | Signalchem | I40-58-1000 |
| 12 | IGF1Rtide | Signalchem | I15-58 |
| 13 | Poly (4:1 Glu, Tyr) | Sigma | P0275 |
| 15 | 384-Well polystyrene shallow flat white | Greiner | 784075 |
| 16 | 384-Well Polypropylene microplate | Labcyte | PP-0200 |
| 17 | Biotek Microplate Reader | Biotek | Synergy 4 |
| 18 | Microplate Low Speed Centrifuge | XiangZhi | TD5B |

2.2 Experimental Methods
2.2.1 Kinase Reaction Reagent Formulation
2.2.1.1 1× Kinase Reaction Buffer (400 mL)

It was the same as the formulation of the 1× kinase reaction buffer in Example 59.

2.2.1.2 2× Kinase Formulation

| JAK1 kinase solution ||||| 
|---|---|---|---|---|
| Name | Stock concentration | Volume | 2X Final Concentration | Final Concentration |
| JAK1 | 3225 nM (884X) | 5.21 μL | 40 nM | 20 nM |
| 1X Kinase Reaction Buffer | | 414.79 μL | | |

| JAK2 kinase solution ||||| 
|---|---|---|---|---|
| Name | Stock concentration | Volume | 2X Final Concentration | Final Concentration |
| JAK2 | 4256 nM (4955X) | 0.2 μL | 2 nM | 1 nM |
| 1X Kinase Reaction Buffer | | 419.8 μL | | |

| JAK3 kinase solution ||||| 
|---|---|---|---|---|
| Name | Stock concentration | Volume | 2X Final Concentration | Final Concentration |
| JAK3 | 3195 nM (5341.2X) | 0.5 μL | 4 nM | 2 nM |
| 1X Kinase Reaction Buffer | | 419.5 μL | | |

| TYK2 kinase solution ||||| 
|---|---|---|---|---|
| Name | Stock concentration | Volume | 2X Final Concentration | Final Concentration |
| TYK2 | 3174 nM (763X) | 2.65 μL | 20 nM | 10 nM |
| 1X Kinase Reaction Buffer | | 417.35 μL | | |

2.2.1.3 4× Substrate Mixture Formulation

| JAK1 substrate mixture solution ||||| 
|---|---|---|---|---|
| Name | Stock concentration | Volume | 4X Final Concentration | Final Concentration |
| ATP | 10 mM (125X) | 2.4 μL | 80 μM | 20 μM |
| IRS1 | 1 mg/mL (5X) | 60 μL | 0.2 mg/mL | 0.05 mg/mL |
| 1X Kinase Reaction Buffer | | 237.6 μL | | |

| JAK2 substrate mixture solution ||||| 
|---|---|---|---|---|
| Name | Stock concentration | Volume | 4X Final Concentration | Final Concentration |
| ATP | 10 mM (500X) | 6 μL | 20 μM | 5 μM |
| IGF1Rtide | 1 mg/mL (25X) | 12 μL | 0.04 mg/mL | 0.01 mg/mL |
| 1X Kinase Reaction Buffer | | 287.4 μL | | |

| JAK3 substrate mixture solution ||||| 
|---|---|---|---|---|
| Name | Stock concentration | Volume | 4X Final Concentration | Final Concentration |
| ATP | 10 mM (250X) | 1.2 μL | 40 μM | 10 μM |
| Poly (4:1 Glu, Tyr) Peptide | 5 mg/mL (41.6X) | 6 μL | 0.12 mg/mL | 0.03 mg/mL |
| 1X Kinase Reaction Buffer | | 292.8 μL | | |

| TYK2 substrate mixture solution ||||| 
|---|---|---|---|---|
| Name | Stock concentration | Volume | 4X Final Concentration | Final Concentration |
| ATP | 10 mM (250X) | 1.2 μL | 40 μM | 10 μM |
| IRS1 | 1 mg/mL (5X) | 60 μL | 0.08 mg/mL | 0.02 mg/mL |
| 1X Kinase Reaction Buffer | | 238.8 μL | | |

2.2.1.4 Compounds to be Tested

| Name | Mass/mg | Molecular weight | Concentration/mM |
|---|---|---|---|
| Filgotinib | 5.0 | 420.5 | 10 |
| MDI-208 | 1.6 | 417.49 | 10 |
| MDI-210 | 1.4 | 431.52 | 10 |
| MDI-214 | 1.5 | 469.48 | 10 |
| MDI-215 | 1.5 | 469.48 | 10 |
| MDI-218 | 1.5 | 467.52 | 10 |
| MDI-219 | 1.7 | 481.55 | 10 |
| MDI-220 | 1.5 | 495.57 | 10 |
| MDI-221 | 1.5 | 457.51 | 10 |
| MDI-224 | 1.5 | 431.52 | 10 |
| MDI-225 | 1.6 | 447.51 | 10 |
| MDI-216 | 1.5 | 476.51 | 10 |
| MDI-226 | 1.7 | 405.43 | 10 |
| MDI-227 | 1.6 | 419.46 | 10 |
| MDI-228 | 1.5 | 433.49 | 10 |
| MDI-229 | 1.5 | 445.50 | 10 |
| MDI-230 | 1.4 | 447.51 | 10 |
| MDI-233 | 1.6 | 474.54 | 10 |
| MDI-235 | 1.8 | 489.56 | 10 |
| MDI-231 | 1.5 | 460.51 | 10 |
| MDI-232 | 1.8 | 446.49 | 10 |
| MDI-234 | 1.5 | 476.51 | 10 |
| MDI-236 | 1.8 | 503.58 | 10 |
| MDI-237 | 2.3 | 432.5 | 10 |
| MDI-239 | 1.5 | 445.5 | 10 |
| MDI-240 | 1.6 | 490.5 | 10 |
| MDI-242 | 1.4 | 432.5 | 10 |
| MDI-243 | 1.7 | 476.5 | 10 |
| MDI-244 | 1.8 | 462.5 | 10 |
| MDI-245 | 1.6 | 490.5 | 10 |
| MDI-246 | 1.5 | 420.5 | 10 |
| MDI-247 | 1.8 | 434.5 | 10 |
| MDI-248 | 1.5 | 450.5 | 10 |
| MDI-249 | 1.9 | 471.5 | 10 |
| MDI-250 | 1.6 | 485.5 | 10 |
| MDI-251 | 2.1 | 476.5 | 10 |
| MDI-252 | 1.8 | 421.4 | 10 |
| MDI-253 | 1.6 | 435.5 | 10 |
| MDI-255 | 1.4 | 477.5 | 10 |
| MDI-256 | 1.4 | 430.4 | 10 |
| MDI-257 | 1.6 | 434.5 | 10 |
| MDI-258 | 1.5 | 459.5 | 10 |
| MDI-259 | 1.7 | 446.5 | 10 |
| MDI-260 | 1.7 | 460.5 | 10 |
| MDI-261 | 1.6 | 487.5 | 10 |
| MDI-262 | 1.7 | 460.5 | 10 |
| MDI-263 | 1.3 | 460.5 | 10 |

2.2.2 Kinase Reaction Experiment Procedure

2.2.2.1 JAK1 & JAK2 Kinase Reaction Experimental Procedure a) Dilute a compound solution to be tested by 5 times with 100% DMSO. Then, using 100% DMSO as diluent, perform a series of dilutions at a ratio of 1:3 for Filgotinib (10 mM stock solution) and the compound solution to be tested in a 96-well dilution plate. Take out 1 μL of the compound solution and add it to 49 μL of kinase reaction buffer, and shake the resulting mixture on a microplate shaker for 20 minutes.

b) Transfer 2 μL of kinase (prepared according to 2.2.1.2) to a 384-well reaction plate, add 1 μL of the compound solution to be tested (prepared in step a) to the 384-well reaction plate (Greiner, 784075), centrifuge it at 1000 rpm/min for 1 min and incubate it at 25° C. for 10 min.

c) Transfer 1 μL of the substrate mixture (prepared according to 2.2.1.3) to the 384-well reaction plate, centrifuge it at 1000 rpm/min for 1 min, and incubate it at 25° C. for 60 min. In the reaction system, the final concentrations of Filgotinib are 50, 12.5, 3.125, 0.7812, 0.1953, 0.0488, 0.0122, 0.003, 0.00076, 0.00019, and 0.000047 μM. The final concentrations of the compound to be tested are: 10, 2.5, 0.625, 0.15625, 0.039, 0.0097, 0.0024, 0.0006, 0.0015, 0.000038, and 0.0000095 μM. The final concentration of DMSO is 0.50.

d) Transfer 4 μL of ADP-Glo to the 384-well reaction plate, centrifuge it at 1000 rpm/min for 1 min, and incubate it at 25° C. for 40 min.

e) Transfer 8 μL of Detection solution to the 384-well reaction plate, centrifuge it at 1000 rpm/min for 1 min, and incubate it at 25° C. for 40 min.

f) Use Biotek multi-function plate reader to read the RLU (Relative luminescence unit) signal. The signal intensity is used to characterize the degree of kinase activity.

2.2.2.2 JAK3 & TYK2 Kinase Reaction Experimental Procedure a) Dilute a compound solution to be tested by 5 times with 100% DMSO. Then, using 100% DMSO as diluent, perform a series of dilutions at a ratio of 1:3 for Filgotinib (10 mM stock solution) and the compound solution to be tested in a 96-well dilution plate. Take out 1 μL of the compound solution and add it to 49 μL of kinase reaction buffer, and shake the resulting mixture on a microplate shaker for 20 minutes.

b) Transfer 2 μL of kinase (prepared according to 2.2.1.2) to a 384-well reaction plate, and add 1 μL of the compound solution to be tested (prepared in step a) to the 384-well reaction plate (Greiner, 784075), centrifuge it at 1000 rpm/min for 1 min and incubate it at 25° C. for 10 min.

c) Transfer 1 μL of the substrate mixture (prepared according to 2.2.1.3) to the 384-well reaction plate, centrifuge it at 1000 rpm/min for 1 min, and incubate it at 25° C. for 60 min. In the reaction system, the final concentrations of Filgotinib are 50, 16.67, 5.555, 1.851, 0.617, 0.205, 0.0686, 0.0228, 0.00762, and 0.0025 μM. The final concentrations of the compound to be tested are 10, 3.33, 1.11, 0.37, 0.12, 0.04, 0.014, 0.0046, 0.0015, and 0.0005 μM. The final concentration of DMSO is 0.5%.

d) Transfer 4 μL of ADP-Glo to the 384-well reaction plate, centrifuge it at 1000 rpm/min for 1 min, and incubate it at 25° C. for 40 min.

e) Transfer 8 μL of Detection solution to the 384-well reaction plate, centrifuge it at 1000 rpm/min for 1 min, and incubate it at 25° C. for 40 min.

f) Use Biotek multi-function plate reader to read the RLU (Relative luminescence unit) signal. The signal intensity is used to characterize the degree of kinase activity.

2.2.3 Experimental Data Processing Method

The same as the experimental data processing method used in Example 59.

3. Experimental Results

| Item | Tested Compound | IC50 (nM) |
|---|---|---|
| JAK1 Experiment | Filgotinib | 88 |
| | MDI-208 | 0.153 |
| | MDI-210 | 0.347 |
| | MDI-214 | 0.303 |
| | MDI-215 | 0.197 |
| | MDI-218 | 0.825 |
| | MDI-219 | 1.38 |
| | MDI-220 | 2.02 |
| | MDI-221 | 0.128 |
| | MDI-224 | 0.248 |
| | MDI-225 | 0.226 |
| | MDI-216 | 0.134 |
| | MDI-226 | 0.308 |
| | MDI-227 | 0.224 |

| Item | Tested Compound | IC50 (nM) |
|---|---|---|
| | MDI-228 | 0.398 |
| | MDI-229 | 0.753 |
| | MDI-230 | 0.819 |
| | MDI-233 | 1.31 |
| | MDI-235 | 0.0395 |
| | MDI-231 | 0.530 |
| | MDI-232 | 0.745 |
| | MDI-234 | 0.206 |
| | MDI-236 | 0.0403 |
| JAK2 Experiment | Filgotinib | 71 |
| | MDI-208 | 0.440 |
| | MDI-210 | 1.11 |
| | MDI-214 | 0.273 |
| | MDI-215 | 0.277 |
| | MDI-218 | 0.614 |
| | MDI-219 | 1.38 |
| | MDI-220 | 1.38 |
| | MDI-221 | 0.363 |
| | MDI-224 | 0.754 |
| | MDI-225 | 0.390 |
| | MDI-216 | 0.233 |
| | MDI-226 | 0.371 |
| | MDI-227 | 0.246 |
| | MDI-228 | 0.355 |
| | MDI-229 | 0.356 |
| | MDI-230 | 0.555 |
| | MDI-233 | 1.33 |
| | MDI-235 | 0.166 |
| | MDI-231 | 1.17 |
| | MDI-232 | 1.04 |
| | MDI-234 | 0.737 |
| | MDI-236 | 0.329 |
| JAK3 Experiment | Filgotinib | 1463 |
| | MDI-208 | 1.11 |
| | MDI-210 | 0.979 |
| | MDI-214 | 0.352 |
| | MDI-215 | 0.308 |
| | MDI-218 | 0.948 |
| | MDI-219 | 2.29 |
| | MDI-220 | 3.15 |
| | MDI-221 | 0.379 |
| | MDI-224 | 2.01 |
| | MDI-225 | 0.487 |
| | MDI-216 | 0.247 |
| | MDI-226 | 0.676 |
| | MDI-227 | 0.441 |
| | MDI-228 | 0.565 |
| | MDI-229 | 0.481 |
| | MDI-230 | 0.821 |
| | MDI-233 | 2.60 |
| | MDI-235 | 0.183 |
| | MDI-231 | 0.893 |
| | MDI-232 | 0.868 |
| | MDI-234 | 0.375 |
| | MDI-236 | 0.141 |
| TYK2 Experiment | Filgotinib | 532 |
| | MDI-208 | 9.31 |
| | MDI-210 | 31.5 |
| | MDI-214 | 2.8 |
| | MDI-215 | 1.58 |
| | MDI-218 | 1.75 |
| | MDI-219 | 1.88 |
| | MDI-220 | 5.56 |
| | MDI-221 | 7.60 |
| | MDI-224 | 16.1 |
| | MDI-225 | 3.50 |
| | MDI-216 | 1.62 |
| | MDI-226 | 4.18 |
| | MDI-227 | 3.89 |
| | MDI-228 | 4.76 |
| | MDI-229 | 4.71 |
| | MDI-230 | 6.57 |
| | MDI-233 | 3.50 |
| | MDI-235 | 0.142 |
| | MDI-231 | 1.31 |
| | MDI-232 | 2.26 |
| | MDI-234 | 0.438 |
| | MDI-236 | 0.0954 |
| JAK1 Experiment | Filgotinib | 46.2 |
| | MDI-237 | 0.758 |
| | MDI-239 | 1.15 |
| | MDI-240 | 0.450 |
| | MDI-242 | 67.2 |
| | MDI-243 | 0.118 |
| | MDI-244 | 0.248 |
| | MDI-245 | 0.178 |
| | MDI-246 | 0.241 |
| | MDI-247 | 0.557 |
| | MDI-248 | 0.093 |
| | MDI-249 | 0.307 |
| | MDI-250 | 0.395 |
| | MDI-251 | 0.144 |
| | MDI-252 | 1.8 |
| | MDI-253 | 2.9 |
| | MDI-255 | 57.2 |
| | MDI-256 | 0.700 |
| | MDI-257 | 0.185 |
| | MDI-258 | 0.939 |
| | MDI-259 | 0.659 |
| | MDI-260 | 2.28 |
| | MDI-261 | 0.154 |
| | MDI-262 | 0.319 |
| | MDI-263 | 0.120 |
| JAK2 Experiment | Filgotinib | 47.6 |
| | MDI-237 | 0.588 |
| | MDI-239 | 1.20 |
| | MDI-240 | 0.842 |
| | MDI-242 | 28.6 |
| | MDI-243 | 0.499 |
| | MDI-244 | 0.915 |
| | MDI-245 | 0.648 |
| | MDI-246 | 0.973 |
| | MDI-247 | 1.88 |
| | MDI-248 | 0.560 |
| | MDI-249 | 0.697 |
| | MDI-250 | 0.974 |
| | MDI-251 | 0.818 |
| | MDI-252 | 2.6 |
| | MDI-253 | 1.6 |
| | MDI-255 | 37.4 |
| | MDI-256 | 3.06 |
| | MDI-257 | 0.600 |
| | MDI-258 | 3.31 |
| | MDI-259 | 1.30 |
| | MDI-260 | 2.99 |
| | MDI-261 | 0.703 |
| | MDI-262 | 1.54 |
| | MDI-263 | 0.717 |
| JAK3 Experiment | Filgotinib | 1051 |
| | MDI-237 | 1.39 |
| | MDI-239 | 4.94 |
| | MDI-240 | 2.02 |
| | MDI-242 | 152 |
| | MDI-243 | 0.269 |
| | MDI-244 | 0.550 |
| | MDI-245 | 0.306 |
| | MDI-246 | 0.709 |
| | MDI-247 | 1.30 |
| | MDI-248 | 0.303 |
| | MDI-249 | 0.398 |
| | MDI-250 | 0.497 |
| | MDI-251 | 0.406 |
| | MDI-252 | 2.2 |
| | MDI-253 | 1.5 |
| | MDI-256 | 2.71 |
| | MDI-257 | 0.381 |
| | MDI-258 | 2.36 |
| | MDI-259 | 1.29 |
| | MDI-260 | 2.47 |
| | MDI-261 | 0.473 |
| | MDI-262 | 1.22 |
| | MDI-263 | 0.458 |

-continued

| Item | Tested Compound | IC50 (nM) |
|---|---|---|
| TYK2 Experiment | Filgotinib | 233 |
| | MDI-237 | 9.68 |
| | MDI-239 | 19.2 |
| | MDI-240 | 5.34 |
| | MDI-242 | 583 |
| | MDI-243 | 0.167 |
| | MDI-244 | 1.31 |
| | MDI-245 | 0.365 |
| | MDI-246 | 1.52 |
| | MDI-247 | 2.35 |
| | MDI-248 | 0.578 |
| | MDI-249 | 1.93 |
| | MDI-250 | 0.993 |
| | MDI-251 | 1.33 |
| | MDI-252 | 22 |
| | MDI-253 | 31 |
| | MDI-256 | 6.14 |
| | MDI-257 | 0.684 |
| | MDI-258 | 6.27 |
| | MDI-259 | 2.94 |
| | MDI-260 | 8.98 |
| | MDI-261 | 1.16 |
| | MDI-262 | 2.59 |
| | MDI-263 | 0.717 |

The above experimental results show that among the compounds of the present disclosure tested in Example 60, except that few example compound has a comparable activity as Filgotinib, most of the tested compounds can inhibit JAK1, JAK2, JAK3, and TYK3 at very low concentrations and the inhibitory activities of these compounds are much higher than that of Filgotinib.

Although specific embodiments of the present disclosure have been illustrated and described, it does not mean that these embodiments illustrate and describe all possible implementation forms of the present disclosure. More precisely, the language used in this specification are only descriptive words and not restrictive. It will be obvious to those skilled in the art that various kinds of changes and modifications can be made without departing from the general scope of the present disclosure. Therefore, the appended claims are intended to include all these changes and modifications within the scope of the present disclosure.

What is claimed is:

1. A compound of formula (G),

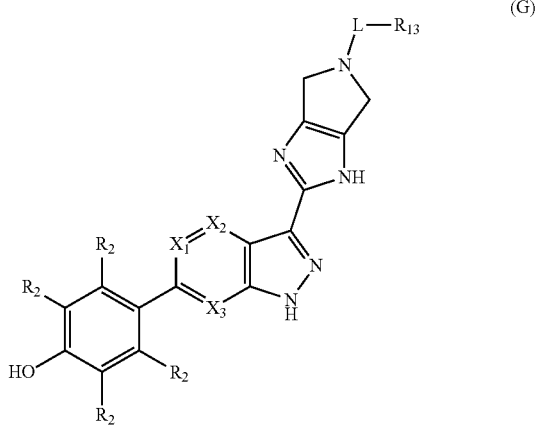

or a pharmaceutically acceptable salt, optical isomer, geometric isomer, or tautomer thereof, wherein each $R_2$ is independently H, halogen, CN, $NO_2$, $C_{1-6}$ alkyl, $C_{2-6}$ alkenyl, $C_{2-6}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 4-10 membered heterocycloalkyl, a monocyclic $C_{5-7}$ aryl, a bicyclic $C_{7-11}$ aryl, a monocyclic 5-7 membered heteroaryl, or a bicyclic 7-11 membered heteroaryl;

wherein each $C_{1-6}$ alkyl, $C_{2-6}$ alkenyl, $OC_{1-6}$ alkyl, $OC_{1-6}$ haloalkyl, and $SC_{1-4}$ alkyl is optionally and independently substituted with 1, 2, or 3 substituents independently selected from the group consisting of halogen, CN, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-7}$ cycloalkyl; and wherein each $C_{3-7}$ cycloalkyl, 4-10 membered heterocycloalkyl, $C_{5-7}$ aryl, $C_{7-11}$ aryl, 5-7 membered heteroaryl, and 7-11 membered heteroaryl is optionally and independently substituted with 1, 2, or 3 substituents independently selected from the group consisting of halogen, CN, $C_{1-4}$ alkyl, $C_{1-4}$ haloalkyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-7}$ cycloalkyl;

L is a bond, —$CH_2$—, —C(O)—, or —$S(O)_2$—;

$R_{13}$ is H, halogen, CN, $NO_2$, $C_{1-6}$ alkyl, $NR_{17}R_{18}$, OH, $OC_{1-6}$ alkyl, $OC_{1-4}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, $C_{5-11}$ bicycloalkyl, a 3-7 membered heterocycloalkyl, a bicyclic 5-11 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricyclyl; wherein $R_{13}$ is optionally substituted with 1, 2, 3, or 4 independently selected $R_1$ substituents;

each $R_1$ is independently halogen, CN, $NO_2$, $C_{1-8}$ alkyl, $C_{2-8}$ alkenyl, $C_{2-8}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-8}$ alkyl, $OC_{1-4}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, $C_{5-11}$ bicycloalkyl, a 3-10 membered heterocycloalkyl, a bicyclic 5-11 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricyclyl;

wherein each $C_{1-8}$ alkyl, $C_{2-8}$ alkenyl, $C_{2-8}$ alkynyl, $OC_{1-8}$ alkyl, and $SC_{1-4}$ alkyl is optionally and independently substituted with 1, 2, 3, or 4 independently selected $R_3$ substituents; and wherein each $C_{3-7}$ cycloalkyl, 3-10 membered heterocycloalkyl, $C_{5-7}$ aryl, $C_{7-11}$ aryl, 5-7 membered heteroaryl, and 7-11 membered heteroaryl is optionally and independently substituted with 1, 2, 3, or 4 independently selected $R_4$ substituents; and each $R_3$ is independently halogen, CN, $NO_2$, $C(O)R_{12}$, $C(O)NR_7R_8$, $C(O)OR_{12}$, $NR_5R_6$, $NR_{11}C(O)R_{12}$, $NR_{11}S(O)_2R_{12}$, OH, $OC_{1-6}$ alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 3-10 membered heterocycloalkyl, a monocyclic $C_{5-7}$ aryl, a bicyclic $C_{7-11}$ aryl, a monocyclic 5-7 membered heteroaryl, or a bicyclic 7-11 membered heteroaryl;

wherein each $C_{3-7}$ cycloalkyl, 3-10 membered heterocycloalkyl, $C_{5-7}$ aryl, $C_{7-11}$ aryl, 5-7 membered heteroaryl, or 7-11 membered heteroaryl is optionally and independently substituted with 1, 2, 3, or 4 substituents independently selected from the group consisting of halogen, CN, $C_{1-4}$ alkyl, $C_{1-4}$ haloalkyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-6}$ cycloalkyl;

each $R_4$ is independently halogen, CN, $NO_2$, $C_{1-6}$ alkyl, $C_{2-6}$ alkenyl, $C_{2-6}$ alkynyl, $C(O)R_{12}$, $C(O)NR_7R_8$, $C(O)OR_{12}$, $NR_5R_6$, $NR_{11}C(O)R_{12}$, $NR_{11}S(O)_2R_{12}$, OH, $OC_{1-6}$alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 3-10 membered heterocycloalkyl, a monocyclic $C_{5-7}$ aryl, a bicyclic $C_{7-11}$ aryl, a monocyclic 5-7 membered heteroaryl, or a bicyclic 7-11 membered heteroaryl;

wherein each $C_{1-6}$ alkyl is optionally and independently substituted with 1, 2, 3, or 4 substituents independently selected from the group consisting of halogen, CN, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-4}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-6}$ cycloalkyl;

wherein each $C_{3-7}$ cycloalkyl, 3-10 membered heterocycloalkyl, $C_{5-7}$ aryl, $C_{7-11}$ aryl, 5-7 membered heteroaryl, and 7-11 membered heteroaryl is optionally and independently substituted with 1, 2, 3, or 4 substitutes substituents independently selected from the group consisting of halogen, CN, $C_{1-4}$ alkyl, $C_{1-4}$ haloalkyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-4}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-6}$ cycloalkyl;

each $R_5$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substitutes substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NH(CH$_3$), N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substitutes substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NH(CH$_3$), N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

each $R_6$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

each $R_7$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

each $R_8$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

$X_1$ is $CR_{14}$ or N;

$X_2$ is $CR_{15}$ or N;

$X_3$ is $CR_{16}$ or N;

$R_{14}$ is H, halogen, CN, NO$_2$, $C_{1-6}$ alkyl, $C_{2-8}$ alkenyl, $C_{2-8}$ alkynyl, C(O)$R_{12}$, C(O)N$R_9R_{10}$, C(O)O$R_{12}$, N$R_9R_{10}$, N$R_{11}$C(O)$R_{12}$, N$R_{11}$S(O)$_2R_{12}$, OH, O$C_{1-6}$ alkyl, O$C_{1-4}$haloalkyl, O$C_{1-4}$ alkylene-$C_{3-7}$ cycloalkyl, O$C_{1-4}$ alkylene-4-10 membered heterocycloalkyl, O$C_{1-4}$ alkylene-$C_{6-10}$ aryl, O$C_{1-4}$ alkylene-5-10 membered heteroaryl, OC(O)$R_{12}$, O$C_{3-7}$ cycloalkyl, O-4-14 membered heterocycloalkyl, O$C_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 3-7 membered heterocycloalkyl, a monocyclic $C_{5-7}$ aryl, or a monocyclic 5-7 membered heteroaryl, wherein the $C_{1-6}$ alkyl, $OC_{1-6}$ alkyl, or $SC_{1-4}$ alkyl is optionally substituted with 1, 2, or 3 substituents independently selected from the group consisting of halogen, CN, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)(C(O)$ $C_{1-4}$ alkyl), OH, $OC_{1-4}$ alkyl, $OC_{1-4}$ haloalkyl, $SC_{1-4}$ alkyl, and $C_{3-7}$ cycloalkyl; and wherein the $C_{3-7}$ cycloalkyl, or 3-7 membered heterocycloalkyl is optionally substituted with 1, 2, or 3 substituents independently selected from the group consisting of halogen, CN, $C_{1-4}$ alkyl, $C_{1-4}$ haloalkyl, $C_{1-4}$ hydroxyalkyl, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)$-$C(O)C_{1-4}$ alkyl, OH, $OC_{1-4}$ alkyl, $OC_{1-4}$ haloalkyl, $SC_{1-4}$ alkyl, and $C_{3-7}$ cycloalkyl;

$R_{15}$ is H, halogen, CN, $NO_2$, $C_{1-6}$ alkyl, $C_{2-8}$ alkenyl, $C_{2-8}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 3-7 membered heterocycloalkyl, a monocyclic $C_{5-7}$ aryl, or a monocyclic 5-7 membered heteroaryl, wherein the $C_{1-6}$ alkyl, $OC_{1-6}$ alkyl, or $SC_{1-4}$ alkyl is optionally substituted with 1, 2, or 3 substituents independently selected from the group consisting of halogen, CN, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)(C(O)$ $C_{1-4}$ alkyl), OH, $OC_{1-4}$ alkyl, $OC_{1-4}$ haloalkyl, $SC_{1-4}$ alkyl, and $C_{3-7}$ cycloalkyl; and wherein the $C_{3-7}$ cycloalkyl, or 3-7 membered heterocycloalkyl is optionally substituted with 1, 2, or 3 substituents independently selected from the group consisting of halogen, CN, $C_{1-4}$ alkyl, $C_{1-4}$ haloalkyl, $C_{1-4}$ hydroxyalkyl, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)$-$C(O)C_{1-4}$ alkyl, OH, $OC_{1-4}$ alkyl, $OC_{1-4}$ haloalkyl, $SC_{1-4}$ alkyl, and $C_{3-7}$ cycloalkyl;

$R_{16}$ is H, halogen, CN, $NO_2$, $C_{1-6}$ alkyl, $C_{2-8}$ alkenyl, $C_{2-8}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-4}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 3-7 membered heterocycloalkyl, a monocyclic $C_{5-7}$ aryl, or a monocyclic 5-7 membered heteroaryl, wherein the $C_{1-6}$ alkyl, $OC_{1-6}$ alkyl, or $SC_{1-4}$ alkyl is optionally substituted with 1, 2, or 3 substituents independently selected from the group consisting of halogen, CN, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)(C(O)$ $C_{1-4}$ alkyl), OH, $OC_{1-4}$ alkyl, $OC_{1-4}$ haloalkyl, $SC_{1-4}$ alkyl, $C_{3-7}$ cycloalkyl; and wherein the $C_{3-7}$ cycloalkyl, or 3-7 membered heterocycloalkyl is optionally substituted with 1, 2, or 3 substituents independently selected from the group consisting of halogen, CN, $C_{1-4}$ alkyl, $C_{1-4}$ haloalkyl, $C_{1-4}$ hydroxyalkyl, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, $N(C_{1-4}$ alkyl$)$-$C(O)C_{1-4}$ alkyl, OH, $OC_{1-4}$ alkyl, $OC_{1-4}$ haloalkyl, $SC_{114}$ alkyl, and $C_{3-7}$ cycloalkyl;

$R_{17}$ is H, $C_{1-6}$ alkyl, $C_{2-6}$ alkenyl, $C_{2-6}$ alkynyl, $OC_{1-6}$ alkyl, $OC_{1-6}$ haloalkyl, $C_{3-7}$ cycloalkyl, $C_{5-11}$ bicycloalkyl, a 3-7 membered heterocycloalkyl, a bicyclic 5-11 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricycyl;

wherein the $C_{1-6}$ alkyl, $C_{2-6}$ alkenyl, $C_{2-6}$ alkynyl, $OC_{1-6}$ alkyl, or $OC_{1-6}$ haloalkyl is optionally substituted with 1, 2, 3, or 4 substituents independently selected from the group consisting of halogen, CN, $NO_2$, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, a 4-10 membered heterocycloalkyl, a monocyclic $C_{5-7}$ aryl, a bicyclic $C_{7-11}$ aryl, a monocyclic 5-7 membered heteroaryl, and a bicyclic 7-11 membered heteroaryl;

wherein the $C_{3-7}$ cycloalkyl, $C_{5-11}$ bicycloalkyl, 3-7 membered heterocycloalkyl, 5-11 membered heteroaryl, $C_{5-7}$ aryl, $C_{7-11}$ aryl, 5-7 membered heteroaryl, 7-11 membered heteroaryl, or 11-15 membered tricyclyl is optionally substituted with 1, 2, 3, or 4 substituents independently selected from the group consisting of halogen, CN, $NO_2$, $C_{1-6}$ alkyl, $C_{2-6}$ alkenyl, $C_{2-6}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, C$_{3-7}$ cycloalkyl, a 4-10 membered heterocycloalkyl, a monocyclic C$_{5-7}$ aryl, a bicyclic C$_{7-11}$ aryl, a monocyclic 5-7 membered heteroaryl, and a bicyclic 7-11 membered heteroaryl;

wherein each C$_{1-6}$ alkyl, C$_{2-6}$ alkenyl, C$_{2-6}$ alkynyl, OC$_{1-6}$ alkyl, OC$_{1-6}$ haloalkyl and SC$_{1-4}$ haloalkyl substituent is optionally substituted with 1, 2, or 3 substituents independently selected from the group consisting of halogen, CN, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, and C$_{3-6}$ cycloalkyl; and wherein each C$_{3-7}$ cycloalkyl, 4-10 membered heterocycloalkyl, C$_{5-7}$ aryl, C$_{7-11}$ aryl, 5-7 membered heteroaryl, and 7-11 membered heteroaryl substituent is optionally and independently substituted with 1, 2, or 3 substituents independently selected from the group consisting of halogen, CN, C$_{1-4}$ alkyl, C$_{1-4}$ haloalkyl, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, and C$_{3-6}$ cycloalkyl;

R$_{18}$ is H, C$_{1-6}$ alkyl, C$_{2-6}$ alkenyl, C$_{2-6}$ alkynyl, OC$_{1-6}$ alkyl, OC$_{1-6}$ haloalkyl, C$_{3-7}$ cycloalkyl, C$_{5-11}$ bicycloalkyl, a 3-7 membered heterocycloalkyl, a bicyclic 5-11 membered heterocycloalkyl, a monocyclic C$_{5-7}$ aryl, a bicyclic C$_{7-11}$ aryl, a monocyclic 5-7 membered heteroaryl, a bicyclic 7-11 membered heteroaryl, or an 11-15 membered tricycyl;

wherein the C$_{1-6}$ alkyl, C$_{2-6}$ alkenyl, C$_{2-6}$ alkynyl, OC$_{1-6}$ alkyl, or OC$_{1-6}$ haloalkyl is optionally substituted with 1, 2, 3, or 4 substituents independently selected from the group consisting of halogen, CN, NO$_2$, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, C$_{3-7}$ cycloalkyl, a 4-10 membered heterocycloalkyl, a monocyclic C$_{5-7}$ aryl, a bicyclic C$_{7-11}$ aryl, a monocyclic 5-7 membered heteroaryl, and a bicyclic 7-11 membered heteroaryl;

wherein the C$_{3-7}$ cycloalkyl, C$_{5-11}$ bicycloalkyl, 3-7 membered heterocycloalkyl, 5-11 membered heteroaryl, C$_{5-7}$ aryl, C$_{7-11}$ aryl, 5-7 membered heteroaryl, 7-11 membered heteroaryl, or 11-15 membered tricyclyl is optionally substituted with 1, 2, 3, or 4 substituents independently selected from the group consisting of halogen, CN, NO$_2$, C$_{1-6}$ alkyl, C$_{2-6}$ alkenyl, C$_{2-6}$ alkynyl, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$ haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, C$_{3-7}$ cycloalkyl, a 4-10 membered heterocycloalkyl, a monocyclic C$_{5-7}$ aryl, a bicyclic C$_{7-11}$ aryl, a monocyclic 5-7 membered heteroaryl, and a bicyclic 7-11 membered heteroaryl;

wherein each C$_{1-6}$ alkyl, C$_{2-6}$ alkenyl, C$_{2-6}$ alkynyl, OC$_{1-6}$ alkyl, OC$_{1-6}$ haloalkyl, and SC$_{1-4}$ haloalkyl substituent is optionally substituted with 1, 2, or 3 substituents independently selected from the group consisting of halogen, CN, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, SC$_{6-10}$ aryl, S-5-10 membered heteroaryl, and C$_{3-6}$ cycloalkyl; and wherein each C$_{3-7}$ cycloalkyl, 4-10 membered heterocycloalkyl, C$_{5-7}$ aryl, C$_{7-11}$ aryl, 5-7 membered heteroaryl, and 7-11 membered heteroaryl substituent is optionally and independently substituted with 1, 2, or 3 substituents independently selected from the group consisting of halogen, CN, C$_{1-4}$ alkyl, C$_{1-4}$ haloalkyl, C(O)R$_{12}$, C(O)NR$_9$R$_{10}$, C(O)OR$_{12}$, NR$_9$R$_{10}$, NR$_{11}$C(O)R$_{12}$, NR$_{11}$S(O)$_2$R$_{12}$, OH, OC$_{1-6}$ alkyl, OC$_{1-6}$haloalkyl, OC$_{1-4}$ alkylene-C$_{3-7}$ cycloalkyl, OC$_{1-4}$ alkylene-4-10 membered heterocycloalkyl, OC$_{1-4}$ alkylene-C$_{6-10}$ aryl, OC$_{1-4}$ alkylene-5-10 membered heteroaryl, OC(O)R$_{12}$, OC$_{3-7}$ cycloalkyl, O-4-14 membered heterocycloalkyl, OC$_{6-10}$ aryl, O-5-10 membered heteroaryl, SH, SC$_{1-4}$ alkyl, SC$_{1-4}$ haloalkyl, SC$_{1-4}$ alkylene-C$_{3-7}$ cycloalkyl, SC$_{1-4}$ alkylene-4-10 membered heterocycloalkyl, SC$_{1-4}$ alkylene-C$_{6-10}$ aryl, SC$_{1-4}$ alkylene-5-10 membered heteroaryl, SF$_5$, S(O)$_2$NR$_9$R$_{10}$, SC$_{3-7}$ cycloalkyl, S-4-14 membered heterocycloalkyl, $SC_{6-10}$ aryl, S-5-10 membered heteroaryl, and $C_{3-6}$ cycloalkyl; or $R_{17}$ and $R_{18}$ together with the nitrogen atom to which they are attached, form a 3-14 membered heterocyclyl;

each $R_9$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

each $R_{10}$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl;

each $R_{11}$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and each $R_{12}$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of halogen, CN, $C_{1-4}$ alkyl, $C_{1-4}$ haloalkyl, $C_{1-4}$ hydroxyalkyl, $C_{2-6}$ alkenyl, $C_{2-6}$ alkynyl, C(O)H, C(O)$C_{1-4}$ alkyl, C(O)NH$_2$, C(O)N($C_{1-4}$ alkyl)$_2$, C(O)O$C_{1-4}$ alkyl, NH$_2$, NHCH$_3$, N(CH$_3$)$_2$, OH, O$C_{1-4}$ alkyl, O$C_{1-4}$ haloalkyl, =O, S$C_{1-4}$ alkyl, S$C_{3-7}$ cycloalkyl.

2. The compound according to claim 1, or a pharmaceutically acceptable salt, optical isomer, geometric isomer, or tautomer thereof, wherein one $R_2$ is H; and the other $R_2$(s) are independently H, halogen, CN, $NO_2$, $C_{1-6}$ alkyl, $C_{2-6}$ alkenyl, $C_{2-6}$ alkynyl, OH, $OC_{1-6}$ alkyl, $OC_{1-6}$haloalkyl, SH, $SC_{1-4}$ alkyl, $SF_5$, $C_{3-7}$ cycloalkyl, or a 4-10 membered heterocycloalkyl;

wherein each $C_{1-6}$ alkyl, and $SC_{1-4}$ alkyl is optionally and independently substituted with 1, 2, or 3 substituents independently selected from the group consisting of halogen, CN, $C_{1-4}$ alkyl, $C_{1-4}$ haloalkyl, $NH_2$, $NHCH_3$, $N(CH_3)_2$, OH, $OC_{1-4}$ alkyl, and $OC_{1-4}$haloalkyl; and wherein each $C_{3-7}$ cycloalkyl and a 4-10 membered heterocycloalkyl is optionally and independently substituted with 1, 2, or 3 substituents independently selected from the group consisting of halogen, CN, $C_{1-4}$ alkyl, $C_{1-4}$ haloalkyl, $NH_2$, $NHCH_3$, $N(CH_3)_2$, OH, $OC_{1-4}$ alkyl, and $OC_{1-4}$ haloalkyl.

3. The compound according to claim 1, or a pharmaceutically acceptable salt, optical isomer, geometric isomer, or tautomer thereof, wherein one $R_2$ is H; and the other $R_2$(s) are independently H, halogen, $C_{1-6}$ alkyl, or $C_{3-6}$ cycloalkyl;

wherein each $C_{1-6}$ alkyl is optionally and independently substituted with 1, 2, or 3 substituents independently selected from the group consisting of halogen, CN, $C_{1-4}$ alkyl, $C_{1-4}$ haloalkyl, $NH_2$, $NHCH_3$, $N(CH_3)_2$, OH, $OC_{1-4}$ alkyl, and $OC_{1-4}$ haloalkyl; and wherein each $C_{3-6}$ cycloalkyl is optionally and independently substituted with 1, 2, or 3 substituents independently selected from the group consisting of halogen, CN, $C_{1-4}$ alkyl, $C_{1-4}$ haloalkyl, $NH_2$, $NHCH_3$, $N(CH_3)_2$, OH, $OC_{1-4}$ alkyl, and $OC_{1-4}$ haloalkyl.

4. The compound according to claim 1, or a pharmaceutically acceptable salt, optical isomer, geometric isomer, or tautomer thereof, wherein one $R_2$ is H; and the other $R_2$(s) are independently H, halogen, or $C_{1-6}$ alkyl wherein each $C_{1-6}$ alkyl is optionally and independently substituted with 1, 2, or 3 substituents independently selected from the group consisting of halogen, CN, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-4}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, 0-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-7}$ cycloalkyl.

5. The compound according to claim 1, or a pharmaceutically acceptable salt, optical isomer, geometric isomer, or tautomer thereof, wherein L is —$CH_2$—, —C(O)—, or —$S(O)_2$—.

6. The compound according to claim 1, or a pharmaceutically acceptable salt, optical isomer, geometric isomer, or tautomer thereof, wherein $R_{13}$ is H, halogen, CN, $NO_2$, $C_{1-6}$ alkyl, $NR_{17}R_{18}$, OH, $OC_{1-6}$ alkyl, SH, $SC_{1-4}$ alkyl, $SF_5$, $C_{3-7}$ cycloalkyl, a 3-7 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricyclyl, wherein the $C_{1-6}$ alkyl, $OC_{1-6}$ alkyl, $SC_{1-4}$ alkyl, $C_{3-7}$ cycloalkyl, 3-7 membered heterocycloalkyl, $C_{5-7}$ aryl, $C_{7-11}$ aryl, 5-7 membered heteroaryl, 7-11 membered heteroaryl, or 11-15 membered tricyclyl is optionally substituted with 1, 2, 3, or 4 independently selected $R_1$ substituents.

7. The compound according to claim 1, or a pharmaceutically acceptable salt, optical isomer, geometric isomer, or tautomer thereof, wherein $R_{13}$ is H, $C_{1-6}$ alkyl, $NR_{17}R_{18}$, $OC_{1-6}$ alkyl, $C_{3-7}$ cycloalkyl, a 3-7 membered heterocycloalkyl, a monocyclic $C_{5-7}$ aryl, or a monocyclic 5-7 membered heteroaryl, wherein the $C_{1-6}$ alkyl, $OC_{1-6}$ alkyl, $C_{3-7}$ cycloalkyl, 3-7 membered heterocycloalkyl, $C_{5-7}$ aryl, or 5-7 membered heteroaryl is optionally substituted with 1, 2, 3, or 4 independently selected $R_1$ substituents.

8. The compound according to claim 1, or a pharmaceutically acceptable salt, optical isomer, geometric isomer, or tautomer thereof, wherein $R_{13}$ is optionally substituted with 1 $R_1$ substituent;

$R_1$ is halogen, $C_{1-6}$ alkyl, OH, $C_{3-7}$ cycloalkyl, or a 5-7 membered heteroalkyl;

wherein the $C_{1-6}$ alkyl is optionally and independently substituted with 1, 2, or 3 independently selected $R_3$ substituents; and wherein the $C_{3-7}$ cycloalkyl or 5-7 membered heterocycloalkyl is optionally and independently substituted with 1, 2, 3, or 4 independently selected $R_4$ substituents; and each $R_4$ is independently $C_{1-3}$ alkyl.

9. The compound according to claim 1, or a pharmaceutically acceptable salt, optical isomer, geometric isomer, or tautomer thereof, wherein $R_{17}$ is H, $C_{1-6}$ alkyl, $C_{3-7}$ cycloalkyl, or a 3-7 membered heterocycloalkyl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, or 3-7 membered heterocycloalkyl is optionally substituted with 1, 2, 3, or 4 substituents independently selected from the group consisting of halogen, CN, $NO_2$, OH, SH, and $SF_5$; and $R_{18}$ is H, $C_{1-6}$ alkyl, $C_{3-7}$ cycloalkyl, or a 3-7 membered heterocycloalkyl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, or 3-7 membered heterocycloalkyl is optionally substituted with 1, 2, 3, or 4 substituents independently selected from the group consisting of halogen, CN, $NO_2$, OH, SH, and $SF_5$.

10. The compound according to claim 1, or a pharmaceutically acceptable salt, optical isomer, geometric isomer, or tautomer thereof, wherein $R_{13}$ is H, halogen, CN, $NO_2$, $C_{1-6}$ alkyl, $NR_{17}R_{18}$, OH, $OC_{1-6}$ alkyl, SH, $SC_{1-4}$ alkyl, $SF_5$, $C_{3-7}$ cycloalkyl, $C_{5-11}$ bicycloalkyl, a 3-7 membered heterocycloalkyl, a bicyclic 5-11 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricyclyl, wherein the $C_{1-6}$ alkyl, $OC_{1-6}$ alkyl, $SC_{1-4}$ alkyl, $C_{3-7}$ cycloalkyl, $C_{5-11}$ bicycloalkyl, 3-7 membered heterocycloalkyl, 5-11 membered heterocycloalkyl, $C_{5-7}$ aryl, $C_{7-11}$ aryl, 5-7 membered heteroaryl, 7-11 membered heteroaryl, or 11-15 membered tricyclyl is optionally substituted with 1, 2, 3, or 4 independently selected $R_1$ substituents;

$R_{17}$ is H, $C_{1-6}$ alkyl, $OC_{1-6}$ alkyl, $C_{3-7}$ cycloalkyl, a 3-7 membered heterocycloalkyl, a monocyclic $C_{5-7}$ aryl, or a monocyclic 5-7 membered heteroaryl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, 3-7 membered heterocycloalkyl, $C_{5-7}$ aryl, or 5-7 membered heteroaryl is optionally substituted with 1, 2, 3, or 4 substituents independently selected from the group consisting of halogen, CN, $NO_2$, OH, SH, and $SF_5$; and $R_{18}$ is H, $C_{1-6}$ alkyl, $OC_{1-6}$ alkyl, $C_{3-7}$ cycloalkyl, a 3-7 membered heterocycloalkyl, a monocyclic $C_{5-7}$ aryl, or a monocyclic 5-7 membered heteroaryl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, 3-7 membered heterocycloalkyl, $C_{5-7}$ aryl, or 5-7 membered heteroaryl is optionally substituted with 1, 2, 3, or 4 substituents independently selected from the group consisting of halogen, CN, $NO_2$, OH, SH, and $SF_5$.

11. The compound according to claim 1, or a pharmaceutically acceptable salt, optical isomer, geometric isomer, or tautomer thereof, wherein L is —C(O)—

$R_{13}$ is H, halogen, CN, $NO_2$, $NR_{17}R_{18}$, OH, $OC_{1-6}$ alkyl, SH, $SC_{1-4}$ alkyl, or $SF_5$, wherein the $OC_{1-6}$ alkyl or $SC_{1-4}$ alkyl is optionally substituted with 1, 2, 3, or 4 independently selected $R_1$ substituents;

$R_{17}$ is H, $C_{1-6}$ alkyl, $OC_{1-6}$ alkyl, $C_{3-7}$ cycloalkyl, a 3-7 membered heterocycloalkyl, a monocyclic $C_{5-7}$ aryl, or a monocyclic 5-7 membered heteroaryl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, 3-7 membered heterocycloalkyl, $C_{5-7}$ aryl, or 5-7 membered heteroaryl is optionally substituted with 1, 2, 3, or 4 substituents independently selected from the group consisting of halogen, CN, $NO_2$, OH, SH, and $SF_5$; and $R_{18}$ is H, $C_{1-6}$ alkyl, $OC_{1-6}$ alkyl, $C_{3-7}$ cycloalkyl, a 3-7 membered heterocycloalkyl, a monocyclic $C_{5-7}$ aryl, or a monocyclic 5-7 membered heteroaryl;

wherein the $C_{1-6}$ alkyl, or $OC_{1-6}$ alkyl is optionally substituted with 1, 2, 3, or 4 substituents independently selected from the group consisting of halogen, CN, $NO_2$, OH, SH, and $SF_5$; and wherein the $C_{3-7}$ cycloalkyl, 3-7 membered heterocycloalkyl, $C_{5-7}$ aryl, or 5-7 membered heteroaryl is optionally substituted with 1, 2, 3, or 4 substituents independently selected from the group consisting of halogen, CN, $NO_2$, OH, SH, and $SF_5$; or $R_{17}$ and $R_{18}$ together with the nitrogen atom to which they are attached, form a 3-14 membered heterocyclyl.

12. The compound according to claim 1, or a pharmaceutically acceptable salt, optical isomer, geometric isomer, or tautomer thereof, wherein $X_1$ is $CR_{14}$; and
$X_2$ is $CR_{16}$.

13. The compound according to claim 1, or a pharmaceutically acceptable salt, optical isomer, geometric isomer, or tautomer thereof, wherein $X_1$ is $CR_{14}$;
$X_2$ is $CR_{15}$;
$X_3$ is $CR_{16}$;
$R_{14}$ is H;
$R_{15}$ is H; and
$R_{16}$ is H.

14. The compound according to claim 1, wherein the compound is of the following Formula:

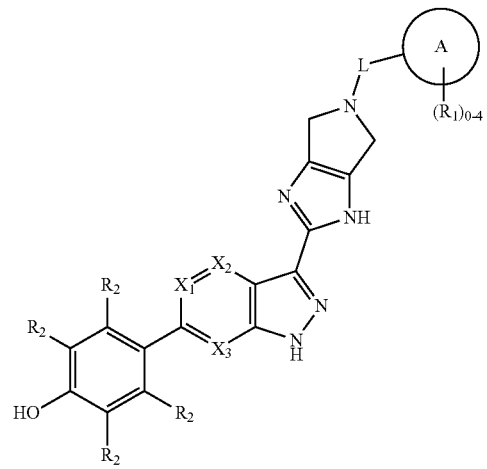

or a pharmaceutically acceptable salt, optical isomer, geometric isomer, or tautomer thereof, wherein each $R_2$ is independently H, halogen, CN, $NO_2$, $C_{1-6}$ alkyl, $C_{2-6}$ alkenyl, $C_{2-6}$ alkynyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-6}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, $C_{3-7}$ cycloalkyl, or a 4-10 membered heterocycloalkyl;

wherein each $C_{1-6}$ alkyl is optionally and independently substituted with 1, 2, or 3 substituents independently selected from the group consisting of halogen, CN, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-4}$ alkyl, $OC_{1-4}$ haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-7}$ cycloalkyl; and wherein each $C_{3-7}$ cycloalkyl and 4-10 membered heterocycloalkyl is optionally and independently substituted with 1, 2, or 3 substituents independently selected from the group consisting of halogen, CN, $C_{1-4}$ alkyl, $C_{1-4}$ haloalkyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-4}$ alkyl, $OC_{1-4}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-7}$ cycloalkyl;

L is a bond;

ring A is $C_{3-7}$ cycloalkyl, a 3-7 membered heterocycloalkyl, a monocyclic $C_{5-7}$ aryl, a bicyclic $C_{7-11}$ aryl, a monocyclic 5-7 membered heteroaryl, a bicyclic 7-11 membered heteroaryl, or an 11-15 membered tricyclyl, wherein the $C_{3-7}$ cycloalkyl, 3-7 membered heterocycloalkyl, $C_{5-7}$ aryl, $C_{7-11}$ aryl, 5-7 membered heteroaryl, 7-11 membered heteroaryl, and 11-15 membered tricyclyl is optionally substituted with 1, 2, 3, or 4 independently selected $R_1$ substituents;

each $R_1$ is independently halogen, $C_{1-8}$ alkyl, $C_{2-8}$ alkenyl, $C_{2-8}$ alkynyl, $OC_{1-8}$ alkyl, $C_{3-7}$ cycloalkyl, a 3-10 membered heterocycloalkyl, a monocyclic $C_{5-7}$ aryl, a bicyclic $C_{7-11}$ aryl, a monocyclic 5-7 membered heteroaryl, or a bicyclic 7-11 membered heteroaryl;

wherein each $C_{1-8}$ alkyl, $C_{2-8}$ alkenyl, $C_{2-8}$ alkynyl, and $OC_{1-8}$ alkyl is optionally and independently substituted with 1, 2, 3, or 4 independently selected $R_3$ substituents; and wherein each $C_{3-7}$ cycloalkyl, 3-7 membered heterocycloalkyl, $C_{5-7}$ aryl, $C_{7-11}$ aryl, 5-7 membered heteroaryl, and 7-11 membered heteroaryl is optionally and independently substituted with 1, 2, 3, or 4 independently selected $R_4$ substituents; and each $R_3$ is independently halogen, CN, $C(O)NR_7R_8$, $NR_5R_6$, OH, $OC_{1-6}$ alkyl, or a 3-7 membered heterocycloalkyl;

wherein each 3-7 membered heterocycloalkyl is optionally and independently substituted with 1, 2, 3, or 4 substituents independently selected from the group consisting of halogen, CN, $C_{1-4}$ alkyl, $C_{1-4}$ haloalkyl, $C(O)R_{12}$, $C(O)NR_9R_{10}$, $C(O)OR_{12}$, $NR_9R_{10}$, $NR_{11}C(O)R_{12}$, $NR_{11}S(O)_2R_{12}$, OH, $OC_{1-6}$ alkyl, $OC_{1-4}$haloalkyl, $OC_{1-4}$ alkylene-$C_{3-7}$ cycloalkyl, $OC_{1-4}$ alkylene-4-10 membered heterocycloalkyl, $OC_{1-4}$ alkylene-$C_{6-10}$ aryl, $OC_{1-4}$ alkylene-5-10 membered heteroaryl, $OC(O)R_{12}$, $OC_{3-7}$ cycloalkyl, O-4-14 membered heterocycloalkyl, $OC_{6-10}$ aryl, O-5-10 membered heteroaryl, SH, $SC_{1-4}$ alkyl, $SC_{1-4}$ haloalkyl, $SC_{1-4}$ alkylene-$C_{3-7}$ cycloalkyl, $SC_{1-4}$ alkylene-4-10 membered heterocycloalkyl, $SC_{1-4}$ alkylene-$C_{6-10}$ aryl, $SC_{1-4}$ alkylene-5-10 membered heteroaryl, $SF_5$, $S(O)_2NR_9R_{10}$, $SC_{3-7}$ cycloalkyl, S-4-14 membered heterocycloalkyl, $SC_{6-10}$ aryl, S-5-10 membered heteroaryl, and $C_{3-6}$ cycloalkyl;

each $R_4$ is independently halogen, $C_{1-3}$ alkyl, $NH_2$, $NH(CH_3)$, $N(CH_3)_2$, OH, or $OC_{1-4}$ alkyl;

each $R_5$ is independently halogen or $C_{1-4}$ alkyl;

each $R_6$ is independently halogen or $C_{1-4}$ alkyl;

each $R_7$ is independently halogen or $C_{1-4}$ alkyl;

each $R_8$ is independently halogen or $C_{1-4}$ alkyl;

$X_1$ is $CR_{14}$ or N;

$X_2$ is $CR_{15}$ or N;

$X_3$ is $CR_{16}$ or N;

$R_{14}$ is H;

$R_{15}$ is H;

$R_{16}$ is H;

each $R_9$ is independently H, $C_{1-4}$ alkyl, $C_{1-4}$ haloalkyl, or $C_{3-7}$ cycloalkyl;

each $R_{10}$ is independently H, $C_{1-6}$ alkyl, $C_{1-4}$ haloalkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-10 membered heterocycloalkyl, $C_{6-10}$ aryl, or 5-10 membered heteroaryl;

wherein each $C_{1-6}$ alkyl, $C_{1-4}$ haloalkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, 3, or 4 substituents independently selected from the group consisting of halogen, CN, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, OH, $OC_{1-4}$ alkyl, $OC_{1-4}$ haloalkyl, $SC_{1-4}$ alkyl, and $C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, 3, or 4 substituents independently selected from the group consisting of CN, $C_{1-4}$ alkyl, $C_{1-4}$ haloalkyl, $C_{1-4}$ hydroxyalkyl, C(O)H, $C(O)C_{1-4}$ alkyl, $C(O)NH_2$, $C(O)N(C_{1-4}$ alkyl$)_2$, $C(O)OC_{1-4}$ alkyl, $NH_2$, $NHCH_3$, $N(CH_3)_2$, OH, $OC_{1-4}$ alkyl, $OC_{1-4}$haloalkyl, $SC_{1-4}$ alkyl, and $C_{3-7}$ cycloalkyl;

each $R_{11}$ is independently H, $C_{1-4}$ alkyl, or $C_{3-7}$ cycloalkyl; and each $R_{12}$ is independently H, $C_{1-6}$ alkyl, $C_{1-4}$ alkylene-$C_{3-7}$ cycloalkyl, $C_{1-4}$ alkylene-4-10 membered heterocycloalkyl, $C_{1-4}$ alkylene-$C_{6-10}$ aryl, $C_{1-4}$ alkylene-5-10 membered heteroaryl, $C_{3-7}$ cycloalkyl, a 4-14 membered heterocycloalkyl, $C_{6-10}$ aryl, or 5-10 membered heteroaryl;

wherein each $C_{1-6}$ alkyl, $C_{1-4}$ alkylene of $C_{1-4}$ alkylene-$C_{3-7}$ cycloalkyl, $C_{1-4}$ alkylene of $C_{1-4}$ alkylene-4-10 membered heterocycloalkyl, $C_{1-4}$ alkylene of $C_{1-4}$ alkylene-$C_{6-10}$ aryl, and $C_{1-4}$ alkylene of $C_{1-4}$ alkylene-5-10 membered heteroaryl is optionally and independently substituted with 1, 2, or 3 substituents independently selected from the group consisting of halogen, CN, $NH_2$, $NHCH_3$, $N(CH_3)_2$, OH, $OC_{1-4}$ alkyl, $OC_{1-4}$ haloalkyl, =O, $SC_{1-4}$ alkyl, and $C_{3-7}$ cycloalkyl; and wherein each $C_{3-7}$ cycloalkyl of $C_{1-4}$ alkylene-$C_{3-7}$ cycloalkyl, 4-10 membered heterocycloalkyl of $C_{1-4}$ alkylene-4-10 membered heterocycloalkyl, $C_{6-10}$ aryl of $C_{1-4}$ alkylene-$C_{6-10}$ aryl, 5-10 membered heteroaryl of $C_{1-4}$ alkylene-5-10 membered heteroaryl, $C_{3-7}$ cycloalkyl, 4-14 membered heterocycloalkyl, $C_{6-10}$ aryl, and 5-10 membered heteroaryl is optionally and independently substituted with 1, 2, or 3 substituents independently selected from the group consisting of halogen, CN, $C_{1-4}$ alkyl, $C_{1-4}$ haloalkyl, $C_{2-6}$ alkenyl, $C_{2-6}$ alkynyl, $NH_2$, $NHCH_3$, $N(CH_3)_2$, OH, $OC_{1-4}$ alkyl, $OC_{1-4}$ haloalkyl, =O, $SC_{1-4}$ alkyl, and $C_{3-7}$ cycloalkyl.

15. The compound according to claim 14, or a pharmaceutically acceptable salt, optical isomer, geometric isomer, or tautomer thereof, wherein X$_1$ is CR$_{14}$;
X$_2$ is CR$_{15}$; and
X$_3$ is CR$_{16}$.

16. The compound according to claim 14, or a pharmaceutically acceptable salt, optical isomer, geometric isomer, or tautomer thereof, wherein ring A is $C_{3-7}$ cycloalkyl, a 3-7 membered heterocycloalkyl, a monocyclic $C_{5-7}$ aryl, or a monocyclic 5-7 membered heteroaryl, wherein the $C_{3-7}$ cycloalkyl, 3-7 membered heterocycloalkyl, $C_{5-7}$ aryl, or 5-7 membered heteroaryl, is optionally substituted with 1, 2, 3, or 4 independently selected R$_1$ substituents.

17. The compound according to claim 14, or a pharmaceutically acceptable salt, optical isomer, geometric isomer, or tautomer thereof, wherein ring A is phenyl or a monocyclic 5-6 membered heteroaryl, wherein the phenyl or 5-6 membered heteroaryl is optionally substituted with 1, 2, 3, or 4 independently selected R$_1$ substituents.

18. The compound according to claim 1, or an optical isomer thereof, wherein the compound, or optical isomer thereof, is selected from the group consisting of:

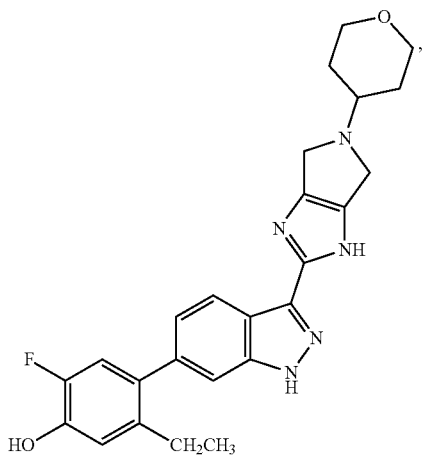

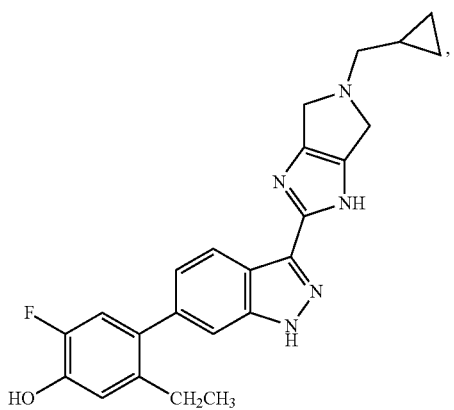

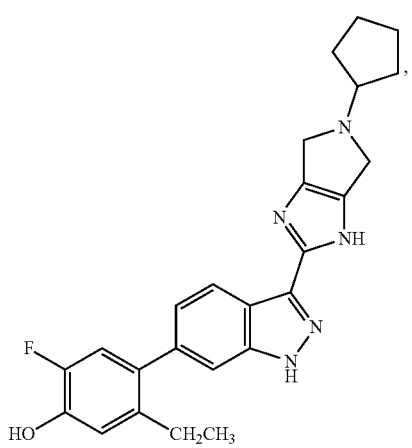

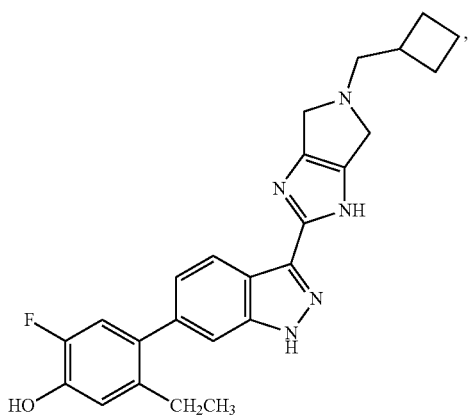

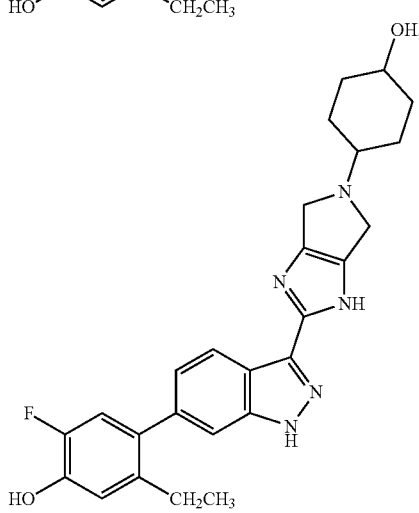

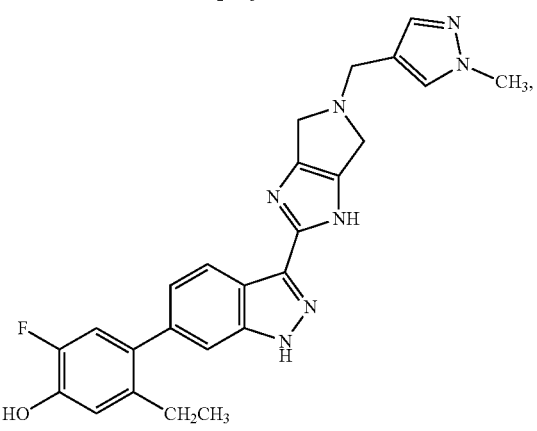

259
-continued
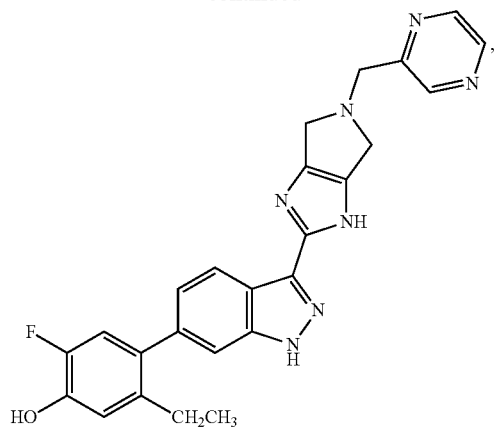
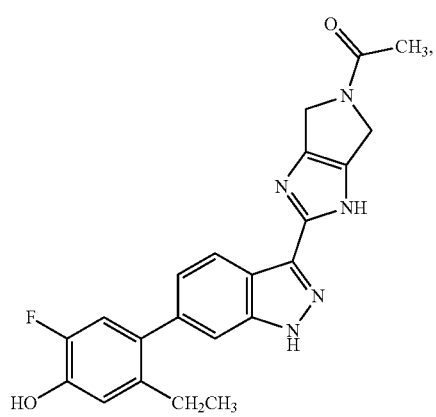
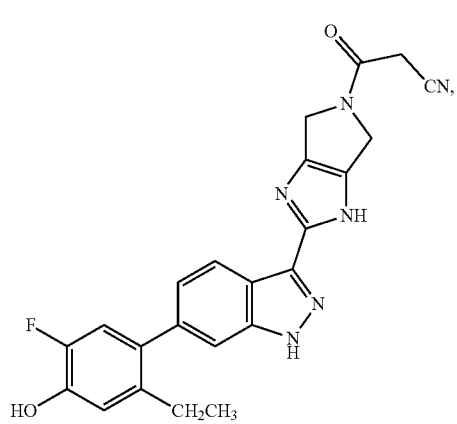
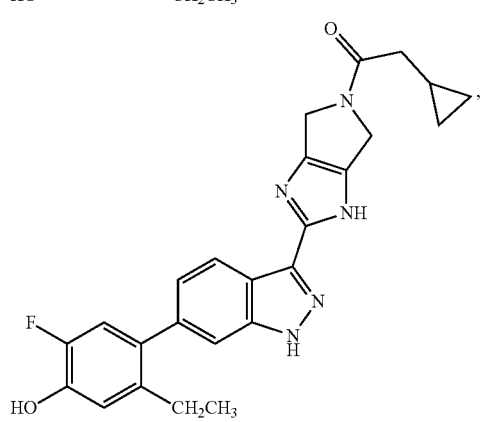
260
-continued
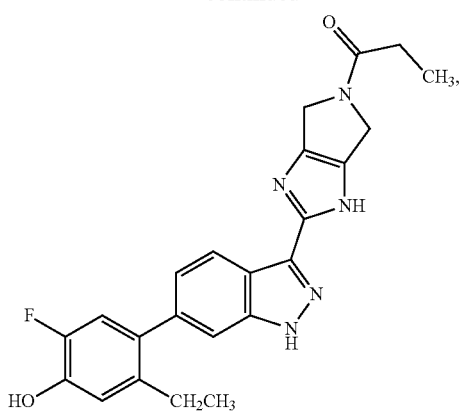
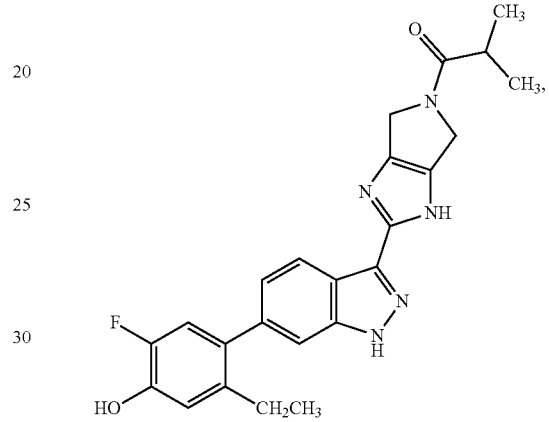
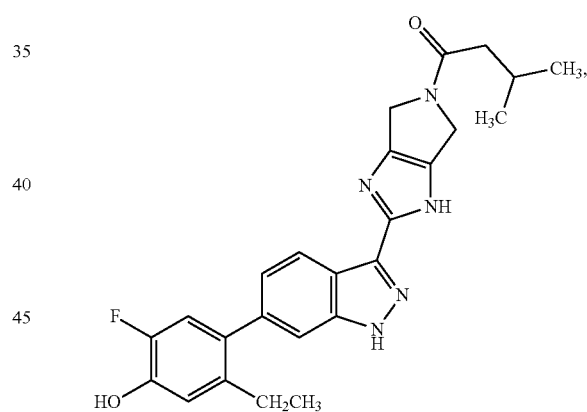
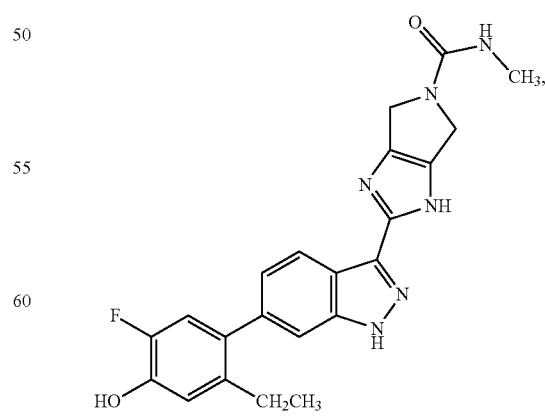

261
-continued
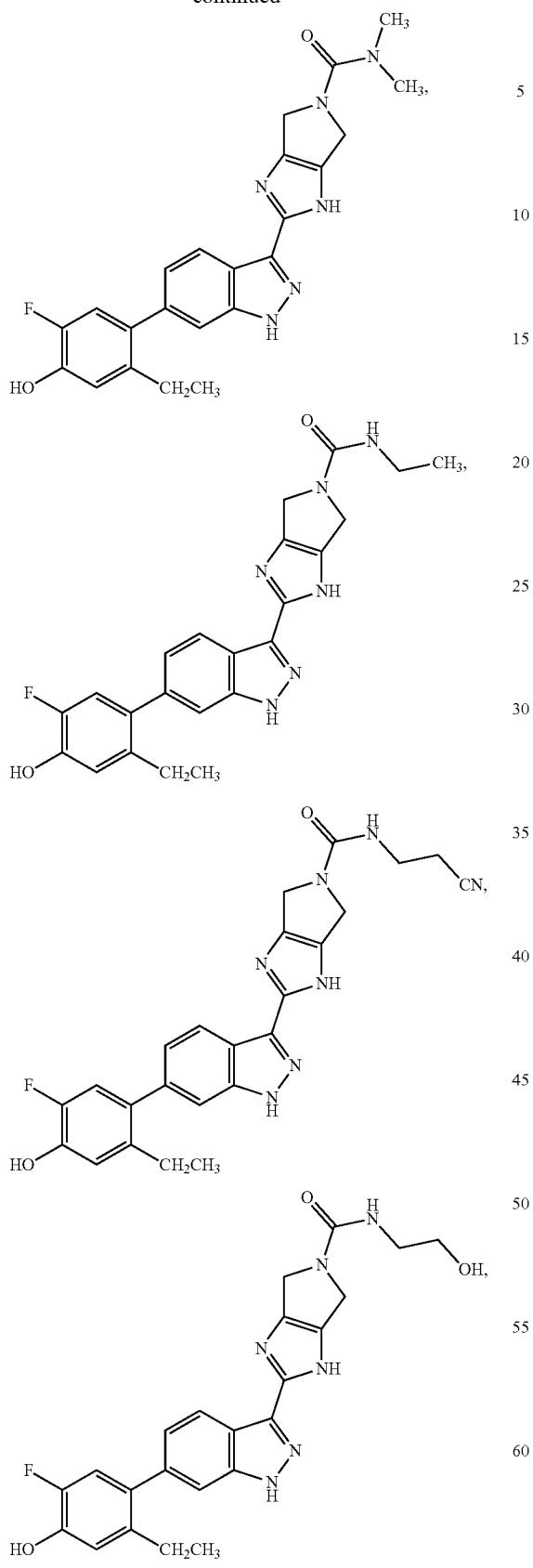
262
-continued
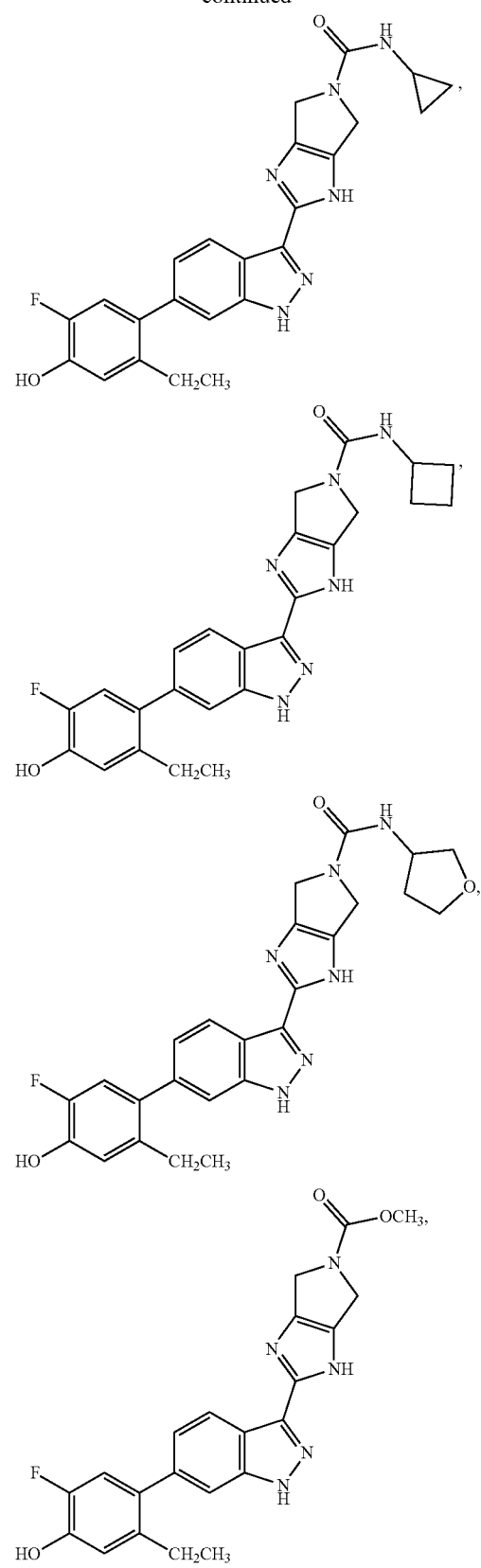

263
-continued
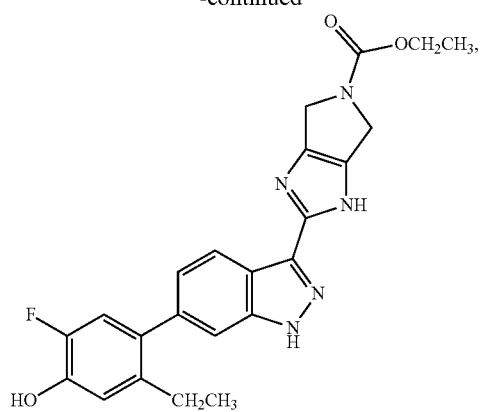
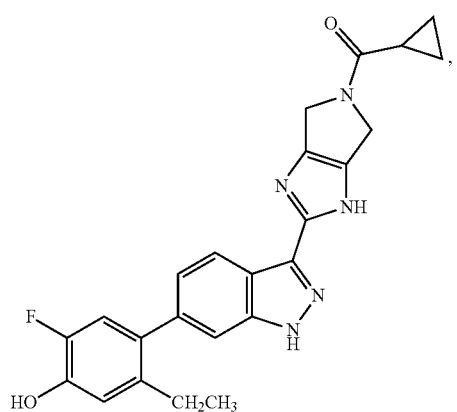
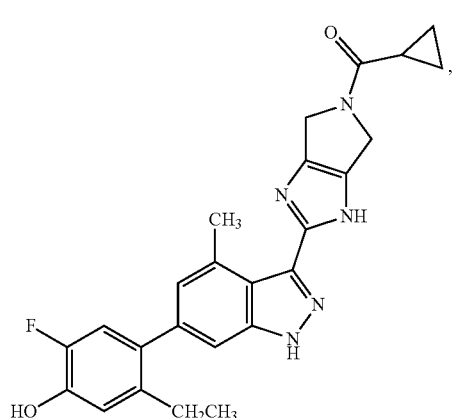
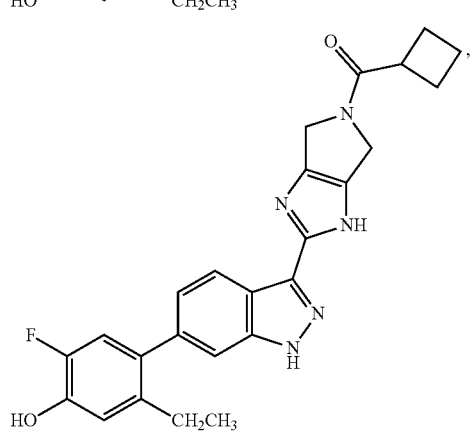
264
-continued
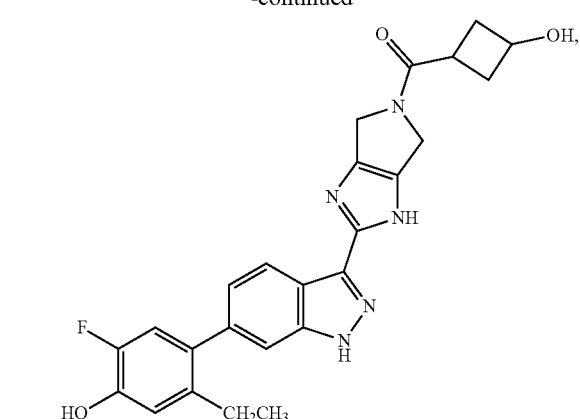
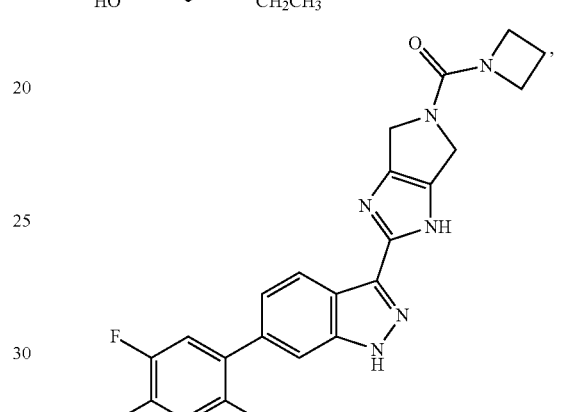
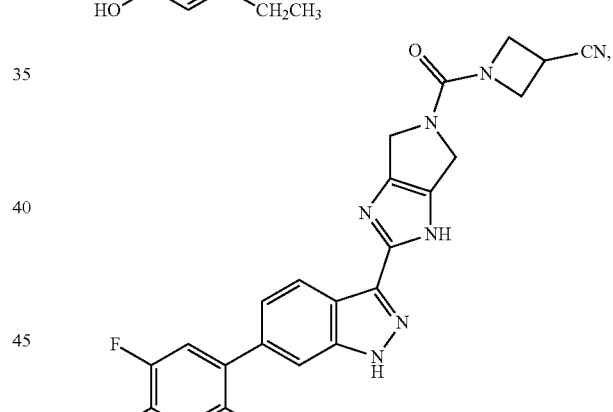
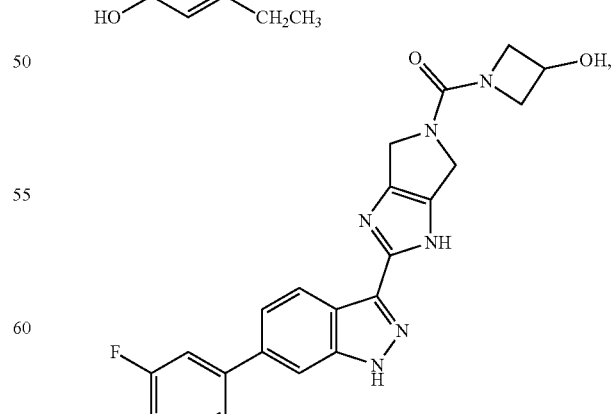

265
-continued
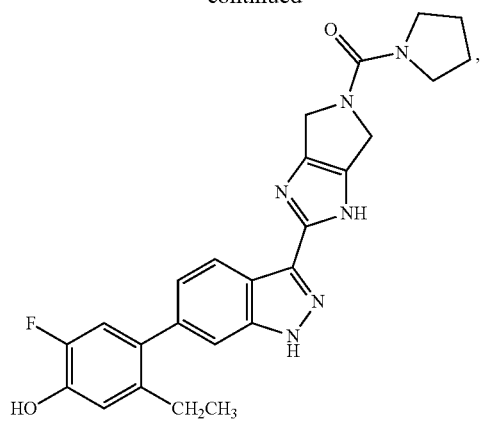
266
-continued
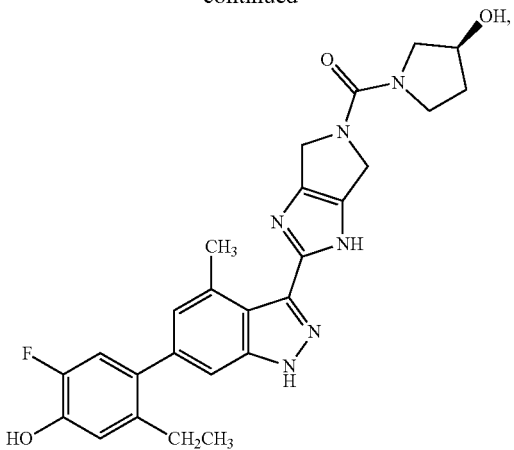

267
268
-continued
-continued
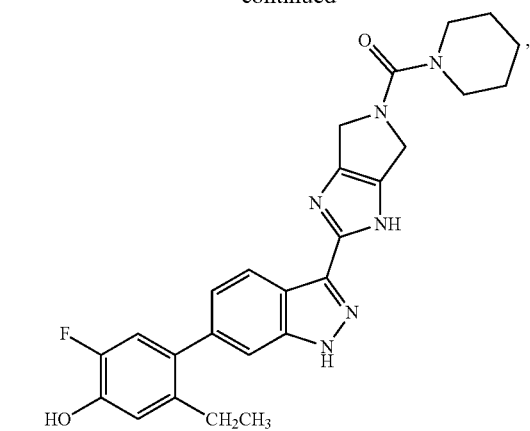
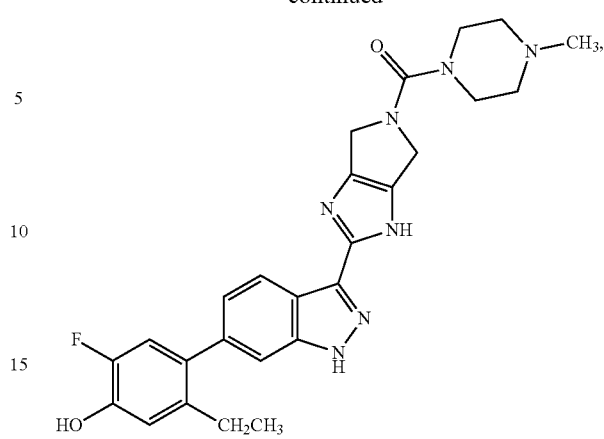
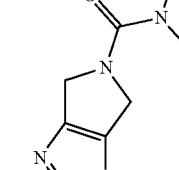

269
-continued
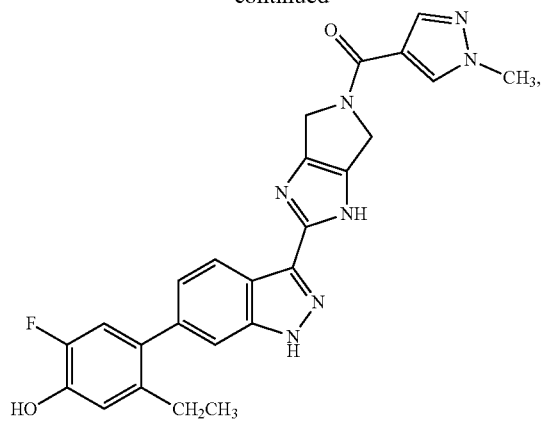
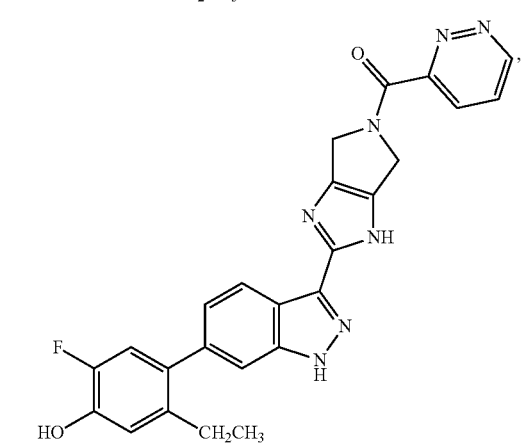
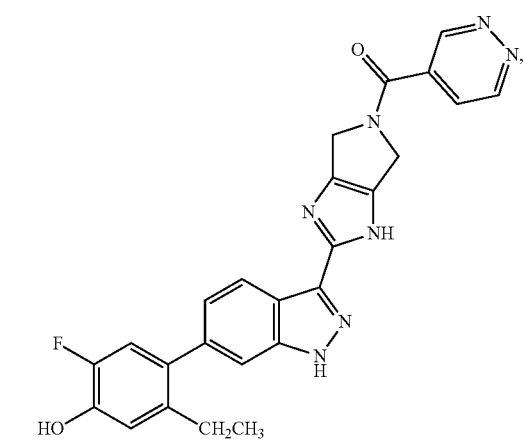
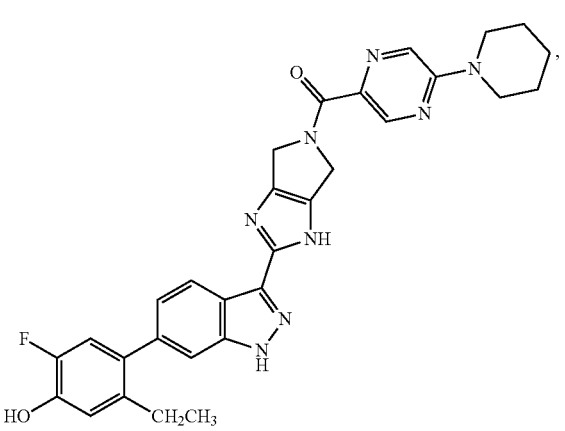
270
-continued
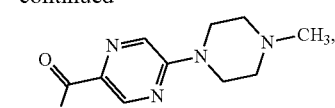
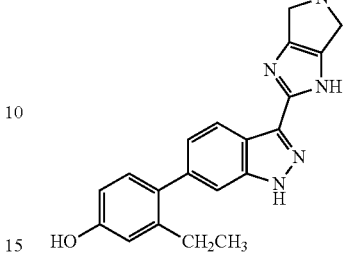
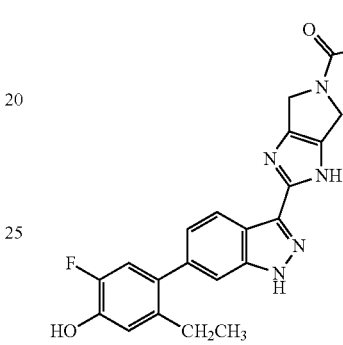
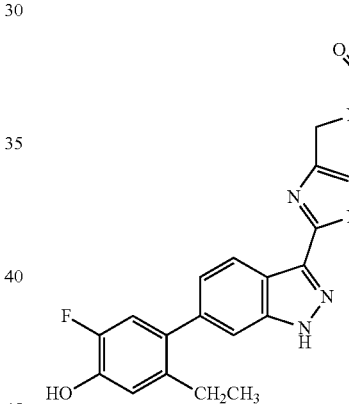
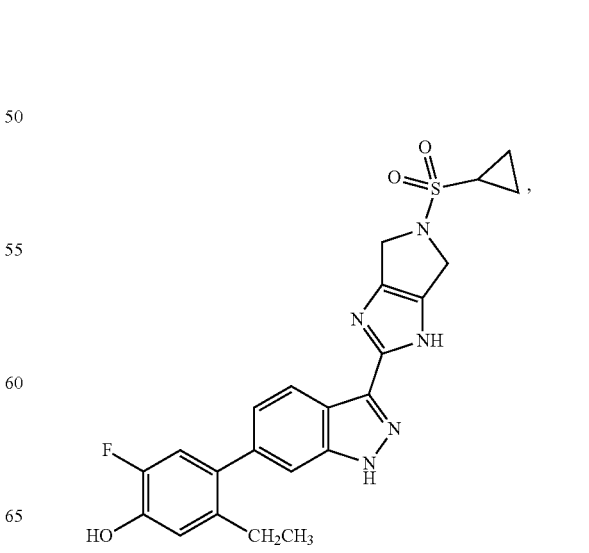

-continued
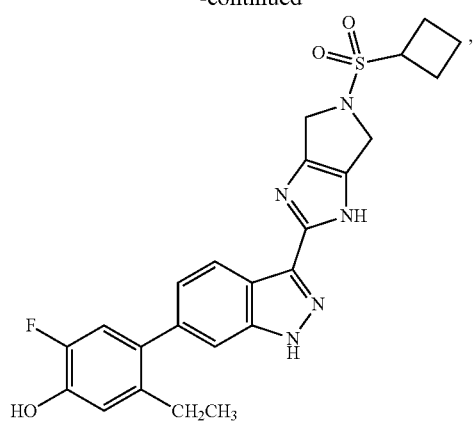
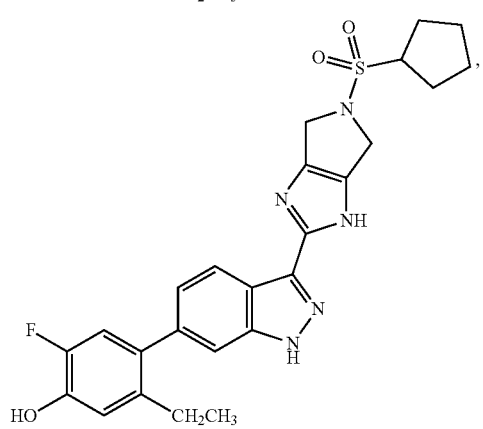
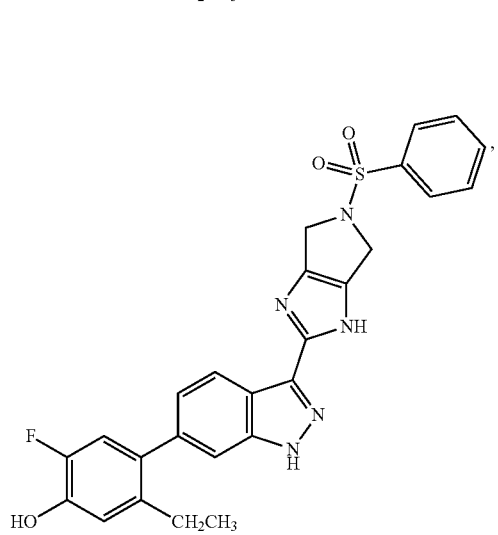
-continued
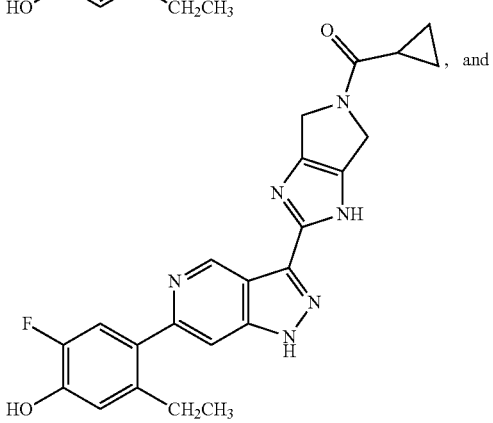
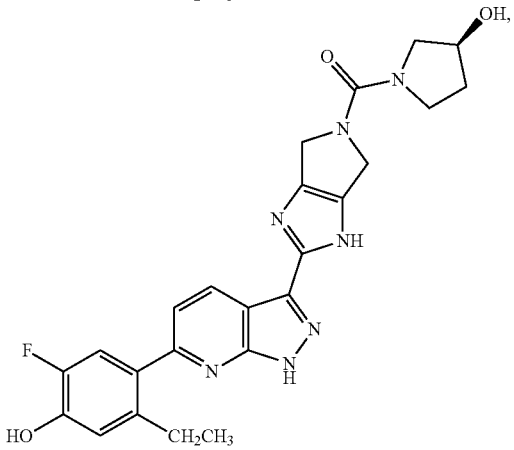
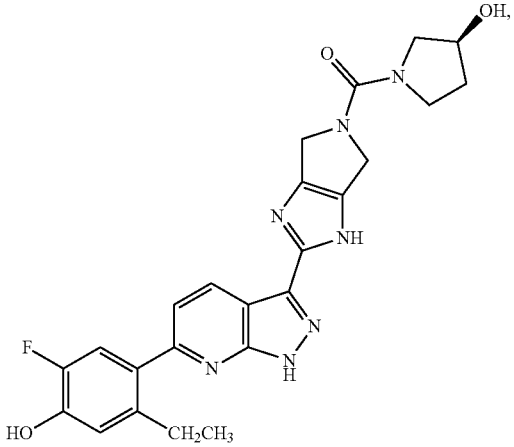
or a pharmaceutically acceptable salt thereof.
19. A pharmaceutical composition comprising one or more pharmaceutically acceptable carriers, adjuvants or excipients and the compound according to claim 1, or a pharmaceutically acceptable salt, optical isomer, geometric isomer, or tautomer thereof.
* * * * *